US012760370B2

(12) United States Patent
Hodis et al.

(10) Patent No.: US 12,760,370 B2
(45) Date of Patent: Oct. 13, 2026

(54) METHODS OF PRODUCING HUMAN CANCER CELL MODELS AND METHODS OF USE

(71) Applicants: The Broad Institute, Inc., Cambridge, MA (US); Massachusetts Institute of Technology, Cambridge, MA (US); Dana-Farber Cancer Institute, Inc., Boston, MA (US)

(72) Inventors: Eran Hodis, Boston, MA (US); Levi Garraway, Boston, MA (US); Aviv Regev, Cambridge, MA (US)

(73) Assignees: THE BROAD INSTITUTE, INC., Cambridge, MA (US); MASSACHUSETTS INSTITUTE OF TECHNOLOGY, Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 1164 days.

(21) Appl. No.: 16/631,916

(22) PCT Filed: Jul. 18, 2018

(86) PCT No.: PCT/US2018/042737

§ 371 (c)(1),
(2) Date: Jan. 17, 2020

(87) PCT Pub. No.: WO2019/018553

PCT Pub. Date: Jan. 24, 2019

(65) Prior Publication Data

US 2020/0157563 A1 May 21, 2020

Related U.S. Application Data

(60) Provisional application No. 62/534,023, filed on Jul. 18, 2017.

(51) Int. Cl.

| | |
|---|---|
| ***C12Q 1/6886*** | (2018.01) |
| ***C07K 14/82*** | (2006.01) |
| ***C12N 9/22*** | (2006.01) |
| ***C12N 15/113*** | (2010.01) |
| ***C12N 15/85*** | (2006.01) |

(52) U.S. Cl.

CPC ............ *C12Q 1/6886* (2013.01); *C07K 14/82* (2013.01); *C12N 9/22* (2013.01); *C12N 15/113* (2013.01); *C12N 15/85* (2013.01); *C07K 2319/81* (2013.01); *C12N 2310/20* (2017.05); *C12N 2320/12* (2013.01); *C12Q 2600/112* (2013.01); *C12Q 2600/156* (2013.01)

(58) Field of Classification Search

CPC .......................... C12Q 1/6886; C12N 2310/20

See application file for complete search history.

(56) References Cited

U.S. PATENT DOCUMENTS

| | | | |
|---|---|---|---|
| 5,869,326 | A | 2/1999 | Hofmann |
| 5,976,782 | A | 11/1999 | Parish et al. |
| 6,133,437 | A | 10/2000 | Korneluk et al. |
| 6,225,118 | B1 | 5/2001 | Grant et al. |
| 6,444,434 | B1 | 9/2002 | Jakobsen et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |

(Continued)

FOREIGN PATENT DOCUMENTS

| | | | |
|---|---|---|---|
| EP | 2 764 103 | B1 | 8/2014 |
| EP | 2 771 468 | B1 | 9/2014 |

(Continued)

OTHER PUBLICATIONS

Duquette et al. Metastasis-associated MCL1 and P16 copy number alterations dictate resistance to vemurafenib in a BRAFV600E patient-derived papillary thyroid carcinoma preclinical model. Oncotarget 6 (2015) 42445-42467 (Year: 2015).*

(Continued)

*Primary Examiner* — Peter Paras, Jr.
*Assistant Examiner* — Briana N Ebbinghaus
(74) *Attorney, Agent, or Firm* — Foley & Lardner LLP; Sunit Talapatra

(57) ABSTRACT

The present invention provides methods for introducing mutations to primary cells and selecting for the mutations to obtain a population of cells for modeling cancer. Such methods may comprise at least one round of introducing one or more mutations into one or more cells in a population of cells in vitro and culturing the cells until the mutation(s) are positively selected in the population. The cells may be cultured in vitro. The cells may be cultured in vivo. In certain embodiments, the cells are positively selected in vivo in order to select for cells capable of evading the immune system. In certain embodiments, cells are selected in an immune competent animal model. The cells may primary cells. The population of cells may be used for drug screening and for studying cancer.

12 Claims, 67 Drawing Sheets

Specification includes a Sequence Listing.

(56) References Cited

U.S. PATENT DOCUMENTS

| | | | |
|---|---|---|---|
| 8,999,641 | B2 | 4/2015 | Zhang et al. |
| 2006/0105360 | A1 | 5/2006 | Croce et al. |
| 2011/0105342 | A1 | 5/2011 | Lubinski et al. |
| 2012/0010240 | A1 | 1/2012 | Coughlin et al. |
| 2014/0137274 | A1 | 5/2014 | Ishikawa |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0310830 | A1 | 10/2014 | Zhang et al. |
| 2016/0040250 | A1 | 2/2016 | Xing |

FOREIGN PATENT DOCUMENTS

| | | | | |
|---|---|---|---|---|
| EP | 2 784 162 | B1 | 10/2014 | |
| WO | WO-97/49450 | A1 | 12/1997 | |
| WO | 98/52609 | A1 | 11/1998 | |
| WO | WO-2004/015075 | A2 | 2/2004 | |
| WO | WO-2011/008730 | A2 | 1/2011 | |
| WO | WO-2014/018423 | A2 | 1/2014 | |
| WO | WO-2014/093595 | A1 | 6/2014 | |
| WO | WO-2014/093622 | A2 | 6/2014 | |
| WO | WO-2014/093635 | A1 | 6/2014 | |
| WO | WO-2014/093655 | A2 | 6/2014 | |
| WO | WO-2014/093661 | A2 | 6/2014 | |
| WO | WO-2014/093694 | A1 | 6/2014 | |
| WO | WO-2014/093701 | A1 | 6/2014 | |
| WO | WO-2014/093709 | A1 | 6/2014 | |
| WO | WO-2014/093712 | A1 | 6/2014 | |
| WO | WO-2014/093718 | A1 | 6/2014 | |
| WO | WO-2014/204723 | A1 | 12/2014 | |
| WO | WO-2014/204724 | A1 | 12/2014 | |
| WO | WO-2014/204725 | A1 | 12/2014 | |
| WO | WO-2014/204726 | A1 | 12/2014 | |
| WO | WO-2014/204727 | A1 | 12/2014 | |
| WO | WO-2014/204728 | A1 | 12/2014 | |
| WO | WO-2014/204729 | A1 | 12/2014 | |
| WO | WO-2014/210353 | A2 | 12/2014 | |
| WO | WO-2016/040476 | A1 | 3/2016 | |
| WO | WO-2016049024 | A2 * | 3/2016 | ......... A01K 67/0275 |
| WO | 2016/108926 | A1 | 7/2016 | |
| WO | WO-2016/168584 | A1 | 10/2016 | |
| WO | WO-2016/186745 | A1 | 11/2016 | |
| WO | 2017/075294 | A1 | 5/2017 | |
| WO | 2019/018553 | A1 | 1/2019 | |

OTHER PUBLICATIONS

Xing et al. BRAF V600E and TERT Promoter Mutations Cooperatively Identify the Most Aggressive Papillary Thyroid Cancer With Highest Recurrence. Journal of Clinical Oncology 32 (2014) 2718-2726 (Year: 2014).*

Jinek et al. RNA-programmed genome editing in human cells. eLife 2013;2:e00471 (Year: 2013).*

Omur and Baran. An update on molecular biology of thyroid cancers. Critical Reviews in Oncology/Hematology 90 (2014) 233-252 (Year: 2014).*

Wu et al. Molecular profiling of thyroid cancer subtypes using large-scale text mining. BMC Medical Genomics 2014, 7(Suppl 3):S3 (Year: 2014).*

In vitro Jul. 2012. accessed at https://www.dictionary.com/browse/in-vitro on Sep. 12, 2023 (Year: 2012).*

Hosler et al. A Primary Melanoma and its Asynchronous Metastasis Highlight the Role of BRAF, CDKN2A, and TERT. J Cutan Pathol. Feb. 2015;42(2):108-17.(Year: 2015).*

Ming et al. PTEN: New Insights into Its Regulation and Function in Skin Cancer. J Invest Dermatol. Sep. 2009; 129(9): 2109-2112. (Year: 2009).*

Daniotti et al. BRAF alterations are associated with complex mutational profiles in malignant melanoma. Oncogene. Aug. 5, 2004;23(35):5968-77. (Year: 2004).*

Kent et al. Order Matters: The Order of Somatic Mutations Influences Cancer Evolution. Cold Spring Harb Perspect Med. Apr. 3, 2017;7(4):a027060. (Year: 2017).*

Rinner et al. MUG-Mel2, a novel highly pigmented and well characterized NRAS mutated human melanoma cell line. Sci Rep. May 1, 20178;7(1):2098. (Year: 2018).*

Malanga, et al., "Activating E17K Mutation in the Gene Encoding the Protein Kinase AKT in a Subset of Squamous Cell Carcinoma of the Lung", Cell Cycle, vol. 7, No. 5, Mar. 1, 2008, 665-669.

Do, et al., "Detection of the Transforming AKT1 Mutation E17K in Non-Small Cell Lung Cancer by High Resolution Melting", BMC Research Notes, vol. 1, No. 14, 2008, 5 pages.

Drier, et al., "Somatic Rearrangements Across Cancer Reveal Classes of Samples with Distinct Patterns of DNA Breakage and Rearrangement-Induced Hypermutability", Genome Research, vol. 23, No. 2, Feb. 2013, 228-235.

Drost, et al., "Sequential Cancer Mutations in Cultured Human Intestinal Stem Cells", Nature, vol. 521, No. 7550, May 7, 2015, 23 pages.

Edmunds, et al., "Mutational Analysis of Selected Genes in the TGFBETA, WNET, PRB, and P53 Pathways in Primary Uveal Melanoma", Investigative Ophthalmology & Visual Science, vol. 43, No. 9, Sep. 2002, 2845-2851.

Emery, et al., "Identification Myelin Gene Regulatory Factor is a Critical Transcriptional Regulator Required for CNS Myelination", Cell, vol. 138, No. 1, Jul. 10, 2009, 20 pages.

Fernandez-Peralta, et al., "Significance of Mutations In TGFBR2 And BAX in Neoplastic Progression and Patient Outcome in Sporadic Colorectal Tumors with High-Frequency Microsatellite Instability", Cancer Genetics and Cytogenetics, vol. 157, No. 1, Feb. 2005, 18-24.

Forbes, et al., "Cosmic: Somatic Cancer Genetics at High-Resolution", Nucleic Acids Research, vol. 45, Nov. 29, 2016, D777-D783.

Fusco, et al., "A New Mechanism of BRAF Activation in Human Thyroid Papillary Carcinomas", Journal of Clinical Investigation, vol. 115, No. 1, Jan. 3, 2005, 20-23.

Gao, et al., "Integrative Analysis of Complex Cancer Genomics and Clinical Profiles using the CBioPortal", Science Signaling, vol. 6, No. 269, Apr. 2, 2013, 34 pages.

Garraway, et al., "Integrative Genomic Analyses Identify MITFL as a Lineage Survival Oncogene Amplified in Malignant Melanoma", Nature, vol. 436, No. 7047, Jul. 7, 2005, 117-122.

Garraway, et al., "Lessons from the Cancer Genome", Cell, vol. 153, Mar. 28, 2013, 17-37.

Geyer, et al., "Microglandular Adenosis or Microglandular Adenoma? A Molecular Genetic Analysis of a Case Associated with Atypia and Invasive Carcinoma", Histopathology, vol. 55, No. 6, Dec 2009, 732-743.

Gibney, et al., "Paradoxical Oncogenesis and The Long Term Consequences of BRAF Inhibition in Melanoma", Nature Reviews Clinical Oncology, vol. 10, No. 7, Jul. 2013, 20 pages.

Girard, et al., "Apparent Ruminal Synthesis and Intestinal Disappearance of Vitamin B12 and its Analogs in Dairy Cows", Journal of Dairy Science, vol. 92, No. 9, Sep. 2009, 4524-4529.

Girard, et al., "Thymic Tumors Relevant Molecular Data in the Clinic", Journal of Thoracic Oncology, vol. 5, Issue 10, Oct. 2010, S291-S295.

(56) References Cited

OTHER PUBLICATIONS

Growney, et al., "Activation Mutations of Human C-KIT Resistant to Imatinib Mesylate are Sensitive to the Tyrosine Kinase Inhibitor PKC412", Blood, vol. 106, No. 2, Jul. 15, 2005, 721-724.
Guo, et al., "Phase II, Open-Label, Single-Arm Trial of Imatinib Mesylate in Patients with Metastatic Melanoma Harboring C-KIT Mutation or Amplification", Journal of Clinical Oncology, vol. 29, No. 21, Jul. 20, 2011, 2904-2909.
Haigis, et al., "Differential Effects of Oncogenic K-RAS And N-RAS on Proliferation, Differentiation and Tumor Progression in the Colon", Nature Genetics, vol. 40, No. 5, May 2008, 18 pages.
Henley, et al., "Tyrosine Kinase Receptor Expression in Thymomas", Journal of Cancer Research and Clinical Oncology, vol. 130, No. 4, Apr. 2004, 222-224.
Hirota, et al., "Gain-of-Function Mutation at the Extracellular Domain of KIT in Gastrointestinal Stromal Tumours", The Journal of Pathology, vol. 193, No. 4, Apr. 2001, 505-510.
Hirota, et al., "Gain-of-Function Mutations of C-KIT in Human Gastrointestinal Stromal Tumors", Science, vol. 279, No. 5350, Jan. 23, 1998, 577-580.
Hodi, et al., "Imatinib for Melanomas Harboring Mutationally Activated or Amplified Kit Arising on Mucosal, Acral, and Chronically Sun-Damaged Skin", Journal of Clinical Oncology, vol. 31, No. 26, Sep. 10, 2013, 12 pages.
Hodis, et al., "A Landscape of Driver Mutations in Melanoma", Cell, vol. 150, Jul. 20, 2012, 22 pages.
Horbinski, et al., "To BRAF or Not to BRAF: Is That Even a Question Anymore", Journal of Neuropathology & Experimental Neurology, vol. 72, No. 1, Jan. 2013, 12 pages.
Horn, et al., "TERT Promoter Mutations in Familial and Sporadic Melanoma", Science, vol. 339, No. 6122, Feb. 22, 2013, 959-961.
Huang, et al., "Highly Recurrent TERT Promoter Mutations in Human Melanoma", Science, vol. 339, No. 6122, Feb. 22, 2013, 6 pages.
Huang, et al., "New Era in Drug Interaction Evaluation: US Food and Drug Administration Update on CYP Enzymes, Transporters, and the Guidance Process", The Journal of Clinical Pharmacology, vol. 48, No. 6, Jun. 2008, 662-670.
Irahara, et al., "NRAS Mutations are Rare in Colorectal Cancer", Diagnostic Molecular Pathology, vol. 19, No. 3, Sep. 2010, 13 pages.
Janku, et al., "PIK3CA Mutations Frequently Coexist with RAS And BRAF Mutations in Patients with Advanced Cancers", PLoS One, vol. 6, No. 7, Jul. 2011, 8 pages.
Jemal, et al., "Cancer Statistics, 2010", CA: A Cancer Journal for Clinicians, vol. 60, No. 5, Sep.-Oct. 2010, 277-300.
Jin, et al., "PTEN Mutations and Relationship To EGFR, ERBB2, KRAS, and TP53 Mutations in Non-Small Cell Lung Cancers", Lung Cancer, vol. 69, No. 3, Sep. 2010, 279-283.
Kerr-Conte, et al., "Upgrading Pretransplant Human Islet Culture Technology Requires Human Serum Combined with Media Renewal", Transplantation, vol. 89, No. 9, May 15, 2010, 1154-1160.
Kimura, et al., "High Prevalence of BRAF Mutations in Thyroid Cancer: Genetic Evidence for Constitutive Activation of The RET/PTC-RAS-BRAF Signaling Pathway in Papillary Thyroid Carcinoma", Cancer Research, vol. 63, No. 7, Apr. 1, 2003, 1454-1457.
Kitayama, et al., "Constitutively Activating Mutations of C-KIT Receptor Tyrosine Kinase Confer Factor-Independent growth and Tumorigenicity of Factor-Dependent Hematopoietic Cell Lines", Blood, vol. 85, No. 3, Feb. 1, 1995, 790-798—Abstract only.
Kohno, et al., "Inactivation of the PTEN/MMAC1/TEP1 Gene in Human Lung Cancers", Genes Chromosomes and Cancer, vol. 22, No. 2, Jun. 1998, 152-156.
Kosmider, et al., "TET2 Mutation is an Independent Favorable Prognostic Factor in Myelodysplastic Syndromes (MDSS)", Blood, vol. 114, No. 15, Oct. 8, 2009, 3285-3291.
Krauthammer, et al., "Exome Sequencing Identifies Recurrent Mutations In NF1 and RASopathy Genes in Sun-Exposed Melanomas", Nature Genetics, vol. 47, No. 9, Sep. 2015, 25 pages.
Krauthammer, et al., "Exome Sequencing Identifies Recurrent Somatic RAC1 Mutations in Melanoma", Nature Genetics, vol. 44, No. 9, Sep. 2012, 30 pages.
Kuo, et al., "The Relationships Among Service Quality, Perceived Value, Customer Satisfaction, and Post-Purchase Intention in Mobile Value-Added Services", Computers in Human Behavior, vol. 25, Issue 4, Jul. 2009, 887-896.
Kurman, "Molecular Pathogenesis and Extraovarian Origin of Epithelial Ovarian Cancer-Shifting the Paradigm", Human Pathology, vol. 42, No. 7, Jul. 2011, 918-931.
Landen, et al., "Early Events in the Pathogenesis of Epithelial Ovarian Cancer", Journal of Clinical Oncology, vol. 26, No. 6, Feb. 20, 2008, 995-1005.
Laurent-Puig, et al., "Analysis of PTEN, BRAF, and EGFR Status in Determining Benefit from Cetuximab Therapy In Wild-Type KRAS Metastatic Colon Cancer", Journal of Clinical Oncology, vol. 27, No. 35, Dec 10, 2009, 5924-5930.
Lebbe, et al., "Phase II Multicentric Uncontrolled National Trial Assessing the Efficacy of Nilotinib in the Treatment of Advanced Melanomas with C-KIT Mutation or Amplification", Journal of Clinical Oncology, May 2014, 9032—Abstract.
Lee, et al., "Somatic Mutations in Epidermal Growth Factor Receptor Signaling Pathway Genes in Non-Small Cell Lung Cancers", Journal of Thoracic Oncology, vol. 5, No. 11, Nov. 2010, 1734-1740.
Leslie, et al., "Non-Genomic Loss of PTEN function in Cancer: Not in my Genes", Trends in Pharmacological Sciences, vol. 32, No. 3, Mar. 2011, 131-140.
Lovly, et al., "Routine Multiplex Mutational Profiling of Melanomas Enables Enrollment in Genotype-Driven Therapeutic Trials", PLoS One, vol. 7, No. 4, Apr. 2012, 9 pages.
Maehama, "PTEN: its Deregulation and Tumorigenesis", Biological and Pharmaceutical Bulletin, vol. 30, No. 9, Sep. 2007, 1624-1627.
Maertens, et al., "Elucidating Distinct Roles for NF1 in Melanomagenesis", Cancer Discovery, vol. 3, No. 3, Mar. 2013, 20 pages.
Maldonado, et al., "Determinants of BRAF Mutations in Primary Melanomas", Journal of the National Cancer Institute, vol. 95, No. 24, Dec 17, 2003, 1878-1880.
Terheyden et al., "Response to Imatinib Mesylate Depends on the Presence of the V559A-Mutated KIT Oncogene," Journal of Investigative Dermatology, 2010, 130, 314-316.
Torres-Cabala, et al., "Correlation between KIT Expression and KIT Mutation in Melanoma: A Study of 173 Cases with Emphasis on the Acral-Lentiginous/Mucosal Type", Modern Pathology, vol. 22, No. 11, Nov. 2009, 21 pages.
Torres-Ruiz, et al., "Efficient Recreation of t(11;22) EWSR1-FLI1+ in Human Stem Cells Using CRISPR/Cas9", Stem Cell Reports, vol. 8, No. 5, May 9, 2017, 1408-1420.
Tsao, et al., "Genetic Interaction between NRAS and BRAF Mutations and PTEN/MMAC1 Inactivation in Melanoma", Journal of Investigative Dermatology, vol. 122, No. 2, Feb. 2004, 9 pages.
Van 'T Veer, et al., "N-Ras Mutations in Human Cutaneous Melanoma from Sun-Exposed Body Sites", Molecular and Cellular Biology, vol. 9, No. 7, Jul. 1989, 3114-3116.
Vaughn, et al., "Frequency of KRAS, BRAF, and NRAS Mutations in Colorectal Cancer", Genes Chromosomes Cancer, vol. 50, No. 5, May 2011, 307-312.
Viros, et al., "Ultraviolet Radiation Accelerates BRAF-Driven Melanomagenesis by Targeting TP53", Nature, vol. 511, No. 7510, Jul. 24, 2014, 17 pages.
Vogelstein, et al., "Cancer Genome Landscapes", Science, vol. 339, Mar. 29, 2013., 1546-1558.
Wakimoto, et al., "Targetable Signaling Pathway Mutations are Associated with Malignant Phenotype in IDH-Mutant Gliomas", Clinical Cancer Research, vol. 20, No. 11, Jun. 1, 2014, 22 pages.
Walter, et al., "The Unfolded Protein Response: From Stress Pathway to Homeostatic Regulation", Science, vol. 334, No. 6059, Nov. 25, 2011, 1081-1086.
Wan, et al., "Mechanism of Activation of the RAF-ERK Signaling Pathway by Oncogenic Mutations of B-RAF", Cell, vol. 116, No. 6, Mar. 19, 2009, 855-867.

(56) References Cited

OTHER PUBLICATIONS

Whittaker, et al., "A Genome-Scale RNA Interference Screen Implicates NF1 Loss in Resistance to RAF Inhibition", Cancer Discovery, vol. 3, No. 3, Mar. 2013, 21 pages.
Worm, et al., "Genetic and Epigenetic Alterations of the APC Gene in Malignant Melanoma", Oncogene, vol. 23, No. 30, Jul. 1, 2004, 5215-5226.
Xing, et al., "ROXY1, a Member of the Plant Glutaredoxin Family, is Required for Petal Development in *Arabidopsis thaliana*", Development, vol. 132, No. 7, Apr. 2005, 1555-1565.
Yap, et al., "The NF1 Gene Revisited—from Bench to Bedside", Oncotarget, vol. 5, No. 15, Aug. 2014, 5873-5892.
Yauch, et al., "Smoothened Mutation Confers Resistance to a Hedgehog Pathway Inhibitor in Medulloblastoma", Science, vol. 326, No. 5952, Oct. 23, 2009, 7 pages.
Yeh, et al., "Combined Activation of MAP Kinase Pathway and β-Catenin Signaling Cause Deep Penetrating Nevi", Nature Communications, vol. 8, No. 644, 2017, 8 pages.
Zeng, et al., "Bi-Allelic Loss of CDKN2A Initiates Melanoma Invasion via BRN2 Activation", Cancer Cell, vol. 34, No. 1, Jul. 9, 2018, 38 pages.
Makishima, et al., "Mutations in the Spliceosome Machinery, A Novel and Ubiquitous Pathway in Leukemogenesis", Blood, vol. 119, No. 14, Apr. 5, 2012, 3203-3210.
Malcovati, et al., "Clinical Significance of SF3B1 Mutations in Myelodysplastic Syndromes and Myelodysplastic/Myeloproliferative Neoplasms", Blood, vol. 118, No. 24, Dec 8, 2011, 6239-6246.
Tsao et al., Monitoring response to therapy in melanoma by quantifying circulating tumour DNA with droplet digital PCR for BRAF and NRAS mutations, Scientific Reports, pp. 1-11, 2015.
Negri et al., "PTEN Status in Advanced Colorectal Cancer Treated with Cetuximab," British Journal of Cancer, 102, 2010, 162-164.
Si et al., "mTOR Pathway Activation in KIT-Mutated Melanoma with Acquired Imatinib Resistance," American Society of Clinical Oncology, 2012, 8562, Abstract.
Caffrey, "Promising News in Treating Multiple Myeloma," The American Journal of Managed Care, vo. 20, Issue 7, 2014, 1 page.
The Broad Institute, Inc, "International Preliminary Report on Patentability issued in International Application No. PCT/US2018/042737", mailed on Jan. 30, 2020, 10 pages.
Adamson, et al., "A Multiplexed Single-Cell CRISPR Screening Platform Enables Systematic Dissection of the Unfolded Protein Response", Cell, vol. 167, No. 7, Dec 15, 2016, 49 pages.
Agaimy, et al., "V600E BRAF Mutations are Alternative Early Molecular Events in a Subset of KIT/PDGFRA Wild-Type Gastrointestinal Stromal Tumours", Journal of Clinical Pathology, vol. 62, No. 7, Jul. 2009, 613-616.
Akbani, et al., "Genomic Classification of Cutaneous Melanoma", Cell, vol. 161, No. 7, Jun. 2015, 1681-1696.
Baba, et al., "Phosphorylated AKT Expression is Associated with PIK3CA Mutation, Low Stage and Favorable Outcome in 717 Colorectal Cancers", Cancer, vol. 117, No. 7, Apr. 1, 2011, 17 pages.
Ball, et al., "RAS Mutations in Human Melanoma: A Marker of Malignant Progression", Journal of Investigative Dermatology, vol. 102, No. 3, Mar. 1994, 285-290.
Bastian, "The Molecular Pathology of Melanoma: An Integrated Taxonomy of Melanocytic Neoplasia", Annual Review of Pathology, vol. 2014, 2014, 37 pages.
Beadling, et al., "KIT Gene Mutations and Copy number in Melanoma Subtypes", Clinical Cancer Research, vol. 14. No. 21, Nov. 1, 2008, 6821-6828.
Begum, et al., "BRAF Mutations in Anaplastic Thyroid Carcinoma: Implications for Tumor Origin, Diagnosis and Treatment", Modern Pathology, vol. 17, 2004, 1359-1363.
Bejar, et al., "Clinical Effect of Point Mutations in Myelodysplastic Syndromes", The New England Journal of Medicine, vol. 364, No. 26, Jun. 30, 2011, 15 pages.
Bennett, "Genetics of Melanoma Progression: The Rise and Fall of Cell Senescence", Pigment Cell & Melanoma Research, vol. 29, Issue 2, Mar. 2016, 122-140.
Berg, et al., "Revised Terminology and Concepts for Organization of Seizures and Epilepsies: Report of the ILAE Commission on Classification and Terminology, 2005-2009", Epilepsia, vol. 51, No. 4, Apr. 2010, 676-685.
Berger, et al., "The Genomic Complexity of Primary Human Prostate Cancer", Nature, vol. 470, Feb. 10, 2011, 214-220.
Bhaijee, et al., "Molecular Analysis of Thyroid Tumors", Endocrine Pathology, vol. 22, No. 3, Sep. 2011, 126-133.
Bleeker, et al., "AKT1(E17K) in Human Solid Tumours", Oncogene, vol. 27, No. 42, Sep. 18, 2008, 5648-5650.
Brose, et al., "BRAF and RAS Mutations in Human Lung Cancer and Melanoma", Cancer Research, vol. 62, No. 23, Dec 1, 2002, 6997-7000.
Cancer Genome Atlas Network, "Genomic Classification of Cutaneous Melanoma", Cell, vol. 161, No. 7, Jun. 18, 2015, 30 pages.
Cardarella, et al., "Clinical, Pathologic, and Biologic Features Associated with BRAF Mutations in Non-Small Cell Lung Cancer", Clinical Cancer Research, vol. 19, No. 16, Aug. 15, 2013, 19 pages.
Carvajal, et al., "KIT as a Therapeutic Target in Metastatic Melanoma", JAMA, vol. 305, No. 22, Jun. 8, 2011, 17 pages.
Cazzola, et al., "The Genetic Basis of Myelodysplasia and its Clinical Relevance", Blood, vol. 122, No. 25, Dec 12, 2013, 4021-4034.
Cerami, et al., "The cBio Cancer Genomics Portal: An Open Platform for Exploring Multidimensional Cancer Data", Cancer Discovery, vol. 2, No. 5, May 2012, 7 pages.
Chalhoub, et al., "PTEN and The PI3-Kinase Pathway in Cancer", Annual Review of Pathology, vol. 4, 2009, 30 pages.
Chapman, et al., "Improved Survival with Vemurafenib in Melanoma with BRAF V600E Mutation", The New England Journal of Medicine, vol. 364, No. 26, Jun. 30, 2011, 17 pages.
Cheng, et al., "EGFR Exon 18 Mutations in East Asian Patients with Lung Adenocarcinomas: A Comprehensive Investigation of Prevalence, Clinicopathologic Characteristics and Prognosis", Scientific Reports, vol. 5, No. 13959, Sep. 10, 2015, 8 pages.
Chudnovsky, et al., "Use of Human Tissue to Assess the Oncogenic Activity of Melanoma-Associated Mutations", Nature Genetics, vol. 37, No. 7, Jul. 2005, 12 pages.
Ciampi, et al., "Alterations of the BRAF Gene in Thyroid Tumors", Endocrine Pathology, vol. 16, 2005, 163-171.
Ciampi, et al., "RET/PTC Rearrangements and BRAF Mutations in Thyroid Tumorigenesis", Endocrinology, vol. 148, No. 3, Mar. 2007, 936-941.
Clark, "Tumour Progression and the Nature of Cancer", British Journal of Cancer, vol. 64, No. 4, May 16, 1991, 631-644.
Cohen, et al., "BRAF Mutation in Papillary Thyroid Carcinoma", Journal of the National Cancer Institute, vol. 95, No. 3, Apr. 16, 2003, 625-627.
Cong, et al., "Multiplex Genome Engineering Using CRISPR/Cas Systems", Science, vol. 339, No. 6121, Feb. 15, 2013, 819-823.
Courtney, et al., "The PI3K Pathway as Drug Target in Human Cancer", Journal of Clinical Oncology, vol. 28, No. 6, Feb. 28, 2010, 1075-1083.
Curtin, et al., "Distinct Sets of Genetic Alterations in Melanoma", The New England Journal of Medicine, vol. 353, No. 20, Nov. 17, 2005, 2135-2147.
Curtin, et al., "Somatic Activation of KIT in Distinct Subtypes of Melanoma", Journal of Clinical Oncology, vol. 24, No. 26, Sep. 10, 2006, 4340-4346.
Damm, et al., "BCOR and BCORL 1 Mutations in Myelodysplastic Syndromes and Related Disorders", Blood, vol. 122, No. 18, Oct. 31, 2018, 3169-3177.
Damsky, et al., "β-Catenin Signaling Controls Metastasis in Braf-Activated Pten-Deficient Melanomas", Cancer cell, vol. 20, No. 6, Dec 13, 2011, 25 pages.
Daniel, et al., "Lessons from Tissue Compartment-Specific Analysis of Androgen Receptor Alterations in Prostate Cancer", The Journal of Steroid Biochemistry and Molecular Biology, vol. 166, Feb. 2017, 22 pages.
Dankort, et al., "Braf(V600E) Cooperates with Pten Loss to Induce Metastatic Melanoma", Nature Genetics, vol. 41, No. 5, May 2009, 21 pages.

(56) References Cited

OTHER PUBLICATIONS

Daoud, et al., “Pancreatic Islet Culture and Preservation Strategies: Advances, Challenges, and Future Outlook”, Cell Transplantation, vol. 19, No. 12, 2010, 1523-1535.
Daver, et al., “Molecular Targeted Therapy in Acute Myeloid Leukemia”, Hematology, vol. 17, Apr. 2012, S59-S62.
Davies, et al., “Mutations of the BRAF Gene in Human Cancer”, Nature, vol. 417, No. 6892, Jun. 27, 2002, 949-954.
De Mattos-Arruda, et al., “Development of Molecular Biomarkers in Individualized Treatment of Colorectal Cancer”, Clinical Colorectal Cancer, vol. 10, No. 4, Dec 2011, 279-289.
De Roock, et al., “Effects of KRAS, BRAF, NRAS, and PIK3CA Mutations on the Efficacy of Cetuximab Plus Chemotherapy in Chemotherapy-Refractory Metastatic Colorectal Cancer: a Retrospective Consortium Analysis”, The Lancet Oncology, vol. 11, No. 8, Aug. 2010, 753-762.
De Roock, et al., “KRAS, BRAF, PIK3CA, and PTEN Mutations: Implications for Targeted Therapies in Metastatic Colorectal Cancer”, The Lancet Oncology, vol. 12, No. 6, Jun. 2011, 594-603.
Delmas, et al., “β-Catenin Induces Immortalization of Melanocytes by Suppressing P16INK4A Expression and Cooperates with N-RAS in Melanoma Development”, Genes and Development, vol. 21, No. 22, Nov. 15, 2007, 2923-2935.
Demunter, et al., “Loss of Membranous Expression of β-Catenin Is Associated with Tumor Progression in Cutaneous Melanoma and Rarely Caused by Exon 3 Mutations”, Modern Pathology, vol. 15, Apr. 1, 2002, 454-461.
Dever, “Crispr/Cas9 β-Globin Gene Targeting in Human Haematopoietic Stem Cells”, Nature, vol. 539, No. 7629, Nov. 17, 2016, 33 pages.
Dicuonzo, et al., “Antibiotic Resistance and Genotypic Characterization by PFGE of Clinical and Environmental Isolates of Enterococci”, FEMS Microbiology Letters, vol. 201, No. 2, Jul. 24, 2001, 205-211.
Dienstmann, et al., “Molecular Predictors of Response to Chemotherapy in Colorectal Cancer”, The Cancer Journal, vol. 17, No. 2, Mar.-Apr. 2011, 114-126.
Ding, et al., “Somatic Mutations Affect Key Pathways in Lung Adenocarcinoma”, Nature, vol. 455, No. 7216, Oct. 23, 2008, 17 pages.
Dixit, et al., “Perturb-Seq; Dissecting Molecular Circuits with Scalable Single-Cell RNA Profiling of Pooled Genetic Screens”, Cell, vol. 167, No. 7, Dec 15, 2016, 40 pages.
Thenappan, et al., “New Therapeutics Targeting Colon Cancer Stem Cells”, Current Colorectal Cancer Reports, vol. 5, No. 4, Oct. 1, 2009, 12 pages.
Mali, et al., “RNA-Guided Human Genome Engineering via Cas9”, Science, vol. 339, No. 6121, Feb. 15, 2013, 8 pages.
Mao, et al., “SIRT6 Promotes DNA Repair Under Stress by Activating PARP1”, Science, vol. 332, No. 6036, Jun. 17, 2011, 14 pages.
Matano, et al., “Modeling Colorectal Cancer using CRISPR-Cas9-Mediated Engineering of Human Intestinal Organoids”, Nature Medicine, vol. 21, No. 3, Mar. 2015, 256-262.
Metcalfe, et al., “Hedgehog Fights Back: Mechanisms of Acquired Resistance against Smoothened Antagonist”, Cancer Research, vol. 71, No. 15, Aug. 1, 2011, 5057-5061.
Minor, et al., “Sunitinib Therapy for Melanoma Patients with KIT Mutations”, Clinical Cancer Research, vol. 18, No. 5, Mar. 1, 2012, 1457-1463.
Moura, et al., “High Prevalence of RAS Mutations in RET-Negative Sporadic Medullary Thyroid Carcinomas”, The Journal of Clinical Endocrinology and Metabolism, vol. 96, No. 5, May 2011, E863-E868.
Murdoch, et al., “Methods of Human Islet Culture for Transplantation”, Cell Transplant, vol. 13, No. 6, 2004, 605-617.
Namba, et al., “Clinical Implication of Hot Spot BRAF Mutation, V599E, in Papillary Thyroid Cancers”, The Journal of Clinical Endocrinology and Metabolism, vol. 88, No. 9, Sep. 2003, 4393-4397.
Naoe, et al., “Gene Mutations of Acute Myeloid Leukemia in the Genome Era”, International Journal of Hematology, vol. 97, No. 2, Feb. 2013, 164-174.
Naoki, et al., “Missense Mutations of the BRAF Gene in Human Lung Adenocarcinoma”, Cancer Research, vol. 62, No. 23, Dec 1, 2002, 7001-7003.
Neshat, et al., “Enhanced Sensitivity of PTEN-Deficient Tumors to Inhibition of FRAP/mTOR”, Proceedings of the National Academy of Sciences of the United States of America, vol. 98, No. 18, Aug. 28, 2001, 10314-10319.
Nikiforov, et al., “Molecular Diagnostics of Thyroid Tumors”, Archives of Pathology & Laboratory Medicine, vol. 135, No. 5, May 2011, 569-577.
Nikiforova, et al., “BRAF Mutations in Thyroid Tumors are Restricted to Papillary Carcinomas and Anaplastic or Poorly Differentiated Carcinomas Arising from Papillary Carcinomas”, The Journal of Clinical Endocrinology and Metabolism, vol. 88, No. 11, Nov. 2003, 5399-5404.
Nikolaev, et al., “Exome Sequencing Identifies Recurrent Somatic MAP2K1 And MAP2K2 Mutations in Melanoma”, Nature Genetics, vol. 44, No. 2, Dec 25, 2011, 133-139.
Nissan, et al., “Loss of NF1 in Cutaneous Melanoma is Associated with RAS Activation and MEK Dependence”, Cancer Research, vol. 74, No. 8, Apr. 15, 2014, 18 pages.
Obaid, et al., “Strategies for Overcoming Resistance in Tumours Harboring BRAF Mutations”, International Journal of Molecular Sciences, vol. 18, No. 3, Mar. 2017, 15 pages.
Ohashi, et al., “Characteristics of Lung Cancers Harboring NRAS Mutations”, Clinical Cancer Research, vol. 19, No. 9, May 1, 2013, 17 pages.
Omholt, et al., “Cytoplasmic and Nuclear Accumulation of Beta-Catenin is Rarely caused by CTNNB1 Exon 3 Mutations in Cutaneous Malignant Melanoma”, International Journal of Cancer, vol. 92, No. 6, Jun. 15, 2001, 839-842.
Paik, et al., “Clinical Characteristics of Patients With Lung Adenocarcinomas Harboring BRAF Mutations”, Journal of Clinical Oncology, vol. 29, No. 15, May 20, 2011, 2046-2051.
Pan, et al., “Kit (CD117) is Frequently Overexpressed in Thymic Carcinomas but is Absent in Thymomas”, The Journal of Pathology, vol. 202, No. 3, Mar. 2004, 375-381.
Papageorgis, et al., “Smad4 Inactivation Promotes Malignancy and Drug Resistance of Colon Cancer”, Cancer Research, vol. 71, No. 3, Feb. 1, 2011, 17 pages.
Peeters, et al., “Randomized Phase III Study of Panitumumab with Fluorouracil, Leucovorin, and Irinotecan (FOLFIRI) Compared with FOLFIRI alone as Second-Line Treatment in Patients with Metastatic Colorectal Cancer”, Journal of Clinical Oncology, vol. 28, No. 31, Nov. 1, 2010, 4706-4713.
Petrini, et al., “Expression and Mutational Status of C-Kit in Thymic Epithelial Tumors”, Journal of Thoracic Oncology, vol. 5, No. 9, Sep. 2010, 1447-1453.
Pollock, et al., “Mutations in Exon 3 of the Beta-Catenin Gene are Rare in Melanoma Cell Lines”, Melanoma Research, vol. 12, No. 2, Apr. 2002, 183-186.
Pratilas, et al., “Genetic Predictors of MEK Dependence in Non-Small Cell Lung Cancer”, Cancer Research, vol. 68, No. 22, Nov. 15, 2008, 17 pages.
Quintas-Cardama, et al., “Complete Response of Stage IV Anal Mucosal Melanoma Expressing KIT VAL560AAP to the Multikinase Inhibitor Sorafenib”, Nature Reviews Clinical Oncology, vol. 5, No. 12, Dec 2008, 737-740.
Ran, et al., “In Vivo Genome Editing using *Staphylococcus aureus* Cas9”, Nature, vol. 520, No. 7546, Apr. 9, 2015, 30 pages.
Reifenberger, et al., “Missense Mutations in SMOH in Sporadic Basal Cell Carcinomas of the Skin and Primitive Neuroectodermal Tumors of the Central Nervous System”, Cancer Research, vol. 58, No. 9, May 1, 1998, 1798-1803.
Reifenberger, et al., “Molecular Genetic Analysis of Malignant Melanomas for Aberrations of the WNT Signaling Pathway Genes CTNB1, APC, ICAT and BTRC”, Cancer Genetics, vol. 100, Issue 5, Aug. 2002, 549-556.
Ricarte-Filho, et al., “Mutational Profile of Advanced Primary and Metastatic Radioactive Lodine-Refractory Thyroid Cancers Reveals

(56) References Cited

OTHER PUBLICATIONS

Distinct Pathogenetic Roles for BRAF, PIK3CS, and AKT1", Cancer Research, vol. 69, No. 11, Jun. 1, 2009, 18 pages.
Rimm, et al., "Frequent Nuclear/Cytoplasmic Localization of β-Catenin without Exon 3 Mutations in Malignant Melanoma", The American Journal of Pathology, vol. 154, No. 2, Feb. 1999, 325-329.
Rimm, et al., "Moderate Alcohol Intake and Lower Risk of Coronary Heart Disease: Meta-Analysis of Effects on Lipids and Haemostatic Factors", The BMJ, vol. 319, No. 7224, Dec 11, 1999, 1523-1528.
Rizzo, et al., "Endogenous Antioxidants and Radical Scavengers", Advances in Experimental Medicine and Biology, vol. 698, 2010, 52-67.
Roh, et al., "High-Grade Fimbrial-Ovarian Carcinomas are unified by altered P53, PTEN and PAX2 Expression", Modern Pathology, vol. 23, No. 10, Oct. 2010, 1316-1324.
Willmore-Payne, et al., "Human Malignant Melanoma: Detection of BRAF- and C-Kit-Activating Mutations by High-Resolution Amplicon Melting Analysis", Human Pathology, vol. 36, No. 5, May 2005, 486-493.
Rongvaux, et al., "Development and Function of Human Innate Immune Cells in a Humanized Mouse Model", Nature Biotechnology, vol. 32, No. 4, Apr. 2014, 23 pages.
Rubinfeld, et al., "Stabilization of Beta-Catenin by Genetic Defects in Melanoma Cell Lines", Science, vol. 275, No. 5307, Mar. 21, 1997, 1790-1792.
Rubinstein, et al., "Incidence of the V600K Mutation among Melanoma Patients With BRAF Mutations, and Potential Therapeutic Response to the Specific BRAF Inhibitor PLX4032", Journal of Translational Medicine, vol. 8, No. 67, 2010, 3 pages.
Salmena, et al., "Tenets of PTEN Tumor Suppression", Cell, vol. 133, No. 3, May 2, 2008, 403-414.
Sanborn, et al., "Phylogenetic Analyses of Melanoma Reveal Complex Patterns of Metastatic Dissemination", Proceedings of the National Academy of Sciences of the United States of America, vol. 112, No. 35, Sep. 1, 2015, 10995-11000.
Sartore-Bianchi, et al., "PIK3CA Mutations in Colorectal Cancer are Associated with Clinical Resistance to EGFR- Targeted Monoclonal Antibodies", Cancer Research, vol. 69, No. 5, Mar. 1, 2009, 1851-1857.
Satzger, et al., "Analysis of c-KIT Expression and KIT Gene Mutation in Human Mucosal Melanomas", British Journal of Cancer, vol. 99, No. 12, Dec 9, 2008, 2065-2069.
Shain, et al., "From Melanocytes to Melanomas", Nature Reviews Cancer, vol. 16, No. 6, Apr. 29, 2016, 14 pages.
Shain, et al., "The Genetic Evolution of Melanoma from Precursor Lesions", The New England Journal of Medicine, vol. 373, Nov. 12, 2015, 1926-1936.
Shi, et al., "Preexisting MEK1 Exon 3 Mutations in V600E/KBRAF Melanomas Do Not Confer Resistance to BRAF Inhibitors", Cancer Discovery, vol. 2, No. 5, May 2012, 17 pages.
Shih, et al., "The Role of Mutations in Epigenetic Regulators in Myeloid Malignancies", Nature Reviews Cancer, vol. 12, No. 9, Sep. 2012, 599-612.
Sosman, et al., "Survival in BRAF V600-Mutant Advanced Melanoma Treated with Vemurafenib", The New England Journal of Medicine, vol. 366, No. 8, Feb. 23, 2012, 14 pages.
Stein, et al., "Novel and Emerging Drugs for Acute Myeloid Leukemia", Current Cancer Drug Targets, vol. 12, No. 5, Jun. 2012, 19 pages.
Thol, et al., "Prognostic Significance of ASXL1 Mutations in Patients with Myelodysplastic Syndrome", Journal of Clinical Oncology, vol. 29, No. 18, Jun. 20, 2011, 2499-2506.
Greene-Colozzi, et al., "Using the CRISPR/Cas9 System to Service and Isogenic BRCA1 Mutant (187 delAG) Strain from a Wild Type BRCA1 Mammary Epithelial Strain", Master's thesis, Harvard Extension School, 2016, 60 pages.
Samowitz, et al., "Poor Survival Associated with the BRAF V600E Mutation in Microsatellite-Stable Colon Cancers", Cancer Research, 2005, 6063-6071.
Snoo, et al., "Increased Risk of Cancer Other than Melanoma in CDKN2A Founder Mutation (p16-Leiden)-Positive Melanoma Families", Clinical Cancer Research, 2008, pp. 7151-7158.
The Broad Institute, Inc, "Notification of Transmittal of the International Search Report and The Written Opinion of the International Searching Authority, or the Declaration for PCT/US18/42737", Oct. 4, 2018, 13 pages.
Abdel-Wahab et al., "ASXL1 mutations promote myeloid transformation through loss of PRC2-mediated gene repression," Cancer Cell, Aug. 14, 2012, vol. 22 (p. 180-193).
Adar et al., "Differential activation of cysteine-substitution mutants of fibroblast growth factor receptor 3 is determined by cysteine localization," Journal of Bone and Mineral Research, May 2002, vol. 17, No. 5 (pp. 860-868).
Alazzouzi et al., "SMAD4 as a prognostic marker in colorectal cancer," Clinical Cancer Research, Apr. 1, 2005, vol. 11, No. 7 (pp. 2606-2611).
Amado et al., "Wild-Type KRAS Is Required for Panitumumab Efficacy in Patients With Metastatic Colorectal Cancer," Journal of Clinical Oncology, Apr. 1, 2008, vol. 26, No. 10 (pp. 1626-1634).
American Cancer Society, Cancer Facts and Figures, 2016, Lymphoma, p. 16 (72 pages).
Antonarakis et al., "Androgen receptor splice variant, AR-V7, and resistance to enzalutamide and abiraterone in men with metastatic castration-resistant prostate cancer (mCRPC)," Journal of Clinical Oncology, May 20, 2014, vol. 32, No. 15 (pp. 1-3).
Arcila et al., "MAP2K1 (MEK1) Mutations Define a Distinct Subset of Lung Adenocarcinoma Associated with Smoking," Clinical Cancer Research, Apr. 15, 2015, vol. 21, No. 8 (pp. 1935-1943).
Arruga et al., "Functional impact of NOTCH1 mutations in chronic lymphocytic leukemia," Leukemia, article preview Oct. 30, 2013 (pp. 1-38).
Azad et al., "Outcomes with abiraterone acetate in metastatic castration-resistant prostate cancer patients who have poor performance status," European Urology, 2015 (pp. 1-6).
Baliakas et al., "Not all IGHV3-21 chronic lymphocytic leukemias are equal: prognostic considerations," Blood, Jan. 29, 2015, vol. 125, No. 5 (pp. 856-959).
Baliakas et al., "Recurrent mutations refine prognosis in chronic lymphocytic leukemia," Leukemia, 2014 (pp. 1-8).
Baliakas et al., "Splenic marginal-zone lymphoma: ontogeny and genetics," Leukemia & Lymphoma, 2015, vol. 56, No. 2.
Bamford et al., "The COSMIC (catalogue of somatic mutations in cancer) database and website", British Journal of Cancer, 2004, vol. 91, pp. 355-358.
Bang et al., "Trastuzumab in combination with chemotherapy versus chemotherapy alone for treatment of HER2-positive advanced gastric or gastro-oesophageal junction cancer (ToGA): a phase 3, open-label, randomised controlled trial," The Lancet, Aug. 28, 2010, vol. 376 (pp. 687-697).
Bean et al., "MET amplification occurs with or without T790M mutations in EGFR mutant lung tumors with acquired resistance to gefitinib or erlotinib," Proceedings of the National Association of Sciences, USA, Dec 26, 2007, vol. 104, No. 52 (pp. 20932-20937).
Behlke et al., "Chemical Modification of siRNAs for In Vivo Use", Oligonucleotides, 2008 vol. 18 (pp. 305-320).
Bejar et al., "Validation of a Prognostic Model and the Impact of Mutations in Patients with Lower-Risk Myelodysplastic Syndromes," Journal of Clinical Oncology, Sep. 20, 2012 vol. 30, No. 27 (pp. 3376-3382).
Beltran et al., "Targeted next-generation sequencing of advanced prostate cancer identifies potential therapeutic targets and disease heterogeneity," European Urology, May 2013, vol. 63, No. 5 (pp. 920-926).
Berg et al., "DNA Sequence Profiles of the Colorectal Cancer Critical Gene Set KRAS-BRAF-PIK3CA-PTEN-TP53 Related to Age at Disease Onset," PLoS One, Nov. 2010, vol. 5, No. 11 (pp. 1-8).
Bergethon et al., "ROS1 rearrangements define a unique molecular class of lung cancers," Journal of Clinical Oncology, Mar. 10, 2012, vol. 30, No. 8 (pp. 863-870).

(56) References Cited

OTHER PUBLICATIONS

Bertrand et al., "cIAP1/2 are direct E3 ligases conjugating diverse types of ubiquitin chains to receptor interacting proteins kinases 1 to 4 (RIP-4)," Sep. 2011, vol. 6, No. 9 (pp. 1-11).
Bierie et al., "TGF beta: the molecular Jekyll and Hyde of cancer," Nature, Jul. 206, vol. 6 (pp. 506-520).
Billerey et al., "Frequent FGFR3 Mutations in Papillary Non-Invasive Bladder (pTa) Tumors," American Journal of Pathology, Jun. 2001, vol. 158, No. 6 (pp. 1955-1959).
Birchmeier et al., "Characterization of ROS1 cDNA from a human glioblastoma cell line," Proceedings of the National Academy of Sciences, USA , Jun. 1990, vol. 87 (pp. 4799-4803).
Birchmeier et al., "Expression and rearrangement of the ROS1 gene in human glioblastoma cells," Proceedings of the National Academy of Sciences, USA, Dec 1987, vol. 84 (pp. 9270-9274).
Boch, et al., "Breaking the Code of DNA Binding Specificity of TAL-Type III Effectors," Science, vol. 326, Dec 11, 2009 (pp. 1509-1512).
Bokemeyer et al., "Efficacy according to biomarker status of cetuximab plus FOLFOX-4 as first-line treatment for metastatic colorectal cancer: the OPUS study," Annals of Oncology, Jul. 2011, vol. 22, No. 7 (pp. 1535-1546).
Bokemeyer et al., "Fluorouracil, leucovorin, and oxaliplatin with and without cetuximab in the first-line treatment of metastatic colorectal cancer," Journal of Clinical Oncology, Feb. 10, 2009, vol. 27, No. 5 (pp. 663-671).
Bose et al., "Activating HER2 Mutations in HER2 Gene Amplification Negative Breast Cancer," Cancer Discovery, Feb. 2013, (pp. 224-237).
Bravo et al. "Integrating genetics and epigenetics in myelodysplastic syndromes: advances in pathogenesis and disease evolution," British Journal of Haematology, Sep. 2014, vol. 166, No. 5 (pp. 646-659).
Buggins et al., "Interaction with Vascular Endothelium Enhances Survival in Primary Chronic Lymphocytic Leukemia Cells via NF-kappaBAB Activation and De novo Gene Transcription," Cancer research, Molecular and Cellular Pathobiology, Sep. 29, 2010, vol. 70, No. 19 (pp. 7523-7533).
Buttitta et al., "Mutational analysis of the HER2 gene in lung tumors from Caucasian patients: Mutations are mainly present in adenocarcinomas with bronchioloalveolar features," International Journal of Cancer, 2006, vol. 119 (pp. 2586-2591).
Campana et al., "Double and triple staining methods for studying the proliferative activity of human B and T lymphoid cells," Journal of Immunological Methods, 1988, vol. 107 (pp. 79-88).
Cao et al., "Comprehensive single cell transcriptional profiling of a multicellular organism by combinatorial indexing," bioRxiv preprint first posted online Feb. 2, 2017 (35 pages).
Capelletti et al., "Identification of Recurrent FGFR3-TACC3 Fusion Oncogenes from Lung Adenocarcinoma," Clinical Cancer Research, 2014 (pp. 6551-6559).
Capuzzo et al., "MET increased gene copy number and primary resistance to gefitinib therapy in non-small-cell lung cancer patients," Annals of Oncology, 2009, vol. 20 (pp. 298-304).
Carpenter et al., "Targeting ALK in neuroblastoma-preclinical and clinical advancements," Nature Reviews Clinical Oncology, 2012, vol. 9 (pp. 391-399).
Carpten et al., "A transforming mutation in the pleckstrin homology domain of AKT1 in cancer," Nature, Jul. 2007, vol. 448 (pp. 439-444).
Carr et al., "Genome Engineering," Nature Biotechnology, Dec 2009, vol. 27, No. 12 (pp. 1151-1162).
Carreno et al., "Immunodeficient Mouse Strains Display Marked Variability in Growth of Human Melanoma Lung Metastases," Clinical Cancer Research, May 2009, vol. 15, No. 10 (pp. 3277-3286).
Cejas et al., KRAS Mutations in Primary Colorectal Cancer Tumors and Related Metastases: A Potential Role in Prediction of Lung Metastasis, PLoS one, Dec 2009, No. 12 (pp. 1-6).
Cerreira et al., "Tumor clone dynamics in lethal prostate cancer," Science Translational Medicine, Sep. 17, 2014, vol. 6, No. 254 (pp. 1-21).
Chadee et al., "Increased Phosphorylation of Histone H1 in Mouse Fibroblasts Transformed with Oncogenes or Constitutively Active Mitogen-activated Protein Kinase Kinase," Journal of Biological Chemistry, Aug. 25, 1995, vol. 270, No. 34 (pp. 20098-20105).
Charest et al., "Fusion of FIG to the receptor tyrosine kinase ROS in a glioblastoma with an interstitial del (6) (q21q21)," Genes, Chromosomes and Cancer, May 2003, vol. 37, No. 1 (pp. 58-71).
Chen et al., "Clinicopathologic and Molecular Features of Epidermal Growth Factor Receptor T790M Mutation and c-MET Amplification in Tyrosine Kinase Inhibitor-resistant Chinese Non-small Cell Lung Cancer," Pathology and Oncology Research, 2009, vol. 15 (pp. 651-658).
Chen et al., "Genome-wide CRISPR Screen in a Mouse Model of Tumor Growth and Metastasis," Cell, 2015, vol. 160 (pp. 1-15).
Chen et al., "Oncogenic mutations of ALK kinase in neuroblastoma," Nature, Oct. 16, 2008, vol. 455 (pp. 971-974).
Cheng et al., "Long non-coding Rna UCA1 induces non-T790M acquired resistance to EGFR-TKIs by activating the AKT/mTOR pathway in EGFR-mutant non-small cell lung cancer," Oncotarget, Jun. 8, 2015, vol. 6, No. 27 (pp. 23582-23593).
Chesnais et al., "Spliceosome mutations in myelodysplastic syndromes and chronic myelomonocytic leukemia," Oncotarget, Nov. 2012, vol. 3, No. 11 (pp. 1284-1293).
Chiaretti et al., "Diagnosis and subclassification of acute lymphoblastic leukemia," Mediterranean Journal of Hematology and Infectious Diseases, 2014 (pp. 1-14).
Chiaretti et al., "NOTCH1, SF3B1, BIRC3 and TP53 mutations in patients with chronic lymphocytic leukemia undergoing first-line treatment: correlation with biological parameters and response to treatment," Leukemia & Lymphoma, Dec 2014, vol. 55, No. 12 (pp. 2785-2792).
Chiorazzi et al., "Chronic lymphocytic leukemia," The New England Journal of Medicine, Feb. 24, 2005, vol. 352, No. 8 (pp. 804-815).
Chiosea et al., "KRAS mutant allele-specific imbalance in lung adenocarcinoma," Modern Pathology, 2011, vol. 24 (pp. 1571-1577).
Choi et al., "Identification of Novel Isoforms of the EML4-ALK Transforming Gene in Non-Small Cell Lung Cancer," Cancer Research, Jul. 1, 2008, vol. 68, No. 13 (pp. 4971-4976).
Conze et al., "Non-canonical NF-kappaB activation and abnormal B cell accumulation in mice expressing ubiquitin protein ligase-inactive c-IAP2," PLoS Biology, Oct. 2010, vol. 8, No. 10 (pp. 1-13).
Corao et al., "ALK expression in rhabdomyosarcomas: correlation with histologic subtype and fusion status," Pediatric and Developmental Pathology, May 1, 2011, vol. 12, No. 4 (pp. 275-283).
Corless et al., "PDGFRA Mutations in Gastrointestinal Stromal Tumors: Frequency, Spectrum and In Vitro Sensitivity to Imatinib," Journal of Clinical Oncology . Aug./Sep. 2005, vol. 23, No. 23 (pp. 5357-5364).
Cortese et al., "On the way towards a 'CLL prognostic index': focus on TP53, BIRC3, SF3B1, NOTCH1 and MYD88 in a population-based cohort," Leukemia, 2014, vol. 28, (pp. 710-713).
Crew et al., "Epidemiology of gastric cancer," World Journal of Gastroenterology, Jan. 21, 2006, vol. 12, No. 3 (pp. 354-362).
Cunningham et al., "MKK4 status predicts survival after resection of gastric adenocarcinoma," Archives of Surgery, 2006, vol. 141, No. 11 (pp. 1095-1099).
Dang et al., "IDH mutations in glioma and acute myeloid leukemia," Trends in Molecular Medicine, Aug. 6, 2010, vol. 16, No. 9 (pp. 387-397).
Darding et al., "IAPs: guardians of RIPK1," Cell Death and Differentiation, 2012, vol. 19 (pp. 58-66).
Davies et al., "Identifying and targeting ROS1 gene fusions in non-small cell lung cancer," Clinical Cancer Research, Sep. 1, 2012, vol. 18, No. 17 (pp. 4570-4579).
De Bosscher et al., "Molecular and functional consequences of Smad4 C-terminal missense mutations in colorectal tumour cells," Journal of Biochemistry, 2004, vol. 379 (pp. 209-216).

(56) References Cited

OTHER PUBLICATIONS

Debelenko et al., "Renal cell carcinoma with novel VCL-ALK fusion: new representative of ALK-associated tumor spectrum," Modern Pathology, 2011, vol. 24 (pp. 430-442).
Del Giudice et al., "NOTCH1 mutations in 12 chronic lymphocytic leukemia (CLL) confer an unfavorable prognosis, induce a distinctive transcriptional profiling and refine the intermediate prognosis of 12 CLL," Haematologica, 2012, vol. 97, No. 3 (pp. 437-441).
Dellinger et al., "Streamlined process for the chemical synthesis of RNA using 2'-O-thionocarbamate-protected nucleoside phosphoramidites in the solid phase," Journal of the American Chemical Society, Aug. 3, 2011, vol. 133, No. 30 (pp. 11540-11556).
Deshpande et al., "Vandetanib (ZD6474) in the treatment of medullary thyroid cancer," Clinical Medicine Insights: Oncology, 2011, vol. 5 (pp. 214-221).
Di Martino et al., "A Decade of FGF Receptor Research in Bladder Cancer: Past, Present, and Future Challenges," Advances in Urology, 2012, vol. 2012, Article ID 429213 (pp. 1-10).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Dores et al., "Chronic lymphocytic leukaemia and small lymphocytic lymphoma: overview of the descriptive epidemiology," British Journal of Haematology, Dec. 2007, vol. 139, No. 5 (pp. 809-819).
Douillard et al., "Randomized, Phase III Trial of Panitumumab with Infusional Fluorouracil, Leucovorin, and Oxaliplatin (FOLFOX4) Versus FOLFOX4 Alone As First-Line Treatment in Patients With Previously Untreated Metastatic Colorectal Cancer: The Prime Study," Hournal of Clinical Oncology, Nov. 1, 2010, vol. 28, No. 31 (pp. 4697-4705).
Doyon et al., "Enhancing zinc-finger-nuclease activity with improved obligate heterodimeric architectures," Nature Methods, Jan. 2011, vol. 8, No. 1 (pp. 74-79).
Drexler et al., "Pathobiology of NPM-ALK and variant fusion genes in anaplastic large cell lymphoma and other lymphomas," Leukemia, Sep. 2000, vol. 14, No. 9 (pp. 1533-1359).
Elliot et al., "Role of Transforming Growth Factor Beta in Human Cancer," Journal of Clinical Oncology, 2005, vol. 23 (pp. 2078-2093).
Engelman et al., "MET Amplification Leads to Gefitinib Resistance in Lung Cancer by Activating ERBB3 Signaling," Science, 2007, vol. 316 (pp. 1039-1043).
Espinosa et al., "Targeting BRAF in thyroid cancer", British Journal of Cancer, 2007, vol. 96, No. 1 (pp. 16-20).
Faderl et al., "The biology of chronic myeloid leukemia," The New England Journal of Medicine, Jul. 15, 1999, vol. 341, No. 3 (pp. 164-172).
Falini et al., "Anaplastic large cell lymphoma: changes in the World Health Organization classification and perspectives for targeted therapy," Haematologica, Jul. 2009, vol. 94, No. 7 (pp. 897-900).
Fearon et al., "A genetic model for colorectal tumorigenesis," Cell, Jun. 1, 1990, vol. 61 (pp. 759-767).
Foa et al., "Clinical implications of the molecular genetics of chronic lymphocytic leukemia," Haematologica, 2013; vol. 98, No. 5 (pp. 675-685).
Fumagalli et al., "A rapid, sensitive, reproducible and cost-effective method for mutation profiling of colon cancer and metastatic lymph nodes," BMC Cancer, 2010, vol. 10, No. 101 (pp. 1-14).
George et al., "Activating mutations in ALK provide a therapeutic target in neuroblastoma," Nature, Oct. 16, 2008, vol. 455 (pp. 975-978).
Gianfelici, V., Activation of the NOTCH1 pathway in chronic lymphocytic leukemia, Haematologica, 2012, vol. 97, No. 3 (pp. 328-330).
Gibney et al., "An unholy alliance: cooperation between BRAF and NF1 in melanoma development and BRAF inhibitor resistance," Cancer Discovery, Mar. 2013, vol. 3, No. 3 (pp. 260-263).
Gilbert et al., "CRISPR-Mediated Modular RNA-Guided Regulation of Transcription in Eukaryotes," Cell, Jul. 18, 2013, vol. 154 (pp. 442-451).
Gleason et al., "Inflammatory myofibroblastic tumours: where are we now?," Journal of Clinical Pathology, 2008, vol. 61 (pp. 428-437).
Goustin et al., "Growth Factors and Cancer," Cancer Research, 1986, vol. 46, (pp. 1015-1029 ).
Grasso et al., "The mutational landscape of lethal castration-resistant prostate cancer," Nature, Jul. 2012, vol. 487, No. 7406 (pp. 239-243).
Graubert et al., "Recurrent mutations in the U2AF1 splicing factor in myelodysplastic syndromes," Nature Genetics, Dec 11, 2011, vol. 44, No. 1 (pp. 53-57).
Gravalos et al., "HER2 in gastric cancer: a new prognostic factor and a novel therapeutic target," Annals of Oncology, 2008, vol. 19 (pp. 1523-1529).
Gruber et al., "The Vienna RNA Websuite," Nucleic Acids Research, Apr. 19, 2008, vol. 36 (pp. W70-W74).
Gu et al., "Survey of tyrosine kinase signaling reveals ROS kinase fusions in human cholangiocarcinoma," PLoS One, Jan. 2011, vol. 6, No. 1 (pp. 1-9).
Guieze et al., "Genomic and epigenomic heterogeneity in chronic lymphocytic leukemia," Blood, Jul. 23, 2015, vol. 126, No. 4 (pp. 445-453).
Habib et al., "Div-Seq: Single-nucleus RNA-Seq reveals dynamics of rare adult newborn neurons," Science, Aug. 26, 2016, vol. 353, No. 6302 (pp. 925-928).
Haferlach et al., "Landscape of genetic lesions in 944 patients with myelodysplastic syndromes," Leukemia, 2014, vol. 28 (pp. 241-247).
Hahn et al., "Homozygous Deletion Map at 18q21.1 in Pancreatic Cancer," Cancer Research, Feb. 1, 1996, vol. 56 (pp. 490-494).
Hammerman et al. "Mutations in the DDR2 Kinase Gene Identify a Novel Therapeutic Target in Squamous Cell Lung Cancer", Cancer Discovery, Jun. 2011 (pp. 79-89).
Handolias et al., "Clinical responses observed with imatinib or sorafenib in melanoma patients expressing mutations in KIT," British Journal of Cancer, 2010, vol. 102 (pp. 1219-1223).
Hankey et al., "The Surveillance, Epidemiology, and End Results Program: A National Resource," Cancer Epidemiology, Biomarkers & Prevention, Dec. 1999, vol. 8 (pp. 1117-1121).
Hartman et al., "Mutant allele-specific imbalance modulates prognostic impact of KRAS mutations in colorectal adenocarcinoma and is associated with worse overall survival," International Journal of Cancer, Oct. 15, 2012, vol. 131, No. 8 (pp. 1810-1817).
He et al., "Conjugation and Evaluation of Triazole-Linked Single Guide RNA for CRISPR-Cas9 Gene Editing," Chembiochem, Oct. 4, 2016, vol. 17, No. 19 (pp. 1809-1812).
Heinrich, et al., "PDGFRA Activating Mutations in Gastrointestinal Stromal Tumors," Science, Jan. 9, 2003, vol. 299 (pp. 708-710).
Heiskanen et al., "CGH, cDNA and Tissue Microarray Analyses Implicate FGFR2 Amplification in a Small Subset of Breast Tumors," Analytical Cellular Pathology, 2001, vol. 22 (pp. 229-234).
Helsten et al., "The FGFR landscape in cancer: analysis of 4,853 tumors by next-generation sequencing," Clinical cancer Research, Downloaded from clincancerres.aacrjournals.org on Jul. 15, 2017, vol. 22 (pp. 259-267).
Hendel et al., "Chemically modified guide RNAs enhance CRISPR-Cas genome editing in human primary cells," Nature Biotechnology Sep. 2015, vol. 33, No. 9 (pp. 985-989).
Hernandez et al., "Prospective Study of FGFR3 Mutations As a Prognostic Factor in Nonmuscle Invasive Urothelial Bladder Carcinomas," Journal of Clinical Oncology, Aug. 1, 2006, vol. 24, No. 22 (pp. 3664-3671).
Hess et al., "Directed evolution using dCas9-targeted somatic hypermutation in mammalian cells," Nature Methods, Dec 2016, vol. 13, No. 12 (pp. 1036-1042).
Hicke et al., "Escort aptamers: a delivery service for diagnosis and therapy," The Journal of Clinical Investigation, Oct. 2000, vol. 106, No. 8 (pp. 923-928).
Hodi et al., "Imatinib for Melanomas Harboring Mutationally Activated or Amplified KIT Arising on Mucosal, Acral, and Chroni-

(56) References Cited

OTHER PUBLICATIONS cally Sun-Damaged Skin," Journal of Clinical Oncology, Sep. 10, 2013, vol. 31, No. 26 (pp. 3182-3190).
Hofman et al., "Assessment of a HER2 scoring system for gastric cancer: results from a validation study," Histopathology, Jun. 2008, vol. 52, No. 7 (pp. 797-805).
Horbinski et al., "Interplay among BRAF, p16, p53, and MIB1 in pediatric low-grade gliomas," Neuro-Oncology, Feb. 23, 2012, vol. 14, No. 6 (pp. 777-789).
Horn et al. "EML4-ALK: Honing In on a New Target in Non-Small-Cell Lung Cancer," Journal of Clinical Oncology, Sep. 10, 2009, vol. 27, No. 26 (pp. 4232-4235).
Hoshino et al., "S-phase fraction of human brain tumors in situ measured by uptake of bromodeoxyuridine," International Journal of Cancer, Sep. 15, 1986, vol. 38, No. 3 (pp. 369-374).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases," Nature Biotechnology, Sep. 2013, vol. 31, No. 9 (pp. 827-832).
Huizinga et al., "W/kit gene required for interstitial cells of Cajal and for intestinal pacemaker activity," Nature, Jan. 26, 1995, vol. 373, (pp. 347-349).
Hynes et al., "Potential for targeting the fibroblast growth factor receptors in breast cancer," American Association for Cancer Research, Published Online First on Jun. 22, 2010 (pp. 5199-5203).
Inamura et al., "EML4-ALK lung cancers are characterized by rare other mutations, a TTF-1 cell lineage, an acinar histology, and young onset," Modern Pathology, Apr. 2009, vol. 22, No. 4 (pp. 508-515).
Inoue et al., "An inducible translocation strategy to rapidly activate and inhibit small GTPase signaling pathways," Nature Methods, Jun. 2005, vol. 2, No. 6 (pp. 415-418).
Irahara et al., "NRAS Mutations Are Rare in Colorectal Cancer," Diagnostic Molecular Pathology, Sep. 2010, vol. 19, No. 3 (pp. 157-163).
Iyer et al., "Genome sequencing identifies a basis for everolimus sensitivity," Science, Oct. 12, 2012, vol. 338, No. 6104 (pp. 1-3).
Jain et al., "Challenges and opportunities in the targeting of fibroblast growth factor receptors in breast cancer," Breast Cancer Research, 2012, vol. 14, No. 208 (pp. 1-9).
Janoueix-Lerosey et al., "Somatic and germline activating mutations of the ALK kinase receptor in neuroblastoma," Nature 2008, vol. 455 (pp. 967-970).
Jebar et al., "FGFR3 and Ras gene mutations are mutually exclusive genetic events in urothelial cell carcinoma," Oncogene, 2005, vol. 24 (pp. 5218-5225).
Jeoung et al., "Effects of Tumor Necrosis Factor-alpha on Antimitogenicity and Cell Cycle-related Proteins in MCF-7 Cells," Journal of Biological Chemistry, Aug. 1995, vol. 270, No. 31 (pp. 18367-18373).
Jeselsohn et al., "Emergence of Constitutively Active Estrogen Receptor-alpha mutations in Pretreated Advanced Estrogen Receptor-Positive Breast Cancer," Clinical Cancer Research, Jan. 7, 2014, vol. 20, No. 7 (pp. 1757-1767).
Jiang et al., "RNA-guided editing of bacterial genomes using CRISPR-Cas systems," Nature Biotechnology, Mar. 2013, vol. 31 [30 pages, including supplementary information] (pp. 233-239).
Johnson et al., "Treatment of NRAS-mutant melanoma," Current Treatment Options, Oncology, Apr. 2015, vol. 16, No. 4 (pp. 1-14).
Jorgenson et al., Targeted HER2 treatment in advanced gastric cancer, Oncology, Feb. 25, 2010, vol. 7 (pp. 26-33).
Ju et al., "A transforming KIF5B and RET gene fusion in lung adenocarcinoma revealed from whole-genome and transcriptome sequencing," Genome, 2012, vol. 22 (pp. 436-445).
Kalinec et al., "Mutated alpha subunit of the Gq protein induces malignant transformation in Nih 3T3 cells," Molecular Cell Biology, Oct. 1992, vol. 12, No. 10 (pp. 4687-4693).
Kamanger et al., "Patterns of cancer incidence, mortality, and prevalence across five continents: defining priorities to reduce cancer disparities in different geographic regions of the world," Journal of Clinical Oncology, May 10, 2006, vol. 24, No. 14 (pp. 1-16).
Kang et al., "Phosphatidylinositol 3-kinase mutations identified in human cancer are oncogenic," Proceedings of the National Academy of Sciences, Jan. 18, 2005, vol. 102, No. 3 (pp. 802-807).
Kawano et al., "PIK3CA mutation status in Japanese lung cancer patients," Lung Cancer, Nov. 2006, vol. 54, No. 2 (pp. 209-215).
Keefe et al., "Aptamers as therapeutics," Nature Reviews, Jul. 2010, vol. 9 (pp. 537-550).
Kim et al., "Chimeric restriction endonuclease," Proceedings of the National Academy of Sciences, USA, Biochemistry, Feb. 1994, vol. 91 (pp. 883-887).
Kim et al., "Integrative and comparative genomic analysis of lung squamous cell carcinomas in East Asian patients," Journal of Clinical Oncology, Jan. 10, 2014, vol. 32, No. 2 (pp. 121-128).
Kim et al., "Mutational analysis of oncogenic AKT E17K mutation in common solid cancers and acute leukaemias," British Journal of Cancer, 2008, vol. 98 (pp. 1533-1535).
Kim et al., "Nonmelanoma skin cancer," Dermatologic Clinics, Jan. 2012, vol. 30, No. 1 (pp. 125-139).
Kim et al., "Phase 3 Trial of Postoperative Chemotherapy Alone Versus Chemoradiation Therapy in Stage III-IV Gastric Cancer Treated With R0 Gastrectomy and D2 Lymph Node Dissection," International Journal of Radiation Oncology, Biology, Physics, Dec. 1, 2012, vol. 84, No. 5 (pp. e585-e592).
Kim et al., "Hybrid restriction enzymes: zinc finger fusions to Fok I cleavage domain," Proceedings of the National Academy of Sciences, USA, Feb. 6, 1996, vol. 93, No. 3 (pp. 1156-1160).
Klein et al., "Droplet Barcoding for Single-Cell Transcriptomics Applied to Embryonic Stem Cells," Cell, 2015, vol. 161, No. 5 (pp. 1187-1201).
Kohno et al., "KIF5B-RET fusions in lung adenocarcinoma," Nature Medicine, published online Feb. 2, 2012, vol. 18, No. 3 (pp. 1-7).
Koivunen et al., "EML4-ALK Fusion Gene and Efficacy of an ALK Kinase Inhibitor in Lung Cancer," Clinical Cancer Research, Jul. 1, 2008, vol. 14, No. 13 (pp. 4275-4283).
Komor et al., "Programmable editing of a target base in genomic DNA without double-stranded DNA cleavage," Nature, 2016, vol. 533 (pp. 420-424).
Kondo et al., "Therapy for thymic epithelial tumors: a clinical study of 1,320 patients from Japan," The Annals of Thoracic Surgery, 2003, vol. 76 (pp. 878-885).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Kong-Beltran et al., "Somatic mutations lead to an oncogenic deletion of met in lung cancer," Cancer Research, Jan. 1, 2006, vol. 66, No. 1 (pp. 283-289).
Ahn et al., "Smad4 may help to identify a subset of colorectal cancer patients with early recurrence after curative therapy," Hepato-gastroenterology, Nov. 1, 2011, vol. 58, No. 112 (pp. 1933-1936).
Chen et al., "Effects of ectopic overexpression of p21(WAF1/CIP1) on aneuploidy and the malignant phenotype of human brain tumor cells," Oncogene, Oct. 3, 1996, vol. 13, No. 7 (pp. 1395-1403).
Coffin et al., "Inflammatory myofibroblastic tumor: comparison of clinicopathologic, histologic, and immunohistochemical features including ALK expression in atypical and aggressive cases," The American Journal of Surgical Pathology, Apr. 2007, vol. 31, No. 4 (pp. 509-520).
D'Avis et al., "Constitutive activation of fibroblast growth factor receptor 3 by mutations responsible for the lethal skeletal dysplasia thanatophoric dysplasia type I," Cell Growth Differ, Jan. 1998, vol. 9, No. 1 (pp. 71-78).
Falsey et al., "Peptide and small molecule microarray for high throughput cell adhesion and functional assays," Bioconjugate Chemistry, May-Jun. 2001, vol. 12, No. 3 (pp. 346-353).
Ferreri et al., "Anaplastic large cell lymphoma, ALK-positive," Critical Reviews in Oncology/Hematology, Aug. 2012, vol. 83, No. 2 (pp. 293-302).

(56) References Cited

OTHER PUBLICATIONS

Heidenreich et al., "EAU guidelines on prostate cancer. Part II: Treatment of advanced, relapsing, and castration-resistant prostate cancer," European Urology, Feb. 2014, 1, vol. 65, No. 2 (pp. 467-479).
Kovach et al., "Inflammatory myofibroblastic tumors," Journal of Surgical Oncology, Sep. 11, 2006, vol. 94, No. 5 (pp. 385-391).
Nassiri et al., "Tissue detection of biomolecular predictors in breast cancer," Expert Review of Anticancer Therapy, Aug. 2006, vol. 6, No. 8 (pp. 1225-1232).
Rhodes et al., "Dedicated Dual-Head Gamma Imaging for Breast Cancer Screening in Women with Mammographically Dense Breasts, " Radiology, Jan. 2011, vol. 258, No. 1 (pp. 106-118).
Rossi et al., "Molecular genetics of high-risk chronic lymphocytic leukemia," Expert Review of Hematology, Dec 2012, vol. 5, No. 6 (pp. 593-602).
Sipos et al., "The therapeutic management of differentiated thyroid cancer," Expert Opinion on Pharmacotherapy, 2008, vol. 9, No. 15 (pp. 2627-2637).
Konstantinopoulos et al., "Gene expression profile of BRCAness that correlates with responsiveness to chemotherapy and with outcome in patients with epithelial ovarian cancer," Journal of Clinical Oncology, Aug. 1, 2010, vol. 28, No. 22 (pp. 3555-3561).
Koretzky et al., "The legacy of the Philadelphia chromosome," The Journal of Clinical Investigation, Aug. 2007, vol. 117, No. 8 (pp. 2030-2032).
Koyama et al., "Inactivation of both alleles of the DPC4/SMAD4 gene in advanced colorectal cancers: identification of seven novel somatic mutations in tumors from Japanese patients," Mutation Research/Mutation Research Genomics, Aug. 1999, vol. 406, Nos. 2-4 (pp. 71-77).
Krasinskas et al., "KRAS mutational analysis and immunohistochemical studies can help distinguish pancreatic metastases from primary lung adenocarcinomas," Modern Pathology, Feb. 2014, vol. 27, No. 2 (pp. 262-270).
Kubo et al., "MET gene amplification or EGFR mutation activate MET in lung cancers untreated with EGFR tyrosine kinase inhibitors," International Journal of Cancer, 2009, vol. 124 (pp. 1778-1784).
Kumar et al., "Substantial interindividual and limited intraindividual genomic diversity among tumors from men with metastatic prostate cancer," Nature Medicine, Apr. 2016, vol. 22, No. 4 (pp. 369-378).
Kwak et al., "Targeted inhibition in tumors with ALK dependency," Lung Cancer: Targets and Therapy, 2013, vol. 4 (pp. 1-8).
Ladanyi et al., "Lung adenocarcinoma: guiding EGFR-targeted therapy and beyond," Modern Pathology, May 2008, vol. 21, Supplement 2 (pp. S16-S22).
Landis et al., "GTPase inhibiting mutations activate the alpha chain of Gs and stimulate adenylyl cyclase in human pituitary tumours," Nature, Aug. 31, 1989, vol. 340, No. 6236 (pp. 692-696).
Lau et al., "cIAP2 represses IKKalpha/beta-mediated activation of MDM2 to prevent p53 degradation," Cell Cycle, Nov. 1, 2012, vol. 11, No. 21 (pp. 4009-4019).
Lawrence et al., "TPM3-ALK and TPM4-ALK Oncogenes in Inflammatory Myofibroblastic Tumors," American Journal of Pathology, Aug. 2000, vol. 157, No. 2 (pp. 377-384).
Lazebnik et al., "Cleavage of poly (ADP-ribose) polymerase by a proteinase with properties like ICE," Nature, Sep. 22, 1994, vol. 371, No. 6495 (pp. 346-347).
Levy-Nissenbaum et al., Nanotechnology and aptamers: applications in drug delivery, Trends in Biotechnology, Aug. 2008, vol. 26, No. 8 (pp. 442-449).
Li et al., "TNF-RII and c-IAP1 mediate ubiquitination and degradation of TRAF2," Nature, Letters, Mar. 21, 2002, vol. 416 (pp. 345-347).
Liao et al., "Inhibitor-sensitive FGFR2 and FGFR3 mutations in lung squamous cell carcinoma," Cancer Research, Aug. 15, 2013, vol. 73, No. 16 (pp. 5195-5205).
Lievens et al., "K644E/M FGFR3 Mutants Activate Erk1/2 from the Endoplasmic Reticulum through FRS2alpha and PLCgamma-independent Pathways," Journal of Molecular Biology, Mar. 31, 2006, vol. 357, No. 3, (pp. 783-792).
Lievre et al. "KRAS Mutation Status Is Predictive of Response to Cetuximab Therapy in Colorectal Cancer," Cancer Research, 2006, vol. 66, No. 8 (pp. 3992-3995).
Lin et al., "Exon Array Profiling Detects EML4-ALK Fusion in Breast, Colorectal, and Non-Small Cell Lung Cancers," Molecular Cancer Research, Sep. 8, 2009, vol. 7, No. 9 (pp. 1466-1476).
Lipson et al., "Identification of new ALK and RET gene fusions from colorectal and lung cancer biopsies," Nature Medicine, 2012, vol. 18 (pp. 382-384).
Losada, A., "Cohesin in cancer: chromosome segregation and beyond," Nature reviews Cancer, Jun. 2014, vol. 14 (pp. 389-393).
Lucas et al., "Multiple Forms of Angiostatin Induce Apoptosis in Endothelial Cells," Blood, Dec 15, 1998, vol. 92, No. 12 (pp. 4730-4741).
Lynch et al., "Activating mutations in the epidermal growth factor receptor underlying responsiveness of non-small-cell lung cancer to gefitinib," New England Journal of Medicine, May 20, 2004, vol. 350, No. 21 (pp. 2129-2139).
Ma et al., "c-MET Mutational Analysis in Small Cell Lung Cancer: Novel Juxtamembrane Domain Mutations Regulating Cytoskeletal Functions," Cancer research, Oct. 1, 2003, vol. 63 (pp. 6272-6281).
Ma et al., "Myelodysplastic syndromes: incidence and survival in the United States," Cancer, Apr. 15, 2007, vol. 109, No. 8 (pp. 1536-1542).
Ma et al., "PIK3CA as an oncogene in cervical cancer," Oncogene, 2000, vol. 19 (pp. 2739-2744).
Ma et al., "Targeted AID-mediated mutagenesis (TAM) enables efficient genomic diversification in mammalian cells," Nature Methods, Dec 2016, vol. 13, No. 12 (pp. 1029-1035).
MacDonald et al., "Chemoradiotherapy after Surgery Compared with Surgery Alone for Adenocarcinoma of the Stomach or Gastroesophageal Junction," The New England Journal of Medicine, Sep. 6, 2001, vol. 345, No. 1 (pp. 725-730).
Macosko et al., "Highly Parallel Genome-wide Expression Profiling of Individual Cells Using Nanoliter Droplets," Cell, May 21, 2015, vol. 161 (pp. 1202-1214).
Maitra et al., "Loss of Dpc4 expression in colonic adenocarcinomas correlates with the presence of metastatic disease," American Journal of Pathology, Oct. 2000, vol. 157, No. 4 (pp. 1105-1111).
Majewski et al., "Identification of recurrent FGFR3 fusion genes in lung cancer through kinome-centred RNA sequencing," Journal of Pathology, 2013, vol. 230 (pp. 270-276).
Manoharan, M., "RNA interference and chemically modified small interfering RNAs," Current Opinion in Chemical Biology, Dec 2004, vol. 8, No. 6 (pp. 570-579).
Mariani et al., "Concordant analysis of KRAS status in primary colon carcinoma and matched metastasis," AntiCancer Research, 2010, vol. 30 (pp. 4229-4236).
Marks et al., "Novel MEK1 Mutation Identified by Mutational Analysis of Epidermal Growth Factor Receptor Signaling Pathway Genes in Lung Adenocarcinoma," Cancer Research, Jul. 15, 2008, vol. 68, No. 14 (pp. 5524-5528).
Masaoka et al., "Follow-up study of thymomas with special reference to their clinical stages," Cancer, 1981, vol. 48 (pp. 2485-2492).
Matsuda et al., "Controlled expression of transgenes introduced by in vivo electroporation," Proceedings of the National Academy of Sciences, Jan. 16, 2007, vol. 104, No. 3 (pp. 1027-1032).
Merenbakh-Lamin et al., "D538G mutation in estrogen receptor-alpha: A novel mechanism for acquired endocrine resistance in breast cancer," Cancer Research, Dec. 1, 2013, vol. 73, No. 23 (pp. 6856-6865).
Merkel et al., "Novel therapeutic options in anaplastic large cell lymphoma: molecular targets and immunological tools," Molecular Cancer Therapy, vol. 10, No. 7 (pp. 1127-1136).
Mesker et al., "Presence of a high amount of stroma and downregulation of SMAD4 predict for worse survival for stage I-II colon cancer patients," Cellular Oncology, 2009, vol. 31 (169-178).
Miyaki et al., "Higher frequency of Smad4 gene mutation in human colorectal cancer with distant metastasis," Oncogene, 1999, vol. 18 (pp. 3098-3103).

(56) References Cited

OTHER PUBLICATIONS

Miyaki et al., "Role of Smad4 (DPC4) inactivation in human cancer," Biochemical and Biophysical Research Communications, 2003, vol. 306 (pp. 799-804).
Miyamoto et al., "Rapid and orthogonal logic gating with a gibberellin-induced dimerization system," Nature Chemical Biology, 2012, vol. 8, No. 5 (pp. 465-470).
Mochizuki et al., "RET rearrangements and BRAF mutation in undifferentiated thyroid carcinomas having papillary carcinoma components," Histopathology, Sep. 2010, vol. 57, No. 3 (pp. 444-450).
Morocz et al., "Brain edema development after MRI-guided focused ultrasound treatment," Journal of Magnetic Resonance Imaging, Jan.-Feb. 1998, vol. 8, No. 1 (pp. 136-142).
Morris et al., "Fusion of a Kinase Gene, ALK, to a Nucleolar Protein Gene, NPM, in Non-Hodgkin's Lymphoma," Science, 1994, vol. 263 (pp. 1281-1284).
Moscou et al., "A Simple Cipher Governs DNA Recognition by TAL Effectors", Science, Dec. 11, 2009, vol. 326 (p. 1501).
Mosse et al., "Inhibition of ALK signaling for cancer therapy," Clinical cancer Research, Sep. 15, 2009, vol. 15, No. 18 (pp. 5609-5614).
Moussatov et al., "A Possible Approach To The Treatment of Polycystic Ovarian Syndrome Using Focused Ultrasound," Ultrasonics, 1998, vol. 36, No. 8 (pp. 893-900).
Mullighan et al., "JAK mutations in high-risk childhood acute lymphoblastic leukemia," Proceedings of the National Academy of Sciences, Jun. 9, 2009, vol. 106, No. 23 (pp. 9414-9418).
Nadji et al., "Immunohistochemistry of Estrogen and Progesterone Receptors Reconsidered: Experience With 5,993 Breast Cancers," American Journal of Clinical Pathology, Feb. 2005, vol. 123, No. 1 (pp. 21-27).
Nasmyth et al., "Cohesin: its roles and mechanisms," Annual Review of Genetics, 2009, vol. 43 (pp. 525-558).
Neumann et al., "Frequency and type of KRAS mutations in routine diagnostic analysis of metastatic colorectal cancer," Pathology—Research and Practice, Dec 15, 2009, vol. 205, No. 12 (pp. 858-862).
Nikiforov et al., "Risk factors for thyroid cancer," Trends in Endocrinology & Metabolism, Jan. 1997, vol. 8, No. 1 (pp. 20-25).
Nikiforov, "Thyroid carcinoma: molecular pathways and therapeutic targets," Modern Pathology, 2008, vol. 21 (pp. S37-S43).
Nilsson et al., "Gastrointestinal stromal tumors: The incidence, prevalence, clinical course, and prognostication in the preimatinib mesylate era," Cancer, Feb. 2005, vol. 103, No. 4 (pp. 653-875).
Nishida et al., "Targeted nucleotide editing using hybrid prokaryotic and vertebrate adaptive immune systems," Science, Sep. 16, 2016, vol. 353, No. 6305 (9 Pages).
Nishimasu et al., "Crystal Structure of Cas9 in Complex with Guide RNA and Target DNA," Cell, Feb. 27, 2014, vol. 156 (pp. 935-949).
Nishimasu et al.,"Crystal Structure of *Staphylococcus aureus* Cas9", Cell, 2015, vol. 162 (pp. 1113-1126).
Nose, V., "Familial thyroid cancer: a review," Modern Pathology, 2011, vol. 24, Suppl. 2 (pp. S19-S33).
Okines et al., "Trastuzumab in gastric cancer," The Lancet, Nov. 20, 2010, vol. 376 (p. 1736).
Okuda et al., "Epidermal growth factor receptor gene amplification and gefitinib sensitivity in patients with recurrent lung cancer," Journal for Cancer Research and Clinical Oncology, 2008, vol. 134 (pp. 569-577).
Omlin et al., "Improved survival in a cohort of trial participants with metastatic castration-resistant prostate cancer demonstrates the need for updated prognostic nomograms," European Urology, Aug. 2013, vol. 64, No. 2 (pp. 300-306).
Onken et al., "Oncogenic mutations in GNAQ occur early in uveal melanoma," Anatomy and Pathology/Oncology, Dec. 2008, vol. 49, No. 12 (pp. 5230-5234).
Onozato et al., "Activation of MET by gene amplification or by splice mutations deleting the juxtamembrane domain in primary resected lung cancers," Journal of Thoracic Oncology, Jan. 2009, vol. 4, No. 1 (pp. 5-11).
Orton et al., "Computational modelling of the receptor-tyrosine-kinase-activated MAPK pathway," Biochemistry Journal, 2005, vol. 392 (pp. 249-261).
Ostrom et al., "CBTRUS statistical report: primary brain and central nervous system tumors diagnosed in the United States in 2008-2012," Neuro-Oncology, The Centers for Disease Control, Published by Oxford University Press on behalf of the Society for Neuro-Oncology in cooperation with the Central Brain Tumor Registry, 2015 (62 pages).
Owens et al., "HER2 amplification ratios by fluorescence in situ hybridization and correlation with immunohistochemistry in a cohort of 6556 breast cancer tissues," Clinical Breast Cancer, Apr. 2004, vol. 5, No. 1 (pp. 63-69).
Paez et al., "EGFR Mutations in Lung Cancer: Correlation with Clinical Response to Gefitinib Therapy," Science, Jun. 4, 2004, vol. 304 (pp. 1497-1500).
Paige et al., "RNA mimics of green fluorescent protein," Science, Jul. 29, 2011, vol. 333, No. 6042 (pp. 642-646).
Paik et al., "Sphingosine 1-phosphate-induced endothelial cell migration requires the expression of EDG-1 and EDG-3 receptors and Rho-dependent activation of alpha-v beta 3-and beta 1 containing integrins," Journal of Biological Chemistry, Apr. 13, 2001, vol. 276, No. 15 (pp. 11830-11837).
Pao et al., "EGF receptor gene mutations are common in lung cancers from 'never smokers' and are associated with sensitivity of tumors to gefitinib and erlotinib," Proceedings of the National Academy of Sciences, Sep. 7, 2004, vol. 101, No. 36 (pp. 13306-13311).
Parnas et al., "A Genome-Wide CRISPR Screen in Primary Immune Cells to Dissect Regulatory Networks," 2015, vol. 162 (pp. 675-686) [with Supplementary Information].
Parsonnet et al., "Helicobacter pylori Infection and the Risk of Gastric Carcinoma," The New England Journal of Medicine, Oct. 17, 1991, vol. 325, No. 16 (pp. 1127-1131).
Piccolo et al., "Production of plasma membrane vesicles with chloride salts and their utility as a cell membrane mimetic for biophysical characterization of membrane protein interactions," Analytical Chemistry, Oct. 16, 2012, vol. 84, No. 20 (pp. 8650-8655).
Pierotti et al., "Cytogenetics and molecular genetics of carcinomas arising from thyroid epithelial follicular cells," Genes, Chromosomes & Cancer, May 1996, vol. 16, No. 1 (pp. 1-14).
Pillay et al., "ALK protein expression in rhabdomyosarcomas," Histopathology Nov. 2002, vol. 41, No. 5 (pp. 461-467).
Pitt et al., "Medullary, anaplastic, and metastatic cancers of the thyroid," Seminars in Oncology, Dec 2010, vol. 37, No. 6 (pp. 567-579).
Platt et al., "CRISPR-Cas9 Knockin Mice for Genome Editing and Cancer Modeling," Cell, 2014, vol. 159 (pp. 440-455).
Puchalpalli et al., "NSG Mice Provide a Better Spontaneous Model of Breast Cancer Metastasis than Athymic (Nude) Mice," PLos One, Sep. 23, 2016 (pp. 1-15).
Puente et al., "Whole-genome sequencing identifies recurrent mutations in chronic lymphocytic leukaemia," Nature, Jul. 7, 2011, vol. 475 (pp. 101-105).
Puiggros et al., "Genetic abnormalities in chronic lymphocytic leukemia: where we are and where we go," BioMed Research International, 2014, vol. 2014, Article ID 435983 (pp. 1-13).
Qi et al., "Repurposing CRISPR as an RNA-Guided Platform for Sequence-Specific Control of Gene Expression," Cell, 2013, vol. 152 (pp. 1173-1183).
Rahal et al., "Pharmacological and genomic profiling identifies NF-kappaB 3targeted treatment strategies for mantle cell lymphoma," Nature Medicine, 2014, (pp. 1-9).
Ramanan et al., "CRISPR-Cas9 cleavage of viral DNA efficiently suppresses hepatitis B virus," Nature/Scientific Reports, Jun. 2015 (9 pages).

(56) References Cited

OTHER PUBLICATIONS

Ran et al., "Double Nicking by RNA-guided CRISPR Cas9 for enhanced genome editing specificity," Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Reichardt et al., "Gastrointestinal stromal tumors I: pathology, pathobiology, primary therapy, and surgical issues," Seminars in Oncology, Aug. 2009, vol. 36, No. 4 (pp. 290-301).
Ren et al., "Identification of Anaplastic Lymphoma Kinase as a Potential Therapeutic Target in Ovarian Cancer," Cancer Research, Jul. 1, 2012, vol. 72, No. 13 (pp. 3312-3323).
Riely et al., "Frequency and Distinctive Spectrum of KRAS Mutations in Never Smokers with Lung Adenocarcinoma," Clinical Cancer Research, Sep. 15, 2008, vol. 14, No. 18 (pp. 5731-5734).
Rikova et al., "Global Survey of Phosphotyrosine Signaling Identifies Oncogenic Kinases in Lung Cancer," Cell, Dec 14, 2007, vol. 131 (pp. 1190-1203).
Rizzo et al., "Prognostic vs predictive molecular biomarkers in colorectal cancer: is KRAS and BRAF wild type status required for anti-EGFR therapy?," Cancer Treatment Reviews, Nov. 2010, vol. 36, Suppl. 3 (pp. S56-S61).
Robinson et al., "Activating ESR1 mutations in hormone-resistant metastatic breast cancer," Nature Genetics, Dec. 2013, vol. 45 (pp. 1446-1451).
Robinson et al., "Integrative clinical genomics of advanced prostate cancer," Cell 2015, vol. 161 (pp. 1215-1228).
Romanel et al., "Plasma AR and abiraterone-resistant prostate cancer," Science translational Medicine, Nov. 4, 2015, vol. 7, No. 312 (pp. 1-15).
Rose-Zerilli et al., "ATM mutation rather than BIRC3 deletion and/or mutation predicts reduced survival in 11q-deleted chronic lymphocytic leukemia: data from the UK LRF CLL4 trial," Haematologica, 2014, vol. 99, No. 4 (pp. 736-742).
Rosenbaum et al., "The structure and function of G-protein-coupled receptors," Nature, May 21, 2009, vol. 459, No. 7245 (pp. 356-363).
Rosenberg et al., "Scaling single cell transcriptomics through split pool barcoding," bioRxiv preprint first posted online Feb. 2, 2017 (13 pages).
Rossi et al., "Mutations of NOTCH1 are an independent predictor of survival in chronic lymphocytic leukemia," Blood, Jan. 12, 2012, vol. 119, No. 2 (pp. 521-529).
Saab et al., "IgG4 plasma cells in inflammatory myofibroblastic tumor: inflammatory marker or pathogenic link?," Modern Pathology, Apr. 4, 2011, vol. 24, No. 4 (pp. 606-612).
Samuels et al., "High frequency of mutations of the PIK3CA gene in human cancers," Science, Apr. 23, 2004, vol. 304, No. 5670 (p. 554).
Santarius et al., "A census of amplified and overexpressed human cancer genes," Nature Reviews, Cancer, Jan. 2010, vol. 10 (pp. 59-64).
Santini et al., "High Concordance of KRAS Status Between Primary Colorectal Tumors and Related Metastatic Sites: Implications for Clinical Practice," The Oncologist, Gastrointestinal Cancer, Dec. 2008, vol. 13, No. 12 (pp. 1270-1275).
Scaringe et al., "Advanced 5'-silyl-2'-orthoester approach to RNA oligonucleotide synthesis," Methods in Enzymology, 2000, vol. 317 (pp. 3-18).
Scaringe et al., "Novel RNA Synthesis Method Using 5'0-Silyl-2'-O-orthoester Protecting Groups," Journal of the American Chemical Society, 1998, vol. 120, No. 45 (pp. 11820-11821).
Schonherr et al., "The neuroblastoma Alk (I1250T) mutation is a kinase-dead RTK in vitro and in vivo," Translational Oncology, Aug. 2011, vol. 4, No. 4 (pp. 258-265).
Sequist et al., "Genotypic and histological evolution of lung cancers acquiring resistance to EGFR inhibitors," Science Translational Medicine, Mar. 23, 2011, vol. 3, No. 75 (pp. 1-27).
Shalem et al., "Genome-Scale CRISPR-Cas9 Knockout Screening in Human Cells," Science, Jan. 3, 2014, vol. 343 (pp. 84-87).
Shalem et al., "High-throughput functional genomics using CRISPR-Cas9" Nature Review Genetics, 2015, vol. 16, No. 5 (pp. 299-311).
Shaw et al., "Clinical Features and Outcome of Patients with Non-Small-Cell Lung Cancer Who Harbor EML4-ALK," Journal of Clinical Oncology, Sep. 10, 2009, vol. 27, No. 26 (pp. 4247-4253).
Shi et al., "A structural basis for mutational inactivation of the tumour suppressor Smad4," Nature, Letters, Jul. 1997, vol. 388 (pp. 87-93).
Shi et al., "Mechanisms of TGF-beta signaling from cell membrane to the nucleus," Cell, Jun. 13, 2003, vol. 113 (pp. 685-700).
Shigematsu et al., "Somatic mutations of the HER2 kinase domain in lung adenocarcinomas," Cancer Research, Mar. 1, 2005, vol. 65, No. 5 (pp. 1642-1646).
Shinmura et al., "A novel somatic FGFR3 mutation in primary lung cancer," Oncology Reports, 2014, vol. 31 (pp. 1219-1224).
Shinmura et al., "EML4-ALK fusion transcripts, but no NPM-, TPM3-, CLTC-, ATIC-, or TFG-ALK fusion transcripts, in non-small cell lung carcinomas," Lung Cancer, Aug. 2008, vol. 61, No. 2 (pp. 163-169).
Shmakov et al., "Discovery and Functional Characterization of Diverse Class 2 CRISPR-Cas Systems," Molecular Cell, Nov. 1, 2015, vol. 60, No. 3 (pp. 385-397).
Shukla et al., "Exploring chemical modifications for siRNA therapeutics: a structural and functional outlook," ChemMedChem, Mar. 1, 2010, vol. 5, No. 3 (pp. 328-349).
Shukla et al., "Oncogene Mutation Profiling of Pediatric Solid Tumors Reveals Significant Subsets of Embryonal Rhabdomyosarcoma and Neuroblastoma with Mutated Genes in Growth Signaling Pathways," Clinical Cancer Research, Jan./Feb. 2012, vol. 18, No. 3 (pp. 748-757).
Siegel et al., "Cancer statistics, 2012", CA: A Cancer Journal for Clinocians, Jan.-Feb. 2012, vol. 62, No. 1 (pp. 10-29).
Sjodahl et al., "A Systematic Study of Gene Mutations in Urothelial Carcinoma; Inactivating Mutations in TSC2 and PIK3R1," PloS One, Apr. 2011, vol. 6, No. 4 (pp. 1-6).
Slamon et al., "Human Breast Cancer: Correlation of Relapse and Survival with Amplification of the HER-2/neu Oncogene," Science, Jan. 9, 1987, vol. 235, (pp. 177-182).
Sletten et al., "Bioorthogonal Chemistry: Fishing for selectivity in a sea of functionality," Angewandte Chemie International Edition, 2009, vol. 48, (pp. 6974-6998).
Soda et al., "Identification of the transforming EML4-ALK fusion gene in non-small-cell lung cancer," Nature, Aug. 2, 2007, vol. 448 (pp. 561-566).
Soh et al., "Oncogene Mutations, Copy Number Gains and Mutant Allele Specific Imbalance (MASI) Frequently Occur Together in Tumor Cells," PLoS One, Oct. 2009, vol. 4, No. 10 (pp. 1-13).
Solary et al., "The Ten-Eleven Translocation-2 (TET2) gene in hematopoiesis and hematopoietic diseases," Leukemia, 2014, vol. 28 (pp. 485-496).
Sordella et al., "Gefitinib-Sensitizing EGFR Mutations in Lung Cancer Activate Anti-Apoptotic Pathways," Science, Aug. 20, 2004, vol. 305, No. 5687 (pp. 1163-1167).
Stanley et al., "Radio-Wave Heating of Iron Oxide Nanoparticles Can Regulate Plasma Glucose in Mice," Science, May 4, 2012 vol. 336, No. 6081 (pp. 604-608).
Stein et al., "Remission induction in acute myeloid leukemia," International Journal of Hematology, 2012, vol. 96 (pp. 164-170).
Stephens et al., "Intragenic ERBB2 kinase mutations in tumours," Nature, Sep. 30, 2004, vol. 431, No. 7008 (pp. 525-526).
Strefford, J., "The genomic landscape of chronic lymphocytic leukaemia: biological and clinical implications," British Journal of Haematology, Apr. 2015, vol. 169, No. 1 (pp. 14-31).
Stupp et al., "Effects of radiotherapy with concomitant and adjuvant temozolomide versus radiotherapy alone on survival in glioblastoma in a randomised phase III study: 5-year analysis of the EORTC-NCIC trial," The Lancet, Oncology, May 2009, vol. 10, No. 1 (pp. 459-466).
Sukov et al., "ALK alterations in adult renal cell carcinoma: frequency, clinicopathologic features and outcome in a large series of consecutively treated patients," Modern Pathology, 2012, vol. 25 (pp. 1516-1525).

(56) References Cited

OTHER PUBLICATIONS

Sun et al., "Lung adenocarcinoma from East Asian never-smokers is a disease largely defined by targetable oncogenic mutant kinases," Journal of Clinical Oncology, Oct. 20, 2010, vol. 28, No. 30 (pp. 4616-4620).

Swiech et al., "In vivo interrogation of gene function in the mammalian brain using CRISPR-Cas9," Nature Biotechnology, 2014, vol. 33 (pp. 102-106) [Including Supplemental information, 4 pages].

Takagi et al., "Somatic alterations of the DPC4 gene in human colorectal cancers in vivo," Gastroenterology, Nov. 1996, vol. 111, No. 5 (pp. 1369-7132).

Takeuchi et al., "KIF5B-ALK, a Novel Fusion Oncokinase Identified by an Immunohistochemistry-based Diagnostic System for ALK-positive Lung Cancer," Clinical Cancer Research, May 1, 2009, vol. 15, No. 9 (pp. 3143-3149).

Takeuchi et al., "Multiplex Reverse Transcription-PCR Screening for EML4-ALK Fusion Transcripts," Clinical Cancer Research, 2008, vol. 14, No. 2 (pp. 6618-6624).

Takeuchi et al., "RET, ROS1 and ALK fusions in lung cancer," Nature Medicine, Feb. 12, 2012, vol. 18, No. 3 (pp. 378-381).

Tanner et al., "Amplification of HER-2 in gastric carcinoma: association with Topoisomerase IIalpha gene amplification, intestinal type, poor prognosis and sensitivity to trastuzumab," Annals of Oncology, 2005, vol. 16 (pp. 273-278).

Tasian et al., "Aberrant STAT5 and PI3K/mTOR pathway signaling occurs in human CRLF2-rearranged B-precursor acute lymphoblastic leukemia," Blood, Jul. 26, 2012, vol. 120, No. 4 (pp. 833-842).

Tate et al., "COSMIC: the Catalogue Of Somatic Mutations In Cancer," Nucleic Acids Research, 2019, vol. 47 (pp. D941-D947).

Taylor et al., "Integrative genomic profiling of human prostate cancer," Cancer Cell, Jul. 13, 2010, vol. 18 (pp. 11-22).

Tefferi et al., "Myelodysplastic syndromes," The New England Journal of Medicine, Nov. 5, 2009, vol. 361, No. 19 (pp. 1872-1885).

Tejpar et al., "Mutant KRAS and BRAF gene expression profiles in colorectal cancer: Results of the translational study on the PETACC 3-EORTC 40993-SAKK 60-00 trial," Journal of Clinical Oncology, Meeting Abstract: 2010 ASCO Annual Meeting I, vol. 28, No. 15_suppl (3 pages).

Ten Hacken et al., "Microenvironment interactions and B-cell receptor signaling in Chronic Lymphocytic Leukemia: Implications for disease pathogenesis and treatment," Biochimica et Biophysica Acta, Mar. 2016, vol. 1863, No. 3 (pp. 401-413).

Tiacci et al., "The corepressors BCOR and BCORL1: two novel players in acute myeloid leukemia," Haematologica, Jan. 2012, vol. 97, No. 1 (pp. 3-5).

Tomita et al., "Mechanisms of action and resistance to all-trans retinoic acid (ATRA) and arsenic trioxide (As2O 3) in acute promyelocytic leukemia," International Journal of Hematology, 2013, vol. 97 (pp. 717-725).

Tomlinson et al., "Alternative Splicing of Fibroblast Growth Factor Receptor 3 Produces a Secreted Isoform That Inhibits Fibroblast Growth Factor-Induced Proliferation and Is Repressed in Urothelial Carcinoma Cell Lines," Cancer Research, Nov. 15, 2005, vol. 65, No. 22 (pp. 10441-10449).

Tomlinson et al., "FGFR3 protein expression and its relationship to mutation status and prognostic variables in bladder cancer," Journal of Pathology, Sep. 2007, vol. 213, No. 1 (pp. 91-98).

Tomlinson et al., "Knockdown by shRNA identifies S249C mutant FGFR3 as a potential therapeutic target in bladder cancer," Oncogene, Aug. 30, 2007, vol. 26, No. 40 (pp. 5889-5899).

Touat et al., Targeting FGFR signaling in cancer, Clinical cancer Research, Jun. 15, 2015, vol. 21, No. 12 (pp. 2684-2694).

Toy et al., "ESR1 ligand-binding domain mutations in hormone-resistant breast cancer," Nature Genetics, Dec. 2013, vol. 45, No. 12 (pp. 1439-1445).

Tran-Huu-Hue et al., "Practical Systems for the Generation of High Power Continuous Wave-Non Focused Ultrasound in the MHz Range," Acustica, acta acustica, 1997, vol. 83 (pp. 1103-1106).

Tsai et al., "Dimeric CRISPR RNA-guided FokI nucleases for highly specific genome editing," Nature Biotechnology, 2014, vol. 32, No. 6 (pp. 569-576).

Tucker et al., "Identical reactivity of monoclonal antibodies HNK-1 and NC-1: conservation in vertebrates on cells derived from the neural primordium and on some leukocytes," Cell Differentiation, 1984, vol. 14 (pp. 223-230).

Tuerk et al., "Systematic evolution of ligands by exponential enrichment: RNA ligands to bacteriophage T4 DNA polymerase," Science, Aug. 3, 1990, vol. 249, No. 4968 (pp. 505-510).

Turner et al., "Integrative molecular profiling of triple negative breast cancers identifies amplicon drivers and potential therapeutic targets," Oncogene, Apr. 8, 2010, vol. 29, No. 14 (pp. 2013-2023).

Vaishnavi et al., "Oncogenic and drug-sensitive NTRK1 rearrangements in lung cancer," Nature Medicine, Nov. 2013, vol. 19, No. 11 (pp. 1469-1472).

Vallabhapurapu et al., "Regulation and function of NF-kappaB transcription factors in the immune system," Annual Review, Immunonlogy, 2009, vol. 27 (pp. 693-733).

Van Gaal et al., "Anaplastic Lymphoma Kinase Aberrations in Rhabdomyosarcoma: Clinical and Prognostic Implications," Journal of Clinical Oncology, Jan. 20, 2012, vol. 30, No. 3 (pp. 308-315).

Van Oers et al., "FGFR3 mutations indicate better survival in invasive upper urinary tract and bladder tumours," European Urology, Mar. 2009, vol. 55, No. 3 (pp. 650-658).

Van Raamsdonk et al., "Frequent somatic mutations of GNAQ in uveal melanoma and blue naevi," Nature, Jan. 29, 2009, vol. 457, No. 7229 (pp. 599-602).

Van Raamsdonk et al., "Mutations in GNA11 in uveal melanoma," New England Journal of Medicine, Dec. 2, 2010, vol. 363, No. 23 (pp. 2191-2199).

Van Rhijn et al., "Frequent FGFR3 mutations in urothelial papilloma," The Journal of Pathology, Oct. 2002, vol. 198, No. 2 (pp. 245-251).

Visconte et al., "Emerging roles of the spliceosomal machinery in myelodysplastic syndromes and other hematological disorders," Leukemia, Dec. 2012, vol. 26, No. 12 (pp. 2447-2454).

Voytik-Harbin, "Application and Evaluation of the Alamarblue Assay for Cell Growth and Survival of Fibroblasts," In Vitro Cellular & Developmental Biology-Animal, Mar. 1998, vol. 34, No. 3, Part 1 (pp. 239-246).

Walker et al., "Management of patients with cytogenetically normal acute myeloid leukemia who have neither favorable nor unfavorable markers," urnal of the National Comprehensive Cancer Network, Apr. 2014, vol. 12, No. 4 (pp. 527-534).

Wall et al., "Chronic Lymphocytic Leukemia and Other Lymphoproliferative Disorders," Clinics in Geriatric Medicine, Feb. 2016, vol. 32, No. 1 (pp. 175-189).

Walter et al., "Clonal diversity of recurrently mutated genes in myelodysplastic syndromes," Leukemia, Jun. 2013, vol. 27, No. 6 (pp. 1275-1282).

Wang et al., "Genetic screens in human cells using the CRISPR/Cas9 system," Science, Jan. 3, 2014, vol. 343 No. 6166 (pp. 80-84).

Wang et al., "HER2 kinase domain mutation results in constitutive phosphorylation and activation of HER2 and EGFR and resistance to EGFR tyrosine kinase inhibitors," Cancer Cell, Jul. 2006, vol. 10, No. 1 (pp. 25-38).

Wang et al., "FGFR1/3 Tyrosine Kinase Fusions Define a Unique Molecular Subtype of Non-Small Cell Lung Cancer," Clinical Cancer Research, 2014, vol. 20, No. 15 (pp. 4107-4114).

Wang et al., "One-Step Generation Of Mice Carrying Mutations In Multiple Genes By CRISPR/Cas-Mediated Genome Engineering," Cell, May 9, 2013, vol. 153 (pp. 910-918).

Watts et al., "Chemically modified siRNA: tools and applications," Drug Discovery Today, Oct. 2008, vol. 13, Nos. 19-20 (pp. 842-855).

Webster et al., "Constitutive activation of fibroblast growth factor receptor 3 by the transmembrane domain point mutation found in achondroplasia," The EMBO Journal, 1996, vol. 15, No. 3 (pp. 520-527).

Williams et al., "Oncogenic FGFR3 gene fusions in bladder cancer," Human Molecular Genetics, 2013, vol. 22, No. 4 (pp. 795-803).

(56) References Cited

OTHER PUBLICATIONS

Wong et al., "The EML4-ALK fusion gene is involved in various histologic types of lung cancers from nonsmokers with wild-type EGFR and KRAS," Cancer, Apr. 15, 2009, vol. 115, No. 8 (pp. 1723-1733).
Wu et al., "Early Helicobacter pylori eradication decreases risk of gastric cancer in patients with peptic ulcer disease," Gastroenterology, 2009, vol. 137 (pp. 1641-1648).
Wu et al., "Identification of targetable FGFR gene fusions in diverse cancers," Cancer Discovery, Jun. 2013, vol. 3, No. 6 (pp. 636-647).
Wu et al., "Genome-wide binding of the CRISPR endonuclease Cas9 in mammalian cells," Nature Biotechnology, 2014, Including Supplemental information (pp. 1-9).
Wyatt et al., "Circulating tumor DNA (ctDNA) burden and actionable mutations in treatment-naive metastatic castration-resistant prostate cancer (mCRPC)," Journal of Clinical Oncology, Meeting Abstract: 2016 ASCO Annual Meeting, May 20, 2016, vol. 34, No. 15 (2 pages).
Xia et al., "Frequencies of SF3B1, NOTCH1, MYD88, BIRC3 and IGHV mutations and TP53 disruptions in Chinese with chronic lymphocytic leukemia: disparities with Europeans," Oncotarget, 2015, vol. 6, No. 7 (pp. 5426-5434).
Xing et al., "A genetically defined mouse ovarian carcinoma model for the molecular characterization of pathway-targeted therapy and tumor resistance," Proceedings of the National Academy of Sciences, USA, May 10, 2005, vol. 102, No. 19 (pp. 6936-6941).
Xu et al., "Sequence determinants of improved CRISPR sgRNA design," Genome Research, Aug. 2015, vol. 25 (pp. 1147-1157).
Yang et al., "Engineering and optimising deaminase fusions for genome editing," Nature Communications, 2017 vol. 7. No. 13330 (pp. 1-12).
Yaziji et al., "HER-2 testing in breast cancer using parallel tissue-based methods," JAMA, Apr. 28, 2004, vol. 291, No. 16 (pp. 1972-1977).
Yonehara et al., "A cell-killing monoclonal antibody (anti-Fas) to a cell surface antigen co-downregulated with the receptor of tumor necrosis factor," The Journal of Experimental Medicine, May 1989, vol. 169 (pp. 1747-1756).
Yoshida et al., 633. Myelodysplastic Syndromes: Role of RNA Splicing and Epigenetics "Frequent pathway mutations of splicing machinery in myelodysplasia," Blood, Nov. 18, 2011, vol. 118, No. 21, Abstract 458 (pp. 1-3).
Zardavas et al., "PIK3CA mutations in breast cancer: reconciling findings from preclinical and clinical data," Breast Cancer Research, 2014, vol. 16, No. 201 (pp. 1-10).
Zarnegar et al., "Noncanonical NF-kappaB activation requires coordinated assembly of a regulatory complex of the adaptors cIAP1, cIAP2, TRAF2 and TRAF3 and the kinase NIK," Nature Immunology, 2008, vol. 9, No. 12 (pp. 1371-1378).
Zent et al., "Mutations in chronic lymphocytic leukemia and how they affect therapy choice: focus on NOTCH1, SF3B1, and TP53," Hematology, 2014 (pp. 119-124).
Zenz et al., "From pathogenesis to treatment of chronic lymphocytic leukaemia," Nature Reviews Cancer, 2010, vol. 10 (pp. 37-50).
Zetsche et al., "A split-Cas9 architecture for inducible genome editing and transcription modulation," Nature Biotechnology, Feb. 2015, vol. 33, No. 2 (pp. 139-142).
Zetsche et al., "Cpf1 is a single RNA-guided endonuclease of a class 2 CRISPR-Cas system," Cell, Oct. 22, 2015, vol. 163 (pp. 759-771).
Zhang and Kipps, "The pathogenesis of chronic lymphocytic leukemia," Annual Reviews, Pathology, 2014, vol. 9 (pp. 103-118).
Zhang et al., "Efficient Construction of Sequence-Specific TAL Effectors for Modulating Mammalian Transcription," Nature Biotechnology, Feb. 2011, vol. 29, No. 2 (pp. 149-154).
Zheng et al. "Haplotyping germline and cancer genomes with high-throughput linked-read sequencing," Nature Biotechnology, Feb. 1, 2016, vol. 34, No. 3 (pp. 303-311) [with Supplemental Material].
Zheng et al., "Massively parallel digital transcriptional profiling of single cells," Nature Communications, Jan. 16, 2017, vol. 8, No. 14049 (12 pages).
Zhou et al., "Aptamer-targeted cell-specific RNA interference," Silence, Feb. 1, 2010, vol. 1, No. 4 (10 pages).
Zhou et al., "IKKepsilon-mediated tumorigenesis requires K63-linked polyubiquitination by a cIAP1/cIAP2/TRAF2 E3 ubiquitin ligase complex," Cell Reports, Mar. 28, 2013, vol. 3 (pp. 724-733).
Zhu et al., "Efficacy, safety, and potential biomarkers of sunitinib monotherapy in advanced hepatocellular carcinoma: a phase II study," Journal of Clinical Oncology, Jun. 20, 2009, vol. 27, No. 18 (pp. 3027-3035).
Zilionis et al., "Single-cell barcoding and sequencing using droplet microfluidics," Nature Protocols, 2017, vol. 12, No. 1 (pp. 44-73).
Zuker et al., "Optimal computer folding of large RNA sequences using thermodynamics and auxiliary information," Nucleic Acids Research, Jan. 10, 1981, vol. 9, No. 1 (pp. 133-148).

* cited by examiner

SEQ ID NO: 240

Day 9

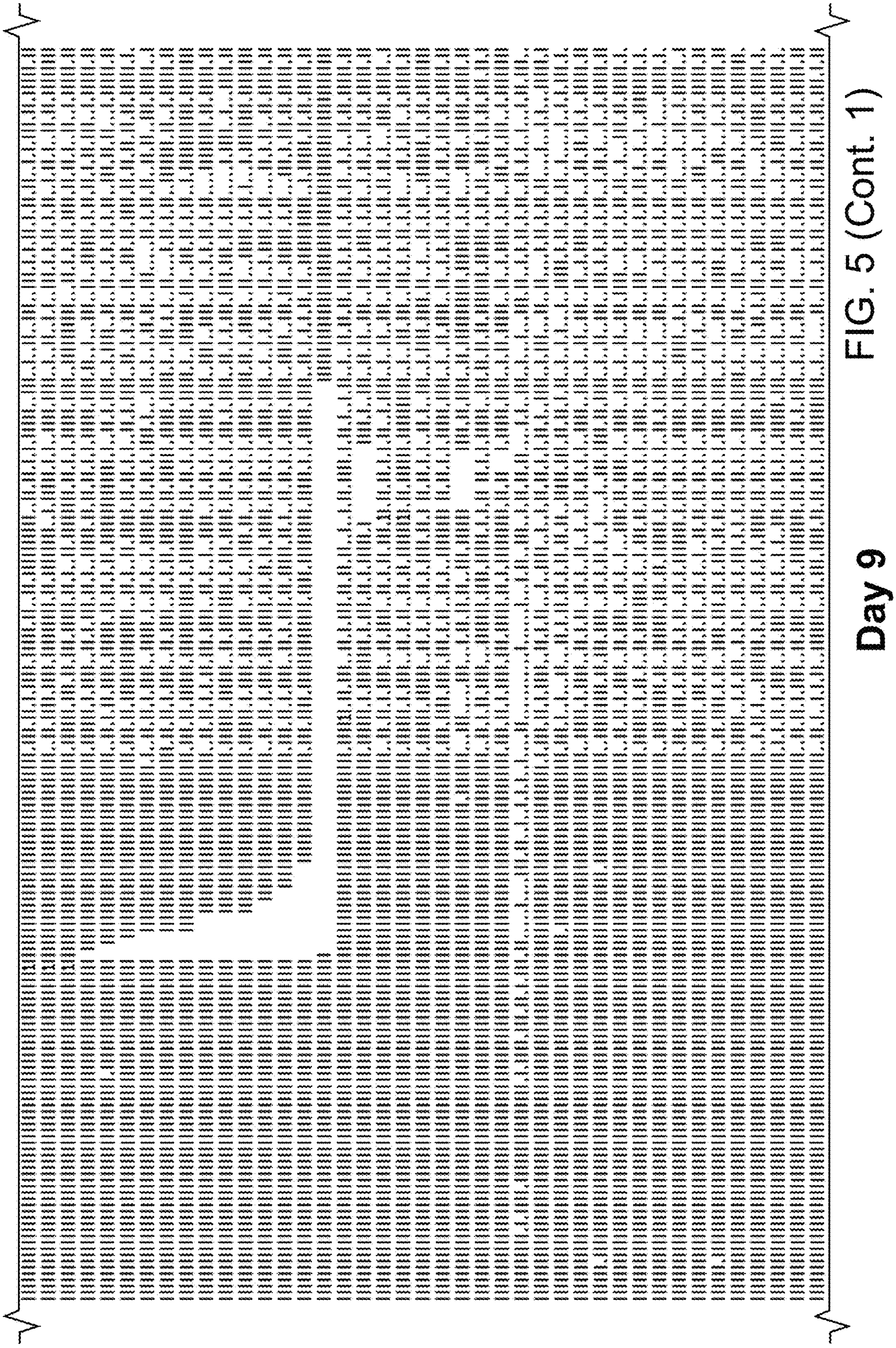
Day 9
FIG. 5 (Cont. 1)

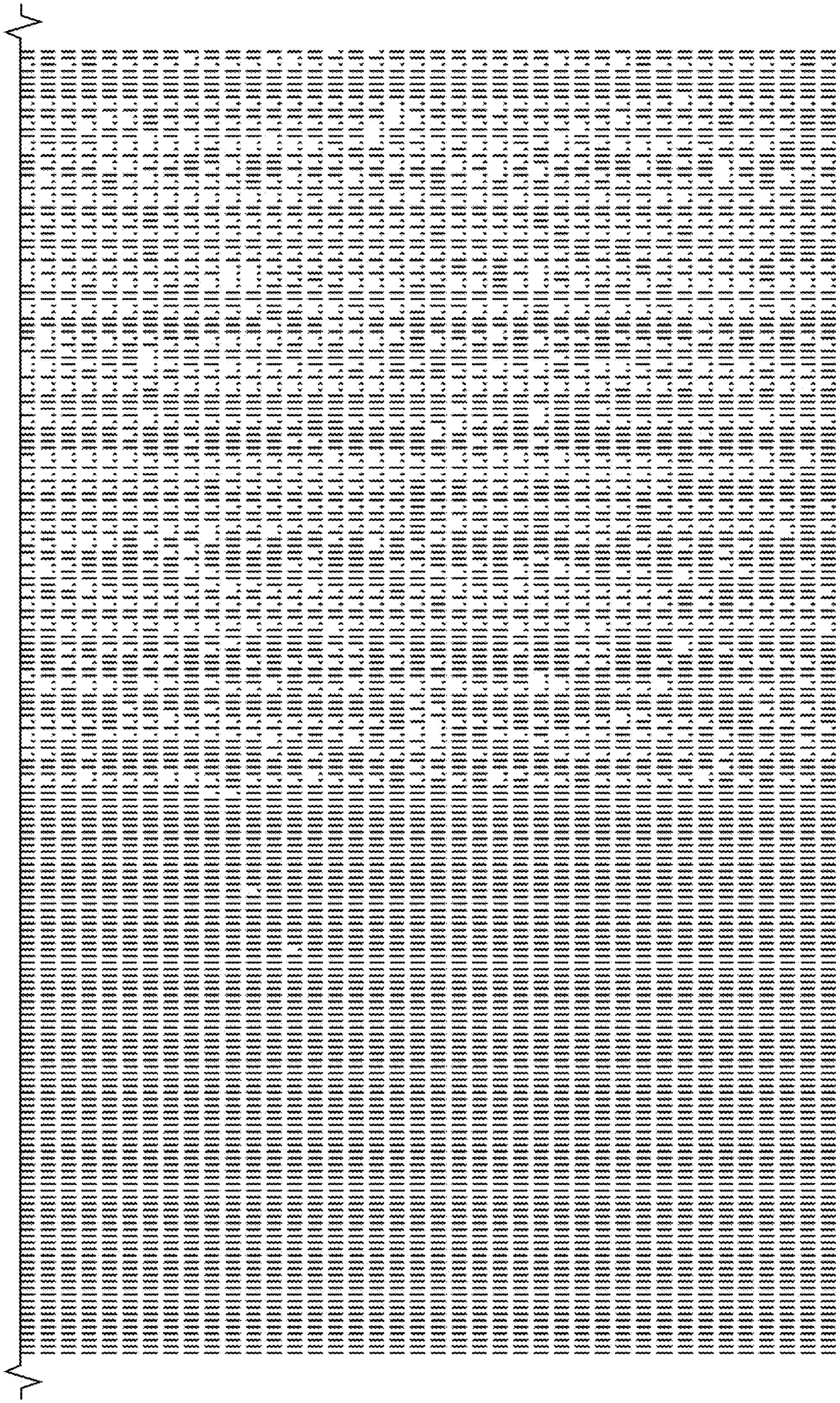
Day 9
FIG. 5 (Cont. 2)

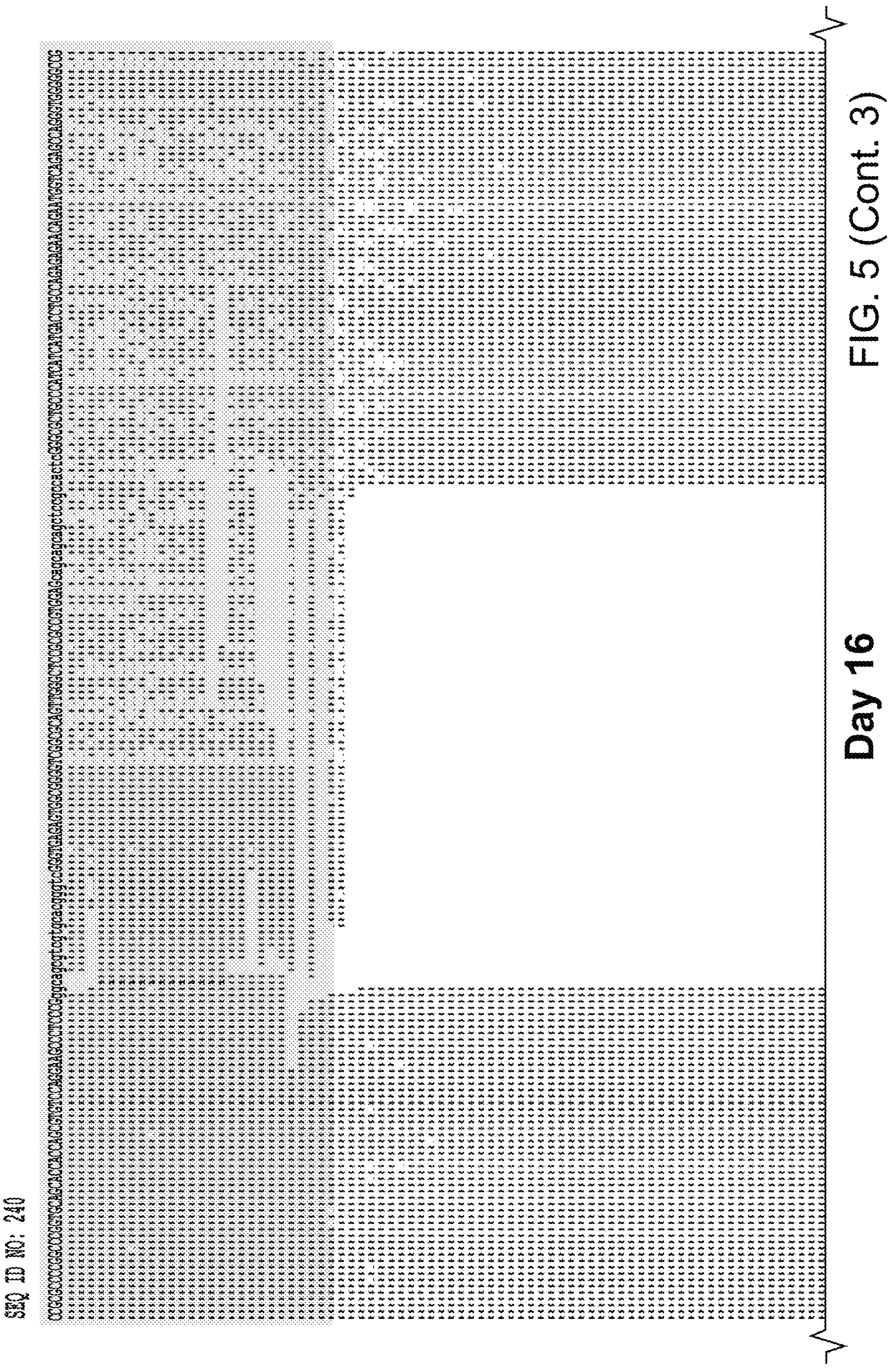
FIG. 5 (Cont. 3)

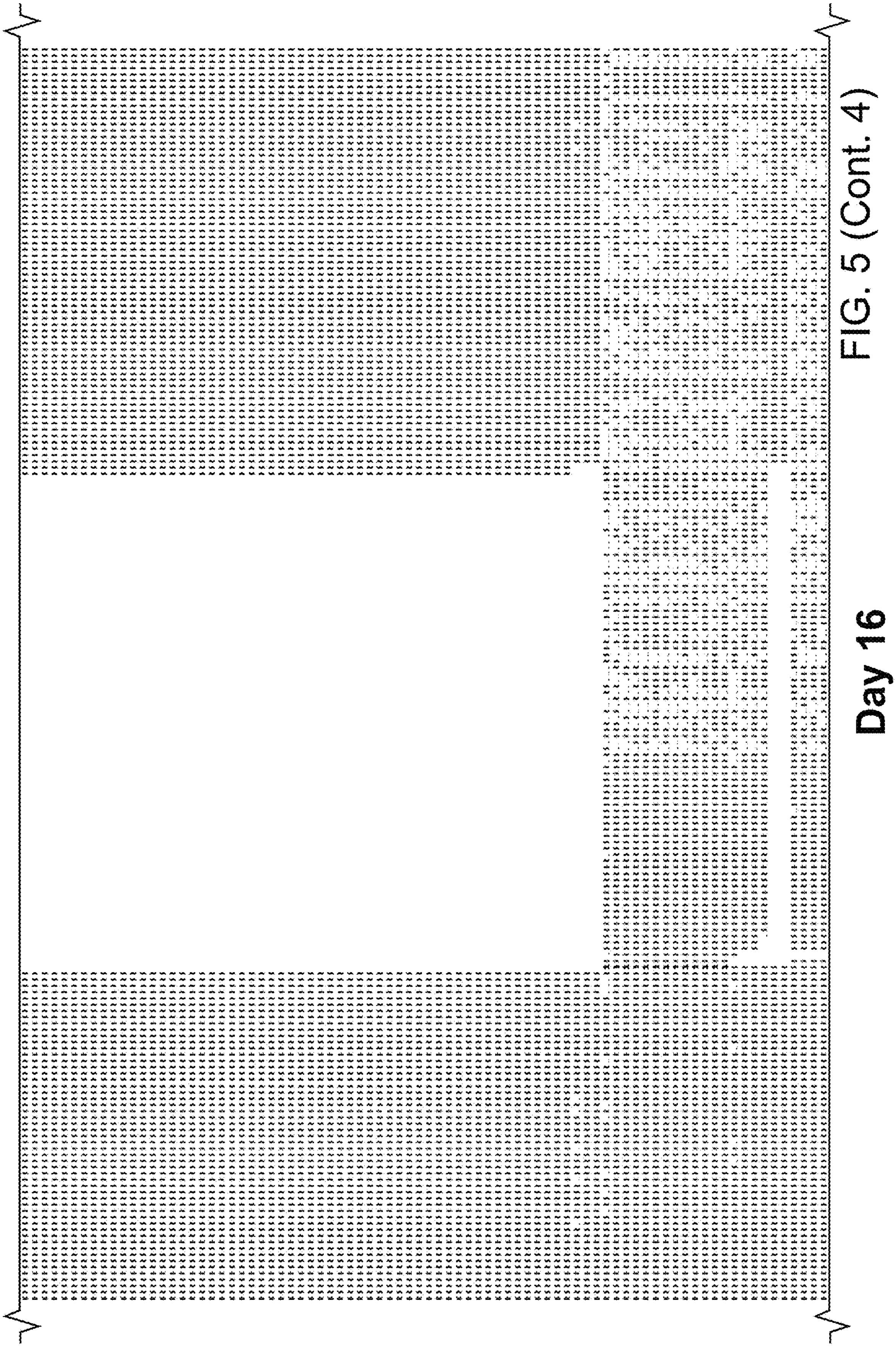
Day 16
FIG. 5 (Cont. 4)

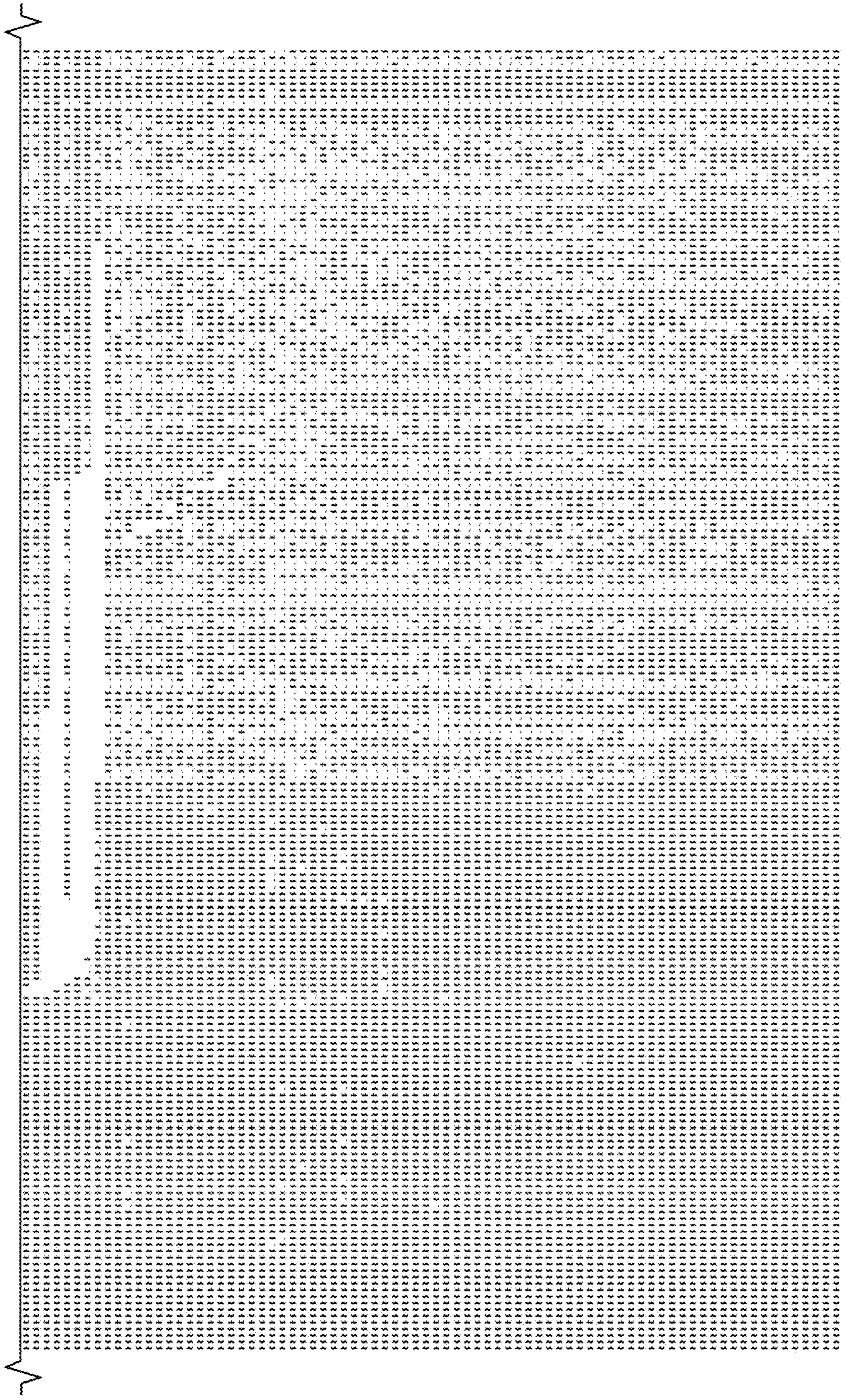
Day 16
FIG. 5 (Cont. 5)

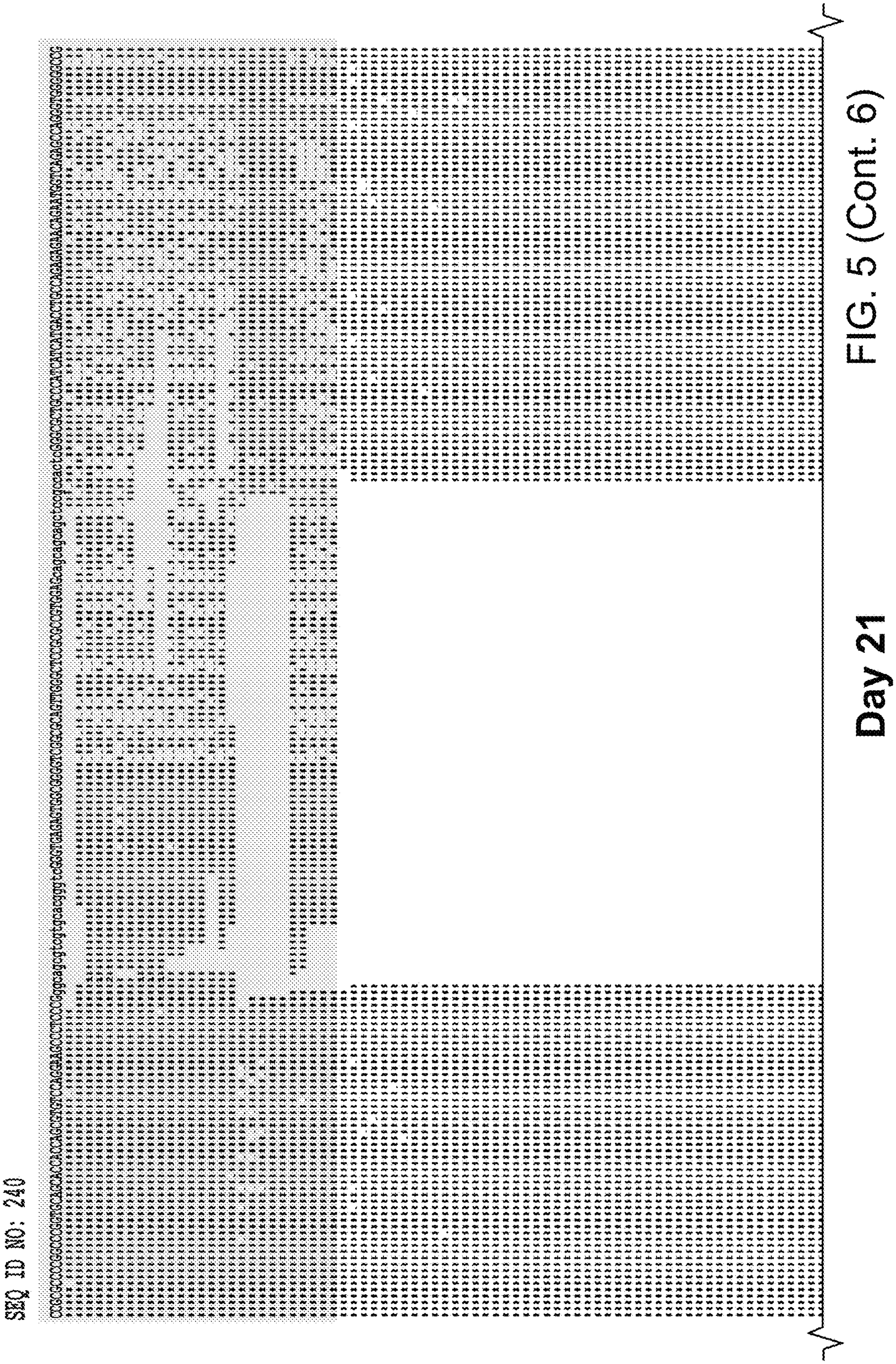
Day 21
FIG. 5 (Cont. 6)

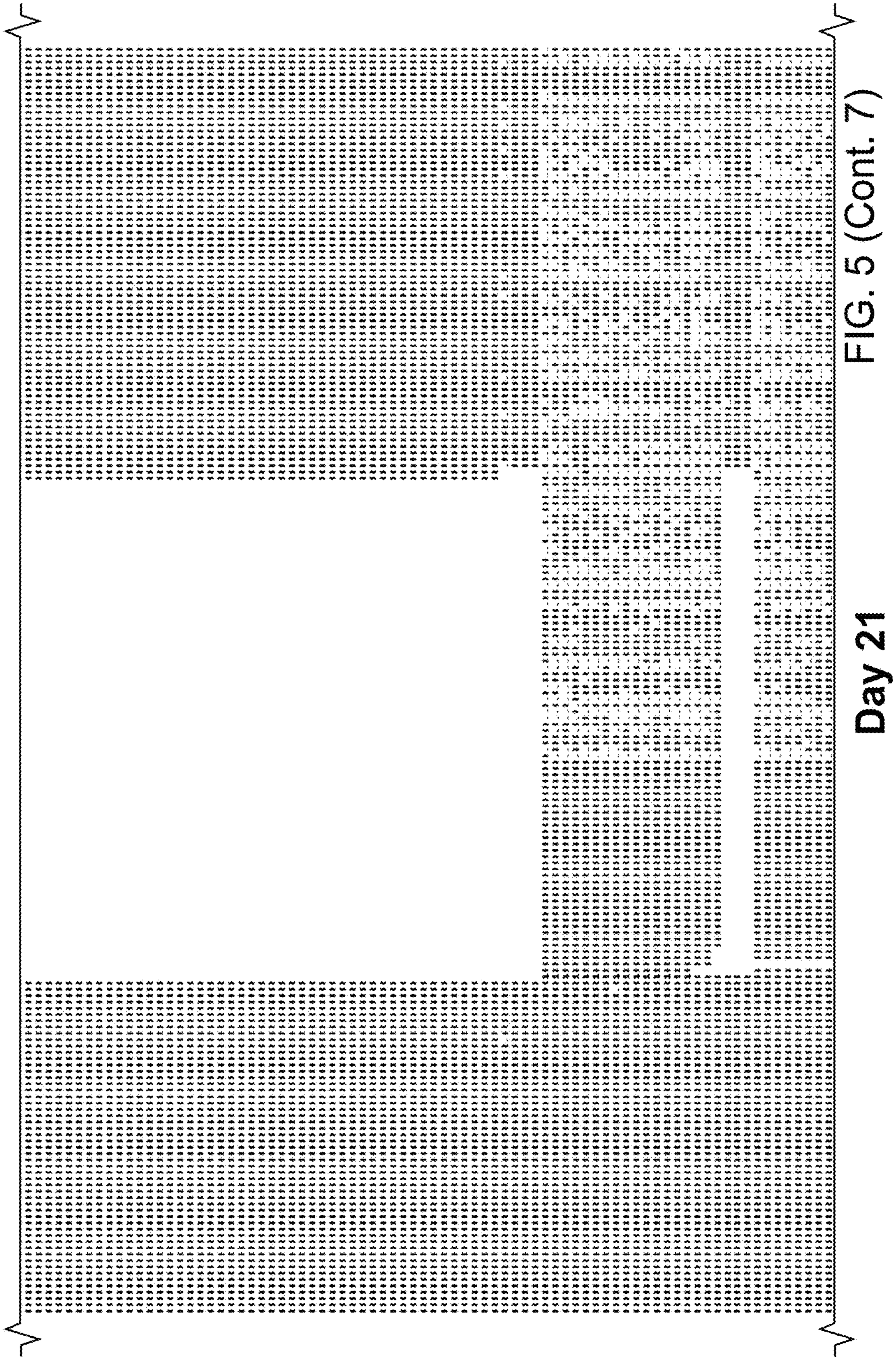
Day 21
FIG. 5 (Cont. 7)

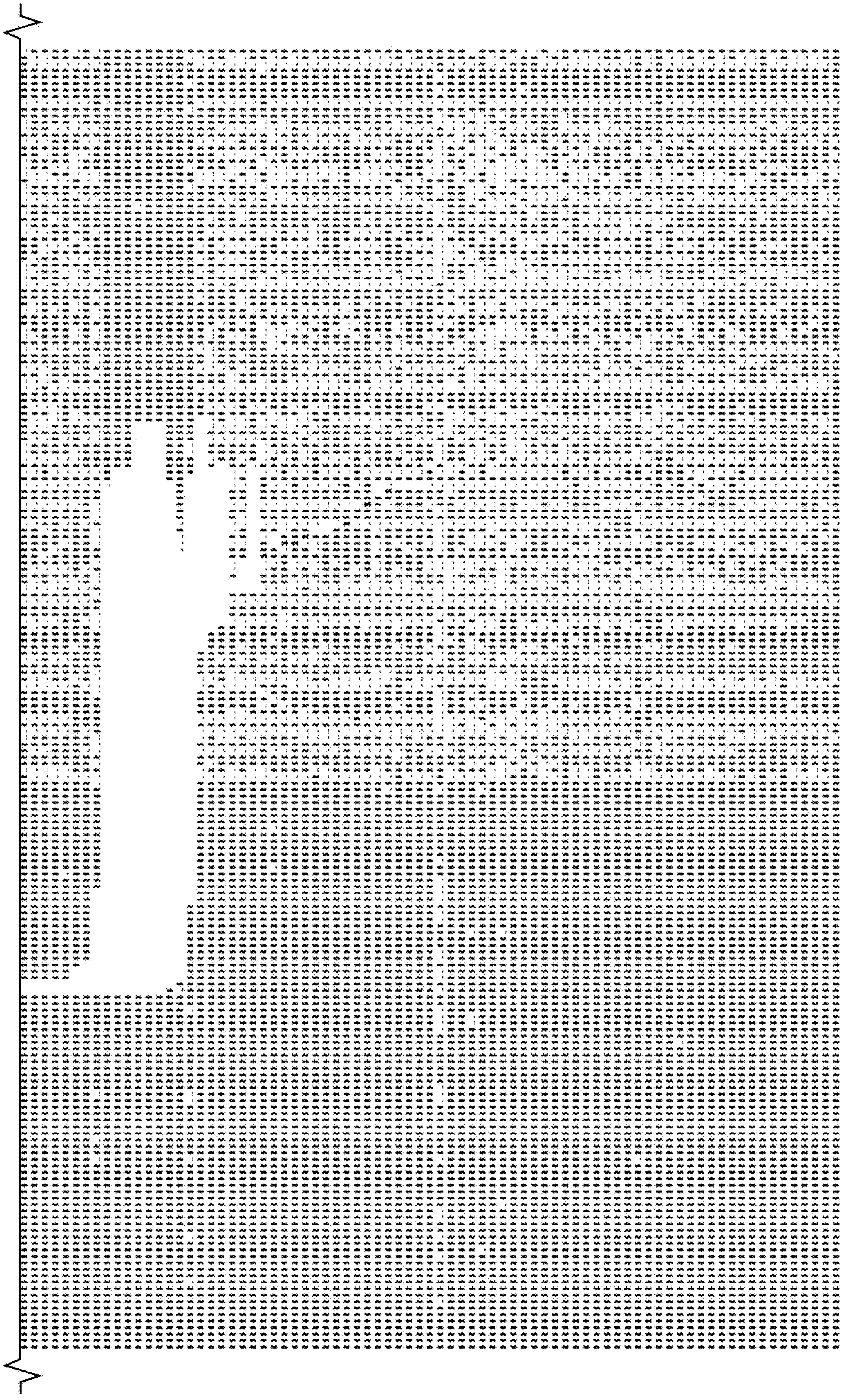
Day 21
FIG. 5 (Cont. 8)

SEQ ID NO: 240
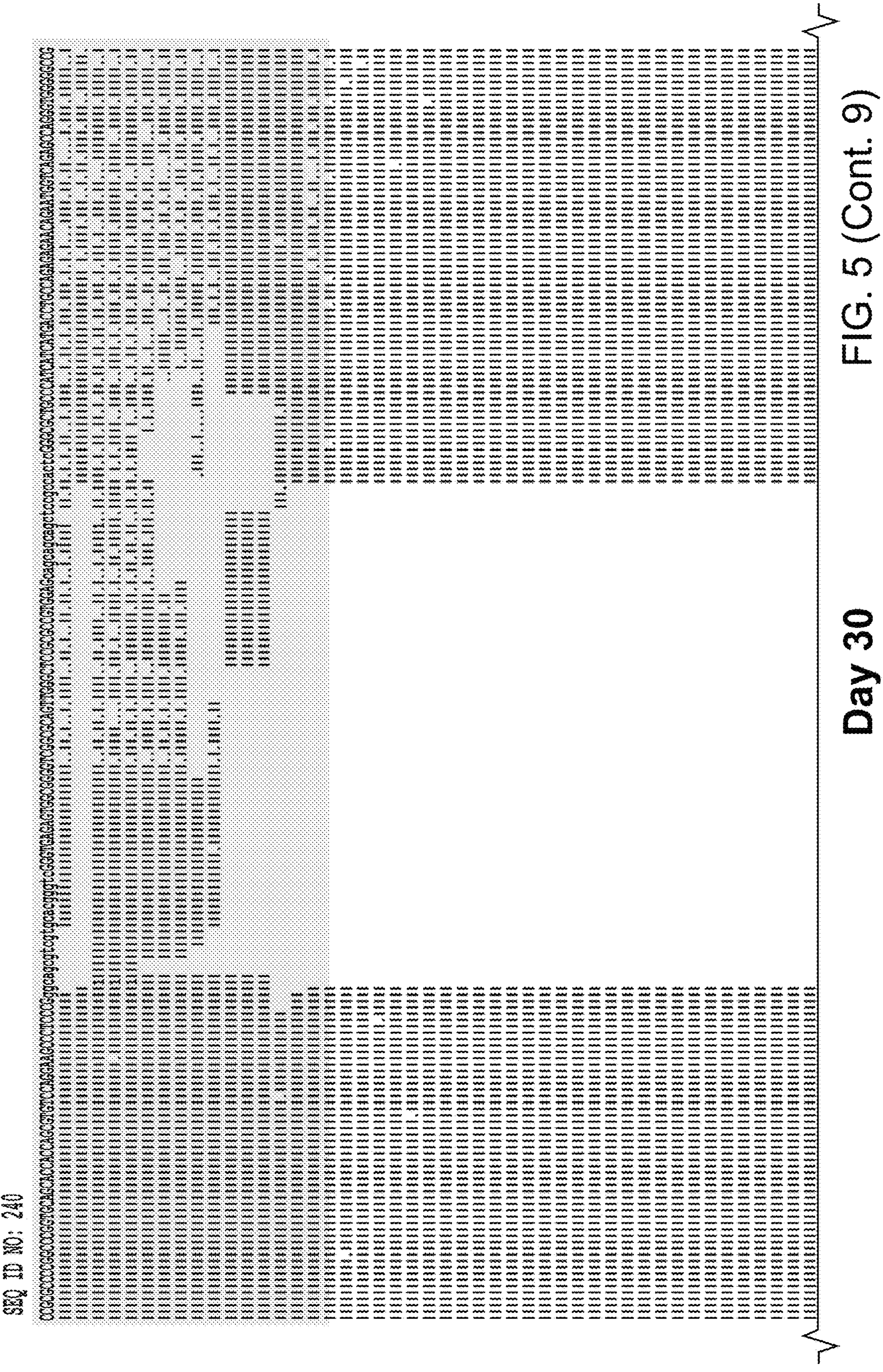
Day 30
FIG. 5 (Cont. 9)

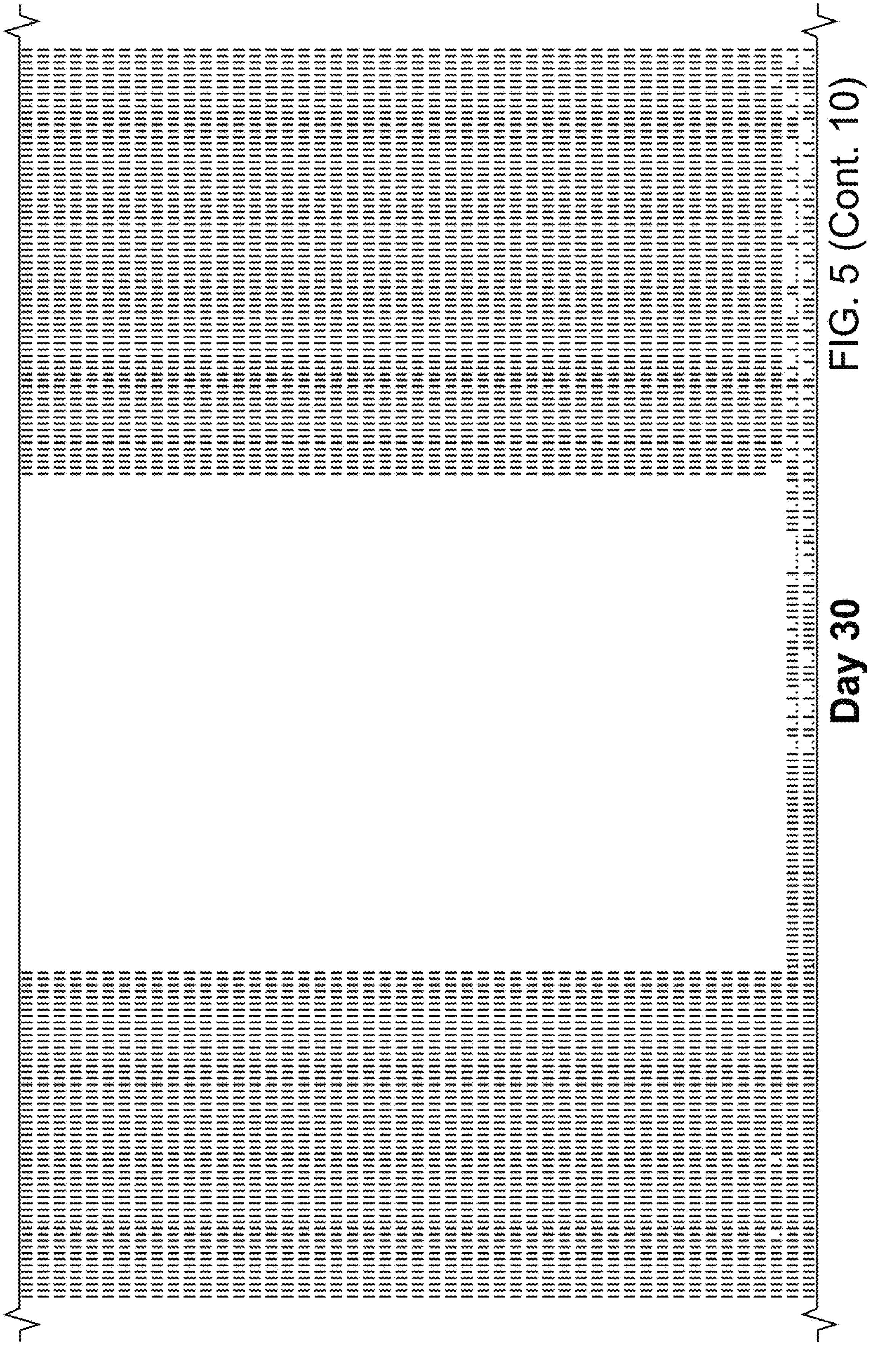
FIG. 5 (Cont. 10)

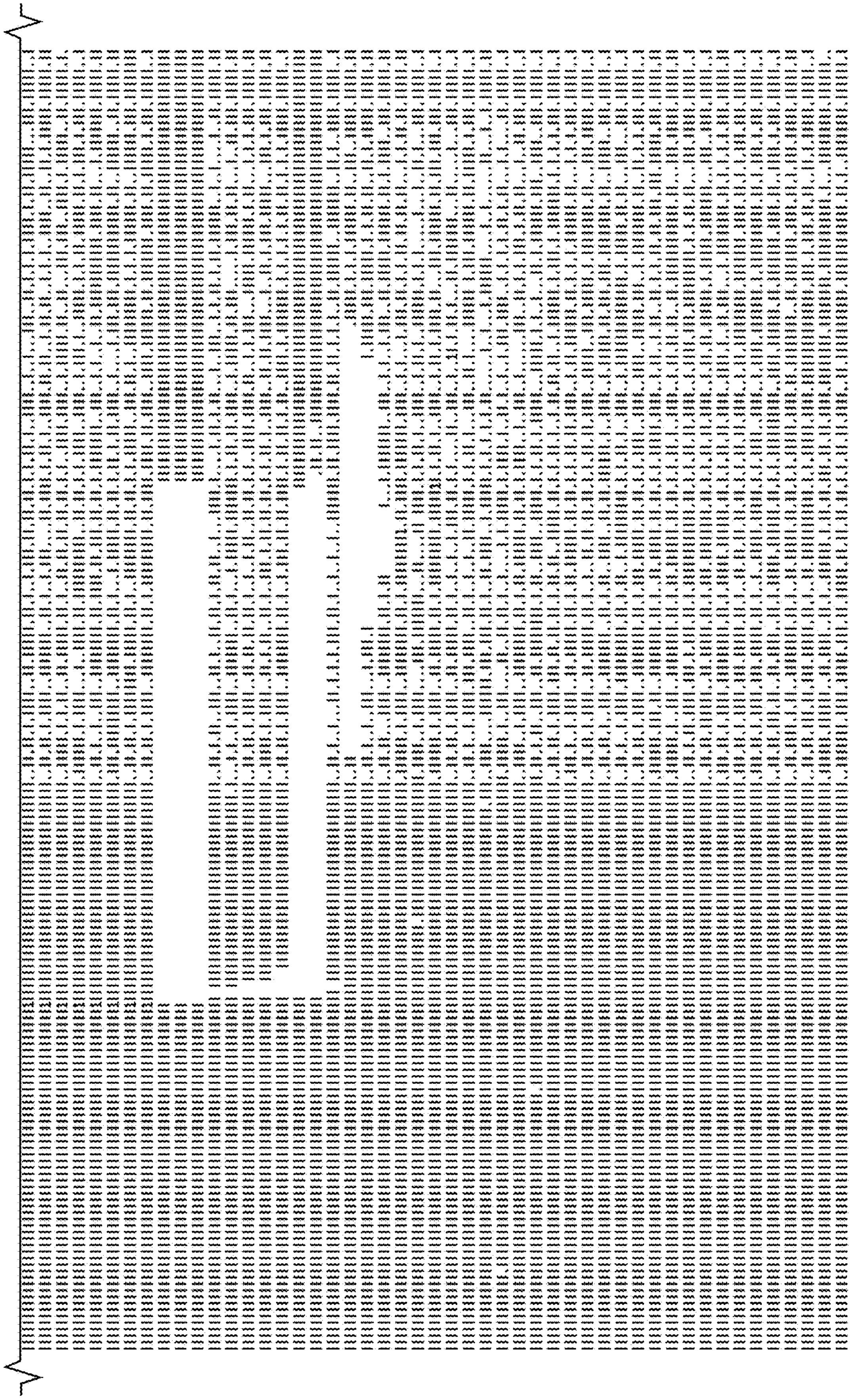
Day 30
FIG. 5 (Cont. 11)

CBTP grows in mouse dermis, CBT does not

CBT
(0/4 flanks)

CBTP
(4/4 flanks)

Intradermal xenograft
12.5 weeks
NSG mice, no Matrigel
1 million cells / injection CBTP+TP53-KO yields fast growing large tumors

CBTP CBTP-TP53

Intradermal xenograft
7 weeks
NSG mice, no Matrigel
1 million cells/injection

CBTP+TP53-KO tumors are amelanotic, with some pigmented cells at the core

WT - - - - - - - - - - - - - -▸ C - - - - - - - - - - - - - -▸ CB - - - - - - - - - - - - - -▸ CBT

CBTP

CBT3

CBTA

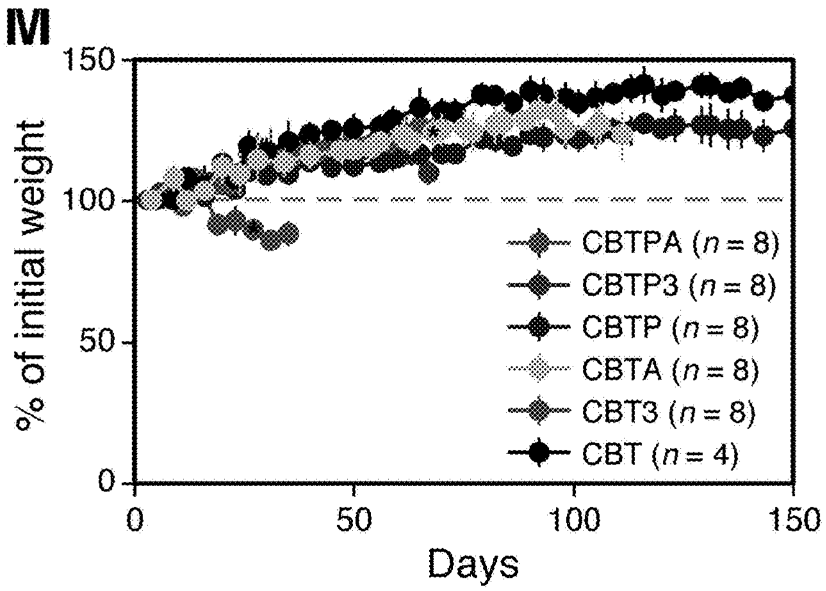

FIG. 28M

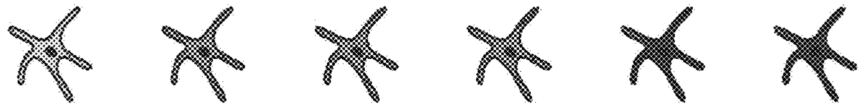

| | CBT | CBT3 | CBTA | CBTP | CBTP3 | CBTPA |
|---|---|---|---|---|---|---|
| | *CDKN2A*$^{-/-}$ *BRAF*$^{V600E}$ *TERT*$^{C228T}$ | *CDKN2A*$^{-/-}$ *BRAF*$^{V600E}$ *TERT*$^{C228T}$ *TP53*$^{-/-}$ | *CDKN2A*$^{-/-}$ *BRAF*$^{V600E}$ *TERT*$^{C228T}$ *APC*$^{-/-}$ | *CDKN2A*$^{-/-}$ *BRAF*$^{V600E}$ *TERT*$^{C228T}$ *PTEN*$^{-/-}$ | *CDKN2A*$^{-/-}$ *BRAF*$^{V600E}$ *TERT*$^{C228T}$ *PTEN*$^{-/-}$ *TP53*$^{-/-}$ | *CDKN2A*$^{-/-}$ *BRAF*$^{V600E}$ *TERT*$^{C228T}$ *PTEN*$^{-/-}$ *APC*$^{-/-}$ |
| Replicative immortality: | + | + | + | + | + | + |
| Malignant: | + | + | + | + | + | + |
| Primary tumor growth: | – | – | + | + | + | + |
| Metastasis: | – | | | –/+ | –/+ | + |
| Weight loss: | – | – | – | – | – | + |
| Rapid tumor growth: | – | – | – | – | – | + |

FIG. 28N

| Genotype | Days post-injection |
|---|---|
| CBTA | 111 |

Mouse ID: 337

| Genotype | Days post-injection | |
|---|---|---|
| CBTPA | 36 |  |

METHODS OF PRODUCING HUMAN CANCER CELL MODELS AND METHODS OF USE

CROSS-REFERENCE TO RELATED APPLICATIONS

This application is a U.S. National Stage of International Application No. PCT/US2018/042737, filed Jul. 18, 2018, which claims the benefit of U.S. Provisional Application No. 62/534,023, filed Jul. 18, 2017. The entire contents of the above-identified application are hereby fully incorporated herein by reference.

REFERENCE TO AN ELECTRONIC SEQUENCE LISTING

The content of the electronic sequence listing ("BROD-2110US_ST25.txt", 55,139 bytes, created on Dec. 19, 2023) is herein incorporated by reference in its entirety.

TECHNICAL FIELD

The subject matter disclosed herein is generally directed to defined human cancer models and methods of producing such models.

BACKGROUND

Cancer models can provide systems to dissect cancer development and identify therapeutic targets. Prior studies have attempted to generate cancer associated mutations in human cells (Torres-Ruiz et al., Stem Cell Reports (2017) Vol. 8, 1408-1420). In this study, the authors achieved a population of cells with the defined mutation in 100% of the cells using induced pluripotent stem cells (iPSCs). iPSCs are not normal human cells and are altered to make them similar to stem-cells. The authors failed to introduce mutations in human mesenchymal stem cells (hMSCs). The authors also used sub-cloning to achieve a clonal population. In other words, they delivered the editing reagents and then separated out the cells into single cells so that the colonies that grew out all had cells with the same exact genotype ('clonal'). Sub cloning is known to generate artifacts, such that two sub clones may be quite different from each other when grown out. The mutant cells they generated had no phenotypic difference compared to the parental cells they started with. Finally, the authors introduced only one mutational event. Thus, there is a further need for defined models for use in understanding cancer development and for screening of drugs.

Each human cancer has as its root cause a combination of genetic alterations. In aggregate, human cancers harbor seemingly innumerable combinations of genetic alterations in patterns that likely accord with tissue-specific requirements for malignant transformation (Garraway et al. *Cell* 153:17-37 (2013); Vogelstein et al. *Science* 339:1546-1558 (2013)). It is generally possible to infer which alterations have undergone positive selection over the lifetime of a tumor through examination of data across tumors and to categorize altered genes as oncogenes or tumor suppressor genes. However, it remains exceedingly challenging to identify the particular set of genetic alterations responsible for an observed malignant phenotype. Addressing this challenge would be considerably easier were it possible to model multiple, precise genetic alterations in healthy human cells, yet such a technical feat has historically been out of reach.

Recent advances in genome editing in mammalian cells (Cong et al. *Science* 339:819-823 (2013); Mali et al. *Science* 339:823-826 (2013); Drost et al. *Nature* 521:43-47 (2015); Matano et al. *Nat Med* 21:256-262 (2015); Dever et al. *Nature* 539:384-389 (2016)) open up an opportunity to sequentially introduce mutations in endogenous gene loci in a human cellular context.

Melanoma provides an illustrative case in point (Clark, et al. *Br J Cancer* 64:631-644 (1991)). Melanoma genome sequencing, mostly of advanced cancers, has revealed a complicated genetic landscape of somatic alterations. With tens of thousands of mutations per genome and many copy number changes, melanoma ranks among the most mutated of all cancer types, largely due to sunlight-induced DNA damage (Berger et al. *Nature* 485:502-506 (2012); Alexandrov et al. *Nature* 500:415-421 (2013)). Dozens of genes are recognized as pathogenically mutated across patients in melanoma, making it difficult to describe disease initiation or progression in terms of a restricted set of genetic events (Hodis et al. *Cell* 150:251-263 (2012); Krauthammer et al. *Nat Genet* 44:1006-1014 (2012); Akbani et al. *Cell* 161:1681-1696 (2015)). Nevertheless, mutation patterns observed across hundreds of individual human melanoma specimens strongly hint at three core genetic requirements (Bastian et al. *Annu Rev Pathol* 9:239-271 (2014); Shain et al. *Nat Rev Cancer* 16:345-358 (2016); Shain et al. *N Eng J Med* 373:1926-1936 (2015); Bennett *Pigment Cell & Melanoma Res* 29:122-140 (2016); Hodis and Garraway *Melanoma* (2017)) (FIG. 18A): (1) activation of the mitogen-activated protein kinase (MAPK) pathway (~90% of melanomas have a mutation in one, and often only one, of BRAF, NRAS, NF1, KIT, MAP2K1, RAF1, HRAS, or KRAS (Hodis et al. *Cell* 150:251-263 (2012); Krauthammer et al. *Nat Genet* 44:1006-1014 (2012); Akbani et al. *Cell* 161:1681-1696 (2015); Krauthammer et al. *Nat Genet* 47:996-1002 (2015)); (2) activation of telomerase (~70% of melanomas have one of two specific nucleotide substitutions in the promoter of TERT (Horn et al. *Science* 339:959-961 (2013); Huang et al. *Science* 339:957-959 (2013)), and (3) disruption of the p16/cyclinD/CDK4/RB pathway (~70% of melanomas have a lesion in one, and generally only one, of CDKN2A, RB1, CDK4, or CCND1 (Akbani et al. *Cell* 161:1681-1696 (2015)). However, it remains unclear whether genetic alteration of these three functional pathways alone suffices to generate human melanoma, and what are the contributions of an expansive palette of additional common mutations, for example those in PTEN (deleted or mutated in ~20% of melanomas) or TP53 (mutated in ~10-15% of melanomas), to the phenotypes of genesis or progression of human melanoma (FIG. 18A) (Hodis et al. *Cell* 150:251-263 (2012); *Cell* 161:1681-1696 (2015)). Also unclear are the phenotypic contributions of melanoma genes like APC that are mutated at a relatively lower frequency (~1-2% of melanomas) but act within a frequently activated molecular pathway (~30% of melanomas have active Wnt signaling) (Hodis et al. *Cell* 150:251-263 (2012); Akbani et al. *Cell* 161:1681-1696 (2015); Dankort et al. *Nat Genet* 41:544-552 (2009); Damsky et al. *Cancer Cell* 20:741-754 (2011); Viros et al. *Nature* 511:478-482 (2014)). Among the key open questions are: Which mutations suffice for malignant transformation of a melanocyte? The earliest diagnosed melanomas tend to be small lesions whose malignancy is ascertained by a combination of histology, cellular morphology and immunophenotypic staining. Which combinations of mutations enable the growth of such an initial lesion into a large primary melanoma? Which yield accelerated growth? Which promote metastasis? And which mutations cause systemic manifestations of disease, such as weight loss?

Experimental modeling has produced conflicting conclusions regarding the phenotypes conferred by specific sets of melanoma genetic alterations. On the one hand, experiments with genetically engineered murine models have shown that Braf V600E paired with biallelic inactivation of Pten suffices to generate aggressive, metastatic murine melanoma, which can be exacerbated by an activating mutation in Ctnnb1 (Chudnovsky et al. *Nat Genet* 37:745-749 (2005); Zeng et al. *Cancer Cell* 34:56-68 (2018)) pairing Braf V600E instead with a dominant negative mutation of Trp53 was similarly shown to initiate murine melanoma. On the other hand, when primary melanocytes derived from a human donor were made to ectopically overexpress BRAF V600E and dominant negative TP53 in addition to TERT and constitutively active CDK4 (substituting for CDKN2A loss), only benign neoplasia resulted (Knight et al. *Science* 350: 823-826 (2015)). Additional overexpression of the catalytic subunit of PI3K (substituting for PTEN loss) in this human model produced a malignant, but non-metastatic, transformation, for which BRAF V600E overexpression was inconsequential and could be withheld. These conflicting results could reflect the distinct limitations of each model: the human model lacked endogenous control of expression, while the genetically engineered murine models did not fully mirror the biology of a human cell.

Genome editing of human cells could sidestep these liabilities. Its potential for modeling human cancer has been demonstrated by generation of colorectal cancer models starting from human intestinal stem cells (Drost et al. *Nature* 521:43-47 (2015); Matano et al. *Nat Med* 21:256-262 (2015)). These pioneering initial approaches are however limited: (1) only specific mutations can be introduced, since the selection of mutations relies on functional equivalence between the introduced mutation and a known growth factor or chemical compound that is removed from or added to the media; and (2) many cancers do not arise from stem cells that can be cultured indefinitely. Genome editing in differentiated primary human cells, such as melanocytes, is more challenging than in stem cells due to their limited lifespan in culture and a frequent inability to grow single cells into clones. However, very recent work has demonstrated the feasibility of genome editing human melanocytes to study the molecular and phenotypic consequences of CDKN2A loss (Tsao et al. *J Invest Dermatol* 122:337-341 (2004)).

SUMMARY

In certain example embodiments, the present invention provides for novel defined cancer models and methods to obtain the models. In one aspect, the present invention provides for a method of obtaining a population of cells for modeling cancer, said method comprising at least one round of introducing one or more mutations into one or more cells in a population of cells in vitro and culturing the cells until the mutation(s) are positively selected in the population. The cells may be cultured in vitro. The cells may be cultured in vivo. In certain embodiments, the cells are positively selected in vivo in order to select for cells capable of evading the immune system. In certain embodiments, cells are selected in an immune competent animal model. The cells may be primary cells.

In certain embodiments, the one or more mutations are selected from the group consisting of known cancer mutations listed in Tables 1 to 6. The one or more mutations may be selected from the group consisting of a CDKN2A inactivating mutation, BRAF activating mutation, TERT activating mutation, PTEN inactivating mutation, CTNNB1 activating mutation, and TP53 inactivating mutation. The CDKN2A inactivating mutation may be selected from the group consisting of a deletion in exon 1, a deletion in exon 2, a deletion in exon 1 and 2, a deletion in exon 3, a deletion in the whole gene, a missense mutation, a frameshift mutation and a nonsense mutation. The BRAF activating mutation may be selected from the group consisting of BRAF V600E, BRAF V600K, BRAF V600R and BRAF K601E. In certain example embodiments, the TERT activating mutation may be selected from the group consisting of TERT C228T and TERT C250T. In certain example embodiments, the PTEN inactivating mutation may be selected from the group consisting of a deletion, a missense mutation, a frameshift mutation, a nonsense mutation. The CTNNB1 activating mutation may be selected from the group consisting of CTNNB1 S45P, CTNNB1 S45F, CTNNB1 S45Y, CTNNB1 S37F, CTNNB1 S37Y and CTNNB1 S33C. The TP53 inactivating mutation may be selected from the group consisting of a deletion, a missense mutation, a frameshift mutation and a nonsense mutation.

In some embodiments, the population of cells may comprise one or more mutations in genes including NRAS, NF1, KIT, CCND1, CDK4, and/or RB1. In some embodiments, the population of cells may comprise one or more additional mutations in genes such as ARID2, PPP6C, RAC1, IDH1, MITF, DDX3X, MDM2, EZH2, PI3KCA, and/or APC.

In certain embodiments, the method may comprise introducing a first mutation into one or more cells in the population of cells and culturing the cells until the first mutation is positively selected in the population. The method may further comprise introducing a second mutation into one or more cells in the positively selected population of cells and culturing the cells until the first and second mutations are positively selected in the population. The method may further comprise introducing a third mutation into one or more cells in the positively selected population of cells and culturing the cells until the first, second and third mutations are positively selected in the population. The method may further comprise introducing a fourth mutation into one or more cells in the positively selected population of cells and culturing the cells until the first, second, third and fourth mutations are positively selected in the population. The method may further comprise introducing a fifth mutation into one or more cells in the positively selected population of cells and culturing the cells until the first, second, third, fourth and fifth mutations are positively selected in the population. The method may further comprise repeating the steps of introducing and culturing for N number of mutations, wherein N is greater than 5. Not being bound by a theory the method may be used to introduce any number of mutations.

In certain embodiments, the method may comprise introducing a first and second mutation and culturing the cells until the first and second mutations are positively selected in the population. The method may further comprise introducing a third mutation into one or more cells in the positively selected population of cells and culturing the cells until the first, second and third mutations are positively selected in the population. In certain embodiments, the method may comprise introducing a first, second and third mutation and culturing the cells until the first second and third mutations are positively selected in the population. The method may further comprise introducing a fourth mutation into one or more cells in the positively selected population of cells and culturing the cells until the first, second, third and fourth mutations are positively selected in the population. The method may further comprise introducing a third and fourth mutation into one or more cells in the positively selected population of cells and culturing the cells until the first, second, third and fourth mutations are positively selected in the population. The method may further comprise introducing a fifth mutation into one or more cells in the positively selected population of cells and culturing the cells until the first, second, third, fourth and fifth mutations are positively selected in the population.

In any embodiment described herein, the first mutation may be a CDKN2A inactivating mutation. The second mutation may be BRAF activating mutation. The third mutation may be a TERT activating mutation. The fourth mutation may be a PTEN inactivating mutation. The fifth mutation may be a TP53 inactivating mutation or CTNNB1 activating mutation. The fifth mutation may be a mutation in the APC gene. The mutation may be any mutation described herein.

In some embodiments, the population may comprise a CDKN2A knockout mutation, a BRAF V600E mutation, and a −124C>T TERT mutation. In some embodiments, the population may comprise mutations in CDKN2A, BRAF, TERT, PTEN, and APC genes.

In certain embodiments, any of the mutation(s) may confer resistance to a cancer treatment agent and the method may further comprise culturing with the cancer treatment agent, whereby the mutation may be positively selected. The cancer treatment agent may be selected from the group consisting of a chemotherapy, immunotherapy, and targeted therapy. Not being bound by a theory, the immunotherapy is administered in vivo, whereby, the resistance mutation is selected in cells able to avoid an immune response.

In certain embodiments, 90-100% of the positively selected cells in the population comprise the mutation(s). Not being bound by a theory, positively selected cells will take over the entire population of cells but may also take over only a majority of the cells (e.g., greater than 50%).

In certain embodiments, the cells may be human cells. The cells may be melanocytes. The cancer may be melanoma.

In certain embodiments, the one or more mutations may be introduced using a gene editing system capable of targeting the locus to be mutated. The gene editing system may comprise a CRISPR system and one or more guide RNAs capable of targeting the locus to be mutated. The gene editing system may comprise a TALEN, Zinc finger, or recombination system capable of targeting the locus to be mutated. The CRISPR system may be introduced into cells via a nucleic acid molecule encoding the CRISPR system, and the one or more guide RNAs may be introduced into cells via one or more nucleic acid molecules with sequences comprising or encoding the one or more guide RNAs, optionally wherein nucleic acid molecules are comprised within one or more expression vectors and wherein sequences encoding the one or more guide RNAs and/or the CRISPR system are operably linked to a promoter. The nucleic acid molecules may be introduced into cells by transfection, electroporation or viral delivery, optionally via lentiviral vector delivery, adenoviral vector delivery or AAV vector delivery. The CRISPR system and the one or more guide RNAs may be introduced into cells via electroporation. The method may comprise introducing mutations by a method comprising: electroporating the cells with CRISPR RNPs comprising guide RNAs targeting the locus to be mutated; optionally adding to the electroporated cells AAV comprising homologous donor DNA comprising knock-in mutations; plating the cells in growth media; incubating the cells at ~30° C. for 1 to 3 days; and transferring the cells to 37° C.

In another aspect, the present invention provides for a population of cells obtained by the any method described herein.

In another aspect, the present invention provides for an engineered, non-naturally occurring population of cells for modeling human cancer comprising an in vitro population of primary cells comprising a first defined mutation. Not being bound by a theory, an in vitro population of primary cells all comprising a single defined mutation does not exist in nature. The population may further comprise a second defined mutation. The population may further comprise a third defined mutation, wherein the primary cells are immortal. The population may further comprise a fourth defined mutation, wherein the primary cells are transformed. The population may further comprise a fifth defined driver mutation. The first mutation may be a CDKN2A inactivating mutation. The second mutation may be a BRAF activating mutation. The third mutation may be a TERT activating mutation. The fourth mutation may be a PTEN inactivating mutation. The fifth mutation may be a TP53 inactivating mutation or CTNNB1 activating mutation. The primary cells may be human cells. The primary cells may be melanocytes. The cancer may be melanoma.

In another aspect, the present invention provides for a method of studying cancer development in pre-transformed or transformed cells comprising detecting genetic, epigenetic, gene expression, proteomic and/or phenotypic changes at one or more time points in a population of cells according to any embodiment herein. The phenotypic changes may be detected by growth in soft agar or a xenograft.

In certain embodiments, the population of cells according to any embodiment herein may be treated with one or more perturbations. The perturbations may comprise a physical, chemical or biologic perturbation. The one or more perturbations may comprise a CRISPR system and one or more guide RNAs, wherein single cells in the population receive a single guide RNA.

In another aspect, the present invention provides for a method of drug screening comprising treating a population of cells according to any embodiment herein with one or more drug candidates and assaying for viability, proliferation, secretion and/or migration. The population of cells may comprise one or more mutations selected from the group consisting of a CDKN2A inactivating mutation, BRAF activating mutation, TERT activating mutation, PTEN inactivating mutation, CTNNB1 activating mutation, TP53 inactivating mutation and combinations thereof. The drug may target mutant activated BRAF kinase, optionally wherein the mutant activated BRAF kinase may be BRAF V600E, preferably wherein the drug may be a small molecule drug. The drug may be an inhibitor of a MEK kinase or wherein the drug may be an inhibitor of a MAP (ERK) kinase, preferably wherein the drug may be a small molecule drug.

In another aspect, the present invention provides for a method of determining mutations capable of acting as a first event in the transformation of primary cells comprising: introducing one or more mutations to a population of primary cells; culturing the cells; and detecting mutations positively selected in the culture. In certain embodiments, a plurality of mutations is introduced to a population of cells and the cells are cultured to allow for mutations to be positively selected. The positively selected mutations may then be identified by a method, such as sequencing, thus identifying mutations capable of acting as a first event.

In another aspect, the present invention provides for a method of determining mutations capable of acting as a second event in the transformation of primary cells comprising: introducing one or more mutations to a population of primary cells comprising a first event mutation; culturing the cells; and detecting mutations positively selected in the culture. In certain embodiments, the first event mutation may be a CDKN2A inactivating mutation.

In certain embodiments, any of the one or more mutations described herein are heterozygous or homozygous mutations.

In another aspect, the present invention provides for a non-naturally occurring or engineered composition comprising a CRISPR system, the system comprising: a CRISPR enzyme; and one or more guide RNAs, each capable of targeting the enzyme to a locus to be mutated; wherein the system may be configured to introduce one or more mutations at one or more loci in one or more cells in a cell population when the system is expressed in said one or more cells; wherein the one or more mutations are selected from the group consisting of a CDKN2A inactivating mutation, BRAF activating mutation, TERT activating mutation, PTEN inactivating mutation, CTNNB1 activating mutation, and TP53 inactivating mutation. The CDKN2A inactivating mutation may be selected from the group consisting of a deletion in exon 1, a deletion in exon 2, a deletion in exon 1 and 2, a deletion in exon 3, a deletion in the whole gene, a missense mutation, a frameshift mutation and a nonsense mutation. The BRAF activating mutation may be selected from the group consisting of BRAF V600E, BRAF V600K, BRAF V600R and BRAF K601E. The TERT activating mutation may be selected from the group consisting of TERT C228T and TERT C250T. The PTEN inactivating mutation may be selected from the group consisting of a deletion, a missense mutation, a frameshift mutation, and a nonsense mutation. The CTNNB1 activating mutation may be selected from the group consisting of CTNNB1 S45P, CTNNB1 S45F, CTNNB1 S45Y, CTNNB1 S37F, CTNNB1 S37Y and CTNNB1 S33C. The TP53 inactivating mutation may be selected from the group consisting of a deletion, a missense mutation, a frameshift mutation, and a nonsense mutation.

In certain embodiments, the composition or population of cells according to any embodiment herein, may comprise one or more mutations that are heterozygous or homozygous mutations.

In another aspect, the method of introducing mutations may involve electroporating the cells with CRISPR RNPs comprising guide RNAs targeting the locus to be mutated; optionally adding to the electroporated cells AAV comprising homologous donor DNA comprising knock-in mutations; plating the cells in growth media; incubating the cells at ~30° C. for 1 to 3 days; and transferring the cells to 37° C. In some embodiments, these steps may be repeated one or more times to introduce additional mutations. In some embodiments, the CRISPR RNP may be a Cas9 RNP.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

(FIG. 18A) Model of genetic alterations found in human melanomas. (FIG. 18B) Experimental approach for introducing sequential melanoma mutations into the genomes of primary human melanocytes using CRISPR/Cas9. (FIG. 18C) Sequence of introduced mutations and cell lines in this study.

(FIG. 19A-19C) Sequential introduction of mutations in CDKN2A ('C'), BRAF ('B'), and TERT ('T') using CRISPR/Cas9 genome editing of wild-type ('WT') melanocytes. Shown are the allele frequencies of each engineered mutation (y axis) over time (x axis) (30) #: measurement of allele frequency discontinued due to senescence. (FIG. 19D) Loss of CDKN2A disrupts the $p16^{INK4A}$/RB axis. Immunoblot analysis of protein lysates of WT cells and C cells using the indicated antibodies (rows). Data are representative of at least two independent experiments. (FIG. 19E) Addition of the $BRAF^{V600E}$ mutation enhances MAPK pathway signaling. Immunoblot analysis of C cells and CB cells ($BRAF^{V600E}$ at ~50% frequency) using the indicated antibodies. Data are representative of at least two independent experiments. (FIG. 19F) Addition of the −124C>T TERT promoter mutation activates TERT expression. Mean of log number of TERT mRNA and actin control (ACTB) transcripts (y axis) measured by qPCR in CB and CBT cells. Error bars: SD. n=3. *p<0.01, one-tailed, one-sample Student's t-test. (FIG. 19G) Some CBT melanocytes are malignant. Representative micrographs of hematoxylin and eosin (H&E) or immunohistochemically stained (antibody indicated on top) sections of tumors harvested 67 days after intradermal injection of CBT cells into immunodeficient (NSG) mice. Insets are at two-fold magnification.

(FIG. 20A) Genome editing of TERT −146C>T promoter mutation into CB melanocytes. Shown is the allele frequency of −146C>T (y axis) over time (x axis) (see Materials and Methods). Control cells stopped dividing due to senescence. (FIG. 20B) Introduction of the −146C>T TERT promoter mutation activates TERT expression. Mean of log number of TERT mRNA and actin (ACTB) control transcripts (y axis) measured by qPCR in CB, CBT−146C>T, CBT−124C>T, and HEK293T cells (known to express TERT). Error bars: SD. n=3. *p<0.01, one-tailed, one-sample Student's t-test. **p<0.01, two-tailed, two-sample Student's t-test.

FIG. 21A-21O—illustrate that a fourth mutation in PTEN, TP53, or APC leads to three distinct phenotypes of disease progression. (FIG. 21A-21C) Knockout of PTEN ('P'), TP53 ('3'), or APC ('A'). Shown are the allele frequencies of each mutation (y axis) engineered into CBT cells over time (x axis), as assessed by indels in the respective loci in genomic DNA (Rimm et al. *Am J Pathol* 154:325-329 (1999)). (FIG. 21D-21F) Each gene knockout has the expected effect on the relevant downstream molecular pathway (PI3K/AKT, p53, or Wnt, respectively). Immunoblot (FIG. 21D, 21E) or RT-qPCR (FIG. 21F) analysis of CBT, CBTP, CBT3, and CBTA cells, as indicated. Data are representative of at least two or three independent experiments for immunoblotting and RT-qPCR, respectively (Error bars: SD). (FIG. 21G-21O) Primary tumor growth of CBTP, CBT3, and CBTA cells in NSG mice. (FIG. 21G-21I) Tumor size ($mm^3$, y axis) over time (x axis) following two intradermal injections, one in each flank. Control: CBT cells that received non-targeting Cas9 RNP. (#two CBTA mice (FIG. 21I), one from each guide group, were sacrificed for histological inspection). (FIG. 21J-21L) Representative images of (shaved) mice harboring mutant cells as marked. (FIG. 21M-21O) Representative micrographs of H&E stained primary tumor tissue sections. Insets are at two-fold magnification. *p<0.01, NS not significant, two-tailed, two-sample Student's t-test.

(FIG. 23A) Aggregates of hyperchromatic malignant melanoma cells virtually replaced the subcutaneous fat. Magnification: 40×. (FIG. 23B) Upper left exhibited areas of malignant epithelioid melanocytes in large nests. The rest of the lesion was composed of nevoid malignant melanocytes. Magnification: 200×. (FIG. 23C) A nest of malignant melanoma cells showed retraction from the adjacent tumor cells. Magnification: 600×.

(FIG. 24A) Extensive involvement of the subcutis by hyperchromatic nevus-like cells in linear array resembled the pattern sometimes seen in human congenital melanocytic nevi. Magnification: 40×. (FIG. 24B) Tumor cells exhibited variable pigmentation and showed neurotropism. Magnification: 200×. (FIG. 24C) Marked pleomorphism was observed in the nevoid cells, a sign of malignancy. There were scattered cells with pigmented cytoplasm. Magnification: 600×.

(FIG. 25A) Malignant melanoma nodules in subcutaneous tissue showed marked variation in size and shape. Magnification: 40×. (FIG. 25B) Higher power identified a variety of melanoma cells. Some had small hyperchromatic nuclei with variable pigmentation resembling melanocytic nevus cells. Others exhibited large pleomorphic epithelioid cells. Magnification: 200×. (FIG. 25C) The hyperchromatic smaller cells were punctuated by large malignant epithelioid cells. Note that the hyperchromatic cells exhibited a rare mitosis, a feature of malignancy. Magnification: 600×. (FIG. 25D) The epithelioid cells showed ample eosinophilic cytoplasm with nuclei containing nucleoli. Magnification: 600×.

(FIG. 26A) A plaque of malignant melanoma cells was present in the subcutis just beneath, as well as infiltrating, the skeletal muscle. The cells appeared uniformly hyperchromatic. Magnification: 40×. (FIG. 26B) Toward one end of the plaque, there were place cells with multinucleated giant cells with remarkable pleomorphism of the giant cell nuclei, a feature of malignancy. Magnification: 400×. (FIG. 26C) In the denser areas, there were small hyperchromatic cells resembling benign melanocytic nevus cells. However, giant malignant cells were scattered throughout. Magnification: 400×. (FIG. 26D) Very marked variability in the giant cell nuclei, a characteristic feature of malignant melanoma giant cells. Magnification: 600×. (FIG. 26E) Bizarre nuclei in giant cells. Magnification: 600×.

(FIG. 27A) Multiple nodules of melanoma were present on both sides of the skeletal muscle in the subcutaneous tissue. Magnification: 40×. (FIG. 27B) Zones of spindle cells admixed with epithelioid cells was seen, characteristic of the architecture of melanoma nodules. There was scattered pigmentation, mainly in some of the smaller epithelioid and nevoid cells. Magnification: 200×. (FIG. 27C) A central nest of epithelioid cells highlighted the contrast with the adjacent spindle cells. Magnification: 200×. (FIG. 27D) Striking nuclear pleomorphism associated with vacuolization of the cell cytoplasm. Magnification: 600×.

FIG. 28A-28N—CDKN2A, $BRAF^{V600E}$, $TERT^{-124C>T}$, PTEN, and APC mutations together produce aggressive melanocytic disease. (FIG. 28A, 28B) Knockout of either TP53 ('3') or APC ('A')_in CBTP cells. Shown are the allele frequencies of each mutation (y axis) engineered into CBTP cells over time (x axis), as assessed by indels in the respective loci in genomic DNA (Rimm et al. *Am J Pathol* 154:325-329 (1999) (FIG. 28C, 28D) Each gene knockout has the expected effect on the downstream molecular pathways (p53 and Wnt). Immunoblot (FIG. 28C) or relative RT-qPCR analysis (FIG. 28D) of CBTP, CBTP3, and CBTPA cells, as indicated. Data are representative of at least two or three independent experiments for immunoblotting and RT-qPCR, respectively (Error bars: SD). (FIG. 28E-28J) Primary tumor growth of CBTP3 or CBTPA cells in NSG mice. (FIG. 28E-28F) Tumor size ($mm^3$, y axis) over time (x axis) following two intradermal injections, one in each flank. Control: CBTP cells that received non-targeting Cas9 RNP. (#one mouse was euthanized due to primary tumor ulceration). (FIG. 28G, 28H) Representative images of (shaved) mice harboring mutant cells as marked. (FIG. 28I, 28J) Representative micrographs of H&E stained primary tumor tissue sections. Insets are at two-fold magnification. (FIG. 28M) Injected CBTPA melanocytes cause rapid weight loss in mice. Shown is the change in mouse weight (y axis, determined after subtracting primary tumor weights (estimated at 1 g/$cm^3$) from measured mouse weights). Data shown are from the four independent experiments in FIGS. 21G, 21I, 28E, and 28F. (# on line: one mouse euthanized due to primary tumor ulceration. # on orange line: two mice sacrificed for histological inspection.) (FIG. 28N) Summary of phenotypic observations across generated human melanocyte genotypes. *p<0.01, NS not significant, two-tailed, two-sample Student's t-test.

(FIG. 29A) Mouse lungs with gross metastases. (FIG. 29B) Small intestine (top left), stomach (bottom left), and subcutaneous tissue (top and bottom right) with gross metastases in two mice.

(FIG. 30A) Prominent melanoma nodule distorted completely the subcutaneous fat and displaced the skeletal muscle fibers. Magnification: 20×. (FIG. 30B) The nodule was composed of spindle cells with a neuroidal appearance. Magnification: 200×. (FIG. 30C) In other areas, there was a population of malignant epithelioid cells. Notable were the nucleoli and the striking variability of nuclear sizes, all signs of malignancy. Magnification: 600×. (FIG. 30D) Mitotic activity was noted. Magnification: 600×. (FIG. 30E) Spindle cells varied in the cytoplasmic masses, from very thin small dendrite-like shapes to very ample granular cytoplasm, a feature of malignant transformation. Magnification: 600×.

(FIG. 31A) Two expansile nodules of malignant melanoma were present. One extended from the dermis into the subcutis and the other was present in the subcutis surrounded by fibrous tissue. The larger nodule spanned the skeletal muscle disrupting its architecture. Scattered pigmentation is present in the larger nodule. Magnification: 40×. (FIG. 31B) The malignant melanocytes infiltrated through the skeletal muscle and were composed predominantly of epithelioid cells with rare giant cells. Scattered pigment was present in the tumor cells and in melanophages. Note the mitotic activity and the marked nuclear pleomorphism. Magnification: 600×.

(FIG. 32A) This extensive melanoma extended from the epidermis into the deep subcutis entrapping skeletal muscle. Notable were two distinct areas, one heavily diffusely pigmented, the other focally pigmented. Magnification: 20×. (FIG. 32B) Large zones of alternating heavily pigmented and less pigmented tumor cells. Magnification: 200×. (FIG. 32C) Prominent nests with nucleoli and large malignant nuclei surrounded by other heavily pigmented cells. Magnification: 600×. (FIG. 32D) Even areas of less pigmentation exhibited nests of melanoma cells outlined by surrounding pigmented cells. Magnification: 600×.

(FIG. 34A) A large malignant melanoma nodule occupied virtually the entire subcutaneous tissue and was associated with zones of central necrosis. Magnification: 20×. (FIG. 34B) There was extensive central zonal necrosis of the tumor. Magnification: 100×. (FIG. 34C) Malignant melanoma cell nuclei exhibited large nucleoli, often multiple, associated with giant malignant epithelioid melanoma cells. Magnification: 600×. (FIG. 34D) Numerous mitoses in different phases were evident in these melanoma cells. Magnification: 600×.

(FIG. 35A) Striking replacement of the entire dermis was noted in this large multinodular melanoma that also demonstrated extensive foci of necrosis. Magnification: 20×. (FIG. 35B) Viable nodules of melanoma cells highlighted zones of necrosis. Magnification: 100×. (FIG. 35C) The tumor extended to the basal layer of the epidermis and focally encroached on the spinous layer. Multiple mitoses and malignant melanocytes with prominent nucleoli were features of an aggressive malignant melanoma. Magnification: 400×. (FIG. 35D) Numerous mitoses surrounded some areas of zonal necrosis. Note large nucleoli and vacuolated ample cytoplasm. Magnification: 600×.

DETAILED DESCRIPTION OF THE EXAMPLE EMBODIMENTS

General Definitions

Figure 1:
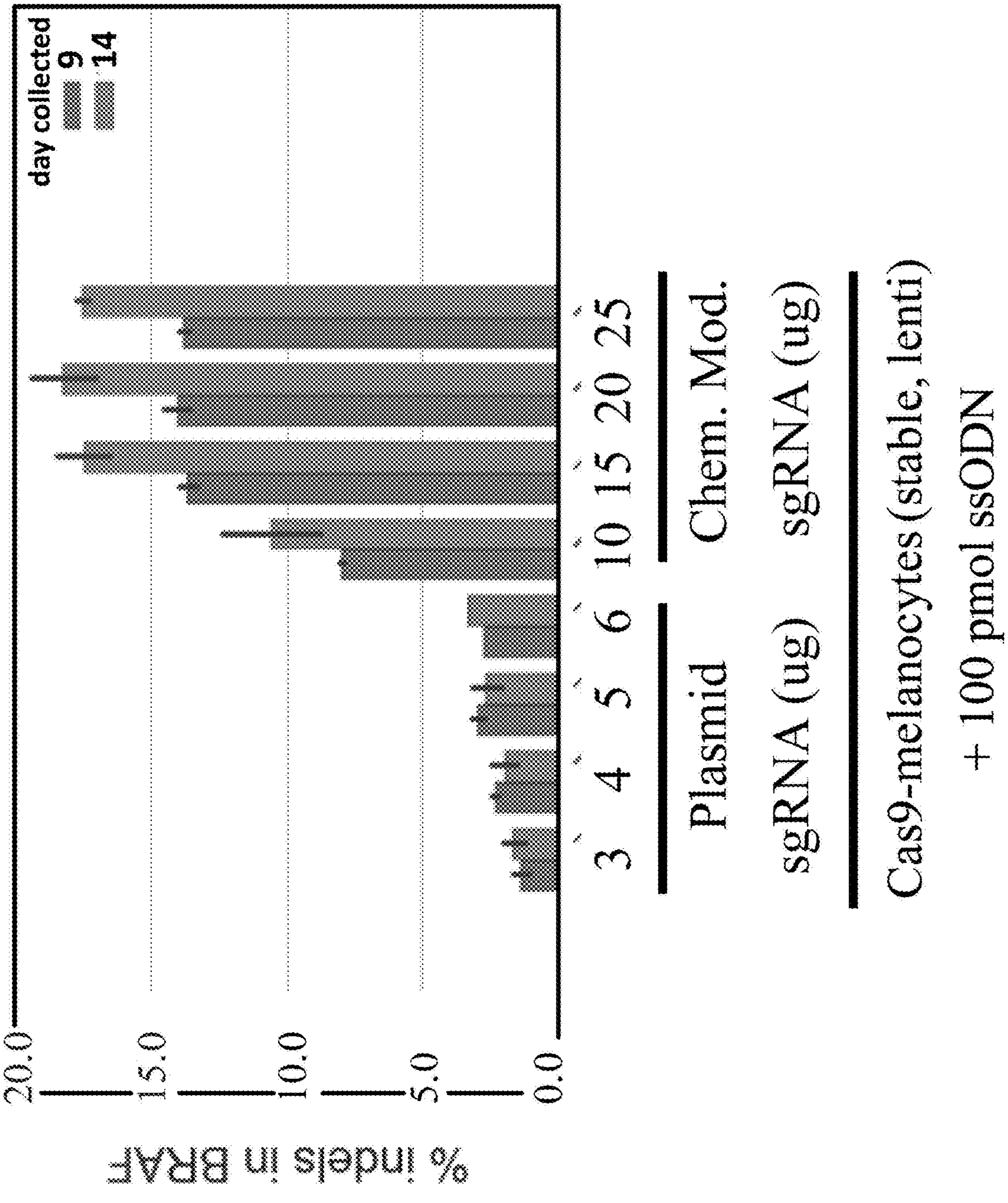
FIG. 1 illustrates introducing indels into Cas9 expressing melanocytes (Mel-Cas9) using sgRNAs expressed from a plasmid or chemically modified sgRNA.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other, features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide models of cancer development for use in target identification, drug screening, and determining early event mutations. Cancer models may be generated and have advantages over other methods. For example, cell lines grown directly from patient tumors may be from real tumors, however these cells have complex genetics, there is no ability to design and is an in vitro model. In another example, mouse tumors arising in laboratory mice provide real mouse melanomas with a syngeneic mouse line with an immune system, however, there is no ability to control the genetics, mouse cells are different than human cells, and there are few models. In another example, genetically-engineered mouse tumors arising in laboratory mice can provide an inducible model with proper tissue environment and immune system. Genetically-engineered mouse tumors arising in laboratory mice can also provide control over the genetics and they have a syngeneic mouse line. However, mouse cells are different than human cells and building models takes a long time, especially if combining multiple gene mutations. In another example, overexpression-/shRNA-based human tumor models provide for human cells, and the ability to introduce combinations of genes. However, overexpression-/shRNA-based gene perturbations do not accurately mimic the mutations that occur in patient tumors, multiple viral integrations into the genome can cause undesired/unknown mutations and is an in vitro model.

Applicants have generated for the first time a knock-in, human tumor model of melanoma. The model provides for human cells, the mutations mimic those seen in patient melanomas, and different combinations of gene mutations can be introduced. The model is obtained using normal human cells, directly from people and unaltered (e.g., primary cells). Furthermore, the approach allows for the mutations introduced to naturally take over about 100% of the cell population, without resorting to sub cloning. Additionally, the model provides for phenotypic changes that emerge as additional mutations are added to the cells (e.g. at 3 mutations the cells become immortal, at 4 mutations they can form small tumors in mouse skin, at 5 mutations they form large, rapidly growing tumors in mouse skin). In certain example embodiments, the methods allow for introducing at least five mutations in sequence.

Primary Cells

In certain embodiments, a cancer model is generated by introducing mutations to primary cells in vitro and incubating (either in vitro or in vivo) until the mutation is positively selected. As used herein, the term "primary cell" refers to cells dissociated from the parental tissue using mechanical or enzymatic methods and that are cultured directly from a subject. Primary cells for use in the present invention may be obtained and cultured from fresh tissue (see e.g., Freshney, R. (1987) Culture of Animal Cells: A Manual of Basic Technique, p. 117, Alan R. Liss, Inc., New York; and Freshney, R. Culture of Animal Cells: A Manual of Basic Technique, 6th Ed. John Wiley & Sons, Hoboken, New Jersey, 2010) and may also be purchased from commercial sources (e.g., American Type Culture Collection (ATCC), Manassas, VA; and Lonza, Walkersville, MD). Primary cells may include, but are not limited to, chondrocytes, endothelial cells, epithelial cells, fibroblasts, hematopoietic and immune cells, hepatocytes, neural cells, osteoblasts, pancreatic islets, progenitor cells, skeletal cells and smooth muscle cells. Epithelial cells may include bronchial epithelial cells (NHBE), small-airway epithelial cells (SAEC), gastrointestinal cells (InEpC), keratinocytes, mammary epithelial cells, melanocytes, prostate cells, renal cells and retinal cells. Endothelial cells may include cardiac endothelial cells, aortic endothelial (HAEC), coronary, iliac artery (HCAEC, HIAEC), umbilical vein (HUVEC), cardiac microvascular (HMVEC-C), bladder, uterine microvascular, dermal microvascular (HMVEC-D), lung microvascular (HMVEC-L) and pulmonary artery (HPAEC, PASMC). Methods for culturing primary Pancreatic Islets (or Islets of Langerhans) have been described (Daoud et al., Cell Transplant. 2010; 19(12):1523-35; Kerr-Conte et al., Transplantation. 2010 May 15; 89(9):1154-60; and Murdoch et al., Transplant. 2004; 13(6):605-17).

Mutations

In certain embodiments, a cancer model is generated by introducing cancer mutations to primary cells. As used herein, the term "mutation" refers to a modification to an endogenous genome locus. Hence, the endogenous target genomic locus (e.g., gene, regulatory sequence, non-coding RNA) may be modified or "mutated". Any types of mutations achieving the intended effects are contemplated herein (e.g., inactivation, activation). For example, suitable mutations may include deletions, insertions, substitutions, amplifications, frameshift mutations, germline mutations, missense mutations, nonsense mutations, somatic mutations, splicing mutations and/or translocations. The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the open reading frame (ORF) encoding the target protein. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon are apparent to a skilled person. For example, but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF encoding the target protein. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift are apparent to a skilled person. For example, but without limitation, a suitable insertion or deletion of one or more (not multiple of 3) nucleotides in the ORF may lead to a frame shift.

In further embodiments, a mutation may delete at least a portion of the ORF encoding the target protein. Such deletion may lead to production of an N-terminally truncated form, a C-terminally truncated form and/or an internally deleted form of said polypeptide (this may preferably affect, such as diminish or abolish, some or all biological function (s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In further embodiments, a mutation may delete at least a portion of the promoter of the target gene, leading to impaired transcription of the target gene.

In certain other embodiments, a mutation may be a substitution of one or more nucleotides in the ORF encoding the target protein, resulting in substitution of one or more amino acids of the target protein. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding the target protein. In the absence of native splicing, the pre-mRNA may be degraded, or the pre-mRNA may be alternatively spliced, or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing. The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions +2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2.

Typically, mutations which abolish the expression of a target gene or gene product, e.g., by deleting at least a portion of the ORF or the entire ORF, may be referred to as "knock-out" (KO) mutations.

In certain other embodiments, a mutation may introduce an insertion, deletion, substitution that leads to an activated protein (i.e., activating mutation). In certain embodiments, a regulatory region of a protein is eliminated by mutation. In certain embodiments, a protein is activated by a mutation that results in substitution of an amino acid in the protein sequence (e.g., missense mutation).

Cancer Mutations

In certain embodiments, the present invention may be used to model any type of cancer. In certain embodiments, cancer specific mutations may be introduced to a population of cells and positively selected. As used herein, the term "positive selection" refers to the process by which new advantageous genetic variants take over a population. The mutations may be introduced step wise as single mutations in order to study cancer development (e.g., first, second, third event mutations). More than one mutation may be introduced in parallel and positively selected (e.g., two, three, four mutations in a single step of introducing and positively selecting).

Mutations associated across the spectrum of human cancer types have been identified (e.g., Hodis E. et al., Cell. (2012) July 20; 150(2):251-63; and Vogelstein, et al., Science (2013) March 29: Vol. 339, Issue 6127, pp. 1546-1558)

(Tables 1-6; adapted from Vogelstein, 2013). A directory of cancer mutations, including gene specific mutations may be found at cancer.sanger.ac.uk/cosmic, the Catalogue of Somatic Mutations in Cancer (COSMIC) (Forbes, et al.; COSMIC: somatic cancer genetics at high-resolution. Nucleic Acids Res 2017; 45 (D1): D777-D783. doi: 10.1093/nar/gkwll21) and world wide web.mycancergenome.org. In certain embodiments, any of these known mutations may be introduced to a population of cells and positively selected for. In preferred embodiments, mutations are introduced to the cell of origin associated with a specific cancer type.

TABLE 1

Driver genes affected by subtle mutations

| Gene Symbol | Gene Name | # Mutated Tumor Samples** | Ocogene score* | Tumor Suppressor Gene score* | Classification* | Core pathway | Process |
|---|---|---|---|---|---|---|---|
| ABL1 | c-abl oncogene 1, receptor tyrosine kinase | 851 | 93% | 0% | Oncogene | Cell Cycle/ Apoptosis | Cell Survival |
| ACVR1B | activin A receptor, type IB | 17 | 0% | 42% | Tumor suppressor gene (TSG) | TGF-b | Cell Survival |
| AKT1 | v-akt murine thymoma viral oncogene homolog 1 | 155 | 93% | 1% | Oncogene | PI3K | Cell Survival |
| ALK | anaplastic lymphoma receptor tyrosine kinase | 189 | 72% | 1% | Oncogene | PI3K; RAS | Cell Survival |
| APC | adenomatous polyposis coli | 2561 | 2% | 92% | TSG | APC | Cell Fate |
| AR | androgen receptor | 23 | 54% | 0% | Oncogene | Transcriptional Regulation | Cell Fate |
| ARID1A | AT rich interactive domain 1A (SWI-like) | 234 | 1% | 83% | TSG | Chromatin Modification | Cell Fate |
| ARID1B | AT rich interactive domain 1B (SWI1-like) | 17 | 0% | 50% | TSG | Chromatin Modification | Cell Fate |
| ARID2 | AT rich interactive domain 2 (ARID, RFX-like) | 45 | 0% | 56% | TSG | Chromatin Modification | Cell Fate |
| ASXL1 | additional sex combs like 1 (*Drosophila*) | 442 | 5% | 87% | TSG | Chromatin Modification | Cell Fate |
| ATM | similar to Serine-protein kinase ATM (Ataxia telangiectasia mutated) (A-T, mutated); ataxia telangiectasia mutated | 242 | 24% | 30% | TSG | DNA Damage Control | Genome Maintenance |
| ATRX | alpha thalassemia/mental retardation syndrome X-linked (RAD54 homolog, *S. cerevisiae*) | 50 | 4% | 47% | TSG | Chromatin Modification | Cell Fate |
| AXIN1 | axin 1 | 117 | 20% | 27% | TSG | APC | Cell Fate |
| B2M | beta-2-microglobulin | 30 | 18% | 39% | TSG | PI3K; RAS; MAPK | Cell Survival |
| BAP1 | BRCA1 associated protein-1 (ubiquitin carboxy-terminal hydrolase) | 99 | 8% | 70% | TSG | DNA Damage Control | Genome Maintenance |
| BCL2 | B-cell CLL/lymphoma 2 | 45 | 27% | 1% | Oncogene | Cell Cycle/ Apoptosis | Cell Survival |
| BCOR | BCL6 co-repressor | 21 | 0% | 70% | TSG | Transcriptional Regulation | Cell Fate |
| BRAF | v-raf murine sarcoma viral oncogene homolog B1 | 24288 | 100% | 0% | Oncogene | RAS | Cell Survival |
| BRCA1 | breast cancer 1, early onset | 62 | 0% | 69% | TSG | DNA Damage Control | Genome Maintenance |
| BRCA2 | breast cancer 2, early onset | 67 | 0% | 30% | TSG | DNA Damage Control | Genome Maintenance |

TABLE 1-continued

Driver genes affected by subtle mutations

| Gene Symbol | Gene Name | # Mutated Tumor Samples** | Ocogene score* | Tumor Suppressor Gene score* | Classification* | Core pathway | Process |
|---|---|---|---|---|---|---|---|
| CARD11 | caspase recruitment domain family, member 11 | 74 | 30% | 1% | Oncogene | Cell Cycle/ Apoptosis | Cell Survival |
| CASP8 | caspase 8, apoptosis-related cysteine peptidase | 21 | 0% | 52% | TSG | Cell Cycle/ Apoptosis | Cell Survival |
| CBL | Cas-Br-M (murine) ecotropic retroviral transforming sequence | 168 | 57% | 9% | Oncogene | PI3K; RAS | Cell Survival |
| CDC73 | cell division cycle 73, Paf1/RNA polymerase II complex component, homolog (*S. cerevisiae*) | 45 | 4% | 78% | TSG | Cell Cycle/ Apoptosis | Cell Survival |
| CDH1 | cadherin 1, type 1, E-cadherin (epithelial) | 200 | 14% | 52% | TSG | APC | Cell Fate |
| CDKN2A | cyclin-dependent kinase inhibitor 2A (melanoma, p16, inhibits CDK4) | 968 | 32% | 49% | TSG | Cell Cycle/ Apoptosis | Cell Survival |
| CEBPA | CCAAT/enhancer binding protein (C/EBP), alpha | 448 | 30% | 54% | TSG | PI3K; RAS; MAPK | Cell Survival |
| CIC | capicua homolog (*Drosophila*) | 47 | 12% | 31% | TSG | RAS | Cell Survival |
| CREBBP | CREB binding protein | 151 | 24% | 34% | TSG | Chromatin Modification; Transcriptional Regulation | Cell Fate |
| CRLF2 | cytokine receptor-like factor 2 | 10 | 100% | 0% | Oncogene | STAT | Cell Survival |
| CSF1R | colony stimulating factor 1 receptor | 48 | 50% | 15% | Oncogene | PI3K; RAS | Cell Survival |
| CTNNB1 | catenin (cadherin-associated protein), beta 1, 88 kDa | 3262 | 92% | 1% | Oncogene | APC | Cell Fate |
| CYLD | cylindromatosis (turban tumor syndrome) | 26 | 0% | 85% | TSG | Cell Cycle/ Apoptosis | Cell Survival |
| DAXX | death-domain associated protein | 28 | 7% | 61% | TSG | Chromatin Modification; Cell Cycle/ Apoptosis | Cell Fate |
| DNMT1 | DNA (cytosine-5-)-methyltransferase 1 | 22 | 36% | 5% | Oncogene | Chromatin Modification | Cell Fate |
| DNMT3A | DNA (cytosine-5-)-methyltransferase 3 alpha | 788 | 74% | 12% | Oncogene | Chromatin Modification | Cell Fate |
| EGFR | epidermal growth factor receptor (erythroblastic leukemia viral (v-erb-b) oncogene homolog, avian) | 10628 | 97% | 0% | Oncogene | PI3K; RAS | Cell Survival |
| EP300 | E1A binding protein p300 | 88 | 12% | 32% | TSG | Chromatin Modification; APC; TGF-b; NOTCH | Cell Survival/ Fate |
| ERBB2 | v-erb-b2 erythroblastic leukemia viral oncogene homolog 2, neuro/ glioblastoma derived oncogene homolog (avian) | 164 | 67% | 3% | Oncogene | PI3K; RAS | Cell Survival |

TABLE 1-continued

Driver genes affected by subtle mutations

| Gene Symbol | Gene Name | # Mutated Tumor Samples** | Ocogene score* | Tumor Suppressor Gene score* | Classification* | Core pathway | Process |
|---|---|---|---|---|---|---|---|
| EZH2 | enhancer of zeste homolog 2 (*Drosophila*) | 276 | 67% | 12% | Oncogene | Chromatin Modification | Cell Fate |
| FAM123B | family with sequence similarity 123B | 55 | 4% | 66% | TSG | APC | Cell Fate |
| FBXW7 | F-box and WD repeat domain containing 7 | 312 | 55% | 18% | TSG | NOTCH | Cell Fate |
| FGFR2 | fibroblast growth factor receptor 2 | 121 | 49% | 6% | Oncogene | PI3K; RAS; STAT | Cell Survival |
| FGFR3 | fibroblast growth factor receptor 3 | 2948 | 99% | 0% | Oncogene | PI3K; RAS; STAT | Cell Survival |
| FLT3 | fms-related tyrosine kinase 3 | 11520 | 98% | 0% | Oncogene | RAS; PI3K; STAT | Cell Survival |
| FOXL2 | forkhead box L2 | 330 | 100% | 0% | Oncogene | TGF-b | Cell Fate |
| FUBP1 | far upstream element (FUSE) binding protein 1 | 9 | 0% | 70% | TSG | Cell Cycle/ Apoptosis | Cell Survival |
| GATA1 | GATA binding protein 1 (globin transcription factor 1) | 203 | 8% | 84% | TSG | NOTCH, TGF-b | Cell Fate |
| GATA2 | GATA binding protein 2 | 45 | 53% | 4% | Oncogene | NOTCH, TGF-b | Cell Fate |
| GATA3 | GATA binding protein 3 | 33 | 9% | 66% | TSG | Transcriptional Regulation | Cell Fate |
| GNA11 | guanine nucleotide binding protein (G protein), alpha 11 (Gq class) | 110 | 92% | 1% | Oncogene | PI3K; RAS; MAPK | Cell Survival |
| GNAQ | guanine nucleotide binding protein (G protein), q polypeptide | 245 | 95% | 1% | Oncogene | PI3K; RAS; MAPK | Cell Survival |
| GNAS | GNAS complex locus | 422 | 93% | 2% | Oncogene | APC; PI3K; TGF-b, RAS | Cell Survival/ Cell Fate |
| H3F3A | H3 histone, family 3B (H3.3B); H3 histone, family 3A pseudogene; H3 histone, family 3A; similar to H3 histone, family 3B; similar to histone H3.3B | 122 | 93% | 0% | Oncogene | Chromatin Modification | Cell Fate |
| HIST1H3B | histone cluster 1, H3j; histone cluster 1, H3i; histone cluster 1, H3h; histone cluster 1, H3g; histone cluster 1, H3f; histone cluster 1, H3e; histone cluster 1, H3d; histone cluster 1, H3c; histone cluster 1, H3b; histone cluster 1, H3a; histone cluster 1, H2ad; histone cluster 2, H3a; histone cluster 2, H3c; histone cluster 2, H3d | 25 | 60% | 0% | Oncogene | Chromatin Modification | Cell Fate |
| HNF1A | HNF1 homeobox A | 126 | 29% | 55% | TSG | APC | Cell Fate |
| HRAS | v-Ha-ras Harvey rat sarcoma viral oncogene homolog | 812 | 96% | 0% | Oncogene | RAS | Cell Survival |

TABLE 1-continued

| Driver genes affected by subtle mutations | | | | | | | |
|---|---|---|---|---|---|---|---|
| Gene Symbol | Gene Name | # Mutated Tumor Samples** | Ocogene score* | Tumor Suppressor Gene score* | Classification* | Core pathway | Process |
| IDH1 | isocitrate dehydrogenase 1 (NADP+), soluble | 4509 | 100% | 0% | Oncogene | Chromatin Modification | Cell Fate |
| IDH2 | isocitrate dehydrogenase 2 (NADP+), mitochondrial | 1029 | 99% | 0% | Oncogene | Chromatin Modification | Cell Fate |
| JAK1 | Janus kinase 1 | 61 | 26% | 18% | Oncogene | STAT | Cell Survival |
| JAK2 | Janus kinase 2 | 32692 | 100% | 0% | Oncogene | STAT | Cell Survival |
| JAK3 | Janus kinase 3 | 89 | 60% | 6% | Oncogene | STAT | Cell Survival |
| KDM5C | lysine (K)-specific demethylase 5C | 26 | 0% | 62% | TSG | Chromatin Modification | Cell Fate |
| KDM6A | lysine (K)-specific demethylase 6A | 66 | 0% | 72% | TSG | Chromatin Modification | Cell Fate |
| KIT | similar to Mast/stem cell growth factor receptor precursor (SCFR) (Proto-oncogene tyrosine-protein kinase Kit) (c-kit) (CD117 antigen); v-kit Hardy-Zuckerman 4 feline sarcoma viral oncogene homolog | 4720 | 90% | 0% | Oncogene | PI3K; RAS; STAT | Cell Survival |
| KLF4 | Kruppel-like factor 4 | 61 | 80% | 4% | Oncogene | Transcriptional Regulation; WNT | Cell Fate |
| KRAS | v-Ki-ras2 Kirsten rat sarcoma viral oncogene homolog | 23261 | 100% | 0% | Oncogene | RAS | Cell Survival |
| MAP2K1 | mitogen-activated protein kinase kinase 1 | 13 | 67% | 0% | Oncogene | RAS | Cell Survival |
| MAP3K1 | mitogen-activated protein kinase kinase kinase 1 | 11 | 0% | 63% | TSG | RAS; MAPK | Cell Survival |
| MED12 | mediator complex subunit 12 | 337 | 84% | 0% | Oncogene | Cell Cycle/Apoptosis; TGF-b | Cell Survival |
| MEN1 | multiple endocrine neoplasia I | 290 | 7% | 68% | TSG | Chromatin Modification | Cell Fate |
| MET | met proto-oncogene (hepatocyte growth factor receptor) | 159 | 61% | 4% | Oncogene | PI3K; RAS | Cell Survival |
| MLH1 | mutL homolog 1, colon cancer, nonpolyposis type 2 (*E. coli*) | 61 | 18% | 37% | TSG | DNA Damage Control | Genome Maintenance |
| MLL2 | myeloid/lymphoid or mixed-lineage leukemia 2 | 165 | 1% | 70% | TSG | Chromatin Modification | Cell Fate |
| MLL3 | myeloid/lymphoid or mixed-lineage leukemia 3 | 111 | 5% | 44% | TSG | Chromatin Modification | Cell Fate |
| MPL | myeloproliferative leukemia virus oncogene | 531 | 96% | 0% | Oncogene | STAT | Cell Survival |
| MSH2 | mutS homolog 2, colon cancer, nonpolyposis type 1 (*E. coli*) | 37 | 0% | 65% | TSG | DNA Damage Control | Genome Maintenance |
| MSH6 | mutS homolog 6 (*E. coli*) | 135 | 3% | 68% | TSG | DNA Damage Control | Genome Maintenance |
| MYD88 | myeloid differentiation primary response gene (88) | 134 | 92% | 1% | Oncogene | Cell Cycle/Apoptosis | Cell Survival |
| NCOR1 | nuclear receptor co-repressor 1 | 35 | 11% | 32% | TSG | Chromatin Modification | Cell Fate |
| NF1 | neurofibromin 1 | 362 | 2% | 73% | TSG | RAS | Cell Survival |
| NF2 | neurofibromin 2 (merlin) | 609 | 4% | 89% | TSG | APC | Cell Fate |

TABLE 1-continued

| Driver genes affected by subtle mutations | | | | | | | |
|---|---|---|---|---|---|---|---|
| Gene Symbol | Gene Name | # Mutated Tumor Samples** | Ocogene score* | Tumor Suppressor Gene score* | Classification* | Core pathway | Process |
| NFE2L2 | nuclear factor (erythroid-derived 2)-like 2 | 102 | 74% | 1% | Oncogene | Cell Cycle/ Apoptosis | Cell Survival |
| NOTCH1 | Notch homolog 1, translocation-associated (*Drosophila*) | 661 | 44% | 27% | TSG | NOTCH | Cell Fate |
| NOTCH2 | Notch homolog 2 (*Drosophila*) | 51 | 0% | 27% | TSG | NOTCH | Cell Fate |
| NPM1 | nucleophosmin 1 (nucleolar phosphoprotein B23, numatrin) pseudogene 21; hypothetical LOC100131044; similar to nucleophosmin 1; nucleophosmin (nucleolar phosphoprotein B23, numatrin) | 2471 | 2% | 98% | TSG | Cell Cycle/ Apoptosis | Cell Survival |
| NRAS | neuroblastoma RAS viral (v-ras) oncogene homolog | 2738 | 99% | 0% | Oncogene | RAS | Cell Survival |
| PAX5 | paired box 5 | 49 | 42% | 26% | TSG | Chromatin Modification | Cell Fate |
| PBRM1 | polybromo 1 | 171 | 0% | 83% | TSG | Chromatin Modification | Cell Fate |
| PDGFRA | platelet-derived growth factor receptor, alpha polypeptide | 653 | 84% | 1% | Oncogene | PI3K; RAS | Cell Survival |
| PHF6 | PHD finger protein 6 | 57 | 18% | 61% | TSG | Transcriptional Regulation | Cell Fate |
| PK3CA | phosphoinositide-3-kinase, catalytic, alpha polypeptide | 4560 | 95% | 1% | Oncogene | PI3K | Cell Survival |
| PIK3R1 | phosphoinositide-3-kinase, regulatory subunit 1 (alpha) | 88 | 14% | 37% | TSG | PI3K | Cell Survival |
| PPP2R1A | protein phosphatase 2 (formerly 2A), regulatory subunit A, alpha isoform | 86 | 85% | 2% | Oncogene | Cell Cycle/ Apoptosis | Cell Survival |
| PRDM1 | PR domain containing 1, with ZNF domain | 46 | 0% | 64% | TSG | Chromatin Modification | Cell Fate |
| PTCH1 | patched homolog 1 (*Drosophila*) | 318 | 7% | 60% | TSG | HH | Cell Fate |
| PTEN | phosphatase and tensin homolog; phosphatase and tensin homolog pseudogene 1 | 1719 | 30% | 55% | TSG | PI3K | Cell Survival |
| PTPN11 | protein tyrosine phosphatase, non-receptor type 11; similar to protein tyrosine phosphatase, non-receptor type 11 | 410 | 90% | 0% | Oncogene | RAS | Cell Survival |
| RB1 | retinoblastoma 1 | 208 | 4% | 80% | TSG | Cell Cycle/ Apoptosis | Cell Survival |
| RET | ret proto-oncogene | 500 | 86% | 1% | Oncogene | RAS; PI3K | Cell Survival |
| RNF43 | ring finger protein 43 | 27 | 7% | 43% | TSG | APC | Cell Fate |
| RUNX1 | runt-related transcription factor 1 | 304 | 34% | 41% | TSG | Transcriptional Regulation | Cell Fate |
| SETD2 | SET domain containing 2 | 47 | 3% | 47% | TSG | Chromatin Modification | Cell Fate |

TABLE 1-continued

| Driver genes affected by subtle mutations | | | | | | | | |
|---|---|---|---|---|---|---|---|---|
| Gene Symbol | Gene Name | # Mutated Tumor Samples** | Ocogene score* | Tumor Suppressor Gene score* | Classification* | Core pathway | Process |
| SETBP1 | SET binding protein 1 | 95 | 25% | 4% | Oncogene | Chromatin Modification; Replication | Cell Fate |
| SF3B1 | splicing factor 3b, subunit 1, 155 kDa | 516 | 91% | 0% | Oncogene | Transcriptional Regulation | Cell Fate |
| SMAD2 | SMAD family member 2 | 16 | 0% | 41% | TSG | TGF-b | Cell Survival |
| SMAD4 | SMAD family member 4 | 207 | 24% | 39% | TSG | TGF-b | Cell Survival |
| SMARCA4 | SWI/SNF related, matrix associated, actin dependent regulator of chromatin, subfamily a, member 4 | 68 | 22% | 22% | TSG | Chromatin Modification | Cell Fate |
| SMARCB1 | SWI/SNF related, matrix associated, actin dependent regulator of chromatin, subfamily b, member 1 | 247 | 16% | 74% | TSG | Chromatin Modification | Cell Fate |
| SMO | smoothened homolog (*Drosophila*) | 34 | 51% | 3% | Oncogene | HH | Cell Fate |
| SOCS1 | suppressor of cytokine signaling 1 | 41 | 15% | 46% | TSG | STAT | Cell Survival |
| SOX9 | SRY (sex determining region Y)-box9 | 9 | 0% | 70% | TSG | APC | Cell Survival |
| SPOP | speckle-type POZ protein | 35 | 66% | 3% | Oncogene | Chromatin Modification; HH | Cell Fate |
| SRSF2 | SRSF2 serine/ arginine-rich splicing factor 2 | 273 | 95% | 2% | Oncogene | Transcriptional Regulation | Cell Fate |
| STAG2 | stromal antigen 2 | 21 | 0% | 33% | TSG | DNA Damage Control | Genome Maintenance |
| STK11 | serine/threonine kinase 11 | 220 | 24% | 52% | TSG | mTOR | Cell Survival |
| TET2 | tet oncogene family member 2 | 864 | 14% | 70% | TSG | Chromatin Modification | Cell Fate |
| TNFAIP3 | tumor necrosis factor, alpha-induced protein 3 | 136 | 1% | 80% | TSG | Cell Cycle/ Apoptosis; MAPK | Cell Survival |
| TRAF7 | TNF receptor-associated factor 7 | 123 | 61% | 9% | TSG | Apoptosis | Cell Survival |
| TP53 | tumor protein p53 | 14438 | 73% | 20% | TSG | Cell Cycle/ Apoptosis; DNA Damage Control | Cell Survival |
| TSC1 | tuberous sclerosis 1 | 20 | 0% | 45% | TSG | PI3K | Cell SUrvival |
| TSHR | thyroid stimulating hormone receptor | 301 | 86% | 0% | Oncogene | PI3K; MAPK | Cell Survival |
| U2AF1 | U2 small nuclear RNA auxiliary factor 1 | 96 | 92% | 1% | Oncogene | Transcriptional Regulation | Cell Fate |

TABLE 1-continued

| Driver genes affected by subtle mutations | | | | | | | |
|---|---|---|---|---|---|---|---|
| Gene Symbol | Gene Name | # Mutated Tumor Samples** | Ocogene score* | Tumor Suppressor Gene score* | Classification* | Core pathway | Process |
| VHL | von Hippel-Lindau tumor suppressor | 1287 | 27% | 60% | TSG | PI3K; RAS; STAT | Cell Survival |
| WT1 | Wilms tumor 1 | 312 | 10% | 79% | TSG | Chromatin Modification | Cell Fate |

*Genes were classified as Oncogenes if they had an Oncogene Score >20% and classified as a Tumor Suppressor Gene (TSG) if the TSG Score was >20% (the 20/20 rule). The Oncogene Score was defined as the number of clustered mutations (i.e., missense mutations at the same amino acid or identical in-frame insertions or deletions) divided by the total number of mutations. The TSG Score was defined as the number of truncating mutations divided by the total number of mutations. Truncating mutations included nonsense mutations, insertions or deletions that alter the reading frame, splice-site mutations, or mutations at the normal stop codon predicted to result in a longer protein. When a gene had an oncogene score >20% and a TSG Score >5%, it was classified as a TSG because well-studied oncogenes rarely harbor stop codons. The major data source for this classification was the COSMIC database (www.sanger.ac.uk/genetics/CGP/cosmic/). To be classified as an oncogene, there had to be >10 clustered mutations in this database. To be classified as a tumor suppressor gene, there had had to be at least 7 inactivating mutations recorded in this database. In those cases in which 7 to 20 inactivating mutations were recorded in the COSMIC database, manual curation was performed. This curation was used to identify other examples of mutations not yet recorded in the COSMIC database and to exclude the most common artifacts encountered in next-generation sequencing, such as mapping errors and high mutation frequencies observed in normal tissues. Genes with mutations occurring predominantly in tumors with very high rates of mutation, such as in mismatch-repair deficient tumors or melanomas, were excluded. As more individual tumors are sequenced in the future, the 20/20 rule can be improved by (i) considering mutations only in particular tumor types, rather than in all tumor types combined (as done here); (ii) requiring a higher number (e.g., 15) of clustered or inactivating mutations as a threshold for inclusion; and (iii) for genes with thousands of recorded mutations, choose a random subset to calculate the Oncogene Score (if enough tumors are sequenced, all mutations will appear to be clustered)
**The number of samples with any subtle mutation (single base substitution, insertion or deletion <100 bp), in the COSMIC database.

TABLE 2

| Driver genes affected by amplification or homozygous deletion* | | | | | |
|---|---|---|---|---|---|
| Gene Symbol | Gene Name | Genetic alteration | Classification | Core pathway | Process |
| CCND1 | cyclin D1 | Amplification | Oncogene | Cell Cycle/ Apoptosis | Cell Survival |
| CDKN2C | cyclin-dependent kinase inhibitor 2C (p18, inhibits CDK4) | Homozygous deletion | TSG | Cell Cycle/ Apoptosis | Cell Survival |
| IKZF1 | IKAROS family zinc finger 1 (Ikaros) | Homozygous deletion | TSG | Transcriptional Regulation | Cell Fate |
| LMO1 | LIM domain only 1 (rhombotin 1) | Amplification | Oncogene | Transcriptional Regulation | Cell Fate |
| MAP2K4 | mitogen-activated protein kinase kinase 4 | Homozygous deletion | TSG | MAPK | Cell Survival |
| MDM2 | Mdm2 p53 binding protein homolog (mouse) | Amplification | Oncogene | Cell Cycle/ Apoptosis | Cell Survival |
| MDM4 | Mdm4 p53 binding protein homolog (mouse) | Amplification | Oncogene | Cell Cycle/ Apoptosis | Cell Survival |
| MYC | v-myc myelocytomatosis viral oncogene homolog (avian) | Amplification | Oncogene | Cell Cycle/ Apoptosis | Cell Survival |
| MYCL1 | v-myc myelocytomatosis viral oncogene homolog 1, lung carcinoma derived (avian) | Amplification | Oncogene | Cell Cycle/ Apoptosis | Cell Survival |
| MYCN | v-myc myelocytomatosis viral related oncogene, neuroblastoma derived (avian) | Amplification | Oncogene | Cell Cycle/ Apoptosis | Cell Survival |

TABLE 2-continued

Driver genes affected by amplification or homozygous deletion*

| Gene Symbol | Gene Name | Genetic alteration | Classification | Core pathway | Process |
|---|---|---|---|---|---|
| NCOA3 | nuclear receptor coactivator 3 | Amplification | Oncogene | Chromatin Modification | Cell Fate |
| NKX2-1 | NK2 homeobox 1 | Amplification | Oncogene | PI3K; MAPK | Cell Survival |
| SKP2 | S-phase kinase-associated protein 2 (p45) | Amplification | Oncogene | Cell Cycle/ Apoptosis | Cell Survival |

*A gene was classified as an Oncogene if it was included in the Cancer Gene Census (www.sanger.ac.uk/genetics/CGP/Census/) and met the criteria for a high confidence amplified gene (Class I or II) described in Santarius et al., *Nat Rev Cancer* 2010;10(1):59-64. A gene was classified as a TSG if had at least 10 documented homozygous deletions in the COSMIC database (http://www.sanger.ac.uk/genetics/CGP/cosmic/) and was not co-deleted with other genes that had at least 10 documented instances of homozygous deletion. The genes in this table exclude those that are amplified or deleted but are listed as driver genes affected by intragenic alterations (table S2A) or copy number changes (table S2B).

TABLE 3

Rearrangements in carcinomas

| Gene Fusion* | Gene 1 | Gene 2 | # Tumor samples** | # Tumor samples with fusion of Gene 1*** | # Tumor samples with fusion of Gene 2*** | Characteristic tumor type | Core pathway | Process |
|---|---|---|---|---|---|---|---|---|
| TMPRSS2:ERG | TMPRSS2 | ERG | 2601 | 2638 | 2825 | prostate | Transcriptional Regulation | Cell Fate |
| CRTC1:MAML2 | CRTC1 | MAML2 | 253 | 253 | 266 | salivary gland | NOTCH | Cell Fate |
| PAX8:PPARG | PAX8 | PPARG | 71 | 107 | 71 | thyroid | Transcriptional Regulation | Cell Fate |
| SLC45A3:ERG | SLC45A3 | ERG | 47 | 60 | 2825 | prostate | Transcriptional Regulation | Cell Fate |
| TPM3:NTRK1 | TPM3 | NTRK1 | 32 | 51 | 42 | colon | MAPK | Cell Survival |
| TMPRSS2:ETV1 | TMPRSS2 | ETV1 | 21 | 2638 | 34 | prostate | Transcriptional Regulation | Cell Fate |
| BRD4:C15orf55 | BRD4 | C15orf55 | 19 | 19 | 21 | midline organs**** | Cell Cycle/ Apoptosis | Cell Survival |
| CD74:ROS1 | CD74 | ROS1 | 15 | 15 | 35 | lung | PI3K; RAS | Cell Survival |
| CRTC3:MAML2 | CRTC3 | MAML2 | 13 | 13 | 266 | salivary gland | NOTCH | Cell Fate |
| MYB:NFIB | MYB | NFIB | 11 | 29 | 15 | salivary gland | Transcriptional Regulation | Cell Fate |
| PRCC:TFE3 | PRCC | TFE3 | 11 | 11 | 100 | kidney | TGF-b; APC | Cell Fate/ Cell Survival |
| FGFR1:PLAG1 | FGFR1 | PLAG1 | 10 | 11 | 42 | salivary gland | Transcriptio nal Regulation | Cell Fate |
| TMPRSS2:ETV4 | TMPRSS2 | ETV4 | 10 | 2638 | 17 | prostate | Transcriptional Regulation | Cell Fate |
| SLC45A3:ELK4 | SLC45A3 | ELK4 | 9 | 60 | 9 | prostate | MAPK | Cell Survival |
| HMGA2:WIF1 | HMGA2 | WIF1 | 7 | 95 | 7 | salivary gland | APC | Cell Fate |
| TPR:NTRK1 | TPR | NTRK1 | 7 | 7 | 42 | thyroid | MAPK | Cell Survival |
| PTPRK:RSPO3 | PTPRK | RSPO3 | 5 | 5 | 5 | large intestine | APC | Cell Fate |
| SLC34A2:ROS1 | SLC34A2 | ROS1 | 5 | 5 | 35 | lung | PI3K; RAS | Cell Survival |
| CHCHD7:PLAG1 | CHCHD7 | PLAG1 | 4 | 4 | 42 | salivary gland | Transcriptional Regulation | Cell Fate |
| LIFR:PLAG1 | LIFR | PLAG1 | 4 | 4 | 42 | salivary gland | Transcriptional Regulation | Cell Fate |
| TFE3:ASPSCR1 | TFE3 | ASPSCR1 | 4 | 100 | 78 | kidney | TGF-b; APC; PI3K | Cell Fate/ Cell Survival |
| VTI1A:TCF7L2 | VTI1A | TCF7L2 | 4 | 4 | 4 | large intestine | APC | Cell Fate |
| NDRG1:ERG | NDRG1 | ERG | 3 | 3 | 2825 | prostate | Transcriptional Regulation | Cell Fate |
| SDC4:ROS1 | SDC4 | ROS1 | 3 | 3 | 35 | lung | PI3K; RAS | Cell Survival |
| SFPQ:TFE3 | SFPQ | TFE3 | 3 | 3 | 100 | kidney | TGF-b; APC | Cell Fate/ Cell Survival |

*The rearranged genes exclude driver genes affected by intragenic alterations or copy number changes.

**The number of samples with the indicated gene fusion, as determined from the data in the COSMIC database (www.sanger.ac.uk/genetics/CGP/cosmic/).

***One of the two genes involved in a translocation is often fused to other genes (in addition to the fusion partner indicated). These columns provide information about the number of tumors which contain rearrangements in either of the two fused genes indicated in the columns on the left. This number is always at least as high as the # of tumor samples harboring the indicated gene fusion.

****examples of midline organs: nasal cavity, paranasal sinuses, mediastinum, or intrathoracic organs

TABLE 4

Rearrangements in Mesenchymal Tumors

| Gene Fusion* | Gene 1 | Gene 2 | # Tumor samples** | # Tumor samples with fusion of Gene 1*** | # Tumor samples with fusion of Gene 2*** | Characteristic tumor type | Core pathway | Process |
|---|---|---|---|---|---|---|---|---|
| EWSR1:FLI1 | EWSR1 | FLI1 | 1332 | 1920 | 1332 | Ewings sarcoma | TGF-b; HH; Transcriptional Regulation | Cell Fate/Cell Survival |
| SS18:SSX1 | SS18 | SSX1 | 589 | 951 | 590 | synovia sarcoma | Transcriptional Regulation | Cell Fate |
| PAX3:FOXO1 | PAX3 | FOXO1 | 380 | 386 | 479 | rhabdomyosarcoma | PI3K | Cell Survival |
| FUS:DDIT3 | FUS | DDIT3 | 351 | 611 | 377 | liposarcoma | PI3K; RAS; MAPK | Cell Survival |
| SS18:SSX2 | SS18 | SSX2 | 348 | 951 | 348 | synovial sarcoma | Transcriptional Regulation | Cell Fate |
| COL1A1:PDGFB | COL1A1 | PDGFB | 255 | 255 | 255 | dermatofibrosarcoma protuberans | PI3K; RAS; STAT | Cell Survival |
| EWSR1:ATF1 | EWSR1 | ATF1 | 150 | 1920 | 152 | melanoma | MAPK; Transcriptional Regulation | Cell Fate/Cell Survival |
| EWSR1:ERG | EWSR1 | ERG | 122 | 1920 | 2825 | Ewing's sarcoma | Transcriptional Regulation | Cell Fate |
| ETV6:NTRK3 | ETV6 | NTRK3 | 121 | 126 | 121 | congenital (infantile) fibrosarcoma | MAPK | Cell Survival |
| PAX7:FOXO1 | PAX7 | FOXO1 | 99 | 99 | 479 | rhabdomyosarcoma | PI3K | Cell Survival |
| FUS:CREB3L2 | FUS | CREB3L2 | 97 | 611 | 99 | fibrosarcoma | PI3K; RAS; MAPK | Cell Survival |
| EWSR1:NR4A3 | EWSR1 | NR4A3 | 86 | 1920 | 104 | chondrosarcoma | Transcriptional Regulation | Cell Fate |
| ASPSCR1:TFE3 | ASPSCR1 | TFE3 | 74 | 78 | 100 | alveolar soft part sarcoma | TGF-b; APC | Cell Fate/Cell Survival |
| JAZF1:SUZ12 | JAZF1 | SUZ12 | 71 | 71 | 72 | endometrial stromal sarcoma | Transcriptional Regulation | Cell Fate |
| HMGA2:LPP | HMGA2 | LPP | 70 | 95 | 73 | lipoma | Cell Cycle/ Apoptosis | Cell Survival |
| FUS:ERG | FUS | ERG | 52 | 611 | 2825 | Askins tumor | Transcriptional Regulation | Cell Fate |
| FUS:FUS | FUS | FUS | 49 | 611 | 611 | liposarcoma | Transcriptional Regulation | Cell Fate |
| EWSR1:CREB1 | EWSR1 | CREB1 | 28 | 1920 | 28 | melanoma | PI3K; RAS; MAPK | Cell Survival |
| EWSR1:DDIT3 | EWSR1 | DDIT3 | 26 | 1920 | 377 | liposarcoma | PI3K; RAS; MAPK | Cell Survival |
| TAF15:NR4A3 | TAF15 | NR4A3 | 16 | 16 | 104 | chondrosarcoma | Transcriptional Regulation | Cell Fate |
| YWHAE:FAM22B | YWHAE | FAM22B | 13 | 15 | 13 | endometrial stromal sarcoma | PI3K; MAPK | Cell Survival |
| EWSR1:FEV | EWSR1 | FEV | 6 | 1920 | 7 | Ewings sarcoma | Transcriptional Regulation | Cell Fate |
| SS18:SSX4 | SS18 | SSX4 | 6 | 951 | 6 | synovial sarcoma | Transcriptional Regulation | Cell Fate |
| EWSR1:POU5F1 | EWSR1 | POU5F1 | 5 | 1920 | 5 | sarcoma | Transcriptional Regulation | Cell Fate |
| HEY1:NCOA2 | HEY1 | NCOA2 | 5 | 5 | 7 | chondrosarcoma | Transcriptional Regulation | Cell Fate |
| EWSR1:ETV1 | EWSR1 | ETV1 | 4 | 1920 | 34 | Ewings sarcoma | Transcriptional Regulation | Cell Fate |
| EWSR1:NFATC2 | EWSR1 | NFATC2 | 4 | 1920 | 4 | Ewings sarcoma | Transcriptional Regulation | Cell Fate |
| FUS:CREB3L1 | FUS | CREB3L1 | 4 | 611 | 4 | fibrosarcoma | PI3K; RAS; MAPK | Cell Survival |
| GOPC:ROS1 | GOPC | ROS1 | 7 | 7 | 35 | glioma | PI3K; RAS | Cell Survival |
| HAS2:PLAG1 | HAS2 | PLAG1 | 4 | 4 | 42 | lipoblastoma | Transcriptional Regulation | Cell Fate |
| HMGA2:NFIB | HMGA2 | NFIB | 4 | 95 | 15 | lipoma | Cell Cycle/ Apoptosis | Cell Survival |
| PAX3:NCOA1 | PAX3 | NCOA1 | 4 | 386 | 4 | rhabdomyosarcoma | Transcriptional Regulation | Cell Fate |
| SRGAP3:RAF1 | SRGAP3 | RAF1 | 4 | 6 | 6 | glioma | RAS | Cell Survival |

TABLE 4-continued

| Rearrangements in Mesenchymal Tumors | | | | | | | | |
|---|---|---|---|---|---|---|---|---|
| Gene Fusion* | Gene 1 | Gene 2 | # Tumor samples** | # Tumor samples with fusion of Gene 1*** | # Tumor samples with fusion of Gene 2*** | Characteristic tumor type | Core pathway | Process |
| SS18:SS18 | SS18 | SS18 | 4 | 951 | 951 | synovial sarcoma | Transcriptional Regulation | Cell Fate |
| EWSR1:ETV4 | EWSR1 | ETV4 | 3 | 1920 | 17 | Ewings sarcoma | Transcriptional Regulation | Cell Fate |
| HMGA2:RAD51L1 | HMGA2 | RAD51L1 | 3 | 95 | 5 | leiomyoma | Cell Cycle/ Apoptosis | Cell Survival |
| NAB2:STAT6 | NAB2 | STAT6 | 58 | 0**** | 0**** | solitary fibrous tumors | STAT | Cell Survival |
| LPP:HMGA2 | LPP | HMGA2 | 3 | 73 | 9 | lipoma | Cell Cycle/ Apoptosis | Cell Survival |

*The rearranged genes exclude those wherein one of the two genes is a driver gene affected by subtle sequence alterations, amplifications, or homozygous deletions.
**The number of samples with the indicated gene fusion, as determined from the data in the COSMIC database (www.sanger.ac.uk/genetics/CGP/cosmic/).
***One of the two genes involved in a translocation is often fused to other genes (in addition to the fusion partner indicated). These columns provide information about the number of tumors which contain rearrangements in either of the two fused genes indicated in the columns on the left. This number is always at least as high as the number of tumor samples harboring the indicated gene fusion.
****not in COSMIC

TABLE 5

| Rearrangements in liquid tumors* | | |
|---|---|---|
| Gene | Fusion gene partner(s) | Characteristic tumor type |
| ABL2 | ETV6 | AML |
| AF15Q14 | MLL | AML |
| AF1Q | MLL | ALL |
| AF3p21 | MLL | ALL |
| AF5q31 | MLL | ALL |
| ARHGEF12 | MLL | AML |
| ARHH | BCL6 | NHL |
| ARNT | ETV6 | AML |
| BCL10 | Ig loci | MALT |
| BCL11A | Ig loci | B-CLL |
| BCL11B | TLX3 | T-ALL |
| BCL3 | IG loci | CLL |
| BCL6 | IG loci, ZNFN1A1, LCP1, PIM1, TFRC, CIITA, NACA, HSPCB, HSPCA, HIST1H4I, IL21R, POU2AF1, ARHH, EIF4A2, SFRS3 | NHL, CLL |
| BCL9 | IG loci | B-ALL |
| BCR | FGFR1 | CML, ALL, AML |
| BIRC3 | MALT1 | MALT |
| C16orf75 | CIITA | PMBL, Hodgkin's Lymphoma |
| CBFA2T1 | MLL | AML |
| CBFB | MYH11 | AML |
| CCND2 | Ig loci | NHL,CLL |
| CCND3 | Ig loci | MM |
| CD273 | CIITA | PMBL, Hodgkin's Lymphoma |
| CD274 | CIITA | PMBL, Hodgkin's Lymphoma |
| CDK6 | MLLT10 | ALL |
| CDX2 | ETV6 | AML |
| CEP1 | FGFR1 | MPD, NHL |
| CHIC2 | ETV6 | AML |
| CIITA | FLJ27352, CD274, CD273, RALGDS, RUNDC2A, C16orf75, BCL6 | PMBL, Hodgkin's Lymphoma |
| CLTC | ALK, TFE3 | ALCL, renal |
| DDX10 | NUP98 | AML^ |
| DDX6 | Ig loci | B-NHL |
| DEK | NUP214 | AML |
| EIF4A2 | BCL6 | NHL |
| ELF4 | ERG | AML |
| ELL | MLL | AL |
| ELN | PAX5 | B-ALL |
| EPS15 | MLL | ALL |
| EVI1 | ETV6, PRDM16, RPN1 | AML, CML |

TABLE 5-continued

| Rearrangements in liquid tumors* | | |
|---|---|---|
| Gene | Fusion gene partner(s) | Characteristic tumor type |
| FACL6 | ETV6 | AML, AEL |
| FGFR1 | BCR, FOP, ZNF198, CEP1 | MPD, NHL |
| FGFR1OP | FGFR1 | MPD, NHL |
| FIP1L1 | PDGFRA | idiopathic hypereosinophilic syndrome |
| FLJ27352 | CIITA | PMBL, Hodgkin's Lymphoma |
| FNBP1 | MLL | AML |
| FOX03A | MLL | AL |
| FOXP1 | PAX5 | ALL |
| FSTL3 | CCND1 | B-CLL |
| FVT1 | Ig loci | B-NHL |
| GAS7 | MLL | AML^ |
| GMPS | MLL | AML |
| GPHN | MLL | AL |
| GRAF | MLL | AML, MDS |
| HCMOGT-1 | PDGFRB | JMML |
| HEAB | MLL | AML |
| HIP1 | PDGFRB | CMML |
| HIST1H4I | BCL6 | NHL |
| HLF | TCF3 | ALL |
| HLXB9 | ETV6 | AML |
| HOXA11 | NUP98 | CML |
| HOXA13 | NUP98 | AML |
| HOXA9 | NUP98, MSI2 | AML^ |
| HOXC11 | NUP98 | AML |
| HOXC13 | NUP98 | AML^ |
| HOXD11 | NUP98 | AML |
| HOXD13 | NUP98 | AML^ |
| HSPCA | BCL6 | NHL |
| HSPCB | BCL6 | NHL |
| Ig loci | FGFR3,PAX5, IRTA1, IRF4, CCND1, CCND2, BCL9, BCL8, BCL6, BCL2, BCL3, BCL9, BCL10, BCL11A. LHX4, DDX6, NFKB2, PAFAH1B2, PCSK, FVT!, | MM, Burkitt lymphoma, NHL, CLL, B-ALL, MALT, MLCLS |
| IL2 | TNFRSF17 | intestinal T-cell lymphoma |
| IL21R | BCL6 | NHL |
| IRF4 | Ig loci | MM |
| IRTA1 | Ig loci | B-NHL |
| ITK | SYK | peripheral T-cell lymphoma |
| KDM5A | NUP98 | AML |
| LAF4 | MLL | ALL, T-ALL |

TABLE 5-continued

| Rearrangements in liquid tumors* | | |
|---|---|---|
| Gene | Fusion gene partner(s) | Characteristic tumor type |
| LASP1 | MLL | AML |
| LCK | TCR loci | T-ALL |
| LCP1 | BCL6 | NHL |
| LCX | MLL | AML |
| LMO2 | TCR loci | T-ALL |
| LYL1 | TCR loci | T-ALL |
| MAF | Ig loci | MM |
| MAFB | Ig loci | MM |
| MALT1 | BIRC3 | MALT |
| MDS2 | ETV6 | MDS |
| MKL1 | RBM15 | acute mega-karyocytic leukemia |
| MLL | MLL, MLLT 1, MLLT2, MLLT3, MLLT4, MLLT7, MLLT10, MLLT6, ELL, EPS15, AF1Q, CREBBP, SH3GL1 , FNBP1 , PNUTL1, MSF, GPHN, GMPS, SSH3BP1, ARHGEF12, GAS7, FOXO3A, LAF4, LCX, SEPT6, LPP, CBFA2T1, GRAF, EP300, PICALM, HEAB | AML, ALL |
| MLLT1 | MLL | AL |
| MLLT10 | MLL, PICALM, CDK6 | AL |
| MLLT2 | MLL | AL |
| MLLT3 | MLL | ALL |
| MLLT4 | MLL | AL |
| MLLT6 | MLL | AL |
| MLLT7 | MLL | AL |
| MSF | MLL | AML^ |
| MSI2 | HOXA9 | CML |
| MTCP1 | TCR loci | T cell prolymph-ocytic leukemia |
| MUC1 | Ig loci | B-NHL |
| MYH11 | CBFB | AML |
| MYST4 | CREBBP | AML |
| NACA | BCL6 | NHL |
| NCOA2 | RUNXBP2, HEY1 | AML, Chondro-sarcoma |
| NFKB2 | Ig loci | B-NHL |
| NIN | PDGFRB | MPD |
| NSD1 | NUP98 | AML |
| NUMA1 | RARA | APL |
| NUP214 | DEK, SET | AML, T-ALL |
| NUP98 | HOXA9, NSD1, WHSC1L1, DDX10, TOP1, HOXD13, PMX1, HOXA13, HOXD11, HOXA11, RAP1GDS1, HOXC11 | AML |
| OLIG2 | TCR loci | T-ALL |
| P2RY8 | CRLF2 | B-ALL, Downs associated ALL |
| PAFAH1B2 | Ig loci | MLCLS |
| PCSK7 | Ig loci | MLCLS |
| PDE4DIP | PDGFRB | MPD |
| PDGFRB | ETV6, TRIP11, HIP1, RABSEP, H4, NIN, HCMOGT-1, PDE4DIP | MPD, AML, CMML, CML |
| PER1 | ETV6 | AML, CMML |
| PICALM | MLLT10, MLL | TALL, AML, |
| PIM1 | BCL6 | NHL |
| PML | RARA, PAX5 | APL, ALL |
| PMX1 | NUP98 | AML |
| PNUTL1 | MLL | AML |
| POU2AF1 | BCL6 | NHL |
| PRDM16 | EVI1 | MDS, AML |
| PSIP2 | NUP98 | AML |
| RAB5EP | PDGFRB | CMML |
| RALGDS | CIITA | PMBL, Hodgkin's Lymphoma |
| RANBP17 | TCR loci | ALL |
| RAP1GDS1 | NUP98 | T-ALL |
| RARA | PML, ZNF145, TIF1, NUMA1 | APL |

TABLE 5-continued

| Rearrangements in liquid tumors* | | |
|---|---|---|
| Gene | Fusion gene partner(s) | Characteristic tumor type |
| RBM15 | MKL1 | acute mega-karyocytic leukemia |
| RPN1 | EVI1 | AML |
| RUNDC2A | CIITA | PMBL, Hodgkin's Lymphoma |
| RUNXBP2 | CREBBP, NCOA2, EP300 | AML |
| SEPT6 | MILL | AML |
| SET | NUP214 | AML |
| SFRS3 | BCL6 | follicular lymphoma |
| SH3GL1 | MILL | AL |
| SIL | TALI | T-ALL |
| SSH3BP1 | MILL | AML |
| STL | ETV6 | B-ALL |
| SYK | ETV6, ITK | MDS, peripheral T-cell lymphoma |
| TALI | TR loci, SIL | lymphoblastic leukemia/biphasic |
| TAL2 | TCR loci | T-ALL |
| TCF3 | PBX1, HLF, TFPT | pre B-ALL |
| TCL1A | TCR loci | T-CLL |
| TCL6 | TCR loci | T-ALL |
| TFPT | TCF3 | pre-B ALL |
| TFRC | BCL6 | NHL |
| TIF1 | RARA | APL |
| TLX1 | TRB genes, TRD genes | T-ALL |
| TLX3 | BCL11B | T-ALL |
| TNFRSF17 | IL2 | intestinal T-cell lymphoma |
| TOP1 | NUP98 | AML |
| TCR loci | ATL, HOX11, LCK, LMO1, LMO2, LYL1, OLIG2, TCL1A, TCL6, MTCP1, RANBP17, TAL1, TAL2, TCL6, TLX2, | T-ALL |
| TRIP11 | PDGFRB | AML |
| TTL | ETV6 | ALL |
| WHSC1 | IGH genes | MM |
| WHSC1L1 | NUP98 | AML |
| ZNF145 | RARA | APL |
| ZNF198 | FGFR1 | MPD, NHL |
| ZNF384 | EWSR1, TAF15 | ALL |
| ZNF521 | PAX5 | ALL |

*The rearranged genes exclude those wherein one of the two genes is a driver gene affected by subtle sequence alterations, amplifications, or homozygous deletions (table S2). This list was derived from the Cancer Gene Census, and excluded genes affected by subtle sequence alterations, amplifications, or homozygous deletions. Abbreviations: ALL, acute lymphocytic leukemia; AML, Acute Myelocytic Leukemia; AML^, acute myelogenous leukemia (primarily treatment associated); APL, acute promyelocytic leukemia; B-ALL, B-cell acute lymphocytic leukemia; B-CLL, B-cell Lymphocytic leukemia; B-NHL, B-cell Non-Hodgkin Lymphoma; CLL, chronic lymphatic leukemia; CML, chronic myeloid leukemia; CMML, chronic myelomonocytic leukemia; DLBCL, diffuse large B-cell lymphoma; JMML, juvenile myelomonocytic leukemia; Ig loci, genes encoding immunoglobulin proteins; MALT, mucosa-associated lymphoid tissue lymphoma; MDS, myelodysplastic syndrome; MLCLS, mediastinal large cell lymphoma with sclerosis: MM, multiple myeloma; MPD, Myeloproliferative disorder; NHL, non-Hodgkin lymphoma; PMBL, primary mediastinal B-cell lymphoma; pre-B All, pre-B-cell acute lymphoblastic leukemia; T-ALL, T-cell acute lymphoblastic leukemia; T-CLL, T-cell chronic lymphocytic leukemia;TGCT, testicular germ cell tumor; T-PLL, T cell prolymphocytic leukemia; TCR loci, genes encoding T-cell receptor proteins.

TABLE 6

| Cancer predisposition genes | | | | |
|---|---|---|---|---|
| Gene Symbol | Gene name | Cancer Syndrome | Core pathway | Process |
| FLCN | folliculin, Birt-Hogg-Dube syndrome | Birt-Hogg-Dube syndrome | PI3K | Cell Survival |
| BLM | Bloom Syndrome | Bloom Syndrome | DNA Damage Control | Genome Maintenance |
| BMPR1A | bone morphogenetic protein receptor, type IA | Juvenile polyposis | TGF-b | Cell Survival |
| BRIP1 | BRCA1 interacting protein C-terminal helicase 1 | Fanconi anaemia J, breast cancer susceptibility | DNA Damage Control | Genome Maintenance |
| BUB1B | BUB1 budding uninhibited by benzimidazoles 1 homolog beta (yeast) | Mosaic variegated aneuploidy | DNA Damage Control | Genome Maintenance |
| CDH1 | cadherin 1, type 1, E-cadherin (epithelial) (ECAD) | Familial gastric carcinoma | APC | Cell Fate |
| CDK4 | cyclin-dependent kinase 4 | Familial malignant melanoma | Cell Cycle/ Apoptosis | Cell Survival |
| CHEK2 | CHK2 checkpoint homolog (S. pombe) | familial breast cancer | Cell Cycle/ Apoptosis | Cell Survival |
| DICER1 | dicer 1, ribonuclease type III | Familial Pleuropulmonary Blastoma | Transcriptional Regulation | Cell Fate |
| ERCC2 | excision repair cross-complementing rodent repair deficiency, complementation group 2 (xeroderma pigmentosum D) | Xeroderma pigmentosum (D) | DNA Damage Control | Genome Maintenance |
| ERCC3 | excision repair cross-complementing rodent repair deficiency, complementation group 3 (xeroderma pigmentosum group B complementing) | Xeroderma pigmentosum (B) | DNA Damage Control | Genome Maintenance |
| ERCC4 | excision repair cross-complementing rodent repair deficiency, complementation group 4 | Xeroderma pigmentosum (F) | DNA Damage Control | Genome Maintenance |
| ERCC5 | excision repair cross-complementing rodent repair deficiency, complementation group 5 (xeroderma pigmentosum, complementation group G (Cockayne syndrome)) | Xeroderma pigmentosum, (G) | DNA Damage Control | Genome Maintenance |
| EXT1 | multiple exostoses type 1 gene | Multiple Exostoses Type 1 | HH | Cell Fate |
| EXT2 | multiple exostoses type 2 gene | Multiple Exostoses Type 2 | HH | Cell Fate |
| FANCA | Fanconi anemia, complementation group A | Fanconi anaemia A | DNA Damage Control | Genome Maintenance |
| FANCC | Fanconi anemia, complementation group C | Fanconi anaemia C | DNA Damage Control | Genome Maintenance |
| FANCD2 | Fanconi anemia, complementation group D2 | Fanconi anaemia D2 | DNA Damage Control | Genome Maintenance |
| FANCE | Fanconi anemia, complementation group E | Fanconi anaemia E | DNA Damage Control | Genome Maintenance |
| FANCF | Fanconi anemia, complementation group F | Fanconi anaemia F | DNA Damage Control | Genome Maintenance |
| FANCG | Fanconi anemia, complementation group G | Fanconi anaemia G | DNA Damage Control | Genome Maintenance |
| FH | fumarate hydratase | hereditary leiomyomatosis and renal cell cancer | PI3K; RAS | Cell Survival |
| GPC3 | glypican 3 | Simpson-Golabi-Behmel syndrome | PI3K | Cell Survival |
| CDC73 | hyperparathyroidism 2 | Hyperparathy roidism-jaw tumor syndrome | Cell Cycle/ Apoptosis | Cell Survival |
| MUTYH | mutY homolog (+i E. coli+l ) | Adenomatous polyposis coli | DNA Damage Control | Genome Maintenance |
| NBS1 | Nijmegen breakage syndrome 1 (nibrin) | Nijmegen breakage syndrome | DNA Damage Control | Genome Maintenance |

TABLE 6-continued

Cancer predisposition genes

| Gene Symbol | Gene name | Cancer Syndrome | Core pathway | Process |
|---|---|---|---|---|
| PALB2 | partner and localizer of BRCA2 | Fanconi anaemia N, breast cancer susceptibility | DNA Damage Control | Genome Maintenance |
| PHOX2B | paired-like homeobox 2b | familial neuroblastoma | Transcriptional Regulation | Cell Fate |
| PMS1 | PMS1 postmeiotic segregation increased 1 (S. cerevisiae) | Hereditary non-polyposis colorectal cancer | DNA Damage Control | Genome Maintenance |
| PMS2 | PMS2 postmeiotic segregation increased 2 (+i S. cerevisiae+l ) | Hereditary non-polyposis colorectal cancer, Turcot syndrome | DNA Damage Control | Genome Maintenance |
| PRKAR1A | protein kinase, cAMP-dependent, regulatory, type I, alpha (tissue specific extinguisher 1) | Carney complex | PI3K; APC | Cell Survival; Cell Fate |
| RECQL4 | RecQ protein-like 4 | Rothmund-Thompson Syndrome | DNA Damage Control | Genome Maintenance |
| SBDS | Shwachman-Bodian-Diamond syndrome protein | Schwachman-Diamond syndrome | Transcriptional Regulation | Cell Fate |
| SDH5 | chromosome 11 open reading frame 79 | Familial paraganglioma | PI3K; RAS | Cell Survival |
| SDHB | succinate dehydrogenase complex, subunit B, iron sulfur (Ip) | Familial paraganglioma | PI3K; RAS | Cell Survival |
| SDHC | succinate dehydrogenase complex, subunit C, integral membrane protein, 15kDa | Familial paraganglioma | PI3K; RAS | Cell Survival |
| SDHD | succinate dehydrogenase complex, subunit D, integral membrane protein | Familial paraganglioma | PI3K; RAS | Cell Survival |
| SUFU | suppressor of fused homolog (+i Drosophila+l ) | Medulloblastoma predisposition | HH | Cell Fate |
| TSC2 | tuberous sclerosis 2 gene | Tuberous sclerosis 2 | PI3K | Cell Survival |
| WAS | Wiskott-Aldrich syndrome | Wiskott-Aldrich syndrome | PI3K; MAPK | Cell Survival |
| WRN | Werner syndrome (RECQL2) | Werner Syndrome | DNA Damage Control | Genome Maintenance |
| XPA | xeroderma pigmentosum, complementation group A | Xeroderma pigmentosum (A) | DNA Damage Control | Genome Maintenance |
| XPC | xeroderma pigmentosum, complementation group C | Xeroderma pigmentosum (C) | DNA Damage Control | Genome Maintenance |

*These genes exclude those which are considered drivers on the basis of their somatic mutation patterns. The source for this list was the Cancer Gene Census (www.sanger.ac.uk/genetics/CGP/Census/).

Normal cells will commit cell suicide (programmed cell death) when they are no longer needed. Until then, they are protected from cell suicide by several protein clusters and pathways. One of the protective pathways is the PI3K/AKT pathway; another is the RAS/MEK/ERK pathway. Sometimes the genes along these protective pathways are mutated in a way that turns them permanently "on", rendering the cell incapable of committing suicide when it is no longer needed. This is one of the steps that causes cancer in combination with other mutations. Normally, the PTEN protein turns off the PI3K/AKT pathway when the cell is ready for programmed cell death. In some breast cancers, the gene for the PTEN protein is mutated, so the PI3K/AKT pathway is stuck in the "on" position, and the cancer cell does not commit suicide.

In certain embodiments, cancer development may be studied using a population of cells having a mutation in the MAPK pathway. As used herein the "MAPK pathway" may be used interchangeably with "MAPK/ERK pathway" and "Ras-Raf-MEK-ERK pathway." The MAPK/ERK pathway is a chain of proteins in the cell that communicates a signal from a receptor on the surface of the cell to the DNA in the nucleus of the cell (see, e.g., Orton R J, et al., (2005). "Computational modelling of the receptor-tyrosine-kinase-activated MAPK pathway" The Biochemical Journal. 392 (Pt 2): 249-61). The signal starts when a signaling molecule binds to the receptor on the cell surface and ends when the DNA in the nucleus expresses a protein and produces some change in the cell, such as cell division. The pathway includes many proteins, including MAPK (mitogen-activated protein kinases, originally called ERK, extracellular signal-regulated kinases), which communicate by adding phosphate groups to a neighboring protein, which acts as an "on" or "off" switch. When one of the proteins in the pathway is mutated, it can become stuck in the "on" or "off" position, which is a necessary step in the development of many cancers. In preferred embodiments, the cancer has a mutation in BRAF, KRAS or NRAS. In specific embodiments, the mutations are BRAF V600E, KRAS G12S or NRAS Q61L. BRAF mutations are most common in melanoma. Currently, it is estimated that eight percent of all cancers have mutations in the BRAF gene, and they are present in a wide range of malignant tumors including ~50% of melanomas, ~40% of papillary thyroid cancer (PTC), ~30% of serous ovarian cancer, ~10% of colorectal cancers (CRC), and ~2%-3% of lung cancers (Obaid et al., Strategies for Overcoming Resistance in Tumours Harboring BRAF Mutations. Int J Mol Sci. 2017 Mar. 8; 18(3)). Somatic KRAS mutations are found at high rates in leukemias, colorectal cancer, pancreatic cancer and lung cancer (Chiosea S I, et al., (2011) Modern Pathology. 24 (12): 1571-7; Hartman D J, et al., (2012) International Journal of Cancer. 131 (8): 1810-7; and Krasinskas A M, et al., (2013) Modern Pathology. 26 (10): 1346-54). NRAS mutations arise in 15-20% of all melanomas (Johnson and Puzanov, (2015) Curr Treat Options Oncol. 16(4):15) and also occur in colorectal cancer (De Roock W, et al. Lancet Oncol 2010; 11: 753-762).

In certain embodiments, the cell population of the present invention has a mutation in PIK3CA. As used herein PIK3CA may refer to the gene or protein according accession number NM_006218.3 and may also include associated fragments and splicing variants, proteins with conservative substitutions and proteins having at least 90% sequence identity. Mutations in PIK3CA occur in colorectal cancer, cervical cancers and breast cancers (De Roock W, et al. Lancet Oncol 2010; 11: 753-762; Samuels, et al., (2010) in Human Cancers. Current Topics in Microbiology and Immunology. Springer Berlin Heidelberg. pp. 21-41; Ma Y Y, et al., (2000) Oncogene. 19 (23): 2739-44; and Zardavas, et al., (2014) Breast Cancer Research. 16 (1)).

In certain embodiments, different cancers may be modeled or populations of pre-transformation or transformed cells may be obtained by introducing combinations of mutations specific to a cancer type to a population of cells (e.g., primary cells). The mutations may be introduced one at a time, two at a time, three at a time, four at a time, five at a time, or more than 6 at a time.

Breast Cancer

In certain embodiments, breast cancer is modeled or breast cancer mutations are introduced to cells. In preferred embodiments, the cells are primary cells associated with breast cancer. Most breast cancers are carcinomas. These cancers start in epithelial cells. Breast cancers are often a type of carcinoma called adenocarcinoma, which starts in cells of glandular tissue (e.g., milk ducts or the lobules). Breast sarcomas start in the cells of the muscle, fat, or connective tissue. Breast cancer is the most frequently diagnosed cancer and the leading cause of cancer death in females worldwide, accounting for 23% (1.38 million) of the total new cancer cases and 14% (458,400) of the total cancer deaths in 2008 (Jemal et al. 2011; Jemal, Siegel, and Ward 2010). In the U.S., 249,260 new cases and 40,890 deaths are estimated for 2016 (ACS 2016). Traditionally, treatment decisions have been based on tumor histology and the status of three main biomarkers: ER (estrogen receptor 1, or ESR1), PR (progesterone receptor, or PGR), and HER2 (erb-b2 receptor tyrosine kinase 2, or ERBB2, also known as neu).

In the United States, 10 to 20 percent of people with breast cancer and people with ovarian cancer have a first- or second-degree relative with one of these diseases. The familial tendency to develop these cancers is called hereditary breast-ovarian cancer syndrome. The best known of these, the BRCA mutations, confer a lifetime risk of breast cancer of between 60 and 85 percent and a lifetime risk of ovarian cancer of between 15 and 40 percent. Some mutations associated with cancer, such as p53, BRCA1 and BRCA2, occur in mechanisms to correct errors in DNA. The inherited mutation in BRCA1 or BRCA2 genes can interfere with repair of DNA cross links and DNA double strand breaks (known functions of the encoded protein). However, mutations in BRCA genes account for only 2 to 3 percent of all breast cancers.

Mutations that can lead to breast cancer have been experimentally linked to estrogen exposure. Abnormal growth factor signaling in the interaction between stromal cells and epithelial cells can facilitate malignant cell growth. In breast adipose tissue, overexpression of leptin leads to increased cell proliferation and cancer.

GATA-3 directly controls the expression of estrogen receptor (ER) and other genes associated with epithelial differentiation, and the loss of GATA-3 leads to loss of differentiation and poor prognosis due to cancer cell invasion and metastasis.

Other significant mutations include p53 (Li-Fraumeni syndrome), PTEN (Cowden syndrome), and STK11 (Peutz-Jeghers syndrome), CHEK2, ATM, BRIP1, and PALB2.

Human epidermal receptor growth factor 2 (HER2, ERBB2) overexpression occurs in 18-20% of breast cancer (Owens et al. 2004; Slamon et al. 1987; Yaziji et al. 2004). HER2 overexpression arises from multiple mechanisms; gene amplification is the most common. Activating mutations in HER2 are estimated to occur at a frequency of 1.6-2.0% in breast cancer (Bose et al. 2013; COSMIC).

HER2 overexpression in breast cancer carries prognostic and predictive significance. In the adjuvant setting, HER2 status is prognostic for outcomes and predictive for outcomes with HER2-targeting therapies such as trastuzumab-based therapy and with anthracycline-based therapies (NCCN 2012). In the metastatic setting, HER2 status predicts outcomes with trastuzumab and HER2-targeting agents (NCCN 2012).

Recently, in patients without HER2 gene amplification, activating HER2 mutations have also been identified (Bose et al. 2013). Preclinical studies have indicated that some HER2 mutations may result in sensitivity or resistance to trastuzumab, neratinib, or lapatinib, depending on the specific mutation (Bose et al. 2013).

Both ER expression and ESR1 mutations are observed in breast cancer. ER expression is common in primary breast cancers and occurs in 73-75% of invasive breast cancers (Nadji et al. 2005; Rhodes et al. 2000). ESR1 mutations are observed primarily in breast cancers that have developed resistance to antiestrogen therapy (Jeselsohn et al. 2014; Merenbakh-Lamin et al. 2013; Robinson et al. 2013; Toy et al. 2013).

The chromosomal region at 8p11-12 containing the FGFR1 gene locus is amplified in up to 10% of breast cancer patients (Hynes and Dey 2010). Turner et al. (2010) noted that FGFR1 overexpression has been associated with ER-positive status and luminal B-type breast cancer. Preclinical data suggest that cancer cells with amplified FGFR1 can display "addiction" to FGFR signaling.

The chromosomal region at 1026 containing the FGFR2 gene locus is amplified in about 1-2% of breast cancer patients (Jain and Turner 2012; Heiskenen et al. 2001; TCGA-cBio). Jain and Turner (2012) noted that FGFR2 amplification is uncommon in breast cancer but occurs a little more frequently in triple-negative breast cancer.

Progesterone receptor (PR) protein expression occurs in 55-58% of breast cancers (Nadji et al. 2005; Rhodes et al. 2000). PR (PGR) mutations are not known to be important in breast cancer.

Mutant PIK3CA has been implicated in the pathogenesis of several cancers, including colon cancer, gliomas, gastric cancer, breast cancer, endometrial cancer, and lung cancer (COSMIC; Samuels et al. 2004). Somatic mutations in PIK3CA have been found in a substantial fraction of breast cancers. Mutated PIK3CA proteins have increased catalytic activity resulting in enhanced downstream signaling and oncogenic transformation in vitro (Kang, Bader, and Vogt 2005).

Cancer-associated alterations in PTEN often result in PTEN inactivation and thus increased activity of the PI3K-AKT pathway. Somatic mutations of PTEN occur in multiple malignancies, including gliomas, melanoma, prostate, endometrial, breast, ovarian, renal, and lung cancers. Germline mutations of PTEN lead to inherited hamartoma and Cowden syndrome (for reviews see Chalhoub and Baker 2009 and Maehama 2007). PTEN activity can also be lost through other mechanisms such as epigenetic changes or post-translational modifications (Leslie and Foti 2010).

Pancreatic Cancer

In certain embodiments, pancreatic cancer is modeled or pancreatic cancer mutations are introduced to cells. Exocrine cancers are by far the most common type of pancreas cancer. Most of the cells in the pancreas form the exocrine glands and ducts. In certain embodiments, the pancreatic cancer is pancreatic intraepithelial neoplasia. More than 90% of cases at all grades carry a faulty KRAS gene, while in grades 2 and 3 damage to three further genes—CDKN2A (p16), p53 and SMAD4—are increasingly found. In certain embodiments, a first event mutation may be KRAS.

In certain embodiments, the pancreatic cancer is an intraductal papillary mucinous neoplasm (IPMN). IPMNs are macroscopic lesions, which occur in about 2% of all adults, rising to about 10% by age 70, and have about a 25% risk of developing into invasive cancer. They also have KRAS gene mutations, in about 40-65% of cases, and in the GNAS G, alpha subunit and RNF43.

The genetic events found in ductal adenocarcinoma have been well characterized. Four genes have each been found to be mutated in the majority of adenocarcinomas: KRAS (in 95% of cases), CDKN2A (also in 95%), TP53 (75%), and SMAD4 (55%). The last of these are especially associated with a poor prognosis. SWI/SNF mutations/deletions occur in about 10-15% of the adenocarcinomas.

Pancreatic Neuroendocrine Tumors (PanNET)

Tumors of the endocrine pancreas are uncommon, making up less than 5% of all pancreatic cancers. As a group, they are often called pancreatic neuroendocrine tumors (NETs) or islet cell tumors. The genes often found mutated in PanNETs are different from those in pancreatic adenocarcinoma. For example, a KRAS mutation is normally absent. Instead, hereditary MEN1 gene mutations give rise to MEN1 syndrome, in which primary tumors occur in two or more endocrine glands. About 40-70% of people born with a MEN1 mutation eventually develop a PanNet. Other genes that are frequently mutated include DAXX, mTOR and ATRX. One in six well-differentiated pancreatic NETs have mutations in mTOR pathway genes, such as TSC2, PTEN and PIK3CA. Mutations involving ATRX and DAXX genes were found in about 40% of pancreatic NETs. The proteins encoded by ATRX and DAXX participate in chromatin remodeling of telomeres; these mutations are associated with a telomerase-independent maintenance mechanism termed ALT (alternative lengthening of telomeres) that results in abnormally long telomeric ends of chromosomes. ATRX/DAXX and MEN1 mutations were associated with a better prognosis.

Colorectal Cancer

In certain embodiments, colorectal cancer is modeled or colorectal cancer mutations are introduced to cells. Colorectal cancer is the second leading cause of cancer related mortality in the United States, with an estimated 134,490 new cases and 49,190 deaths anticipated in 2016 (ACS 2016). Colorectal cancer is a disease originating from the epithelial cells lining the colon or rectum of the gastrointestinal tract, most frequently as a result of mutations in the Wnt signaling pathway that increase signaling activity. The mutations can be inherited or acquired, and most probably occur in the intestinal crypt stem cell. The most commonly mutated gene in all colorectal cancer is the APC gene, which produces the APC protein. The APC protein prevents the accumulation of β-catenin protein. Without APC, β-catenin accumulates to high levels and translocates (moves) into the nucleus, binds to DNA, and activates the transcription of proto-oncogenes. These genes are normally important for stem cell renewal and differentiation, but when inappropriately expressed at high levels, they can cause cancer. While APC is mutated in most colon cancers, some cancers have increased 0-catenin because of mutations in β-catenin (CTNNB1) that block its own breakdown or have mutations in other genes with function similar to APC such as AXIN1, AXIN2, TCF7L2, or NKD1.

The main histologic subtype of colorectal cancer is adenocarcinoma. Colorectal adenocarcinomas arise through the acquisition of a series of mutations that occur over the space of many years, and results in the evolution of normal epithelium to adenoma to carcinoma to metastasis (Fearon and Vogelstein 1990). Some somatic mutations may be prognostic or predictive markers for specific therapies available in colorectal cancer. These mutations involve genes such as KRAS, BRAF, PIK3CA, AKT1, SMAD4, PTEN, NRAS, and TGFBR2 (Baba et al. 2011; De Roock et al. 2010; Dienstmann et al. 2011; Fernandez-Peralta et al. 2005; Haigis et al. 2008; Negri et al. 2010; Papageorgis et al. 2011; Sartore-Bianchi et al. 2009). Furthermore, there has been increasing recognition that some of these mutant gene products may be targets for drug development. (De Roock et al. 2010; Huang et al. 2008; Thenappan et al. 2009).

Beyond the defects in the Wnt signaling pathway, other mutations must occur for the cell to become cancerous. The p53 protein, produced by the TP53 gene, normally monitors cell division and kills cells if they have Wnt pathway defects. Eventually, a cell line acquires a mutation in the TP53 gene and transforms the tissue from a benign epithelial tumor into an invasive epithelial cell cancer. Sometimes the gene encoding p53 is not mutated, but another protective protein named BAX is mutated instead.

Other proteins responsible for programmed cell death that are commonly deactivated in colorectal cancers are TGF-β and DCC (Deleted in Colorectal Cancer). TGF-β has a deactivating mutation in at least half of colorectal cancers. Sometimes TGF-β is not deactivated, but a downstream protein named SMAD is deactivated. DCC commonly has a deleted segment of a chromosome in colorectal cancer.

KRAS, RAF, and PI3K, which normally stimulate the cell to divide in response to growth factors, can acquire mutations that result in over-activation of cell proliferation. The chronological order of mutations is sometimes important. If a previous APC mutation occurred, a primary KRAS mutation often progresses to cancer rather than a self-limiting hyperplastic or borderline lesion. PTEN, a tumor suppressor, normally inhibits PI3K, but can sometimes become mutated and deactivated.

Comprehensive, genome-scale analysis has revealed that colorectal carcinomas can be categorized into hypermutated and non-hypermutated tumor types. In addition to the oncogenic and inactivating mutations described for the genes above, non-hypermutated samples also contain mutated CTNNB1, FAM123B, SOX9, ATM, and ARID1A. Progressing through a distinct set of genetic events, hypermutated tumors display mutated forms of ACVR2A, TGFBR2, MSH3, MSH6, SLC9A9, TCF7L2, and BRAF. The common theme among these genes, across both tumor types, is their involvement in WNT and TGF-β signaling pathways, which results in increased activity of MYC, a central player in colorectal cancer.

Somatic mutations in AKT1 have been found in <1-6% of all colorectal cancer (Carpten et al. 2007; COSMIC; Fumagalli et al. 2008; Kim et al. 2008). In colorectal cancer, the only AKT1 mutation observed up to this time is the E17K mutation, which has also been observed in other types of cancer. This mutation in the Pleckstrin homology domain alters the ligand binding site and leads to constitutive kinase activity.

Approximately 8-15% of colorectal cancer (CRC) tumors harbor BRAF mutations (De Roock et al. 2009; Rizzo et al. 2010; Tejpar et al. 2010). The most frequently reported BRAF mutation is an activating missense mutation in which the amino acid glutamic acid is substituted for valine at amino acid position 600 (V600E; Mao et al. 2011; Rizzo et al. 2010). This mutation is also associated with unresponsiveness to anti-EGFR therapy in wild type KRAS patients with mCRC, as indicated by the results of a meta-analysis by Mao et al. (2011).

Approximately 36-40% of patients with colorectal cancer have tumor-associated KRAS mutations (Amado et al. 2008; COSMIC; Faulkner et al. 2010; Neumann et al. 2009). The concordance between primary tumor and metastases is high (Cejas et al. 2009; Mariani et al. 2010; Santini et al. 2008), with only 3-7% of the tumors discordant. The majority of the mutations occur at codons 12, 13, and 61 of the KRAS gene. The result of these mutations is constitutive activation of KRAS signaling pathways.

Multiple studies have now shown that patients with tumors harboring mutations in KRAS are unlikely to benefit from anti-EGFR antibody therapy, either as monotherapy (Amado et al. 2008) or in combination with chemotherapy (Bokemeyer et al. 2009; Bokemeyer et al. 2011; Douillard et al. 2010; Lievre et al. 2006; Peeters et al. 2010). Further, in trials of oxaliplatin based chemotherapy, the patients with KRAS mutated tumors appeared to do worse when treated with EGFR antibody therapy combined with an oxaliplatin based chemotherapy compared to the patients treated with an oxaliplatin based treatment alone.

NRAS mutations occur in ~1-6% of colorectal cancers (COSMIC; De Roock et al. 2010; Irahara et al. 2009; Janku et al. 2007; Vaughn et al. 2011). Wild type NRAS, together with wild type BRAF and KRAS, is associated response to EGFR antibody therapy (De Mattos-Arruda, Dienstmann, and Tabemero 2011; De Roock et al. 2010). Several studies have shown that patients with NRAS-mutated tumors are less likely to respond to cetuximab or panitumumab, but this may not have an effect on PFS or overall survival (De Mattos-Arruda, Dienstmann, and Tabernero 2011; De Roock et al. 2010; Peeters et al. 2010).

Somatic mutations in PIK3CA have been found in 10-30% of colorectal cancers (COSMIC; Samuels et al. 2004). These mutations usually occur within two "hotspot" areas within exon 9 (the helical domain) and exon 20 (the kinase domain). Mutant PIK3CA proteins have increased catalytic activity resulting in enhanced downstream signaling and oncogenic transformation in vitro (Kang, Bader, and Vogt 2005).

PTEN mutations occur in 5-14% of colorectal cancers (Berg et al. 2010; COSMIC; De Roock et al. 2011; Dicuonzo et al. 2001). PTEN is a tumor suppressor gene, and loss of PTEN results in upregulation of the PI3K/AKT pathway (Salmena et al., Cell 2008; 133(3):403-414). PTEN loss of expression is observed with KRAS, BRAF, and PIK3CA mutations (De Roock et al. 2011; Laurent-Puig et al. 2009; Sartore-Bianchi et al. 2009).

SMAD4 is a signal transduction protein that is the central mediator for downstream transcriptional output in the TGF-β family signaling pathways via its interaction with upstream receptors and fellow SMAD transcription factors (Goustin et al. 1986; Tucker et al. 1984a; Tucker et al. 1984b). The TGF-β pathway plays a complex role in cancer development, progression, and metastasis (Bierie and Moses 2006; Elliott and Blobe 2005; Massague 2008; Miyaki and Kuroki 2003).

Mutations in SMAD4 are involved in several hereditary syndromes with cancer predisposition, including juvenile polyposis syndrome and hemorrhagic hereditary telangiectasia (HHT) syndrome. SMAD4 loss or mutation is also seen in approximately 50% of pancreatic tumors and in 10-35% of invasive CRC (Elliott and Blobe 2005; Hahn et al. 1996; Miyaki et al. 1999). The MH2, C-terminal domain of SMAD4 is the target of tumorigenic inactivation, and mutations in this region disrupt RSMAD oligomerization, which interrupts normal signaling pathways (Shi et al. 1997; Shi and Massague 2003).

SMAD4 mutations are found in ~10-35% of colorectal cancer (CRC) tumors (COSMIC; De Bosscher, Hill, and Nicolas 2004; Koyama et al. 1999; Miyaki and Kuroki 2003; Takagi et al. 1996).

In CRC, loss of SMAD4 has been historically thought to be a late event in tumor development with rates of SMAD4 loss of 0%, 8%, 6%, and 22% in stages I-IV CRC, respectively (Maitra et al. 2000). However, downregulation of SMAD4 is associated with worse survival in stages I-II colon cancer patients (Mesker et al. 2009). Loss of SMAD4 protein expression evaluated by immunohistochemistry in stage III (lymph node positive disease) is associated with worse overall and disease-free survival (Alazzouzi et al. 2005). Low SMAD4 expression may also identify a subset of patients with early recurrence after curative therapy (Ahn et al. 2011).

Acute Lymphoblastic Leukemia

In certain embodiments, Acute lymphoblastic leukemia (ALL) is modeled or Acute lymphoblastic leukemia (ALL) mutations are introduced to cells. Acute lymphoblastic leukemia (ALL) is a cancer of the blood that originates in the hematopoietic cells in bone marrow. It is the most common type of cancer in children (NCI 2012).

Cytokine receptor-like factor 2 (CRLF2) encodes for a receptor protein that participates in activating STAT, possibly through JAK pathways. These pathways are important in immune system regulation. In cancer, CRLF2 rearrangements and one recurring mutation leading to CRLF2 overexpression have been identified in a subset of patients with high risk acute lymphoblastic leukemia who have an exceptionally dismal prognosis.

In B-cell precursor ALL, CRLF2 is rearranged in 30% of cases and has high expression in 17.5% of cases (Chen et al. 2012). CRLF2 fusion partners include P2RY8 and IGH (Chen et al. 2012; Mullighan et al. 2009). It is also sometimes mutated (Chen et al. 2012). High CRLF2 expression independently is correlated with longer recurrence free survival in high-risk B-cell precursor ALL (Chen et al. 2012).

Janus kinase 2 (JAK2) encodes for a protein tyrosine kinase involved in cytokine receptor signaling. Mutations in JAK2 have been identified in ALL and other hematologic malignancies. JAK2 is mutated in 85% of BCR-ABL1-negative, high-risk B-cell precursor pediatric ALL patients (Mullighan et al. 2009). It is mutated in 4-9% of B-cell precursor ALL, overall (Chen et al 2012; COSMIC). Most of the observed JAK2 mutations are thought to result in enhanced JAK2 kinase activity (Mullighan et al. 2009). JAK2 mutations are associated with higher risk of relapse (Mullighan et al. 2009).

Acute Myeloid Leukemia

In certain embodiments, Acute myeloid leukemia (AML) is modeled or Acute myeloid leukemia mutations are introduced to cells. Acute myeloid leukemia is a clinically and biologically heterogeneous disease and the most common cause of leukemia-related mortality in the United States, with an estimated 19,950 new cases and 10,430 deaths anticipated in 2016 (ACS 2016). In AML, somatic genetic changes are often thought to contribute to leukemogenesis through a "two-hit" process. In other words, for leukemogenesis to occur, two types of mutations, or "two hits," are needed: 1) a mutation that improves hematopoietic cells' ability to proliferate (class I, including FLT3 and KIT), and 2) a mutation that prevents the cells from maturing (class II, including CBFB-MYH11, CEBPA, DEK-NUP214, MLL-MLLT3, NPM1, PML-RARA, RUNX1-RUNX1T1; Naoe and Kiyoi 2013; Shih et al. 2012). Other mutations include mutations in epigenetic modifiers such as IDH1, IDH2, and DNMT3A (Naoe and Kiyoi 2013; Shih et al. 2012).

Despite increasing knowledge of the effects of genetic variation on prognosis of AML, there are few options for tailoring treatment based on genetic characteristics. Standard treatment options include combination chemotherapy (cytarabine with either idarubicin or daunorubicin) or hematopoietic stem cell transplant (NCCN 2012). Survival rates remain low; novel therapies and treatment strategies are needed. Acute promyelocytic leukemia (APL), a subtype of AML defined by the presence of the t(15;17) translocation, is an exception. In addition to the standard treatments, APL may also be treated using all trans-retinoic acid or arsenic trioxide (NCI 2013a).

No kinase inhibitors, therapeutic antibodies, or immunotherapies are currently in routine clinical use in AML, although several are in preclinical or clinical development. DOT1L inhibitors; FLT3, JAK2, MEK, and mTOR kinase inhibitors; and multi-kinase inhibitors of FLT3, KIT, PDGFRB, RAF, RET, and VEGF are being investigated for use in AML (Cancer Discovery 2013; Daver and Cortes 2012; Stein and Tallman 2012).

Anaplastic Large Cell Lymphoma

In certain embodiments, Anaplastic large cell lymphoma (ALCL) is modeled or Anaplastic large cell lymphoma (ALCL) mutations are introduced to cells. Anaplastic large cell lymphoma (ALCL) is a non-Hodgkin's lymphoma (NHL); NHL includes many cancers of white blood cells. Approximately 750-800 children are diagnosed with NHL each year in the U.S. (SEER 1999), and about 13% of these are diagnosed with ALCL (Drexler et al. 2000). The five-year survival rate for children diagnosed with NHL is 72% (SEER 1999). In all age groups, 72,580 cases of NHL were estimated for 2016, and 20,150 deaths (ACS 2016). ALCL makes up approximately 2% of adult NHL (Drexler et al. 2000).

ALCL is further divided into ALK-positive and ALK-negative ALCL (Falini and Martelli 2009). The predominant genetic alteration observed in ALCL is the NPM1-ALK fusion seen in 31% of adult and 83% of pediatric ALCL patients (Drexler et al. 2000). Development of targeted therapeutics for ALK-positive ALCL has focused on ALK (Ferreri et al. 2012). CD30 antibodies have been explored as a potential treatment in ALK-positive and ALK-negative ALCL (Merkel et al. 2011).

The anaplastic lymphoma kinase (ALK) is a receptor tyrosine kinase that is aberrant in a variety of malignancies. For example, activating missense mutations within full length ALK are found in a subset of neuroblastomas (Chen et al. 2008; George et al. 2008; Janoueix-Lerosey et al. 2008; Mosse et al. 2008). By contrast, ALK fusions are found in anaplastic large cell lymphoma (e.g., NPM-ALK; Morris et al. 1994), colorectal cancer (Lin et al. 2009; Lipson et al. 2012), inflammatory myofibroblastic tumor (IMT; Lawrence et al. 2000) non-small cell lung cancer (NSCLC; Choi et al, 2008; Koivunen et al. 2008; Rikova et al. 2007; Soda et al. 2007; Takeuchi et al. 2009), and ovarian cancer (Ren et al. 2012). All ALK fusions contain the entire ALK tyrosine kinase domain. To date, those tested biologically possess oncogenic activity in vitro and in vivo (Choi et al. 2008; Morris et al. 1994; Soda et al. 2007; Takeuchi et al. 2009). ALK fusions and copy number gains have been observed in renal cell carcinoma (Debelenko et al. 2011; Sukov et al. 2012). Finally, ALK copy number and protein expression aberrations have also been observed in rhabdomyosarcoma (van Gaal et al. 2012).

The various N-terminal fusion partners promote dimerization and therefore constitutive kinase activity (for review, see Mosse, Wood, and Maris 2009). Signaling downstream of ALK fusions results in activation of cellular pathways known to be involved in cell growth and cell proliferation.

Basal Cell Carcinoma

In certain embodiments, Basal cell carcinoma (BCC) is modeled or Basal cell carcinoma (BCC) mutations are introduced to cells. Basal cell carcinoma (BCC) is the most common type of cancer in the United States. BCC and squamous cell carcinoma are grouped together as non-melanoma skin cancers; BCC makes up about 80% of non-melanoma skin cancers (Kim and Armstrong 2012). Approximately 2.2 million individuals are diagnosed with non-melanoma skin cancer in the United States each year (Kim and Armstrong 2012).

The main subtypes of BCC include nodular, superficial, morpheaform, infiltrative, and pigmented; individual lesions can have several BCC subtypes (Marghoob 2011). The most common cause of BCC is exposure to UV radiation such as sunlight. BCC is slow-growing. It may spread locally, but it is rarely metastatic. As a result, BCC is usually curable.

The genes most frequently mutated in BCC are TP53 (39% of BCC), PTCH1 (39% of BCC), and SMO (12% of BCC). PTCH1 encodes a negative regulator of SMO, and loss of function mutations and/or gene deletion of PTCH1 lead to constitutive activation of SMO.

Bladder Cancer

In certain embodiments, bladder cancer is modeled or bladder cancer mutations are introduced to cells. Urothelial bladder cancer is the most common type of urinary tract cancer. In the United States, 76,960 cases and 16,390 deaths were estimated for 2016 (ACS 2016).

Most bladder cancer is uroepithelial; less common subtypes are squamous cell and adenocarcinoma (NCI 2012). Early stages of bladder cancer are treated with surgery, radiation, or a combination of treatments including chemotherapy (NCI 2012). Tumor resection often leads to cure in early stage patients. Intravesical chemotherapy is also sometimes used. For patients with more advanced tumors, removal of the bladder is the most common treatment. Surgery may be followed by radiation or chemotherapy.

FGFR3 mutations are found in about 50% of upper and lower urinary tract tumors (di Martino, Tomlinson, and Knowles 2012). These mutations cluster in exons 7 and 10, which encode portions of the extracellular domain and the entirety of the transmembrane domain, and exon 15, which encodes a portion of the tyrosine kinase domain (Billerey et al. 2001; Burger et al. 2008; Hernandez et al. 2006; di Martino, Tomlinson, and Knowles 2012; Tomlinson et al. 2007a; van Oers et al. 2009; van Rhijn et al. 2002). The most common mutations are found in exons 7 and 10 and introduce non-native cysteine or glutamate residues, allowing the formation of intermolecular disulfide bonds or hydrogen bonds; these disulfide bonds may induce ligand-free dimerization and constitutive activation of FGFR3 (Adar et al. 2002; d'Avis et al. 1998; di Martino, Tomlinson, and Knowles 2012; Tomlinson et al. 2007a; Touat et al. 2015). However; more recent biophysical work demonstrates that cysteine mutations in the extracellular and transmembrane domains, formerly thought to act by promoting constitutive dimerization, only result in modest dimer stabilization in absence of ligand and instead lead to structural changes of the dimers (Piccolo, Placone, and Hristova 2014). The most prevalent of these mutations encodes the amino acid change S249C, which accounts for ~61% of all FGFR3 mutations in bladder cancers. The other commonly found exon 7 and 10 mutations include those encoding the amino acid changes Y375C (~19%), R248C (~8%), and G372C (~6%) (di Martino, Tomlinson, and Knowles 2012). Mutations in exon 15 (encoding K652E, K652Q, K652T, or K652M) account for only about 2% of FGFR3 mutations in bladder cancer (di Martino, Tomlinson, and Knowles 2012). Exon 15 mutations are thought to act by altering the conformation of the kinase domain into a constitutively active state or by inducing aberrant FGFR3 cellular localization (Lievans, Roncador, and Liboi 2006; di Martino, Tomlinson, and Knowles 2012; Webster et al. 1996). FGFR3 fusions have also been described in association with bladder cancer, including an FGFR3-transforming acid coiled-coil 3 (TACC3) fusion and an FGFR-BAI1-associated protein 2-like 1 (BAIAP2L1) fusion (Williams et al. 2013). The FGFR3-BAIAP2L1 fusion protein appears to promote constitutive activation via dimerization (Nakanishi et al. 2015). Mutated FGFR3 also correlates with increased FGFR3 protein expression, although up to 40% of wild-type tumors also display FGFR3 overexpression (di Martino, Tomlinson, and Knowles 2012). In a large-scale analysis by next generation sequencing, FGFR3 amplification was found in around 2% of urothelial carcinomas (Helsten et al. 2016). Combined, FGFR3-signaling dysregulation by mutation or overexpression is found in 81% of non-invasive and 54% of invasive urothelial cancers (Tomlinson et al. 2007a). Additionally, in vitro evidence suggests that splice variant switching to an isoform with a broader ligand profile (specifically from FGFR3b to the FGFR3c isoform) may play a role in enhanced signaling through the FGFR3 pathway in bladder cancers (Tomlinson et al. 2005).

Tuberous sclerosis 1 (TSC1) encodes for a protein, hamartin, that interacts with a protein encoded by the TSC2 gene, tuberin (Genetics Home Reference 2013). TSC1 acts as a tumor suppressor, through regulation of the mTOR pathway, which is involved in cell proliferation (Genetics Home Reference 2013; Sjodahl et al. 2011). Mutations in TSC1 are observed in 7-12% of bladder cancers. The frequency of mutations is the same for low grade, non-invasive, and high grade, invasive, tumors (COSMIC; Iyer et al. 2012; Sjodahl et al. 2011).

Chronic Lymphocytic Leukemia

In certain embodiments, Chronic lymphocytic leukemia (CLL) is modeled or Chronic lymphocytic leukemia (CLL) mutations are introduced to cells. Chronic lymphocytic leukemia (CLL) is a cancer of the blood that originates in the hematopoietic cells in bone marrow. In the West, CLL is the most common type of adult leukemia (Zenz et al. 2010). In the United States, 18,960 cases of CLL and 4,660 deaths due to CLL were estimated for 2016 (ACS 2016). In the U.S., there is an estimated incidence rate for CLL of 4.5 per 100,000 people, with a median age at diagnosis of 72 years, making CLL a disease of the elderly (ten Hacken and Burger 2016). Men are nearly twice as susceptible to CLL as women and the disease is more common in white populations (Dores et al. 2007). Five-year survival rates for patients with CLL is nearly 90% (Wall and Woyach 2016); however, CLL is quite heterogeneous in its presentation, ranging from an indolent disease with little to no therapeutic intervention to a more aggressive clinical course (Guibze and Wu 2015; Wall and Woyach 2016; Zhang and Kipps 2014).

The pathological hallmark of CLL is clonal expansion of B cells in blood (FIG. 1), marrow, and secondary lymphoid tissues (Chiorazzi, Ria, and Ferrarini 2005; Zhang and Kipps 2014);

BIRC3 frameshift mutations typically result in the premature truncation of the BIRC3-encoded protein product, cIAP2; BIRC3 nonsense mutations can also have this effect. This truncation occurs prior to the C-terminal RING domain responsible for the E3 ubiquitin ligase activity of cIAP2 (Bertrand et al. 2011; Buggins et al. 2010; Conze, Zhao, and Ashwell 2010; Foà et al. 2013; Li, Yang, and Ashwell 2002; Rossi et al. 2012; Zarnegar et al. 2008; Zhou et al. 2013).

BIRC3 can be altered in several different ways in chronic lymphocytic leukemia (CLL), with most mutations being inactivating (Bertrand et al. 2011; Buggins et al. 2010; Conze, Zhao, and Ashwell 2010; Foà et al. 2013; Li, Yang, and Ashwell 2002; Rossi et al. 2012; Zarnegar et al. 2008; Zhou et al. 2013). These alterations are primarily whole-gene deletions or frameshift or nonsense mutations resulting in the premature truncation of the BIRC3-encoded protein product, cIAP2; this truncation occurs prior to the C-terminal RING domain responsible for the E3 ubiquitin ligase activity of cIAP2 (Bertrand et al. 2011; Buggins et al. 2010; Conze, Zhao, and Ashwell 2010; Foà et al. 2013; Li, Yang, and Ashwell 2002; Rossi et al. 2012; Zarnegar et al. 2008; Zhou et al. 2013). Because one function of cIAP2 is to act as a negative regulator of NF-κB signaling in B-cells by ubiquitinating the downstream protein kinase MAP3K14, the result of cIAP2 inactivation is the constitutive activation of the non-canonical NF-κB pathway; non-canonical NF-κB pathway signaling likely mediates resistance to treatment in these patients (Darding and Meier 2012; Foà et al. 2013; Conze, Zhao, and Ashwell 2010; Hewamana et al. 2008; Lau, Niu, and Prat 2012; Rossi et al. 2012; Rossi and Gaidano 2012; Rossi, Fangazio, and Gaidano 2012; Vallabhapurapu and Karin 2009; Zarnegar et al. 2008; Zent and Burack 2014). BIRC3 lesions are much more prevalent in relapsed and fludarabine-refractory CLL (~24%) relative to newly diagnosed CLL (~4%) (Rossi et al. 2012), although variable rates of BIRC3 mutation in CLL have been reported in other studies (0.4%-8.6%); these variations are likely due to the unselected nature of cohorts with variations in time since diagnosis (Baliakas et al. 2015; Chiaretti et al. 2014;

Cortese et al. 2014; Xia et al. 2015). Additionally, BIRC3 disruptions are associated with high risk CLL and patients with BIRC3 lesions present at diagnosis had poor survival outcomes (Chiaretti et al. 2014; Foà et al. 2013; Rossi et al. 2012). BIRC3 deletion can also occur from larger deletions involving 11 q; these deletions occur in 10% of patients on diagnosis and in 95% of cases encompass hundreds of genes, including BIRC3, outside the ATM locus (Strefford 2015). However, the risk conferred by BIRC3 loss in patients with concomitant ATM loss appears to be insignificant, with ATM loss being the most important marker of poor response (Rose-Zerilli et al. 2014).

Evidence indicates that BIRC3 mutations can occur in the context of other genetic aberrations. For example, BIRC3 mutation is correlated with CLL with unmutated Immunoglobulin heavy-chain variable region genes (IGHVs) (U-CLL), trisomy 12, and 11q deletions (Baliakas et al. 2015; Chiaretti et al. 2014). However, other studies have shown that BIRC3 mutations are mutually exclusive from TP53 lesions and from 17p deletion (Baliakas et al. 2015; Rossi et al. 2012), and another study showed an inverse correlation between BIRC3 mutation and 13q deletion (Chiaretti et al. 2014).

BIRC3 mutations are associated with chemorefractoriness and poor prognosis (Rossi et al. 2012). As a result, a recent review classified CLL containing BIRC3 aberrations as very high risk, with the recommended therapeutic strategies including p53-independent drugs, BTK inhibitors, and allogenic stem cell transplantation (Puiggros, Blanco, and Espinet 2014). Recent evidence in mantle cell lymphoma has suggested that BIRC3 aberrations may result in decreased sensitivity to the BTK inhibitor ibrutinib and identified the protein kinase MAP3K14 as a potential therapeutic target in BIRC3-mutated lymphomas (Rahal et al. 2014).

NOTCH1 can be altered in several different ways in chronic lymphocytic leukemia (CLL), including insertions, duplications, deletions, frameshift, missense, and nonsense mutations, although NOTCH1 mutation events are predominated by frameshift and nonsense mutations in a hotspot in exon 34 (Chiaretti et al. 2014; Gianfelici 2012; Puente et al. 2011; Rossi et al. 2012a; Rossi and Gaidano 2012; Zent and Burack 2014). Indeed, the exon 34 frameshift deletion c.7544_7545delCT (p.Pro2514Argfs*4) has been reported to account for about ~80-94% of NOTCH1 mutations in CLL (Baliakas et al. 2015; Rossi et al. 2012a; COSMIC). Exon 34 mutations in NOTCH1 in CLL primarily result in premature protein truncation, generating a NOTCH1 protein lacking the C-terminal PEST domain, where inactivating phosphorylation of NOTCH1 can occur to turn off NOTCH1 signaling; truncated NOTCH1 is thus more stable and constitutively active (Arruga et al. 2014; Gianfelici 2012; Puente et al. 2011; Rossi and Gaidano 2012; Zent and Burack 2014).

Chronic Myeloid Leukemia

In certain embodiments, Chronic myeloid leukemia (CML) is modeled or Chronic myeloid leukemia mutations are introduced to cells. Chronic myeloid leukemia (CML; also known as chronic myelogenous leukemia) is an uncommon cause of cancer-related mortality in the United States, with an estimated 8,220 new cases and 1,070 deaths anticipated in 2016 (ACS 2016; NCI 2012).

CML is characterized by the presence of the Philadelphia chromosome, a translocation between chromosomes 9 and 22 in humans, resulting in a fusion between the 5' end of the BCR gene and the 3' end of the ABL1 gene. The Philadelphia chromosome was discovered in 1960, but the molecular genetic features were not understood until more recently. In the 1980s it was discovered that the Philadelphia chromosome resulted in the BCR-ABL1 fusion gene (Koretzky 2007).

Prior to the approval of imatinib in 2001, CML was treated using interferon-alpha or bone marrow transplant. Since then, imatinib and several additional ABL1 kinase inhibitors have become the most common treatments for CML.

Although the Philadelphia chromosome may be found in other types of leukemias, presence of a BCR-ABL1 fusion gene is an absolute diagnostic criterion for CML, so it is present in all cases. Point mutations in ABL1 can confer resistance to ABL1 kinase inhibitors used to treat CML.

Presence of a BCR-ABL1 fusion gene is necessary for the pathogenesis of CML. In up to 95% of cases, a t(9;22)(q34;q11) translocation results in the BCR-ABL1 fusion gene (Faderl et al. 1999). This translocation results in the Philadelphia chromosome. In rare CML cases lacking the traditional t(9;22) translocation, other translocations result in the creation of the BCR-ABL1 fusion gene, which sometimes involve multiple chromosomes.

ABL1 is a tyrosine kinase, and, in normal cells, it plays a role in cellular differentiation and regulation of the cell cycle. The BCR-ABL1 fusion gene creates a constitutively active tyrosine kinase, which leads to uncontrolled proliferation.

Gastric Cancer

In certain embodiments, gastric cancer is modeled or gastric cancer mutations are introduced to cells. Gastric cancer is the fourth most commonly diagnosed cancer and the second most common cause of cancer death worldwide, with an estimated 989,600 new cases and 738,000 deaths in 2008 (Kamangar, Dores, and Anderson 2006; ACS 2011). Gastric cancer incidence varies throughout the world, with Japan and Korea having the highest incidences (Crew and Neugut 2006). In the U.S., 26,370 new cases and 10,730 deaths are estimated for 2016 (ACS 2016). There are two main sites of gastric cancer: cardia (proximal, gastroesophageal junction) and noncardia (fundus, body, distal, and lesser or greater curvature). The incidence of noncardia tumors is decreasing, possibly due to lower incidence of *H. pylori* infection caused by improved diet, food storage, and overall sanitation (Parsonnet et al. 1991). *H. pylori* infection is a major etiologic factor in the development of intestinal type gastric cancer (Parsonnet et al. 1991). Nonetheless, the incidence of proximal tumors has been increasing since the 1970s, suggesting etiologic heterogeneity among gastric malignancies (Wu et al. 2009).

Most patients with this tumor present with inoperable, locally advanced, or metastatic disease (SEER Stat Fact Sheet: Stomach, accessed 2012). Diagnosis is often delayed because many patients with early stage disease present with vague, non-specific symptoms or no symptoms at all. Late-stage disease at presentation, relative chemoresistance, and frequent co-morbidities causing poor functional status have contributed to poor overall survival (Okines and Cunningham 2010; Kim et al. 2012; Bang et al. 2010). Even patients with operable disease will only have about a one in three chance of surviving 5 years (McDonald et al. 2001; Cunningham et al. 2006). Metastatic disease is treated with systemic chemotherapy and supportive measures.

In various studies, 8-53% of gastric cancers have been shown to exhibit HER2 gene amplification or overexpression (Gravalos and Jimeno 2008; Hofmann et al. 2008; Tanner et al. 2005). A weighted mean for 24 studies reporting prevalence of HER2 amplification in gastric cancer is 19.0% (Jorgensen 2010), on par with prevalence estimates for HER2-positive breast cancer. HER2 mutations have not been described in upper gastrointestinal malignancies.

Gastrointestinal Stromal Tumor (GIST)

In certain embodiments, GIST is modeled or GIST mutations are introduced to cells. Gastrointestinal stromal tumor (GIST) is the most common mesenchymal neoplasm of the gastrointestinal tract, if not the most common sarcoma overall (Reichardt et al. 2009). GIST is believed to arise from the interstitial cells of Cajal or their precursors. These pacemaker cells of the bowel have features of smooth muscle cells, fibroblasts, and neurons to various degrees (Huizinga et al. 1995).

GIST characteristically stains positive for the KIT receptor tyrosine kinase by immunohistochemistry. At the genomic level, mutations in KIT or the receptor tyrosine kinase PDGFRA are the hallmark of this diagnosis (Hirota et al. 1998). KIT and PDGFRA are mutated in ~85% and ~5%, respectively, of GIST. Mutations are also rarely found in the serine-threonine kinase, BRAF (<1%).

The incidence of GIST is on the order of 10-15/million (3,000-4,500 cases/year in the US; Nilsson et al. 2005), although autopsy series may identify as many as 10% of people examined with microscopic GIST.

Somatic mutations in BRAF have been found in <1% of GIST (Agaimy et al. 2009), and are similar to those seen in melanoma.

KIT is mutated in ~85% of GIST (Heinrich et al. 2003). The vast majority of KIT mutations are found in exon 11 (juxtamembrane domain; ~70%), exon 9 (extracellular dimerization motif; 10-15%), exon 13 (tyrosine kinase 1 (TK1) domain; 1-3%), and exon 17 (tyrosine kinase 2 (TK2) domain and activation loop; 1-3%; Heinrich et al. 2003). Secondary KIT mutations in exons 13, 14, 17, and 18 are commonly identified in post-imatinib biopsy specimens, after patients have developed acquired resistance.

PDGFRA is mutated in ~5% of GIST, most frequently in gastric GIST. Specifically, PDGFRA mutations are found mostly in exons 18 (tyrosine kinase 2 (TK2) domain; ~5%), 12 (juxtamembrane domain; 1%) and 14 (tyrosine kinase 1 (TK1) domain; <1%). Mutations except for D842V in exon 18 are sensitive to imatinib (Corless et al. 2005).

Glioma

In certain embodiments, glioma is modeled or glioma mutations are introduced to cells. Glioma is a set of tumors that occur in glial cells; glial cells surround and support nerve cells' (NCI 2013). The most common subtype of glioma is glioblastoma (GBM), and it is also one of the most difficult cancers to treat. Approximately 22,400 gliomas are diagnosed in the U.S. each year; of those, approximately 12,075 are GBMs (CBTRUS 2012). The 2-year survival rate for GBM is about 27% with standard therapy (Stupp et al. 2009).

Classical tumors are characterized by chromosome 7 gain with amplification of the epidermal growth factor receptor (EGFR), EGFR mutation, and chromosome 10 loss. Mesenchymal tumors are characterized by low levels of NF1 expression together with high expression of genes in the tumor necrosis factor (TNF) family and NF-κB pathway. The neural subtype of glioblastoma expresses proteins associated with neuronal differentiation and shows features intermediate between proneural and mesenchymal tumors. The majority of "secondary" GBMs (those that progress from lower-grade II and III astrocytomas) are of the proneural subtype. Proneural tumors are characterized by mutations in isocitrate dehydrogenase genes IDH1 and IDH2, and the tumor suppressor p53. Moreover, IDH mutated GBMs have a unique DNA methylation status termed CIMP (CpG island methylator phenotype) and CIMP positive tumors are also proneural but not all proneural GBMs have the CIMP epitype. Proneural GBMs with the CIMP epitype have the best prognosis of all subtypes of glioblastomas including proneural GBMs without CIMP.

IDH1/2 mutations have been shown to be early events in gliomagenesis. Two major genetic subtypes of IDH-mutated gliomas have been identified. One subtype defined by TP53 and alpha-thalassemia/mental retardation syndrome x-linked (ATRX) mutations that correlates with an astrocytoma histology (Wakimoto et al. 2014); a second type is characterized by concurrent mutations in homolog of *Drosophila capicua* (CIC), far upstream element binding protein (FUBP1), telomerase reverse transcriptase (TERT) promoter, and 1p/19q codeletion and is associated with an oligodendroglioma histology. IDH/CIC-mutated tumors are associated with PIK3CA/KRAS mutations, whereas IDH/TP53 tumors are associated with PDGFRA/MET amplification.

BRAF is mutated in 3% of glioma cases (COSMIC). BRAF is mutated in most low-grade pediatric gliomas and in many adult gliomas (Horbinski 2012). Both BRAF V600E mutations and BRAF fusions have been observed (Horbinski 2012).

IDH1 is mutated in the majority of lower grade diffuse gliomas (grades II-III) and also in most secondary glioblastomas. It is rare (5-8%) in newly diagnosed glioblastoma. IDH1 mutations occur in 32% of glioma cases (COSMIC). Mutations of the R132 residue in IDH1 result in a protein with different function; the new function is believed to contribute to carcinogenesis and tumor growth. The majority (80-90%) of IDH1 mutations in glioma are R132H.

IDH2 is mutated in 1.7% of glioma cases (COSMIC). IDH2 mutations account for 5-10% of all IDH mutations in glioma and occur at codon 172 with similar functional consequences (Dang, Jin, and Su 2010). Mutations of the R140 or R172 residues both result in a protein with different function; the new function is believed to contribute to carcinogenesis and tumor growth (Dang, Jin, and Su 2010).

Inflammatory Myofibroblastic Tumor

In certain embodiments, Inflammatory myofibroblastic tumor (IMT) is modeled or Inflammatory myofibroblastic tumor (IMT) mutations are introduced to cells. Inflammatory myofibroblastic tumor (IMT) is a rare benign or locally aggressive neoplasm (Kovach et al. 2006). It occurs primarily in children and young adults, but it can occur at any age (Coffin, Hornick, and Fletcher 2007). IMTs most commonly arise in the lung, abdomen, pelvis, and retroperitoneum. However, IMT also arises in other sites, including but not limited to soft tissue, CNS, and bone (Gleason and Hornick 2008).

Histologically, IMTs are characterized by the presence of a dense inflammatory infiltrate amidst spindle cells in a myxoid to collagenous stroma (Gleason and Hornick 2008). A prominent molecular feature of IMTs involves rearrangements of the ALK gene on chromosome 2p23 in approximately 50% of cases.

The anaplastic lymphoma kinase (ALK) is a receptor tyrosine kinase that is aberrant in a variety of malignancies. For example, activating missense mutations within full length ALK are found in a subset of neuroblastomas (Chen et al. 2008; George et al. 2008; Janoueix-Lerosey et al. 2008; Mosse et al. 2008). By contrast, ALK fusions are found in anaplastic large cell lymphoma (e.g., NPM-ALK; Morris et al. 1994), colorectal cancer (Lin et al. 2009; Lipson et al. 2012), inflammatory myofibroblastic tumor (IMT; Lawrence et al. 2000) non-small cell lung cancer (NSCLC; Choi et al. 2008; Koivunen et al. 2008; Rikova et al. 2007; Soda et al. 2007; Takeuchi et al. 2009), and ovarian cancer (Ren et al. 2012). All ALK fusions contain the entire ALK tyrosine kinase domain. To date, those tested biologically possess oncogenic activity in vitro and in vivo (Choi et al. 2008; Morris et al. 1994; Soda et al. 2007; Takeuchi et al. 2009). ALK fusions and copy number gains have been observed in renal cell carcinoma (Debelenko et al. 2011; Sukov et al. 2012). Finally, ALK copy number and protein expression aberrations have also been observed in rhabdomyosarcoma (van Gaal et al. 2012).

The various N-terminal fusion partners promote dimerization and therefore constitutive kinase activity (for review, see Mosse, Wood, and Maris 2009). Signaling downstream of ALK fusions results in activation of cellular pathways known to be involved in cell growth and cell proliferation.

50-60% of IMTs carry translocations involving the ALK gene on chromosome 2p23 (Coffin, Hornick, and Fletcher 2007; Saab et al. 2011). These translocations juxtapose portions of the ALK gene to various 5' translocation partners, including RANBP2, TPM3, TPM4, ATIC, CLTC, CARS, and SEC3L1 (COSMIC). The result is constitutive activation of the ALK tyrosine kinase.

Lung Cancer

In certain embodiments, lung cancer is modeled or lung cancer mutations are introduced to cells. Lung cancer is the leading cause of cancer related mortality in the United States, with an estimated 224,390 new cases and 158,080 deaths anticipated in 2016 (ACS 2016). Classically, treatment decisions have been empiric and based upon histology of the tumor. Platinum based chemotherapy remains the cornerstone of treatment. However, survival rates remain low. Novel therapies and treatment strategies are needed.

Lung cancer is comprised of two main histologic subtypes: non-small cell lung cancer (NSCLC) and small cell lung cancer (SCLC). Over the past decade, it has become evident that subsets of NSCLC can be further defined at the molecular level by recurrent 'driver' mutations that occur in multiple oncogenes, including AKT1, ALK, BRAF, EGFR, HER2, KRAS, MEK1, MET, NRAS, PIK3CA, RET, and ROS1. Another altered kinase gene involves MET. 'Driver' mutations lead to constitutive activation of mutant signaling proteins that induce and sustain tumorigenesis. These mutations are rarely found concurrently in the same tumor. Mutations can be found in all NSCLC histologies (including adenocarcinoma, squamous cell carcinoma (SCC), and large cell carcinoma) and in current, former, and never smokers (defined by individuals who smoked less than 100 cigarettes in a lifetime). Never smokers with adenocarcinoma have the highest incidence of EGFR, HER2, ALK, RET, and ROS1 mutations. Importantly, targeted small molecule inhibitors are currently available or being developed for specific molecularly defined subsets of lung cancer patients.

Mutations in the K-Ras proto-oncogene are responsible for 10-30% of lung adenocarcinomas. About 4% of non-small-cell lung carcinomas involve an EML4-ALK tyrosine kinase fusion gene.

Epigenetic changes—such as alteration of DNA methylation, histone tail modification, or microRNA regulation—may lead to inactivation of tumor suppressor genes.

The epidermal growth factor receptor (EGFR) regulates cell proliferation, apoptosis, angiogenesis, and tumor invasion. Mutations and amplification of EGFR are common in non-small-cell lung carcinoma and provide the basis for treatment with EGFR-inhibitors. Her2/neu is affected less frequently. Other genes that are often mutated or amplified are c-MET, NKX2-1, LKB1, PIK3CA, and BRAF.

Somatic mutations in AKT1 have been found in ~1% of all NSCLC (Bleeker et al. 2008; Do et al. 2008; Malanga et al. 2008), in both adenocarcinoma and squamous cell carcinoma histology.

Approximately 3-7% of lung tumors harbor ALK fusions (Koivunen et al. 2008; Kwak et al. 2010; Shinmura et al. 2008; Soda et al. 2007; Takeuchi et al. 2008; Wong et al. 2009). ALK fusions are more commonly found in light smokers (<10 pack years) and/or never-smokers (Inamura et al. 2009; Koivunen et al. 2008; Kwak et al. 2010; Soda et al. 2007; Wong et al. 2009). ALK fusions are also associated with younger age (Inamura et al. 2009; Kwak et al. 2010; Wong et al. 2009) and adenocarcinomas with acinar histology (Inamura et al. 2009; Wong et al. 2009) or signet-ring cells (Kwak et al. 2010). Clinically, the presence of EML4-ALK fusions is associated with EGFR tyrosine kinase inhibitor (TKI) resistance (Shaw et al. 2009).

Multiple different ALK rearrangements have been described in NSCLC. The majority of these ALK fusion variants are comprised of portions of the echinoderm microtubule-associated protein-like 4 (EML4) gene with the ALK gene. At least nine different EML4-ALK fusion variants have been identified in NSCLC (Choi et al. 2008; Horn and Pao 2009; Koivunen et al. 2008; Soda et al. 2007; Takeuchi et al. 2008; Takeuchi et al. 2009; Wong et al. 2009). In addition, non-EML4 fusion partners have also been identified, including KIF5B-ALK (Takeuchi et al. 2009) and TFG-ALK (Rikova et al. 2007).

Somatic mutations in BRAF have been found in 1-4% of all NSCLC (Brose et al. 2002; Cardarella et al. 2013; Davies et al. 2002; Naoki et al. 2002; Paik et al. 2011; Pratilas et al. 2008), most of which are adenocarcinomas. BRAF mutations are more likely to be found in former/current smokers (Paik et al. 2011; Pratilas et al. 2008).

In contrast to melanoma where the majority of BRAF mutations occur at valine 600 (V600) within exon 15 of the kinase domain, BRAF mutations in lung cancer also occur at other positions within the kinase domain. In one study of 697 patients with lung adenocarcinoma, BRAF mutations were present in 18 patients (3%). Of these 18 patients, the BRAF mutations identified were V600E (50%), G469A (39%), and D594G (11%; Paik et al. 2011).

CD274 molecule (CD274; also known as PDL1) is a gene that encodes a protein that is known as programmed cell death 1 ligand 1 (PD-L1). The protein functions in the transmission of the costimulatory signal that is needed for T-cell proliferation. Interaction with the protein inhibits T-cell activation and proliferation. Fusions, missense mutations, nonsense mutations, silent mutations, and frameshift deletions are observed in cancers such as intestinal cancer, skin cancer, and stomach cancer. As many as ~50% of lung cancers express membranous programmed cell death 1 ligand 1 (PD-L1) when less stringent cut-offs (>1%) for PD-L1 positivity are used (Huynh et al. 2016).

DDR2 mutations have been found in 2.5-3.8% of squamous cell carcinomas of the lung and in 4% of lung tumors with adenocarcinoma histology (COSMIC; Hammerman et al. 2011). No hotspots have been identified, with mutations spanning both the kinase and discoidin domains (the latter of which forms part of the extracellular region that binds to collagen; Ichikawa et al. 2007). Neither overexpression of DDR2 nor copy number alterations of the DDR2 locus (1q23) has been reported.

Approximately 10% of patients with NSCLC in the US and 35% in East Asia have tumor associated EGFR mutations (Lynch et al. 2004; Paez et al. 2004; Pao et al. 2004). These mutations occur within EGFR exons 18-21, which encodes a portion of the EGFR kinase domain (FIG. 1). EGFR mutations are usually heterozygous, with the mutant allele also showing gene amplification (Soh et al. 2009). Approximately 90% of these mutations are exon 19 deletions or exon 21 L858R point mutations (Ladanyi and Pao 2008). These mutations increase the kinase activity of EGFR, leading to hyperactivation of downstream pro-survival signaling pathways (Sordella et al. 2004).

HER2 mutations are detected in approximately 2-4% of NSCLC (Buttitta et al. 2006; Shigematsu et al. 2005; Stephens et al. 2004). The most common mutation is an in-frame insertion within exon 20. HER2 mutations appear to be found more commonly in never smokers (defined as less than 100 cigarettes in a patient's lifetime) with adenocarcinoma histology (Buttitta et al. 2006; Shigematsu et al. 2005; Stephens et al. 2004). However, HER2 mutations can also be found in other subsets of NSCLC, including in former and current smokers as well as in other histologies (Buttitta et al. 2006; Shigematsu et al. 2005; Stephens et al. 2004). The exon 20 insertion results in increased HER2 kinase activity and enhanced signaling through downstream pathways, resulting in increased survival, invasiveness, and tumorigenicity (Wang et al. 2006).

Amplifications of FGFR1 are predominantly found in squamous cell lung cancers from former/current smokers. The chromosomal region at 8p12 spanning the FGFR1 gene locus is amplified in up to ~20% of squamous cell lung cancer patients.

FGFR3 can be genomically altered in several different ways in lung cancer, including activating point mutations and gene fusions. In one profile of 100 NSCLC samples, FGFR3-transforming acid coiled-coil 3 (TACC3) fusions were identified in 2 cases (2%), both squamous cell carcinomas (SCC; Majewski et al. 2013). Additionally, 2% of cases harbored the known activating S249C mutation (Majewski et al. 2013). In a study of 576 lung adenocarcinomas, the FGFR3-TACC3 was identified in 0.5% of cases (Capelletti et al. 2014). Additionally, in a screen of 214 primary lung cancers, 0.9% harbored the novel somatic mutation R248H, which has an unknown effect on FGFR activity (Shinmura et al. 2014). In a recent next-generation sequencing analysis of 675 NSCLC samples, several mutations were identified in FGFR3, including R248C, S249C, G370C, and K650E (Helsten et al. 2016). In a cohort of 66 samples of lung SCC in East Asian patients, RNA sequencing uncovered two (3.0%) instances of FGFR3-TACC3 fusions (Kim et al. 2014). Finally, in reports by the Cancer Genome Atlas (TGCA), FGFR3 missense mutations were observed in 3% of lung squamous cell carcinoma (SCC) samples and reported alterations included R248C, S249C, S435C, and K717M (Liao et al. 2013). TGCA reports also demonstrated FGFR3 amplifications (0.6%), fusions (2.2%), and deletions (1.7%) in lung SCC and FGFR3 amplifications (1.3%) and a single mutation event to S779R (0.4%) in lung adenocarcinoma (cBio; Kim et al. 2014; TGCA 2012; TGCA 2014). FGFR3 gene fusion events are diverse, and fusions other than FGFR3-TACC3 have been reported in other cancers (Wang et al. 2014; Wu et al. 2013).

Approximately 15-25% of patients with lung adenocarcinoma have tumor associated KRAS mutations. KRAS mutations are uncommon in lung squamous cell carcinoma (Brose et al. 2002). In the majority of cases, these mutations are missense mutations which introduce an amino acid substitution at position 12, 13, or 61. The result of these mutations is constitutive activation of KRAS signaling pathways.

In the vast majority of cases, KRAS mutations are found in tumors wild type for EGFR or ALK; in other words, they are non-overlapping with other oncogenic mutations found in NSCLC. Therefore, KRAS mutation defines a distinct molecular subset of the disease. KRAS mutations are found in tumors from both former/current smokers and never smokers. They are rarer in never smokers and are less common in East Asian vs. US/European patients (Riely et al. 2008; Sun et al. 2010).

Somatic mutations in MEK1 (MAP2K1) have been found in approximately 1% of all NSCLC and are more common in adenocarcinoma than squamous cell carcinoma (Arcila et al. 2014; Marks et al. 2008). In a retrospective study of 36 MEK1-mutated lung adenocarcinoma patient cases, MEK1 mutations were more prevalent in tumors from smokers or former smokers, and there were no other associations with age, sex, race, or stage (Arcila et al. 2014). In this series, the most frequently observed mutations were K57N (64%) and Q56P (19%), and MEK1 mutations were mutually exclusive with mutations in EGFR, KRAS, BRAF and other driver mutations (Arcila et al. 2014).

In non-small cell lung cancer (NSCLC), multiple mechanisms of MET activation have been reported, including gene amplification (Bean et al. 2007; Cappuzzo et al. 2009; Chen et al. 2009; Engelman et al. 2007; Kubo et al. 2009; Okuda et al. 2008; Onozato et al. 2009) and mutation (Kong-Beltran et al. 2006; Ma et al. 2003).

Somatic mutations in NRAS have been found in ~1% of all NSCLC (Brose et al. 2002; Ding et al. 2008; Ohashi et al. 2013). NRAS mutations are more commonly found in lung cancers with adenocarcinoma histology and in those with a history of smoking (Ohashi et al. 2013). In the majority of cases, these mutations are missense mutations that introduce an amino acid substitution at position 61. Mutations at position 12 have also been described (Ohashi et al. 2013). The result of these mutations is constitutive activation of NRAS signaling pathways. Currently, there are no direct anti-NRAS therapies available, but preclinical models suggest that MEK inhibitors may be effective (Ohashi et al. 2013).

NTRK1 fusions in lung cancer are found in 3.3% of cases with adenocarcinoma histology (3 out of 91 patients; Vaishnavi et al. 2013). In two of three cases described, the patients were female with lung adenocarcinoma who had never smoked (Vaishnavi et al. 2013). The patients' tumors tested negative for EGFR and KRAS mutations as well as ALK or ROS1 fusions (Vaishnavi et al. 2013).

Two different NTRK1 fusions have been described in non-small cell lung cancer using next-generation sequencing, MPRIP-NTRK1 and CD74-NTRK1 (FIG. 1; Vaishnavi et al. 2013). Preclinical studies support the role of these fusions in TRKA autophosphorylation leading to oncogenic processes (Vaishnavi et al. 2013).

Somatic mutations in PIK3CA have been found in 1-3% of all NSCLC (COSMIC; Kawano et al. 2006; Samuels et al. 2004). These mutations usually occur within two "hotspot" areas within exon 9 (the helical domain) and exon 20 (the kinase domain). PIK3CA mutations appear to be more common in squamous cell histology compared to adenocarcinoma (Kawano et al. 2006) and occur in both never smokers and ever smokers. PIK3CA mutations can co-occur with EGFR mutations (Kawano et al. 2006; Sun et al. 2010). In addition, PIK3CA mutations have been detected in a small percentage (~5%) of EGFR-mutated lung cancers with acquired resistance to EGFR TKI therapy (Sequist et al. 2011).

Somatic mutations in PTEN have been found in 4-8% of all NSCLC (Jin et al. 2010; Kohno et al. 1998; Lee et al. 2010). PTEN mutations are found more commonly in ever smokers and in tumors with squamous cell histology (Jin et al. 2010; Lee et al. 2010). PTEN mutation can occur in multiple exons within the gene (i.e., no 'hotspot' mutations in PTEN have been found; Jin et al. 2010). In vitro studies have shown that inactivating mutations in the PTEN gene confer sensitivity to PI3K-AKT inhibitors [for review, see (Courtney, Corcoran, and Engelman 2010)] as well as FRAP/mTOR inhibitors (Neshat et al. 2001).

Approximately 1.3% of lung tumors evaluated have chromosomal changes which lead to RET fusion genes (Ju et al. 2012; Kohno et al. 2012; Takeuchi et al. 2012; Lipson et al. 2012). These gene rearrangements appear to occur almost entirely in adenocarcinoma histology tumors. Histology has not been thoroughly evaluated, but all of the reported lung tumors with RET fusions have been adenocarcinomas (more than 400 lung cancers with histologies other than adenocarcinoma have been tested). Where overlap was evaluated, RET fusions have been shown to occur in tumors without other common driver oncogenes (e.g., EGFR, KRAS, ALK). The three reported fusion genes are CCDC6-RET, KIF5B-RET and TRIM33-RET. While the functional consequences of RET fusion proteins in lung adenocarcinoma are not fully understood, RET fusions are oncogenic in vitro and in vivo.

RPTOR independent companion of MTOR, complex 2 (RICTOR) is a gene that encodes the protein RICTOR (rapamycin-insensitive companion of mTOR). RICTOR is a member of the protein complex mTORC2 that functions in the regulation of actin organization, cell proliferation and survival. The mTORC2 is composed of mTOR, LST8, Deptor, RICTOR, Protor, and SIN1. The mTORC2 has PDK2 kinase activity and is responsible for AKT phosphorylation at Ser473 and its subsequent full activation. The mTORC2 appears to be upstream regulated by PI3K. RICTOR also carries mTOR-independent functions to modify cell morphology, migration and protein degradation.

Missense mutations, nonsense mutations, silent mutations, amplifications, and frameshift deletions and insertions have been observed in cancers such as breast cancer, endometrial cancer, intestinal cancer, lung cancer, and stomach cancer.

Genomic alterations in RICTOR are found in 10.9-14.3% lung adenocarcinoma cases and 10.6-16.9% of lung squamous cell carcinoma (c-Bio). The vast majority of RICTOR alterations in NSCLC are amplifications though missense mutations are spread throughout the gene (c-Bio).

In a review of 1070 lung cancer samples assayed by FoundationOne® next generation sequencing, RICTOR amplification was the sole actionable target alteration in 11% of RICTOR-amplified cases, while 34% had additional alterations in other genes in the PI3K/AKT/mTOR pathway (Cheng et al. 2015). Further, 26% had additional alterations in EGFR and 14% had additional alterations in KRAS (Cheng et al. 2015). RICTOR amplification was also found in 14.6% of small cell lung cancer cases (Cheng et al. 2015).

ROS1 is a receptor tyrosine kinase (RTK) of the insulin receptor family. Chromosomal rearrangements involving the ROS1 gene, on chromosome 6q22, were originally described in glioblastomas (e.g., FIG-ROS1; Birchmeier, Sharma, and Wigler 1987; Birchmeier et al. 1990; Charest et al. 2003). More recently, ROS1 fusions were identified as a potential "driver" mutation in non-small cell lung cancer (Rikova et al. 2007) and cholangiocarcinoma (Gu et al. 2011).

Approximately 2% of lung tumors harbor ROS1 fusions (Bergethon et al. 2012). Like ALK fusions, ROS1 fusions are more commonly found in light smokers (<10 pack years) and/or never-smokers. ROS1 fusions are also associated with younger age and adenocarcinomas (Bergethon et al. 2012).

Several different ROS1 rearrangements have been described in NSCLC. These include SLC34A2-ROS1, CD74-ROS1, EZR-ROS1, TPM3-ROS1, and SDC4-ROS1 (FIG. 1; Davies et al. 2012; Rikova et al. 2007; Takeuchi et al. 2012).

Medulloblastoma

In certain embodiments, medulloblastoma is modeled or medulloblastoma mutations are introduced to cells. Medulloblastoma is the most common central nervous system cancer among children between the ages of 0 and 4 years (CBTRUS 2012). Medulloblastoma is the most common type of a set of brain cancers known as primitive or embryonal. Together with the other embryonal and primitive type brain tumors, annual incidence in the United States is approximately 430 in children aged 0-14 and 660 overall (CBTRUS 2012). Mortality data are not available, but the percentage of medulloblastoma and other primitive and embryonal tumor patients alive 10 years after diagnosis is over 55% (CBTRUS 2012).

The most commonly mutated genes in medulloblastoma are TP53 (100% of 8 samples tested), PTCH1 (16% of 125 samples tested), and CTNNB1 (6% of 366 samples tested; COSMIC). Due to a lack of data, the frequency of SMO mutations is not known. In COSMIC, one mutation is reported out of 65 samples tested, a c.1598G>A (S533N) mutation, located in the seventh transmembrane domain (COSMIC, Reifenberger et al. 1998; UniProt Consortium 2012). One mutation conferring resistance to the SMO inhibitor vismodegib has been reported in the literature: D473H (Metcalfe and de Sauvage 2011; Yauch et al. 2009).

Melanoma

In certain embodiments, melanoma is modeled or melanoma mutations are introduced to cells. Melanoma is a malignant tumor of melanocytes. The disease is the fifth most common cancer in men and the seventh in women with an estimated 76,380 new cases and 10,130 deaths in 2016 in the U.S. (ACS 2016). Melanoma is treated with a combination of surgery, traditional cytotoxic chemotherapy, targeted therapies, and immune-based therapies. Five-year survival rates for patients with metastatic disease, unfortunately, are below 10% (Jemal et al. 2010). Novel therapies and treatment strategies are needed.

Historically, melanoma has been classified according to pathologic and clinical characteristics such as histology (depth, Clark level, ulceration) and anatomic site of origin. Over the past decade, it has become evident that subsets of melanoma can be further defined at the molecular level by recurrent "driver" mutations that occur in multiple oncogenes, including BRAF, GNA11, GNAQ, KIT, MEK1 (MAP2K1), and NRAS. Such driver mutations lead to constitutive activation of mutant signaling proteins that induce and sustain tumorigenesis.

Mutations in BRAF, GNA11, GNAQ, KIT, MEK1 (MAP2K1), and NRAS can be found in approximately 70% of all melanomas. In addition, mutations in CTNNB1 have also been described in melanoma. Mutations in more than one of these genes are seldom found concurrently in the same tumor. The distribution of mutations varies by site of origin and also by the absence or presence of chronic sun damage.

Somatic mutations in BRAF have been found in 37-50% of all malignant melanomas (COSMIC; Davies et al. 2002; Hodis et al. 2012; Krauthammer et al. 2012; Maldonado et al. 2003). BRAF mutations are found in all melanoma subtypes but are the most common in melanomas derived from skin without chronic sun-induced damage (Curtin et al. 2005; Maldonado et al. 2003). In this category of melanoma, BRAF mutations are found in ~59% of samples (Curtin et al. 2005).

The most prevalent BRAF mutations detected in melanoma are missense mutations that introduce an amino acid substitution at valine 600. Approximately 80-90% of V600 BRAF mutations are V600E (valine to glutamic acid; COSMIC; Lovly et al. 2012; Rubinstein et al. 2010) while 5-12% are V600K (valine to lysine; COSMIC; Lovly et al. 2012; Rubinstein et al. 2010), and 5% or less are V600R (valine to arginine) or V600D (valine to aspartic acid; COSMIC; Lovly et al. 2012; Rubinstein et al. 2010). The result of these mutations is enhanced BRAF kinase activity and increased phosphorylation of downstream targets, particularly MEK (Wan et al. 2004). In the vast majority of cases, BRAF mutations are non-overlapping with other oncogenic mutations found in melanoma (e.g., NRAS mutations, KIT mutations, etc.).

While BRAF inhibitor therapy is associated with clinical benefit in the majority of patients with BRAF V600E-mutated melanoma, resistance to treatment and tumor progression occurs in nearly all patients, usually in the first year (Chapman et al. 2011; Sosman et al. 2012).

Somatic mutations in CTNNB1 have been found in 2-4% of malignant melanomas in most series (COSMIC; Demunter et al. 2002; Omholt et al. 2001; Pollock and Hayward 2002; Reifenberger et al. 2002; Rimm et al. 1999). One study reported a frequency of as high as 23% in melanoma cell lines (Rubinfeld et al. 1997). CTNNB1 mutations are rare in uveal melanoma (Edmunds et al. 2002). Whether the presence of CTNNB1 mutation correlates with sun exposure remains to be determined.

The most common CTNNB1 (β-catenin) mutations detected in melanoma are missense mutations which introduce amino acid substitutions at either serine 37 or serine 45, both of which are putative glycogen synthase kinase 3β (GSK3β) phosphorylation sites. The result of these mutations is stabilization of the β-catenin protein and increased transcription of TCF/LEF-responsive target genes (Rubinfeld et al. 1997; Worm et al. 2004).

Preclinical models have demonstrated that concurrent mutations in B3-catenin and NRAS are synergistic in promoting melanoma formation (Delmas et al. 2007).

Guanine nucleotide binding proteins (G proteins) are a family of heterotrimeric proteins which couple seven transmembrane domain receptors to intracellular cascades, including neurotransmitter, growth factor, and hormone signaling pathways (for a recent review, see Rosenbaum, Rasmussen, and Kobilka 2009). Heterotrimeric G proteins are composed of three subunits, Gα, Gβ, and Gγ (FIG. 1); each of the subunits has many different family members. The GNA11 gene encodes the alpha-11 subunit (Gα11). Receptor activation catalyzes the exchange of GDP (guanosine diphosphate) to GTP (guanosine triphosphate) on the Ga subunit, resulting in the dissociation of the Gα subunit from Gβγ. Both Gα and Gβγ can then activate downstream cellular signaling pathways. The signal is terminated when GTP is hydrolyzed to GDP by the intrinsic GTPase activity of the Gα subunit. Oncogenic mutations result in a loss of this intrinsic GTPase activity, resulting in a constitutively active Gα subunit (Kalinec et al. 1992; Landis et al. 1989).

Somatic mutations in GNA11 have been found in up to 34% of primary uveal melanomas and up to 63% of uveal melanoma metastases (Van Raamsdonk et al. 2010). In all malignant melanoma, GNA11 mutations are found in about 1.2% of samples (COSMIC). GNA11 mutations have not been detected in extraocular melanoma (Van Raamsdonk et al. 2010).

The majority of melanoma-associated mutations in GNA11 have been detected at codon 209 within exon 5 of the gene, a region within the catalytic (GTPase) domain of GNA11. Mutation at this site inactivates the GTPase domain, resulting in a constitutively active GNA11 protein which is 'locked' in the GTP bound form (Kalinec et al. 1992; Landis et al. 1989). Expression of GNA11 Q209L in mice results in melanocyte transformation and increased signaling through the MAPK pathway (Van Raamsdonk et al. 2010).

In the vast majority of cases, GNA11 mutations are non-overlapping with other oncogenic mutations found in melanoma (e.g., BRAF mutations, KIT mutations, etc.). Currently, there are no direct anti-GNA11 therapies available.

Somatic mutations in GNAQ have been found in ~50% of primary uveal melanomas and up to 28% of uveal melanoma metastases (Onken et al. 2008; Van Raamsdonk et al. 2009; van Raamsdonk et al. 2010). In all malignant melanoma, GNAQ mutations are found in about 1.3% of samples (COSMIC). GNAQ mutations are rare in extraocular melanoma (Van Raamsdonk et al. 2009).

The majority of melanoma-associated mutations in GNAQ have been detected at codon 209 within exon 5 of the gene, a region within the catalytic (GTPase) domain of GNAQ. Mutation at this site inactivates the GTPase domain, resulting in a constitutively active GNAQ protein, which is 'locked' in the GTP bound form (Kalinec et al. 1992; Landis et al. 1989). Expression of GNAQ Q209L in mice results in melanocyte transformation and increased signaling through the MAPK pathway (Van Raamsdonk et al. 2009).

In the vast majority of cases, GNAQ mutations are non-overlapping with other oncogenic mutations found in melanoma (e.g., BRAF mutations, KIT mutations, etc.). Currently, there are no direct anti-GNAQ therapies available.

Somatic mutations in KIT have been found in 2-8% (Beadling et al. 2008; COSMIC; Curtin et al. 2006; Handolias et al. 2010; Willmore-Payne et al. 2005) of all malignant melanoma. KIT mutations may be found in all melanoma subtypes but are the most common in acral melanomas (10-20%) and mucosal melanomas (15-20%; Beadling et al. 2008; Curtin et al. 2006; Satzger et al. 2008; Torres-Cabala et al. 2009). Among mucosal melanomas, KIT mutations are more common in anorectal and vulvovaginal primaries (15-25%) than in sinonasal/oropharyngeal tumors (~7%).

Somatic point mutations in melanoma tumor specimens have been detected predominantly in the juxtamembrane domain but also in the kinase domain of KIT. They can induce ligand-independent receptor dimerization, constitutive kinase activity, and transformation (Growney et al. 2005; Hirota et al. 1998; Hirota et al. 2001; Kitayama et al. 1995). The spectrum of mutations overlaps with those found in gastrointestinal stromal tumor (GIST).

An increasing number of case reports, retrospective studies, and phase II clinical trials have demonstrated clinical responses of KIT mutated melanoma to imatinib (Carvajal et al. 2011; Guo et al. 2011; Hodi et al. 2013), sunitinib (Minor et al. 2012; Zhu et al. 2009), sorafenib (Quintas-Cardama et al. 2008), and nilotinib (Lebbe et al. 2014). In one case study, a patient with melanoma harboring a KIT L576P mutation demonstrated a response to everolimus after acquiring resistance to imatinib (Si et al. 2012).

In the majority of cases, KIT mutations are non-overlapping with other oncogenic mutations found in melanoma (e.g., NRAS mutations, BRAF mutations, etc.; Beadling et al. 2008). In addition, in rare cases the KIT genotype of a primary lesion may differ from its metastases (Terheyden et al. 2010).

Somatic mutations in MEK1 have been found in 6-7% of malignant melanomas (COSMIC; Nikolaev et al. 2012). The prevalence of MEK1 mutations in different melanoma subtypes is not yet known. However, most of the reported MEK1 mutations involve C>T and G>A nucleotide changes, which frequently result from exposure to UV radiation (Emery et al. 2009; Nikolaev et al. 2012).

MEK1 mutations often occur together with BRAF or NRAS mutations (Emery et al. 2009; Nikolaev et al. 2012; Shi et al. 2012).

Neurofibromin 1 (NF1) is a gene that codes for a tumor suppressor protein (Genetics Home Reference 2014). NF1 suppresses the function of the Ras protein, which promotes cell growth and differentiation (Genetics Home Reference 2014; Yap et al. 2014). In cancer, the tumor suppression function of the gene is impaired, leading to conditions favorable for uncontrolled cell growth. NF1 mutations have been observed in multiple cancer types, including myelodysplastic syndromes.

In addition, NF1 syndrome is a germline condition resulting in predisposition to several types of cancer, in addition to other effects (Yap et al. 2014). Cancer types associated with NF1 syndrome include glioma, melanoma, lung cancer, ovarian cancer, breast cancer, colorectal cancer, hematologic malignancies, and other cancers (Yap et al. 2014).

NF1 mutations are inactivating or cause loss of NF1 (Nissan et al. 2014). While many mutations have been described in NF1 in melanoma (Cerami et al. 2012; COSMIC; Gao et al. 2013; Nissan et al. 2014), the overall frequencies of these mutations have not yet been established.

NF1 mutations occur in 11.9% of malignant melanomas (COSMIC). Inactivation or loss of NF1 is thought to play a role in melanogenesis (Maertens et al. 2013; Whittaker et al. 2013). Since NF1 is a tumor suppressor gene, mutations to NF1 can result in loss of normal downregulation of the Ras activation of the MAPK and PI3K-Akt-mTOR proliferation and differentiation pathways, among other tumor suppression activities (Gibney and Smalley 2013; Yap et al. 2014).

Somatic mutations in NRAS have been found in ~13-25% of all malignant melanomas (Ball et al. 1994; Curtin et al. 2005; van 't Veer et al. 1989). In the majority of cases, these mutations are missense mutations which introduce an amino acid substitution at positions 12, 13, or 61. The result of these mutations is constitutive activation of NRAS signaling pathways. NRAS mutations are found in all melanoma subtypes but may be slightly more common in melanomas derived from chronic sun-damaged (CSD) skin (Ball et al. 1994; van 't Veer et al. 1989). Currently, there are no direct anti-NRAS therapies available.

In the vast majority of cases, NRAS mutations are non-overlapping with other oncogenic mutations found in melanoma (e.g., BRAF mutations, KIT mutations, etc.).

Myelodysplastic Syndromes

In certain embodiments, Myelodysplastic syndromes (MDS) is modeled or Myelodysplastic syndromes (MDS) mutations are introduced to cells. Myelodysplastic syndromes (MDS) are a group of myeloid neoplasms originating in hematopoietic stem cells, characterized by ineffective hematopoiesis and an increased risk of progression to acute myeloid leukemia (AML). This aberrant hematopoiesis manifests clinically as cytopenias and morphologically as dysplasia. MDS is primarily a disease of the elderly, with a median age of 76 at diagnosis (Ma et al. 2007; Tefferi and Vardiman 2009). In the United States, more than 10,000 cases of MDS are diagnosed each year (Ma et al. 2007), although this incidence is likely underestimated due to the difficulty in making a definitive diagnosis of MDS. In the United States, the 3-year observed survival rate for all types of MDS is 35% (Ma et al. 2007).

Several genetic surveys of MDS have revealed that genes along several cellular pathways can be involved in MDS (Haferlach et al. 2014; Walter et al. 2013). These include genes producing proteins involved in RNA splicing, DNA methylation, chromatin modification, transcription, DNA repair control, cohesin function, the RAS pathway, and DNA replication (Cazzola, Della Porta, and Malcovati 2013). There is significant overlap between the genes mutated commonly in MDS with those found in AML, although their relative frequencies are quite different, with more frequent spliceosome mutations in MDS and more mutations in FLT3 and NPM1 in AML (Walter et al. 2013).

Currently, knowledge of cytogenetic abnormalities or gene mutations can be used as an aid in diagnosis of MDS. Mutations in several genes have been shown to have prognostic significance; these include ASXL1, BCOR, ETV6, EZH2, RUNX1, TET2, and TP53 (Bejar et al. 2011; Cazzola, Della Porta, and Malcovati 2013; Damm et al. 2013; Kosminder et al. 2009; NCCN 2014; Thol et al. 2011; Thol et al. 2012; Zhang et al. 2012). Others have been associated with decreased or improved outcomes, although the associations have not been shown to be statistically significant: DNMT3A, SF3B1, SRSF2, STAG2, U2AF1, and ZRSR2 (Bejar et al. 2012; Cazolla, Della Porta, and Malcovati 2013; Damm et al. 2012; Graubert et al. 2011; Makishima et al. 2012; Malcovati et al. 2011; NCCN 2014; Thol et al. 2012; Walter et al. 2011).

ASXL1 mutations occur in 15.8% of MDS (COSMIC). ASXL1 and EZH2 mutations—both genes that code for chromatin-modifying proteins—are most often observed in refractory cytopenia with multilineage dysplasia (RCMD) and refractory anemia with excess blasts (RAEB), two subtypes of MDS associated with higher risk (Cazzola, Della Porta, and Malcovati 2013). ASXL1 mutations, 70% of which are frameshift mutations (Thol et al. 2011), result in loss of ASXL1 expression, which ultimately results in loss of polycomb repressive complex 2 (PRC2)-mediated gene repression. PRC2 normally represses the expression of several leukemogenic genes. This loss promotes myeloid transformation and leukemogenesis (Abdel-Wahab et al. 2012).

ASXL1 mutations are a prognostic biomarker, associated with shorter overall survival (Bejar et al. 2011; NCCN 2014; Thol et al. 2011).

BCOR mutations occur in 2.8-4.2% of MDS (COSMIC; Damm et al. 2013). BCOR mutations are most often observed in refractory cytopenia with multilineage dysplasia (RCMD) and refractory anemia with excess blasts (RAEB), two subtypes of high risk MDS (Cazzola, Della Porta, and Malcovati 2013). BCOR mutations tend to co-occur with RUNX1 or DNMT3A mutations (Damm et al. 2013). The role of BCOR mutations in cancer is not yet understood;

however, BCOR mutations tend to be frameshift or nonsense mutations (COSMIC; Tiacci et al. 2012) and are located throughout the gene (Damm et al. 2013). This and other features have led to the hypothesis that BCOR mutations result in the loss of function of a tumor suppressor gene (Tiacci et al. 2012).

BCOR mutations are a prognostic biomarker, associated with shorter overall survival and higher likelihood of transformation to AML (Damm et al. 2013).

DNMT3A mutations occur in 7.8% of MDS (COSMIC). DNMT3A mutations are observed in all types of MDS (Cazzola, Della Porta, and Malcovati 2013). DNMT3A mutations most often occur at the R882 residue of the protein in MDS (COSMIC), and they are believed to cause loss of function (Shih et al. 2012). However, other mutations are spread throughout the gene. DNMT3A mutations affect DNA methylation and, as such, play a role in cancer development through deregulation of gene expression.

ETV6 mutations occur in 1.3-4.2% of MDS (Bejar et al. 2011; Bejar et al. 2012; Haferlach et al. 2014; Walter et al. 2013). The role of ETV6 mutations in MDS is not well understood.

EZH2 mutations occur in 5.8% of MDS (COSMIC). ASXL1 and EZH2 mutations—both genes that code for chromatin-modifying proteins—are most often observed in refractory cytopenia with multilineage dysplasia (RCMD) and refractory anemia with excess blasts (RAEB), two subtypes of high risk MDS (Cazzola, Della Porta, and Malcovati 2013). EZH2 is a component of the polycomb repressive complex 2 (PRC2).

NF1 mutations occur in less than 1% of MDS (COSMIC). NF1 mutations are observed in various types of MDS (Cazzola, Della Porta, and Malcovati 2013).

RUNX1 mutations occur in 8.9% of MDS (COSMIC). RUNX1 mutations are most often observed in refractory cytopenia with multilineage dysplasia (RCMD) and refractory anemia with excess blasts (RAEB), subtypes of high risk (Cazzola, Della Porta, and Malcovati 2013). RUNX1 mutations result in deregulation of transcription necessary for normal hematopoiesis (Bravo et al. 2014).

Splicing factor 3b, subunit 1, 155 kDa (SF3B1) is a gene that codes for part of the splicing factor 3b protein complex (Gene 2014). The complex is a member of the spliceosome and is involved in transcription and mRNA processing (Gene 2014). Spliceosome mutations are observed in MDS, chronic lymphocytic leukemia (CLL), AML, and chronic myelomonocytic leukemia (CMML), and these mutations can cause abnormal expression patterns of some genes involved in cancer pathogenesis (Chesnais et al. 2012).

The most frequently mutated positions of SF3B1 are K700 (44.9%; COSMIC) and H662 (12.2%; COSMIC). SF3B1 mutations have been associated with favorable overall survival and a lower likelihood of transformation to AML (Cazzola, Della Porta, and Malcovati 2013; Malcovati et al. 2011).

SF3B1 mutations occur in 19.9% of MDS (COSMIC). SF3B1 mutations are only observed in refractory anemia with ring sideroblasts (RARS), a type of MDS, and a subtype of MDS/MPN known as refractory anemia with ring sideroblasts and thrombocytosis (RARS-T; Cazzola, Della Porta, and Malcovati 2013). SF3B1 mutations are involved in ring sideroblast formation (Cazzola, Della Porta, and Malcovati 2013; Malcovati et al. 2011). Sideroblasts are red blood cell precursor cells, and ring sideroblasts are abnormal sideroblasts characterized by a ring of iron particles around the cell nucleus. SF3B1 contains a common K700E mutation as well as other recurrent mutations in homeodomains (Yoshida 2011), suggesting aberrant function of the gene.

Serine/arginine-rich splicing factor 2 (SRSF2) is a gene that codes for one of the several serine/arginine-rich splicing factors. SRSF2 is a member of the spliceosome and is involved in mRNA processing (Gene 2014). Spliceosome mutations are observed in MDS, chronic lymphocytic leukemia (CLL), AML, and chronic myelomonocytic leukemia (CMML), and these mutations can cause abnormal expression patterns of some genes involved in cancer pathogenesis (Chesnais et al. 2012).

The most frequently mutated position of SRSF2 is P95 (87.9%; COSMIC). SRSF2 mutations have been associated with less favorable overall survival and a higher likelihood of transformation to AML (Damm et al. 2012; NCCN 2014; Thol et al. 2012).

SRSF2 mutations occur in 7.4% of MDS (COSMIC). SRSF2 mutations are most often observed in refractory cytopenia with multilineage dysplasia (RCMD) and refractory anemia with excess blasts (RAEB), two subtypes of high risk MDS (Cazzola, Della Porta, and Malcovati 2013). SRSF2 mutations are also common in patients with CMML, where they often co-occur with TET2 mutations (Cazzola, Della Porta, and Malcovati 2013). The role of SRSF2 mutations in MDS is not yet well understood (Visconte et al. 2012). As in SF3B1, there is a mutational hotspot in SRSF2, involving an amino acid change at P95, found in the vast majority of all cases of SRSF2 mutations in MDS.

Stromal antigen 2 (STAG2) is a gene that codes for a subunit of the cohesin complex, which is involved in many cellular processes, such as DNA double-strand break repair and chromatid segregation during mitosis (Nasmyth and Haering 2009). Mutations in STAG2 have been observed in MDS, AML, bladder cancer, and other cancers (Losada 2014; Walter et al. 2013). Inactivation of cohesin may be a cause of aneuploidy in cancer (Gene 2014; Losada 2014).

STAG2 mutations occur in 2.9% of MDS (COSMIC). STAG2 mutations are most often observed in refractory cytopenia with multilineage dysplasia (RCMD) and refractory anemia with excess blasts (RAEB), two subtypes of high risk MDS (Cazzola, Della Porta, and Malcovati 2013). The role of STAG2 mutations in MDS is not yet well understood, although the cohesin complex (of which STAG2 is a subunit) is believed to be involved in myeloid leukemogenesis (Cazzola, Della Porta, and Malcovati 2013).

Tet methylcytosine dioxygenase 2 (TET2; also known as ten-eleven translocation 2) is a gene that codes for a protein involved in epigenetic regulation of myelopoiesis (Gene 2014; Solary et al. 2014). TET2 is a tumor suppressor, and so in cancer, loss of TET2 function, which can occur via TET2 mutation, TET2 deletion, or IDH1 or IDH2 mutation, can cause myeloid or lymphoid transformations (Solary et al. 2014). Mutations in TET2 have been found in MDS, AML, ALL, and other hematologic malignancies.

TET2 mutations occur in 18.7% of MDS (COSMIC). TET2 mutations are observed in all types of MDS, and they tend to co-occur with SRSF2 in chronic myelomonocytic leukemia (CMML), a subtype of MDS (Cazzola, Della Porta, and Malcovati 2013). TET2 mutations are believed to cause loss of function (Solary et al. 2014). TET2 is a tumor suppressor gene, and so loss-of-function mutations support the abnormal hematopoiesis observed in MDS (Solary et al. 2014). These mutations are found spread throughout the gene.

TET2 mutations are a neutral or favorable prognostic biomarker (Bejar et al. 2011; Kosminder et al. 2009; NCCN 2014). However, Bejar et al. (2014) observed that TET2 mutations predict shorter overall survival following hematopoietic stem cell transplantation.

TP53 mutations occur in 9.0% of MDS (COSMIC). TP53 mutations are most often observed in patients with advanced disease or whose tumors harbor a complex karyotype, chromosome 17 abnormalities, chromosome 5 deletions, or chromosome 7 deletions (Cazzola, Della Porta, and Malcovati 2013). The role of TP53 mutations in MDS is not yet well understood. These mutations are found spread throughout the gene.

U2 small nuclear RNA auxiliary factor 1 (U2AF1) is a gene that encodes for a member of the spliceosome. The protein coded by this gene is part of the U2 auxiliary factor, which plays an important role in RNA splicing (Gene 2014). Spliceosome mutations are observed in MDS, chronic lymphocytic leukemia (CLL), AML, and chronic myelomonocytic leukemia (CMML), and these mutations can cause abnormal expression patterns of some genes involved in cancer pathogenesis (Chesnais et al. 2012).

The most frequently mutated positions of U2AF1 are S34 (60.8%; COSMIC) and Q157 (28.5%; COSMIC). U2AF1 mutations have been associated with less favorable overall survival and a higher likelihood of transformation to AML (Cazzola, Della Porta, and Malcovati 2013; Graubert et al. 2011; Makishima et al. 2012).

U2AF1 mutations occur in 6.2% of MDS (COSMIC). U2AF1 mutations are most often observed in refractory cytopenia with multilineage dysplasia (RCMD) and refractory anemia with excess blasts (RAEB), two subtypes of high risk MDS (Cazzola, Della Porta, and Malcovati 2013). The role of U2AF1 mutations in MDS is not yet well understood (Visconte et al. 2012). U2AF1 mutations are localized in the zinc finger domains, in particular amino acids A26, S34, and Q157, suggesting aberrations in the nucleic acid recognition function of the protein.

Zinc finger (CCCH type), RNA-binding motif and serine/arginine rich 2 (ZRSR2) is a gene that encodes for a member of the spliceosome. ZRSR2 mutations occur in 6.8% of MDS (COSMIC). The role of ZRSR2 mutations in MDS is not yet well understood (Cazzola, Della Porta, and Malcovati 2013). Unlike many of the other spliceosome genes, mutations in ZRSR2 are found throughout the gene without recurrent sites of mutations.

Neuroblastoma

In certain embodiments, Neuroblastoma is modeled or Neuroblastoma mutations are introduced to cells. Neuroblastoma is a cancer of peripheral nerve tissue, and it is most often diagnosed in infants and young children; neuroblastomas make up about 7.8% of all pediatric cancers (SEER 1999). Neuroblastoma is diagnosed in about 650 patients age 0-19 each year (SEER 1999). Survival rates depend upon age at diagnosis—younger patients (<18 months) have a better prognosis—histology, stage, MYCN status, and DNA ploidy, among other factors (Cohn et al. 2009). Five-year survival rates are 83% for infants (up to 1 year), 55% for children 1-4 years, and 40% for children 5 years and over (SEER 1999).

The genetic basis for neuroblastoma is not yet well understood. However, the association of MYCN status and outcome is well established. In addition, ploidy, 11 q, 1p, and 17q gain chromosomal statuses are important in assigning risk. Most recently, ALK mutations in neuroblastoma have been identified (Carpenter and Mosse 2012; Chen et al. 2008; George et al. 2008; Janoueix-Lerosey et al. 2008). ALK mutations have been detected in 6-9% of tumor samples (Chen et al. 2008; George et al. 2008; Janoueix-Lerosey et al. 2008). There has also been some work published on the roles of ATRX mutations (Cheung et al. 2012). ATRX mutations are associated with patient age: younger patients' tumors are less likely to harbor ATRX mutations (Cheung et al. 2012). ATRX mutations and MYCN amplification are mutually exclusive (Cheung et al. 2012).

ALK mutations are found in 8-9% of neuroblastoma tumors (COSMIC; Weiser et al. 2011).

While ALK rearrangements predominate in other diseases, such as non-small cell lung cancer, point mutations predominate in neuroblastoma. The most common ALK mutations found in neuroblastoma are activating mutations (Carpenter and Mosse 2012; Schonherr et al. 2011). Activation of ALK contributes to cell growth, proliferation, survival, and migration (Carpenter and Mosse 2012). ALK activation—most often via germline R1275 mutations—has been identified as the primary cause of hereditary neuroblastoma in children (Carpenter and Mosse 2012; Mosse et al. 2008).

Epithelial Ovarian Cancer

In certain embodiments, Epithelial ovarian cancer (EOC) is modeled or Epithelial ovarian cancer (EOC) mutations are introduced to cells. Epithelial ovarian cancer (EOC) is the most common cause of gynecological cancer death in the United States, with an estimated 22,280 new cases and 14,240 deaths estimated for 2016 (ACS 2016). The vast majority of women are diagnosed with advanced stage EOC. Current practice consists of aggressive surgical removal of tumors, followed by platinum-taxane based chemotherapy (Muggia 2009). Despite initial aggressive treatment, most tumors recur, and the overall 5-year survival rate is 44% (Siegel, Naishadham, and Jemal 2012).

Emerging knowledge about underlying molecular alterations in ovarian cancer could allow for more personalized diagnostic, predictive, prognostic, and therapeutic strategies. Approximately 10-20% of high-grade ovarian cancers are associated with germline mutations in BRCA1/2 (Pal et al. 2005). Somatic alterations in BRCA1/2 and other genes associated with DNA repair are seen in approximately 50% of high-grade ovarian cancers (TCGA 2011) and tumors with a 'BRCAness' molecular profile are relatively sensitive to treatment with DNA damaging agents cisplatin and PARP inhibitors (Konstantinopoulos et al. 2010).

More recently, EOC tumors have been broadly classified into two distinct groups with unique histological, clinical, and molecular profiles. Type I tumors have low grade serous, clear cell, endometrioid, and mucinous histological features. Typically, these tumors are slow growing and confined to the ovary and are less sensitive to standard chemotherapy. BRAF and KRAS somatic mutations are relatively common in these tumors, which may have important therapeutic implications.

Type II tumors are high grade serous cancers of the ovary, peritoneum, and fallopian tube. Other high grade endometrioid and poorly differentiated ovarian cancers as well as carcinosarcomas are included in the type II group. These tumors are clinically aggressive and are often widely metastatic at the time of presentation. High grade serous EOC tumors display high levels of genomic instability with few common mutations, other than TP53, which is altered in over 90% of the cases (Kurman and Shih 2011; Landen, Birrer, and Sood 2008; TCGA 2011). PIK3CA and RAS signaling pathways are altered in 45% of the cases, but somatic mutations are rare and gene amplifications are far more common (TCGA 2011).

Somatic mutations in BRAF have been found in a fraction of ovarian cancers and are associated with Type I tumors. The most common variant is V600E in 95% of cases (COSMIC).

KRAS mutations are found in approximately 40% of patients with Type I EOC tumors. In the majority of cases, these mutations are missense mutations which introduce an amino acid substitution at position 12, 13, or 61. The result of these mutations is constitutive activation of KRAS signaling pathways. The most common mutation is KRAS G12D c.35G>A (COSMIC).

Somatic alterations in PIK3CA have been found in a substantial fraction of ovarian cancers (Samuels et al. 2004; COSMIC). Both genetic and biochemical data suggest that activation of the PI3K/AKT survival pathway contributes to ovarian cancer development and tumorigenesis.

PIK3CA amplifications are more common in type II high grade serous ovarian tumors (TCGA 2011). PTEN loss is more common in type I ovarian tumors (Kurman and Shih 2011).

Somatic mutations in PTEN have been found in a substantial fraction of Type I ovarian cancers. PTEN loss is more common in type I ovarian tumors, but is found in high grade serous, clear cell and endometrioid tumors (Kuo et al. 2009; Geyer et al. 2009; Roh et al. 2010).

Prostate Cancer

In certain embodiments, prostate cancer is modeled or prostate cancer mutations are introduced to cells. Prostate cancer is the second most common cancer in men worldwide, accounting for 15% (1.1 million) of the total new male cancer cases and 6.6% (307,000) of the total cancer deaths in men in 2012 (GLOBOCAN 2012 v1.1). In the U.S., 180,890 new cases and 26,120 deaths are estimated for 2016 (ACS 2016). In the U.S., approximately 92% of prostate cancers are discovered at local or regional stage; the 5-year relative survival rates for these cancers is ~100% (ACS 2016). The 5-year relative survival rates for all stages combined is 99%, with 10- and 15-year survival rates for all stages being 98% and 95%, respectively (ACS 2016). On the other hand, the median overall survival of patients with metastatic castration resistant prostate cancer (mCRPC) is between 2-3 years (WHO 2015; Heidenreich et al. 2013; Omlin et al. 2013).

In certain embodiments, a prostate cancer cell model is obtained by introducing one or more mutations common to prostate cancer. No single gene is responsible for prostate cancer; many different genes have been implicated. Mutations in BRCA1 and BRCA2 have been implicated in prostate cancer. Other linked genes include the Hereditary Prostate cancer gene 1 (HPC1), the androgen receptor, and the vitamin D receptor. TMPRSS2-ETS gene family fusion, specifically TMPRSS2-ERG or TMPRSS2-ETV1/4 promotes cancer cell growth.

Loss of cancer suppressor genes, early in the prostatic carcinogenesis, have been localized to chromosomes 8p, 10q, 13q, and 16q. P53 mutations in the primary prostate cancer are relatively low and are more frequently seen in metastatic settings, hence, p53 mutations are a late event in the pathology of prostate cancer. Other tumor suppressor genes that are thought to play a role in prostate cancer include PTEN and KAI1. Up to 70 percent of prostate cancers have lost one copy of the PTEN gene at the time of diagnosis. Loss of E-cadherin and CD44 has also been observed.

The following genes are the top 20 mutated genes in prostate cancer: TP53 (16%), AR (9%), SPOP (8%), PTEN (7%), KMT2C (6%), FOXA1 (5%), KMT2D (4%), LRP1B (4%), FAT4 (4%), KRAS (3%), ATM (3%), ZFHX3 (3%), CTNNB1 (3%), APC (3%), EGFR (2%), PIK3CA (2%), SPEN (2%), BRCA2 (2%), FAT1 (2%), and GRIN2A (2%).

The mechanisms underlying primary and acquired resistance to antiandrogen therapies and the role of the AR gene, the AR transcript, and/or the AR protein product are incompletely elucidated. Understanding how AR variations contribute to response and resistance may have prognostic or predictive value towards improving the clinical management of patients with mCRPC (Daniel and Dehm 2016). Not being bound by a theory, the present invention can be used to model resistance to antiandrogen therapy.

Clinical case series combined with supporting preclinical data have suggested that AR amplification, AR overexpression, mutations involving the ligand-binding domain, and AR splice variants are associated with primary and/or acquired resistance to second-generation antiandrogen therapies for mCRPC (Antonarakis et al. 2014; Azad et al. 2015; Carreira et al. 2014; Romanel et al. 2015; Wyatt et al. 2016). Together, AR aberrations are found in ~60% of mCRPC; AR mutations are found in 15-20% of mCRPC cases, and AR copy number gains or amplifications are found in 25-50% (Beltran et al. 2013; Robinson et al. 2015).

Amplification of the AR gene, which encodes the androgen receptor, likely results in increased expression of this receptor and corresponding increasing response to androgen receptor ligands. The frequency of AR amplification in prostate cancer is about 25-54% (Azad et al. 2015; Beltran et al. 2013; Robinson et al. 2015; Kumar et al. 2016) and the frequency of AR mutations in castration-resistant prostate cancer is about 10-15% (Grasso et al. 2012; Robinson et al. 2015; Taylor et al. 2010).

Rhabdomyosarcoma

In certain embodiments, Rhabdomyosarcoma is modeled or Rhabdomyosarcoma mutations are introduced to cells. Rhabdomyosarcoma is a soft tissue sarcoma arising from skeletal muscle tissue (NCI 2012). Rhabdomyosarcoma most often affects children, and it is the most common soft tissue sarcoma diagnosed in children (SEER 1999). Approximately 350 cases of rhabdomyosarcoma are diagnosed in children each year, making up about 50% of pediatric soft tissue sarcoma cases and 7.4% of pediatric cancers (SEER 1999). Survival rates depend on age at diagnosis, stage, histology, and site of origin (NCI 2012). Overall, the 5-year survival rate for childhood rhabdomyosarcoma is 64% (SEER 1999).

Rhabdomyosarcoma can occur anywhere in the body: most commonly, the head, genitourinary tract, and the arms and legs (NCI 2012). There are three main rhabdomyosarcoma histologies: embryonal (60-70% of childhood rhabdomyosarcomas), alveolar (~20%), and pleomorphic (anaplastic; rare in children; NCI 2012).

Embryonal and alveolar rhabdomyosarcoma histologies have distinct molecular profiles: 80% of alveolar rhabdomyosarcomas harbor a characteristic translocation between chromosomes 1 or 2 and chromosome 13, resulting in a PAX7:FOXO1 or a PAX3:FOXO1 fusion protein (NCI 2012). The clinical behavior of alveolar rhabdomyosarcomas without translocations are more similar to typical embryonal rhabdomyosarcomas than to alveolar rhabdomyosarcomas with translocations. The impact of tumor genetics in rhabdomyosarcoma on treatment is not well understood. ALK has been suggested as a potential therapeutic target in rhabdomyosarcoma (van Gaal et al. 2012). Aberrant genes observed in embryonal rhabdomyosarcoma include BRAF, CTNNB1 (beta-catenin), FGFR4, HRAS, KRAS, NRAS, PIK3CA, and PTPN11. KRAS mutations have been found in alveolar rhabdomyosarcoma (Shukla et al. 2012).

ALK expression is found in 15-32% of embryonal rhabdomyosarcomas and 45-81% of alveolar rhabdomyosarcomas (Corao et al. 2009; Pillay, Govender, and Chetty 2002; van Gaal et al. 2012). Because ALK is normally only expressed in embryos and neonatal brain tissue, any expression after birth in any tissue other than brain tissue is abnormal. Whole exon deletions in ALK were observed in 21% of embryonal rhabdomyosarcomas and 10% of alveolar rhabdomyosarcomas (van Gaal et al. 2012). ALK mutations in rhabdomyosarcoma are uncommon, although one has been observed: D1225N (Shukla et al. 2012; van Gaal et al. 2012).

Thymic Malignancies

In certain embodiments, thymic malignancies are modeled or thymic malignancy mutations are introduced to cells. Thymic malignancies are rare intra-thoracic epithelial tumors that may be aggressive and difficult to treat when in an advanced stage (Girard et al. 2009a). The current histopathologic classification distinguishes thymomas (types A, AB, B1, B2, B3) and thymic carcinoma (WHO 2004) based upon the morphology of epithelial cells (with an increasing degree of atypia from type A to thymic carcinoma), the relative proportion of the non-tumoral lymphocytic component (decreasing from types B1 to B3), and resemblance to normal thymic architecture (WHO 2004). Tumor invasiveness as evaluated by the Masaoka staging system is a major prognostic indicator (Masaoka et al. 1981).

The most significant prognostic factor in thymic tumors is whether or not the disease may undergo complete resection (Girard et al. 2009a; Kondo and Monden 2003). Surgery is the mainstay of treatment. After surgery, thymomas have a tendency towards local and regional recurrence. By contrast, thymic carcinomas are highly aggressive tumors with frequent systemic involvement at time of diagnosis and poor prognosis despite multimodal treatment including surgery, radiotherapy, and chemotherapy (Masaoka et al. 1981; Kondo and Monden 2003).

The most relevant molecular alterations for clinical practice are KIT activating mutations in thymic carcinomas, which have been found in about 9% of cases. EGFR and RAS mutations have also been identified in thymoma and thymic carcinoma but are much rarer and of unknown therapeutic significance in this setting.

KIT mutations are found in only 8.7% of thymic carcinomas (13/128 collectively analyzed) and are mutually exclusive with RAS mutations (Girard et al. 2009; Girard 2010). By contrast, KIT is overexpressed in 87% of thymic carcinomas by immunohistochemistry (IHC; Pan, Chen, and Chiang 2004; Henley, Cummings, and Loehrer 2004; Petrini et al. 2010). Given such a high frequency, KIT IHC positivity may be considered as a diagnostic marker for thymic carcinoma vs. thymoma or lung carcinoma in the setting of a mediastinal tumor (Henley, Cummings, and Loehrer 2004).

Thymic carcinoma-associated KIT mutations have been detected primarily in the juxtamembrane domain and the kinase domain. They can induce ligand-independent receptor dimerization, constitutive kinase activity, and transformation (Growney et al. 2005; Hirota et al. 1998; Hirota et al. 2001). The spectrum of mutations overlaps with those found in gastrointestinal stromal tumor (GIST).

Thyroid Cancer

In certain embodiments, thyroid cancer is modeled or thyroid cancer mutations are introduced to cells. Thyroid cancer is the most common type of endocrine malignancy with an incidence that has steadily increased for the past three decades. Deaths from thyroid cancers alone account for more deaths than all of the other endocrine malignancies combined. In the U.S., 64,300 new cases and 1,980 deaths are estimated for 2015 (ACS 2016).

Epithelial malignant cancers of the thyroid arise from two different types of parenchymal cells, follicular and parafollicular. Follicular cells line the colloid follicules, concentrate iodine and are predominantly involved in production of thyroid hormones. From these cells arise well differentiated and anaplastic thyroid cancers. The parafollicular or C cells, which are spread among the thyroid follicules, are responsible for the production of calcitonin and from these cells arise medullary thyroid cancers (Pitt and Moley 2010).

Well differentiated thyroid carcinomas (DTC) account for 90% of all thyroid cancers, while medullary thyroid carcinomas (MTC) account for 5 to 9%, and anaplastic carcinomas for the remaining 1 to 2%. Well differentiated carcinomas are further subdivided histologically as papillary thyroid cancer (80-85%), follicular thyroid cancer (10-15%) and Hurtle cell carcinoma (3-5%). Overall, DTCs have a very good prognosis with long-term disease free survival close to 95% for papillary thyroid cancers (PTC) and 80% for follicular thyroid cancers (FTC). Their treatment is based on a three-pronged approach that includes thyroidectomy, radioactive iodine therapy and hormonal suppression (TSH) with thyroid replacement hormone. Their most important prognostic factor is distant metastasis which is found in only 5% of patients but carry a high mortality rate at 1 year (50%). In general, DTCs do not respond to chemotherapy (Espinosa, Porchia, and Ringel 2007; Sippos and Mazzaferri 2008).

Medullary thyroid cancers are clinically classified as sporadic or familial cancers. Sporadic MTCs occur as localized cancers with infrequent lymph node involvement (unifocal) and correspond to 70% of all cases, while familial cancers are typically diagnosed as advance disease (multifocal) in the remaining 30% of the cases. Familial MTCs have been described as part of the MEN 2a syndrome which includes the presence of pheochromocytoma and parathyroid hyperplasias, and of the MEN 2b syndromes that also include pheochromocytoma and mucosal neuromas and/or gastrointestinal ganglioneuromas. These cancers have a 5-year survival of 80 to 90%, and for a few decades, surgery was the only effective therapy (Nosé 2011). Just recently, the tyrosine kinase inhibitor, vandetanib, was approved by the FDA for treatment of metastatic MTC. It is the only targeted agent FDA approved for any thyroid cancer (Deshpande et al. 2011).

Thyroid cancers harbor multiple gene mutations or rearrangements which are mutually exclusive. Affected genes include RET, BRAF, PI3KCA, and RAS (Kimura et al. 2003).

Somatic mutations in BRAF have been found in 40-45% of papillary thyroid cancer (Kimura et al. 2003; Cohen et al. 2003; Ciampi et al. 2005). BRAF mutations are also found in anaplastic thyroid cancer (30-40%) and poorly differentiated tumors (20-40%; Namba et al. 2003; Nikiforova et al. 2003; Begum et al. 2004; Xing 2005; Ricarte-Filho et al. 2009).

The most prevalent BRAF mutations detected in thyroid cancers are missense mutations which introduce an amino acid substitution at valine 600. The vast majority (98%) of BRAF mutations are V600E (valine to glutamic acid). The result of these mutations is enhanced BRAF kinase activity and increased phosphorylation of downstream targets, particularly MEK (Wan et al. 2004).

The AKAP9-BRAF rearrangement is another mechanism of BRAF activation in thyroid cancers. This translocation, which fuses the first 8 exons of the A-kinase anchor protein 9 (AKAP9) gene with the C-terminal region (exons 9-18) of BRAF, is found in up to 11% of tumors associated with radiation exposure but in less than 1% of sporadic tumors (Ciampi et al. 2005; Fusco, Viglietto, and Santoro 2005).

RAS mutations (HRAS, NRAS and KRAS) are found in all epithelial thyroid malignancies. The frequency of HRAS mutations in thyroid carcinomas is 4% (COSMIC). While most non-thyroid cancers have mutations in KRAS codons 12 and 13, most thyroid tumors have been found to have mutations in NRAS codon 61 and HRAS codon 61 (Nikiforov 2011).

RAS mutations are identified in 10-20% of papillary carcinomas, 40-50% of follicular carcinomas and 20-40% of poorly differentiated and anaplastic carcinomas (Nikiforov 2011).

Several studies have found RAS mutations to be prevalent in follicular carcinomas, follicular variant papillary carcinomas, and poorly differentiated thyroid carcinomas. Ras mutant thyroid cancers are prone to distant metastases to lung and bone rather than to locoregional lymph node involvement.

RAS mutations are the second most common mutation detected in fine-needle aspiration (FNA) biopsy samples from thyroid nodules and have a 74-88% positive predictive value for malignancy (Bhaijee and Nikiforov 2011).

RAS point mutations are mutually exclusive with other thyroid mutations such as BRAF, RET/PTC, or TRK rearrangements (Kimura et al. 2003) in papillary thyroid cancers. In follicular carcinomas, RAS mutations are mutually exclusive with PAX8-PPARG rearrangements (Nikiforova et al. 2003).

HRAS mutations are also found in ~25% of sporadic medullary thyroid cancers (Moura et al. 2011).

Approximately 10-20% of sporadic papillary thyroid cancers (PTCs) harbor RET fusions. The prevalence of RET rearrangements is higher in patients with a history of radiation exposure (50-80%) and in young adults and pediatric populations (40-70%; Ciampi and Nikiforov 2007).

Multiple different RET rearrangements have been described in PTCs, but RET/PTC1 (CCDC6-RET; 60-70%; Nikiforov 2008; Nikiforov and Nikiforova 2011; Nikiforov et al. 1997); RET/PTC2 (PRKAR1A-RET; 5%; Nifikorov et al. 1997), and RET/PTC3 (NCOA4-RET; 20-30%; Mochizuki et al. 2010) account for the vast majority of cases. These oncogenic rearrangements consist of various 5' partners fused to the kinase domain of RET, leading to constitutive activation of the RET kinase (Pierotti et al. 1996).

Both germline and somatic mutations can occur in RET. Virtually all patients with multiple endocrine neoplasia 2 (MEN 2) harbor germline mutations in RET. MEN 2 is divided into three distinct syndromes: MEN 2A, MEN 2B, and Familial Medullary Thyroid Cancer. Somatic mutations are associated with as many as 50% of sporadic medullary thyroid cancers.

In certain embodiments, one or more mutations as described herein are introduced to one or more cells of a population of cells using a gene editing system capable of targeting the locus to be mutated. In preferred embodiments, mutations are introduced to primary cells associated with each cancer type.

Gene Editing for Introduction of Mutations

The gene editing system may comprise a CRISPR system and one or more guide RNAs capable of targeting the locus to be mutated. The gene editing system may comprise a TALEN, Zinc finger, or recombination system capable of targeting the locus to be mutated.

In certain embodiments, the present invention provides for a non-naturally occurring or engineered composition comprising a CRISPR system, the system comprising: a CRISPR enzyme; and one or more guide RNAs, each capable of targeting the enzyme to a locus to be mutated; wherein the system is configured to introduce one or more mutations at one or more loci in one or more cells in a cell population when the system is expressed in said one or more cells.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun.

17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

CRISPR Guides that May be Used in the Present Invention

As used herein, the term "crRNA" or "guide RNA" or "single guide RNA" or "sgRNA" or "one or more nucleic acid components" of a Type V or Type VI CRISPR-Cas locus effector protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at world wide web.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In general, the CRISPR-Cas, CRISPR-Cas9 or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes, or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at world wide web.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA (s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA (s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it may be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

Synthetic Guides

In certain embodiments, guides of the invention comprise non-naturally occurring nucleic acids and/or non-naturally occurring nucleotides and/or nucleotide analogs, and/or chemically modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3' phosphorothioate (MS), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015). In certain embodiments, a guide comprises ribonucleotides in a region that binds to a target DNA and one or more deoxyribonucleotides and/or nucleotide analogs in a region that binds to Cpf1. In an embodiment of the invention, deoxyribonucleotides and/or nucleotide analogs are incorporated in engineered guide structures, such as, without limitation, stem-loop regions.

Synthetically Linked Guide

In one aspect, the guide comprises a tracr sequence and a tracr mate sequence that are chemically linked or conjugated via a non-phosphodiester bond. In one aspect, the guide comprises a tracr sequence and a tracr mate sequence that are chemically linked or conjugated via a non-nucleotide loop. In some embodiments, the tracr and tracr mate sequences are joined via a non-phosphodiester covalent linker. Examples of the covalent linker include but are not limited to a chemical moiety selected from the group consisting of carbamates, ethers, esters, amides, imines, amidines, aminotrizines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cycloaddition pairs or ring-closing metathesis pairs, and Michael reaction pairs.

In some embodiments, the tracr and tracr mate sequences are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, the tracr or tracr mate sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once the tracr and the tracr mate sequences are functionalized, a covalent chemical bond or linkage can be formed between the two oligonucleotides. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In some embodiments, the tracr and tracr mate sequences can be covalently linked using various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Oligonucleotides (2008) 18: 305-19; Watts, et al., Drug. Discov. Today (2008) 13: 842-55; Shukla, et al., ChemMedChem (2010) 5: 328-49.

In some embodiments, the tracr and tracr mate sequences can be covalently linked using click chemistry. In some embodiments, the tracr and tracr mate sequences can be covalently linked using a triazole linker. In some embodiments, the tracr and tracr mate sequences can be covalently linked using Huisgen 1,3-dipolar cycloaddition reaction involving an alkyne and azide to yield a highly stable triazole linker (He et al., ChemBioChem (2015) 17: 1809-1812; WO 2016/186745). In some embodiments, the tracr and tracr mate sequences are covalently linked by ligating a 5'-hexyne tracrRNA and a 3'-azide crRNA. In some embodiments, either or both of the 5'-hexyne tracrRNA and a 3'-azide crRNA can be protected with 2'acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in WO2011/008730.

A typical Type II Cas9 sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain aspects of guide architecture are retained, certain aspect of guide architecture cam be modified, for example by addition, subtraction, or substitution of features, whereas certain other aspects of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2.

In certain embodiments, guides of the invention comprise specific binding sites (e.g. aptamers) for adapter proteins, which may comprise one or more functional domains (e.g. via fusion protein). When such a guide forms a CRISPR complex (i.e. CRISPR enzyme binding to guide and target) the adapter proteins bind and, the functional domain associated with the adapter protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target.

The skilled person will understand that modifications to the guide which allow for binding of the adapter+functional domain but not proper positioning of the adapter+functional domain (e.g. due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and most preferably at both the tetra loop and stem loop 2.

The repeat:anti repeat duplex will be apparent from the secondary structure of the sgRNA. It may be typically a first complimentary stretch after (in 5' to 3' direction) the poly U tract and before the tetraloop; and a second complimentary stretch after (in 5' to 3' direction) the tetraloop and before the poly A tract. The first complimentary stretch (the "repeat") is complimentary to the second complimentary stretch (the "anti-repeat"). As such, they Watson-Crick base pair to form a duplex of dsRNA when folded back on one another. As such, the anti-repeat sequence is the complimentary sequence of the repeat and in terms to A-U or C-G base pairing, but also in terms of the fact that the anti-repeat is in the reverse orientation due to the tetraloop.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one aspect, the stemloop 2, e.g., "ACTTgtttAAGT" (SEQ ID NO: 160) can be replaced by any "XXXXgtttYYYY", e.g., where XXXX and YYYY represent any complementary sets of nucleotides that together will base pair to each other to create a stem.

In one aspect, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one aspect, the stem made of the X and Y nucleotides, together with the "gttt," will form a complete hairpin in the overall secondary structure; and this may be advantageous and the amount of base pairs can be any amount that forms a complete hairpin. In one aspect, any complementary X:Y basepairing sequence (e.g., as to length) is tolerated, so long as the secondary structure of the entire sgRNA is preserved. In one aspect, the stem can be a form of X:Y basepairing that does not disrupt the secondary structure of the whole sgRNA in that it has a DR:tracr duplex, and 3 stemloops. In one aspect, the "gttt" tetraloop that connects ACTT and AAGT (or any alternative stem made of X:Y basepairs) can be any sequence of the same length (e.g., 4 basepair) or longer that does not interrupt the overall secondary structure of the sgRNA. In one aspect, the stemloop can be something that further lengthens stemloop2, e.g. can be MS2 aptamer. In one aspect, the stemloop3 "GGCACCGagtCGGTGC" (SEQ ID NO:1) can likewise take on a "XXXXXXXagtYYYYYYY" (SEQ ID NO:2) form, e.g., wherein X7 and Y7 represent any complementary sets of nucleotides that together will base pair to each other to create a stem. In one aspect, the stem comprises about 7 bp comprising complementary X and Y sequences, although stems of more or fewer basepairs are also contemplated. In one aspect, the stem made of the X and Y nucleotides, together with the "agt", will form a complete hairpin in the overall secondary structure. In one aspect, any complementary X:Y basepairing sequence is tolerated, so long as the secondary structure of the entire sgRNA is preserved. In one aspect, the stem can be a form of X:Y basepairing that doesn't disrupt the secondary structure of the whole sgRNA in that it has a DR:tracr duplex, and 3 stemloops. In one aspect, the "agt" sequence of the stemloop 3 can be extended or be replaced by an aptamer, e.g., a MS2 aptamer or sequence that otherwise generally preserves the architecture of stemloop3. In one aspect for alternative Stemloops 2 and/or 3, each X and Y pair can refer to any basepair. In one aspect, non-Watson Crick basepairing is contemplated, where such pairing otherwise generally preserves the architecture of the stemloop at that position.

In one aspect, the DR:tracrRNA duplex can be replaced with the form: gYYYYag(N)NNNNxxxxNNNN(AAN)uuRRRRu (SEQ ID NO:3) (using standard IUPAC nomenclature for nucleotides), wherein (N) and (AAN) represent part of the bulge in the duplex, and "xxxx" represents a linker sequence. NNNN on the direct repeat can be anything so long as it basepairs with the corresponding NNNN portion of the tracrRNA. In one aspect, the DR:tracrRNA duplex can be connected by a linker of any length (xxxx . . . ), any base composition, as long as it doesn't alter the overall structure.

In one aspect, the sgRNA structural requirement is to have a duplex and 3 stemloops. In most aspects, the actual sequence requirement for many of the particular base requirements are lax, in that the architecture of the DR:tracrRNA duplex should be preserved, but the sequence that creates the architecture, i.e., the stems, loops, bulges, etc., may be altered.

Aptamers

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:

Guide 1—MS2 aptamer—MS2 RNA-binding protein—VP64 activator; and

Guide 2—PP7 aptamer—PP7 RNA-binding protein—SID4x repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g. using the Alu repressor (in RNA) that interferes with RNA polymerase II in mammalian cells). The Alu RNA sequence was located: in place of the MS2 RNA sequences as used herein (e.g. at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number of modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS (SEQ ID NO:4) can be used. They can be used in repeats of 3 ($(GGGGS)_3$) (SEQ ID NO:5) or 6, 9 or even 12 or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

Dead Guides: Guide RNAs Comprising a Dead Guide Sequence May be Used in the Present Invention In one aspect, the invention provides guide sequences which are modified in a manner which allows for formation of the CRISPR complex and successful binding to the target, while at the same time, not allowing for successful nuclease activity (i.e. without nuclease activity/without indel activity). For matters of explanation such modified guide sequences are referred to as "dead guides" or "dead guide sequences". These dead guides or dead guide sequences can be thought of as catalytically inactive or conformationally inactive with regard to nuclease activity. Nuclease activity may be measured using surveyor analysis or deep sequencing as commonly used in the art, preferably surveyor analysis. Similarly, dead guide sequences may not sufficiently engage in productive base pairing with respect to the ability to promote catalytic activity or to distinguish on-target and off-target binding activity. Briefly, the surveyor assay involves purifying and amplifying a CRISPR target site for a gene and forming heteroduplexes with primers amplifying the CRISPR target site. After re-anneal, the products are treated with SURVEYOR nuclease and SURVEYOR enhancer S (Transgenomics) following the manufacturer's recommended protocols, analyzed on gels, and quantified based upon relative band intensities.

Hence, in a related aspect, the invention provides a non-naturally occurring or engineered composition Cas9 CRISPR-Cas system comprising a functional Cas9 as described herein, and guide RNA (gRNA) wherein the gRNA comprises a dead guide sequence whereby the gRNA is capable of hybridizing to a target sequence such that the Cas9 CRISPR-Cas system is directed to a genomic locus of interest in a cell without detectable indel activity resultant from nuclease activity of a non-mutant Cas9 enzyme of the system as detected by a SURVEYOR assay. For shorthand purposes, a gRNA comprising a dead guide sequence whereby the gRNA is capable of hybridizing to a target sequence such that the Cas9 CRISPR-Cas system is directed to a genomic locus of interest in a cell without detectable indel activity resultant from nuclease activity of a non-mutant Cas9 enzyme of the system as detected by a SURVEYOR assay is herein termed a "dead gRNA". It is to be understood that any of the gRNAs according to the invention as described herein elsewhere may be used as dead gRNAs/gRNAs comprising a dead guide sequence as described herein below. Any of the methods, products, compositions and uses as described herein elsewhere is equally applicable with the dead gRNAs/gRNAs comprising a dead guide sequence as further detailed below. By means of further guidance, the following particular aspects and embodiments are provided.

The ability of a dead guide sequence to direct sequence-specific binding of a CRISPR complex to a target sequence may be assessed by any suitable assay. For example, the components of a CRISPR system sufficient to form a CRISPR complex, including the dead guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the dead guide sequence to be tested and a control guide sequence different from the test dead guide sequence, and comparing binding or rate of cleavage at the target sequence between the test and control guide sequence reactions. Other assays are possible, and will occur to those skilled in the art. A dead guide sequence may be selected to target any target sequence. In some embodiments, the target sequence is a sequence within a genome of a cell.

As explained further herein, several structural parameters allow for a proper framework to arrive at such dead guides. Dead guide sequences are shorter than respective guide sequences which result in active Cas9-specific indel formation. Dead guides are 5%, 10%, 20%, 30%, 40%, 50%, shorter than respective guides directed to the same Cas9 leading to active Cas9-specific indel formation.

As explained below and known in the art, one aspect of gRNA—Cas9 specificity is the direct repeat sequence, which is to be appropriately linked to such guides. In particular, this implies that the direct repeat sequences are designed dependent on the origin of the Cas9. Thus, structural data available for validated dead guide sequences may be used for designing Cas9 specific equivalents. Structural similarity between, e.g., the orthologous nuclease domains RuvC of two or more Cas9 effector proteins may be used to transfer design equivalent dead guides. Thus, the dead guide herein may be appropriately modified in length and sequence to reflect such Cas9 specific equivalents, allowing for formation of the CRISPR complex and successful binding to the target, while at the same time, not allowing for successful nuclease activity.

The use of dead guides in the context herein as well as the state of the art provides a surprising and unexpected platform for network biology and/or systems biology in both in vitro, ex vivo, and in vivo applications, allowing for multiplex gene targeting, and in particular bidirectional multiplex gene targeting. Prior to the use of dead guides, addressing multiple targets, for example for activation, repression and/or silencing of gene activity, has been challenging and in some cases not possible. With the use of dead guides, multiple targets, and thus multiple activities, may be addressed, for example, in the same cell, in the same animal, or in the same patient. Such multiplexing may occur at the same time or staggered for a desired timeframe.

For example, the dead guides now allow for the first time to use gRNA as a means for gene targeting, without the consequence of nuclease activity, while at the same time providing directed means for activation or repression. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

Thus, one aspect is a gRNA of the invention which comprises a dead guide, wherein the gRNA further comprises modifications which provide for gene activation or repression, as described herein. The dead gRNA may comprise one or more aptamers. The aptamers may be specific to gene effectors, gene activators or gene repressors. Alternatively, the aptamers may be specific to a protein which in turn is specific to and recruits/binds a specific gene effector, gene activator or gene repressor. If there are multiple sites for activator or repressor recruitment, it is preferred that the sites are specific to either activators or repressors. If there are multiple sites for activator or repressor binding, the sites may be specific to the same activators or same repressors. The sites may also be specific to different activators or different repressors. The gene effectors, gene activators, gene repressors may be present in the form of fusion proteins.

In an embodiment, the dead gRNA as described herein or the Cas9 CRISPR-Cas complex as described herein includes a non-naturally occurring or engineered composition comprising two or more adaptor proteins, wherein each protein is associated with one or more functional domains and wherein the adaptor protein binds to the distinct RNA sequence(s) inserted into the at least one loop of the dead gRNA.

Hence, an aspect provides a non-naturally occurring or engineered composition comprising a guide RNA (gRNA) comprising a dead guide sequence capable of hybridizing to a target sequence in a genomic locus of interest in a cell, wherein the dead guide sequence is as defined herein, a Cas9 comprising at least one or more nuclear localization sequences, wherein the Cas9 optionally comprises at least one mutation wherein at least one loop of the dead gRNA is modified by the insertion of distinct RNA sequence(s) that bind to one or more adaptor proteins, and wherein the adaptor protein is associated with one or more functional domains; or, wherein the dead gRNA is modified to have at least one non-coding functional loop, and wherein the composition comprises two or more adaptor proteins, wherein the each protein is associated with one or more functional domains.

In certain embodiments, the adaptor protein is a fusion protein comprising the functional domain, the fusion protein optionally comprising a linker between the adaptor protein and the functional domain, the linker optionally including a GlySer linker.

In certain embodiments, the at least one loop of the dead gRNA is not modified by the insertion of distinct RNA sequence(s) that bind to the two or more adaptor proteins.

In certain embodiments, the one or more functional domains associated with the adaptor protein is a transcriptional activation domain.

In certain embodiments, the one or more functional domains associated with the adaptor protein is a transcriptional activation domain comprising VP64, p65, MyoD1, HSF1, RTA or SET7/9.

In certain embodiments, the one or more functional domains associated with the adaptor protein is a transcriptional repressor domain.

In certain embodiments, the transcriptional repressor domain is a KRAB domain.

In certain embodiments, the transcriptional repressor domain is a NuE domain, NcoR domain, SID domain or a SID4X domain.

In certain embodiments, at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity.

In certain embodiments, the DNA cleavage activity is due to a Fok1 nuclease.

In certain embodiments, the dead gRNA is modified so that, after dead gRNA binds the adaptor protein and further binds to the Cas9 and target, the functional domain is in a spatial orientation allowing for the functional domain to function in its attributed function.

In certain embodiments, the at least one loop of the dead gRNA is tetra loop and/or loop2. In certain embodiments, the tetra loop and loop 2 of the dead gRNA are modified by the insertion of the distinct RNA sequence(s).

In certain embodiments, the insertion of distinct RNA sequence(s) that bind to one or more adaptor proteins is an aptamer sequence. In certain embodiments, the aptamer sequence is two or more aptamer sequences specific to the same adaptor protein. In certain embodiments, the aptamer sequence is two or more aptamer sequences specific to different adaptor protein.

In certain embodiments, the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, PRR1.

In certain embodiments, the cell is a eukaryotic cell. In certain embodiments, the eukaryotic cell is a mammalian cell, optionally a mouse cell. In certain embodiments, the mammalian cell is a human cell.

In certain embodiments, a first adaptor protein is associated with a p65 domain and a second adaptor protein is associated with a HSF1 domain.

In certain embodiments, the composition comprises a Cas9 CRISPR-Cas complex having at least three functional domains, at least one of which is associated with the Cas9 and at least two of which are associated with dead gRNA.

In certain embodiments, the composition further comprises a second gRNA, wherein the second gRNA is a live gRNA capable of hybridizing to a second target sequence such that a second Cas9 CRISPR-Cas system is directed to a second genomic locus of interest in a cell with detectable indel activity at the second genomic locus resultant from nuclease activity of the Cas9 enzyme of the system.

In certain embodiments, the composition further comprises a plurality of dead gRNAs and/or a plurality of live gRNAs.

One aspect of the invention is to take advantage of the modularity and customizability of the gRNA scaffold to establish a series of gRNA scaffolds with different binding sites (in particular aptamers) for recruiting distinct types of effectors in an orthogonal manner. Again, for matters of example and illustration of the broader concept, replacement of the MS2 stem-loops with PP7-interacting stem-loops may be used to bind/recruit repressive elements, enabling multiplexed bidirectional transcriptional control. Thus, in general, gRNA comprising a dead guide may be employed to provide for multiplex transcriptional control and preferred bidirectional transcriptional control. This transcriptional control is most preferred of genes. For example, one or more gRNA comprising dead guide(s) may be employed in targeting the activation of one or more target genes. At the same time, one or more gRNA comprising dead guide(s) may be employed in targeting the repression of one or more target genes. Such a sequence may be applied in a variety of different combinations, for example the target genes are first repressed and then at an appropriate period other targets are activated, or select genes are repressed at the same time as select genes are activated, followed by further activation and/or repression. As a result, multiple components of one or more biological systems may advantageously be addressed together.

In an aspect, the invention provides nucleic acid molecule(s) encoding dead gRNA or the Cas9 CRISPR-Cas complex or the composition as described herein.

In an aspect, the invention provides a vector system comprising: a nucleic acid molecule encoding dead guide RNA as defined herein. In certain embodiments, the vector system further comprises a nucleic acid molecule(s) encoding Cas9. In certain embodiments, the vector system further comprises a nucleic acid molecule(s) encoding (live) gRNA. In certain embodiments, the nucleic acid molecule or the vector further comprises regulatory element(s) operable in a eukaryotic cell operably linked to the nucleic acid molecule encoding the guide sequence (gRNA) and/or the nucleic acid molecule encoding Cas9 and/or the optional nuclear localization sequence(s).

In another aspect, structural analysis may also be used to study interactions between the dead guide and the active Cas9 nuclease that enable DNA binding, but no DNA cutting. In this way amino acids important for nuclease activity of Cas9 are determined. Modification of such amino acids allows for improved Cas9 enzymes used for gene editing.

A further aspect is combining the use of dead guides as explained herein with other applications of CRISPR, as explained herein as well as known in the art. For example, gRNA comprising dead guide(s) for targeted multiplex gene activation or repression or targeted multiplex bidirectional gene activation/repression may be combined with gRNA comprising guides which maintain nuclease activity, as explained herein. Such gRNA comprising guides which maintain nuclease activity may or may not further include modifications which allow for repression of gene activity (e.g. aptamers). Such gRNA comprising guides which maintain nuclease activity may or may not further include modifications which allow for activation of gene activity (e.g. aptamers). In such a manner, a further means for multiplex gene control is introduced (e.g. multiplex gene targeted activation without nuclease activity/without indel activity may be provided at the same time or in combination with gene targeted repression with nuclease activity).

For example, 1) using one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene activators; 2) may be combined with one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene repressors. 1) and/or 2) may then be combined with 3) one or more gRNA (e.g. 1-50, 1-40, 1-30, 1-20, preferably 1-10, more preferably 1-5) targeted to one or more genes. This combination can then be carried out in turn with 1)+2)+3) with 4) one or more gRNA (e.g. 1-50, 1-40, 1-30, 1-20, preferably 1-10, more preferably 1-5) targeted to one or more genes and further modified with appropriate aptamers for the recruitment of gene activators. This combination can then be carried in turn with 1)+2)+3)+4) with 5) one or more gRNA (e.g. 1-50, 1-40, 1-30, 1-20, preferably 1-10, more preferably 1-5) targeted to one or more genes and further modified with appropriate aptamers for the recruitment of gene repressors. As a result, various uses and combinations are included in the invention. For example, combination 1)+2); combination 1)+3); combination 2)+3); combination 1)+2)+3); combination 1)+2)+3)+4); combination 1)+3)+4); combination 2)+3)+4); combination 1)+2)+4); combination 1)+2)+3)+4)+5); combination 1)+3)+4)+5); combination 2)+3)+4)+5); combination 1)+2)+4)+5); combination 1)+2)+3)+5); combination 1)+3)+5); combination 2)+3)+5); combination 1)+2)+5).

In an aspect, the invention provides an algorithm for designing, evaluating, or selecting a dead guide RNA targeting sequence (dead guide sequence) for guiding a Cas9 CRISPR-Cas system to a target gene locus. In particular, it has been determined that dead guide RNA specificity relates to and can be optimized by varying i) GC content and ii) targeting sequence length. In an aspect, the invention provides an algorithm for designing or evaluating a dead guide RNA targeting sequence that minimizes off-target binding or interaction of the dead guide RNA. In an embodiment of the invention, the algorithm for selecting a dead guide RNA targeting sequence for directing a CRISPR system to a gene locus in an organism comprises a) locating one or more CRISPR motifs in the gene locus, analyzing the 20 nt sequence downstream of each CRISPR motif by i) determining the GC content of the sequence; and ii) determining whether there are off-target matches of the 15 downstream nucleotides nearest to the CRISPR motif in the genome of the organism, and c) selecting the 15 nucleotide sequence for use in a dead guide RNA if the GC content of the sequence is 70% or less and no off-target matches are identified. In an embodiment, the sequence is selected for a targeting sequence if the GC content is 60% or less. In certain embodiments, the sequence is selected for a targeting sequence if the GC content is 55% or less, 50% or less, 45% or less, 40% or less, 35% or less or 30% or less. In an embodiment, two or more sequences of the gene locus are analyzed and the sequence having the lowest GC content, or the next lowest GC content, or the next lowest GC content is selected. In an embodiment, the sequence is selected for a targeting sequence if no off-target matches are identified in the genome of the organism. In an embodiment, the targeting sequence is selected if no off-target matches are identified in regulatory sequences of the genome.

In an aspect, the invention provides a method of selecting a dead guide RNA targeting sequence for directing a functionalized CRISPR system to a gene locus in an organism, which comprises: a) locating one or more CRISPR motifs in the gene locus; b) analyzing the 20 nt sequence downstream of each CRISPR motif by: i) determining the GC content of the sequence; and ii) determining whether there are off-target matches of the first 15 nt of the sequence in the genome of the organism; c) selecting the sequence for use in a guide RNA if the GC content of the sequence is 70% or less and no off-target matches are identified. In an embodiment, the sequence is selected if the GC content is 50% or less. In an embodiment, the sequence is selected if the GC content is 40% or less. In an embodiment, the sequence is selected if the GC content is 30% or less. In an embodiment, two or more sequences are analyzed and the sequence having the lowest GC content is selected. In an embodiment, off-target matches are determined in regulatory sequences of the organism. In an embodiment, the gene locus is a regulatory region. An aspect provides a dead guide RNA comprising the targeting sequence selected according to the aforementioned methods.

In an aspect, the invention provides a dead guide RNA for targeting a functionalized CRISPR system to a gene locus in an organism. In an embodiment of the invention, the dead guide RNA comprises a targeting sequence wherein the CG content of the target sequence is 70% or less, and the first 15 nt of the targeting sequence does not match an off-target sequence downstream from a CRISPR motif in the regulatory sequence of another gene locus in the organism. In certain embodiments, the GC content of the targeting sequence 60% or less, 55% or less, 50% or less, 45% or less, 40% or less, 35% or less or 30% or less. In certain embodiments, the GC content of the targeting sequence is from 70% to 60% or from 60% to 50% or from 50% to 40% or from 40% to 30%. In an embodiment, the targeting sequence has the lowest CG content among potential targeting sequences of the locus.

In an embodiment of the invention, the first 15 nt of the dead guide match the target sequence. In another embodiment, first 14 nt of the dead guide match the target sequence. In another embodiment, the first 13 nt of the dead guide match the target sequence. In another embodiment first 12 nt of the dead guide match the target sequence. In another embodiment, first 11 nt of the dead guide match the target sequence. In another embodiment, the first 10 nt of the dead guide match the target sequence. In an embodiment of the invention the first 15 nt of the dead guide does not match an off-target sequence downstream from a CRISPR motif in the regulatory region of another gene locus. In other embodiments, the first 14 nt, or the first 13 nt of the dead guide, or the first 12 nt of the guide, or the first 11 nt of the dead guide, or the first 10 nt of the dead guide, does not match an off-target sequence downstream from a CRISPR motif in the regulatory region of another gene locus. In other embodiments, the first 15 nt, or 14 nt, or 13 nt, or 12 nt, or 11 nt of the dead guide do not match an off-target sequence downstream from a CRISPR motif in the genome.

In certain embodiments, the dead guide RNA includes additional nucleotides at the 3'-end that do not match the target sequence. Thus, a dead guide RNA that includes the first 15 nt, or 14 nt, or 13 nt, or 12 nt, or 11 nt downstream of a CRISPR motif can be extended in length at the 3' end to 12 nt, 13 nt, 14 nt, 15 nt, 16 nt, 17 nt, 18 nt, 19 nt, 20 nt, or longer.

The invention provides a method for directing a Cas9 CRISPR-Cas system, including but not limited to a dead Cas9 (dCas9) or functionalized Cas9 system (which may comprise a functionalized Cas9 or functionalized guide) to a gene locus. In an aspect, the invention provides a method for selecting a dead guide RNA targeting sequence and directing a functionalized CRISPR system to a gene locus in an organism. In an aspect, the invention provides a method for selecting a dead guide RNA targeting sequence and effecting gene regulation of a target gene locus by a functionalized Cas9 CRISPR-Cas system. In certain embodiments, the method is used to effect target gene regulation while minimizing off-target effects. In an aspect, the invention provides a method for selecting two or more dead guide RNA targeting sequences and effecting gene regulation of two or more target gene loci by a functionalized Cas9 CRISPR-Cas system. In certain embodiments, the method is used to effect regulation of two or more target gene loci while minimizing off-target effects.

In an aspect, the invention provides a method of selecting a dead guide RNA targeting sequence for directing a functionalized Cas9 to a gene locus in an organism, which comprises: a) locating one or more CRISPR motifs in the gene locus; b) analyzing the sequence downstream of each CRISPR motif by: i) selecting 10 to 15 nt adjacent to the CRISPR motif, ii) determining the GC content of the sequence; and c) selecting the 10 to 15 nt sequence as a targeting sequence for use in a guide RNA if the GC content of the sequence is 40% or more. In an embodiment, the sequence is selected if the GC content is 50% or more. In an embodiment, the sequence is selected if the GC content is 60% or more. In an embodiment, the sequence is selected if the GC content is 70% or more. In an embodiment, two or more sequences are analyzed and the sequence having the highest GC content is selected. In an embodiment, the method further comprises adding nucleotides to the 3' end of the selected sequence which do not match the sequence downstream of the CRISPR motif. An aspect provides a dead guide RNA comprising the targeting sequence selected according to the aforementioned methods.

In an aspect, the invention provides a dead guide RNA for directing a functionalized CRISPR system to a gene locus in an organism wherein the targeting sequence of the dead guide RNA consists of 10 to 15 nucleotides adjacent to the CRISPR motif of the gene locus, wherein the CG content of the target sequence is 50% or more. In certain embodiments, the dead guide RNA further comprises nucleotides added to the 3' end of the targeting sequence which do not match the sequence downstream of the CRISPR motif of the gene locus.

In an aspect, the invention provides for a single effector to be directed to one or more, or two or more gene loci. In certain embodiments, the effector is associated with a Cas9, and one or more, or two or more selected dead guide RNAs are used to direct the Cas9-associated effector to one or more, or two or more selected target gene loci. In certain embodiments, the effector is associated with one or more, or two or more selected dead guide RNAs, each selected dead guide RNA, when complexed with a Cas9 enzyme, causing its associated effector to localize to the dead guide RNA target. One non-limiting example of such CRISPR systems modulates activity of one or more, or two or more gene loci subject to regulation by the same transcription factor.

In an aspect, the invention provides for two or more effectors to be directed to one or more gene loci. In certain embodiments, two or more dead guide RNAs are employed, each of the two or more effectors being associated with a selected dead guide RNA, with each of the two or more effectors being localized to the selected target of its dead guide RNA. One non-limiting example of such CRISPR systems modulates activity of one or more, or two or more gene loci subject to regulation by different transcription factors. Thus, in one non-limiting embodiment, two or more transcription factors are localized to different regulatory sequences of a single gene. In another non-limiting embodiment, two or more transcription factors are localized to different regulatory sequences of different genes. In certain embodiments, one transcription factor is an activator. In certain embodiments, one transcription factor is an inhibitor. In certain embodiments, one transcription factor is an activator and another transcription factor is an inhibitor. In certain embodiments, gene loci expressing different components of the same regulatory pathway are regulated. In certain embodiments, gene loci expressing components of different regulatory pathways are regulated.

In an aspect, the invention also provides a method and algorithm for designing and selecting dead guide RNAs that are specific for target DNA cleavage or target binding and gene regulation mediated by an active Cas9 CRISPR-Cas system. In certain embodiments, the Cas9 CRISPR-Cas system provides orthogonal gene control using an active Cas9 which cleaves target DNA at one gene locus while at the same time binds to and promotes regulation of another gene locus.

In an aspect, the invention provides an method of selecting a dead guide RNA targeting sequence for directing a functionalized Cas9 to a gene locus in an organism, without cleavage, which comprises a) locating one or more CRISPR motifs in the gene locus; b) analyzing the sequence downstream of each CRISPR motif by i) selecting 10 to 15 nt adjacent to the CRISPR motif, ii) determining the GC content of the sequence, and c) selecting the 10 to 15 nt sequence as a targeting sequence for use in a dead guide RNA if the GC content of the sequence is 30% more, 40% or more. In certain embodiments, the GC content of the targeting sequence is 35% or more, 40% or more, 45% or more, 50% or more, 55% or more, 60% or more, 65% or more, or 70% or more. In certain embodiments, the GC content of the targeting sequence is from 30% to 40% or from 40% to 50% or from 50% to 60% or from 60% to 70%. In an embodiment of the invention, two or more sequences in a gene locus are analyzed and the sequence having the highest GC content is selected.

In an embodiment of the invention, the portion of the targeting sequence in which GC content is evaluated is 10 to 15 contiguous nucleotides of the 15 target nucleotides nearest to the PAM. In an embodiment of the invention, the portion of the guide in which GC content is considered is the 10 to 11 nucleotides or 11 to 12 nucleotides or 12 to 13 nucleotides or 13, or 14, or 15 contiguous nucleotides of the 15 nucleotides nearest to the PAM.

In an aspect, the invention further provides an algorithm for identifying dead guide RNAs which promote CRISPR system gene locus cleavage while avoiding functional activation or inhibition. It is observed that increased GC content in dead guide RNAs of 16 to 20 nucleotides coincides with increased DNA cleavage and reduced functional activation.

It is also demonstrated herein that efficiency of functionalized Cas9 can be increased by addition of nucleotides to the 3' end of a guide RNA which do not match a target sequence downstream of the CRISPR motif. For example, of dead guide RNA 11 to 15 nt in length, shorter guides may be less likely to promote target cleavage, but are also less efficient at promoting CRISPR system binding and functional control. In certain embodiments, addition of nucleotides that don't match the target sequence to the 3' end of the dead guide RNA increase activation efficiency while not increasing undesired target cleavage. In an aspect, the invention also provides a method and algorithm for identifying improved dead guide RNAs that effectively promote CRISPR system function in DNA binding and gene regulation while not promoting DNA cleavage. Thus, in certain embodiments, the invention provides a dead guide RNA that includes the first 15 nt, or 14 nt, or 13 nt, or 12 nt, or 11 nt downstream of a CRISPR motif and is extended in length at the 3' end by nucleotides that mismatch the target to 12 nt, 13 nt, 14 nt, 15 nt, 16 nt, 17 nt, 18 nt, 19 nt, 20 nt, or longer.

In an aspect, the invention provides a method for effecting selective orthogonal gene control. As will be appreciated from the disclosure herein, dead guide selection according to the invention, taking into account guide length and GC content, provides effective and selective transcription control by a functional Cas9 CRISPR-Cas system, for example to regulate transcription of a gene locus by activation or inhibition and minimize off-target effects. Accordingly, by providing effective regulation of individual target loci, the invention also provides effective orthogonal regulation of two or more target loci.

In certain embodiments, orthogonal gene control is by activation or inhibition of two or more target loci. In certain embodiments, orthogonal gene control is by activation or inhibition of one or more target locus and cleavage of one or more target locus.

In one aspect, the invention provides a cell comprising a non-naturally occurring Cas9 CRISPR-Cas system comprising one or more dead guide RNAs disclosed or made according to a method or algorithm described herein wherein the expression of one or more gene products has been altered. In an embodiment of the invention, the expression in the cell of two or more gene products has been altered. The invention also provides a cell line from such a cell.

In one aspect, the invention provides a multicellular organism comprising one or more cells comprising a non-naturally occurring Cas9 CRISPR-Cas system comprising one or more dead guide RNAs disclosed or made according to a method or algorithm described herein. In one aspect, the invention provides a product from a cell, cell line, or multicellular organism comprising a non-naturally occurring Cas9 CRISPR-Cas system comprising one or more dead guide RNAs disclosed or made according to a method or algorithm described herein.

A further aspect of this invention is the use of gRNA comprising dead guide(s) as described herein, optionally in combination with gRNA comprising guide(s) as described herein or in the state of the art, in combination with systems e.g. cells, transgenic animals, transgenic mice, inducible transgenic animals, inducible transgenic mice) which are engineered for either overexpression of Cas9 or preferably knock in Cas9. As a result, a single system (e.g. transgenic animal, cell) can serve as a basis for multiplex gene modifications in systems/network biology. On account of the dead guides, this is now possible in both in vitro, ex vivo, and in vivo.

For example, once the Cas9 is provided for, one or more dead gRNAs may be provided to direct multiplex gene regulation, and preferably multiplex bidirectional gene regulation. The one or more dead gRNAs may be provided in a spatially and temporally appropriate manner if necessary or desired (for example tissue specific induction of Cas9 expression). On account that the transgenic/inducible Cas9 is provided for (e.g. expressed) in the cell, tissue, animal of interest, both gRNAs comprising dead guides or gRNAs comprising guides are equally effective. In the same manner, a further aspect of this invention is the use of gRNA comprising dead guide(s) as described herein, optionally in combination with gRNA comprising guide(s) as described herein or in the state of the art, in combination with systems (e.g. cells, transgenic animals, transgenic mice, inducible transgenic animals, inducible transgenic mice) which are engineered for knockout Cas9 CRISPR-Cas.

As a result, the combination of dead guides as described herein with CRISPR applications described herein and CRISPR applications known in the art results in a highly efficient and accurate means for multiplex screening of systems (e.g. network biology). Such screening allows, for example, identification of specific combinations of gene activities for identifying genes responsible for diseases (e.g. on/off combinations), in particular gene related diseases. A preferred application of such screening is cancer. In the same manner, screening for treatment for such diseases is included in the invention. Cells or animals may be exposed to aberrant conditions resulting in disease or disease like effects. Candidate compositions may be provided and screened for an effect in the desired multiplex environment. For example, a patient's cancer cells may be screened for which gene combinations will cause them to die, and then use this information to establish appropriate therapies.

In one aspect, the invention provides a kit comprising one or more of the components described herein. The kit may include dead guides as described herein with or without guides as described herein.

The structural information provided herein allows for interrogation of dead gRNA interaction with the target DNA and the Cas9 permitting engineering or alteration of dead gRNA structure to optimize functionality of the entire Cas9 CRISPR-Cas system. For example, loops of the dead gRNA may be extended, without colliding with the Cas9 protein by the insertion of adaptor proteins that can bind to RNA. These adaptor proteins can further recruit effector proteins or fusions which comprise one or more functional domains.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

An aspect of the invention is that the above elements are comprised in a single composition or comprised in individual compositions. These compositions may advantageously be applied to a host to elicit a functional effect on the genomic level.

In general, the dead gRNA are modified in a manner that provides specific binding sites (e.g. aptamers) for adapter proteins comprising one or more functional domains (e.g. via fusion protein) to bind to. The modified dead gRNA are modified such that once the dead gRNA forms a CRISPR complex (i.e. Cas9 binding to dead gRNA and target) the adapter proteins bind and, the functional domain on the adapter protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target.

The skilled person will understand that modifications to the dead gRNA which allow for binding of the adapter+functional domain but not proper positioning of the adapter+functional domain (e.g. due to steric hindrance within the three dimensional structure of the CRISPR complex) are modifications which are not intended. The one or more modified dead gRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some cases, it is advantageous that additionally at least one NLS is provided. In some instances, it is advantageous to position the NLS at the N terminus. When more than one functional domain is included, the functional domains may be the same or different.

The dead gRNA may be designed to include multiple binding recognition sites (e.g. aptamers) specific to the same or different adapter protein. The dead gRNA may be designed to bind to the promoter region −1000-+1 nucleic acids upstream of the transcription start site (i.e. TSS), preferably −200 nucleic acids. This positioning improves functional domains which affect gene activation (e.g. transcription activators) or gene inhibition (e.g. transcription repressors). The modified dead gRNA may be one or more modified dead gRNAs targeted to one or more target loci (e.g. at least 1 gRNA, at least 2 gRNA, at least 5 gRNA, at least 10 gRNA, at least 20 gRNA, at least 30 gRNA, at least 50 gRNA) comprised in a composition.

The adaptor protein may be any number of proteins that binds to an aptamer or recognition site introduced into the modified dead gRNA and which allows proper positioning of one or more functional domains, once the dead gRNA has been incorporated into the CRISPR complex, to affect the target with the attributed function. As explained in detail in this application such may be coat proteins, preferably bacteriophage coat proteins. The functional domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified dead gRNA, the (inactivated) Cas9 (with or without functional domains), and the binding protein with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g. lentiviral vector, adenoviral vector, AAV vector). As explained herein, use of different selection markers (e.g. for lentiviral gRNA selection) and concentration of gRNA (e.g. dependent on whether multiple gRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g. gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals, which are not believed prior to the present invention or application. For example, the target cell comprises Cas9 conditionally or inducibly (e.g. in the form of Cre dependent constructs) and/or the adapter protein conditionally or inducibly and, on expression of a vector introduced into the target cell, the vector expresses that which induces or gives rise to the condition of Cas9 expression and/or adaptor expression in the target cell. By applying the teaching and compositions of the current invention with the known method of creating a CRISPR complex, inducible genomic events affected by functional domains are also an aspect of the current invention. One example of this is the creation of a CRISPR knock-in/conditional transgenic animal (e.g. mouse comprising e.g. a Lox-Stop-polyA-Lox(LSL) cassette) and subsequent delivery of one or more compositions providing one or more modified dead gRNA (e.g. −200 nucleotides to TSS of a target gene of interest for gene activation purposes) as described herein (e.g. modified dead gRNA with one or more aptamers recognized by coat proteins, e.g. MS2), one or more adapter proteins as described herein (MS2 binding protein linked to one or more VP64) and means for inducing the conditional animal (e.g. Cre recombinase for rendering Cas9 expression inducible). Alternatively, the adaptor protein may be provided as a conditional or inducible element with a conditional or inducible Cas9 to provide an effective model for screening purposes, which advantageously only requires minimal design and administration of specific dead gRNAs for a broad number of applications.

In another aspect the dead guides are further modified to improve specificity. Protected dead guides may be synthesized, whereby secondary structure is introduced into the 3' end of the dead guide to improve its specificity. A protected guide RNA (pgRNA) comprises a guide sequence capable of hybridizing to a target sequence in a genomic locus of interest in a cell and a protector strand, wherein the protector strand is optionally complementary to the guide sequence and wherein the guide sequence may in part be hybridizable to the protector strand. The pgRNA optionally includes an extension sequence. The thermodynamics of the pgRNA-target DNA hybridization is determined by the number of bases complementary between the guide RNA and target DNA. By employing 'thermodynamic protection', specificity of dead gRNA can be improved by adding a protector sequence. For example, one method adds a complementary protector strand of varying lengths to the 3' end of the guide sequence within the dead gRNA. As a result, the protector strand is bound to at least a portion of the dead gRNA and provides for a protected gRNA (pgRNA). In turn, the dead gRNA references herein may be easily protected using the described embodiments, resulting in pgRNA. The protector strand can be either a separate RNA transcript or strand or a chimeric version joined to the 3' end of the dead gRNA guide sequence.

Tandem Guides and Uses in a Multiplex (Tandem) Targeting Approach

The inventors have shown that CRISPR enzymes as defined herein can employ more than one RNA guide without losing activity. This enables the use of the CRISPR enzymes, systems or complexes as defined herein for targeting multiple DNA targets, genes or gene loci, with a single enzyme, system or complex as defined herein. The guide RNAs may be tandemly arranged, optionally separated by a nucleotide sequence such as a direct repeat as defined herein. The position of the different guide RNAs is the tandem does not influence the activity. It is noted that the terms "CRISPR-Cas system", "CRISP-Cas complex" "CRISPR complex" and "CRISPR system" are used interchangeably. Also, the terms "CRISPR enzyme", "Cas enzyme", or "CRISPR-Cas enzyme", can be used interchangeably. In preferred embodiments, said CRISPR enzyme, CRISP-Cas enzyme or Cas enzyme is Cas9, or any one of the modified or mutated variants thereof described herein elsewhere.

In one aspect, the invention provides a non-naturally occurring or engineered CRISPR enzyme, preferably a class 2 CRISPR enzyme, preferably a Type V or VI CRISPR enzyme as described herein, such as without limitation Cas9 as described herein elsewhere, used for tandem or multiplex targeting. It is to be understood that any of the CRISPR (or CRISPR-Cas or Cas) enzymes, complexes, or systems according to the invention as described herein elsewhere may be used in such an approach. Any of the methods, products, compositions and uses as described herein elsewhere are equally applicable with the multiplex or tandem targeting approach further detailed below. By means of further guidance, the following particular aspects and embodiments are provided.

In one aspect, the invention provides for the use of a Cas9 enzyme, complex or system as defined herein for targeting multiple gene loci. In one embodiment, this can be established by using multiple (tandem or multiplex) guide RNA (gRNA) sequences.

In one aspect, the invention provides methods for using one or more elements of a Cas9 enzyme, complex or system as defined herein for tandem or multiplex targeting, wherein said CRISP system comprises multiple guide RNA sequences. Preferably, said gRNA sequences are separated by a nucleotide sequence, such as a direct repeat as defined herein elsewhere.

The Cas9 enzyme, system or complex as defined herein provides an effective means for modifying multiple target polynucleotides. The Cas9 enzyme, system or complex as defined herein has a wide variety of utility including modifying (e.g., deleting, inserting, translocating, inactivating, activating) one or more target polynucleotides in a multiplicity of cell types. As such the Cas9 enzyme, system or complex as defined herein of the invention has a broad spectrum of applications in, e.g., gene therapy, drug screening, disease diagnosis, and prognosis, including targeting multiple gene loci within a single CRISPR system.

In one aspect, the invention provides a Cas9 enzyme, system or complex as defined herein, i.e. a Cas9 CRISPR-Cas complex having a Cas9 protein having at least one destabilization domain associated therewith, and multiple guide RNAs that target multiple nucleic acid molecules such as DNA molecules, whereby each of said multiple guide RNAs specifically targets its corresponding nucleic acid molecule, e.g., DNA molecule. Each nucleic acid molecule target, e.g., DNA molecule can encode a gene product or encompass a gene locus. Using multiple guide RNAs hence enables the targeting of multiple gene loci or multiple genes. In some embodiments the Cas9 enzyme may cleave the DNA molecule encoding the gene product. In some embodiments expression of the gene product is altered. The Cas9 protein and the guide RNAs do not naturally occur together. The invention comprehends the guide RNAs comprising tandemly arranged guide sequences. The invention further comprehends coding sequences for the Cas9 protein being codon optimized for expression in a eukaryotic cell. In a preferred embodiment the eukaryotic cell is a mammalian cell, a plant cell or a yeast cell and in a more preferred embodiment the mammalian cell is a human cell. Expression of the gene product may be decreased. The Cas9 enzyme may form part of a CRISPR system or complex, which further comprises tandemly arranged guide RNAs (gRNAs) comprising a series of 2, 3, 4, 5, 6, 7, 8, 9, 10, 15, 25, 30, or more than 30 guide sequences, each capable of specifically hybridizing to a target sequence in a genomic locus of interest in a cell. In some embodiments, the functional Cas9 CRISPR system or complex binds to the multiple target sequences. In some embodiments, the functional CRISPR system or complex may edit the multiple target sequences, e.g., the target sequences may comprise a genomic locus, and in some embodiments, there may be an alteration of gene expression. In some embodiments, the functional CRISPR system or complex may comprise further functional domains. In some embodiments, the invention provides a method for altering or modifying expression of multiple gene products. The method may comprise introducing into a cell containing said target nucleic acids, e.g., DNA molecules, or containing and expressing target nucleic acid, e.g., DNA molecules; for instance, the target nucleic acids may encode gene products or provide for expression of gene products (e.g., regulatory sequences).

In preferred embodiments the CRISPR enzyme used for multiplex targeting is Cas9, or the CRISPR system or complex comprises Cas9. In some embodiments, the CRISPR enzyme used for multiplex targeting is AsCas9, or the CRISPR system or complex used for multiplex targeting comprises an AsCas9. In some embodiments, the CRISPR enzyme is an LbCas9, or the CRISPR system or complex comprises LbCas9. In some embodiments, the Cas9 enzyme used for multiplex targeting cleaves both strands of DNA to produce a double strand break (DSB). In some embodiments, the CRISPR enzyme used for multiplex targeting is a nickase. In some embodiments, the Cas9 enzyme used for multiplex targeting is a dual nickase. In some embodiments, the Cas9 enzyme used for multiplex targeting is a Cas9 enzyme such as a DD Cas9 enzyme as defined herein elsewhere.

In some general embodiments, the Cas9 enzyme used for multiplex targeting is associated with one or more functional domains. In some more specific embodiments, the CRISPR enzyme used for multiplex targeting is a dead Cas9 as defined herein elsewhere.

In an aspect, the present invention provides a means for delivering the Cas9 enzyme, system or complex for use in multiple targeting as defined herein or the polynucleotides defined herein. Non-limiting examples of such delivery means are e.g. particle(s) delivering component(s) of the complex, vector(s) comprising the polynucleotide(s) discussed herein (e.g., encoding the CRISPR enzyme, providing the nucleotides encoding the CRISPR complex). In some embodiments, the vector may be a plasmid or a viral vector such as AAV, or lentivirus. Transient transfection with plasmids, e.g., into HEK cells may be advantageous, especially given the size limitations of AAV and that while Cas9 fits into AAV, one may reach an upper limit with additional guide RNAs.

Also provided is a model that constitutively expresses the Cas9 enzyme, complex or system as used herein for use in multiplex targeting. The organism may be transgenic and may have been transfected with the present vectors or may be the offspring of an organism so transfected. In a further aspect, the present invention provides compositions comprising the CRISPR enzyme, system and complex as defined herein or the polynucleotides or vectors described herein. Also provides are Cas9 CRISPR systems or complexes comprising multiple guide RNAs, preferably in a tandemly arranged format. Said different guide RNAs may be separated by nucleotide sequences such as direct repeats.

Also provided is a method of treating a subject, e.g., a subject in need thereof, comprising inducing gene editing by transforming the subject with the polynucleotide encoding the Cas9 CRISPR system or complex or any of polynucleotides or vectors described herein and administering them to the subject. A suitable repair template may also be provided, for example delivered by a vector comprising said repair template. Also provided is a method of treating a subject, e.g., a subject in need thereof, comprising inducing transcriptional activation or repression of multiple target gene loci by transforming the subject with the polynucleotides or vectors described herein, wherein said polynucleotide or vector encodes or comprises the Cas9 enzyme, complex or system comprising multiple guide RNAs, preferably tandemly arranged. Where any treatment is occurring ex vivo, for example in a cell culture, then it will be appreciated that the term 'subject' may be replaced by the phrase "cell or cell culture."

Compositions comprising Cas9 enzyme, complex or system comprising multiple guide RNAs, preferably tandemly arranged, or the polynucleotide or vector encoding or comprising said Cas9 enzyme, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a Cas9 CRISPR system in screening is also provided by the present invention, e.g., gain of function screens. Cells which are artificially forced to overexpress a gene are able to down regulate the gene over time (re-establishing equilibrium) e.g. by negative feedback loops. By the time the screen starts the unregulated gene might be reduced again. Using an inducible Cas9 activator allows one to induce transcription right before the screen and therefore minimizes the chance of false negative hits. Accordingly, by use of the instant invention in screening, e.g., gain of function screens, the chance of false negative results may be minimized.

In one aspect, the invention provides an engineered, non-naturally occurring CRISPR system comprising a Cas9 protein and multiple guide RNAs that each specifically target a DNA molecule encoding a gene product in a cell, whereby the multiple guide RNAs each target their specific DNA molecule encoding the gene product and the Cas9 protein cleaves the target DNA molecule encoding the gene product, whereby expression of the gene product is altered; and, wherein the CRISPR protein and the guide RNAs do not naturally occur together. The invention comprehends the multiple guide RNAs comprising multiple guide sequences, preferably separated by a nucleotide sequence such as a direct repeat and optionally fused to a tracr sequence. In an embodiment of the invention the CRISPR protein is a type V or VI CRISPR-Cas protein and in a more preferred embodiment the CRISPR protein is a Cas9 protein. The invention further comprehends a Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to the multiple Cas9 CRISPR system guide RNAs that each specifically target a DNA molecule encoding a gene product and a second regulatory element operably linked coding for a CRISPR protein. Both regulatory elements may be located on the same vector or on different vectors of the system. The multiple guide RNAs target the multiple DNA molecules encoding the multiple gene products in a cell and the CRISPR protein may cleave the multiple DNA molecules encoding the gene products (it may cleave one or both strands or have substantially no nuclease activity), whereby expression of the multiple gene products is altered; and, wherein the CRISPR protein and the multiple guide RNAs do not naturally occur together. In a preferred embodiment the CRISPR protein is Cas9 protein, optionally codon optimized for expression in a eukaryotic cell. In a preferred embodiment the eukaryotic cell is a mammalian cell, a plant cell, or a yeast cell and in a more preferred embodiment the mammalian cell is a human cell. In a further embodiment of the invention, the expression of each of the multiple gene products is altered, preferably decreased.

In one aspect, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas9 enzyme complexed with the one or more guide sequence(s) that is hybridized to the one or more target sequence(s); and (b) a second regulatory element operably linked to an enzyme-coding sequence encoding said Cas9 enzyme, preferably comprising at least one nuclear localization sequence and/or at least one NES; wherein components (a) and (b) are located on the same or different vectors of the system. Where applicable, a tracr sequence may also be provided. In some embodiments, component (a) further comprises two or more guide sequences operably linked to the first regulatory element, wherein when expressed, each of the two or more guide sequences direct sequence specific binding of a Cas9 CRISPR complex to a different target sequence in a eukaryotic cell. In some embodiments, the CRISPR complex comprises one or more nuclear localization sequences and/or one or more NES of sufficient strength to drive accumulation of said Cas9 CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the Cas9 enzyme, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

In some embodiments, a host cell is transiently or non-transiently transfected with one or more vectors comprising the polynucleotides encoding the Cas9 enzyme, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the Cas9 enzyme, system or complex for use in multiple targeting as defined herein is used to establish a new cell line comprising one or more vector-derived sequences. In some embodiments, a cell transiently transfected with the components of a Cas9 CRISPR system or complex for use in multiple targeting as described herein (such as by transient transfection of one or more vectors, or transfection with RNA), and modified through the activity of a Cas9 CRISPR system or complex, is used to establish a new cell line comprising cells containing the modification but lacking any other exogenous sequence. In some embodiments, cells transiently or non-transiently transfected with one or more vectors comprising the polynucleotides encoding the Cas9 enzyme, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the Cas9 CRISPR complex to the respective target sequence(s) in a eukaryotic cell, wherein the Cas9 CRISPR complex comprises a Cas9 enzyme complexed with the one or more guide sequence(s) that is hybridized to the respective target sequence(s); and/or (b) a second regulatory element operably linked to an enzyme-coding sequence encoding said Cas9 enzyme comprising preferably at least one nuclear localization sequence and/or NES. In some embodiments, the host cell comprises components (a) and (b). Where applicable, a tracr sequence may also be provided. In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a Cas9 CRISPR complex to a different target sequence in a eukaryotic cell. In some embodiments, the Cas9 enzyme comprises one or more nuclear localization sequences and/or nuclear export sequences or NES of sufficient strength to drive accumulation of said CRISPR enzyme in a detectable amount in and/or out of the nucleus of a eukaryotic cell.

In some embodiments, the Cas9 enzyme is a type V or VI CRISPR system enzyme. In some embodiments, the Cas9 enzyme is a Cas9 enzyme. In some embodiments, the Cas9 enzyme is derived from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, Candidatus Methanoplasma *termitum, Eubacterium eligens, Moraxella bovoculi* 237, *Leptospira inadai, Lachnospiraceae bacterium* ND2006, *Porphyromonas crevioricanis* 3, *Prevotella disiens*, or *Porphyromonas macacae* Cas9, and may include further alterations or mutations of the Cas9 as defined herein elsewhere, and can be a chimeric Cas9. In some embodiments, the Cas9 enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the one or more guide sequence(s) is (are each) at least 16, 17, 18, 19, 20, 25 nucleotides, or between 16-30, or between 16-25, or between 16-20 nucleotides in length. When multiple guide RNAs are used, they are preferably separated by a direct repeat sequence. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

In one aspect, the invention provides a kit comprising one or more of the components described herein. In some embodiments, the kit comprises a vector system and instructions for using the kit. In some embodiments, the vector system comprises (a) a first regulatory element operably linked to a direct repeat sequence and one or more insertion sites for inserting one or more guide sequences up- or downstream (whichever applicable) of the direct repeat sequence, wherein when expressed, the guide sequence directs sequence-specific binding of a Cas9 CRISPR complex to a target sequence in a eukaryotic cell, wherein the Cas9 CRISPR complex comprises a Cas9 enzyme complexed with the guide sequence that is hybridized to the target sequence; and/or (b) a second regulatory element operably linked to an enzyme-coding sequence encoding said Cas9 enzyme comprising a nuclear localization sequence. Where applicable, a tracr sequence may also be provided. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme comprises one or more nuclear localization sequences of sufficient strength to drive accumulation of said CRISPR enzyme in a detectable amount in the nucleus of a eukaryotic cell. In some embodiments, the CRISPR enzyme is a type V or VI CRISPR system enzyme. In some embodiments, the CRISPR enzyme is a Cas9 enzyme. In some embodiments, the Cas9 enzyme is derived from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, Candidatus Methanoplasma *termitum, Eubacterium eligens, Moraxella bovoculi* 237, *Leptospira inadai, Lachnospiraceae bacterium* ND2006, *Porphyromonas crevioricanis* 3, *Prevotella disiens*, or *Porphyromonas macacae* Cas9 (e.g., modified to have or be associated with at least one DD), and may include further alteration or mutation of the Cas9, and can be a chimeric Cas9. In some embodiments, the DD-CRISPR enzyme is codon-optimized for expression in a eukaryotic cell. In some embodiments, the DD-CRISPR enzyme directs cleavage of one or two strands at the location of the target sequence. In some embodiments, the DD-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 16, 17, 18, 19, 20, 25 nucleotides, or between 16-30, or between 16-25, or between 16-20 nucleotides in length.

In one aspect, the invention provides a method of modifying multiple target polynucleotides in a host cell such as a eukaryotic cell. In some embodiments, the method comprises allowing a Cas9CRISPR complex to bind to multiple target polynucleotides, e.g., to effect cleavage of said multiple target polynucleotides, thereby modifying multiple target polynucleotides, wherein the Cas9CRISPR complex comprises a Cas9 enzyme complexed with multiple guide sequences each of the being hybridized to a specific target sequence within said target polynucleotide, wherein said multiple guide sequences are linked to a direct repeat sequence. Where applicable, a tracr sequence may also be provided (e.g. to provide a single guide RNA, sgRNA). In some embodiments, said cleavage comprises cleaving one or two strands at the location of each of the target sequence by said Cas9 enzyme. In some embodiments, said cleavage results in decreased transcription of the multiple target genes. In some embodiments, the method further comprises repairing one or more of said cleaved target polynucleotide by homologous recombination with an exogenous template polynucleotide, wherein said repair results in a mutation comprising an insertion, deletion, or substitution of one or more nucleotides of one or more of said target polynucleotides. In some embodiments, said mutation results in one or more amino acid changes in a protein expressed from a gene comprising one or more of the target sequence(s). In some embodiments, the method further comprises delivering one or more vectors to said eukaryotic cell, wherein the one or more vectors drive expression of one or more of: the Cas9 enzyme and the multiple guide RNA sequence linked to a direct repeat sequence. Where applicable, a tracr sequence may also be provided. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of multiple polynucleotides in a eukaryotic cell. In some embodiments, the method comprises allowing a Cas9 CRISPR complex to bind to multiple polynucleotides such that said binding results in increased or decreased expression of said polynucleotides; wherein the Cas9 CRISPR complex comprises a Cas9 enzyme complexed with multiple guide sequences each specifically hybridized to its own target sequence within said polynucleotide, wherein said guide sequences are linked to a direct repeat sequence. Where applicable, a tracr sequence may also be provided. In some embodiments, the method further comprises delivering one or more vectors to said eukaryotic cells, wherein the one or more vectors drive expression of one or more of: the Cas9 enzyme and the multiple guide sequences linked to the direct repeat sequences. Where applicable, a tracr sequence may also be provided.

In one aspect, the invention provides a recombinant polynucleotide comprising multiple guide RNA sequences up- or downstream (whichever applicable) of a direct repeat sequence, wherein each of the guide sequences when expressed directs sequence-specific binding of a Cas9CRISPR complex to its corresponding target sequence present in a eukaryotic cell. In some embodiments, the target sequence is a viral sequence present in a eukaryotic cell. Where applicable, a tracr sequence may also be provided. In some embodiments, the target sequence is a proto-oncogene or an oncogene.

Aspects of the invention encompass a non-naturally occurring or engineered composition that may comprise a guide RNA (gRNA) comprising a guide sequence capable of hybridizing to a target sequence in a genomic locus of interest in a cell and a Cas9 enzyme as defined herein that may comprise at least one or more nuclear localization sequences.

An aspect of the invention encompasses methods of modifying a genomic locus of interest to change gene expression in a cell by introducing into the cell any of the compositions described herein.

An aspect of the invention is that the above elements are comprised in a single composition or comprised in individual compositions. These compositions may advantageously be applied to a host to elicit a functional effect on the genomic level.

As used herein, the term "guide RNA" or "gRNA" has the leaning as used herein elsewhere and comprises any polynucleotide sequence having sufficient complementarity with a target nucleic acid sequence to hybridize with the target nucleic acid sequence and direct sequence-specific binding of a nucleic acid-targeting complex to the target nucleic acid sequence. Each gRNA may be designed to include multiple binding recognition sites (e.g., aptamers) specific to the same or different adapter protein. Each gRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified gRNA may be one or more modified gRNAs targeted to one or more target loci (e.g., at least 1 gRNA, at least 2 gRNA, at least 5 gRNA, at least 10 gRNA, at least 20 gRNA, at least 30 g RNA, at least 50 gRNA) comprised in a composition. Said multiple gRNA sequences can be tandemly arranged and are preferably separated by a direct repeat.

Thus, gRNA, the CRISPR enzyme as defined herein may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral sgRNA selection) and concentration of gRNA (e.g., dependent on whether multiple gRNAs are used) may be advantageous for eliciting an improved effect. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals; see, e.g., Platt et al., Cell (2014), 159(2): 440-455, or PCT patent publications cited herein, such as WO 2014/093622

(PCT/US2013/074667). For example, cells or animals such as non-human animals, e.g., vertebrates or mammals, such as rodents, e.g., mice, rats, or other laboratory or field animals, e.g., cats, dogs, sheep, etc., may be 'knock-in' whereby the animal conditionally or inducibly expresses Cas9 akin to Platt et al. The target cell or animal thus comprises the CRISPR enzyme (e.g., Cas9) conditionally or inducibly (e.g., in the form of Cre dependent constructs), on expression of a vector introduced into the target cell, the vector expresses that which induces or gives rise to the condition of the CRISPR enzyme (e.g., Cas9) expression in the target cell. By applying the teaching and compositions as defined herein with the known method of creating a CRISPR complex, inducible genomic events are also an aspect of the current invention. Examples of such inducible events have been described herein elsewhere.

In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920—retina (eye).

In some embodiments disease targets also include: cancer; Sickle Cell Anemia (based on a point mutation); HBV, HIV; Beta-Thalassemia; and ophthalmic or ocular disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA.

Methods, products and uses described herein may be used for non-therapeutic purposes. Furthermore, any of the methods described herein may be applied in vitro and ex vivo.

In an aspect, provided is a non-naturally occurring or engineered composition comprising:

I. two or more CRISPR-Cas system polynucleotide sequences comprising (a) a first guide sequence capable of hybridizing to a first target sequence in a polynucleotide locus, (b) a second guide sequence capable of hybridizing to a second target sequence in a polynucleotide locus, (c) a direct repeat sequence, and II. a Cas9 enzyme or a second polynucleotide sequence encoding it, wherein when transcribed, the first and the second guide sequences direct sequence-specific binding of a first and a second Cas9 CRISPR complex to the first and second target sequences respectively, wherein the first CRISPR complex comprises the Cas9 enzyme complexed with the first guide sequence that is hybridizable to the first target sequence, wherein the second CRISPR complex comprises the Cas9 enzyme complexed with the second guide sequence that is hybridizable to the second target sequence, and wherein the first guide sequence directs cleavage of one strand of the DNA duplex near the first target sequence and the second guide sequence directs cleavage of the other strand near the second target sequence inducing a double strand break, thereby modifying the organism or the non-human or non-animal organism. Similarly, compositions comprising more than two guide RNAs can be envisaged e.g. each specific for one target and arranged tandemly in the composition or CRISPR system or complex as described herein.

In another embodiment, the Cas9 is delivered into the cell as a protein. In another and particularly preferred embodiment, the Cas9 is delivered into the cell as a protein or as a nucleotide sequence encoding it. Delivery to the cell as a protein may include delivery of a Ribonucleoprotein (RNP) complex, where the protein is complexed with the multiple guides.

In an aspect, host cells and cell lines modified by or comprising the compositions, systems or modified enzymes of present invention are provided, including stem cells, and progeny thereof.

In an aspect, methods of cellular therapy are provided, where, for example, a single cell or a population of cells is sampled or cultured, wherein that cell or cells is or has been modified ex vivo as described herein and is then re-introduced (sampled cells) or introduced (cultured cells) into the organism. Stem cells, whether embryonic or induce pluripotent or totipotent stem cells, are also particularly preferred in this regard. But, of course, in vivo embodiments are also envisaged.

Inventive methods can further comprise delivery of templates, such as repair templates, which may be dsODN or ssODN, see below. Delivery of templates may be via the cotemporaneous or separate from delivery of any or all the CRISPR enzyme or guide RNAs and via the same delivery mechanism or different. In some embodiments, it is preferred that the template is delivered together with the guide RNAs and, preferably, also the CRISPR enzyme. An example may be an AAV vector where the CRISPR enzyme is AsCas9 or LbCas9.

Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or—(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

The invention also comprehends products obtained from using CRISPR enzyme or Cas enzyme or Cas9 enzyme or CRISPR-CRISPR enzyme or CRISPR-Cas system or CRISPR-Cas9 system for use in tandem or multiple targeting as defined herein.

Escorted Guides for the Cas9 CRISPR-Cas System According to the Invention

In one aspect, the invention provides escorted Cas9 CRISPR-Cas systems or complexes, especially such a system involving an escorted Cas9 CRISPR-Cas system guide. By "escorted" is meant that the Cas9 CRISPR-Cas system or complex or guide is delivered to a selected time or place within a cell, so that activity of the Cas9 CRISPR-Cas system or complex or guide is spatially or temporally controlled. For example, the activity and destination of the Cas9 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted Cas9 CRISPR-Cas systems or complexes have a gRNA with a functional structure designed to improve gRNA structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, provided herein is a gRNA modified, e.g., by one or more aptamer(s) designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to a selected effector. The invention accordingly comprehends an gRNA that responds to normal or pathological physiological conditions, including without limitation pH, hypoxia, 02 concentration, temperature, protein concentration, enzymatic concentration, lipid structure, light exposure, mechanical disruption (e.g. ultrasound waves), magnetic fields, electric fields, or electromagnetic radiation.

An aspect of the invention provides non-naturally occurring or engineered composition comprising an escorted guide RNA (egRNA) comprising:

an RNA guide sequence capable of hybridizing to a target sequence in a genomic locus of interest in a cell; and, an escort RNA aptamer sequence, wherein the escort aptamer has binding affinity for an aptamer ligand on or in the cell, or the escort aptamer is responsive to a localized aptamer effector on or in the cell, wherein the presence of the aptamer ligand or effector on or in the cell is spatially or temporally restricted.

The escort aptamer may for example change conformation in response to an interaction with the aptamer ligand or effector in the cell.

The escort aptamer may have specific binding affinity for the aptamer ligand.

The aptamer ligand may be localized in a location or compartment of the cell, for example on or in a membrane of the cell. Binding of the escort aptamer to the aptamer ligand may accordingly direct the egRNA to a location of interest in the cell, such as the interior of the cell by way of binding to an aptamer ligand that is a cell surface ligand. In this way, a variety of spatially restricted locations within the cell may be targeted, such as the cell nucleus or mitochondria.

Once intended alterations have been introduced, such as by editing intended copies of a gene in the genome of a cell, continued CRISPR/Cas9 expression in that cell is no longer necessary. Indeed, sustained expression would be undesirable in certain casein case of off-target effects at unintended genomic sites, etc. Thus time-limited expression would be useful. Inducible expression offers one approach, but in addition Applicants have engineered a Self-Inactivating Cas9 CRISPR-Cas system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self-inactivating Cas9 CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cas9 gene, (c) within 100 bp of the ATG translational start codon in the Cas9 coding sequence, (d) within the inverted terminal repeat (iTR) of a viral delivery vector, e.g., in an AAV genome.

The egRNA may include an RNA aptamer linking sequence, operably linking the escort RNA sequence to the RNA guide sequence.

In embodiments, the egRNA may include one or more photolabile bonds or non-naturally occurring residues.

In one aspect, the escort RNA aptamer sequence may be complementary to a target miRNA, which may or may not be present within a cell, so that only when the target miRNA is present is there binding of the escort RNA aptamer sequence to the target miRNA which results in cleavage of the egRNA by an RNA-induced silencing complex (RISC) within the cell.

In embodiments, the escort RNA aptamer sequence may for example be from 10 to 200 nucleotides in length, and the egRNA may include more than one escort RNA aptamer sequence.

It is to be understood that any of the RNA guide sequences as described herein elsewhere can be used in the egRNA described herein. In certain embodiments of the invention, the guide RNA or mature crRNA comprises, consists essentially of, or consists of a direct repeat sequence and a guide sequence or spacer sequence. In certain embodiments, the guide RNA or mature crRNA comprises, consists essentially of, or consists of a direct repeat sequence linked to a guide sequence or spacer sequence. In certain embodiments the guide RNA or mature crRNA comprises 19 nts of partial direct repeat followed by 23-25 nt of guide sequence or spacer sequence. In certain embodiments, the effector protein is a FnCas9 effector protein and requires at least 16 nt of guide sequence to achieve detectable DNA cleavage and a minimum of 17 nt of guide sequence to achieve efficient DNA cleavage in vitro. In certain embodiments, the direct repeat sequence is located upstream (i.e., 5') from the guide sequence or spacer sequence. In a preferred embodiment the seed sequence (i.e. the sequence essential critical for recognition and/or hybridization to the sequence at the target locus) of the FnCas9 guide RNA is approximately within the first 5 nt on the 5' end of the guide sequence or spacer sequence.

The egRNA may be included in a non-naturally occurring or engineered Cas9 CRISPR-Cas complex composition, together with a Cas9 which may include at least one mutation, for example a mutation so that the Cas9 has no more than 5% of the nuclease activity of a Cas9 not having the at least one mutation, for example having a diminished nuclease activity of at least 97%, or 100% as compared with the Cas9 not having the at least one mutation. The Cas9 may also include one or more nuclear localization sequences. Mutated Cas9 enzymes having modulated activity such as diminished nuclease activity are described herein elsewhere.

The engineered Cas9 CRISPR-Cas composition may be provided in a cell, such as a eukaryotic cell, a mammalian cell, or a human cell.

In embodiments, the compositions described herein comprise a Cas9 CRISPR-Cas complex having at least three functional domains, at least one of which is associated with Cas9 and at least two of which are associated with egRNA.

The compositions described herein may be used to introduce a genomic locus event in a host cell, such as a eukaryotic cell, in particular a mammalian cell, or a non-human eukaryote, in particular a non-human mammal such as a mouse, in vivo. The genomic locus event may comprise affecting gene activation, gene inhibition, or cleavage in a locus. The compositions described herein may also be used to modify a genomic locus of interest to change gene expression in a cell. Methods of introducing a genomic locus event in a host cell using the Cas9 enzyme provided herein are described herein in detail elsewhere. Delivery of the composition may for example be by way of delivery of a nucleic acid molecule(s) coding for the composition, which nucleic acid molecule(s) is operatively linked to regulatory sequence(s), and expression of the nucleic acid molecule(s) in vivo, for example by way of a lentivirus, an adenovirus, or an AAV.

The present invention provides compositions and methods by which gRNA-mediated gene editing activity can be adapted. The invention provides gRNA secondary structures that improve cutting efficiency by increasing gRNA and/or increasing the amount of RNA delivered into the cell. The gRNA may include light labile or inducible nucleotides.

To increase the effectiveness of gRNA, for example gRNA delivered with viral or non-viral technologies, Applicants added secondary structures into the gRNA that enhance its stability and improve gene editing. Separately, to overcome the lack of effective delivery, Applicants modified gRNAs with cell penetrating RNA aptamers; the aptamers bind to cell surface receptors and promote the entry of gRNAs into cells. Notably, the cell-penetrating aptamers can be designed to target specific cell receptors, in order to mediate cell-specific delivery. Applicants also have created guides that are inducible.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity: Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

Cells involved in the practice of the present invention may be a prokaryotic cell or a eukaryotic cell, advantageously an animal cell a plant cell or a yeast cell, more advantageously a mammalian cell.

The chemical or energy sensitive guide may undergo a conformational change upon induction by the binding of a chemical source or by the energy allowing it act as a guide and have the Cas9 CRISPR-Cas system or complex function. The invention can involve applying the chemical source or energy so as to have the guide function and the Cas9 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., world wide web.nature.com/nmeth/journal/v2/n6/full/nmeth763.html), 3. GID1-GAI based system inducible by Gibberellin (GA) (see, e.g., world wide web.nature.com/nchembio/journal/v8/n5/full/nchembio.922.html).

Another system contemplated by the present invention is a chemical inducible system based on change in sub-cellular localization. Applicants also developed a system in which the polypeptide include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

This type of system could also be used to induce the cleavage of a genomic locus of interest in a cell when the effector domain is a nuclease.

A chemical inducible system can be an estrogen receptor (ER) based system inducible by 4-hydroxytamoxifen (4OHT) (see, e.g., world wide web. pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., world wide web.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas9 CRISPR-Cas complex or system, and the binding will induce the change of sub-cellular localization of the polypeptide, leading to the entire polypeptide entering the nucleus of cells. Once inside the nucleus, the guide protein and the other components of the Cas9 CRISPR-Cas complex will be active and modulating target gene expression in cells.

This type of system could also be used to induce the cleavage of a genomic locus of interest in a cell; and, in this regard, it is noted that the Cas9 enzyme is a nuclease. The light could be generated with a laser or other forms of energy sources. The heat could be generated by raise of temperature results from an energy source, or from nano-particles that release heat after absorbing energy from an energy source delivered in the form of radio-wave.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, ‘electric field energy’ is the electrical energy to which a cell is exposed. Preferably the electric field has a strength of from about 1 Volt/cm to about 10 kVolts/cm or more under in vivo conditions (see WO97/49450).

As used herein, the term “electric field” includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term “pulse” includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm$^2$ to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic, and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm$^{-2}$. Even more preferably, the exposure to an ultrasound energy source is at a power density of from about 1 to about 15 Wcm$^{-2}$.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm$^{-2}$ to about 10 Wcm$^{-2}$ with a frequency ranging from about 0.015 to about 10 MHz (see WO 98/52609). However, alternatives are also possible, for example, exposure to an ultrasound energy source at an acoustic power density of above 100 Wcm$^{-2}$, but for reduced periods of time, for example, 1000 Wcm$^{-2}$ for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm$^{-2}$ or 1.25 Wcm$^{-2}$ as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

The rapid transcriptional response and endogenous targeting of the instant invention make for an ideal system for the study of transcriptional dynamics. For example, the instant invention may be used to study the dynamics of variant production upon induced expression of a target gene. On the other end of the transcription cycle, mRNA degradation studies are often performed in response to a strong extracellular stimulus, causing expression level changes in a plethora of genes. The instant invention may be utilized to reversibly induce transcription of an endogenous target, after which point stimulation may be stopped and the degradation kinetics of the unique target may be tracked.

The temporal precision of the instant invention may provide the power to time genetic regulation in concert with experimental interventions. For example, targets with suspected involvement in long-term potentiation (LTP) may be modulated in organotypic or dissociated neuronal cultures, but only during stimulus to induce LTP, so as to avoid interfering with the normal development of the cells. Similarly, in cellular models exhibiting disease phenotypes, targets suspected to be involved in the effectiveness of a particular therapy may be modulated only during treatment. Conversely, genetic targets may be modulated only during a pathological stimulus. Any number of experiments in which timing of genetic cues to external experimental stimuli is of relevance may potentially benefit from the utility of the instant invention.

The in vivo context offers equally rich opportunities for the instant invention to control gene expression. Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the Cas9 CRISPR-Cas system or complex of the invention, or, in the case of transgenic Cas9 animals, guide RNA of the invention may be delivered and the optrode technology can allow for the modulation of gene expression in precise brain regions. A transparent Cas9 expressing organism, can have guide RNA of the invention administered to it and then there can be extremely precise laser induced local gene expression changes.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

The invention may also offer valuable temporal precision in vivo. The invention may be used to alter gene expression during a particular stage of development. The invention may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

Protected Guides: Enzymes According to the Invention can be Used in Combination with Protected Guide RNAs In one aspect, an object of the current invention is to further enhance the specificity of Cas9 given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets.

In one aspect, the invention provides for the guide sequence being modified by secondary structure to increase the specificity of the Cas9 CRISPR-Cas system and whereby the secondary structure can protect against exonuclease activity and allow for 3' additions to the guide sequence.

In one aspect, the invention provides for hybridizing a "protector RNA" to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target DNA binding to the mismatched base pairs at the 3' end. In embodiments of the invention, additional sequences comprising an extended length may also be present.

Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20nt and Z is of length 1-30nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended.

An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length; In a preferred embodiment, the ExL is denoted as 0 or 4 nucleotides in length. In a more preferred embodiment, the ExL is 4 nucleotides in length. The extension sequence may or may not be complementary to the target sequence.

An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

Cas9Cas9In one aspect, the invention provides for enhanced Cas9Cas9 specificity wherein the double stranded 3' end of the protected guide RNA (pgRNA) allows for two possible outcomes: (1) the guide RNA-protector RNA to guide RNA-target DNA strand exchange will occur and the guide will fully bind the target, or (2) the guide RNA will fail to fully bind the target and because Cas9 target cleavage is a multiple step kinetic reaction that requires guide RNA: target DNA binding to activate Cas9-catalyzed DSBs, wherein Cas9 cleavage does not occur if the guide RNA does not properly bind. According to particular embodiments, the protected guide RNA improves specificity of target binding as compared to a naturally occurring CRISPR-Cas system.

According to particular embodiments the protected modified guide RNA improves stability as compared to a naturally occurring CRISPR-Cas. According to particular embodiments the protector sequence has a length between 3 and 120 nucleotides and comprises 3 or more contiguous nucleotides complementary to another sequence of guide or protector. According to particular embodiments, the protector sequence forms a hairpin. According to particular embodiments the guide RNA further comprises a protected sequence and an exposed sequence. According to particular embodiments the exposed sequence is 1 to 19 nucleotides. More particularly, the exposed sequence is at least 75%, at least 90% or about 100% complementary to the target sequence. According to particular embodiments the guide sequence is at least 90% or about 100% complementary to the protector strand. According to particular embodiments the guide sequence is at least 75%, at least 90% or about 100% complementary to the target sequence. According to particular embodiments, the guide RNA further comprises an extension sequence. More particularly, the extension sequence is operably linked to the 3' end of the protected guide sequence, and optionally directly linked to the 3' end of the protected guide sequence. According to particular embodiments the extension sequence is 1-12 nucleotides. According to particular embodiments the extension sequence is operably linked to the guide sequence at the 3' end of the protected guide sequence and the 5' end of the protector strand and optionally directly linked to the 3' end of the protected guide sequence and the 3' end of the protector strand, wherein the extension sequence is a linking sequence between the protected sequence and the protector strand. According to particular embodiments the extension sequence is 100% not complementary to the protector strand, optionally at least 95%, at least 90%, at least 80%, at least 70%, at least 60%, or at least 50% not complementary to the protector strand. According to particular embodiments the guide sequence further comprises mismatches appended to the end of the guide sequence, wherein the mismatches thermodynamically optimize specificity.

In one aspect, the invention provides an engineered, non-naturally occurring CRISPR-Cas system comprising a Cas9 protein and a protected guide RNA that targets a DNA molecule encoding a gene product in a cell, whereby the protected guide RNA targets the DNA molecule encoding the gene product and the Cas9 protein cleaves the DNA molecule encoding the gene product, whereby expression of the gene product is altered; and, wherein the Cas9 protein and the protected guide RNA do not naturally occur together. The invention comprehends the protected guide RNA comprising a guide sequence fused 3' to a direct repeat sequence. The invention further comprehends the Cas9 protein being codon optimized for expression in a Eukaryotic cell. In a preferred embodiment the Eukaryotic cell is a mammalian cell, a plant cell or a yeast cell and in a more preferred embodiment the mammalian cell is a human cell. In a further embodiment of the invention, the expression of the gene product is decreased. In some embodiments, the Cas9 enzyme is *Acidaminococcus* sp. BV3L6, *Lachnospiraceae bacterium* or *Francisella Novicida* Cas9, and may include mutated Cas9 derived from these organisms. The enzyme may be a further Cas9 homolog or ortholog. In some embodiments, the nucleotide sequence encoding the Cfp1 enzyme is codon-optimized for expression in a eukaryotic cell. In some embodiments, the Cas9 enzyme directs cleavage of one or two strands at the location of the target sequence. In some embodiments, the first regulatory element is a polymerase III promoter. In some embodiments, the second regulatory element is a polymerase II promoter. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide sequences downstream of the direct repeat sequence, wherein when expressed, the guide sequence directs sequence-specific binding of a CRISPR complex to a target sequence in a eukaryotic cell, wherein the CRISPR complex comprises a CRISPR enzyme complexed with the guide RNA comprising the guide sequence that is hybridized to the target sequence and/or (b) a second regulatory element operably linked to an enzyme-coding sequence encoding said Cas9 enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme directs cleavage of one or two strands at the location of the target sequence. In some embodiments, the Cas9 enzyme lacks DNA strand cleavage activity. In some embodiments, the first regulatory element is a polymerase III promoter. In some embodiments, the second regulatory element is a polymerase II promoter.

In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant or a yeast. Further, the organism may be a fungus.

In one aspect, the invention provides a kit comprising one or more of the components described herein above. In some embodiments, the kit comprises a vector system and instructions for using the kit. In some embodiments, the vector system comprises (a) a first regulatory element operably linked to a direct repeat sequence and one or more insertion sites for inserting one or more guide sequences downstream of the direct repeat sequence, wherein when expressed, the guide sequence directs sequence-specific binding of a Cas9 CRISPR complex to a target sequence in a eukaryotic cell, wherein the CRISPR complex comprises a Cas9 enzyme complexed with the protected guide RNA comprising the guide sequence that is hybridized to the target sequence and/or (b) a second regulatory element operably linked to an enzyme-coding sequence encoding said Cas9 enzyme comprising a nuclear localization sequence. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme comprises one or more nuclear localization sequences of sufficient strength to drive accumulation of said Cas9 enzyme in a detectable amount in the nucleus of a eukaryotic cell. In some embodiments, the Cas9 enzyme is *Acidaminococcus* sp. BV3L6, *Lachnospiraceae bacterium* MA2020 or *Francisella tularensis* 1 *Novicida* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a Cas9 enzyme complexed with protected guide RNA comprising a guide sequence hybridized to a target sequence within said target polynucleotide. In some embodiments, said cleavage comprises cleaving one or two strands at the location of the target sequence by said Cas9 enzyme. In some embodiments, said cleavage results in decreased transcription of a target gene. In some embodiments, the method further comprises repairing said cleaved target polynucleotide by non-homologous end joining (NHEJ)-based gene insertion mechanisms, more particularly with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the Cas9 enzyme, the protected guide RNA comprising the guide sequence linked to direct repeat sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a Cas9 CRISPR complex to bind to the polynucleotide such that said binding results in increased or decreased expression of said polynucleotide; wherein the CRISPR complex comprises a Cas9 enzyme complexed with a protected guide RNA comprising a guide sequence hybridized to a target sequence within said polynucleotide. In some embodiments, the method further comprises delivering one or more vectors to said eukaryotic cells, wherein the one or more vectors drive expression of one or more of: the Cas9 enzyme and the protected guide RNA.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a Cas9 enzyme and a protected guide RNA comprising a guide sequence linked to a direct repeat sequence; and (b) allowing a CRISPR complex to bind to a target polynucleotide to effect cleavage of the target polynucleotide within said disease gene, wherein the CRISPR complex comprises the Cas9 enzyme complexed with the guide RNA comprising the sequence that is hybridized to the target sequence within the target polynucleotide, thereby generating a model eukaryotic cell comprising a mutated disease gene. In some embodiments, said cleavage comprises cleaving one or two strands at the location of the target sequence by said Cas9 enzyme. In some embodiments, said cleavage results in decreased transcription of a target gene. In some embodiments, the method further comprises repairing said cleaved target polynucleotide by non-homologous end joining (NHEJ)-based gene insertion mechanisms with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a protected guide sequence downstream of a direct repeat sequence, wherein the protected guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a Cas9 enzyme, a protected guide RNA comprising a guide sequence, and an editing template; wherein the editing template comprises the one or more mutations that abolish Cas9 enzyme cleavage; allowing non-homologous end joining (NHEJ)-based gene insertion mechanisms of the editing template with the target polynucleotide in the cell(s) to be selected; allowing a CRISPR complex to bind to a target polynucleotide to effect cleavage of the target polynucleotide within said gene, wherein the CRISPR complex comprises the Cas9 enzyme complexed with the protected guide RNA comprising a guide sequence that is hybridized to the target sequence within the target polynucleotide, wherein binding of the CRISPR complex to the target polynucleotide induces cell death, thereby allowing one or more cell(s) in which one or more mutations have been introduced to be selected. In a preferred embodiment of the invention the cell to be selected may be a eukaryotic cell. Aspects of the invention allow for selection of specific cells without requiring a selection marker or a two-step process that may include a counter-selection system.

With respect to mutations of the Cas9 enzyme, when the enzyme is not FnCas9, mutations may be as described herein elsewhere; conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations are selected from those described herein elsewhere.

In a further aspect, the invention involves a computer-assisted method for identifying or designing potential compounds to fit within or bind to CRISPR-Cas9 system or a functional portion thereof or vice versa (a computer-assisted method for identifying or designing potential CRISPR-Cas9 systems or a functional portion thereof for binding to desired compounds) or a computer-assisted method for identifying or designing potential CRISPR-Cas9 systems (e.g., with regard to predicting areas of the CRISPR-Cas9 system to be able to be manipulated—for instance, based on crystal structure data or based on data of Cas9 orthologs, or with respect to where a functional group such as an activator or repressor can be attached to the CRISPR-Cas9 system, or as to Cas9 truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Cas9 crystal structure, e.g., in the CRISPR-Cas9 system binding domain or alternatively or additionally in domains that vary based on variance among Cas9 orthologs or as to Cas9s or as to nickases or as to functional groups, optionally with structural information from CRISPR-Cas9 system complex(es), thereby generating a data set;

(b) comparing, using said processor, said data set to a computer database of structures stored in said computer data storage system, e.g., structures of compounds that bind or putatively bind or that are desired to bind to a CRISPR-Cas9 system or as to Cas9 orthologs (e.g., as Cas9s or as to domains or regions that vary amongst Cas9 orthologs) or as to the CRISPR-Cas9 crystal structure or as to nickases or as to functional groups;

(c) selecting from said database, using computer methods, structure(s)—e.g., CRISPR-Cas9 structures that may bind to desired structures, desired structures that may bind to certain CRISPR-Cas9 structures, portions of the CRISPR-Cas9 system that may be manipulated, e.g., based on data from other portions of the CRISPR-Cas9 crystal structure and/or from Cas9 orthologs, truncated Cas9s, novel nickases or particular functional groups, or positions for attaching functional groups or functional-group-CRISPR-Cas9 systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-Cas9 system;

or, said method comprising: providing the co-ordinates of at least two atoms of the CRISPR-Cas9 crystal structure, e.g., at least two atoms of the herein Crystal Structure Table of the CRISPR-Cas9 crystal structure or co-ordinates of at least a sub-domain of the CRISPR-Cas9 crystal structure ("selected co-ordinates"), providing the structure of a candidate comprising a binding molecule or of portions of the CRISPR-Cas9 system that may be manipulated, e.g., based on data from other portions of the CRISPR-Cas9 crystal structure and/or from Cas9 orthologs, or the structure of functional groups, and fitting the structure of the candidate to the selected co-ordinates, to thereby obtain product data comprising CRISPR-Cas9 structures that may bind to desired structures, desired structures that may bind to certain CRISPR-Cas9 structures, portions of the CRISPR-Cas9 system that may be manipulated, truncated Cas9s, novel nickases, or particular functional groups, or positions for attaching functional groups or functional-group-CRISPR-Cas9 systems, with output thereof; and optionally synthesizing compound(s) from said product data and further optionally comprising testing said synthesized compound(s) as or in a CRISPR-Cas9 system.

The testing can comprise analyzing the CRISPR-Cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (e.g. POWERPOINT), internet, email, documentary communication such as a computer program (e.g. WORD) document and the like. Accordingly, the invention also comprehends computer readable media containing: atomic co-ordinate data according to the herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three-dimensional structure of CRISPR-Cas9 or at least one sub-domain thereof, or structure factor data for CRISPR-Cas9, said structure factor data being derivable from the atomic co-ordinate data of herein-referenced Crystal Structure. The invention further comprehends a method of doing business comprising providing to a user the computer system or the media or the three dimensional structure of CRISPR-Cas9 or at least one sub-domain thereof, or structure factor data for CRISPR-Cas9, said structure set forth in and said structure factor data being derivable from the atomic co-ordinate data of herein-referenced Crystal Structure, or the herein computer media or a herein data transmission.

A "binding site" or an "active site" comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention and calculating the extent to which such interactions are stable. Interactions include attraction and repulsion, brought about by charge, steric considerations, and the like. Various computer-based methods for fitting are described further.

By "root mean square (or rms) deviation", we mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows, or Apple operating systems.

By "computer readable media", is meant any medium or media, which can be read and accessed directly or indirectly by a computer e.g., so that the media is suitable for use in the above-mentioned computer system. Such media include but are not limited to magnetic storage media such as floppy discs, hard disc storage medium, and magnetic tape; optical storage media such as optical discs or CD-ROM; electrical storage media such as RAM and ROM; thumb drive devices; cloud storage devices and hybrids of these categories such as magnetic/optical storage media.

The invention comprehends the use of the protected guides described herein above in the optimized functional CRISPR-Cas enzyme systems described herein.

Also, with respect to general information on gene editing systems that may be used in the present invention, mention is made of the following:

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013).

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013).

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013).

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13) 01015-5 (2013-A).

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013).

Genome engineering using the CRISPR-Cas9 system. Ran, FA., Hsu, PD., Wright, J., Agarwala, V., Scott, DA., Zhang, F. Nature Protocols November; 8(11): 2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013). [Epub ahead of print];

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014).

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014).

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014).

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014).

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014).

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015).

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015).

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse).

In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

Zetsche et al., "Cpf1 Is a Single RNA-Guided Endonuclease of a Class 2 CRISPR-Cas System," Cell 163, 1-13 (Oct. 22, 2015).

Shmakov et al., "Discovery and Functional Characterization of Diverse Class 2 CRISPR-Cas Systems," Molecular Cell 60, 1-13 (Available online Oct. 22, 2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position, and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, “Dimeric CRISPR RNA-guided FokI nucleases for highly specific genome editing”, Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme Fold. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or “wild type TALEs” are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term “polypeptide monomers”, “TALE monomers” or “monomers” will be used to refer to the highly conserved repetitive polypeptide sequences within the TALE nucleic acid binding domain and the term “repeat variable di-residues” or “RVD” will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine, and thymine with comparable affinity.

Figure 8:
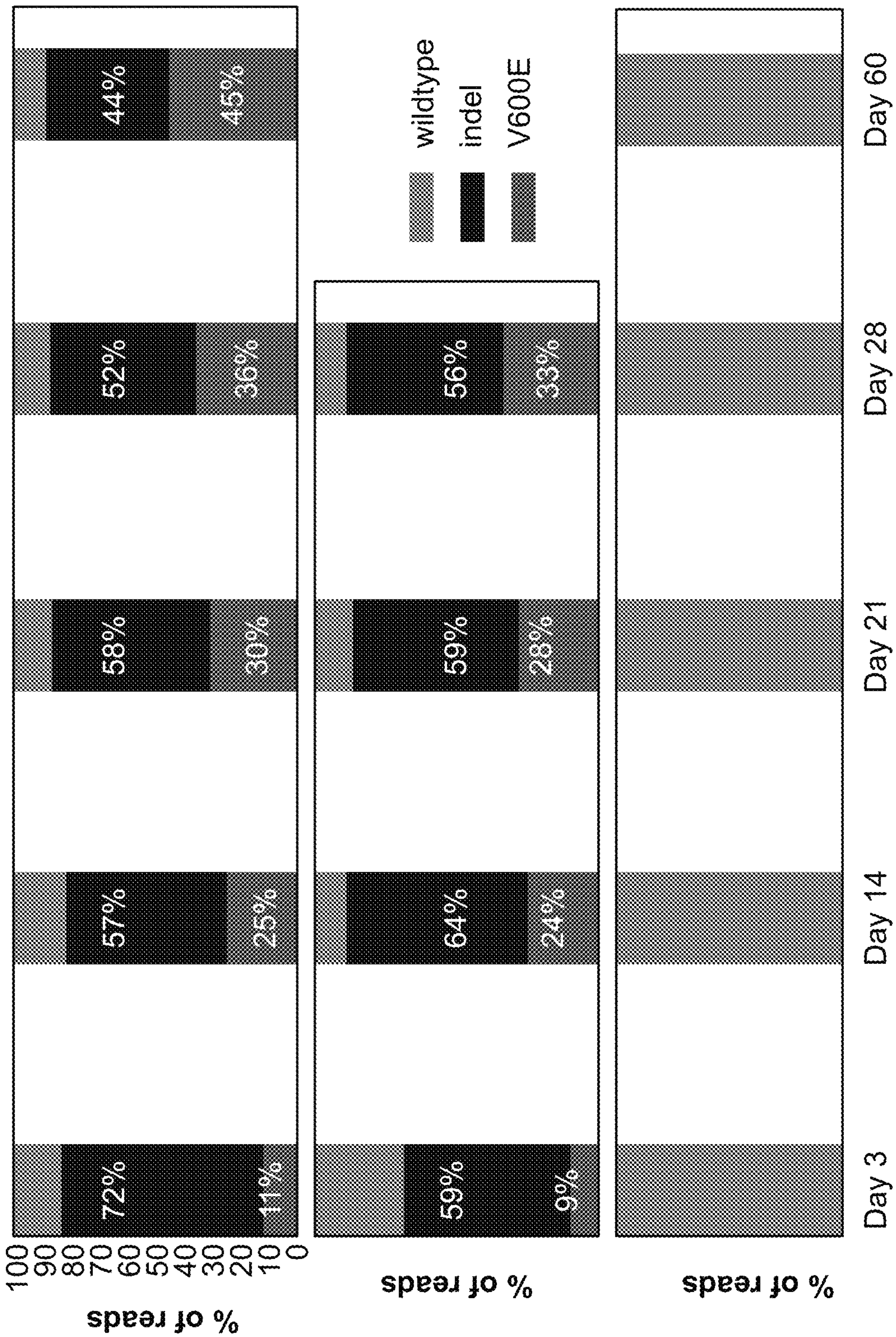
FIG. 8 illustrates that BRAF V600E undergoes selection as second event in CDKNA−/− melanocytes, over weeks in culture.

The predetermined N-terminal to C-terminal order of the one or more polypeptide monomers of the nucleic acid or DNA binding domain determines the corresponding predetermined target nucleic acid sequence to which the polypeptides of the invention will bind. As used herein, the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

As used herein, the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., *Nature Biotechnology* 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments, the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Screening

In certain embodiments, the cells of the present invention may be used for screening phenotypes resulting from perturbation of single cells in a population of the engineered cells. Not being bound by a theory, perturbation of cells along different phases of cancer development can elucidate key networks and targets involved in cancer development. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). In certain embodiments, target genes (e.g., genes for targeting with a drug) may be perturbed in a population of cells according to the present invention and the perturbation may be identified and assigned to the phenotypic readouts of single cells (e.g., proteomic and gene expression). Not being bound by a theory, networks of genes that are disrupted due to perturbation of a target genes in the specific cells of the current invention may be determined. Understanding the network of genes effected by a perturbation may allow for a gene to be linked to a specific pathway that may be targeted to modulate and treat a cancer. Thus, in certain embodiments, Perturb-seq is used to discover novel drug targets to allow treatment of specific cancer patients having the combination of mutations according to the present invention.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq).

In preferred embodiments, the single cell RNA-seq is performed by any method as described herein (e.g., Drop-seq, InDrop, 10×genomics). In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Swiech et al., 2014, "In vivo interrogation of gene function in the mammalian brain using CRISPR-Cas9" Nature Biotechnology Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, all the contents and disclosure of each of which are herein incorporated by reference in their entirety.

In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimising deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)).

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

A CRISPR system may be delivered to the cells of the present invention as described herein. Over 80% transduction efficiency may be achieved with Lenti-CRISPR constructs in CD4 and CD8 T-cells. Despite success with lentiviral delivery, recent work by Hendel et al, (Nature Biotechnology 33, 985-989 (2015) doi:10.1038/nbt.3290) showed the efficiency of editing human T-cells with chemically modified RNA, and direct RNA delivery to T-cells via electroporation. In certain embodiments, perturbation may use these methods.

In certain embodiments, after determining Perturb-seq effects in the cells of the present invention, the cells are infused to a tumor xenograft models to observe the phenotypic effects of genome editing. Not being bound by a theory, detailed characterization can be performed based on the phenotypes related to tumor progression, tumor growth, immune response, etc.

Functional Assays and Screening for Drug Candidates

In certain embodiments, the engineered population of cells of the present invention are used to screen for test agents (e.g., drug candidates, compositions) capable of use as a therapeutic to treat cancer. As used herein "treating" includes ameliorating, curing, preventing it from becoming worse, slowing the rate of progression, or preventing the disorder from re-occurring (i.e., to prevent a relapse). An effective amount of a composition refers to an amount of the composition that results in a therapeutic effect. For example, in methods for treating cancer in a subject, an effective amount of a composition is any amount that provides an anti-cancer effect, such as reduces or prevents proliferation of a cancer cell or is cytotoxic towards a cancer cell. In certain embodiments, the effective amount of a composition is reduced when an inhibitor is administered concomitantly or in combination with one or more additional a composition as compared to the effective amount of the composition when administered in the absence of one or more additional compositions. In certain embodiments, the composition does not reduce or prevent proliferation of a cancer cell when administered in the absence of one or more additional compositions.

Screening assays for drug candidates are designed to identify compounds that inhibit tumor growth, viability, migration, immune evasion, or otherwise interfere with the ability of a tumor to cause cancer. In certain embodiments, such screening assays will include assays amenable to high-throughput screening of chemical libraries, making them particularly suitable for identifying small molecule drug candidates. Small molecules contemplated include synthetic organic or inorganic compounds, including peptides preferably soluble peptides, (poly)peptide-immunoglobulin fusions, and in particular, antibodies including, without limitation poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including in vitro and in vivo cell based assays, which are well characterized in the art. As used herein the term “cell-based” refers to assays using live cells. Screening assays may detect a variety of molecular events, including transcriptional activity (e.g., using a reporter gene), immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

In certain embodiments, a test agent can be added to a population of cells according to the present invention and assayed according to any embodiment herein (e.g., cell proliferation, apoptosis) relative to controls where no test agent is added.

In certain embodiments, cells of the present invention are assayed for apoptosis. Apoptosis assays may be performed by terminal deoxynucleotidyl transferase dUTP Nick End Labeling (TUNEL) assay. The TUNEL assay is used to measure nuclear DNA fragmentation characteristic of apoptosis (Lazebnik et al, 1994, Nature 371, 346), by following the incorporation of fluorescein-dUTP (Yonehara et al, 1989, J. Exp. Med. 169, 1747). Apoptosis may further be assayed by acridine orange staining of tissue culture cells (Lucas, R., et al., 1998, Blood 15:4730-41). A test agent can be added to the apoptosis assay system and changes in induction of apoptosis relative to controls where no test agent is added can be measured to identify candidate modulating agents. In some embodiments of the invention, an apoptosis assay may be used as a secondary assay to test candidate modulating agents. An apoptosis assay may also be used to test whether a specific perturbation (e.g., gene mutation) plays a direct role in apoptosis. For example, an apoptosis assay may be performed on cells that have a specific set of mutations introduced and positively selected. Apoptosis assays are described further in U.S. Pat. No. 6,133,437.

In certain embodiments, cells of the present invention are assayed for cell proliferation. In certain embodiments, cell proliferation is assayed upon addition of mutations to a population of cells. In certain embodiments, cell proliferation is assayed upon addition of a test agent.

Cell proliferation may be assayed via bromodeoxyuridine (BrdU) incorporation. This assay identifies a cell population undergoing DNA synthesis by incorporation of BrdU into newly-synthesized DNA. Newly-synthesized DNA may then be detected using an anti-BrdU antibody (Hoshino et al, 1986, Int. J. Cancer 38, 369; Campana et al, 1988, J. Immunol. Meth. 107, 79), or by other means.

Another measure of cell proliferation is the metabolic activity of a population of cells. Tetrazolium salts or Alamar Blue are compounds that become reduced in the environment of metabolically active cells, forming a formazan dye that subsequently changes the color of the media (Voytik-Harbin S L et al., 1998, In Vitro Cell Dev Biol Anim 34:239-46). The absorption of the media-containing dye solution can be read using a spectrophotometer or microplate reader in low- or high-throughput configurations. MTT is insoluble in standard culture medium, and the formazan crystals produced during reduction must be dissolved in DMSO or isopropanol, thus, MTT is mainly an endpoint assay. The other salts, as well as Alamar Blue, are soluble in culture media and are nontoxic. They can be used for continuous monitoring, to follow dynamic changes in proliferation over time. XTT reduces less efficiently and may need additional factors added. WST1 is more sensitive, reduces more efficiently and shows faster color development compared to the other salts. Alamar Blue is also sensitive, capable of detecting as few as 100 cells in a well of a microtiter plate. The tetrazolium salts and Alamar Blue redox dyes can be quantified with a range of instruments for conventional or high-throughput studies using, for example, standard spectrophotometers or spectrofluorometers or plate readers for spectrophotometric or spectrofluorometric microtiter well plates.

A third way to measure cell proliferation is to detect an antigen present in proliferating cells, but not nonproliferating cells, using a monoclonal antibody to the antigen. For example, a Ki-67 antibody recognizes the protein of the same name, expressed during the S, G2 and M phases of the cell cycle but not during the G0 and G1 (nonproliferative) phases. In certain embodiments, proliferation makers are assayed by flow cytometry. Other common markers for cell proliferation and/or cell cycle regulation, targeted by antibodies, include PCNA (proliferating cell nuclear antigen), topoisomerase IIB and phospho-histone H3. Phospho-histone H3 staining identifies a cell population undergoing mitosis by phosphorylation of histone H3. Phosphorylation of histone H3 at serine 10 is detected using an antibody specific to the phosphorylated form of the serine 10 residue of histone H3 (Chadlee, D. N. 1995, J. Biol. Chem 270: 20098-105).

Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA synthesis. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter).

Another type of cell proliferation assay takes advantage of the tight regulation of intracellular ATP within cells. Dying or dead cells contain little to no ATP, so there is a tight linear relationship between cell number and the concentration of ATP measured in a cell lysate or extract. The bioluminescence-based detection of ATP, using the enzyme luciferase and its substrate luciferin, provides a very sensitive readout. In the presence of ATP, luciferase produces light (proportional to the ATP concentration) that can be detected by a luminometer or any microplate reader capable of reading luminescent signals. This approach is also well suited to high-throughput cell proliferation assays and screening. In certain embodiments high-throughput proliferation assays are used as a primary screen for identifying modulators.

Cell proliferation may also be assayed by colony formation in soft agar (Sambrook et al., Molecular Cloning, Cold Spring Harbor (1989)). For example, cells of the present invention may be seeded in soft agar plates, and colonies measured and counted after about two weeks incubation.

In certain embodiments, cells of the present invention are assayed for angiogenesis. Angiogenesis may be assayed using various human endothelial cell systems, such as umbilical vein, coronary artery, or dermal cells. Suitable assays include Alamar Blue based assays to measure proliferation; migration assays using fluorescent molecules, such as the use of Becton Dickinson Falcon HTS FluoroBlok cell culture inserts to measure migration of cells through membranes in the presence or absence of angiogenesis enhancers or suppressors; and tubule formation assays based on the formation of tubular structures by endothelial cells on Matrigel® (Becton Dickinson). Accordingly, an angiogenesis assay system may comprise a cell according to the present invention. A test agent can be added to the angiogenesis assay system and changes in angiogenesis relative to controls where no test agent is added can be measured. In some embodiments of the invention, the angiogenesis assay may be used as a secondary assay to test candidate modulating agents that are initially identified using another assay system. U.S. Pat. Nos. 5,976,782, 6,225,118 and 6,444,434, among others, describe various angiogenesis assays.

In certain embodiments, cells of the present invention are assayed for cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced and used to coat the wells of a microtiter plate. The wells used for negative control are not coated. Coated wells are then washed, blocked with BSA, and washed again. Compounds are diluted and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader. Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only are the binding specificity of the peptides and modulators against cell lines determined, but also the functional cell signaling of attached cells using immunofluorescence techniques in situ on the microchip (Falsey J R et al., Bioconjug Chem. 2001 May-June; 12(3):346-53).

In certain embodiments, cells of the present invention are assayed for cell migration. An invasion/migration assay (also called a migration assay) tests the ability of cells to overcome a physical barrier and to migrate towards a signal (e.g., pro-angiogenic signal, another cell). Migration assays are known in the art (e.g., Paik J H et al., 2001, J Biol Chem 276:11830-11837). In a typical experimental set-up, cultured cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, MA), and is generally part of an upper chamber that is in fluid contact with a lower chamber containing stimuli. Migration is generally assayed after an overnight incubation with stimuli, but longer or shorter time frames may also be used. Migration is assessed as the number of cells that crossed the lamina and may be detected by staining cells with hematoxylin solution (VWR Scientific, South San Francisco, CA), or by any other method for determining cell number. In another exemplary set up, cells are fluorescently labeled, and migration is detected using fluorescent readings, for instance using the Falcon HTS FluoroBlok (Becton Dickinson). While some migration is observed in the absence of stimulus, migration is greatly increased in response to pro-angiogenic factors.

In certain embodiments, cells of the present invention are assayed for tumorigenicity. Tumor xenograft assays are known in the art (see, e.g., Carreno et al., Clin Cancer Res. 2009 May 15; 15(10):3277-86. doi: 10.1158/1078-0432; and Puchalapalli et al., PLoS One. 2016 Sep. 23; 11(9): e0163521). Xenografts are typically implanted into mice as single cell suspensions either from a preexisting tumor or from in vitro culture. The tumor weight is assessed by measuring perpendicular diameters with a caliper and calculated by multiplying the measurements of diameters in two dimensions. At the end of the experiment, the excised tumors maybe utilized for biomarker identification or further analyses.

Other aspects of the invention relate to methods and compositions for treating cancer in a subject (e.g., with a drug obtained by screening). Cancer is a disease characterized by uncontrolled or aberrantly controlled cell proliferation and other malignant cellular properties. As used herein, the term “cancer” refers to any type of cancer known in the art, including without limitation, breast cancer, biliary tract cancer, bladder cancer, brain cancer, cervical cancer, choriocarcinoma, colon cancer, endometrial cancer, esophageal cancer, gastric cancer, hematological neoplasms, T-cell acute lymphoblastic leukemia/lymphoma, hairy cell leukemia, chronic myelogenous leukemia, multiple myeloma, AIDS-associated leukemias and adult T-cell leukemia/lymphoma, intraepithelial neoplasms, liver cancer, lung cancer, lymphomas, neuroblastomas, oral cancer, ovarian cancer, pancreatic cancer, prostate cancer, rectal cancer, sarcomas, skin cancer, testicular cancer, thyroid cancer, and renal cancer. The cancer cell may be a cancer cell in vivo (i.e., in an organism), ex vivo (i.e., removed from an organism and maintained in vitro), or in vitro. The methods involve administering to a subject a combination of two or more inhibitors of epigenetic genes in an effective amount. In certain embodiments, the subject is a subject having, suspected of having, or at risk of developing cancer. In certain embodiments, the subject is a mammalian subject, including but not limited to a dog, cat, horse, cow, pig, sheep, goat, chicken, rodent, or primate. In certain embodiments, the subject is a human subject, such as a patient. The human subject may be a pediatric or adult subject. Whether a subject is deemed "at risk" of having a cancer may be determined by a skilled practitioner.

The invention is further described in the following examples, which do not limit the scope of the invention described in the claims.

EXAMPLES

Example 1—Protocol to Knock Out a Gene in Human Melanocytes in Culture

Purpose:

1. Controlled knockout of TP53 in CBT cells to test for transformation in ID xenografts.

BRIEF DESCRIPTION

Cells (about −625,000 cells in a 20 μL nucleofection)
CBT−6

Cas9:

1. Cas9 protein from IDT—3.0 ug [0.3 μL @10 μg/μL]—need 1.8 μL sgRNA: TP53 cr1 and TP53 cr7 and NonTargeting cr3

1. IDT Alt-R cr:tracrRNA complex—45 pmol [1.5 μl @30 μM]
   1 ug Cas9 @158.4 kDa=6.31 pmol. Therefore want to add about 2.5x=15.775 pmol of crRNA:tracrRNA complex per 1 ug Cas9

Workflow Timeline:

TABLE 7

| | | |
|---|---|---|
| Day −2 042617 | Passage cells | Done |
| Day 0 042817 | Nucleofect | |
| Day 2 043017 | Move cells from 30C to 37C | |
| Day 3 050117 | Collect gDNA | |

Materials and Instrumentation

1. Plasmids.
2. cells
3. 254M+HMGS-2 media
4. Amaxa 4D nucleofector P3 solution.
5. Amaxa 4D nucleofection X Unit (EO-208).

Step-by-Step:

Day 2 Nucleofection

Steps 1-18 Included Modified Steps from the Lonza Nucleofector Protocol.

1. Make sure that the entire supplement is added to the Nucleofector Solution. The ratio of Nucleofector solution to supplement is 4.5:1 (This lasts for 3 months after you mix).
2. Note that the volume of substrate solution added to each sample should not exceed 10% of the total reaction volume (2 μL for 20 μL reactions; 10 μL for 100 μL reactions—you may need to concentrate plasmid solutions ahead of time accordingly).
3. Use endotoxin-free purification kits. A260:280 ratio should be at least 1.8.
4. Passage cells 2 days before Nucleofection.
5. Prepare cell culture plates by filling them with media and putting in incubator.
6. Let P3 nucleofection solution warm to room temperature.
7. Trypsinize cells with TrypLE.
8. Count and divide as appropriate.
9. Centrifuge at 90×g for 10 min at RT.
10. Prepare nucleofector mastermix with plasmid.
11. Aspirate supernatant from centrifuged cells and add nucleofector master mix.
12. Transfer to cuvette and tap gently to avoid bubbles.
13. Nucleofect in 4D machine (on 10th floor of 75Ames)
14. Add 500 μL media (cuvette) or 80 μL media (16-well strip well)
15. Incubate at 37° C. for 10 minutes.
16. If cell mortality is less of an issue, you can avoid adding more media after nucleofection and do the 10 min incubation at room temp. (Skip this step).
17. Use supplied pipettes (cuvette) or western blot pipette tips (16-well strip) to remove samples from cuvette/wells and plate them. Avoid repeated aspiration.
18. Incubate cells.

Use 625,000 cells per well.

Take:

6-CBT—3,750,000 cells (will go into 6 wells).

centrifuge at 90×g for 10 min and then aspirate supernatant and add:

6-CBT—111 μL nucleofection solution (use 18.5 μL nucleofection solution per well, so 6*18.5=111 uL).

Make 3 RNP Mixtures:

1. 0.6 μL of Life Cas9 @3 μg/μL, 3.0 μL of Alt-R crRNA:tracrRNA NonTarg cr3 @30 μM.
2. 0.6 μL of Life Cas9 @3 μg/μL, 3.0 μL of Alt-R crRNA:tracrRNA TP53 cr1 @30 "M.
3. 0.6 μL of Life Cas9 @3 μg/μL, 3.0 μL of Alt-R crRNA:tracrRNA TP53 cr7 @30 μM.

Incubate at 25° C. thermocycler for 10 minutes.

Add 37 μL cells+nucleofection sol'n to each of the above RNP mixtures.

Load 20 μL per well of 16-well strip, as below.

Add 80 μL media post-nucleofection and incubate for 10 min in 37° C. incubator.

Then 30° C. for 24 hrs.

Then back to 37° C.

Strip #1

A1-H1 (first column) & A2-H2 (second column)

Nucleofection setting: EO-208

TABLE 8

| | |
|---|---|
| 3.0 ug Life Cas9, 45 pmol Alt-R NonTarg cr3 | 3.0 ug Life Cas9, 45 pmol Alt-R NonTarg cr3 |
| 3.0 ug Life Cas9, 45 pmol Alt-R TP53 crl | 3.0 ug Life Cas9, 45 pmol Alt-R TP53 crl |
| 3.0 ug Life Cas9, 45 pmol Alt-R TP53 cr7 | 3.0 ug Life Cas9, 45 pmol Alt-R TP53 cr7 |

To amend this protocol to do a knock-in edit, Applicants add at the very end to each appropriate well: ~10,000 genomic copies per cell of rAAV2/6.2 harboring ~2 kb of homologous sequence to the edited region, containing the desired knock-in mutation(s) as well as a mutation disrupting the binding site of the Cas9 guide, ideally altering the PAM.

Example 2—Method of Generating a Melanoma Model

1. Obtain primary human melanocytes (purchased from Invitrogen).
2. Culture melanocytes in 5% 02, 5% CO2, 37 degrees C., using M254 media+HMGS-2 growth factor supplement (from Invitrogen), switching media every MWF.
3. Once sufficient melanocytes (require ~625,000 cells per experimental condition), passage melanocytes into a new flask.
4. Two days after passaging cells, electroporate with Cas9 RNP with guide(s) targeting CDKN2A exon 2 to knock out the gene, according to our protocol (using Lonza Nucleofector Kit and 4D Nucleofection Machine). Key points here that distinguish the protocol from the standard Lonza protocol:
   A. Using 3 ug Cas9+45 pmol crRNA:tracrRNA complex from IDT per well.
   B. EO208 electroporation shock setting on the Lonza machine.
   C. Do the recommended step where you add 80 uL warm media after electroporation and let the cells sit in the 37° C. incubator for 10 minutes before transferring to plates.
   D. If making a knock-in, add ~10,000 genomic copies per cell of rAAV2/6.2 harboring the necessary homologous DNA donor to the relevant wells. (not necessary for CDKN2A).
   E. After plating, place cells in 30° C. incubator for 2 days ("Cold shock")—this increases the cutting efficiency of Cas9, as the cutting efficiency improves compared to 1 day, and seems to max out at 2 days since 3 days does not increase cutting efficiency. The cold shock may decrease proteasomal degradation of the Cas9 RNP, but this is speculation.
   F. After 2 days at 30° C., transfer the cells to 37° C.
   G. At 3 days, cells may be harvested and replated, with some cells taken for extraction of genomic DNA using QuickExtract, in order to test for efficiency of genomic editing by PCR of the targeted locus and next generation sequencing.
5. Keep cells in culture, periodically extracting genomic DNA to perform PCR on the targeted region (CDKN2A exon 2) followed by library preparation and next generation sequencing to access the percentage of reads with the desired allele.
6. Over time (1-4 weeks), the CDKN2A exon 2 locus will show an increase in indel frequency, eventually stabilizing at 100%. This means the entire cell population has CDKN2A knocked out genetically.
7. Repeat steps 2-6 to introduce BRAF V600E knock-in. (Step 6 will take 4-8 weeks.)
8. Repeat steps 2-6 to introduce TERT C228T knock-in. (Step 6 will take 4-8 weeks.)
9. At this point, the cells have three mutations, and are abbreviated as "CBT" cells. These cells appear to be able to grow indefinitely in culture, whereas "CB" cells senesce around 16-24 months in culture, as do "C" cells and the unaltered, original cells.
10. Repeat steps 2-6 to introduce PTEN knock-out. (Step 6 will take 2-4 weeks).
11. At this point, CBTP quadruple-mutant cells are transformed as judged by a newfound ability to form small, slowly growing tumors within about 1 month when 1 million cells are injected intradermally into the most severely immunocompromised mice (NGS mice).
12. Repeat steps 2-6 to introduce TP53 knock-out. (Step 6 will take 2-4 weeks).
13. At this point, the CBTP+TP53 quintuple mutant cells form substantially larger tumors in mice than the quadruple mutant cells, requiring euthanasia of the mice within 3 months of intradermal injection of 1 million CBTP+TP53 cells into severely immunocompromised mice (NSG).

Applicants also introduced CTNNB1 activating mutations into cells with mutations in CDKN2A/BRAF/TERT/PTEN, and these quintuple-mutant 'CBTPN' cells turned pigmented, which was a feature of melanoma could not be recapitulated until now. These CBTPN cells can be grown in mice and as a result of adding the CTNNB1 activating mutation, the cells become metastatic and spread throughout the mouse's body similar to metastatic melanoma in humans. In conclusion, we have shown that CBT=immortalized, CBTP=immortalized/transformed, and CBTPN=immortalized/transformed/metastatic.

Guide sequences for all genes were determined by empirically testing multiple guides per gene for cutting efficiency (on the extreme end, we tested around 40 Cas9 guide sequences for TERT before settling on one that works).

The following guide sequences were used.

```
1. CDKN2A crRNA 2 (typically delivered in con-
junction with CDKN2A crRNA 8)
DNA genomic sequence:
                                        (SEQ ID NO: 6)
CAGCAGCAGCTCCGCCACTC

RNA version of genomic sequence:
                                        (SEQ ID NO: 7)
CAGCAGCAGCUCCGCCACUC

crRNA sequence:
                                        (SEQ ID NO: 8)
CA GCA GCA GCU CCG CCA CUC GUU WA GAG CUA UGC U

2. CDKN2A crRNA 8 (typically delivered in con-
junction with CDKN2A crRNA 2)
DNA genomic sequence:
                                        (SEQ ID NO: 9)
GACCCGTGCACGACGCTGCC

RNA version of genomic sequence:
                                       (SEQ ID NO: 10)
GACCCGUGCACGACGCUGCC

crRNA sequence:
                                       (SEQ ID NO: 11)
GA CCC GUG CAC GAC GCU GCC GUU UUA GAG CUA UGC U

3. CDKN2A crRNA 1 (typically delivered in con-
junction with CDKN2A crRNA 9)
DNA genomic sequence:
                                       (SEQ ID NO: 12)
GATGATGGGCAGCGCCCGAG

RNA version of genomic sequence:
                                       (SEQ ID NO: 13)
GAUGAUGGGCAGCGCCCGAG

crRNA sequence:
                                       (SEQ ID NO: 14)
GA UGA UGG GCA GCG CCC GAG GUU UUA GAG CUA UGC U
```

-continued

4. CDKN2A crRNA 9 (typically delivered in conjunction with CDKN2A crRNA 1)
DNA genomic sequence:
(SEQ ID NO: 15)
TCGGGTGAGAGTGGCGGGGT RNA version of genomic sequence:
(SEQ ID NO: 16)
UCGGGUGAGAGUGGCGGGGU crRNA sequence:
(SEQ ID NO: 17)
UC GGG UGA GAG UGG CGG GGU GUU UUA GAG CUA UGC U 5. BRAF crRNA 12
DNA genomic sequence:
(SEQ ID NO: 18)
AGACAACTGTTCAAACTGAT RNA version of genomic sequence:

crRNA sequence:
(SEQ ID NO: 19)
AG ACA ACU GUU CAA ACU GAU GUU UUA GAG CUA UGC U 6. TERT crRNA 202
DNA genomic sequence:
(SEQ ID NO: 20)
GCAGCAGGGAGCGCACGGCT RNA version of genomic sequence:
(SEQ ID NO: 21)
GCAGCAGGGAGCGCACGGCU crRNA sequence:
(SEQ ID NO: 22)
GC AGC AGG GAG CGC ACG GCU GUU UUA GAG CUA UGC U 7. PTEN crRNA 6
DNA genomic sequence:
(SEQ ID NO: 23)
AAACAAAAGGAGATATCAAG RNA version of genomic sequence:
(SEQ ID NO: 24)
AAACAAAAGGAGAUAUCAAG crRNA sequence:
(SEQ ID NO: 25)
AA ACA AAA GGA GAU AUC AAG GUU UUA GAG CUA UGC U 8. PTEN crRNA 10
DNA genomic sequence:
(SEQ ID NO: 26)
TTGATGATGGCTGTCATGTC RNA version of genomic sequence:
(SEQ ID NO: 27)
UUGAUGAUGGCUGUCAUGUC crRNA sequence:
(SEQ ID NO: 28)
UU GAU GAU GGC UGU CAU GUC GUU UUA GAG CUA UGC U 9. PTEN crRNA 11
DNA genomic sequence:
(SEQ ID NO: 29)
TGATGATGGCTGTCATGTCT RNA version of genomic sequence:
(SEQ ID NO: 30)
UGAUGAUGGCUGUCAUGUCU crRNA sequence:
(SEQ ID NO: 31)
UG AUG AUG GCU GUC AUG UCU GUU UUA GAG CUA UGC U -continued 10. CTNNB1 crRNA 4
DNA genomic sequence:
(SEQ ID NO: 32)
TTGCCTTTACCACTCAGAGA RNA version of genomic sequence:
(SEQ ID NO: 33)
UUGCCUUUACCACUCAGAGA crRNA sequence:
(SEQ ID NO: 34)
UU GCC UUU ACC ACU CAG AGA GUU UUA GAG CUA UGC U 11. TP53 crRNA 1
DNA genomic sequence:
(SEQ ID NO: 35)
TCCTCAGCATCTTATCCGAG RNA version of genomic sequence:
(SEQ ID NO: 36)
UCCUCAGCAUCUUAUCCGAG crRNA sequence:
(SEQ ID NO: 37)
UC CUC AGC AUC UUA UCC GAG GUU UUA GAG CUA UGC U 12. TP53 crRNA 7
DNA genomic sequence:
(SEQ ID NO: 38)
TCCACTCGGATAAGATGCTG RNA version of genomic sequence:
(SEQ ID NO: 39)
UCCACUCGGAUAAGAUGCUG crRNA sequence:
(SEQ ID NO: 40)
UC CAC UCG GAU AAG AUG CUG GUU UUA GAG CUA UGC U The following donor sequence were used and read in a 5' to 3' direction.

RAF V600E (includes silent mutation S607S)
(SEQ ID NO: 41)
GTTGAAGGATATAAAGAAAATCTTGTCTCACAAAGGGAAGATCTTGTGGAC
CCTCTAAAACGGTGTGAGGGACCCTTTTAAGAATGCTGTTTTAGGGAATGA
TTCATATGACTGAGCTTTCCACAGCTTGCTGCAATGCACACAAGTTTTTGT
TCCCTTCTTTTAGAACTTCTCTTTCTTCTTTTCCACAAAGCAAAAAACAAG
AAGAAAGAAAGAGCTATGCAAGACAGCACAAGGCTGTTAATCTACCTCTCA
TTTTTTTTTGTCTTTCCTCTTCCAGCTGCCCCATAATTATGAGATACTTTC
TAGTCTAAAGGAAGTAACTTTCCAATTTAGGCTTAAATAAGATTGCGAAAC
AGCTTCTCTGTTAAAAGGAGTAGTTCTCTTAGCAAAACCATAATAATGGCT
GTGGATCACACCTGCCTTAAATTGCATACCTGTTTTTTTTTTCAACAGGGT
ACACAGAACATTTTGAACACAAAATACTTTAAACAATTTAGAATAAAATAT
GAAACACTGTTTATAAGACATATATTTTTGTTTGAAATACACTGAAACTGG
TTTCAAAATATTCGTTTTAAGGGTTCATATTTATTTAAGAATAAAATATGA
AACACTGTTTATAAGACATATATTTTTGTTTGAAATACACTGAAACTGGTT
TCAAAATATTCGTTTTAAGGGTAAAGAAAAAAGTTAAAAAATCTATTTACA
TAAAAAATAAGAACACTGATTTTTGTGAATACTGGGAACTATGAAAATACT
ATAGTTGAGACCTTCAATGACTTTCTAGTAACTCAGCAGCATCTCAGGGCC
AAAAATTTAATCAGTGGAAAAATAGCCTCAATTCTTACCATCCACAAAATG -continued

GATCCAGACAACTGTTCAAACTGATGACTCCCACTCCATCGAGATTTCTCT

GTAGCTAGACCAAAATCACCTATTTTTACTGTGAGGTCTTCATGAAGAAAT

ATATCTGAGGTGTAGTAAGTAAAGGAAAACAGTAGATCTCATTTTCCTATC

AGAGCAAGCATTATGAAGAGTTTAGGTAAGAGATCTAATTTCTATAATTCT

GTAATATAATATTCTTTAAAACATAGTACTTCATCTTTCCTCTTAGAGTCA

ATAAGTATGTCTAAAACAATGATTAGTTCTATTTAGCCTATATAACCTGCT

TTTAAGATTTTTGGGGCTTGAAATGTGTTAGGATGAGGTGAGATGCTTTCC

TAAGTTTATAGGAGAACCTAAAACTTTCCCATTAGATTTTAGCAATGTAGG

CCCAGATATTCTCTTGGCACTCCTGGGCGAGCAGTAAAGGCTCTTCATTGG

AATGAAGATGCTGCAGATAGTATCTTAGTCTGCACTTAGGGAAGAGAAATA

TTATGTTTTTCTCACCTCATTGTTATATAATTTAGAGTCTTCAGTTATATC

TCAACTACCACTGAGCAAGGTCAGAGGTCTGAAAGGGACTAATAGATAGCT

ACAAAACTATCAGTTTTATAGTGCTGATAAAATGTAAGCAAGCAATCAAAA

ACTCCTACTATTGTAAAGACTTCTGATAGATTTTCTTGTAATGTTCAGTTG

TCGAGAAACCAAAAGCAGGCTGTGGTATCCTGCTCTCCTATACATGCATGC

ACAATCCTTTATTAATTCTCTTTACAGTATATCGAACTTAGCATGAAAACT

GTTTTTACATAATGTGAAGACAAAATGCAGAAGAAAAAGTCAGGATGTTTT

CAAACTTCGCAGACAAATTTCAGGAAGGATACTATTACTCTTGAGGTCTCT

GTGGATGATTGACTTGGCGTGTAAGTAACTGAAAAACAAAACATCA

TERT C228T (includes silent mutation C7C)
(SEQ ID NO: 42)

CGCGTCCTGCCCGGGTGGGCCCAGGACCCCTGCCCAACGGGCGTCCGCTCC

GGCTCAGGGGCAGCGCCACGCCTGGGCCTCTTGGGCAACGGCAGACTTCGG

CTGGCACTGCCCCCGCGCCTCCTCGCACCCGGGGCTGGCAGGCCCAGGGGG

ACCCCGGCCTCCCTGACGCTATGGTTCCAGGCCCGTTCGCATCCCAGACGC

CTTCGGGGTCCACTAGCGTGTGGCGGGGGCCGGGCCTGAGTGGCAGCGCCG

AGCTGGTACAGCGGCGGCCCGCACACCTGGTAGGCGCAGCTGGGAGCCACC

AGCACAAAGAGCGCGCAGCGTGCCAGCAGGTGAACCAGCACGTCGTCGCCC

ACGCGGCGCAGCAGCAGCCCCCACGCCCCGCTCCCCCGCAGTGCGTCGGTC

ACCGTGTTGGGCAGGTAGCTGCGCACGCTGGTGGTGAAGGCCTCGGGGGGG

CCCCCGCGGGCCCCGTCCAGCAGCGCGAAGCCGAAGGCCAGCACGTTCTTC

GCGCCGCGCTCGCACAGCCTCTGCAGCACTCGGGCCACCAGCTCCTTCAGG

CAGGACACCTGCGGGGGAAGCGCCCTGAGTCGCCTGCGCTGCTCTCCGCAT

GTCGCTGGTTCCCCCCGGCCGCCCTCAACCCCAGCCGGACGCCGACCCCGG

GGAGGCCCACCTGGCGGAAGGAGGGGGCGGCGGGGGGCGGCCGTGCGTCCC

AGGGCACGCACACCAGGCACTGGGCCACCAGCGCGCGGAAAGCCGCCGGGT

CCCCGCGCTGCACCAGCCGCCAGCCCTGGGGCCCCAGGCGCCGCACGAACG

TGGCCAGCGGCAGCACCTCGCGGTAGTGGCTGCGCAGCAGGGAGCGCACGG

CTCGACAGCGGGGAGCGCGCGGCATCGCGGGGGTGGCCGGGGCCAGGGCTT

CCCACGTGCGCAGCAGGACGCAGCGCTGCCTGAAACTCGCGCCGCGAGGAG

AGGGCGGGGCCGCGGAAAGGAAGGGGAGGGGCTGGGAGGGCCCGGAAGGGG

CTGGGCCGGGGACCCGGGAGGGGTCGGGACGGGGCGGGGTCCGCGCGGAGG

-continued

AGGCGGAGCTGGAAGGTGAAGGGGCAGGACGGGTGCCCGGGTCCCCAGTCC

CTCCGCCACGTGGGAAGCGCGGTCCTGGGCGTCTGTGCCCGCGAATCCACT

GGGAGCCCGGCCTGGCCCCGACAGCGCAGCTGCTCCGGGCGGACCCGGGGG

TCTGGGCCGCGCTTCCCCGCCCGCGCGCCGCTCGCGCTCCCAGGGTGCAGG

GACGCCAGCGAGGGCCCCAGCGGAGAGAGGTCGAATCGGCCTAGGCTGTGG

GGTAACCCGAGGGAGGGGCCATGATGTGGAGGCCCTGGGAACAGGTGCGTG

CGGCGACCCTTTGGCCGCTGGCCTGATCCGGAGACCCAGGGCTGCCTCCAG

GTCCGGACGCGGGGCGTCGGCTCCGGGCACCACGAATGCCGGACGTGAAG

GGGAGGACGGAGGCGCGTAGACGCGGCTGGGGACGAACCCGAGGACGCATT

GCTCCCTGGACGGGCACGCGGGACCTCCCGGAGTGCCTCCCTGCAACACTT

CCCCGCGACTTGGGCTCCTTGACACAGGCCCGTCATTTCTCTTTGCAGGTT

CTCAGGCGGCGAGGGGTCCCCACCATGAGCAAACCACCCCAAATCTGTTAA

TCACCCACCGGGGCGGTCCCGTCGAGAAAGGGTGGGAAATGGAGCCAGGCG

CTCCTGCTGGCCGCGCACCGGGCGCCTCACACCAGCCACAACGGCCTTGAC

CCTGGGCCCCGGCACTCTGTCTGGCAGATGAGGCCAACATCTGGTCACA

TERT C250T (includes silent mutation C7C)
(SEQ ID NO: 43)

CGCGTCCTGCCCGGGTGGGCCCAGGACCCCTGCCCAACGGGCGTCCGCTCC

GGCTCAGGGGCAGCGCCACGCCTGGGCCTCTTGGGCAACGGCAGACTTCGG

CTGGCACTGCCCCCGCGCCTCCTCGCACCCGGGGCTGGCAGGCCCAGGGGG

ACCCCGGCCTCCCTGACGCTATGGTTCCAGGCCCGTTCGCATCCCAGACGC

CTTCGGGGTCCACTAGCGTGTGGCGGGGGCCGGGCCTGAGTGGCAGCGCCG

AGCTGGTACAGCGGCGGCCCGCACACCTGGTAGGCGCAGCTGGGAGCCACC

AGCACAAAGAGCGCGCAGCGTGCCAGCAGGTGAACCAGCACGTCGTCGCCC

ACGCGGCGCAGCAGCAGCCCCCACGCCCCGCTCCCCCGCAGTGCGTCGGTC

ACCGTGTTGGGCAGGTAGCTGCGCACGCTGGTGGTGAAGGCCTCGGGGGGG

CCCCCGCGGGCCCCGTCCAGCAGCGCGAAGCCGAAGGCCAGCACGTTCTTC

GCGCCGCGCTCGCACAGCCTCTGCAGCACTCGGGCCACCAGCTCCTTCAGG

CAGGACACCTGCGGGGGAAGCGCCCTGAGTCGCCTGCGCTGCTCTCCGCAT

GTCGCTGGTTCCCCCCGGCCGCCCTCAACCCCAGCCGGACGCCGACCCCGG

GGAGGCCCACCTGGCGGAAGGAGGGGGCGGCGGGGGGCGGCCGTGCGTCCC

AGGGCACGCACACCAGGCACTGGGCCACCAGCGCGCGGAAAGCCGCCGGGT

CCCCGCGCTGCACCAGCCGCCAGCCCTGGGGCCCCAGGCGCCGCACGAACG

TGGCCAGCGGCAGCACCTCGCGGTAGTGGCTGCGCAGCAGGGAGCGCACGG

CTCGACAGCGGGGAGCGCGCGGCATCGCGGGGGTGGCCGGGGCCAGGGCTT

CCCACGTGCGCAGCAGGACGCAGCGCTGCCTGAAACTCGCGCCGCGAGGAG

AGGGCGGGGCCGCGGAAAGGAAGGGGAGGGGCTGGGAGGGCCCGGAgGGGG

CTGGGCCGGGGACCCGGaAGGGGTCGGGACGGGGCGGGGTCCGCGCGGAGG

AGGCGGAGCTGGAAGGTGAAGGGGCAGGACGGGTGCCCGGGTCCCCAGTCC

CTCCGCCACGTGGGAAGCGCGGTCCTGGGCGTCTGTGCCCGCGAATCCACT

GGGAGCCCGGCCTGGCCCCGACAGCGCAGCTGCTCCGGGCGGACCCGGGGG

-continued

```
TCTGGGCCGCGCTTCCCCGCCCGCGCGCCGCTCGCGCTCCCAGGGTGCAGG
GACGCCAGCGAGGGCCCCAGCGGAGAGAGGTCGAATCGGCCTAGGCTGTGG
GGTAACCCGAGGGAGGGGCCATGATGTGGAGGCCCTGGGAACAGGTGCGTG
CGGCGACCCTTTGGCCGCTGGCCTGATCCGGAGACCCAGGGCTGCCTCCAG
GTCCGGACGCGGGGCGTCGGGCTCCGGGCACCACGAATGCCGGACGTGAAG
GGGAGGACGGAGGCGCGTAGACGCGGCTGGGGACGAACCCGAGGACGCATT
GCTCCCTGGACGGGCACGCGGGACCTCCCGGAGTGCCTCCCTGCAACACTT
CCCCGCGACTTGGGCTCCTTGACACAGGCCCGTCATTTCTCTTTGCAGGTT
CTCAGGCGGCGAGGGGTCCCCACCATGAGCAAACCACCCCAAATCTGTTAA
TCACCCACCGGGGCGGTCCCGTCGAGAAAGGGTGGGAAATGGAGCCAGGCG
CTCCTGCTGGCCGCGCACCGGGCGCCTCACACCAGCCACAACGGCCTTGAC
CCTGGGCCCCGGCACTCTGTCTGGCAGATGAGGCCAACATCTGGTCACA
```

The above sequences were cloned into an AAV plasmid with ITR sequences.

Modification of Variables:

1. The choice of which gene mutations to introduce and when is the main variable in the system, and there are many recognized melanoma driver mutations that one might like to introduce into this model system.
2. Order of early gene mutation introduction (We determined the order we use empirically: CDKN2A→BRAF→TERT).
3. Percent O2 during cell growth (current: 5%—have not tested others)
4. Time in cold shock post-delivery of Cas9 RNP (current: 2 days—have tested 1 and 3 days).
5. Temperature in cold shock post-delivery of Cas9 RNP (current: 30° C.—have not tested other cold shock temps below 37° C.).
6. Number of simultaneously gene knockouts/knockins (current: have done as many as 2 simultaneous knockouts).
7. Mode of Cas9/crRNA tracrRNA delivery (current: RNP. Plasmid and mRNA didn't work as well).
8. Alternative genome editing proteins (e.g. Cpf1, etc.).
9. Mode of DNA donor delivery (AAV worked best; plasmid worked okay; ssODN was poorest, but it may be the case that as the model starts to approximate a cancer cell line, ssODN because feasible as a DNA donor for HDR).

Example 3—Obtaining a Melanoma Cell Line

Figure 2:
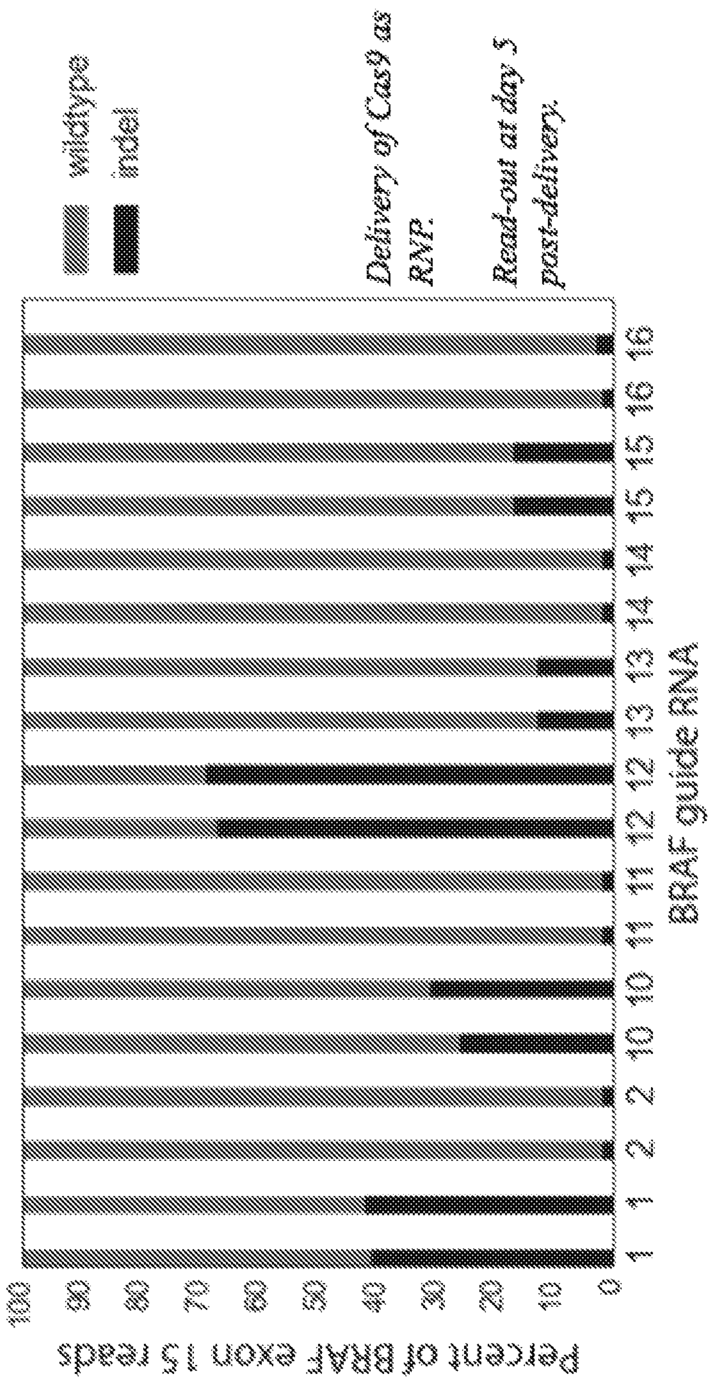
FIG. 2 illustrates selecting guide RNAs to generate indels at exon 15 of BRAF. The guide RNAs and Cas9 were delivered by ribonucleoprotein complexes (RNP).

Applicants determined conditions for introducing indels at the BRAF gene into primary cells (FIGS. 1, 2). Chemically modified sgRNAs allowed indels to be introduced in Cas9 expressing melanocytes. Guide RNAs were assayed to determine the best guide sequences.

Figure 3:
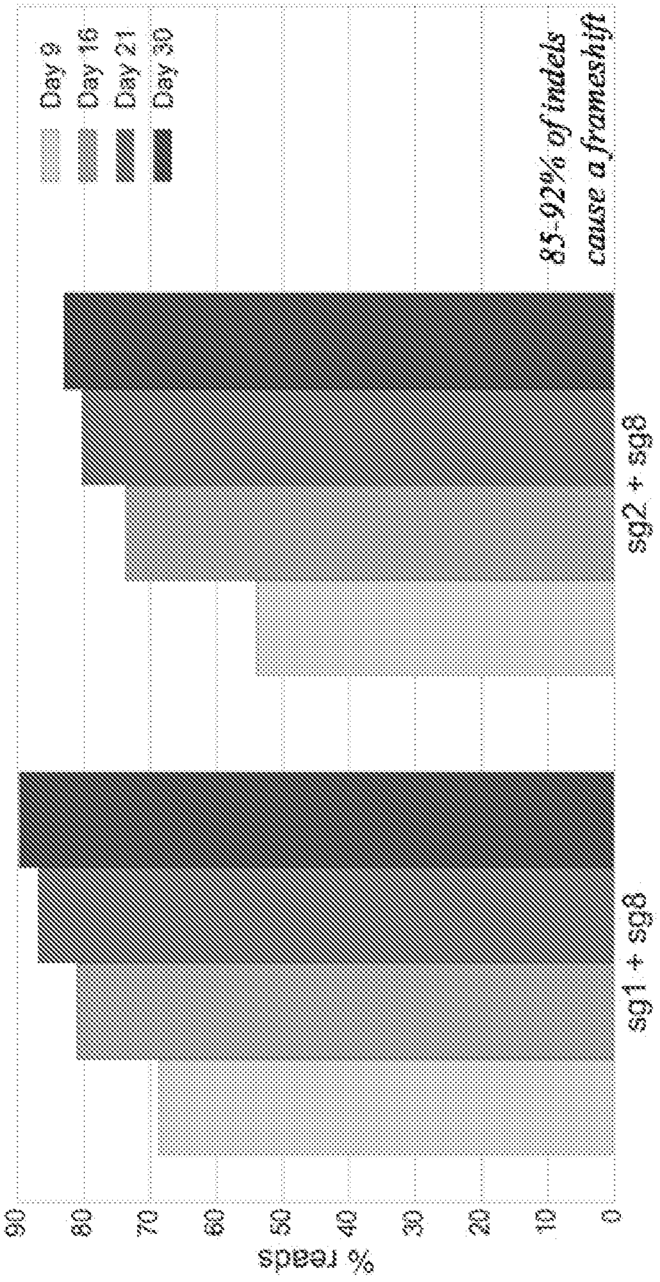
FIG. 3 illustrates Mel-Cas9 nucleofected with 1.5 ug plasmid encoding CDKN2a sg2 and 1.5 ug CDKN2A sg8.
Figure 4:
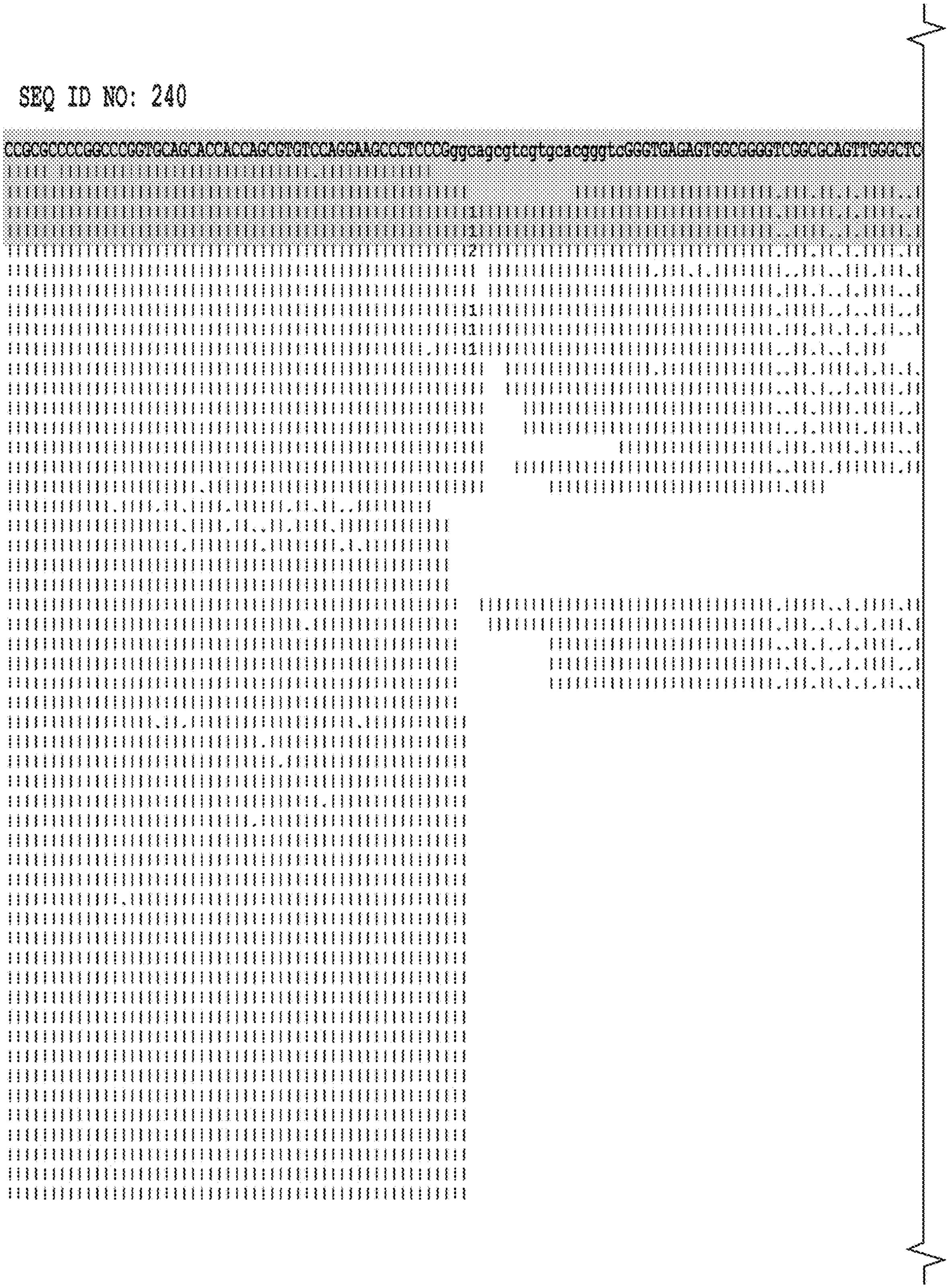
FIG. 4 illustrates an example of next generation sequencing (NGS) data from the CDKN2A locus (SEQ ID NO: 240).
Figure 4:
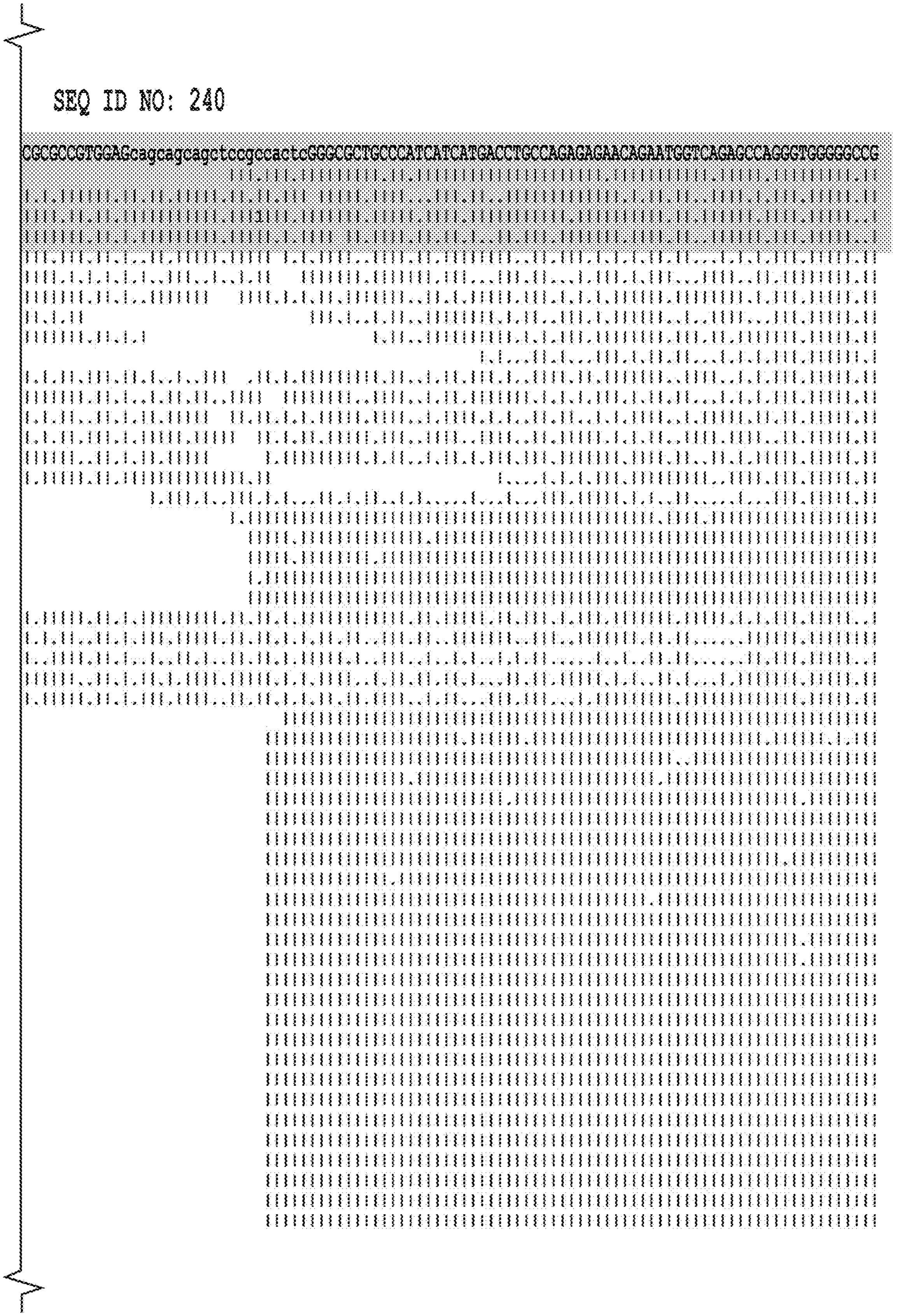
Figure 5:
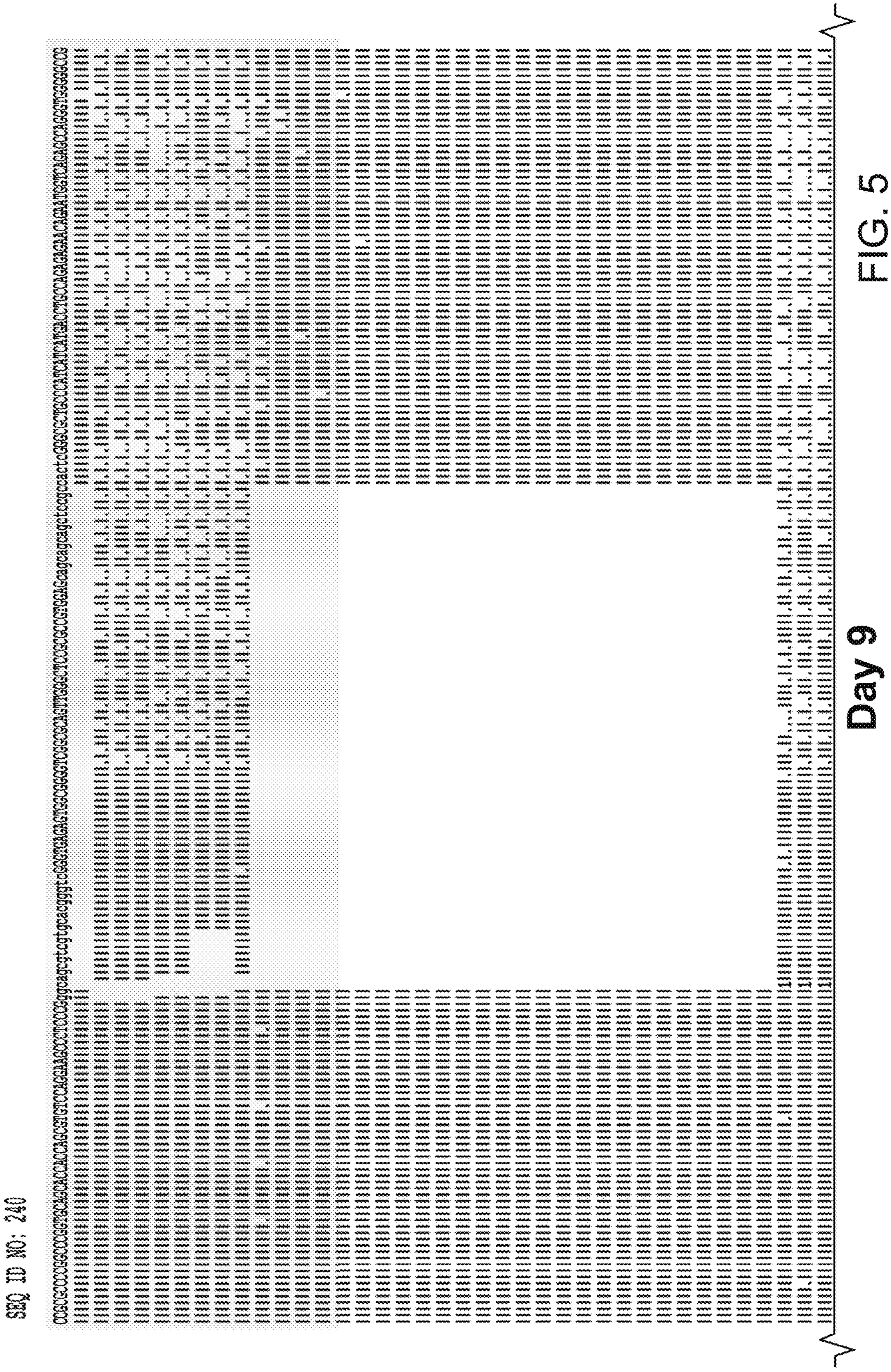
FIG. 5 illustrates CDKN2A reads over time in culture from Mel-Cas9 nucleofected with 1.5 ug plasmid encoding CDKN2a sg2 and 1.5 ug CDKN2A sg8 (SEQ ID NOS: 241-244).

Applicants used guide RNAs specific to the CDKN2A gene and determined that the mutation could be positively selected. Applicants achieved close to 100% selection of the mutation and show that CDKN2A mutations may act as a first event in melanocytes (FIG. 3). Next generation sequencing shows the formation of indels over time (FIGS. 4, 5).

Figure 6:
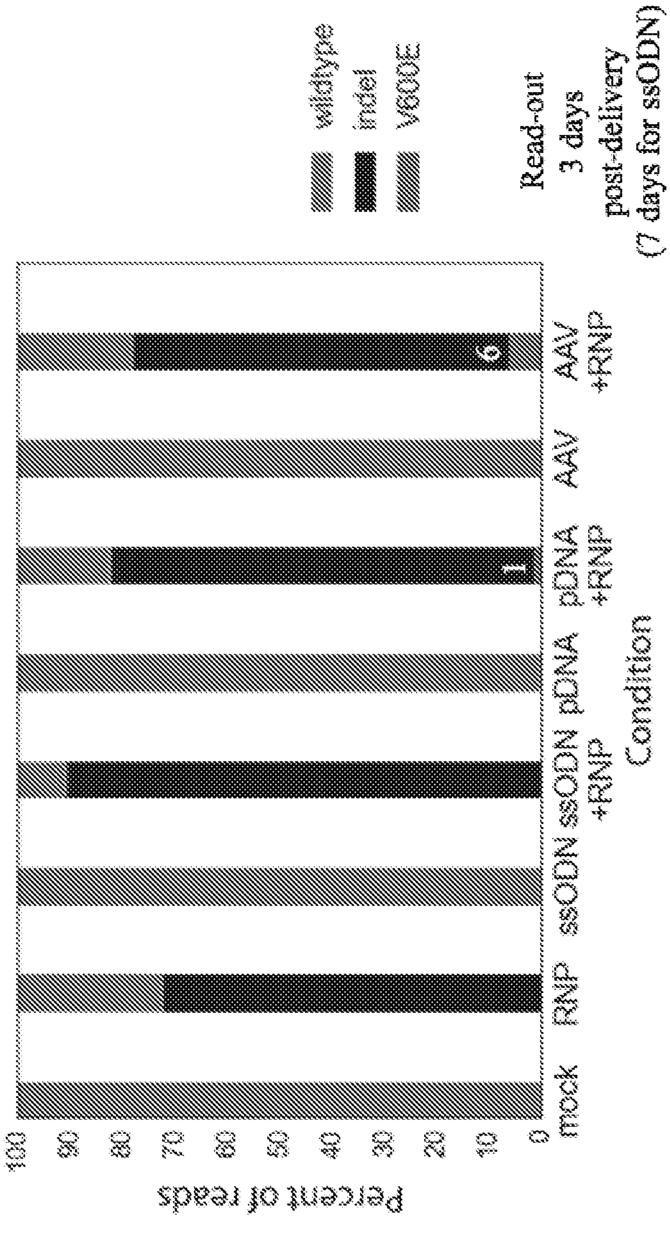
FIG. 6 illustrates that the use of AAV as HR donor enables robust, reproducible BRAF V600E knockin in melanocytes.
Figure 9:
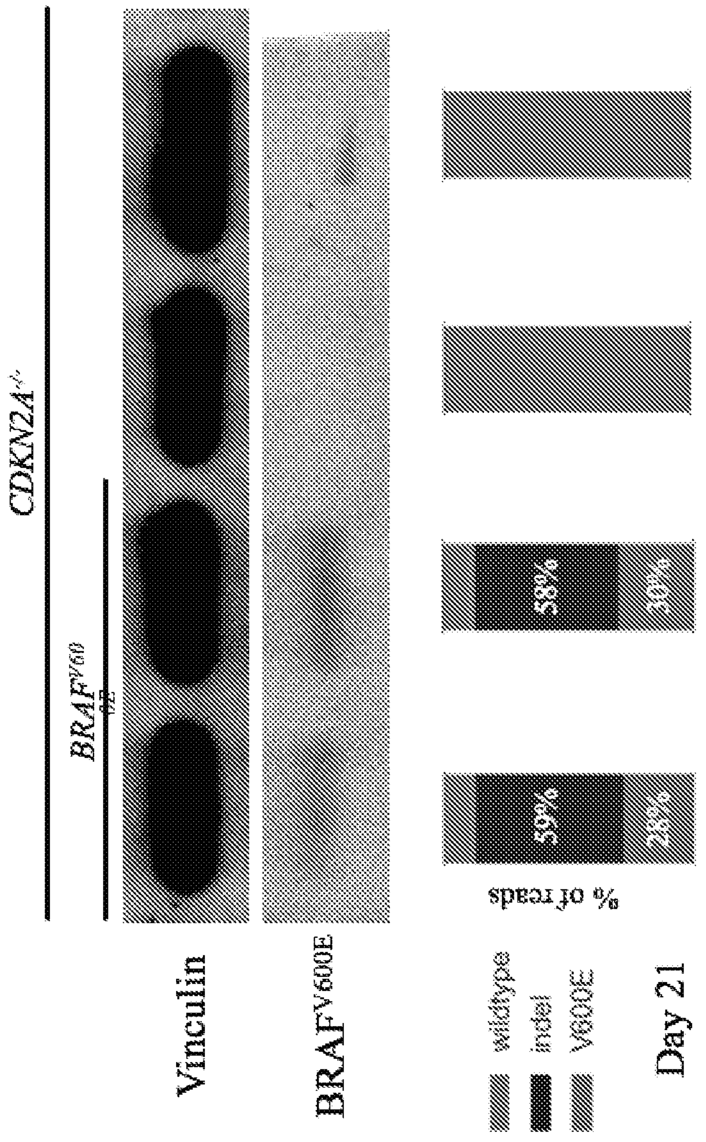
FIG. 9 illustrates that the CDKN2A−/− BRAF V600E cells express BRAF V600E.
Figure 10:
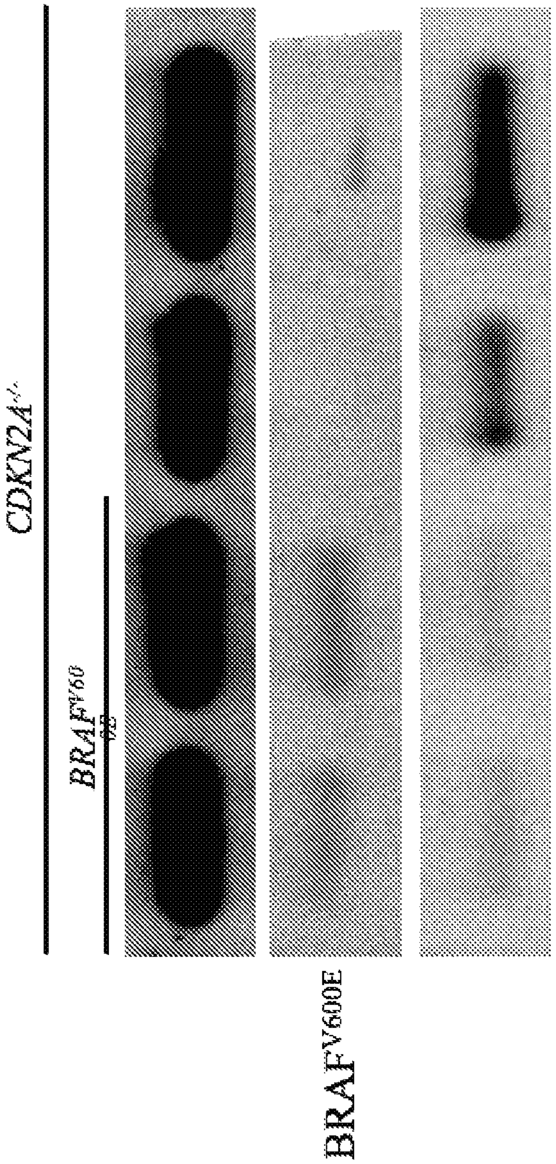
FIG. 10 illustrates that the CDKN2A−/− BRAF V600E population show reduced expression of BRAF protein.
Figure 11:
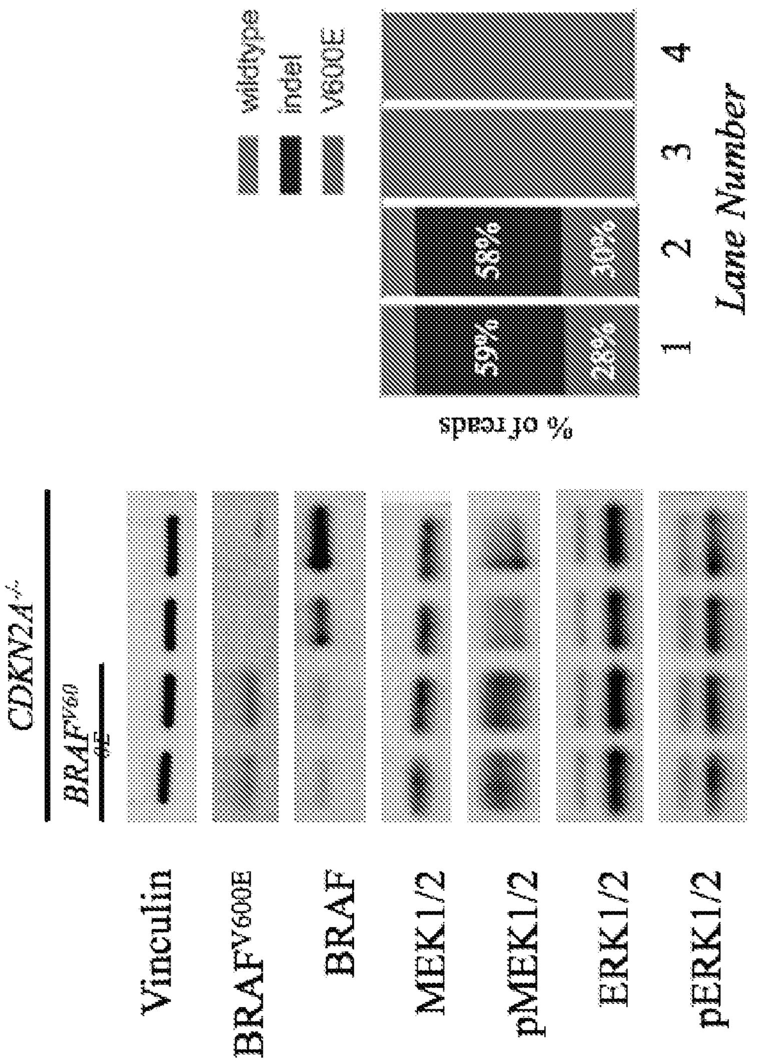
FIG. 11 illustrates that pMEK is up in BRAF V600E population, but no detectable change in pERK is observed.

Applicants show that knockin mutations ($BRAF^{V600E}$) can be introduced to melanocytes using AAV as the homologous recombination donor (FIG. 6). Applicants observed that the $BRAF^{V600E}$ mutation can act as a first event mutation. Applicants also discovered that the BRAFV600E mutation can be positively selected as a second event mutation where the first event mutation is in CDKN2A (FIG. 8). By 60 days 45% of the cells contain the mutation. The mutation and reduction of the BRAF protein can be observed by western blot (FIGS. 9, 10). The mutations in CDKN2A and BRAF lead to phenotypic changes in the cells. For example, phosphorylated MEK1/2 is upregulated in the BRAF V600E population, but no detectable change in pERK is observed (FIG. 11).

Figure 12:
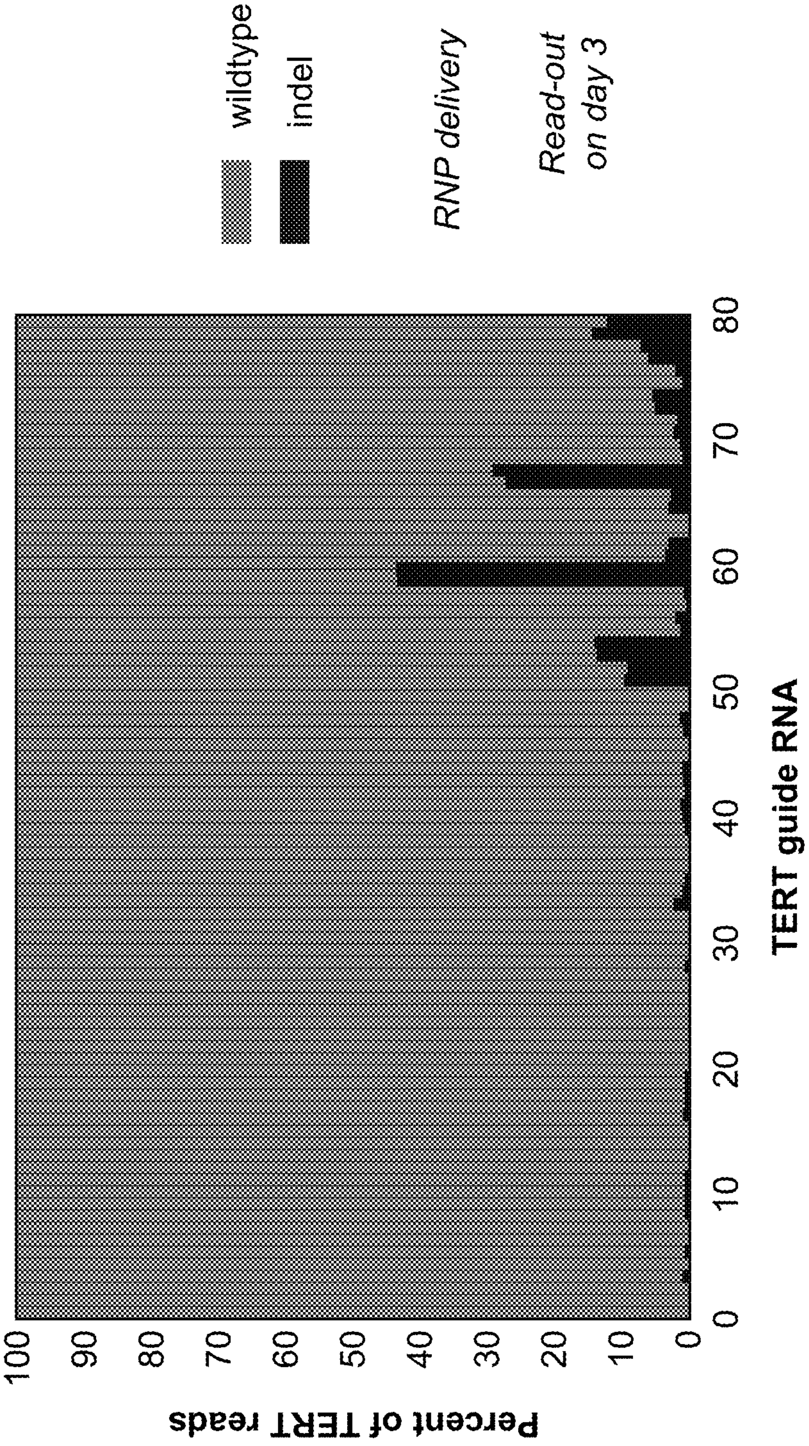
FIG. 12 illustrates testing TERT guide RNAs introduced by RNP for indel formation.
Figure 13A:
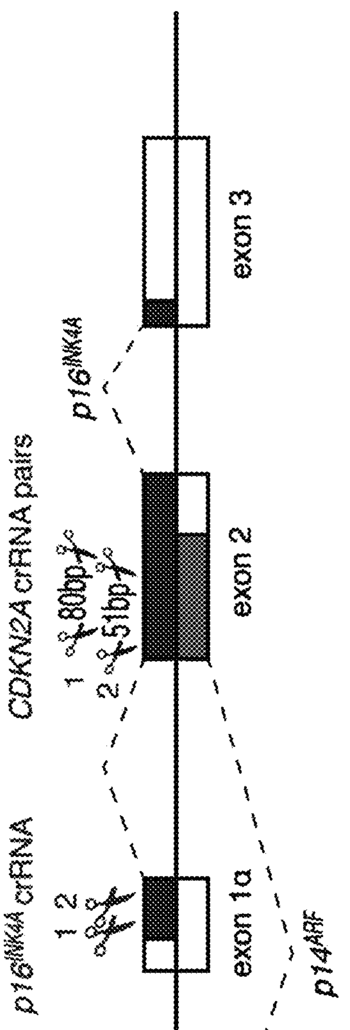
FIG. 13A-13F illustrate an example embodiment for introduction of CDKN2A mutation.
Figure 13B:
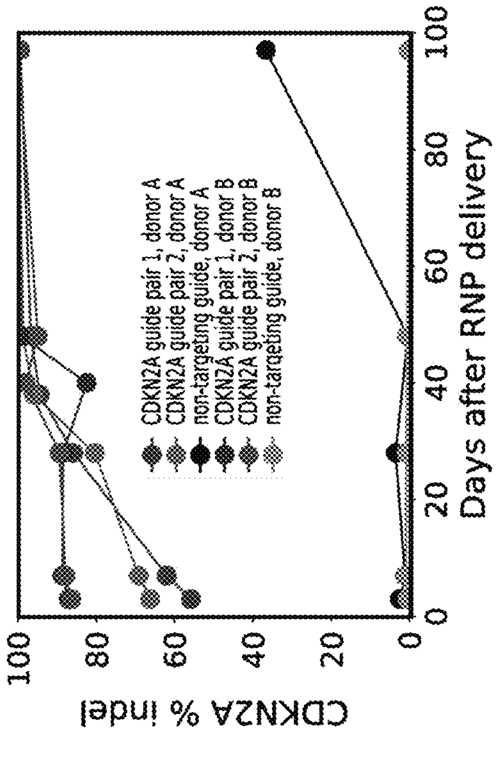
Figure 13C:
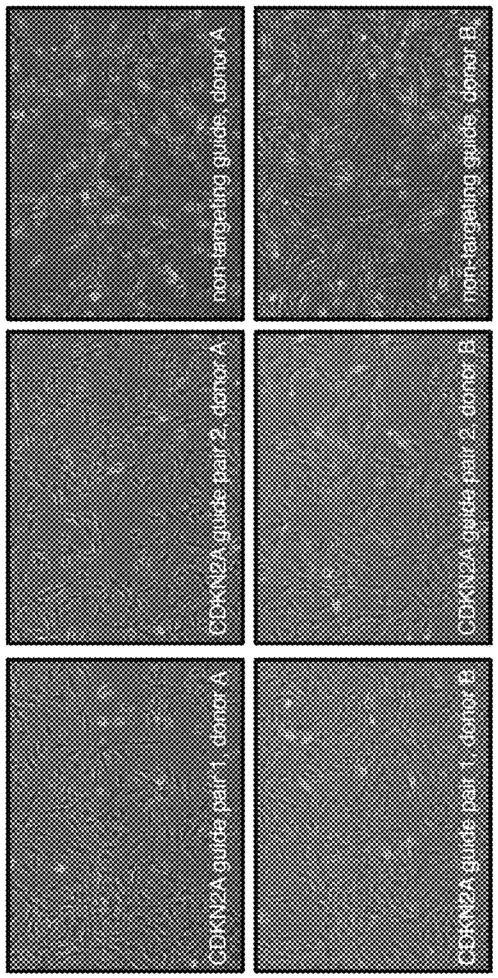
Figure 13D:
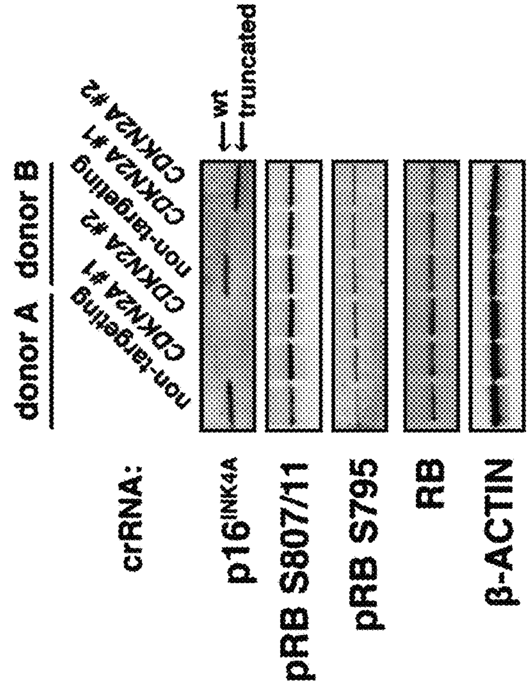
Figure 13E:
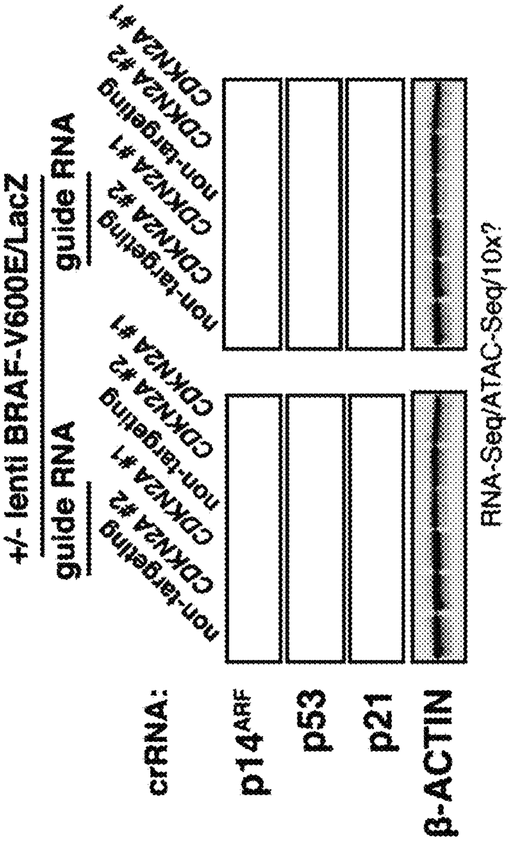
Figure 13F:
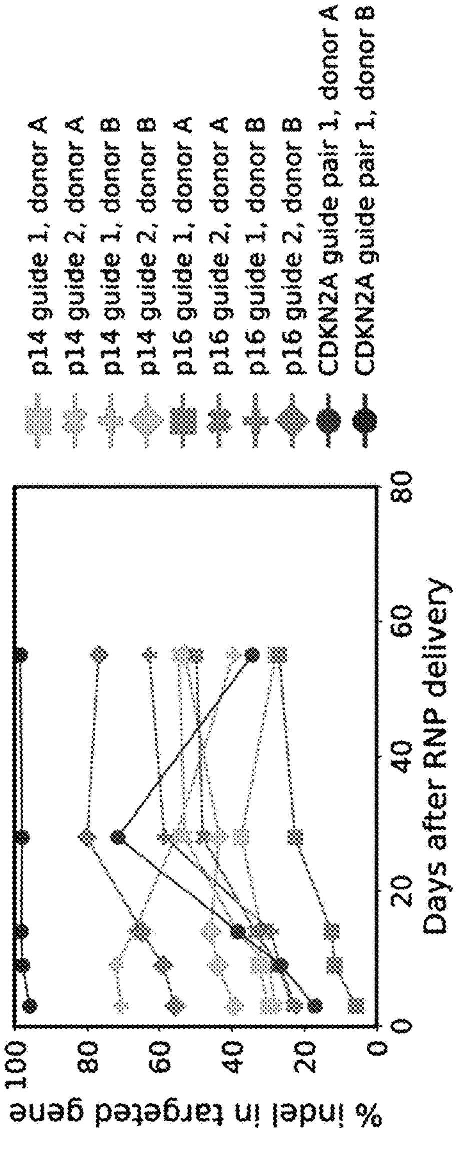
Figure 14A:
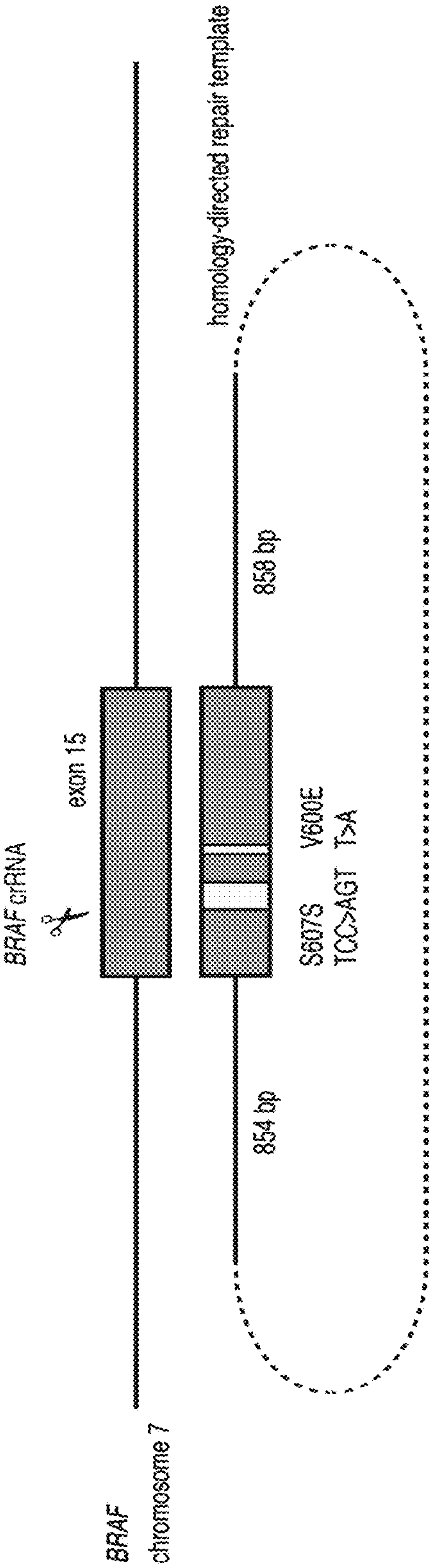
FIG. 14A-14C illustrate selection of BRAF V600E and CDKN2A−/− mutants.
Figure 14B:
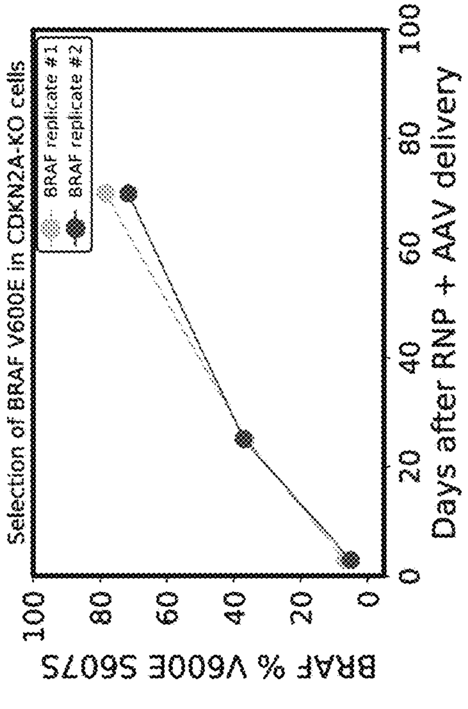
Figure 14C:
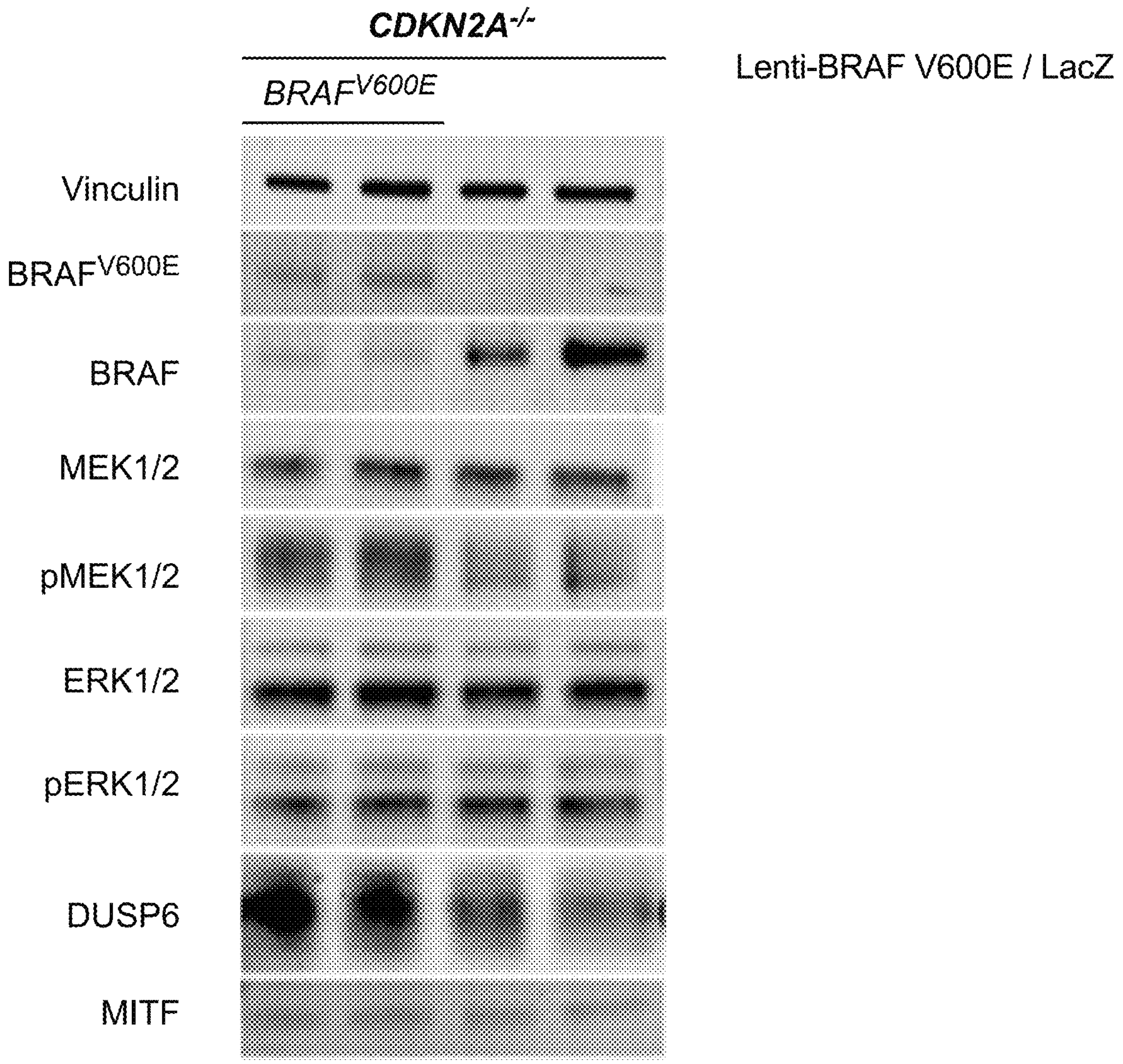
Figure 15A:
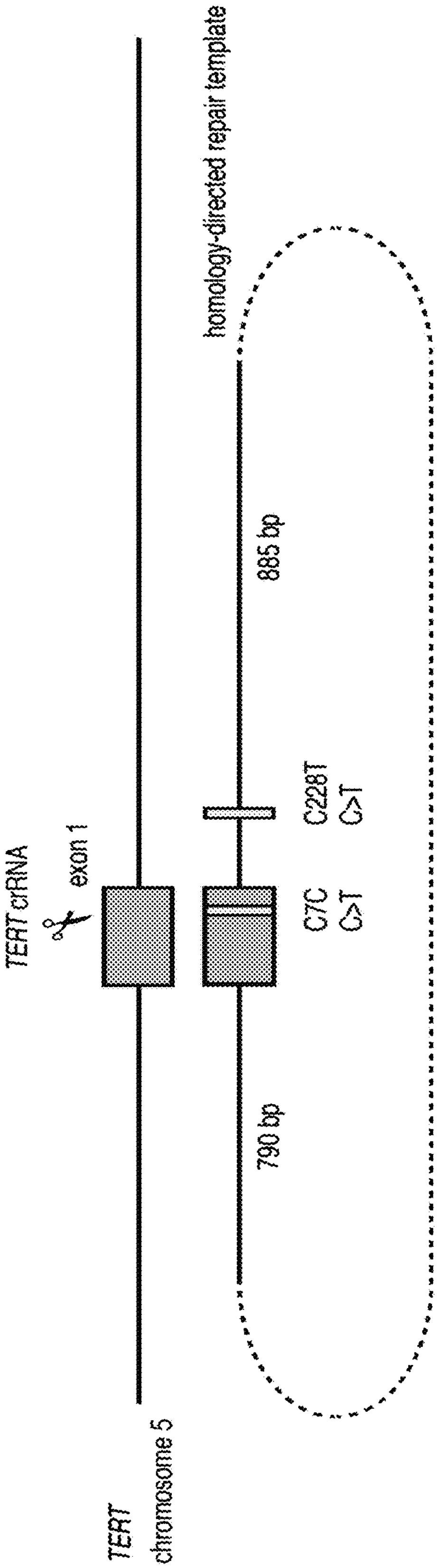
FIG. 15A-15D—illustrate introduction of TERT mutations into BRAF and CDKN2A mutant background.
Figure 15B:
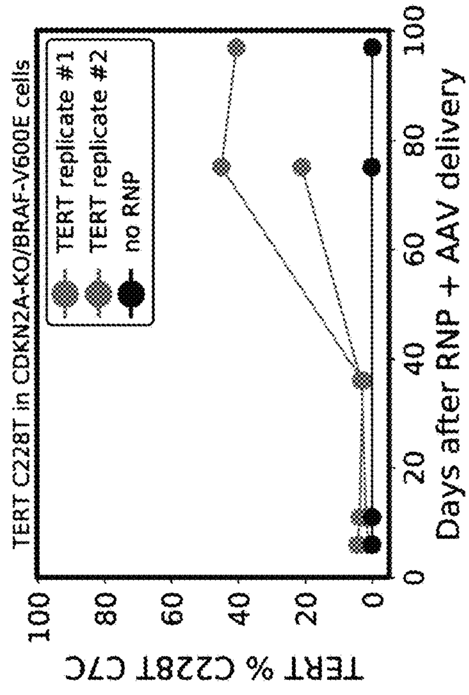
Figure 15C:
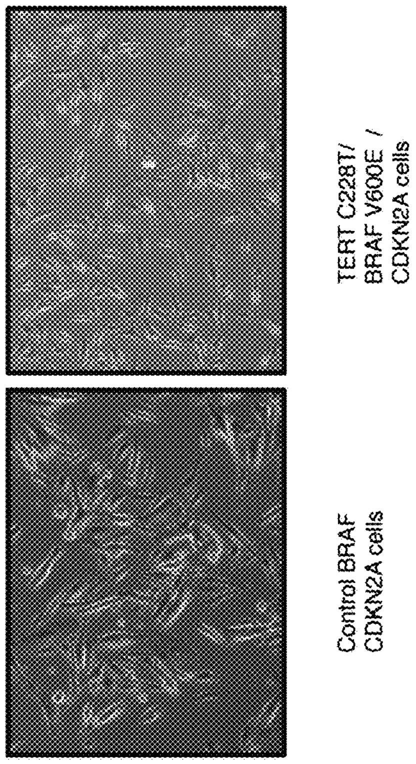
Figure 15D:
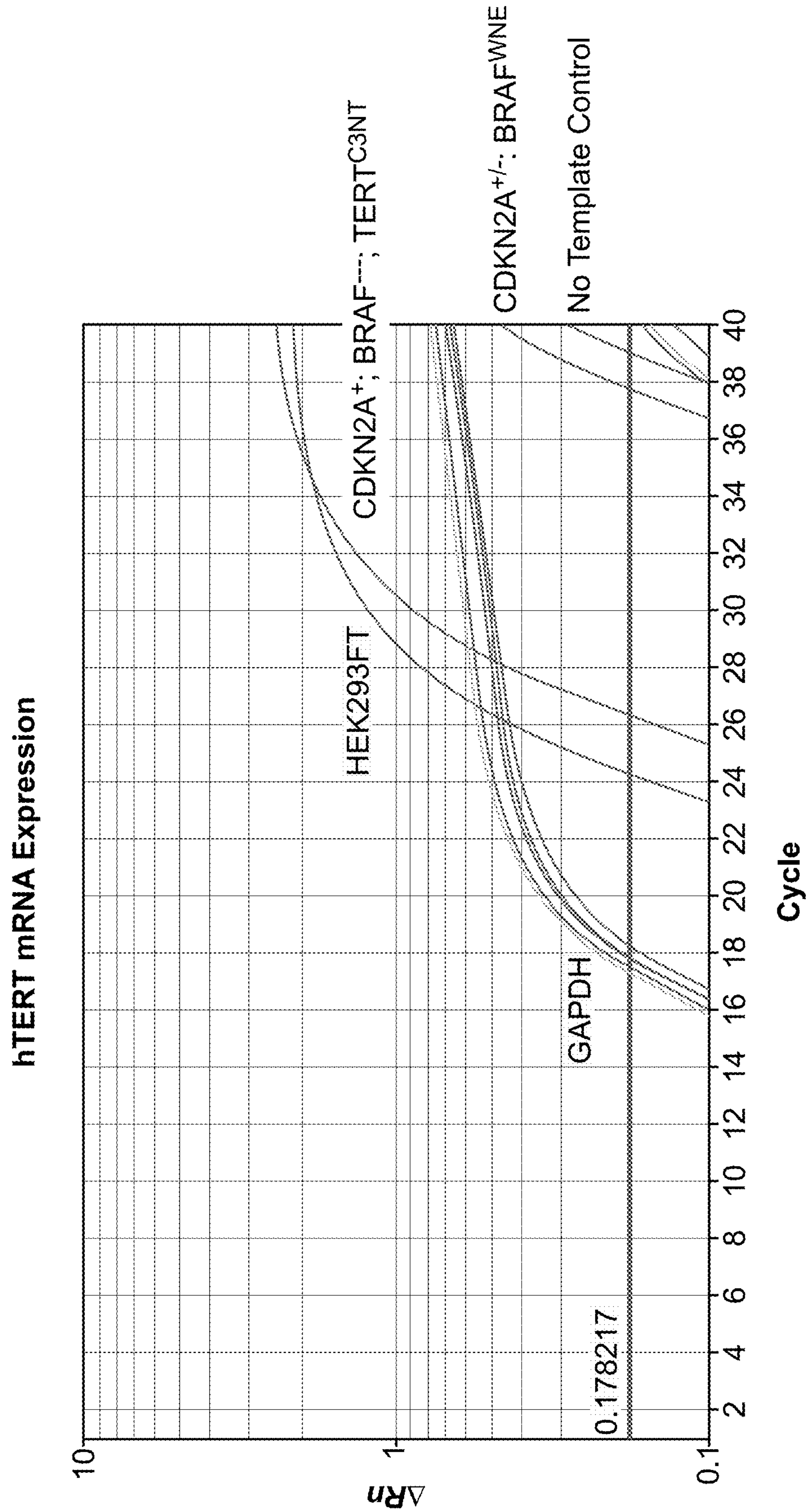
Figure 16A:
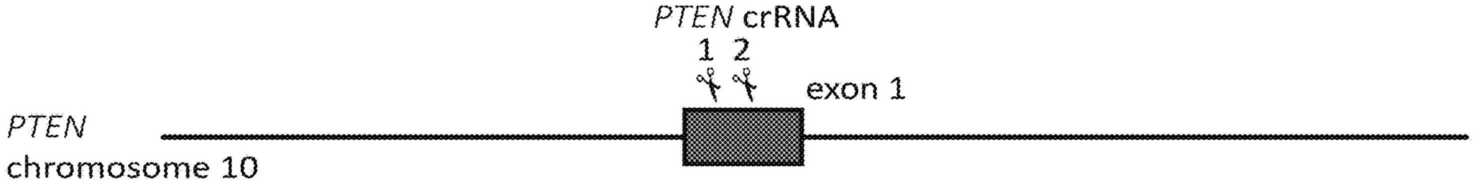
FIG. 16A-16G—illustrate introduction of PTEN mutation and intradermal xenograft in PTEN-KO model.
Figure 16B:
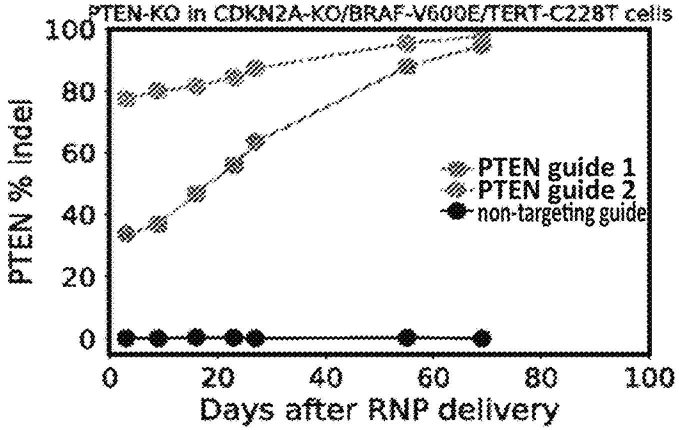
Figure 16C:
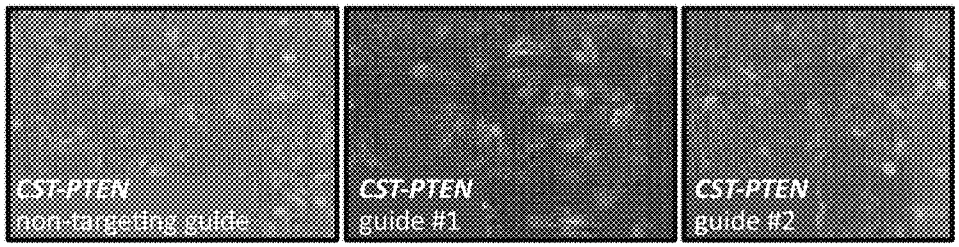
Figure 16D:
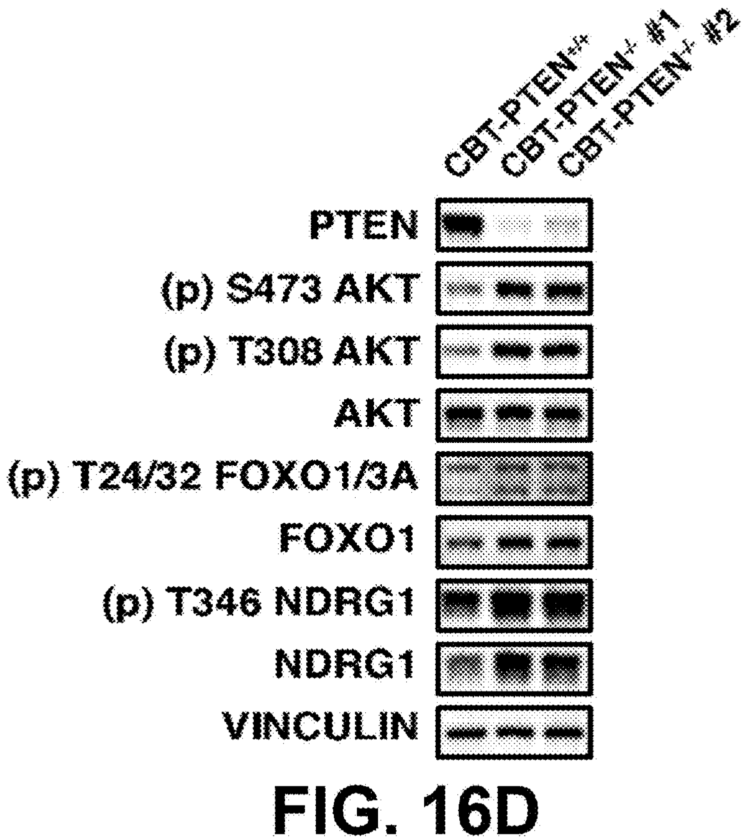
Figure 16E:
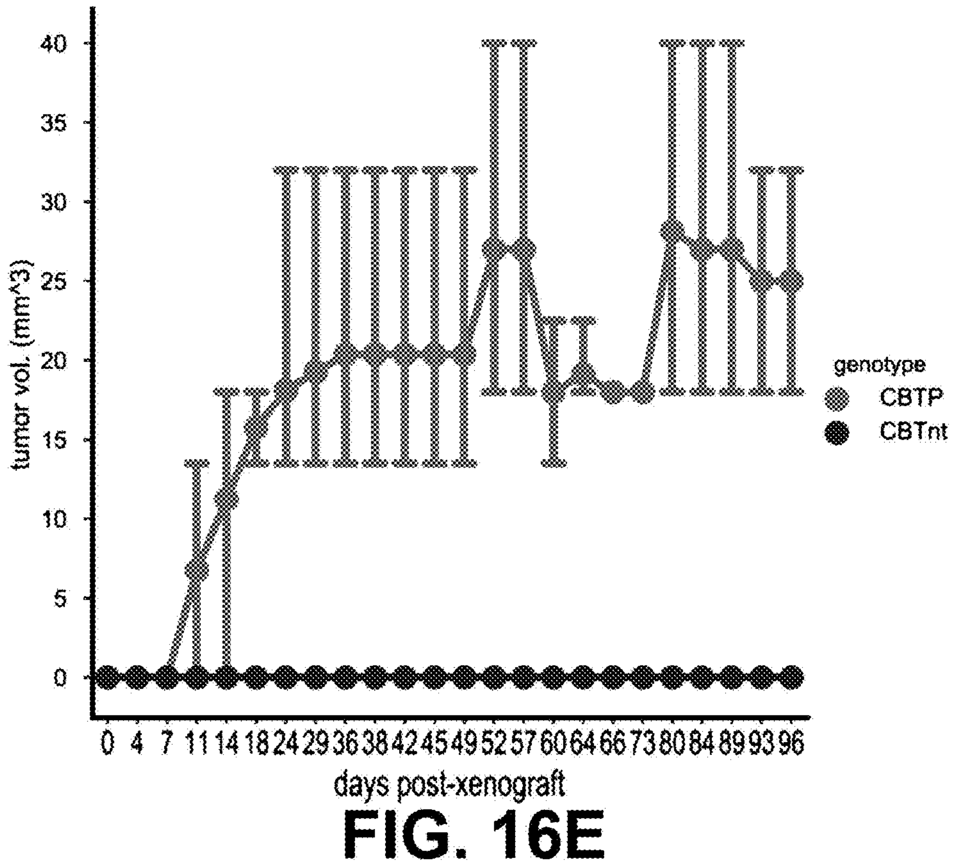
Figure 16F:
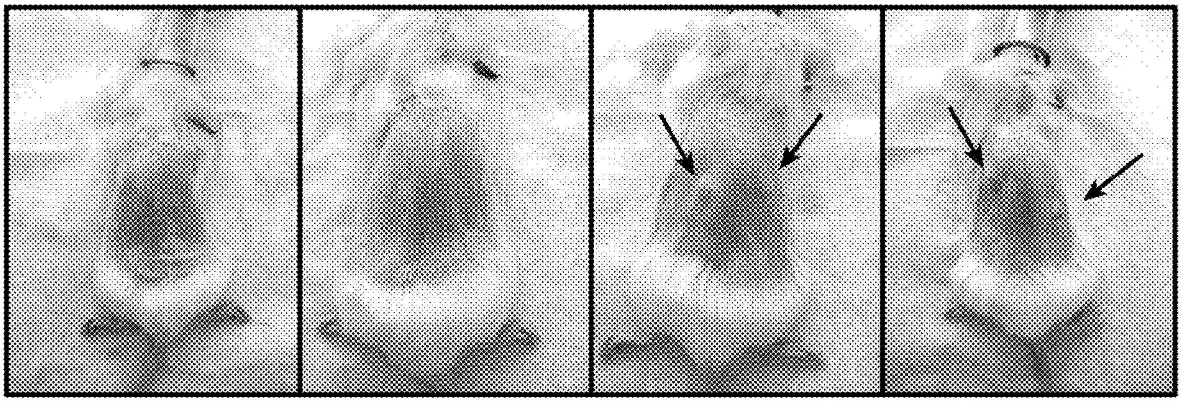
Figure 16G:
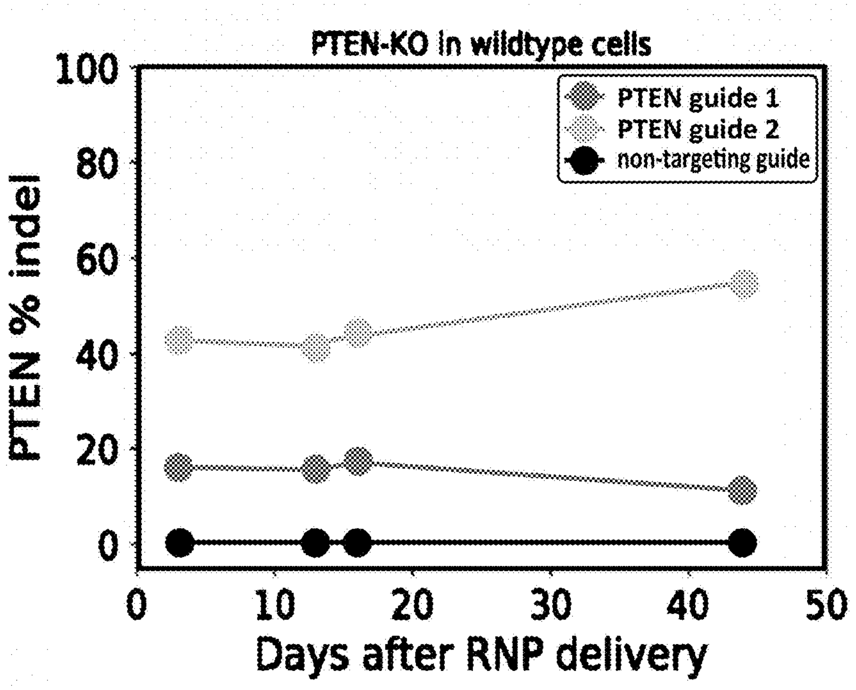
Figure 17A:
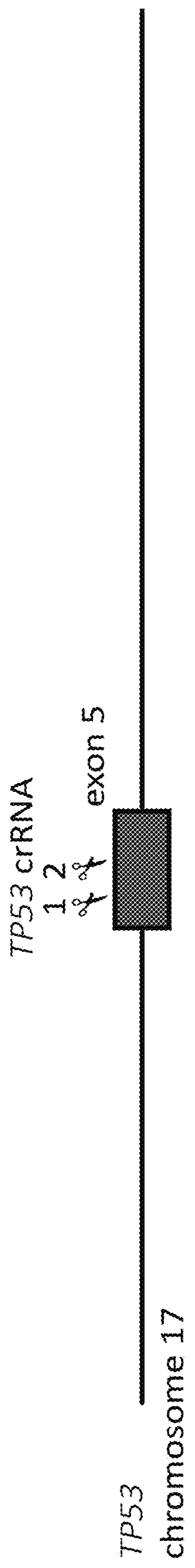
FIG. 17A-17J—illustrate introduction of TP53 mutations.
Figure 17B:
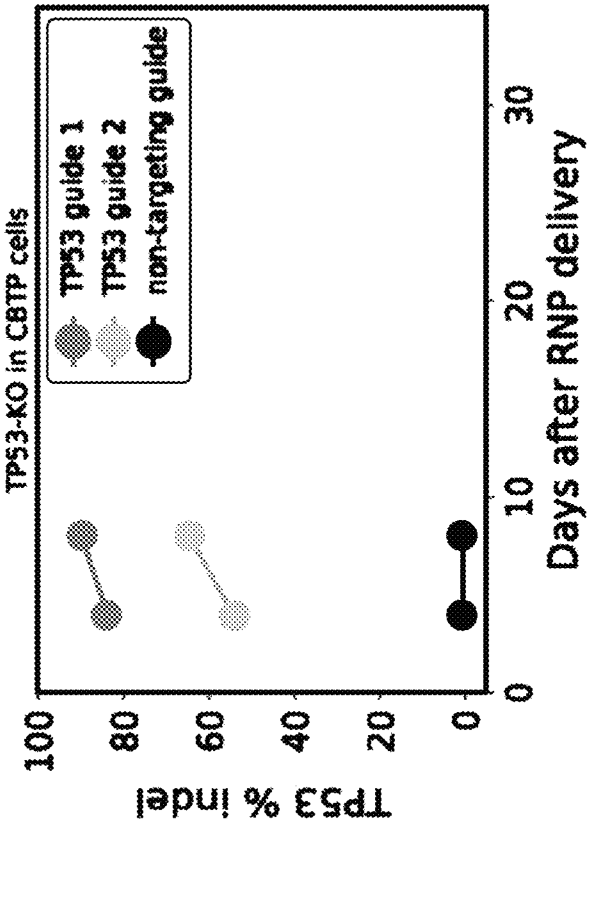
Figure 17C:
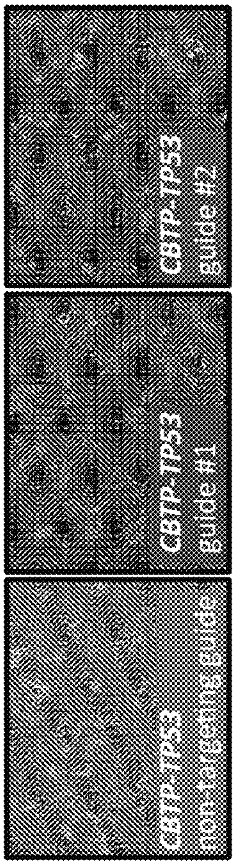
Figure 17D:
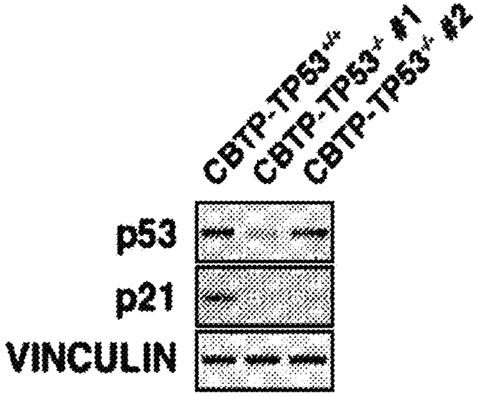
Figure 17E:
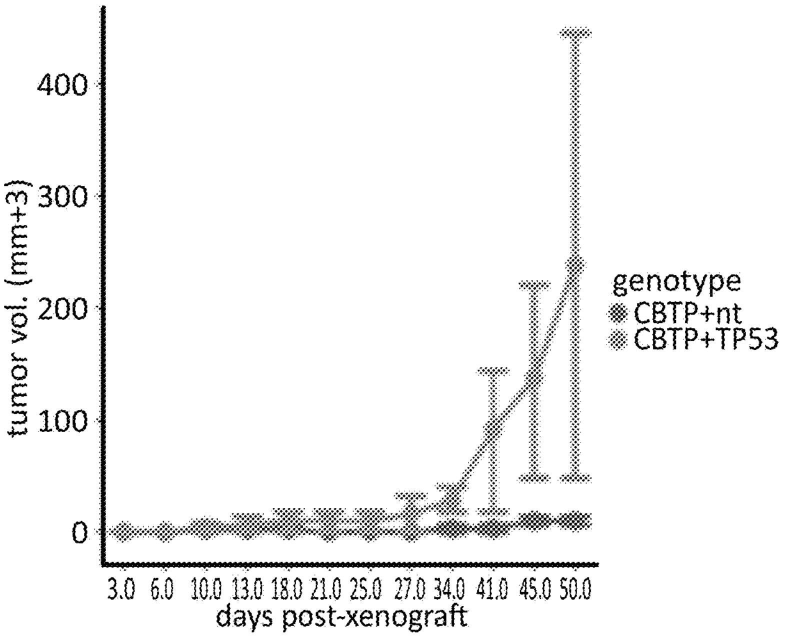
Figure 17F:
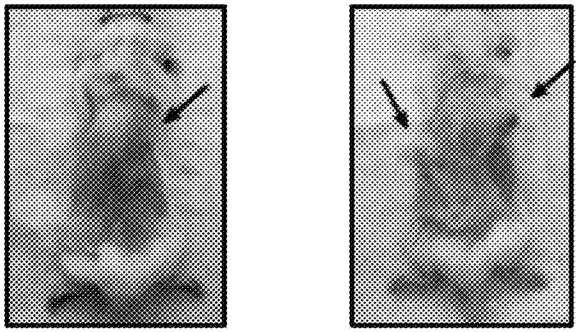
Figure 17G:
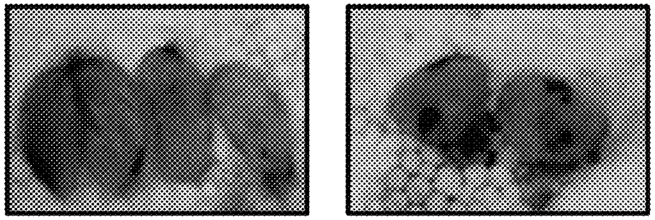
Figure 17I:
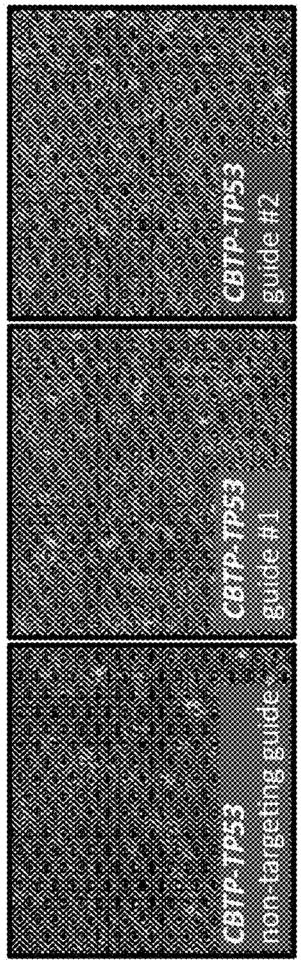
Figure 17J:
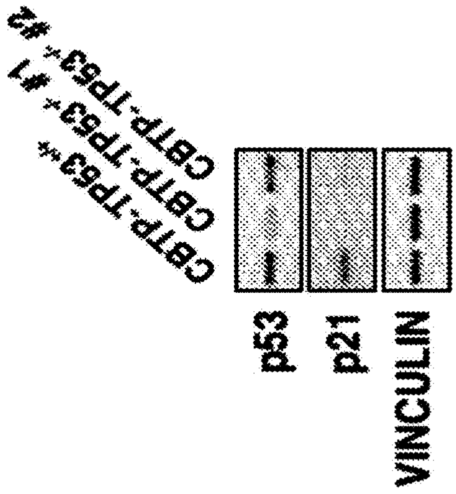
Figure 17H:
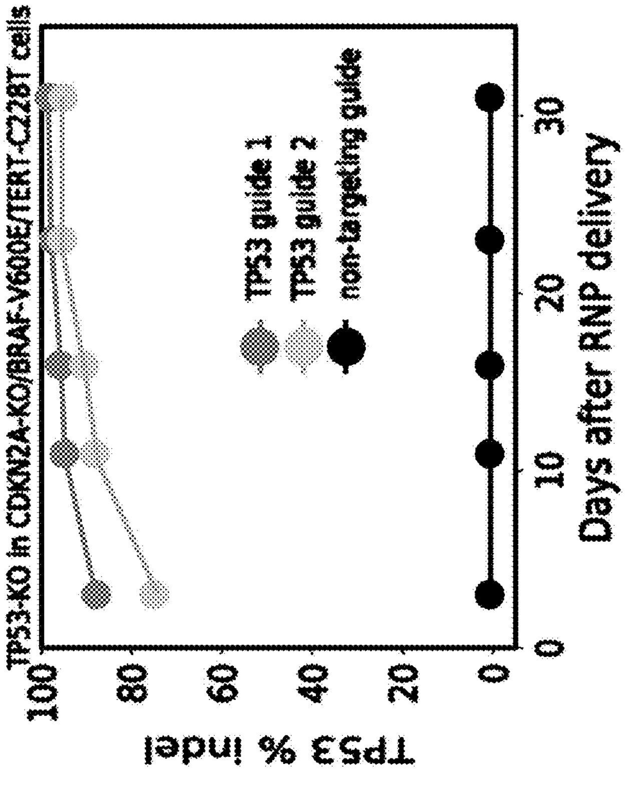

Applicants also determined guide RNAs for introducing indels at the TERT gene (FIG. 12).

Example 4—Genome Edited Human Models of Melanoma Genesis and Progression

Applicants used genome editing to build a stepwise series of melanoma models starting from primary human melanocytes. To introduce each mutation, genome-editing reagents were transiently delivered in vitro and then the cells were cultured until the mutant allele(s) reached near-fixation due to relative fitness advantage, avoiding chemical selection or single cell cloning (FIG. 18B). For each subsequent mutation, the process was repeated. Applicants then phenotypically characterized each mutant state by observing histologic, immunophenotypic, and growth characteristics following intradermal injection in immunodeficient mice (FIG. 18C).

Figure 19A:
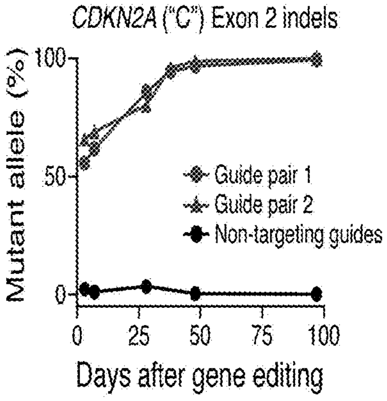
FIG. 19A-19G—illustrate that sequential introduction of CDKN2A, $BRAF^{V600E}$, and $TERT^{-124C>T}$ mutations confers immortality and malignancy to primary human melanocytes.
Figure 19B:
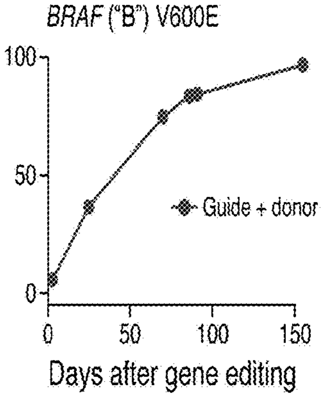

Mutations were first engineered into CDKN2A ('C'), BRAF ('B'), and TERT ('T') (FIGS. 19A-19G). Lesions in these three genes happen early in melanoma pathogenesis and are exceptionally common, co-occurring events (Akbani et al. *Cell* 161:1681-1696 (2015)) that have been hypothesized to suffice for malignant transformation (Shain et al. *Nat Rev Cancer* 16:345-358 (2016); Shain et al. *N Engl J Med* 373:1926-1936 (2015)). After electroporation of Cas9 ribonucleoprotein complex (RNP) (Rimm et al. *Am J Pathol* 154:325-329 (1999)) targeting CDKN2A exon 2, the only exon shared by both p16 and p14 protein products, small insertions and deletions ('indels') in the gene underwent natural positive selection during cell culture from a 90-95% allele frequency at day three to nearly 100% by day 42 (FIG. 19A). Into these CDKN2A knockout ('C') melanocytes, Applicants next introduced the BRAF V600E mutation by co-delivering Cas9 RNP targeting BRAF exon 15 together with a homologous DNA donor encoding the V600E mutation. Recombinant adeno-associated virus (rAAV) was used to deliver the DNA donor (Rimm et al. *Am J Pathol* 154:325-329 (1999)) in order to increase the low editing efficiency over plasmid or single-stranded oligodeoxynucleotide donors (data not shown; Dever et al. *Nature* 539:384-389 (2016)). Over roughly 150 days in culture, the BRAF V600E allele increased from a frequency of 6% at day 3 to nearly 100% at day 155 (FIG. 19B). Finally, into these CDKN2A knockout, BRAF V600E mutant ('CB') melanocytes, Applicants introduced the −124C>T (also known as C228T) TERT promoter mutation by co-delivery of Cas9 RNP targeting TERT exon 1 together with a homologous DNA donor encoding TERT −124C>T. The −124C>T TERT promoter mutation allele shifted from a stable allele frequency of 3-5% over the first 30 days in culture to roughly 50% by day 75 and stayed at roughly 50% for more than 300 days of continuous culture (FIG. 19C; this 50% frequency is further discussed below). Engineering the TERT promoter mutation was the most technically difficult of these three mutations and required testing forty different Cas9 guide sequences to identify a potent reagent for making double stranded breaks near the TERT promoter locus (Table 9), possibly due to the high G:C content or closed chromatin state at this locus (Yeh et al. *Nat Commun* 8:644 (2017)).

TABLE 9

Efficiency of 40 tested Cas9 guide sequences targeting TERT promoter or exon 1

| Gene | Guide Number | Rep-licate | Chromo-some | Strand | Start | End | or Sequence (5' > 3') | % Indel Post-Editing | Days Post-Editing |
|---|---|---|---|---|---|---|---|---|---|
| TERT | 1 | 1 | 5 | + | 1295214 | 1295233 | TGGGAGGGCCCGGAGGGGGC (SEQ ID NO: 161) | 0.168552204 | 3 |
| TERT | 1 | 2 | 5 | + | 1295214 | 1295233 | TGGGAGGGCCCGGAGGGGGC (SEQ ID NO: 162) | 0.205722443 | 3 |
| TERT | 2 | 1 | 5 | − | 1295226 | 1295245 | GTCCCCGGCCCAGCCCCCTC (SEQ ID NO: 163) | 0.289972351 | 3 |
| TERT | 2 | 2 | 5 | − | 1295226 | 1295245 | GTCCCCGGCCCAGCCCCCTC (SEQ ID NO: 164) | 0.608679198 | 3 |
| TERT | 3 | 1 | 5 | − | 1295225 | 1295244 | TCCCCGGCCCAGCCCCCTCC (SEQ ID NO: 165) | 0.283637653 | 3 |
| TERT | 3 | 2 | 5 | − | 1295225 | 1295244 | TCCCCGGCCCAGCCCCCTCC (SEQ ID NO: 166) | 0.472953 | 3 |
| TERT | 4 | 1 | 5 | + | 1295209 | 1295228 | GGGGCTGGGAGGGCCCGGAG (SEQ ID NO: 167) | 0.278685889 | 3 |
| TERT | 4 | 2 | 5 | + | 1295209 | 1295228 | GGGGCTGGGAGGGCCCGGAG (SEQ ID NO: 168) | 0.059719319 | 3 |
| TERT | 5 | 1 | 5 | + | 1295210 | 1295229 | GGGCTGGGAGGGCCCGGAGG (SEQ ID NO: 169) | 0.373768264 | 3 |
| TERT | 5 | 2 | 5 | + | 1295210 | 1295229 | GGGCTGGGAGGGCCCGGAGG (SEQ ID NO: 170) | 0.406504065 | 3 |
| TERT | 6 | 1 | 5 | + | 1295215 | 1295234 | GGGAGGGCCCGGAGGGGGCT (SEQ ID NO: 171) | 0.35623658 | 3 |
| TERT | 6 | 2 | 5 | + | 1295215 | 1295234 | GGGAGGGCCCGGAGGGGGCT (SEQ ID NO: 172) | 0.311157208 | 3 |
| TERT | 7 | 1 | 5 | + | 1295207 | 1295226 | GAGGGGCTGGGAGGGCCCGG (SEQ ID NO: 173) | 0.225727184 | 3 |
| TERT | 7 | 2 | 5 | + | 1295207 | 1295226 | GAGGGGCTGGGAGGGCCCGG (SEQ ID NO: 174) | 0.172761301 | 3 |
| TERT | 8 | 1 | 5 | + | 1295228 | 1295247 | GGGGGCTGGGCCGGGGACCC (SEQ ID NO: 175) | 0.192908677 | 5 |
| TERT | 8 | 2 | 5 | + | 1295228 | 1295247 | GGGGGCTGGGCCGGGGACCC (SEQ ID NO: 176) | 0.225031205 | 5 |
| TERT | 9 | 1 | 5 | + | 1295231 | 1295250 | GGCTGGGCCGGGGACCCGGG (SEQ ID NO: 177) | 0.567387747 | 5 |
| TERT | 9 | 2 | 5 | + | 1295231 | 1295250 | GGCTGGGCCGGGGACCCGGG (SEQ ID NO: 178) | 0.398020465 | 5 |
| TERT | 10 | 1 | 5 | + | 1295232 | 1295251 | GCTGGGCCGGGGACCCGGGA (SEQ ID NO: 179) | 0.31548626 | 5 |
| TERT | 10 | 2 | 5 | + | 1295232 | 1295251 | GCTGGGCCGGGGACCCGGGA (SEQ ID NO: 180) | 0.38895825 | 5 |
| TERT | 11 | 1 | 5 | + | 1295233 | 1295252 | CTGGGCCGGGGACCCGGGAG (SEQ ID NO: 181) | 0.228772908 | 5 |
| TERT | 11 | 2 | 5 | + | 1295233 | 1295252 | CTGGGCCGGGGACCCGGGAG (SEQ ID NO: 182) | 0.273305506 | 5 |
| TERT | 12 | 1 | 5 | + | 1295237 | 1295256 | GCCGGGGACCCGGGAGGGGT (SEQ ID NO: 183) | 0.168158156 | 5 |

TABLE 9-continued

Efficiency of 40 tested Cas9 guide sequences targeting TERT promoter or exon 1

| Gene | Guide Number | Rep-licate | Chromo-some | Strand | Start | End | or Sequence (5' > 3') | % Indel Post-Editing | Days Post-Editing |
|---|---|---|---|---|---|---|---|---|---|
| TERT | 12 | 2 | 5 | + | 1295237 | 1295256 | GCCGGGGACCCGGGAGGGGT (SEQ ID NO: 184) | 0.083386472 | 5 |
| TERT | 13 | 1 | 5 | + | 1295238 | 1295257 | CCGGGGACCCGGGAGGGGTC (SEQ ID NO: 185) | 0.066029111 | 5 |
| TERT | 13 | 2 | 5 | + | 1295238 | 1295257 | CCGGGGACCCGGGAGGGGTC (SEQ ID NO: 186) | 0.055248619 | 5 |
| TERT | 14 | 1 | 5 | - | 1295249 | 1295268 | CGCCCCGTCCCGACCCCTCC (SEQ ID NO: 187) | 0.048508368 | 5 |
| TERT | 14 | 2 | 5 | - | 1295249 | 1295268 | CGCCCCGTCCCGACCCCTCC (SEQ ID NO: 188) | 0.092630712 | 5 |
| TERT | 15 | 1 | 5 | – | 1295248 | 1295267 | GCCCCGTCCCGACCCCTCCC (SEQ ID.NO: 189) | 0.375036061 | 5 |
| TERT | 16 | 1 | 5 | + | 1295189 | 1295208 | GGCCGCGGAAAGGAAGGGGA (SEQ ID NO: 190) | 0.194174757 | 3 |
| TERT | 16 | 2 | 5 | + | 1295189 | 1295208 | GGCCGCGGAAAGGAAGGGGA (SEQ ID NO: 191) | 0.095556617 | 3 |
| TERT | 17 | 1 | 5 | + | 1295162 | 1295181 | GAAACTCGCGCCGCGAGGAG (SEQ ID NO: 192) | 0.0339098 | 3 |
| TERT | 17 | 2 | 5 | + | 1295162 | 1295181 | GAAACTCGCGCCGCGAGGAG (SEQ ID NO: 193) | 0.16298021 | 3 |
| TERT | 18 | 1 | 5 | – | 1295194 | 1295213 | GCCCCTCCCCTTCCTTTCCG (SEQ ID NO: 194) | 2.298850575 | 3 |
| TERT | 18 | 2 | 5 | – | 1295194 | 1295213 | GCCCCTCCCCTTCCTTTCCG (SEQ ID NO: 195) | 1.044776119 | 3 |
| TERT | 19 | 1 | 5 | + | 1295157 | 1295176 | TGCCTGAAACTCGCGCCGCG (SEQ ID NO: 196) | 0.309597523 | 3 |
| TERT | 19 | 2 | 5 | + | 1295157 | 1295176 | TGCCTGAAACTCGCGCCGCG (SEQ ID NO: 197) | 0.258679374 | 3 |
| TERT | 20 | 1 | 5 | + | 1295185 | 1295204 | GCGGGGCCGCGGAAAGGAAG (SEQ ID NO: 198) | 0.137614679 | 3 |
| TERT | 20 | 2 | 5 | + | 1295185 | 1295204 | GCGGGGCCGCGGAAAGGAAG (SEQ ID NO: 199) | 0.173410405 | 3 |
| TERT | 21 | 1 | 5 | + | 1295163 | 1295182 | AAACTCGCGCCGCGAGGAGA (SEQ ID NO: 200) | 0.536193029 | 3 |
| TERT | 21 | 2 | 5 | + | 1295163 | 1295182 | AAACTCGCGCCGCGAGGAGA (SEQ ID NO: 201) | 0.595744681 | 3 |
| TERT | 22 | 1 | 5 | + | 1295184 | 1295203 | GGCGGGGCCGCGGAAAGGAA (SEQ ID NO: 202) | 1.212121212 | 3 |
| TERT | 22 | 2 | 5 | + | 1295184 | 1295203 | GGCGGGGCCGCGGAAAGGAA (SEQ ID NO: 203) | 0.304371887 | 3 |
| TERT | 23 | 1 | 5 | + | 1295190 | 1295209 | GCCGCGGAAAGGAAGGGGAG (SEQ ID NO: 204) | 0.735294118 | 3 |
| TERT | 23 | 2 | 5 | + | 1295190 | 1295209 | GCCGCGGAAAGGAAGGGGAG (SEQ ID NO: 205) | 0.808734331 | 3 |
| TERT | 24 | 1 | 5 | + | 1295188 | 1295207 | GGGCCGCGGAAAGGAAGGGG (SEQ ID NO: 206) | 0.190013723 | 3 |
| TERT | 24 | 2 | 5 | + | 1295188 | 1295207 | GGGCCGCGGAAAGGAAGGGG (SEQ ID NO: 207) | 0.263178882 | 3 |
| TERT | 25 | 1 | 5 | + | 1295195 | 1295214 | GGAAAGGAAGGGGAGGGGCT (SEQ ID NO: 208) | 0.694483338 | 3 |

TABLE 9-continued

Efficiency of 40 tested Cas9 guide sequences targeting TERT promoter or exon 1

| Gene | Guide Number | Rep-licate | Chromo-some | Strand | Start | End | or Sequence (5' > 3') | % Indel Post-Editing | Days Post-Editing |
|---|---|---|---|---|---|---|---|---|---|
| TERT | 25 | 2 | 5 | + | 1295195 | 1295214 | GGAAAGGAAGGGGAGGGGCT (SEQ ID NO: 209) | 1.088031652 | 3 |
| TERT | 26 | 1 | 5 | - | 1295047 | 1295066 | GCTGCGCAGCCACTACCGCG (SEQ ID NO: 210) | 9.608671688 | 3 |
| TERT | 26 | 2 | 5 | - | 1295047 | 1295066 | GCTGCGCAGCCACTACCGCG (SEQ ID NO: 211) | 9.23021453 | 3 |
| TERT | 27 | 1 | 5 | - | 1295029 | 1295048 | TGGCCAGCGGCAGCACCTCG (SEQ ID NO: 212) | 13.6092238 | 3 |
| TERT | 27 | 2 | 5 | + | 1295029 | 1295048 | TGGCCAGCGGCAGCACCTCG (SEQ ID NO: 213) | 13.92764247 | 3 |
| TERT | 28 | 1 | 5 | + | 1295089 | 1295108 | GGGGAGCGCGCGGCATCGCG (SEQ ID NO: 214) | 1.17506812 | 3 |
| TERT | 28 | 2 | 5 | + | 1295089 | 1295108 | GGGGAGCGCGCGGCATCGCG (SEQ ID NO: 215) | 1.845949535 | 3 |
| TERT | 29 | 1 | 5 | + | 1295057 | 1295076 | GCTGCGCAGCAGGGAGCGCA (SEQ ID NO: 216) | 0.516528926 | 3 |
| TERT | 29 | 2 | 5 | + | 1295057 | 1295076 | GCTGCGCAGCAGGGAGCGCA (SEQ ID NO: 217) | 0.584136093 | 3 |
| TERT | 30 *selected* | 1 | 5 | + | 1295062 | 1295081 | GCAGCAGGGAGCGCACGGCT (SEQ ID NO: 218) | 43.3586832 | 3 |
| TERT | 30 *selected* | 2 | 5 | + | 1295062 | 1295081 | GCAGCAGGGAGCGCACGGCT (SEQ ID NO: 219) | 43.64339974 | 3 |
| TERT | 31 | 1 | 5 | - | 1295012 | 1295031 | CCACGTTCGTGCGGCGCCTG (SEQ ID NO: 220) | 3.555234955 | 3 |
| TERT | 31 | 2 | 5 | - | 1295012 | 1295031 | CCACGTTCGTGCGGCGCCTG (SEQ ID NO: 221) | 3.026278342 | 3 |
| TERT | 32 | 1 | 5 | - | 1295021 | 1295040 | TGCCGCTGGCCACGTTCGTG (SEQ ID NO: 222) | 0.166488286 | 3 |
| TERT | 32 | 2 | 5 | - | 1295021 | 1295040 | TGCCGCTGGCCACGTTCGTG (SEQ ID NO: 223) | 0.106094542 | 3 |
| TERT | 33 | 1 | 5 | + | 1295016 | 1295035 | CGCCGCACGAACGTGGCCAG (SEQ ID NO: 224) | 2.924819773 | 3 |
| TERT | 33 | 2 | 5 | + | 1295016 | 1295035 | CGCCGCACGAACGTGGCCAG (SEQ ID NO: 225) | 2.488785993 | 3 |
| TERT | 34 | 1 | 5 | + | 1295048 | 1295067 | GCGGTAGTGGCTGCGCAGCA (SEQ ID NO: 226) | 27.04076829 | 3 |
| TERT | 34 | 2 | 5 | + | 1295048 | 1295067 | GCGGTAGTGGCTGCGCAGCA (SEQ ID NO: 227) | 29.26941692 | 3 |
| TERT | 35 | 1 | 5 | - | 1295035 | 1295054 | CTACCGCGAGGTGCTGCCGC (SEQ ID NO: 228) | 1.037644788 | 3 |
| TERT | 35 | 2 | 5 | - | 1295035 | 1295054 | CTACCGCGAGGTGCTGCCGC (SEQ ID NO: 229) | 1.547315785 | 3 |
| TERT | 36 | 1 | 5 | + | 1295035 | 1295054 | GCGGCAGCACCTCGCGGTAG (SEQ ID NO: 230) | 2.113120269 | 3 |
| TERT | 36 | 2 | 5 | + | 1295035 | 1295054 | GCGGCAGCACCTCGCGGTAG (SEQ ID NO: 231) | 1.683682608 | 3 |
| TERT | 37 | 1 | 5 | + | 1295068 | 1295087 | GGGAGCGCACGGCTCGGCAG (SEQ ID NO: 232) | 5.207835643 | 3 |
| TERT | 37 | 2 | 5 | + | 1295068 | 1295087 | GGGAGCGCACGGCTCGGCAG (SEQ ID NO: 233) | 5.47759167 | 3 |

TABLE 9-continued

Efficiency of 40 tested Cas9 guide sequences targeting TERT promoter or exon 1

| Gene | Guide Number | Rep-licate | Chromo-some | Strand | Start | End | or Sequence (5' > 3') | % Indel Post-Editing | Days Post-Editing |
|---|---|---|---|---|---|---|---|---|---|
| TERT | 38 | 1 | 5 | + | 1295069 | 1295088 | GGAGCGCACGGCTCGGCAGC (SEQ ID NO: 234) | 0.835322196 | 3 |
| TERT | 38 | 2 | 5 | + | 1295069 | 1295088 | GGAGCGCACGGCTCGGCAGC (SEQ ID NO: 235) | 1.797124601 | 3 |
| TERT | 39 | 1 | 5 | + | 1295070 | 1295089 | GAGCGCACGGCTCGGCAGCG (SEQ ID NO: 236) | 6.049213944 | 3 |
| TERT | 39 | 2 | 5 | + | 1295070 | 1295089 | GAGCGCACGGCTCGGCAGCG (SEQ ID NO: 237) | 7.137254902 | 3 |
| TERT | 40 | 1 | 5 | + | 1295079 | 1295098 | GCTCGGCAGCGGGGAGCGCG (SEQ ID NO: 238) | 14.09248191 | 3 |
| TERT | 40 | 2 | 5 | + | 1295079 | 1295098 | GCTCGGCAGCGGGGAGCGCG (SEQ ID NO: 239) | 12.15295966 | 3 |

The CDKN2A knockout, BRAF V600E mutant, −124C>T TERT promoter mutant ('CBT') melanocytes were immortal. Control CB cells that did not receive the TERT −124C>T mutation exhibited morphological signs of senescence ('fried egg' appearance) and a noticeable decrease in division rate by day 100 (FIG. 19C, black curve and hash mark, and data not shown), by which point the cells had been in continuous culture for approximately six months since the original thaw of the wildtype parental melanocytes. In contrast, CBT cells proliferated normally in continuous culture for more than 1.5 years (data not shown). Thus, the combination of CDKN2A knockout, BRAF V600E mutation, and −124C>T TERT promoter mutation confers replicative immortality upon human melanocytes.

Because the mutant TERT allele stayed at an allele frequency of roughly 50%—unlike the BRAF and CDKN2A alleles, which were selected to 100%—we queried the TERT genotype of single cells within the CBT population, expecting to observe a uniform population of heterozygous cells. Instead, all single CBT cells were obtained as clones by sparse plating (n=8) had an approximately 100% mutant TERT allele frequency (Table 10), indicative of homozygosity and in conflict with the observed 50% allele frequency in the aggregate CBT population. Taken together with the observation that TERT wildtype CB cells were incapable of limitless cellular division, the most parsimonious explanation is that the majority of the aggregate CBT population was indeed heterozygous in the TERT mutant allele, and thus could not produce clones, with a small subpopulation of clonogenic, homozygous cells, which is selected upon cloning.

TABLE 10

TERT-124C>T allele frequency in CBT single cell clones.

| Mutant Line | Clone Number | TERT-124C>T Allele Frequency |
|---|---|---|
| CBT | 1 | 96.77942176 |
| CBT | 2 | 98.12505029 |
| CBT | 3 | 98.2724944 |
| CBT | 4 | 95.30814763 |
| CBT | 5 | 97.63974856 |
| CBT | 6 | 97.49311295 |

TABLE 10-continued

TERT-124C>T allele frequency in CBT single cell clones.

| Mutant Line | Clone Number | TERT-124C>T Allele Frequency |
|---|---|---|
| CBT | 7 | 96.85648029 |
| CBT | 8 | 97.17518903 |

Each sequentially introduced mutation leading to the generation of CBT melanocytes had the expected molecular and functional effect in the cells. C melanocytes showed loss of full-length p16 and increased levels of phosphorylated RB (FIG. 19D), indicating inactivation of the RB pathway. Applicants could not detect p14 in either wildtype or C melanocytes (data not shown). CB melanocytes showed expression of the BRAF V600E mutant kinase and increased phosphorylation of its substrates MEK1/2, indicating increased MAPK pathway activity (FIG. 19E). However, Applicants detected no increased phosphorylation of ERK1/2, the substrates of MEK1/2 (FIG. 19E), suggesting that the increase in MAPK pathway activity is rather minor. Finally, CBT melanocytes showed detectable TERT mRNA, whereas CB cells showed none (FIG. 19F), indicating that the −124C>T TERT promoter mutation is sufficient to activate telomerase reverse transcriptase expression in this cellular context. These results confirmed that the engineered C, B, and T mutations had respectively resulted in dysregulation of the RB pathway, the MAPK pathway, and telomerase reverse transcriptase expression in primary human melanocytes.

Figure 20A:
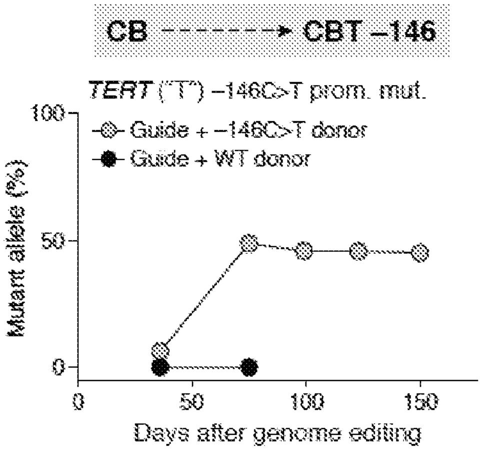
FIG. 20A, 20B—illustrate that −146C>T promoter mutation activates TERT expression and immortalizes CB melanocytes.
Figure 20B:
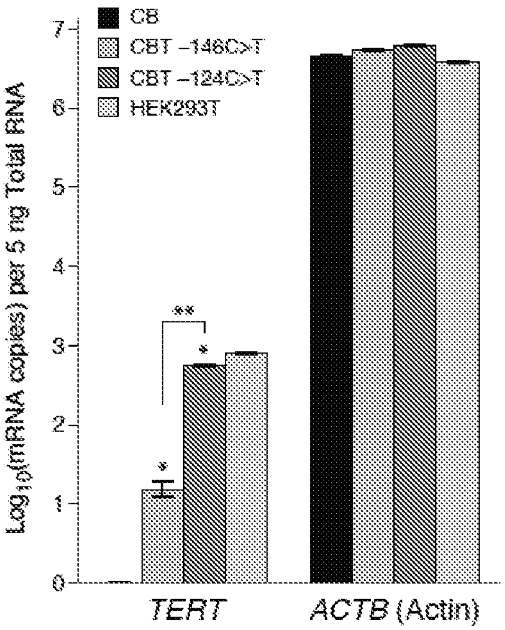
Figure 21G:
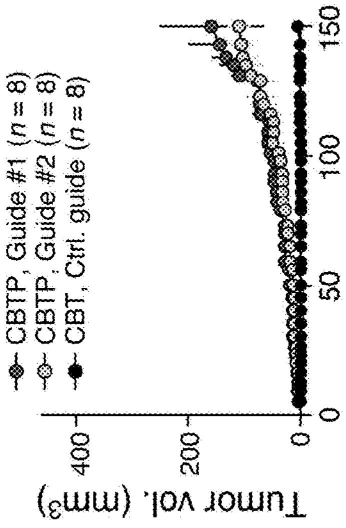
Figure 21H:
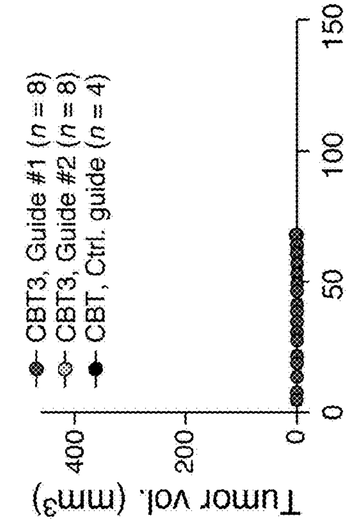
Figure 21I:
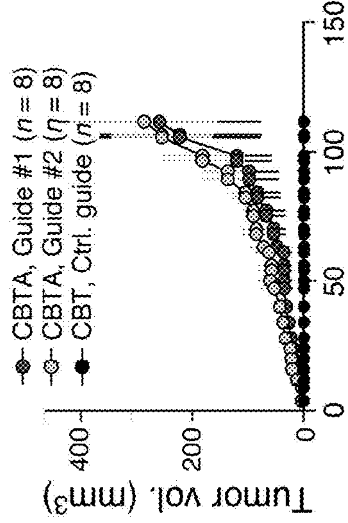
Figure 22:
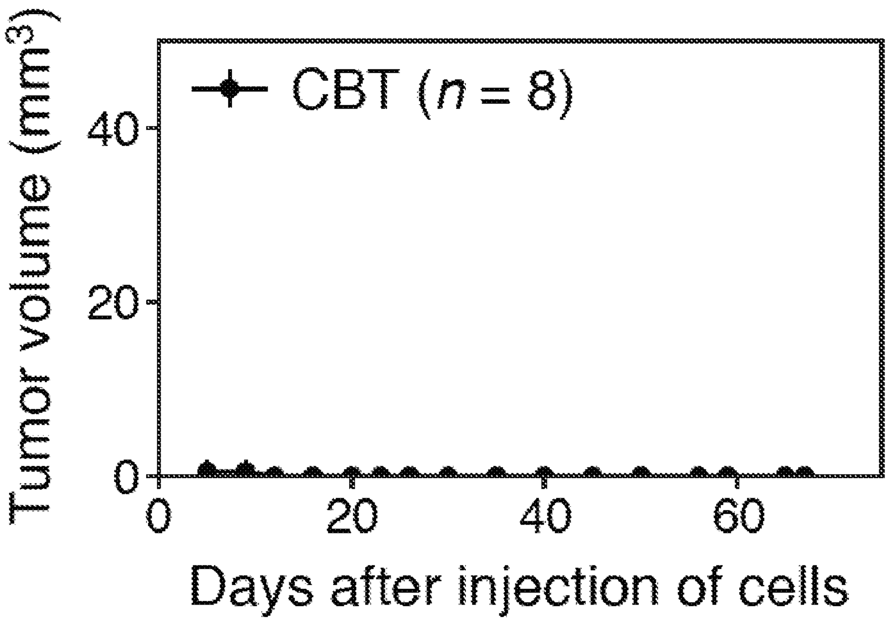
FIG. 22—a graph showing that CBT melanocytes do not readily form primary tumors in vivo. Primary tumor size of CBT cells ($mm^3$, y axis) over time (days, x axis) following two intradermal injections, one in each flank of NSG mice.
Figure 23A:
FIG. 23A-23C—micrographs showing that CBT melanocytes demonstrate malignant cellular pathology in vivo: mouse 108, tumor 1. Micrographs of H&E stained sections of small nodules of CBT cells at 67 days after injection into NSG mice.
Figure 23B:
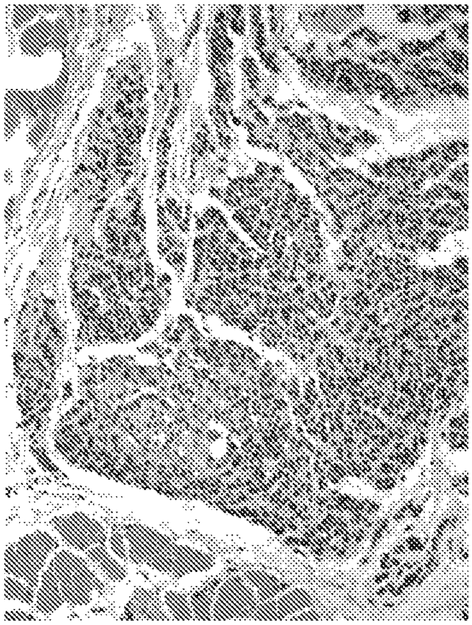
Figure 23C:
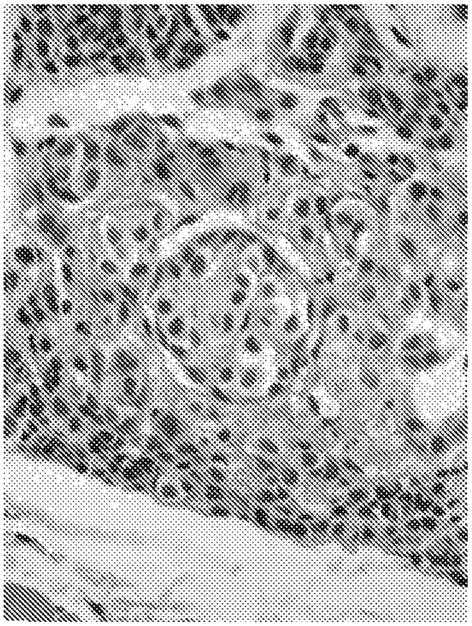
Figure 24A:
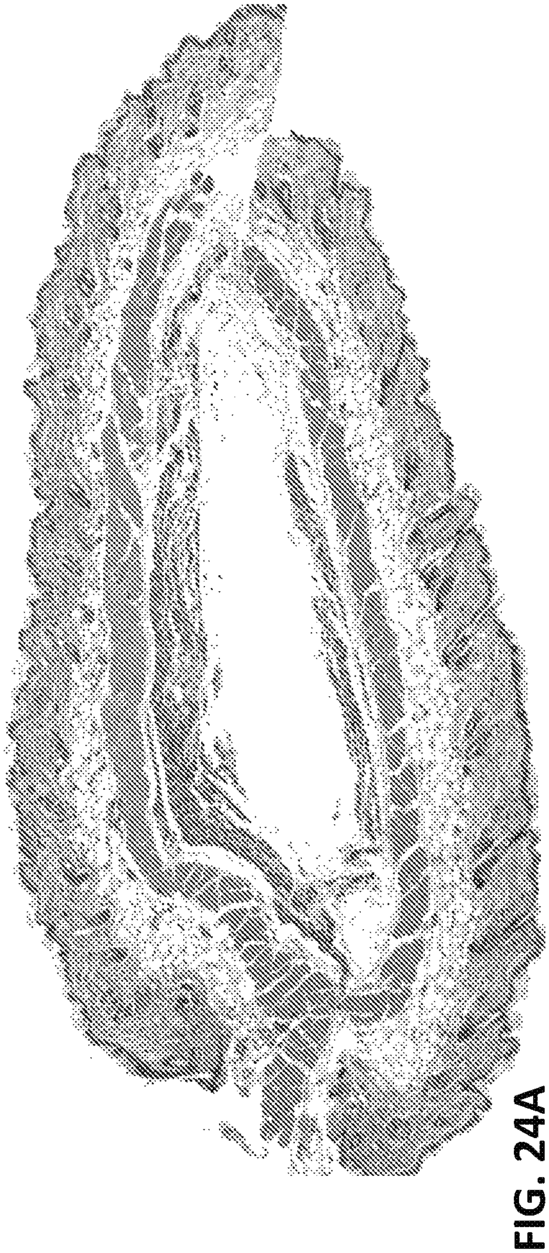
FIG. 24A-24C—micrographs showing that CBT melanocytes demonstrate malignant cellular pathology in vivo: mouse 108, tumor 2. Micrographs of H&E stained sections of small nodules of CBT cells at 67 days after injection into NSG mice.
Figure 24B:
Figure 24C:
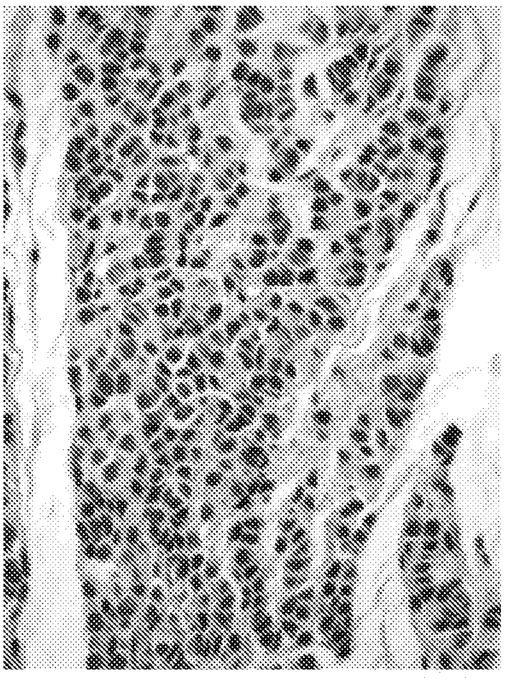
Figure 25A:
FIG. 25A-25D— micrographs showing that CBT melanocytes demonstrate malignant cellular pathology in vivo: mouse 218. Micrographs of H&E stained sections of small nodules of CBT cells at 67 days after injection into NSG mice.
Figure 25B:
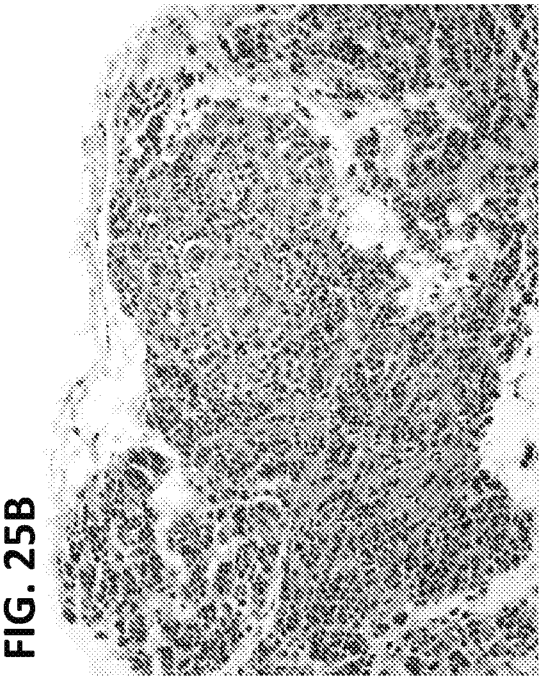
Figure 25C:
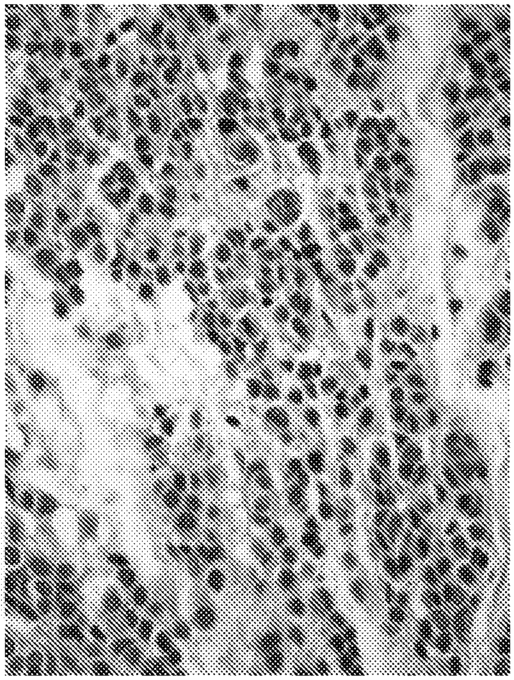
Figure 25D:
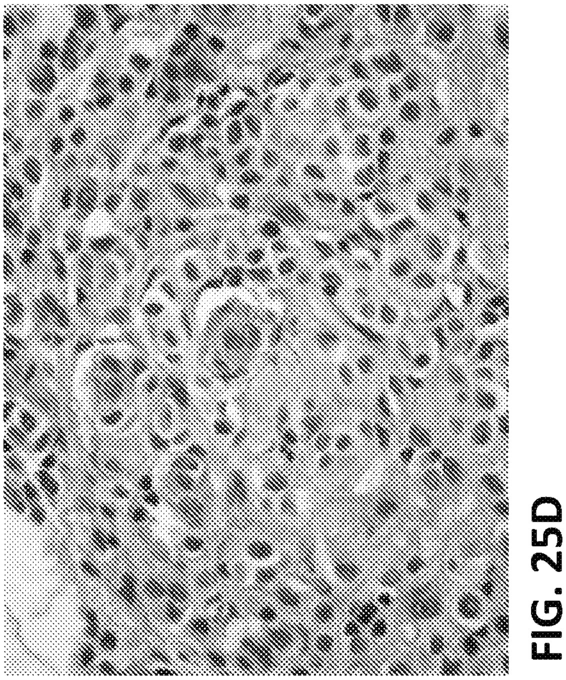
Figure 26A:
FIG. 26A-26E—micrographs showing that CBT melanocytes demonstrate malignant cellular pathology in vivo: mouse 107. Micrographs of H&E stained sections of small nodules of CBT cells at 69 days after injection into NSG mice.
Figure 26B:
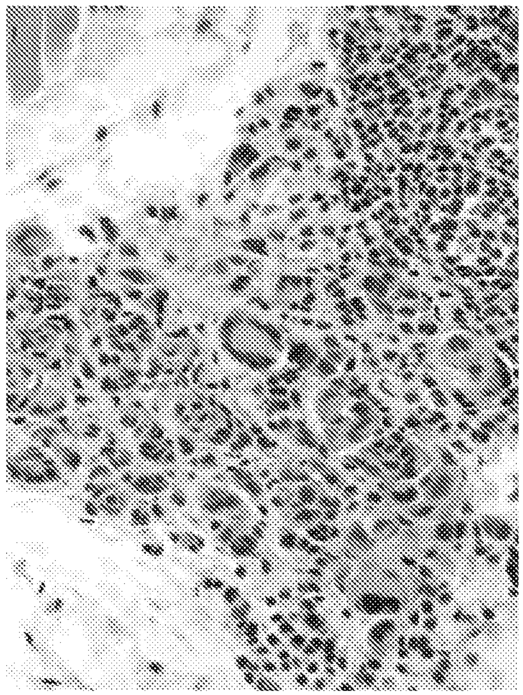
Figure 26C:
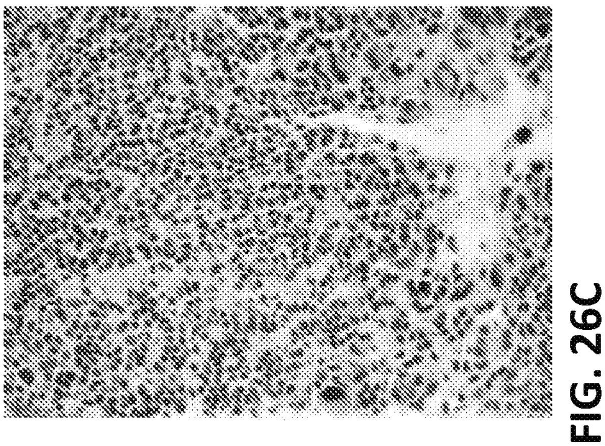
Figure 26D:
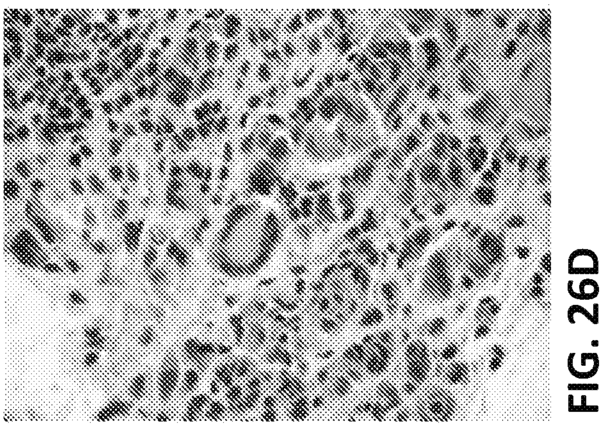
Figure 26E:
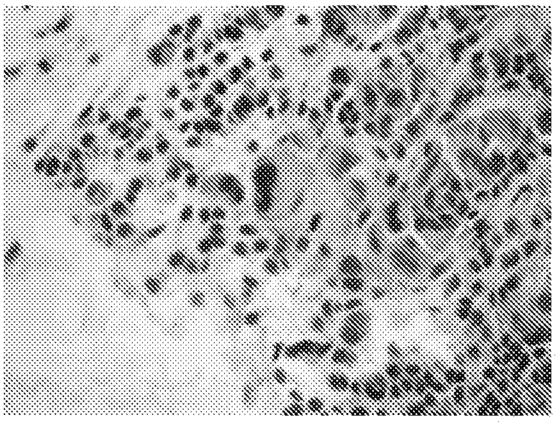
Figure 27A:
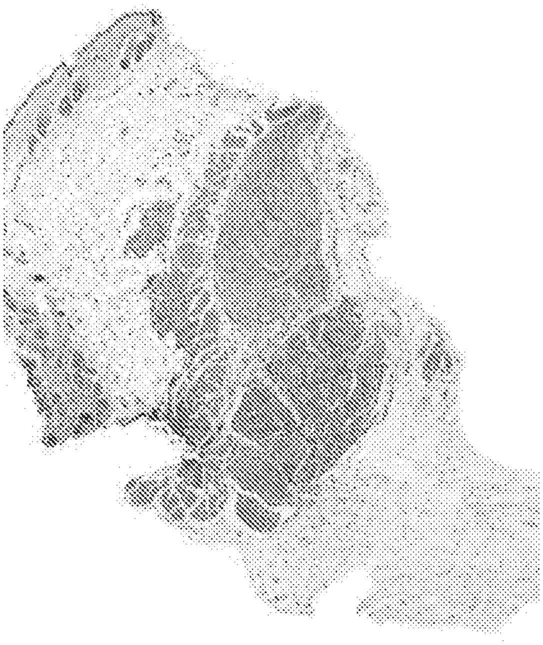
FIG. 27A-27D—micrographs showing that small primary tumors of CBT melanocytes demonstrate malignant cellular pathology in vivo. Micrographs of representative H&E stained sections of small primary tumors (up to 14 $mm^3$) that occasionally became apparent prior to tissue harvest at 151 days after injection of CBT cells into NSG mice. Green color is marking ink.
Figure 27B:
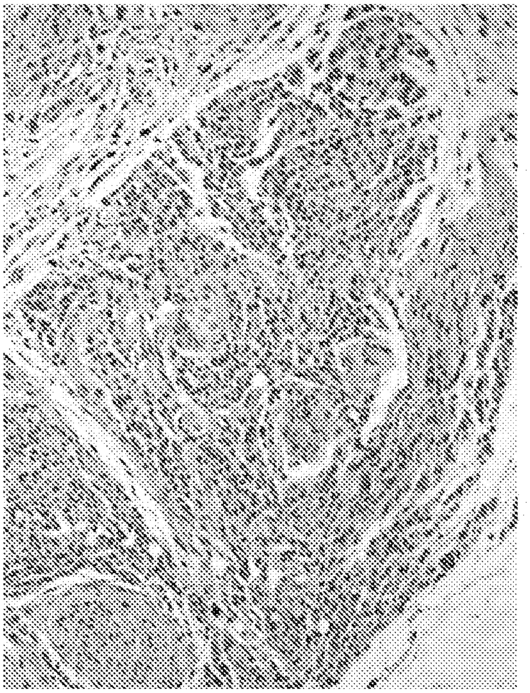
Figure 27C:
Figure 27D:
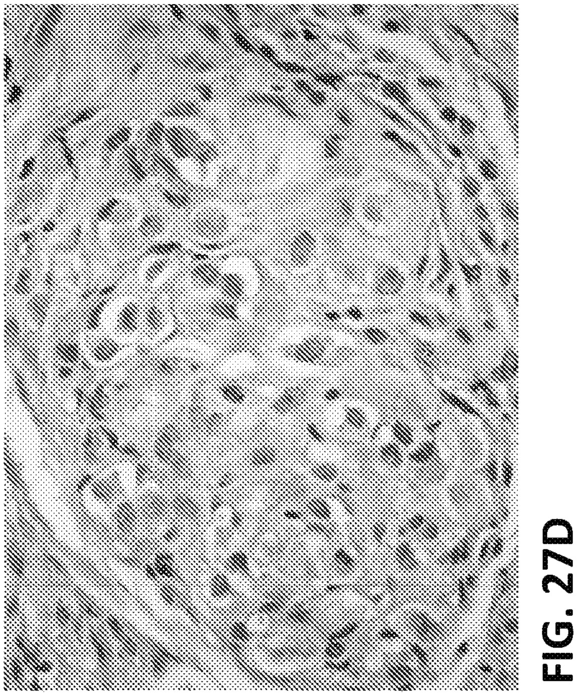

While CBT cells harbored the −124C>T mutation, one of two highly recurrent mutations in the TERT promoter in human melanoma that occur in a mutually exclusive pattern (Horn et al. *Science* 339:959-961 (2013); Huang et al. *Science* 339:957-959 (2013)), the other mutation, −146C>T (also known as C250T), could substitute for −124C>T in triggering TERT mRNA expression and conferring replicative immortality to CB cells. Specifically, after genome editing of CB melanocytes, the −146C>T TERT promoter mutation rose in allele frequency from 5% at day 36 to stabilize at roughly 50% by day 75 (FIG. 20A). Applicants detected TERT mRNA in these CBT−146 melanocytes, but at lower levels than in CBT melanocytes (FIG. 20B). This is in line with prior observations made in patient-derived melanomas (Akbani et al. *Cell* 161:1681-1696 (2015)) supporting the loyal nature of this model. Nevertheless, CBT-146 melanocytes were continuously grown in culture for over one year (data not shown), while CB cells that had received a control DNA donor sequence senesced much earlier. These results confirm that either of the two recurrent TERT promoter mutations is sufficient to activate TERT expression and immortalize CB melanocytes. CBT melanocytes were malignant in vivo. Applicants injected CBT cells into the dermis of immunodeficient mice to assay for malignant transformation. Over 67 to 111 days, no primary tumor growth was detectable (FIG. 21I [n=8], FIG. 21H [n=4]: black curves; FIG. 22 [n=8]); however, upon tissue harvest, small nodules could be seen at the injection sites. Histologic and immunophenotypic evaluation confirmed the presence of melanoma cells in these nodules (6 of 6 tumors examined; FIGS. 19G, 23A-26E, and Tables 11 and 12), often in the setting of what resembled a congenital nevus (3 of 6). Over a longer time course of at least 150 days, a small tumor (up to 14 $mm^3$) did occasionally become apparent at the injection site prior to tissue harvest (7 of 12 injections, FIG. 21G [n=8]: slight uptick of black curve at day 151, and not shown [n=4]). These occasionally arising tumors most closely resembled melanoma by dermatopathologic evaluation (4 of 4 tumors examined; FIGS. 27A-27D, Table 13). Thus, in contrast to previously reported observations in an ectopic expression human cell model (Tsao et al. *Science* 350:823-826 (2015)) but in line with observations in human melanoma (Shain et al. *N Engl J Med* 373:1926-1936 (2015)) melanocytes with common melanoma mutations in the endogenous loci of CDKN2A, BRAF, and TERT displayed phenotypic characteristics of early melanoma.

TABLE 11

Dermatopathological review of CBT primary tumors.

| Genotype | Days Post Injection | Slide Num | Slide Label | Stain | Tissue | Heterogenous/ Homogenous (1-10 scale?) | Benign or Malignant? | Most similar to which human melanocytic neoplastic category |
|---|---|---|---|---|---|---|---|---|
| CBT | 67 | 1 | EH_108_XLR1 | H&E | primary tumor | 6 | Malignant | Melanoma: Small foci of large epithelioid cells arising in nevoid background |
| CBT | 67 | 2 | EH_108_XLR1 | Ki67 | primary tumor | | | |
| CBT | 67 | 3 | EH_108_XLR1 | HMB45 | primary tumor | | | |
| CBT | 67 | 4 | EH_108_XLR1 | SOX10 | primary tumor | | | |
| CBT | 67 | 5 | EH_108_XLR1 | Melan-A | primary tumor | | | |
| CBT | 67 | 6 | EH_108_XLR2 | H&E | primary tumor | 9 | Malignant | Resembles nevoid melanoma |
| CBT | 67 | 7 | EH_108_XLR2 | Ki67 | primary tumor | | | |
| CBT | 67 | 8 | EH_108_XLR2 | HMB45 | primary tumor | | | |
| CBT | 67 | 9 | EH_108_XLR2 | SOX10 | primary tumor | | | |
| CBT | 67 | 10 | EH_108_XLR2 | Melan-A | primary tumor | | | |
| CBT | 67 | 11 | EH_212_XLR2 | H&E | primary tumor | 9 | Malignant | Small epithelioid and nevoid resembles congenital nevus |
| CBT | 67 | 12 | EH_212_XLR2 | Ki67 | primary tumor | | | |
| CBT | 67 | 13 | EH_212_XLR2 | HMB45 | primary tumor | | | |
| CBT | 67 | 14 | EH_212_XLR2 | SOX10 | primary tumor | | | |
| CBT | 67 | 15 | EH_212_XLR2 | Melan-A | primary tumor | | | |
| CBT | 67 | 16 | EH_218_XL | H&E | primary tumor | 7 | Malignant | Melanoma: Predominantly small epithelioid cells with scattered large epithelioid cells |
| CBT | 67 | 17 | EH_218_XL | Ki67 | primary tumor | | | |
| CBT | 67 | 18 | EH_218_XL | HMB45 | primary tumor | | | |
| CBT | 67 | 19 | EH_218_XL | SOX10 | primary tumor | | | |
| CBT | 67 | 20 | EH_218_XL | Melan-A | primary tumor | | | |

| Genotype | Days Post Injection | Slide Num | Pigmentation level (0-10) | Mitotic Count/ mm2 | Stain Scale (1-10) | Full note |
|---|---|---|---|---|---|---|
| CBT | 67 | 1 | 1 | 0 | N/A | There are nests of epitheloid cells focally present in a background of a nevus-like population of cells. HMB45 is strongly positive in the nests that resemble early melanoma, and is less positive in the |
| CBT | 67 | 2 | | | 2 | |
| CBT | 67 | 3 | | | 6 | |
| CBT | 67 | 4 | | | 9 | |
| CBT | 67 | 5 | | | 7 | |

TABLE 11-continued

Dermatopathological review of CBT primary tumors.

| | | | | | | |
|---|---|---|---|---|---|---|
| | | | | | | remainder of the lesion. |
| CBT | 67 | 6 | 2 | 0 | N/A | There is focal pigmentation. HMB45, SOX10 and Melan-A are diffusely positive. |
| CBT | 67 | 7 | | | 1 | |
| CBT | 67 | 8 | | | 7 | |
| CBT | 67 | 9 | | | 10 | |
| CBT | 67 | 10 | | | 7 | |
| CBT | 67 | 11 | 0 | 0 | N/A | The lesion is a well differentiated epithelioid cell melanoma with low proliferative index but with diffuse staining for Melan-A, HMB45, and SOX10. |
| CBT | 67 | 12 | | | 1 | |
| CBT | 67 | 13 | | | 7 | |
| CBT | 67 | 14 | | | 9 | |
| CBT | 67 | 15 | | | 9 | |
| CBT | 67 | 16 | 2 | 1 | N/A | This lesion exhibits a uniform population of malignant epithelioid melanocytes that have focal pigmetation but are strongly positive for Melan-A, HMB4, and SOX10. Ki67 shows a low proliferative index. |
| CBT | 67 | 17 | | | 2 | |
| CBT | 67 | 18 | | | 8 | |
| CBT | 67 | 19 | | | 10 | |
| CBT | 67 | 20 | | | 9 | |

TABLE 12

Dermatopathological review of CBT3 and control CBT primary tumors.

| Genotype | Days Post Injection | Slide Num | Slide Label | Stain | Tissue | Heterogenous/ Homogenous (1-10 scale?) | Benign or Malignant? | Most similar to which human melanocytic neoplastic category |
|---|---|---|---|---|---|---|---|---|
| CBT | 69 | 1 | EH_105_XLR | H&E | primary tumor | 8 | Malignant | Congenital nevus with epithelioid cells |
| CBT | 69 | 2 | EH_105_XLR | Ki67 | primary tumor | | | |
| CBT | 69 | 3 | EH_105_XLR | HMB45 | primary tumor | | | |
| CBT | 69 | 4 | EH_105_XLR | SOX10 | primary tumor | | | |
| CBT | 69 | 5 | EH_105_XLR | Melan-A | primary tumor | | | |
| CBT | 69 | 6 | EH_107_XLR | H&E | primary tumor | 7 | Malignant | Some resemblence to congenital nevus. Nevoid melanocytes with nests of small epithelioid cells |
| CBT | 69 | 7 | EH_107_XLR | Ki67 | primary tumor | | | |
| CBT | 69 | 8 | EH_107_XLR | HMB45 | primary tumor | | | |
| CBT | 69 | 9 | EH_107_XLR | SOX10 | primary tumor | | | |
| CBT | 69 | 10 | EH_107_XLR | Melan-A | primary tumor | | | |
| CBT3 | 69 | 11 | EH_106_XR | H&E | primary tumor | 8 | Malignant | Melanoma: Large epithelioid cells in nests and sheets |
| CBT3 | 69 | 12 | EH_106_XR | Ki67 | primary tumor | | | |
| CBT3 | 69 | 13 | EH_106_XR | HMB45 | primary tumor | | | |
| CBT3 | 69 | 14 | EH_106_XR | SOX10 | primary tumor | | | |
| CBT3 | 69 | 15 | EH_106_XR | Melan-A | primary tumor | | | |
| CBT3 | 69 | 21 | EH_190_XLR | H&E | primary tumor | 7 | Malignant | Majority of small round hyperchromatic cells with scattered epithelioid cells and multinucleated giant cells |
| CBT3 | 69 | 22 | EH_190_XLR | Ki67 | primary tumor | | | |
| CBT3 | 69 | 23 | EH_190_XLR | HMB45 | primary tumor | | | |
| CBT3 | 69 | 24 | EH_190_XLR | SOX10 | primary tumor | | | |

TABLE 12-continued

Dermatopathological review of CBT3 and control CBT primary tumors.

| | | | | | | | | |
|---|---|---|---|---|---|---|---|---|
| CBT3 | 69 | 25 | EH_190_XLR | Melan-A | primary tumor | | | |
| CBT3 | 69 | 26 | EH_191_XLR | H&E | primary tumor | 7 | Malignant | Nevoid cells resembles congenital nevus with few cells with ample cytoplasm |
| CBT3 | 69 | 27 | EH_191_XLR | Ki67 | primary tumor | | | |
| CBT3 | 69 | 28 | EH_191_XLR | HMB45 | primary tumor | | | |
| CBT3 | 69 | 29 | EH_191_XLR | SOX10 | primary tumor | | | |
| CBT3 | 69 | 30 | EH_191_XLR | Melan-A | primary tumor | | | |

| Genotype | Days Post Injection | Slide Num | Pigmentation level (0-10) | Mitotic Count/ mm2 | Stain Scale (1-10) | Full note |
|---|---|---|---|---|---|---|
| CBT | 69 | 1 | 0 | 0 | N/A | The lesion is present below the muscle. It is uniform and resembles a congenital nevus. But there are 3 or 4 large malignant cells present that are positive for all markers. |
| CBT | 69 | 2 | | | 1 | |
| CBT | 69 | 3 | | | 6 | |
| CBT | 69 | 4 | | | 8 | |
| CBT | 69 | 5 | | | 7 | |
| CBT | 69 | 6 | 1 | 2 | N/A | The tumor is present between muscle fibers and in fat. There are two populations of cells. There is a small cell population that is HMB45 virtually negative. However, there are several large cells that are HMB45 positive, as well as Ki67 and Melan-A positive. SOX10 is diffuse throughout the tumor. The large cells are present in the nodule and as single cells in the adjacent fat. |
| CBT | 69 | 7 | | | 1 | |
| CBT | 69 | 8 | | | 6 | |
| CBT | 69 | 9 | | | 10 | |
| CBT | 69 | 10 | | | 4 | |
| CBT3 | 69 | 11 | 4 | 21 | N/A | This lesion represents a small cell melanoma nodule that is homogeneous but shows minimal mitotic activity inspite of the high Ki67. There is patchy irregular pigmentation throughout the lesion. |
| CBT3 | 69 | 12 | | | 8 | |
| CBT3 | 69 | 13 | | | 10 | |
| CBT3 | 69 | 14 | | | 10 | |
| CBT3 | 69 | 15 | | | 9 | |
| CBT3 | 69 | 21 | 0 | 0 | N/A | A small deposit of tumor in subcutaneous fat exhibits a small cell component that looks uniform |
| CBT3 | 69 | 22 | | | 3 | |
| CBT3 | 69 | 23 | | | 4 | |
| CBT3 | 69 | 24 | | | 10 | |
| CBT3 | 69 | 25 | | | 8 | |

TABLE 12-continued

Dermatopathological review of CBT3 and control CBT primary tumors.

| | | | | | | |
|---|---|---|---|---|---|---|
| | | | | | | except for a few prominent maligant cells scattered. The melanoma focally dissects into the muscle. The staining is unusual. SOX10 is diffuse, but HMB45 stains a few nests in the large big cells. Melan-A stains more of the small cells, as well as the large cells. Ki67 is positive in the nests in the periphery. |
| CBT3 | 69 | 26 | 0 | 0 | N/A | The lesion has a nevoid small cell appearance except for a few scattered nests of slightly larger cells. These nests stain for the melanocyte markers. All cells stain for SOX10. There is rare Ki67 positive signal in the nests. |
| CBT3 | 69 | 27 | | | 1 | |
| CBT3 | 69 | 28 | | | 2 | |
| CBT3 | 69 | 29 | | | 9 | |
| CBT3 | 69 | 30 | | | 3 | |

TABLE 13

Dermatopathological review of CBTA and control CBT primary tumors, liver, and lung sections.

| Genotype | Days Post Injection | Slide Num | Slide Label | Stain | Tissue | Heterogenous/ Homogenous (1-10 scale?) | Benign or Malignant? | Most similar to which human melanocytic neoplastic category |
|---|---|---|---|---|---|---|---|---|
| CBT | 151 | 1 | EH_215-222_X4-1 | H&E | primary tumor | 8 | Malignant | Melanoma: spindle cells |
| CBT | 151 | 2 | EH_215-222_X4-1 | Ki67 | primary tumor | | | |
| CBT | 151 | 3 | EH_215-222_X4-1 | HMB45 | primary tumor | | | |
| CBT | 151 | 4 | EH_215-222_X4-1 | SOX10 | primary tumor | | | |
| CBT | 151 | 5 | EH_215-222_X4-1 | Melan-A | primary tumor | | | |
| CBT | 151 | 1 | EH_215-222_X4-2 | H&E | primary tumor | 5 | Malignant | Spitzoid features |
| CBT | 151 | 2 | EH_215-222_X4-2 | Ki67 | primary tumor | | | |
| CBT | 151 | 3 | EH_215-222_X4-2 | HMB45 | primary tumor | | | |
| CBT | 151 | 4 | EH_215-222_X4-2 | SOX10 | primary tumor | | | |
| CBT | 151 | 5 | EH_215-222_X4-2 | Melan-A | primary tumor | | | |
| CBT | 151 | 1 | EH_215-222_X4-3 | H&E | primary tumor | 5 | Malignant | Melanoma: Large and small epithelioid cells with admixed spindle cells (with neuroidal features) |
| CBT | 151 | 2 | EH_215-222_X4-3 | Ki67 | primary tumor | | | |
| CBT | 151 | 3 | EH_215-222_X4-3 | HMB45 | primary tumor | | | |
| CBT | 151 | 4 | EH_215-222_X4-3 | SOX10 | primary tumor | | | |
| CBT | 151 | 5 | EH_215-222_X4-3 | Melan-A | primary tumor | | | |
| CBT | 151 | 1 | EH_215-222_X4-4 | H&E | primary tumor | 4 | Malignant | Melanoma: Central large epithelioid cells in nests surrounded by smaller epithelioid cells with admixed spindle cells |
| CBT | 151 | 2 | EH_215-222_X4-4 | Ki67 | primary tumor | | | |
| CBT | 151 | 3 | EH_215-222_X4-4 | HMB45 | primary tumor | | | |

TABLE 13-continued

Dermatopathological review of CBTA and control CBT primary tumors, liver, and lung sections.

| | | | | | | | | |
|---|---|---|---|---|---|---|---|---|
| CBT | 151 | 4 | EH_215-222_X4-4 | SOX10 | primary tumor | | | |
| CBT | 151 | 5 | EH_215-222_X4-4 | Melan-A | primary tumor | | | |
| CBTP | 151 | 6 | EH_211-213_XT-1 | H&E | primary tumor | 9 | Malignant | epithelioid with peripheral spindle |
| CBTP | 151 | 7 | EH_211-213_XT-1 | Ki67 | primary tumor | | | |
| CBTP | 151 | 8 | EH_211-213_XT-1 | HMB45 | primary tumor | | | |
| CBTP | 151 | 9 | EH_211-213_XT-1 | SOX10 | primary tumor | | | |
| CBTP | 151 | 10 | EH_211-213_XT-1 | Melan-A | primary tumor | | | |
| CBTP | 151 | 6 | EH_211-213_XT-2 | H&E | primary tumor | 8 | Malignant | Melanoma: Admixed |
| CBTP | 151 | 7 | EH_211-213_XT-2 | Ki67 | primary tumor | | | |
| CBTP | 151 | 8 | EH_211-213_XT-2 | HMB45 | primary tumor | | | |
| CBTP | 151 | 9 | EH_211-213_XT-2 | SOX10 | primary tumor | | | |
| CBTP | 151 | 10 | EH_211-213_XT-2 | Melan-A | primary tumor | | | |
| CBTP | 151 | 6 | EH_211-213_XT-3 | H&E | primary tumor | 7 | Malignant | Melanoma: |
| CBTP | 151 | 7 | EH_211-213_XT-3 | Ki67 | primary tumor | | | |
| CBTP | 151 | 8 | EH_211-213_XT-3 | HMB45 | primary tumor | | | |
| CBTP | 151 | 9 | EH_211-213_XT-3 | SOX10 | primary tumor | | | |
| CBTP | 151 | 10 | EH_211-213_XT-3 | Melan-A | primary tumor | | | |
| CBTP | 151 | 6 | EH_211-213_XT-4 | H&E | primary tumor | 7 | Malignant | Melanoma: Large |
| CBTP | 151 | 7 | EH_211-213_XT-4 | Ki67 | primary tumor | | | |
| CBTP | 151 | 8 | EH_211-213_XT-4 | HMB45 | primary tumor | | | |
| CBTP | 151 | 9 | EH_211-213_XT-4 | SOX10 | primary tumor | | | |
| CBTP | 151 | 10 | EH_211-213_XT-4 | Melan-A | primary tumor | | | |
| CBT | 151 | 11 | EH_215_225_LVG | H&E | multiple liver and lung lobes | | | |
| CBT | 151 | 12 | EH_215_225_LVG | Ki67 | multiple liver and lung lobes | | | |
| CBT | 151 | 13 | EH_215_225_LVG | HMB45 | multiple liver and lung lobes | | | |
| CBT | 151 | 14 | EH_215_225_LVG | SOX10 | multiple liver and lung lobes | | | |
| CBT | 151 | 15 | EH_215_225_LVG | Melan-A | multiple liver and lung lobes | | | |
| CBT | 151 | 16 | EH_222_LVG | H&E | multiple liver and lung lobes | | | |
| CBT | 151 | 17 | EH_222_LVG | Ki67 | multiple liver and lung lobes | | | |
| CBT | 151 | 18 | EH_222_LVG | HMB45 | multiple liver and lung lobes | | | |
| CBT | 151 | 19 | EH_222_LVG | SOX10 | multiple liver and lung lobes | | | |
| CBT | 151 | 20 | EH_222_LVG | Melan-A | multiple liver and lung lobes | | | |
| CBT | 151 | 21 | EH_202_203 | H&E | multiple liver and lung lobes | | | |
| CBT | 151 | 22 | EH_202_203 | Ki67 | multiple liver and lung lobes | | | |
| CBT | 151 | 23 | EH_202_203 | HMB45 | multiple liver and lung lobes | | | |
| CBT | 151 | 24 | EH_202_203 | SOX10 | multiple liver and lung lobes | | | |
| CBT | 151 | 25 | EH_202_203 | Melan-A | multiple liver and lung lobes | | | |
| CBT | 151 | 26 | EH_214_LVG | H&E | multiple liver and lung lobes | | | |
| CBT | 151 | 27 | EH_214_LVG | Ki67 | multiple liver and lung lobes | | | |
| CBT | 151 | 28 | EH_214_LVG | HMB45 | multiple liver and lung lobes | | | |
| CBT | 151 | 29 | EH_214_LVG | SOX10 | multiple liver and lung lobes | | | |
| CBT | 151 | 30 | EH_214_LVG | Melan-A | multiple liver and lung lobes | | | |
| CBTP | 151 | 31 | EH_211_LVG | H&E | multiple liver and lung lobes | | | |
| CBTP | 151 | 32 | EH_211_LVG | Ki67 | multiple liver and lung lobes | | | |
| CBTP | 151 | 33 | EH_211_LVG | HMB45 | multiple liver and lung lobes | | | |
| CBTP | 151 | 34 | EH_211_LVG | SOX10 | multiple liver and lung lobes | | | |
| CBTP | 151 | 35 | EH_211_LVG | Melan-A | multiple liver and lung lobes | | | |
| CBTP | 151 | 36 | EH_213_LVG | H&E | multiple liver and lung lobes | | | |
| CBTP | 151 | 37 | EH_213_LVG | Ki67 | multiple liver and lung lobes | | | |

TABLE 13-continued

Dermatopathological review of CBTA and control CBT primary tumors, liver, and lung sections.

| | | | | | |
|---|---|---|---|---|---|
| CBTP | 151 | 38 | EH_213_LVG | HMB45 | multiple liver and lung lobes |
| CBTP | 151 | 39 | EH_213_LVG | SOX10 | multiple liver and lung lobes |
| CBTP | 151 | 40 | EH_213_LVG | Melan-A | multiple liver and lung lobes |
| CBTP | 151 | 41 | EH_204_LVG | H&E | multiple liver and lung lobes |
| CBTP | 151 | 42 | EH_204_LVG | Ki67 | multiple liver and lung lobes |
| CBTP | 151 | 43 | EH_204_LVG | HMB45 | multiple liver and lung lobes |
| CBTP | 151 | 44 | EH_204_LVG | SOX10 | multiple liver and lung lobes |
| CBTP | 151 | 45 | EH_204_LVG | Melan-A | multiple liver and lung lobes |
| CBTP | 151 | 46 | EH_223_LVG | H&E | multiple liver and lung lobes |
| CBTP | 151 | 47 | EH_223_LVG | Ki67 | multiple liver and lung lobes |
| CBTP | 151 | 48 | EH_223_LVG | HMB45 | multiple liver and lung lobes |
| CBTP | 151 | 49 | EH_223_LVG | SOX10 | multiple liver and lung lobes |
| CBTP | 151 | 50 | EH_223_LVG | Melan-A | multiple liver and lung lobes |

| Genotype | Days Post Injection | Slide Num | Pigmentation level (0-10) | Mitotic Count/ mm2 | Stain Scale (1-10) | Full note |
|---|---|---|---|---|---|---|
| CBT | 151 | 1 | 0 | 0 | N/A | Small spindle cell tumor |
| CBT | 151 | 2 | | | 5 | with unexpectedly high |
| CBT | 151 | 3 | | | 0 | Ki67 signal. It is negative |
| CBT | 151 | 4 | | | 8 | for HMB45, but positive for |
| CBT | 151 | 5 | | | 5 | SOX10 and Melan-A focally. |
| CBT | 151 | 1 | 0 | 0 | N/A | This small tumor shows a |
| CBT | 151 | 2 | | | 1 | mixture of spindle and |
| CBT | 151 | 3 | | | 7 | epithelioid cells. It is focally |
| CBT | 151 | 4 | | | 9 | positive for melanocytic |
| CBT | 151 | 5 | | | 6 | markers. |
| CBT | 151 | 1 | 0 | 0 | N/A | This tumor exhibits a |
| CBT | 151 | 2 | | | 1 | prominent neuroidal |
| CBT | 151 | 3 | | | 8 | picture resembling a |
| CBT | 151 | 4 | | | 9 | neuroma. However, it is |
| CBT | 151 | 5 | | | 8 | atypical and consistent with melanoma as confirmed by the melanoma markers. |
| CBT | 151 | 1 | 0 | 0 | N/A | This interesting tumor |
| CBT | 151 | 2 | | | 2 | shows a focus of epitheloid |
| CBT | 151 | 3 | | | 5 | cells in the center of an |
| CBT | 151 | 4 | | | 9 | otherwise multifocal |
| CBT | 151 | 5 | | | 5 | nevoid melanoma. The nevoid melanoma is present in multiple aggregates around the epithelioid cell area. The latter is negative for Melan-A, HMB45, and Ki67 but positive for SOX10. The nevoid melanoma component is positive for all markers. |
| CBTP | 151 | 6 | 0 | 1 | N/A | Large uniform epithelioid |
| CBTP | 151 | 7 | | | 1 | cell tumor in prominent |
| CBTP | 151 | 8 | | | 2 | nests with low mitotic |
| CBTP | 151 | 9 | | | 9 | activity. Staining for |
| CBTP | 151 | 10 | | | 2 | melanocyte markers is patchy. |
| CBTP | 151 | 6 | 0 | 1 | N/A | On H&E, the tumor appears |
| CBTP | 151 | 7 | | | 3 | homogeneous. However, |
| CBTP | 151 | 8 | | | 1 | the melanocytic markers |
| CBTP | 151 | 9 | | | 9 | exhibit multifocal staining |
| CBTP | 151 | 10 | | | 3 | in patches. |
| CBTP | 151 | 6 | 0 | 1 | N/A | This predominantly spindle |
| CBTP | 151 | 7 | | | 2 | cell melanoma has areas of |
| CBTP | 151 | 8 | | | 4 | epithelioid cells that stain |

TABLE 13-continued

Dermatopathological review of CBTA and control CBT primary tumors, liver, and lung sections.

| | | | | | | |
|---|---|---|---|---|---|---|
| CBTP | 151 | 9 | | | 7 | for HMB45, Melan-A, and |
| CBTP | 151 | 10 | | | 4 | SOX10. There is an increase in Ki67 in these areas. |
| CBTP | 151 | 6 | 2 | 1 | N/A | One central area of |
| CBTP | 151 | 7 | | | 2 | epitheliod cells shows |
| CBTP | 151 | 8 | | | 2 | pigmenteation, increased |
| CBTP | 151 | 9 | | | 9 | Ki67, Melan-A and HMB45 |
| CBTP | 151 | 10 | | | 3 | positivity. The tumor is in subcutaneous fat. |
| CBT | 151 | 11 | | | N/A | No metatastatic tumor to |
| CBT | 151 | 12 | | | | liver or lung. |
| CBT | 151 | 13 | | | | |
| CBT | 151 | 14 | | | | |
| CBT | 151 | 15 | | | | |
| CBT | 151 | 16 | | | N/A | No metatastatic tumor to |
| CBT | 151 | 17 | | | | liver or lung. |
| CBT | 151 | 18 | | | | |
| CBT | 151 | 19 | | | | |
| CBT | 151 | 20 | | | | |
| CBT | 151 | 21 | | | N/A | No metatastatic tumor to |
| CBT | 151 | 22 | | | | liver or lung. |
| CBT | 151 | 23 | | | | |
| CBT | 151 | 24 | | | | |
| CBT | 151 | 25 | | | | |
| CBT | 151 | 26 | | | N/A | No metatastatic tumor to |
| CBT | 151 | 27 | | | | liver or lung. |
| CBT | 151 | 28 | | | | |
| CBT | 151 | 29 | | | | |
| CBT | 151 | 30 | | | | |
| CBTP | 151 | 31 | | | N/A | No metatastatic tumor to |
| CBTP | 151 | 32 | | | | liver. Multiple foci of |
| CBTP | 151 | 33 | | | | metastatic tumor |
| CBTP | 151 | 34 | | | | highlighted with HMB45 |
| CBTP | 151 | 35 | | | | and SOX10 to lung. |
| CBTP | 151 | 36 | | | N/A | No metatastatic tumor to |
| CBTP | 151 | 37 | | | | liver. Multiple foci of |
| CBTP | 151 | 38 | | | | metastatic tumor |
| CBTP | 151 | 39 | | | | highlighted with HMB45 |
| CBTP | 151 | 40 | | | | and SOX10 to lung. |
| CBTP | 151 | 41 | | | N/A | No metatastatic tumor to |
| CBTP | 151 | 42 | | | | liver. Multiple foci of |
| CBTP | 151 | 43 | | | | metastatic tumor |
| CBTP | 151 | 44 | | | | highlighted with HMB45, |
| CBTP | 151 | 45 | | | | Melan-A, and SOX10 to lung. |
| CBTP | 151 | 46 | | | N/A | No metatastic tumor to |
| CBTP | 151 | 47 | | | | liver. 2 cells highlighted by |
| CBTP | 151 | 48 | | | | HMB45 metastatic to lung. |
| CBTP | 151 | 49 | | | | |
| CBTP | 151 | 50 | | | | |

Figures 21A, 21B, 21C, 21D, 21E, 21F:
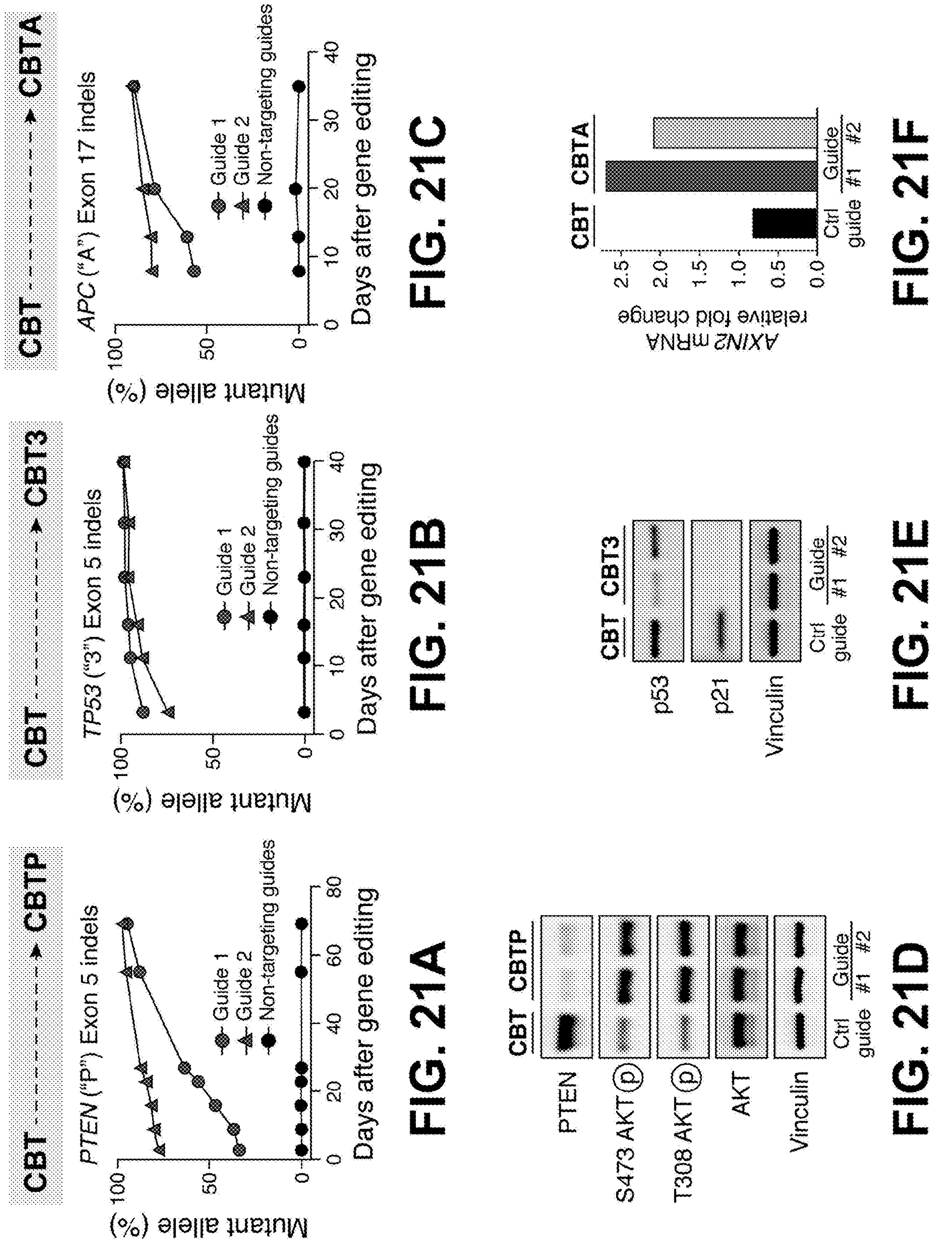
Figure 21J:
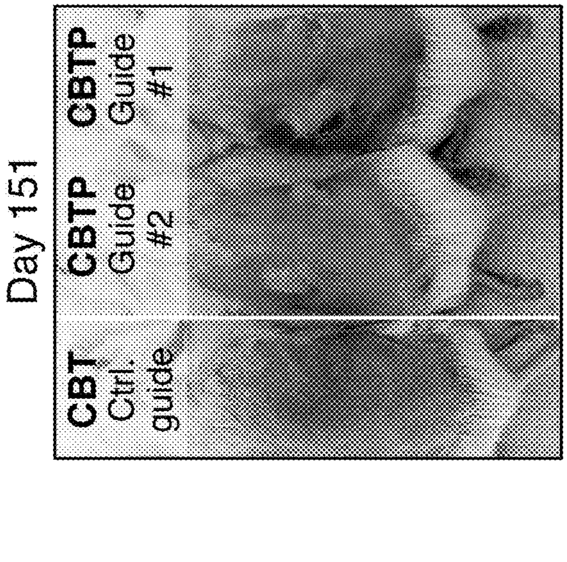
Figure 21K:
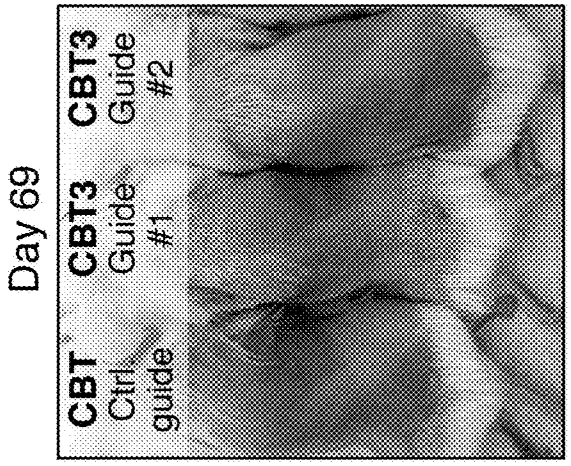
Figure 21L:
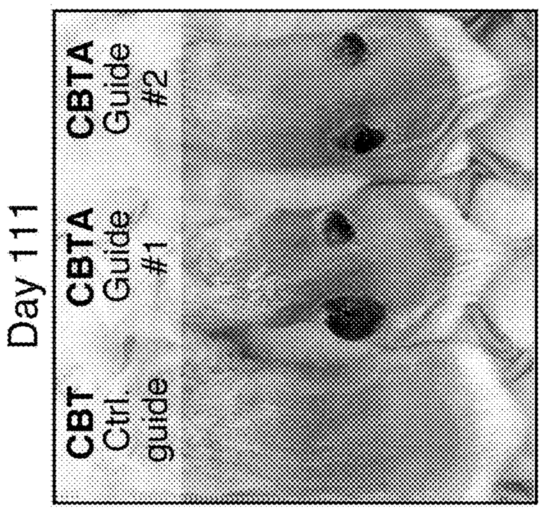
Figure 21M:
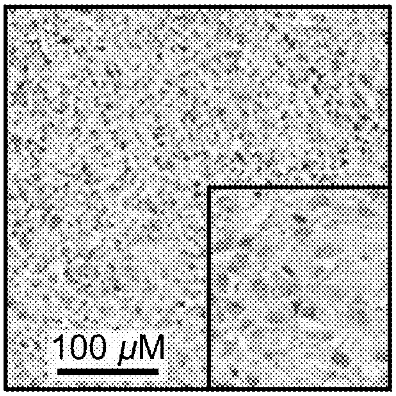
Figure 21N:
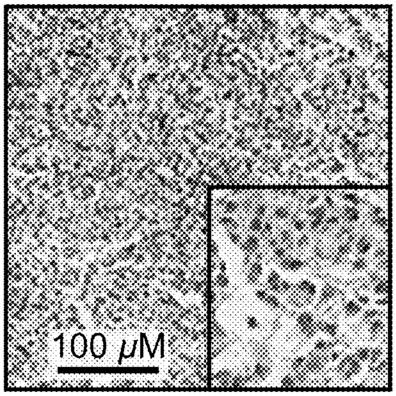
Figure 21O:
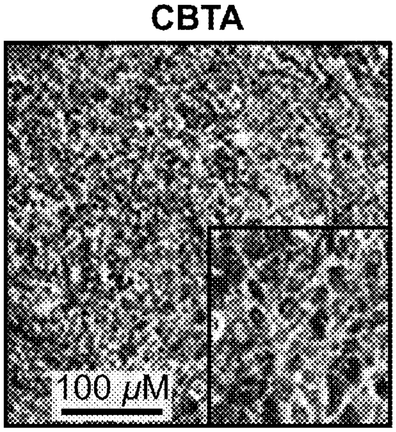

Applicants next engineered additional single knockouts of PTEN ('P'), TP53 ('3'), and APC ('A') in CBT melanocytes to explore if a fourth mutation in any of these melanoma tumor suppressor genes could elicit disease progression (FIGS. 21A-21O). BRAF V600E melanomas tend to harbor PTEN alterations (~40% of them), but otherwise no co-mutation pattern has emerged in human melanoma among PTEN, TP53, and APC (or Wnt pathway activation) (Hodis et al. *Cell* 150:251-263 (2012); Krauthammer et al. *Nat Genet* 44:1006-1014 (2012); Akbani et al. *Cell* 161:1681-1696 (2015); Sanborn et al. *PNAS USA* 112:10995-11000 (2015)). In each case, indels in the fourth gene underwent positive selection in culture, reaching a near 100% mutant allele frequency by at most 70 days (FIGS. 21A-21C). Each knockout had the expected effect on the relevant functional pathway as reflected by increased phosphorylation of AKT (PI3K/AKT pathway), loss of p21 (p53 pathway), and increased AXIN2 mRNA (Wnt pathway) in CBTP, CBT3, and CBTA cells, respectively (FIGS. 21D-21F).

Figure 28K:
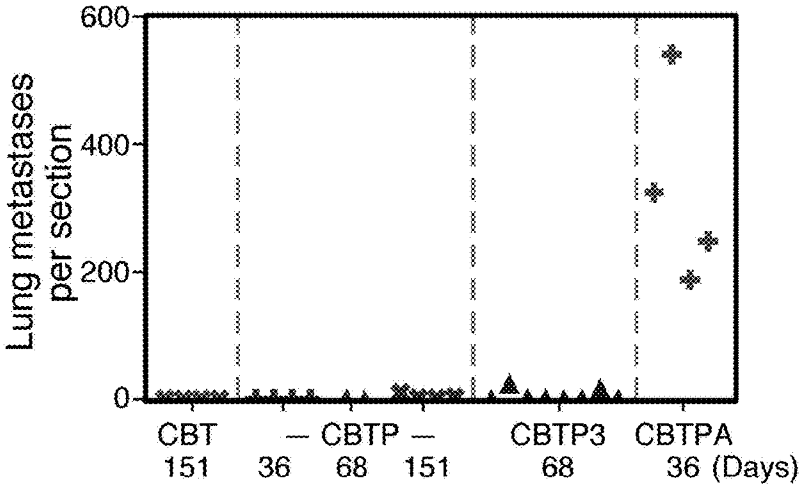
(FIG. 28K, 28L) Loss of APC promotes frequent distant metastases. Number of individual metastatic foci per section of lung (FIG. 28K) or liver (FIG. 28L) tissue in each histologic slide (y axis, counted manually) in tumors from mice injected with different mutant cell lines and collected following the indicated number of days (x axis). Each slide had an average of three lung sections and two liver sections, all from the same mouse, each from a different lobe. Data shown is from the four independent experiments in FIGS. 21G, 21I, 28E, and 28F.
Figure 28L:
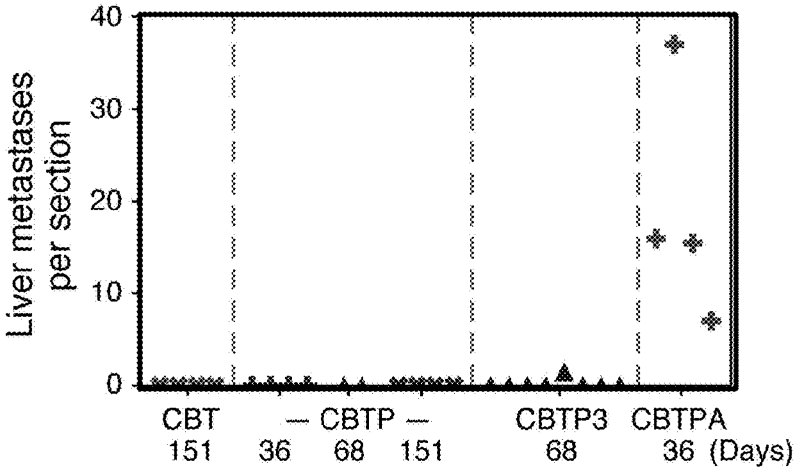
Figure 29A:
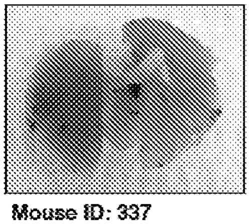
FIG. 29A, 29B—CBTA cells metastasize in vivo. Photographs of mouse organs and tissues 111 days after dermal injection of CBTA cells into both flanks of NSG mice. Black lesions are metastatic nodules.
Figure 29B:
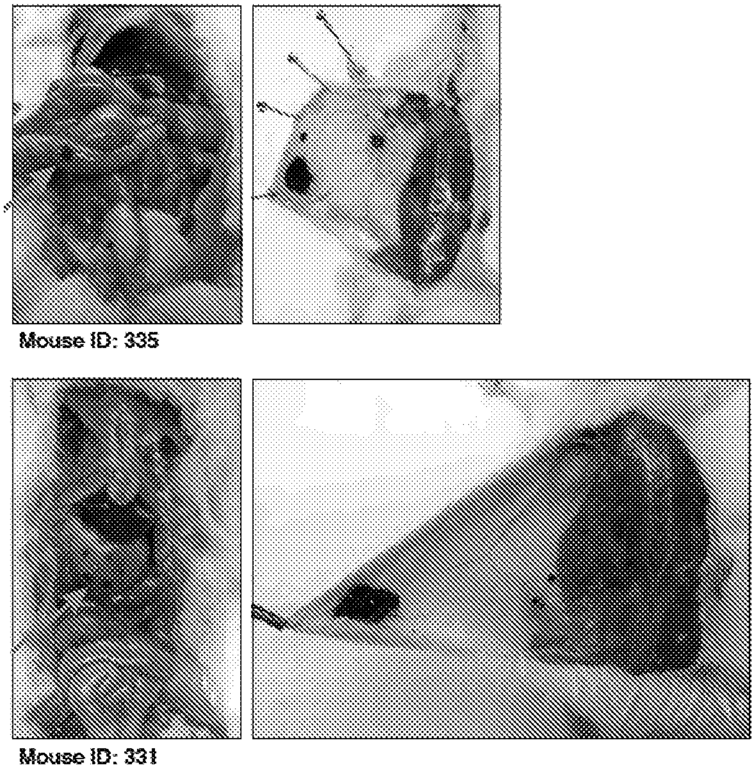
Figure 30A:
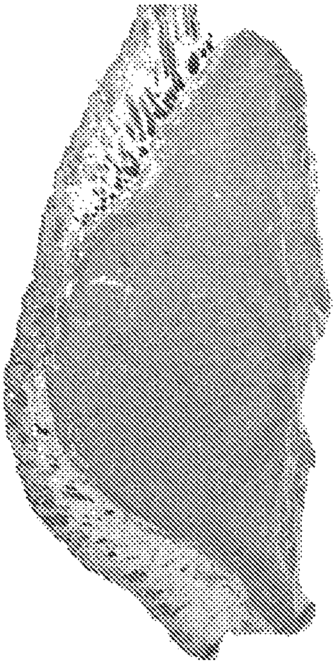
FIG. 30A-30E—Primary tumors of CBTP melanocytes demonstrate malignant cellular pathology in vivo. Micrographs of representative H&E stained sections of primary tumors harvested 151 days after injection of CBTP melanocytes into NSG mice.
Figure 30B:
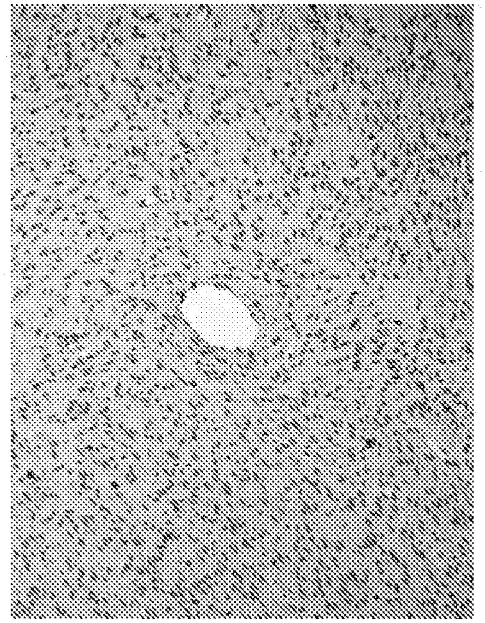
Figure 30C:
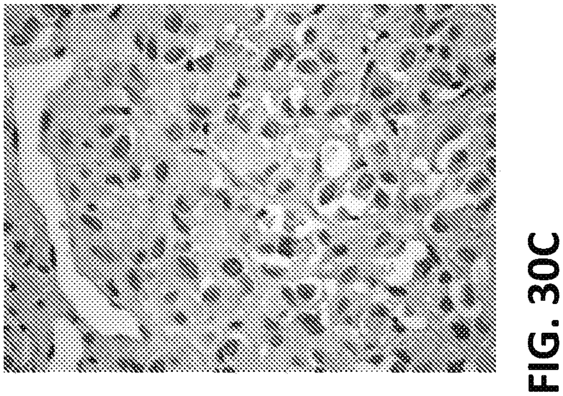
Figure 30D:
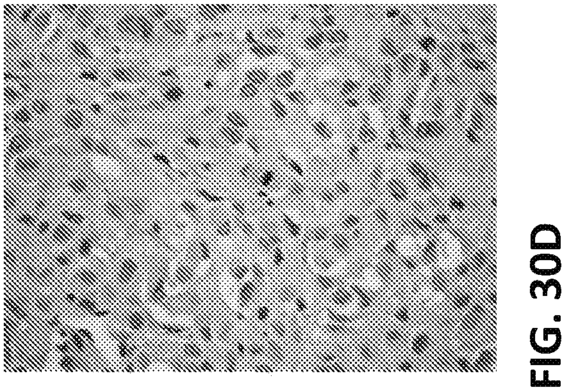
Figure 30E:
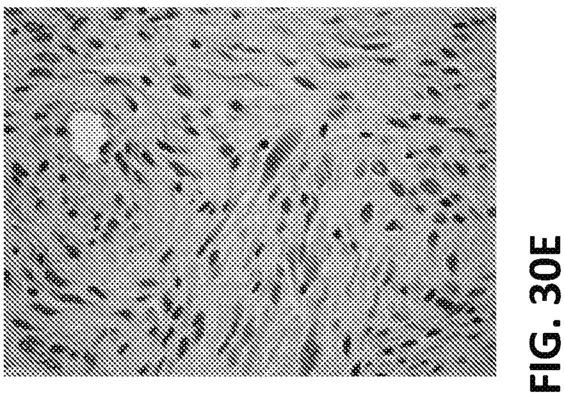
Figure 31A:
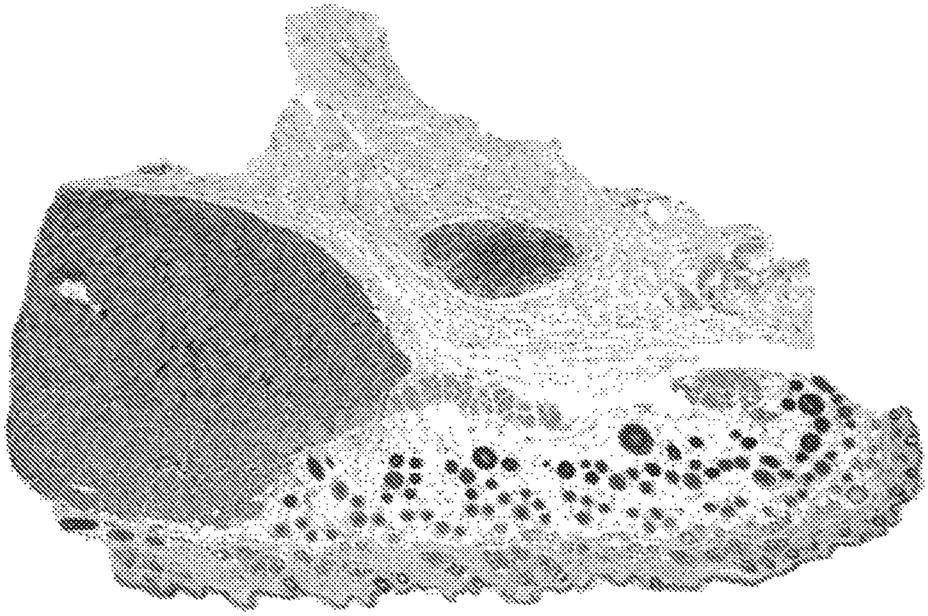
FIG. 31A, 31B—Primary tumors of CBT3 melanocytes demonstrate malignant cellular pathology in vivo. Micrographs of representative H&E stained sections of primary tumors harvested 69 days after injection of CBT3 melanocytes into NSG mice.
Figure 31B:
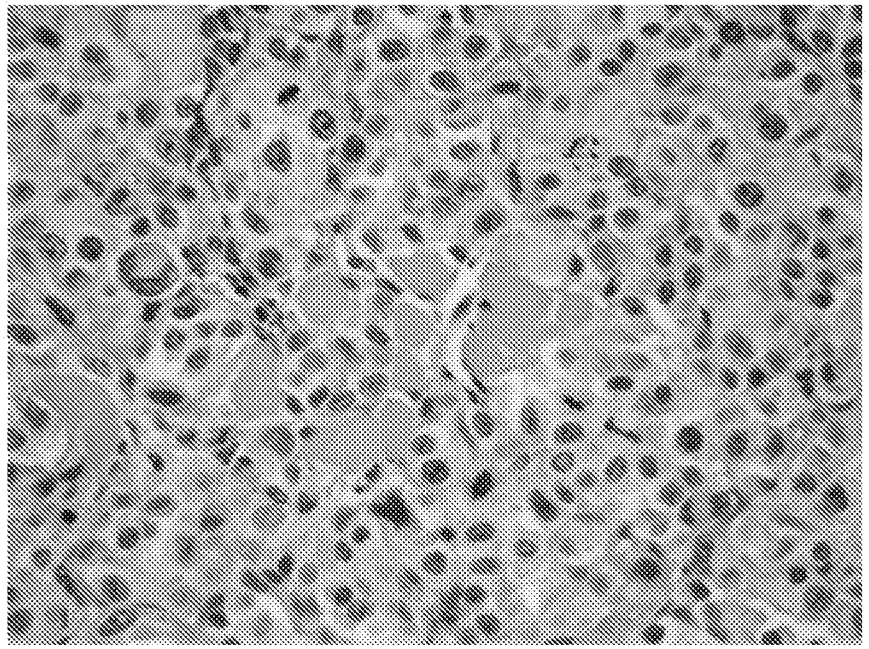
Figure 32A:
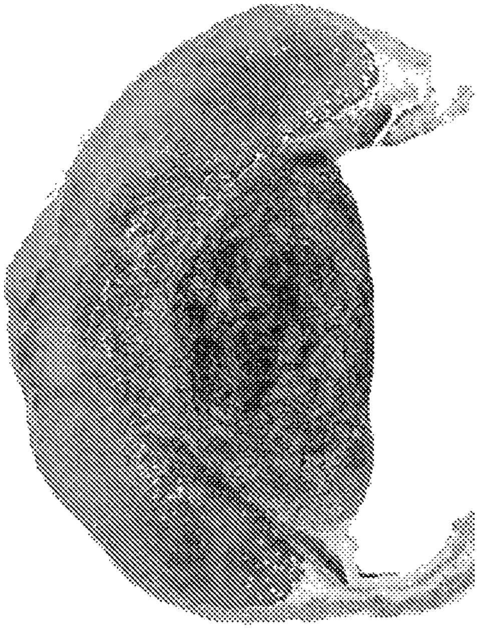
FIG. 32A-32D—Primary tumors of CBTA melanocytes demonstrate malignant cellular pathology in vivo. Micrographs of representative H&E stained sections of primary tumors harvested 111 days after injection of CBTA melanocytes into NSG mice.
Figure 32B:
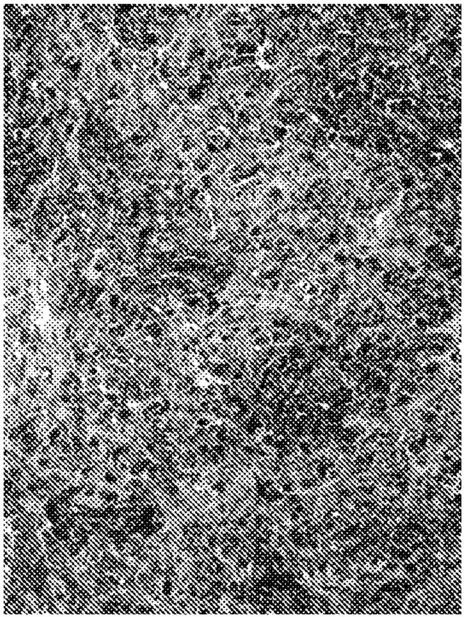
Figure 32C:
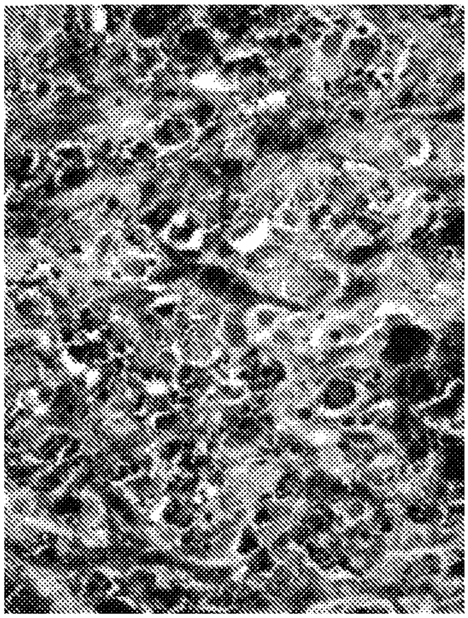
Figure 32D:
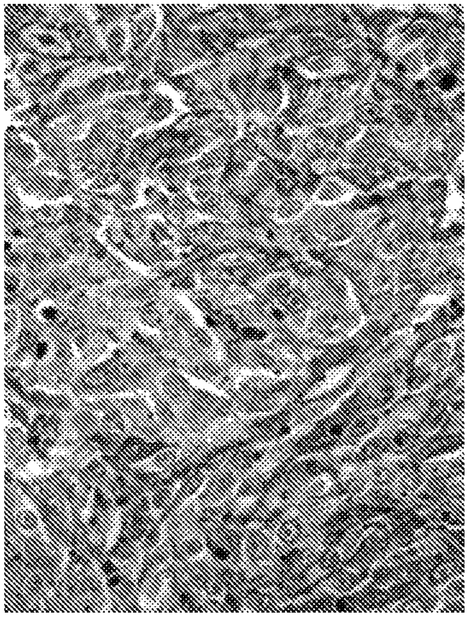

These three different genetic alterations led to distinct effects on disease progression. CBTP melanocytes formed slowly growing, amelanotic tumors in mice (FIGS. 21G, 21J) and yielded a small number of lung metastases by day 151 (FIG. 28K, 28L). CBT3 cells did not produce visible tumors over a period of ~60 days, although by day 69, a few injection sites (3 of 16) began to show small tumors (up to 14 $mm^3$, FIGS. 21H, 21K). Finally, CBTA cells initially formed darkly pigmented, macular (flat) lesions that advanced to slowly growing, darkly pigmented tumors, with a faster growth rate compared to CBTP tumors (compare FIGS. 21I and 21L to FIGS. 21G and 21J). By day 111, CBTA cells metastasized to the lung and liver (FIGS. 28K, 28L), two common sites of melanoma metastasis in humans, as well as to other organs (FIGS. 29A, 29B). In all examined cases, histologic and immunophenotypic features most resembled those of melanoma (4 of 4, CBTP; 3 of 3, CBT3; 3 of 3 CBTA; FIGS. 30A-32D, Tables 12-14). These results are in contrast to observations in genetically engineered mouse models where a $Braf^{V600E}Pten^{-/-}$ genotype caused rapidly lethal, pigmented tumor growth, and $Braf^{V600E}Ctnnb1^{STA}$ (constitutively active Wnt signaling, perhaps similar to APC loss) caused slowly growing, pigmented tumors that did not metastasize to distant organs Chudnovsky et al. *Nat Genet* 37:745-749 (2005); Zeng et al. *Cancer Cell* 34:56-68 (2018)). Applicants' findings suggest that, in the selling of mutant CDKN2A, BRAF, and TERT, loss of APC causes more potent progression of human melanoma than loss of either of the more commonly mutated genes PTEN or TP53.

TABLE 14

Dermatopathological review of CBTP and control CBT primary tumors, liver, and lung sections

| Genotype | Days Post Injection | Slide Num | Slide Label | Stain | Tissue | Heterogenous/ Homogenous (1-10 scale?) | Benign or Malignant | Most similar to which human melanocytic neoplastic category |
|---|---|---|---|---|---|---|---|---|
| CBT | 111 | 1 | EH_326_329_X4_1 | H&E | primary tumor | 8 | Malignant | Epithelioid cells rarely with bizarre shapes |
| CBT | 111 | 2 | EH_326_329_X4_1 | Ki67 | primary tumor | | | |
| CBT | 111 | 3 | EH_326_329_X4_1 | HMB45 | primary tumor | | | |
| CBT | 111 | 4 | EH_326_329_X4_1 | SOX10 | primary tumor | | | |
| CBT | 111 | 5 | EH_326_329_X4_1 | Melan-A | primary tumor | | | |
| CBT | 111 | 1 | EH_326_329_X4_2 | H&E | primary tumor | 8 | Malignant | Round cells few multinucleated, malignant |
| CBT | 111 | 2 | EH_326_329_X4_2 | Ki67 | primary tumor | | | |
| CBT | 111 | 3 | EH_326_329_X4_2 | HMB45 | primary tumor | | | |
| CBT | 111 | 4 | EH_326_329_X4_2 | SOX10 | primary tumor | | | |
| CBT | 111 | 5 | EH_326_329_X4_2 | Melan-A | primary tumor | | | |
| CBT | 111 | 1 | EH_326_329_X4_3 | H&E | primary tumor | 8 | Malignant | Small round hyperchromatic cells with poor nest formation |
| CBT | 111 | 2 | EH_326_329_X4_3 | Ki67 | primary tumor | | | |
| CBT | 111 | 3 | EH_326_329_X4_3 | HMB45 | primary tumor | | | |
| CBT | 111 | 4 | EH_326_329_X4_3 | SOX10 | primary tumor | | | |
| CBT | 111 | 5 | EH_326_329_X4_3 | Melan-A | primary tumor | | | |
| CBTA | 111 | 6 | EH_327_328_X4_1 | H&E | primary tumor | 8 | Malignant | Pigmented spindled and epithelioid cells |
| CBTA | 111 | 7 | EH_327_328_X4_1 | Ki67 | primary tumor | | | |
| CBTA | 111 | 8 | EH_327_328_X4_1 | HMB45 | primary tumor | | | |
| CBTA | 111 | 9 | EH_327_328_X4_1 | SOX10 | primary tumor | | | |
| CBTA | 111 | 10 | EH_327_328_X4_1 | Melan-A | primary tumor | | | |
| CBTA | 111 | 6 | EH_327_328_X4_2 | H&E | primary tumor | 5 | Malignant | Pigmented spindled and epithelioid cells, resembles PEM |
| CBTA | 111 | 7 | EH_327_328_X4_2 | Ki67 | primary tumor | | | |
| CBTA | 111 | 8 | EH_327_328_X4_2 | HMB45 | primary tumor | | | |
| CBTA | 111 | 9 | EH_327_328_X4_2 | SOX10 | primary tumor | | | |
| CBTA | 111 | 10 | EH_327_328_X4_2 | Melan-A | primary tumor | | | |
| CBTA | 111 | 6 | EH_327_328_X4_3 | H&E | primary tumor | 8 | Malignant | Predominantly faintly pigmented spindled cells |
| CBTA | 111 | 7 | EH_327_328_X4_3 | Ki67 | primary tumor | | | |
| CBTA | 111 | 8 | EH_327_328_X4_3 | HMB45 | primary tumor | | | |
| CBTA | 111 | 9 | EH_327_328_X4_3 | SOX10 | primary tumor | | | |
| CBTA | 111 | 10 | EH_327_328_X4_3 | Melan-A | primary tumor | | | |
| CBTA | 111 | 6 | EH_327_328_X4_4 | H&E | primary tumor | 10 | Malignant | Densely pigmented spindled and epithelioid cells |
| CBTA | 111 | 7 | EH_327_328_X4_4 | Ki67 | primary tumor | | | |
| CBTA | 111 | 8 | EH_327_328_X4_4 | HMB45 | primary tumor | | | |
| CBTA | 111 | 9 | EH_327_328_X4_4 | SOX10 | primary tumor | | | |
| CBTA | 111 | 10 | EH_327_328_X4_4 | Melan-A | primary tumor | | | |
| CBT | 111 | 13 | EH_326_LVG | H&E | multiple liver and lung lobes | | | |
| CBT | 111 | 14 | EH_326_LVG | Ki67 | multiple liver and lung lobes | | | |
| CBT | 111 | 15 | EH_326_LVG | HMB45 | multiple liver and lung lobes | | | |
| CBT | 111 | 16 | EH_326_LVG | SOX10 | multiple liver and lung lobes | | | |
| CBT | 111 | 17 | EH_326_LVG | Melan-A | multiple liver and lung lobes | | | |
| CBT | 111 | 18 | EH_329_LVG | H&E | multiple liver and lung lobes | | | |
| CBT | 111 | 19 | EH_329_LVG | Ki67 | multiple liver and lung lobes | | | |

TABLE 14-continued

Dermatopathological review of CBTP and control CBT primary tumors, liver, and lung sections

| | | | | | | |
|---|---|---|---|---|---|---|
| CBT | 111 | 20 | EH_329_LVG | HMB45 | multiple liver and lung lobes | |
| CBT | 111 | 21 | EH_329_LVG | SOX10 | multiple liver and lung lobes | |
| CBT | 111 | 22 | EH_329_LVG | Melan-A | multiple liver and lung lobes | |
| CBT | 111 | 23 | EH_332_LVG | H&E | multiple liver and lung lobes | |
| CBT | 111 | 24 | EH_332_LVG | Ki67 | multiple liver and lung lobes | |
| CBT | 111 | 25 | EH_332_LVG | HMB45 | multiple liver and lung lobes | |
| CBT | 111 | 26 | EH_332_LVG | SOX10 | multiple liver and lung lobes | |
| CBT | 111 | 27 | EH_332_LVG | Melan-A | multiple liver and lung lobes | |
| CBT | 111 | 28 | EH_335_LVG | H&E | multiple liver and lung lobes | |
| CBT | 111 | 29 | EH_335_LVG | Ki67 | multiple liver and lung lobes | |
| CBT | 111 | 30 | EH_335_LVG | HMB45 | multiple liver and lung lobes | |
| CBT | 111 | 31 | EH_335_LVG | SOX10 | multiple liver and lung lobes | |
| CBT | 111 | 32 | EH_335_LVG | Melan-A | multiple liver and lung lobes | |
| CBTA | 111 | 33 | EH_327_LVG | H&E | multiple liver and lung lobes | 10 |
| CBTA | 111 | 34 | EH_327_LVG | Ki67 | multiple liver and lung lobes | |
| CBTA | 111 | 35 | EH_327_LVG | HMB45 | multiple liver and lung lobes | |
| CBTA | 111 | 36 | EH_327_LVG | SOX10 | multiple liver and lung lobes | |
| CBTA | 111 | 37 | EH_327_LVG | Melan-A | multiple liver and lung lobes | |
| CBTA | 111 | 38 | EH_328_LVG | H&E | multiple liver and lung lobes | 8 |
| CBTA | 111 | 39 | EH_328_LVG | Ki67 | multiple liver and lung lobes | |
| CBTA | 111 | 40 | EH_328_LVG | HMB45 | multiple liver and lung lobes | |
| CBTA | 111 | 41 | EH_328_LVG | SOX10 | multiple liver and lung lobes | |
| CBTA | 111 | 42 | EH_328_LVG | Melan-A | multiple liver and lung lobes | |
| CBTA | 111 | 43 | EH_336_LVG | H&E | multiple liver and lung lobes | 8 |
| CBTA | 111 | 44 | EH_336_LVG | Ki67 | multiple liver and lung lobes | |
| CBTA | 111 | 45 | EH_336_LVG | HMB45 | multiple liver and lung lobes | |
| CBTA | 111 | 46 | EH_336_LVG | SOX10 | multiple liver and lung lobes | |
| CBTA | 111 | 47 | EH_336_LVG | Meln-A | multiple liver and lung lobes | |
| CBTA | 111 | 48 | EH_337_LVG | H&E | multiple liver and lung lobes | 8 |
| CBTA | 111 | 49 | EH_337_LVG | Ki67 | multiple liver and lung lobes | |
| CBTA | 111 | 50 | EH_337_LVG | HMB45 | multiple liver and lung lobes | |
| CBTA | 111 | 51 | EH_337_LVG | SOX10 | multiple liver and lung lobes | |
| CBTA | 111 | 52 | EH_337_LVG | Melan-A | multiple liver and lung lobes | |

| Genotype | Days Post Injection | Slide Num | Pigmentation level (0-10) | Mitotic Count/ mm2 | Stain Scale (1-10) | Full note |
|---|---|---|---|---|---|---|
| CBT | 111 | 1 | 1 | 0 | N/A | |
| CBT | 111 | 2 | | | 1 | |
| CBT | 111 | 3 | | | 1 | |
| CBT | 111 | 4 | | | 2 | |
| CBT | 111 | 5 | | | 2 | |
| CBT | 111 | 1 | 1 | 0 | N/A | |
| CBT | 111 | 2 | | | 1 | |

TABLE 14-continued

Dermatopathological review of CBTP and control CBT primary tumors, liver, and lung sections

| | | | | | | |
|---|---|---|---|---|---|---|
| CBT | 111 | 3 | | | 1 | |
| CBT | 111 | 4 | | | 2 | |
| CBT | 111 | 5 | | | 2 | |
| CBT | 111 | 1 | 1 | 0 | N/A | |
| CBT | 111 | 2 | | | 1 | |
| CBT | 111 | 3 | | | 1 | |
| CBT | 111 | 4 | | | 2 | |
| CBT | 111 | 5 | | | 2 | |
| CBTA | 111 | 6 | 10 | 3 | N/A | |
| CBTA | 111 | 7 | | | 5 | |
| CBTA | 111 | 8 | | | 10 | |
| CBTA | 111 | 9 | | | 1 | |
| CBTA | 111 | 10 | | | 8 | |
| CBTA | 111 | 6 | 8 | 0 | N/A | |
| CBTA | 111 | 7 | | | 5 | |
| CBTA | 111 | 8 | | | 10 | |
| CBTA | 111 | 9 | | | 1 | |
| CBTA | 111 | 10 | | | 8 | |
| CBTA | 111 | 6 | 5 | 13 | N/A | |
| CBTA | 111 | 7 | | | 5 | |
| CBTA | 111 | 8 | | | 10 | |
| CBTA | 111 | 9 | | | 1 | |
| CBTA | 111 | 10 | | | 8 | |
| CBTA | 111 | 6 | 10 | 1 | N/A | |
| CBTA | 111 | 7 | | | 5 | |
| CBTA | 111 | 8 | | | 10 | |
| CBTA | 111 | 9 | | | 1 | |
| CBTA | 111 | 10 | | | 8 | |
| CBT | 111 | 13 | | | N/A | No metatastatic tumor to liver or lung. |
| CBT | 111 | 14 | | | | |
| CBT | 111 | 15 | | | | |
| CBT | 111 | 16 | | | | |
| CBT | 111 | 17 | | | | |
| CBT | 111 | 18 | | | N/A | No metatastatic tumor to liver or lung. |
| CBT | 111 | 19 | | | | |
| CBT | 111 | 20 | | | | |
| CBT | 111 | 21 | | | | |
| CBT | 111 | 22 | | | | |
| CBT | 111 | 23 | | | N/A | No metatastatic tumor to liver or lung. |
| CBT | 111 | 24 | | | | |
| CBT | 111 | 25 | | | | |
| CBT | 111 | 26 | | | | |
| CBT | 111 | 27 | | | | |
| CBT | 111 | 28 | | | N/A | No metatastatic tumor to liver or lung. |
| CBT | 111 | 29 | | | | |
| CBT | 111 | 30 | | | | |
| CBT | 111 | 31 | | | | |
| CBT | 111 | 32 | | | | |
| CBTA | 111 | 33 | 0 | | N/A | Multifocal metastases to lung, mostly single cell with some small nests of 3 cells, best seen on HMB45 and SOX10. Few single cell metastases to liver. |
| CBTA | 111 | 34 | | | 5 | |
| CBTA | 111 | 35 | | | 8 | |
| CBTA | 111 | 36 | | | 7 | |
| CBTA | 111 | 37 | | | 5 | |
| CBTA | 111 | 38 | 10 | | N/A | Multifocal metastases to lung, some resembling large emboli best seen on HMB45. There are also small nests and scattered single metastatic cells. Few single cell metastases to liver. |
| CBTA | 111 | 39 | | | 2 | |
| CBTA | 111 | 40 | | | 10 | |
| CBTA | 111 | 41 | | | 8 | |
| CBTA | 111 | 42 | | | 9 | |
| CBTA | 111 | 43 | 9 | | N/A | Multifocal metastases to lung, some resembling large emboli best seen on HMB45.There are also small nests and scattered single metastatic cells. Few single |
| CBTA | 111 | 44 | | | 5 | |
| CBTA | 111 | 45 | | | 8 | |
| CBTA | 111 | 46 | | | 6 | |
| CBTA | 111 | 47 | | | 4 | |

TABLE 14-continued

Dermatopathological review of CBTP and control CBT primary tumors, liver, and lung sections

| | | | | | |
|---|---|---|---|---|---|
| | | | | | cell metastases to liver. |
| CBTA | 111 | 48 | 8 | N/A | Multifocal metastases |
| CBTA | 111 | 49 | | 5 | to lung, some |
| CBTA | 111 | 50 | | 10 | resembling large |
| CBTA | 111 | 51 | | 6 | emboli best seen |
| CBTA | 111 | 52 | | 9 | on HMB45.There are also small nests and scattered single metastatic cells. One single tumor cell in liver. |

Figures 28A, 28B, 28C, 28D, 28E, 28F:
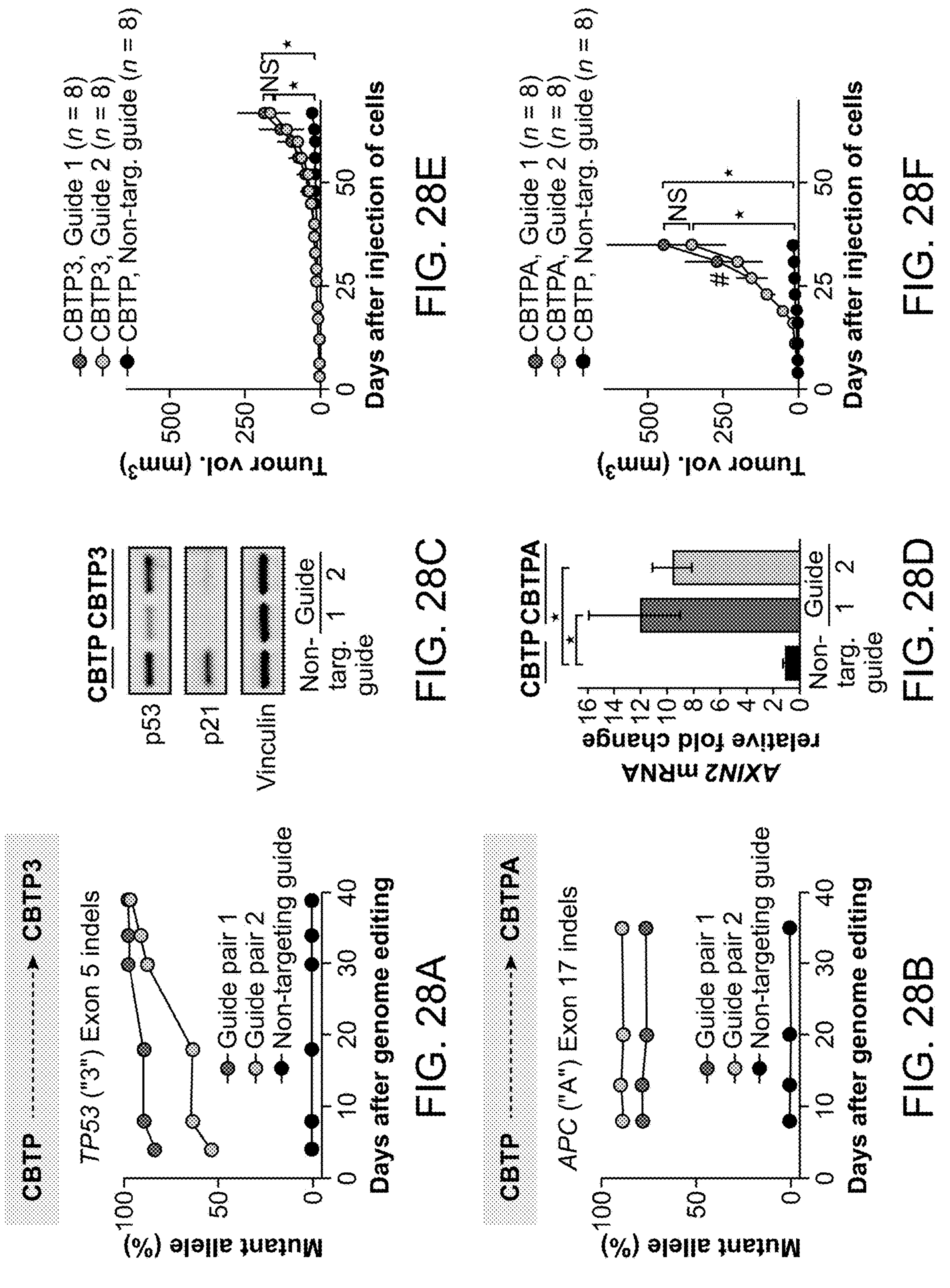

Introducing yet a fifth mutation finally led to truly aggressive disease (FIGS. 28A-28N). Applicants engineered single knockouts of TP53 ('3') and APC ('A') into CBTP melanocytes, opting to proceed with CBTP melanocytes because of the high prevalence of PTEN alterations in melanoma (~20%) (13). Indels in TP53 rose over time in culture to an allele frequency of nearly 100% (FIG. 28A), and indels in APC stayed at a stable allele fraction of ~75-85% (FIG. 28B). Applicants confirmed the expected downstream pathway activation in CBTP3 and CBTPA cells by loss of p21 protein and increase in AXIN2 mRNA levels, respectively (FIGS. 28C, 28D).

Figure 28G:
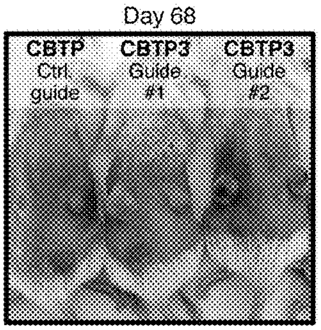
Figure 28H:
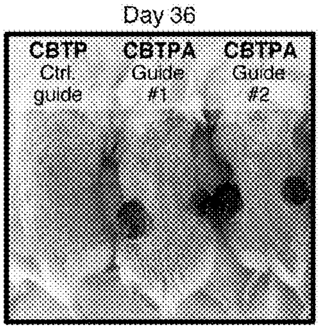
Figure 28I:
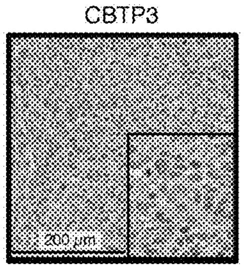
Figure 28J:
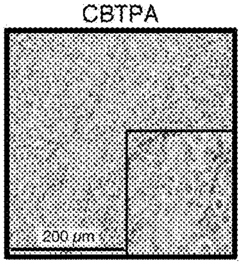
Figures 33A, 33B, 33C:
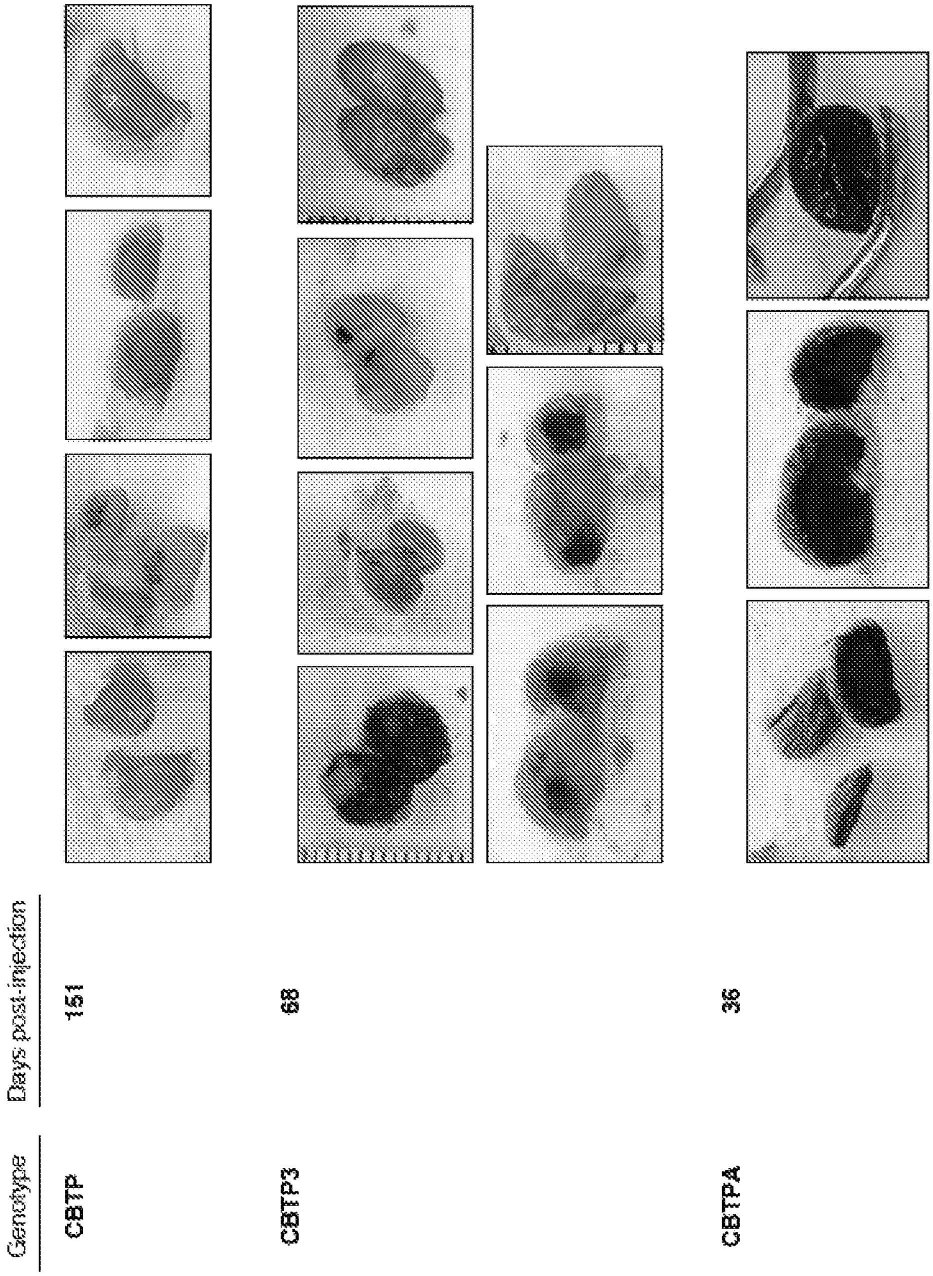
FIG. 33A-33C—CBTP, CBTP3, and CBTPA primary tumor pigmentation patterns. Photographs of primary tumors arising from CBTP (FIG. 33A), CBTP3 (FIG. 33B), and CBTPA (FIG. 33C) cells injected into both flanks of NSG mice. Number of days between injection and tumor harvest is indicated.
Figure 34A:
FIG. 34A-34D—Primary tumors of CBTP3 melanocytes demonstrate malignant cellular pathology in vivo. Micrographs of representative H&E stained sections of primary tumors harvested 68 days after injection of CBTP3 melanocytes into NSG mice.
Figure 34B:
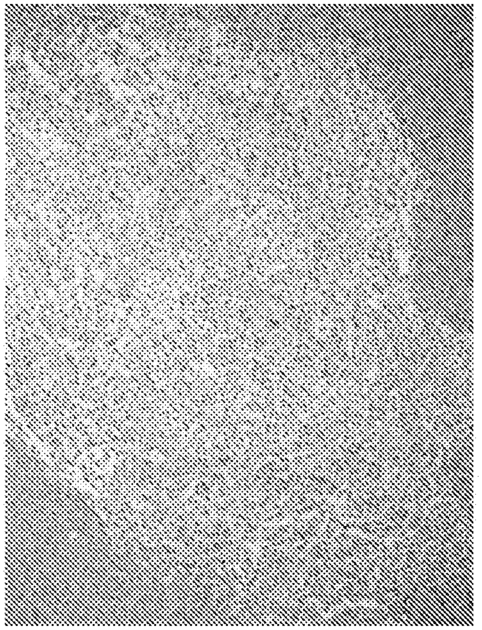
Figure 34C:
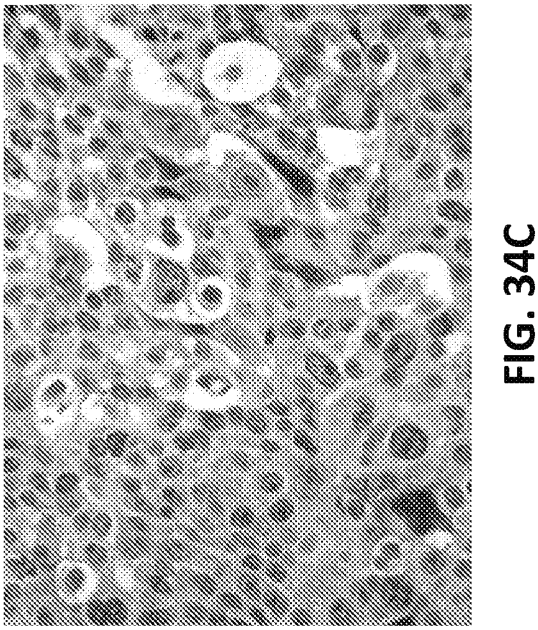
Figure 34D:
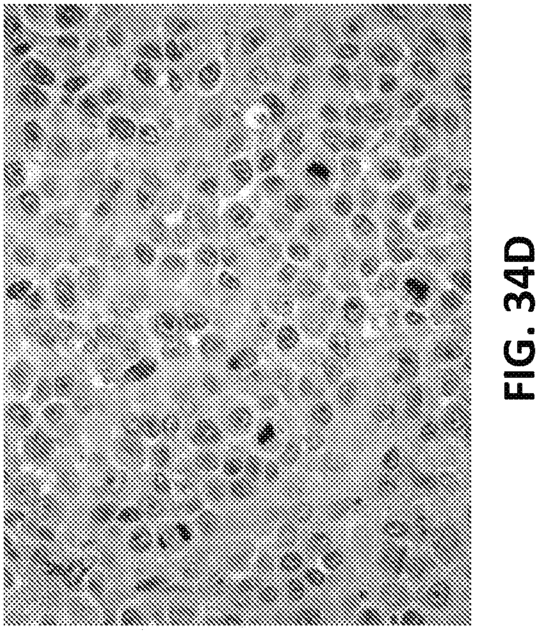
Figure 35A:
FIG. 35A-35D—Primary tumors of CBTPA melanocytes demonstrate malignant cellular pathology in vivo. Micrographs of representative H&E stained sections of primary tumors harvested 36 days after injection of CBTPA melanocytes into NSG mice.
Figure 35B:
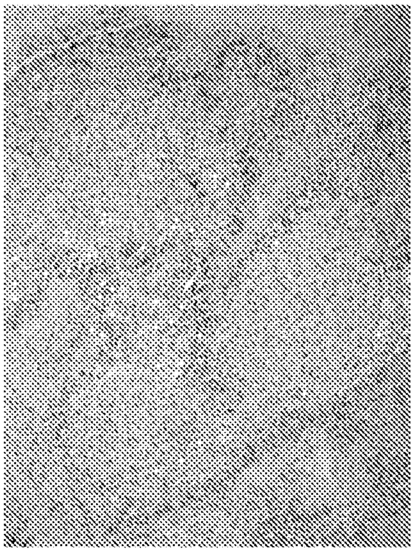
Figure 35C:
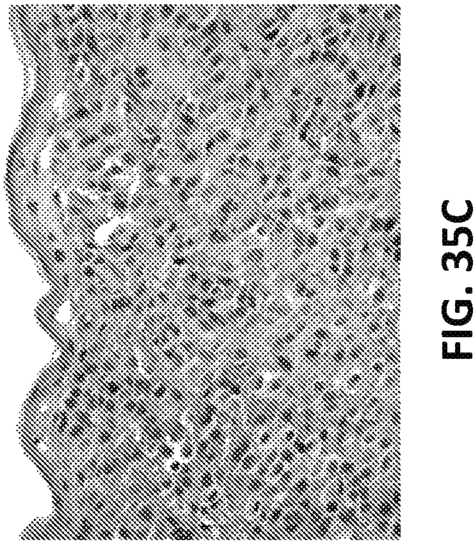
Figure 35D:
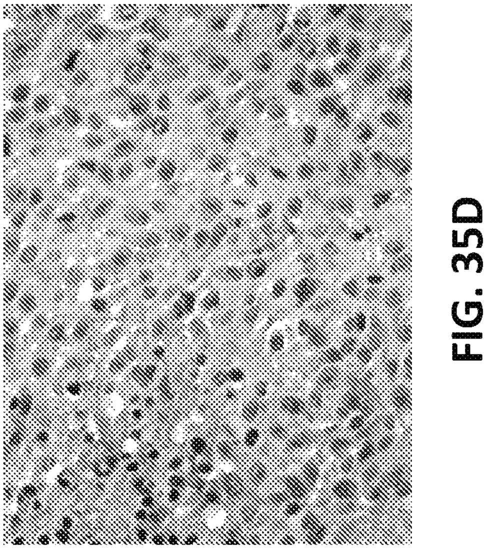

In vivo tumors formed by CBTPA melanocytes had aggressive growth characteristics, while those from CBTP3 melanocytes showed only a modest increase in tumor growth rate compared to CBTP derived tumors (FIGS. 28A-28N). Whereas tumors formed by CBTP3 melanocytes only grew larger than those formed by CBTP control tumors starting around day 50 (FIGS. 28E, 28G), mice that had received CBTPA melanocytes required euthanization by day 36, due to primary tumor burden (FIGS. 28F, 28H). Of note, the APC indel allele fraction in these tumors reached ~100% (6 of 6 examined tumors). CBTPA tumors were all darkly pigmented (FIG. 28H), while CBTP3 tumors were largely amelanotic (FIG. 28G), except for occasional darkly pigmented internal sectors (FIGS. 33A-33C). Both genotypes resembled melanoma by histologic and immunophenotypic features (4 of 4, CBTPA; 4 of 4, CBTP3; FIGS. 28I, 28J, 34A-34D, 35A-35D, and Tables 15 and 16).

TABLE 15

Dermatopathological review of CBTP3 and control CBTP primary tumors, liver, and lung sections.

| Genotype | Days Post Injection | Slide Num | Slide Label | Stain | Tissue | Heterogenous/ Homogenous (1-10 scale?) | Benign or Malignant? | Most similar to which human melanocytic neoplastic category |
|---|---|---|---|---|---|---|---|---|
| CBTP | 68 | 1 | EH_103_200_X4-1 | H&E | primary tumor | 7 | Malignant | Spitzoid: Epithelioid cells in nests that coalesce to form sheets |
| CBTP | 68 | 2 | EH_103_200_X4-1 | Ki67 | primary tumor | | | |
| CBTP | 68 | 3 | EH_103_200_X4-1 | HMB45 | primary tumor | | | |
| CBTP | 68 | 4 | EH_103_200_X4-1 | SOX10 | primary tumor | | | |
| CBTP | 68 | 5 | EH_103_200_X4-1 | Melan-A | primary tumor | | | |
| CBTP | 68 | 1 | EH_103_200_X4-2 | H&E | primary tumor | 7 | Malignant | Spitzoid epithelioid cells with spindle cells |
| CBTP | 68 | 2 | EH_103_200_X4-2 | Ki67 | primary tumor | | | |
| CBTP | 68 | 3 | EH_103_200_X4-2 | HMB45 | primary tumor | | | |
| CBTP | 68 | 4 | EH_103_200_X4-2 | SOX10 | primary tumor | | | |
| CBTP | 68 | 5 | EH_103_200_X4-2 | Melan-A | primary tumor | | | |
| CBTP | 68 | 1 | EH_103_200_X4-3 | H&E | primary tumor | 4 | Malignant | Spitzoid: Epithelioid cells in nests that coalesce to form sheets, with admixed spindle cells |
| CBTP | 68 | 2 | EH_103_200_X4-3 | Ki67 | primary tumor | | | |
| CBTP | 68 | 3 | EH_103_200_X4-3 | HMB45 | primary tumor | | | |
| CBTP | 68 | 4 | EH_103_200_X4-3 | SOX10 | primary tumor | | | |
| CBTP | 68 | 5 | EH_103_200_X4-3 | Melan-A | primary tumor | | | |
| CBTP | 68 | 1 | EH_103_200_X4-4 | H&E | primary tumor | 5 | Malignant | Spitzoid: Epithelioid cells in nests that coalesce to form sheets, with |

TABLE 15-continued

Dermatopathological review of CBTP3 and control CBTP primary tumors, liver, and lung sections.

| | | | | | | | | |
|---|---|---|---|---|---|---|---|---|
| | | | | | | | | admixed spindle cells |
| CBTP | 68 | 2 | EH_103_200_X4-4 | Ki67 | primary tumor | | | |
| CBTP | 68 | 3 | EH_103_200_X4-4 | HMB45 | primary tumor | | | |
| CBTP | 68 | 4 | EH_103_200_X4-4 | SOX10 | primary tumor | | | |
| CBTP | 68 | 5 | EH_103_200_X4-4 | Melan-A | primary tumor | | | |
| CBTP3 | 68 | 6 | EH_109_187_X4-1 | H&E | primary tumor | 5 | Malignant | Melanoma: Large epithelioid cells with medium epithelioid cells and some foci of spindle cells |
| CBTP3 | 68 | 7 | EH_109_187_X4-1 | Ki67 | primary tumor | | | |
| CBTP3 | 68 | 8 | EH_109_187_X4-1 | HMB45 | primary tumor | | | |
| CBTP3 | 68 | 9 | EH_109_187_X4-1 | SOX10 | primary tumor | | | |
| CBTP3 | 68 | 10 | EH_109_187_X4-l | Melan-A | primary tumor | | | |
| CBTP3 | 68 | 6 | EH_109_187_X4-2 | H&E | primary tumor | 5 | Malignant | Melanoma: Large epithelioid cells with medium epithelioid cells and some foci of spindle cells |
| CBTP3 | 68 | 7 | EH_109_187_X4-2 | Ki67 | primary tumor | | | |
| CBTP3 | 68 | 8 | EH_109_187_X4-2 | HMB45 | primary tumor | | | |
| CBTP3 | 68 | 9 | EH_109_187_X4-2 | SOX10 | primary tumor | | | |
| CBTP3 | 68 | 10 | EH_109_187_X4-2 | Melan-A | primary tumor | | | |
| CBTP3 | 68 | 6 | EH_109_187_X4-3 | H&E | primary tumor | 7 | Malignant | Melanoma: Large epithelioid cells with medium epithelioid cells and some foci of spindle cells |
| CBTP3 | 68 | 7 | EH_109_187_X4-3 | Ki67 | primary tumor | | | |
| CBTP3 | 68 | 8 | EH_109_187_X4-3 | HMB45 | primary tumor | | | |
| CBTP3 | 68 | 9 | EH_109_187_X4-3 | SOX10 | primary tumor | | | |
| CBTP3 | 68 | 10 | EH_109_187_X4-3 | Melan-A | primary tumor | | | |
| CBTP3 | 68 | 6 | EH_109_187_X4-4 | H&E | primary tumor | 5 | Malignant | Melanoma: Large epithelioid cells with medium epithelioid cells and some foci of spindle cells |
| CBTP3 | 68 | 7 | EH_109_187_X4-4 | Ki67 | primary tumor | | | |
| CBTP3 | 68 | 8 | EH_109_187_X4-4 | HMB45 | primary tumor | | | |
| CBTP3 | 68 | 9 | EH_109_187_X4-4 | SOX10 | primary tumor | | | |
| CBTP3 | 68 | 10 | EH_109_187_X4-4 | Melan-A | primary tumor | | | |
| CBTP | 68 | 11 | EH_103_LVG | H&E | multiple liver and lung lobes | | | |
| CBTP | 68 | 12 | EH_103_LVG | Ki67 | multiple liver and lung lobes | | | |
| CBTP | 68 | 13 | EH_103_LVG | HMB45 | multiple liver and lung lobes | | | |
| CBTP | 68 | 14 | EH_103_LVG | SOX10 | multiple liver and lung lobes | | | |
| CBTP | 68 | 15 | EH_103_LVG | Melan-A | multiple liver and lung lobes | | | |
| CBTP | 68 | 16 | EH_200_LVG | H&E | multiple liver and lung lobes | | | |
| CBTP | 68 | 17 | EH_200_LVG | Ki67 | multiple liver and lung lobes | | | |
| CBTP | 68 | 18 | EH_200_LVG | HMB45 | multiple liver and lung lobes | | | |
| CBTP | 68 | 19 | EH_200_LVG | SOX10 | multiple liver and lung lobes | | | |
| CBTP | 68 | 20 | EH_200_LVG | Melan-A | multiple liver and lung lobes | | | |
| CBTP3 | 68 | 21 | EH_101_LVG | H&E | multiple liver and lung lobes | | | |
| CBTP3 | 68 | 22 | EH_101_LVG | Ki67 | multiple liver and lung lobes | | | |
| CBTP3 | 68 | 23 | EH_101_LVG | HMB45 | multiple liver and lung lobes | | | |
| CBTP3 | 68 | 24 | EH_101_LVG | SOX10 | multiple liver and lung lobes | | | |
| CBTP3 | 68 | 25 | EH_101_LVG | Melan-A | multiple liver and lung lobes | | | |
| CBTP3 | 68 | 26 | EH_109_LVG | H&E | multiple liver and lung lobes | | | |

TABLE 15-continued

Dermatopathological review of CBTP3 and control CBTP primary tumors, liver, and lung sections.

| | | | | | |
|---|---|---|---|---|---|
| CBTP3 | 68 | 27 | EH_109_LVG | Ki67 | multiple liver and lung lobes |
| CBTP3 | 68 | 28 | EH_109_LVG | HMB45 | multiple liver and lung lobes |
| CBTP3 | 68 | 29 | EH_109_LVG | SOX10 | multiple liver and lung lobes |
| CBTP3 | 68 | 30 | EH_109_LVG | Melan-A | multiple liver and lung lobes |
| CBTP3 | 68 | 31 | EH_176_LVG | H&E | multiple liver and lung lobes |
| CBTP3 | 68 | 32 | EH_176_LVG | Ki67 | multiple liver and lung lobes |
| CBTP3 | 68 | 33 | EH_176_LVG | HMB45 | multiple liver and lung lobes |
| CBTP3 | 68 | 34 | EH_176_LVG | SOX10 | multiple liver and lung lobes |
| CBTP3 | 68 | 35 | EH_176_LVG | Melan-A | multiple liver and lung lobes |
| CBTP3 | 68 | 36 | EH_186_LVG | H&E | multiple liver and lung lobes |
| CBTP3 | 68 | 37 | EH_186_LVG | Ki67 | multiple liver and lung lobes |
| CBTP3 | 68 | 38 | EH_186_LVG | HMB45 | multiple liver and lung lobes |
| CBTP3 | 68 | 39 | EH_186_LVG | SOX10 | multiple liver and lung lobes |
| CBTP3 | 68 | 40 | EH_186_LVG | Melan-A | multiple liver and lung lobes |
| CBTP3 | 68 | 41 | EH_187_188_LVG | H&E | multiple liver and lung lobes |
| CBTP3 | 68 | 42 | EH_187_188_LVG | Ki67 | multiple liver and lung lobes |
| CBTP3 | 68 | 43 | EH_187_188_LVG | HMB45 | multiple liver and lung lobes |
| CBTP3 | 68 | 44 | EH_187_188_LVG | SOX10 | multiple liver and lung lobes |
| CBTP3 | 68 | 45 | EH_187_188_LVG | Melan-A | multiple liver and lung lobes |
| CBTP3 | 68 | 46 | EH_192_LVG | H&E | multiple liver and lung lobes |
| CBTP3 | 68 | 47 | EH_192_LVG | Ki67 | multiple liver and lung lobes |
| CBTP3 | 68 | 48 | EH_192_LVG | HMB45 | multiple liver and lung lobes |
| CBTP3 | 68 | 49 | EH_192_LVG | SOX10 | multiple liver and lung lobes |
| CBTP3 | 68 | 50 | EH_192_LVG | Melan-A | multiple liver and lung lobes |
| CBTP3 | 68 | 51 | EH_198_LVG | H&E | multiple liver and lung lobes |
| CBTP3 | 68 | 52 | EH_198_LVG | Ki67 | multiple liver and lung lobes |
| CBTP3 | 68 | 53 | EH_198_LVG | HMB45 | multiple liver and lung lobes |
| CBTP3 | 68 | 54 | EH_198_LVG | SOX10 | multiple liver and lung lobes |
| CBTP3 | 68 | 55 | EH_198_LVG | Melan-A | multiple liver and lung lobes |
| CBTP3 | 68 | 56 | EH_199_LVG | H&E | multiple liver and lung lobes |
| CBTP3 | 68 | 57 | EH_199_LVG | Ki67 | multiple liver and lung lobes |
| CBTP3 | 68 | 58 | EH_199_LVG | HMB45 | multiple liver and lung lobes |
| CBTP3 | 68 | 59 | EH_199_LVG | SOX10 | multiple liver and lung lobes |
| CBTP3 | 68 | 60 | EH_199_LVG | Melan-A | multiple liver and lung lobes |

| Genotype | Days Post Injection | Slide Num | Does it look 'metastatic'? (if possible to determine) | Pigmentation level (0-10) | Stain Scale (1-10) | Full note |
|---|---|---|---|---|---|---|
| CBTP | 68 | 1 | Yes | 1 | | Diffuse proliferation of |
| CBTP | 68 | 2 | | | 1 | epithelioid cells in nests |
| CBTP | 68 | 3 | | | 7 | with strong HMB45 and |
| CBTP | 68 | 4 | | | 10 | Melan-A staining. No Ki67 |

TABLE 15-continued

Dermatopathological review of CBTP3 and control CBTP primary tumors, liver, and lung sections.

| | | | | | | |
|---|---|---|---|---|---|---|
| CBTP | 68 | 5 | | | 8 | staining. |
| CBTP | 68 | 1 | Yes | 0 | | Small subcutaneous nodule |
| CBTP | 68 | 2 | | | 2 | that is heterogeneous. Only |
| CBTP | 68 | 3 | | | 1 | few Ki67 positive cells. |
| CBTP | 68 | 4 | | | 5 | There is no inflammation. |
| CBTP | 68 | 5 | | | 3 | |
| CBTP | 68 | 1 | Yes | 0 | | Diffuse nodule with strong |
| CBTP | 68 | 2 | | | 1 | HMB45 staining. No visible |
| CBTP | 68 | 3 | | | 9 | mitoses. |
| CBTP | 68 | 4 | | | 9 | |
| CBTP | 68 | 5 | | | 7 | |
| CBTP | 68 | 1 | Yes | 0 | | Fragmented tumor in |
| CBTP | 68 | 2 | | | 1 | subcutaneous fat and |
| CBTP | 68 | 3 | | | 8 | muscle. |
| CBTP | 68 | 4 | | | 10 | |
| CBTP | 68 | 5 | | | 9 | |
| CBTP3 | 68 | 6 | Yes | 2 | | Zones of necrosis in the |
| CBTP3 | 68 | 7 | | | 9 | tumor with small multifocal |
| CBTP3 | 68 | 8 | | | 10 | areas of prominent |
| CBTP3 | 68 | 9 | | | 8 | pigmentation. Subcutaneous |
| CBTP3 | 68 | 10 | | | 9 | nodule. |
| CBTP3 | 68 | 6 | Yes | 1 | | Tumor with ulceration |
| CBTP3 | 68 | 7 | | | 9 | extending into subcutaneous |
| CBTP3 | 68 | 8 | | | 10 | fat and muscle. Central |
| CBTP3 | 68 | 9 | | | 10 | necrosis. |
| CBTP3 | 68 | 10 | | | 9 | |
| CBTP3 | 68 | 6 | Yes | 1 | | Extensive necrosis in a |
| CBTP3 | 68 | 7 | | | 6 | tumor that is otherwise |
| CBTP3 | 68 | 8 | | | 10 | homogeneous. It occupies |
| CBTP3 | 68 | 9 | | | 10 | the subcutaneous fat and |
| CBTP3 | 68 | 10 | | | 10 | invades muscle. |
| CBTP3 | 68 | 6 | Yes | 4 | | There is extensive central |
| CBTP3 | 68 | 7 | | | 8 | necrosis. Rthe necrotic areas |
| CBTP3 | 68 | 8 | | | 10 | are rimmed by pigmnted |
| CBTP3 | 68 | 9 | | | 10 | melanocytes. There is strong |
| CBTP3 | 68 | 10 | | | 6 | staining for melanocytic |
| | | | | | | markers. |
| CBTP | 68 | 11 | | | | No metastatic tumor to |
| CBTP | 68 | 12 | | | | liver. Multiple foci of |
| CBTP | 68 | 13 | | | | metastatic tumor |
| CBTP | 68 | 14 | | | | highlighted with HMB45 and |
| CBTP | 68 | 15 | | | | SOX10 to lung. |
| CBTP | 68 | 16 | | | | No Metastatic tumor to liver |
| CBTP | 68 | 17 | | | | or lung. |
| CBTP | 68 | 18 | | | | |
| CBTP | 68 | 19 | | | | |
| CBTP | 68 | 20 | | | | |
| CBTP3 | 68 | 21 | | | | No metastatic tumor to |
| CBTP3 | 68 | 22 | | | | liver. No metastatic tumor |
| CBTP3 | 68 | 23 | | | | to lung. Melan-A stained |
| CBTP3 | 68 | 24 | | | | nuclei in the lung tissue, an |
| CBTP3 | 68 | 25 | | | | aberrant staining. SOX10 |
| | | | | | | and HMB45 are negative. |
| CBTP3 | 68 | 26 | | | | No metastatic tumor to |
| CBTP3 | 68 | 27 | | | | liver. In the lung there are |
| CBTP3 | 68 | 28 | | | | multiple foci of clustered |
| CBTP3 | 68 | 29 | | | | melanoma cells seen with |
| CBTP3 | 68 | 30 | | | | melanoma markers (HMB45, |
| | | | | | | SOX10, Melan-A and Ki67). |
| CBTP3 | 68 | 31 | | | | No metatstic tumor to liver. |
| CBTP3 | 68 | 32 | | | | Metatstatic focus |
| CBTP3 | 68 | 33 | | | | highlighted by SOX10, |
| CBTP3 | 68 | 34 | | | | HMB45, and Melan-A in the |
| CBTP3 | 68 | 35 | | | | lung. |
| CBTP3 | 68 | 36 | | | | No metastatic tumor to |
| CBTP3 | 68 | 37 | | | | liver. 2 metastatic foci |
| CBTP3 | 68 | 38 | | | | highlighted by HMB45 in the |
| CBTP3 | 68 | 39 | | | | lung. |
| CBTP3 | 68 | 40 | | | | |
| CBTP3 | 68 | 41 | | | | No metastatic tumor to |
| CBTP3 | 68 | 42 | | | | liver. Multiple metastatic |
| CBTP3 | 68 | 43 | | | | foci highlighted by HMB45 |
| CBTP3 | 68 | 44 | | | | and Melan-A in the lung. |
| CBTP3 | 68 | 45 | | | | |
| CBTP3 | 68 | 46 | | | | No metatastatic tumor to |
| CBTP3 | 68 | 47 | | | | lung. Multiple foci of |
| CBTP3 | 68 | 48 | | | | metastatic tumor |
| CBTP3 | 68 | 49 | | | | highlighted with HMB45 and |

TABLE 15-continued

Dermatopathological review of CBTP3 and control CBTP primary tumors, liver, and lung sections.

| | | | |
|---|---|---|---|
| CBTP3 | 68 | 50 | SOX10 to liver. |
| CBTP3 | 68 | 51 | No metatstatic tumor to liver. One metatstatic cell highlighted by HMB45 in the lung. |
| CBTP3 | 68 | 52 | |
| CBTP3 | 68 | 53 | |
| CBTP3 | 68 | 54 | |
| CBTP3 | 68 | 55 | |
| CBTP3 | 68 | 56 | No metastatic tumor to liver. 2 metastatic cells highlighted by HMB45 in the lung. |
| CBTP3 | 68 | 57 | |
| CBTP3 | 68 | 58 | |
| CBTP3 | 68 | 59 | |
| CBTP3 | 68 | 60 | |

TABLE 16

Dermatopathological review of CBTPA and control CBTP primary tumors, liver, and lung sections.

| Genotype | Days Post Injection | Slide Num | Slide Label | Stain | Tissue | Heterogenous/ Homogenous (1-10 scale?) | Benign or Malignant? | Most similar to which human melanocytic neoplastic category |
|---|---|---|---|---|---|---|---|---|
| CBTP | 36 | 1 | EH_276-279_X4_1 | H&E | primary tumor | 5 | Malignant | Melanoma |
| CBTP | 36 | 2 | EH_276-279_X4_1 | Ki67 | primary tumor | | | |
| CBTP | 36 | 3 | EH_276-279_X4_1 | HMB45 | primary tumor | | | |
| CBTP | 36 | 4 | EH_276-279_X4_1 | SOX10 | primary tumor | | | |
| CBTP | 36 | 5 | EH_276-279_X4_1 | Melan-A | primary tumor | | | |
| CBTP | 36 | 1 | EH_276-279_X4_2 | H&E | primary tumor | 5 | Malignant | Melanoma |
| CBTP | 36 | 2 | EH_276-279_X4_2 | Ki67 | primary tumor | | | |
| CBTP | 36 | 3 | EH_276-279_X4_2 | HMB45 | primary tumor | | | |
| CBTP | 36 | 4 | EH_276-279_X4_2 | SOX10 | primary tumor | | | |
| CBTP | 36 | 5 | EH_276-279_X4_2 | Melan-A | primary tumor | | | |
| CBTP | 36 | 1 | EH_276-279_X4_3 | H&E | primary tumor | 5 | Malignant | Melanoma |
| CBTP | 36 | 2 | EH_276-279_X4_3 | Ki67 | primary tumor | | | |
| CBTP | 36 | 3 | EH_276-279_X4_3 | HMB45 | primary tumor | | | |
| CBTP | 36 | 4 | EH_276-279_X4_3 | SOX10 | primary tumor | | | |
| CBTP | 36 | 5 | EH_276-279_X4_3 | Melan-A | primary tumor | | | |
| CBTP | 36 | 1 | EH_276-279_X4_4 | H&E | primary tumor | 5 | Malignant | Melanoma |
| CBTP | 36 | 2 | EH_276-279_X4_4 | Ki67 | primary tumor | | | |
| CBTP | 36 | 3 | EH_276-279_X4_4 | HMB45 | primary tumor | | | |
| CBTP | 36 | 4 | EH_276-279_X4_4 | SOX10 | primary tumor | | | |
| CBTP | 36 | 5 | EH_276-279_X4_4 | Melan-A | primary tumor | | | |
| CBTPA | 36 | 6 | EH_277-278_X4_1 | H&E | primary tumor | 8 | Malignant | Melanoma |
| CBTPA | 36 | 7 | EH_277-278_X4_1 | Ki67 | primary tumor | | | |
| CBTPA | 36 | 8 | EH_277-278_X4_1 | HMB45 | primary tumor | | | |
| CBTPA | 36 | 9 | EH_277-278_X4_1 | SOX10 | primary tumor | | | |
| CBTPA | 36 | 10 | EH_277-278_X4_1 | Melan-A | primary tumor | | | |
| CBTPA | 36 | 6 | EH_277-278_X4_2 | H&E | primary tumor | 8 | Malignant | Melanoma |
| CBTPA | 36 | 7 | EH_277-278_X4_2 | Ki67 | primary tumor | | | |
| CBTPA | 36 | 8 | EH_277-278_X4_2 | HMB45 | primary tumor | | | |
| CBTPA | 36 | 9 | EH_277-278_X4_2 | SOX10 | primary tumor | | | |
| CBTPA | 36 | 10 | EH_277-278_X4_2 | Melan-A | primary tumor | | | |
| CBTPA | 36 | 6 | EH_277-278_X4_3 | H&E | primary tumor | 8 | Malignant | Melanoma |
| CBTPA | 36 | 7 | EH_277-278_X4_3 | Ki67 | primary tumor | | | |
| CBTPA | 36 | 8 | EH_277-278_X4_3 | HMB45 | primary tumor | | | |
| CBTPA | 36 | 9 | EH_277-278_X4_3 | SOX10 | primary tumor | | | |
| CBTPA | 36 | 10 | EH_277-278_X4_3 | Melan-A | primary tumor | | | |
| CBTPA | 36 | 6 | EH_277-278_X4_4 | H&E | primary tumor | 8 | Malignant | Melanoma |
| CBTPA | 36 | 7 | EH_277-278_X4_4 | Ki67 | primary tumor | | | |
| CBTPA | 36 | 8 | EH_277-278_X4_4 | HMB45 | primary tumor | | | |
| CBTPA | 36 | 9 | EH_277-278_X4_4 | SOX10 | primary tumor | | | |
| CBTPA | 36 | 10 | EH_277-278_X4_4 | Melan-A | primary tumor | | | |
| CBTP | 36 | 13 | EH_276_LVG | H&E | multiple liver and lung lobes | | | |
| CBTP | 36 | 14 | EH_276_LVG | Ki67 | multiple liver and lung lobes | | | |
| CBTP | 36 | 15 | EH_276_LVG | HMB45 | multiple liver and lung lobes | | | |
| CBTP | 36 | 16 | EH_276_LVG | SOX10 | multiple liver and lung lobes | | | |
| CBTP | 36 | 17 | EH_276_LVG | Melan-A | multiple liver and lung lobes | | | |

TABLE 16-continued

Dermatopathological review of CBTPA and control CBTP primary tumors, liver, and lung sections.

| | | | | | | |
|---|---|---|---|---|---|---|
| CBTP | 36 | 18 | EH_279_LVG | H&E | multiple liver and lung lobes | |
| CBTP | 36 | 19 | EH_279_LVG | Ki67 | multiple liver and lung lobes | |
| CBTP | 36 | 20 | EH_279_LVG | HMB45 | multiple liver and lung lobes | |
| CBTP | 36 | 21 | EH_279_LVG | SOX10 | multiple liver and lung lobes | |
| CBTP | 36 | 22 | EH_279_LVG | Melan-A | multiple liver and lung lobes | |
| CBTP | 36 | 23 | EH_282_LVG | H&E | multiple liver and lung lobes | |
| CBTP | 36 | 24 | EH_282_LVG | Ki67 | multiple liver and lung lobes | |
| CBTP | 36 | 25 | EH_282_LVG | HMB45 | multiple liver and lung lobes | |
| CBTP | 36 | 26 | EH_282_LVG | SOX10 | multiple liver and lung lobes | |
| CBTP | 36 | 27 | EH_282_LVG | Melan-A | multiple liver and lung lobes | |
| CBTP | 36 | 28 | EH_285_LVG | H&E | multiple liver and lung lobes | |
| CBTP | 36 | 29 | EH_285_LVG | Ki67 | multiple liver and lung lobes | |
| CBTP | 36 | 30 | EH_285_LVG | HMB45 | multiple liver and lung lobes | |
| CBTP | 36 | 31 | EH_285_LVG | SOX10 | multiple liver and lung lobes | |
| CBTP | 36 | 32 | EH_285_LVG | Melan-A | multiple liver and lung lobes | |
| CBTPA | 36 | 33 | EH_277_LVG | H&E | multiple liver and lung lobes | 10 |
| CBTPA | 36 | 34 | EH_277_LVG | Ki67 | multiple liver and lung lobes | |
| CBTPA | 36 | 35 | EH_277_LVG | HMB45 | multiple liver and lung lobes | |
| CBTPA | 36 | 36 | EH_277_LVG | SOX10 | multiple liver and lung lobes | |
| CBTPA | 36 | 37 | EH_277_LVG | Melan-A | multiple liver and lung lobes | |
| CBTPA | 36 | 38 | EH_278_LVG | H&E | multiple liver and lung lobes | |
| CBTPA | 36 | 39 | EH_278_LVG | Ki67 | multiple liver and lung lobes | |
| CBTPA | 36 | 40 | EH_278_LVG | HMB45 | multiple liver and lung lobes | |
| CBTPA | 36 | 41 | EH_278_LVG | SOX10 | multiple liver and lung lobes | |
| CBTPA | 36 | 42 | EH_278_LVG | Melan-A | multiple liver and lung lobes | |
| CBTPA | 36 | 43 | EH_280_LVG | H&E | multiple liver and lung lobes | 10 |
| CBTPA | 36 | 44 | EH_280_LVG | Ki67 | multiple liver and lung lobes | |
| CBTPA | 36 | 45 | EH_280_LVG | HMB45 | multiple liver and lung lobes | |
| CBTPA | 36 | 46 | EH_280_LVG | SOX10 | multiple liver and lung lobes | |
| CBTPA | 36 | 47 | EH_280_LVG | Melan-A | multiple liver and lung lobes | |
| CBTPA | 36 | 48 | EH_281_LVG | H&E | multiple liver and lung lobes | 10 |
| CBTPA | 36 | 49 | EH_281_LVG | Ki67 | multiple liver and lung lobes | |
| CBTPA | 36 | 50 | EH_281_LVG | HMB45 | multiple liver and lung lobes | |
| CBTPA | 36 | 51 | EH_281_LVG | SOX10 | multiple liver and lung lobes | |
| CBTPA | 36 | 52 | EH_281_LVG | Melan-A | multiple liver and lung lobes | |

| Genotype | Days Post Injection | Slide Num | Mitoses/ mm2 | Pigmentation level (0-10) | Stain Scale (1-10) | Full note |
|---|---|---|---|---|---|---|
| CBTP | 36 | 1 | | 0 | N/A | Multiple nests of |
| CBTP | 36 | 2 | | | 3 | spindled and |
| CBTP | 36 | 3 | | | 9 | epithelioid cells with |

TABLE 16-continued

Dermatopathological review of CBTPA and control CBTP primary tumors, liver, and lung sections.

| | | | | | | |
|---|---|---|---|---|---|---|
| CBTP | 36 | 4 | | | 9 | no pigmentation. |
| CBTP | 36 | 5 | | | 8 | |
| CBTP | 36 | 1 | | 0 | N/A | Multiple nests of |
| CBTP | 36 | 2 | | | 3 | spindled and |
| CBTP | 36 | 3 | | | 9 | epithelioid cells with |
| CBTP | 36 | 4 | | | 9 | no pigmentation. |
| CBTP | 36 | 5 | | | 8 | |
| CBTP | 36 | 1 | | 0 | N/A | Multiple nests of |
| CBTP | 36 | 2 | | | 2 | spindled and |
| CBTP | 36 | 3 | | | 9 | epithelioid cells with |
| CBTP | 36 | 4 | | | 9 | no pigmentation. |
| CBTP | 36 | 5 | | | 8 | |
| CBTP | 36 | 1 | | 0 | N/A | Multiple nests of |
| CBTP | 36 | 2 | | | 3 | spindled and |
| CBTP | 36 | 3 | | | 9 | epithelioid cells with |
| CBTP | 36 | 4 | | | 9 | no pigmentation. |
| CBTP | 36 | 5 | | | 8 | |
| CBTPA | 36 | 6 | 14 | 5 | N/A | Predominantly epithelioid |
| CBTPA | 36 | 7 | | | 8 | with admixed spindle cells |
| CBTPA | 36 | 8 | | | 3 | with varying degrees of |
| CBTPA | 36 | 9 | | | 10 | pigmentation in the |
| CBTPA | 36 | 10 | | | 10 | cytoplasm. On the edge of |
| | | | | | | the necrotic areas are |
| | | | | | | melanophages. There is |
| | | | | | | extensive necrosis. |
| CBTPA | 36 | 6 | 18 | 6 | N/A | Predominantly epithelioid |
| CBTPA | 36 | 7 | | | 9 | with admixed spindle cells |
| CBTPA | 36 | 8 | | | 2 | with varying degrees of |
| CBTPA | 36 | 9 | | | 10 | pigmentation in the |
| CBTPA | 36 | 10 | | | 10 | cytoplasm. On the edge of |
| | | | | | | the necrotic areas are |
| | | | | | | melanophages. There is |
| | | | | | | extensive necrosis. |
| CBTPA | 36 | 6 | 19 | 7 | N/A | Predominantly epithelioid |
| CBTPA | 36 | 7 | | | 9 | with admixed spindle cells |
| CBTPA | 36 | 8 | | | 2 | with varying degrees of |
| CBTPA | 36 | 9 | | | 7 | pigmentation in the |
| CBTPA | 36 | 10 | | | 10 | cytoplasm. On the edge of |
| | | | | | | the necrotic areas are |
| | | | | | | melanophages. There is |
| | | | | | | extensive necrosis. |
| CBTPA | 36 | 6 | 17 | 5 | N/A | Predominantly epithelioid |
| CBTPA | 36 | 7 | | | 9 | with admixed spindle cells |
| CBTPA | 36 | 8 | | | 2 | with varying degrees of |
| CBTPA | 36 | 9 | | | 10 | pigmentation in the |
| CBTPA | 36 | 10 | | | 10 | cytoplasm. On the edge of |
| | | | | | | the necrotic areas are |
| | | | | | | melanophages. There is |
| | | | | | | extensive necrosis. |
| CBTP | 36 | 13 | | | N/A | No metastases detected. |
| CBTP | 36 | 14 | | | | |
| CBTP | 36 | 15 | | | | |
| CBTP | 36 | 16 | | | | |
| CBTP | 36 | 17 | | | | |
| CBTP | 36 | 18 | | | N/A | No metastases detected. |
| CBTP | 36 | 19 | | | | |
| CBTP | 36 | 20 | | | | |
| CBTP | 36 | 21 | | | | |
| CBTP | 36 | 22 | | | | |
| CBTP | 36 | 23 | | | N/A | No metastases detected. |
| CBTP | 36 | 24 | | | | |
| CBTP | 36 | 25 | | | | |
| CBTP | 36 | 26 | | | | |
| CBTP | 36 | 27 | | | | |
| CBTP | 36 | 28 | | | N/A | No metastases detected. |
| CBTP | 36 | 29 | | | | |
| CBTP | 36 | 30 | | | | |
| CBTP | 36 | 31 | | | | |
| CBTP | 36 | 32 | | | | |
| CBTPA | 36 | 33 | | 6 | N/A | Multifocal lung and |
| CBTPA | 36 | 34 | | | 9 | liver metastases, some |
| CBTPA | 36 | 35 | | | 10 | as scattered single |
| CBTPA | 36 | 36 | | | 10 | cells, but other foci are |
| CBTPA | 36 | 37 | | | 9 | nests. The lung exhibits |
| | | | | | | more metastases than |
| | | | | | | the liver. |
| CBTPA | 36 | 38 | | | N/A | Multifocal lung and |
| CBTPA | 36 | 39 | | | | liver metastases, some |

TABLE 16-continued

Dermatopathological review of CBTPA and control CBTP primary tumors, liver, and lung sections.

| | | | | | |
|---|---|---|---|---|---|
| CBTPA | 36 | 40 | | | as scattered single |
| CBTPA | 36 | 41 | | | cells, but other foci are |
| CBTPA | 36 | 42 | | | nests. The lung exhibits more metastases than the liver. |
| CBTPA | 36 | 43 | 0 | N/A | Multifocal lung and |
| CBTPA | 36 | 44 | | 8 | liver metastases, some |
| CBTPA | 36 | 45 | | 10 | as scattered single |
| CBTPA | 36 | 46 | | 9 | cells, but other foci are |
| CBTPA | 36 | 47 | | 9 | nests. |
| CBTPA | 36 | 48 | 0 | N/A | Multifocal lung and |
| CBTPA | 36 | 49 | | 8 | liver metastases, some |
| CBTPA | 36 | 50 | | 8 | as scattered single |
| CBTPA | 36 | 51 | | 5 | cells, but other foci are |
| CBTPA | 36 | 52 | | 5 | nests. These are best seen on HMB45. |

Figure 36:
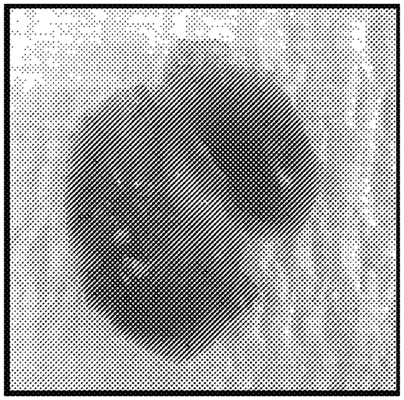
FIG. 36—CBTPA cells metastasize in vivo. Photograph of mouse lungs 36 days after dermal injection of CBTPA cells into both flanks of NSG mice. Black lesions are metastatic nodules.

Along with rapid primary tumor growth, tumors formed by CBTPA melanocytes had further characteristics of aggressive disease. They readily metastasized to visceral organs, with numerous metastases visible in the lungs and liver by day 36 (FIGS. 28K, 28L, and 36), and caused rapid-onset weight loss, apparent almost immediately after xenograft injection (FIG. 28M). Together with our observations of metastasis in the CBTA model (FIGS. 28K, 28L, 29A, and 29B), Applicants' findings point to loss of APC as an important cause of metastatic disease in this genetic context. This is likely due to Wnt pathway activation and is consistent with recent observations in patients with metastatic melanoma (Viros et al. *Nature* 511:478-482 (2014)). Taken together, these findings suggest that the CBTPA combination of mutations in human melanocytes causes an aggressive, metastatic malignancy with systemic manifestations of disease.

Figure 37A:
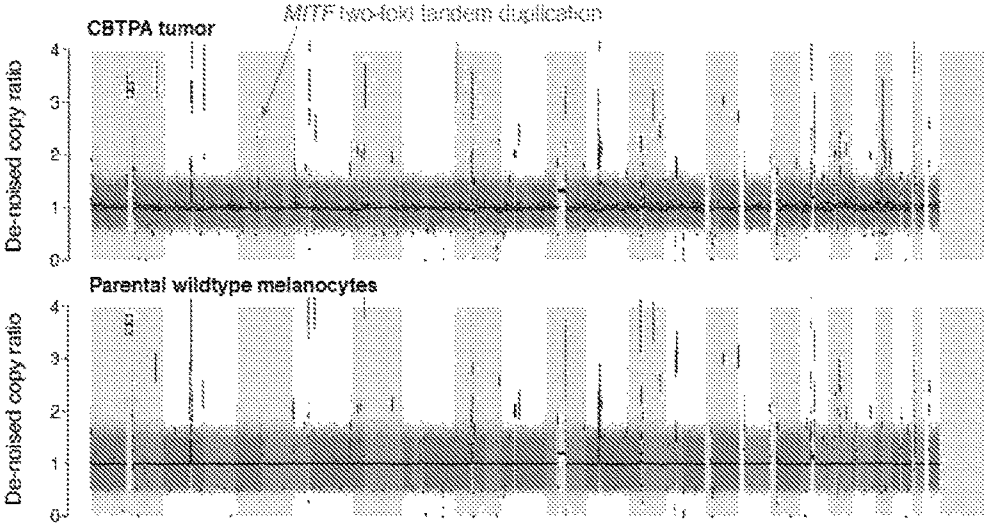
FIG. 37A, 37B—CBTPA tumor has mostly normal chromosomal copy number profile and MITF duplication. Chromosomal copy number profiles based on whole genome sequencing data (see Materials and Methods). Across each chromosome (x axis), plots show copy number (y axis) inferred using either a ratio of sequencing coverage (FIG. 37A) or a fraction of the alternate allele called at each locus (FIG. 37B) for a CBTPA tumor (top) and the parental wildtype melanocytes (bottom). MITF duplication on chromosome 3p is marked.
Figure 37B:
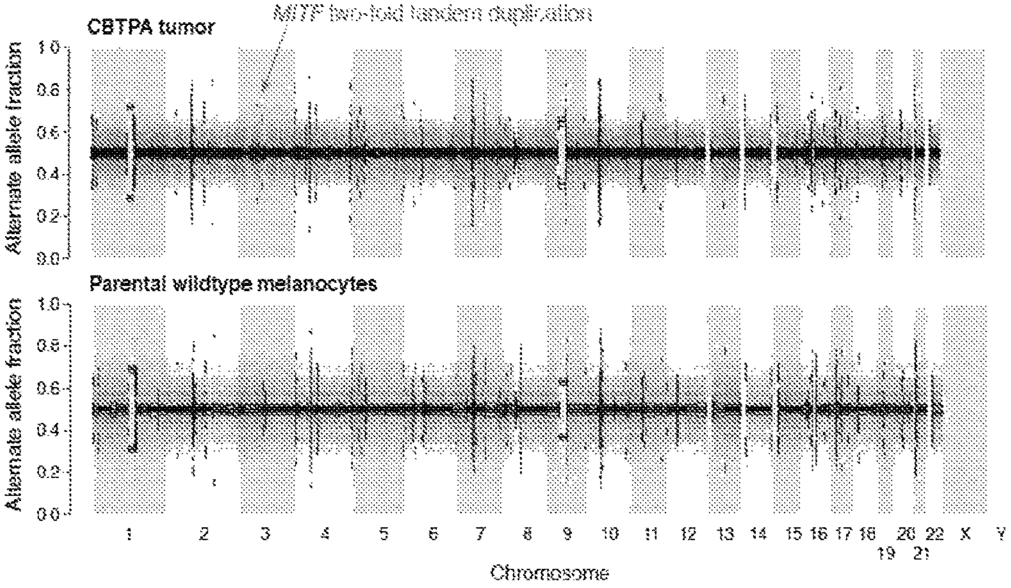
Figure 38:
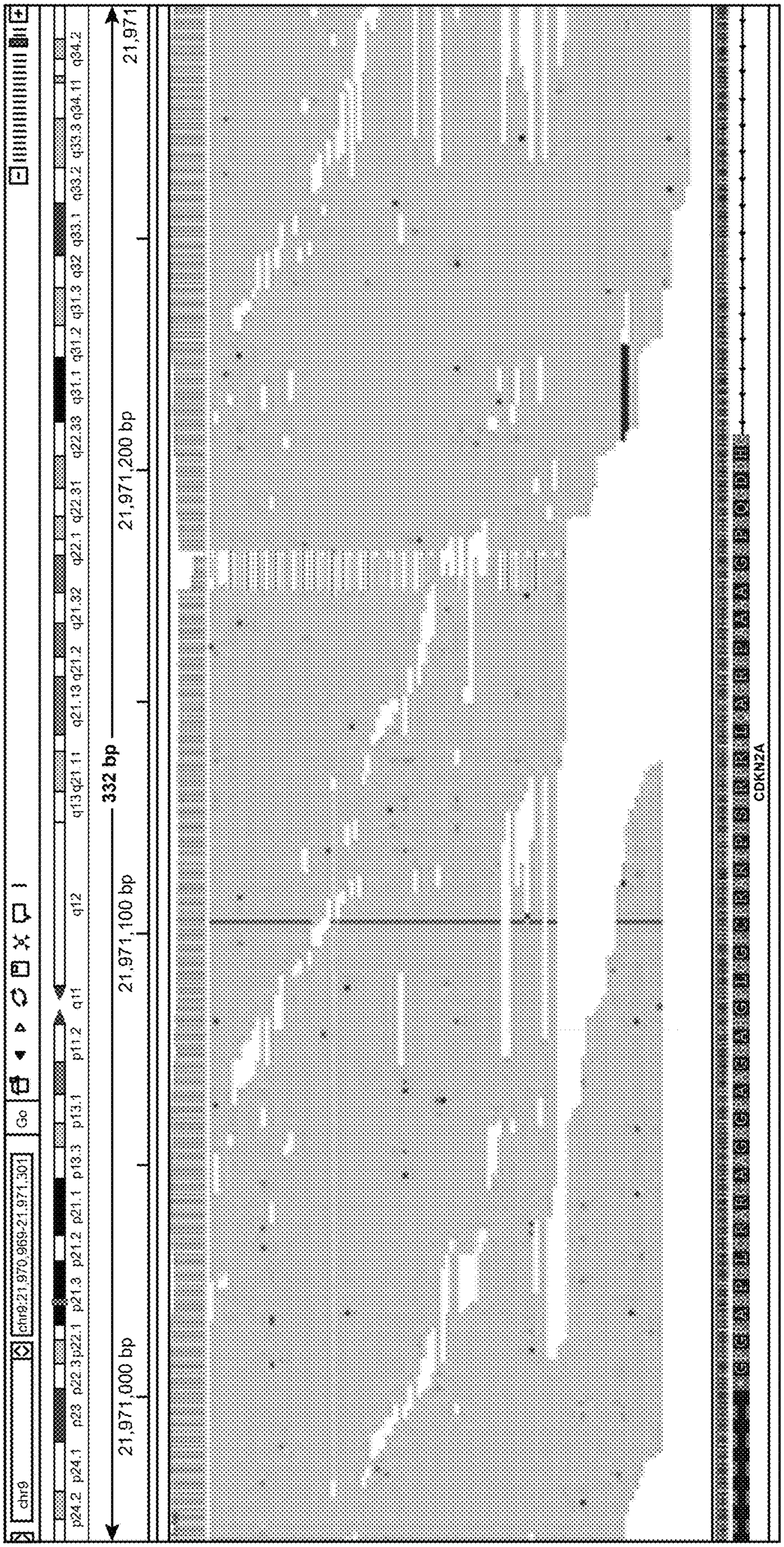
FIG. 38—Whole genome sequencing of CBTPA tumor shows ~100% CDKN2A indel allele fraction. Integrative Genomics Viewer (IGV) screenshot of whole genome sequencing reads from a CBTPA tumor aligned at the CDKN2A exon 2 locus (Table 18). Individual reads are shown as stacked, horizontal bars. Insertion of a single base pair (A:T) is indicated in solid (left). Deletions of length one and length eight are indicated with narrow horizontal line (right). Mismatched bases within a read are shown as squares. Reads whose mate read aligns to a distant locus are shown. Reference sequence and CDKN2A exon model are shown (bottom). Histogram of read coverage is also shown (middle, above stacked read plot).
Figure 39:
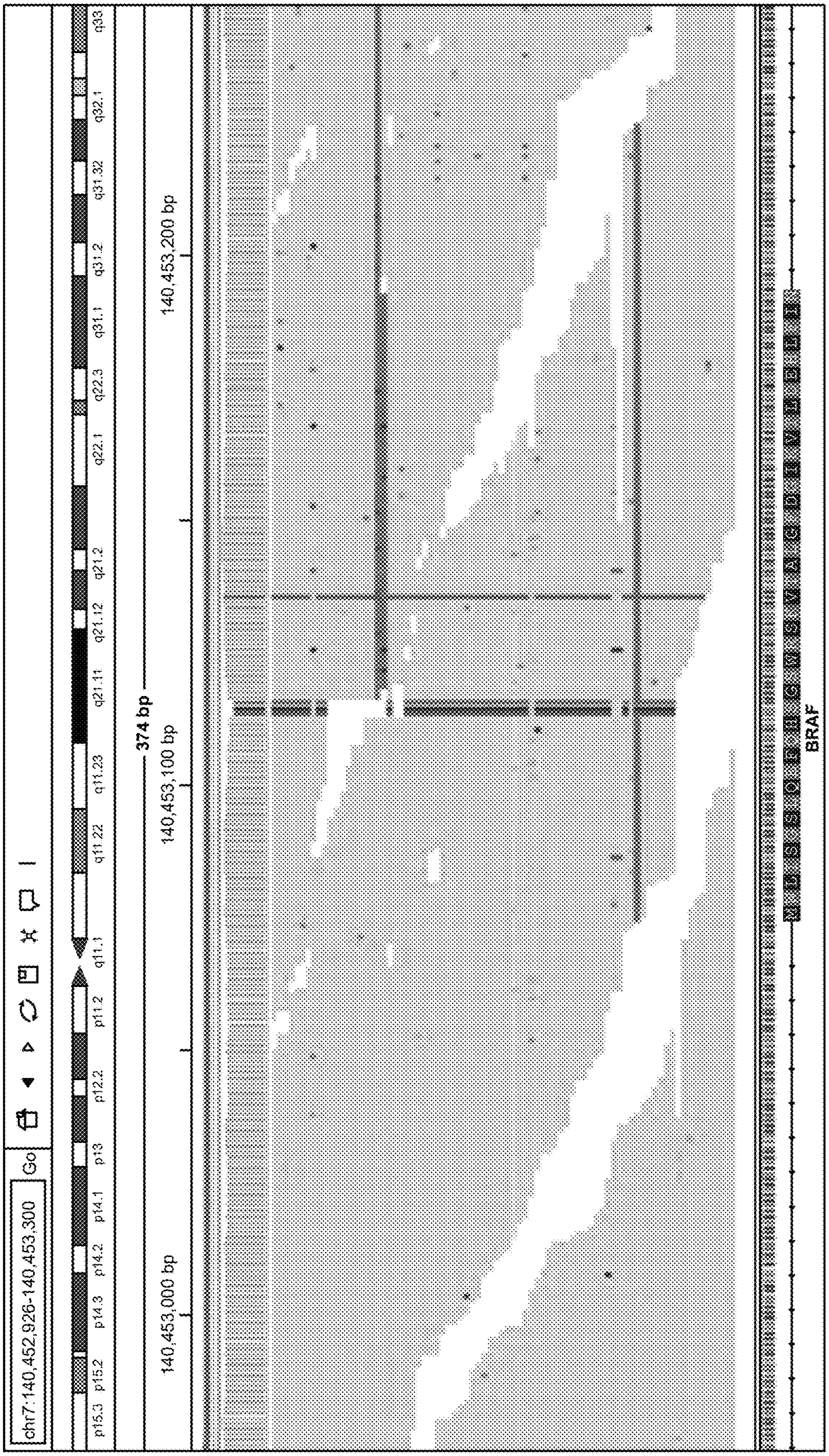
FIG. 39—Whole genome sequencing of CBTPA tumor shows ~100% BRAF V600E, S607S allele fraction. Integrative Genomics Viewer (IGV) screenshot of whole genome sequencing reads from a CBTPA tumor aligned at the BRAF exon 15 locus (see Table 18). Individual reads are shown as stacked, horizontal bars. Mismatched bases within a read, as compared to the reference sequence, are shown as squares. BRAF V600E (vertical stripe, right) and S607S (vertical stripe, left) mutations are present in ~100% of reads. Reads whose mate read aligns to a distant locus are shown. Reference sequence and BRAF exon model is shown (bottom). Histogram of read coverage is also shown (middle, above stacked read plot).
Figure 40:
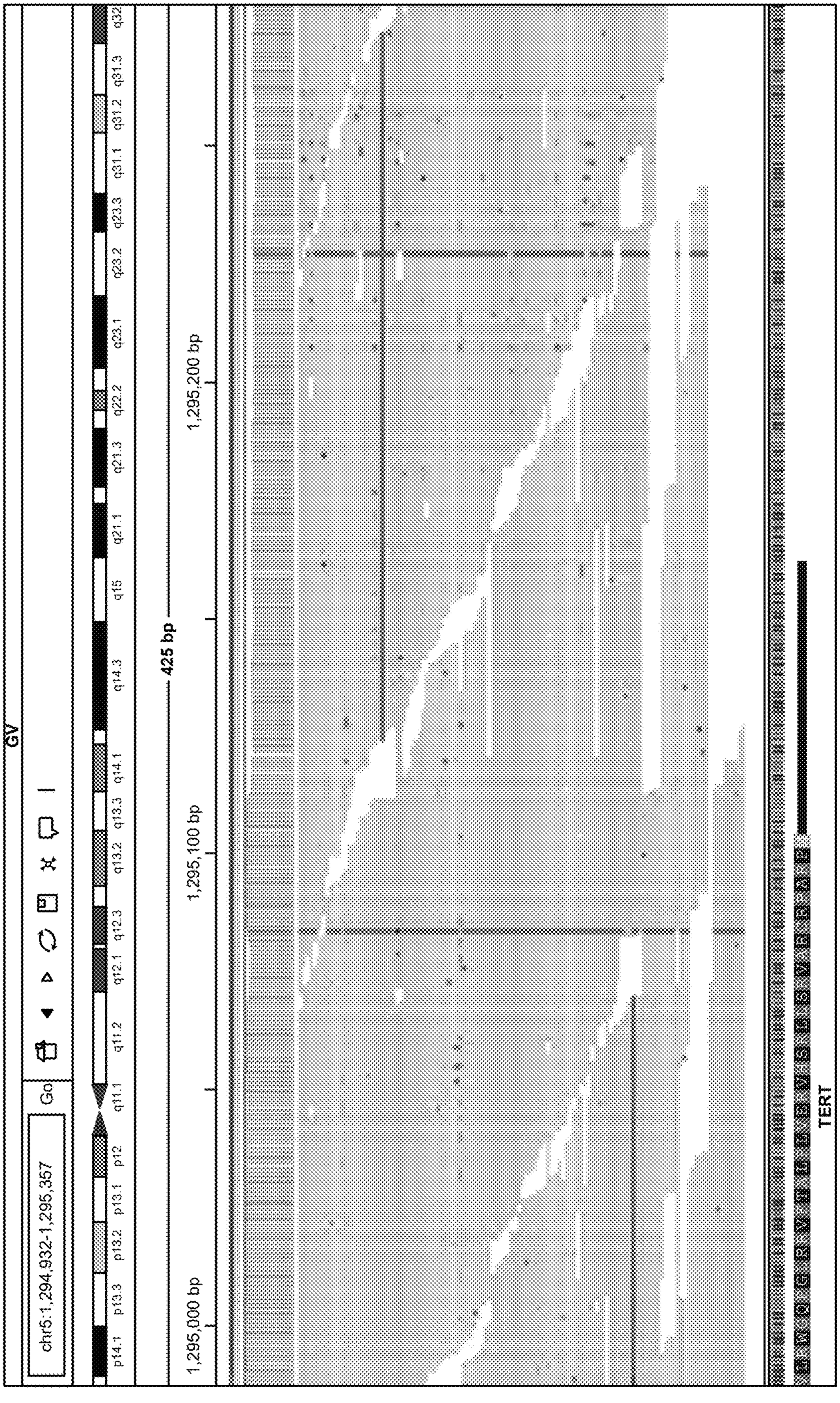
FIG. 40—Whole genome sequencing of CBTPA tumor shows 100% TERT −124C>T, C7C allele fraction. Integrative Genomics Viewer (IGV) screenshot of whole genome sequencing reads from a CBTPA tumor aligned at the TERT exon 1/core promoter locus (see Table 18). Individual reads are shown as stacked, horizontal bars. Mismatched bases within a read, as compared to the reference sequence, are shown as squares. TERT −124C>T (vertical stripe, right) and C7C (vertical stripe, left) mutations are present in ~100% of reads. Reads whose mate read aligns to a distant locus are shown. Reference sequence and TERT exon model is shown (bottom). Histogram of read coverage is also shown (middle, above stacked read plot).
Figure 41:
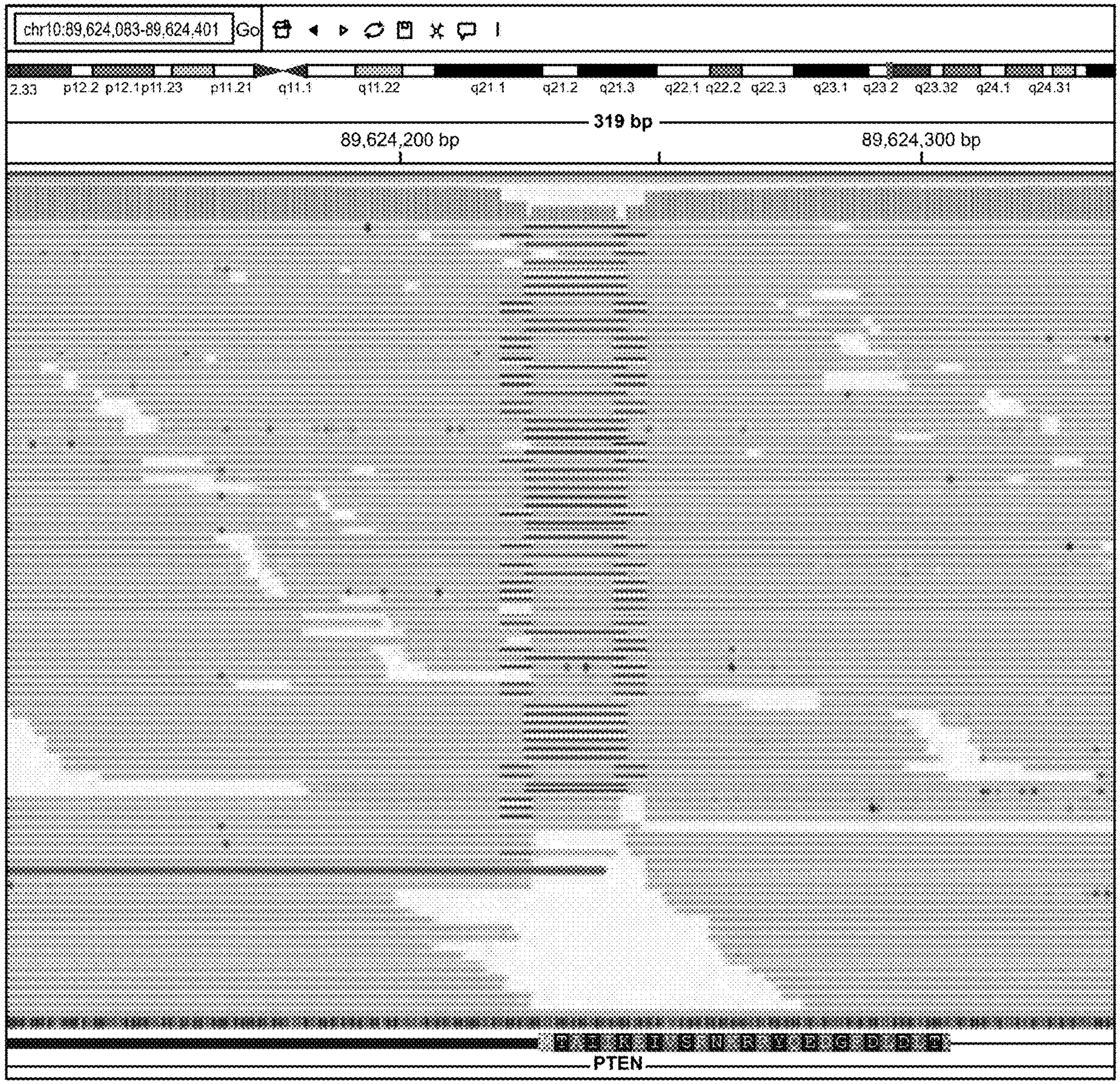
FIG. 41—Whole genome sequencing of CBTPA tumor shows ~100% PTEN indel allele fraction. Integrative Genomics Viewer (IGV) screenshot of whole genome sequencing reads from a CBTPA tumor aligned at the PTEN exon 1 locus (see Table 18). Individual reads are shown as stacked, horizontal bars. Deletions are show as narrow black horizontal lines within a grey read. Mismatched bases, compared to reference, within a read are shown as squares. Reads whose mate read aligns to a distant locus are shown. Reference sequence and PTEN exon model is shown (bottom). Histogram of read coverage is also shown (middle, above stacked read plot).
Figure 42:
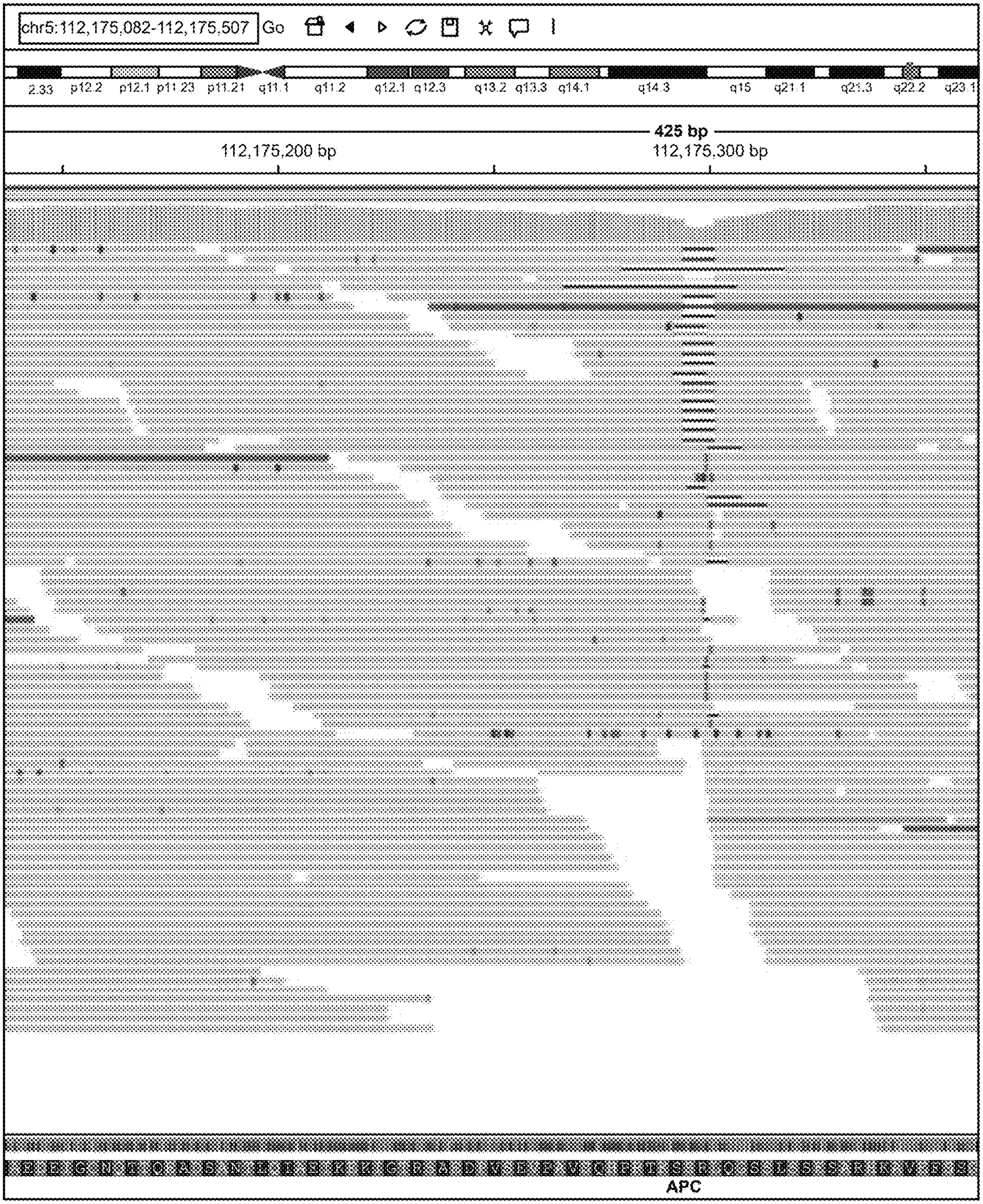
FIG. 42—Whole genome sequencing of CBTPA tumor shows ~100% APC indel allele fraction. Integrative Genomics Viewer (IGV) screenshot of whole genome sequencing reads from a CBTPA tumor aligned at the final APC exon locus (see Table 18). Individual reads are shown as stacked, horizontal bars. Deletions are show as narrow black horizontal lines within a grey read. Insertions are shown as I's. Mismatched bases, compared to reference, within a read are shown as squares. Reads whose mate read aligns to a distant locus are shown. Reference sequence and APC exon model is shown (bottom). Histogram of read coverage is also shown (middle, above stacked read plot).

Applicants sequenced the genome of a CBTPA tumor and compared it to the parental, wildtype melanocyte genome to identify somatic events. Overall, no mutations of apparent in vivo phenotypic consequence were found beyond those that, had been introduced. Notably, Applicants did identify a clonal, two-fold tandem duplication of the melanocyte master regulator (transcription factor) MITF (Table 17, FIGS. 37A, and 37B) (Rimm et al. *Am J Pathol* 154:325-329 (1999) but it had no major phenotypic consequence, as discussed below. No further somatic alterations of known cancer association were identified, with no additional chromosomal segment amplifications or deletions (FIGS. 37A, 37B), only 12 clonal, non-silent somatic point mutations (not including engineered mutations; Table 18, FIGS. 38-42), and only one structural variant (deletion of RIC8B; Table 17).

TABLE 17

Potentially clonal, somatic structural variants identified in CBTPA tumor whole genome sequencing data.

| individual | num | chr1 | str1 | pos1 | chr2 | str2 | pos2 | class | span | tumreads | normreads |
|---|---|---|---|---|---|---|---|---|---|---|---|
| sample | 1 | 3 | 1 | 69915515 | 3 | 0 | 70057122 | tandem_dup | 141610 | 57 | 0 |
| sample | 6 | 12 | 0 | 107185172 | 12 | 1 | 107205157 | deletion | 19990 | 33 | 0 |

| individual | normpanel-bins | min1 | max1 | range1 | stdev1 | min2 | max2 | range2 | stdev2 | gene1 | site1 |
|---|---|---|---|---|---|---|---|---|---|---|---|
| sample | 0 | 69915512 | 69916263 | 752 | 131 | 70056551 | 70057122 | 572 | 120 | MITF | Intron of MITF(+): 15 bp after exon 1 |
| sample | 0 | 107184618 | 107185168 | 551 | 114 | 107205158 | 107205867 | 710 | 123 | RIC8B | Intron of RIC8B(+): 7 Kb after exon 2 |

| individual | gene2 | site2 | fusion | fmapqzT1 | fmapqzN1 | fmapqzT2 | fmapqzN2 | nuwpT1 | nuwpN1 | nuwpT2 | nuwpN2 |
|---|---|---|---|---|---|---|---|---|---|---|---|
| sample | MITF | IGR: 40 Kb after MITF(+) | — | 1.00E−02 | 0 | 1.00E−02 | 4.00E−02 | 3 | 1 | 3 | 1 |
| sample | RIC8B | Intron of RIC8B(+): 3 Kb before exon 3 | Deletion within intron | 0 | 0 | 0 | 0 | 2 | 0 | 3 | 1 |

| individual | zstdev1 | zstdev2 | quality | score | somatic | somatic_score | BPtry | dRpos1 | dRpos2 | T_BPhit | T_BPpos1 |
|---|---|---|---|---|---|---|---|---|---|---|---|
| sample | 0.221626 | −0.125857 | 1 | 57 | 1 | 57 | 1 | 69915512 | 70057122 | 1 | 69915515 |
| sample | −0.315394 | −0.031089 | 1 | 33 | 1 | 33 | 1 | 107185168 | 107205158 | 1 | 107185172 |

TABLE 17-continued

Potentially clonal, somatic structural variants identified in CBTPA tumor whole genome sequencing data.

| individual | T_diffpos1 | T_BPpos2 | T_diffpos2 | T_SWreads | T_SWscore | T_firstseq | T_lenhomology |
|---|---|---|---|---|---|---|---|
| sample | 3 | 70057122 | 0 | 20 | 0.983858 | 1 | 1 |
| sample | 4 | 107205157 | −1 | 20 | 0.944966 | 0 | 0 |

| individual | T_lenhomology_soft | T_lenforeign | T_foreignseq | T_BWAreads |
|---|---|---|---|---|
| sample | 65 | 0 | | 28 |
| sample | 68 | 0 | | 16 |

| individual | N_BPhit | N_BPpos1 | N_diffpos1 | N_BPpos2 | N_diffpos2 | N_SWreads | N_SWscore |
|---|---|---|---|---|---|---|---|
| sample | 1 | −1 | −69915513 | −1 | −70057123 | −1 | −1 |
| sample | 1 | −1 | −107185169 | −1 | −107205159 | −1 | −1 |

| individual | N_firstseq | N_lenhomology | N_lenhomology_soft | N_lenforeign |
|---|---|---|---|---|
| sample | −1 | −1 | −1 | −1 |
| sample | −1 | −1 | −1 | −1 |

| individual | N_foreignseq | N_BWAreads | BPresult | BPsomaticratio | approxflag | VCF_TALT | VCF_TALT_RP |
|---|---|---|---|---|---|---|---|
| sample | failed | 0 | 1 | Inf | 0 | 57 | 33 |
| sample | failed | 0 | 1 | Inf | 0 | 33 | 18 |

| individual | VCF_TALT_SR | VCF_TREF | VCF_TREF_RP | VCF_TREF_SR |
|---|---|---|---|---|
| sample | 24 | 149 | 73 | 76 |
| sample | 15 | 72 | 37 | 35 |

| individual | VCF_NALT | VCF_NALT_RP | VCF_NALT_SR | VCF_NREF | VCF_NREF_RP | VCF_NREF_SR |
|---|---|---|---|---|---|---|
| sample | 0 | 0 | 0 | 83 | 56 | 27 |
| sample | 0 | 0 | 0 | 88 | 56 | 32 |

| individual | VCF_QUAL | VCF_HOMLEN | VCF_HOMSEQ | VCF_FORLEN | VCF_FORSEQ |
|---|---|---|---|---|---|
| sample | 99 | 1 | T | 0 | |
| sample | 99 | 0 | | 0 | |

| individual | VCF_POS1 | VCF_ALT1 | VCF_POS2 | VCF_ALT2 |
|---|---|---|---|---|
| sample | 69915516 | ]chr3: 70057121]T | 70057121 | A[chr3: 69915516[ |
| sample | 107185172 | A[chr12: 107205158[ | 107205158 | ]chr12: 107185172]G |

TABLE 18

Potentially clonal, somatic single nucleotide variants identified in CBTPA tumor whole genome sequencing data.

| Hugo Symbol | Entrez_ Gene_Id | Chromo-some | Start_ position | End_ position | Variant_ Classification | Variant_ Type | Reference_ Allele | Tumor_Seq_ Allele1 | Tumor_Seq_ Allele2 | dbSNP_RS |
|---|---|---|---|---|---|---|---|---|---|---|
| CDKN2A | 1029 | 9 | 21971102 | 21971103 | Frame_Shift_Ins | INS | — | — | A | |
| CDKN2A | 1029 | 9 | 21971175 | 21971182 | Frame_Shift_Del | DEL | CTCCGCCA | CTCCGCCA | — | rs121913382 |
| CDKN2A | 1029 | 9 | 21971182 | 21971182 | Frame_Shift_Del | DEL | A | A | — | rs104894099 |
| BRAF | 673 | 7 | 140453113 | 140453114 | Frame_Shift_Del | DEL | GG | GG | — | |
| BRAF | 673 | 7 | 140453116 | 140453117 | Frame_Shift_Ins | INS | — | — | CT | |
| BRAF | 673 | 7 | 140453136 | 140453136 | Missense_Mutation | SNP | A | A | T | rs121913377 |
| TERT | 7015 | 5 | 1295084 | 1295084 | Silent | SNP | G | G | A | |
| PTEN | 5728 | 10 | 89624220 | 89624225 | 5'UTR | DEL | CCCAGA | CCCAGA | — | |
| PTEN | 5728 | 10 | 89624225 | 89624243 | Start_Codon_Del | DEL | ACATGACAG | ACATGACAG | — | rs121913290 |
| PTEN | 5728 | 10 | 89624242 | 89624247 | In_Frame_Del | DEL | AAAGAG | AAAGAG | — | rs121913290 |
| APC | 324 | 5 | 112175295 | 112175301 | Frame_Shift_Del | DEL | GCAGACT | GCAGACT | — | |
| APC | 324 | 5 | 112175299 | 112175300 | Frame_Shift_Ins | INS | — | — | C | |
| APC | 324 | 5 | 112175301 | 112175307 | Frame_Shift_Del | DEL | TGCAGGG | TGCAGGG | — | rs121913327 |
| APC | 324 | 5 | 112175307 | 112175308 | Frame_Shift_Ins | INS | — | — | G | |
| PRKD1 | 5587 | 14 | 30103721 | 30103721 | Missense_Mutation | SNP | A | A | T | |
| DNAH3 | 55567 | 16 | 21014526 | 21014526 | Missense_Mutation | SNP | C | C | T | |
| SLC25A10 | 1468 | 17 | 79684455 | 79684455 | Missense_Mutation | SNP | G | G | T | |
| DAXX | 1616 | 6 | 33286892 | 33286892 | Missense_Mutation | SNP | G | G | A | rs377663648 |
| CCDC141 | 285025 | 2 | 179733893 | 179733893 | Missense_Mutation | SNP | T | T | C | |
| NPC1L1 | 29881 | 7 | 44578884 | 44578884 | Missense_Mutation | SNP | A | A | G | |
| INADL | 10207 | 1 | 62574146 | 62574146 | Missense_Mutation | SNP | C | C | A | |
| MOV10L1 | 54456 | 22 | 50530457 | 50530457 | Missense_Mutation | SNP | G | G | C | |
| EXOC1 | 55763 | 4 | 56768600 | 56768600 | Missense_Mutation | SNP | C | C | T | |

TABLE 18-continued

Potentially clonal, somatic single nucleotide variants identified in CBTPA tumor whole genome sequencing data.

| | | | | | | | | | |
|---|---|---|---|---|---|---|---|---|---|
| GCDH | 2639 | 19 | 13002786 | 13002786 | Missense_Mutation | SNP | A | A | G |
| UNG | 7374 | 12 | 109541372 | 109541372 | Missense_Mutation | SNP | C | C | T |
| C9orf85 | 138241 | 9 | 74561942 | 74561942 | Silent | SNP | T | T | C |
| LRWD1 | 222229 | 7 | 102109029 | 102109029 | Silent | SNP | C | C | T |
| ERP29 | 10961 | 12 | 112460155 | 112460155 | Missense Mutation | SNP | A | A | T |

| Hugo_Symbol | dbSNP_ Val_Status | Genome_Change | Annotation_Transcript | Transcript_ Strand | Transcript_ Exon | Transcript_ Position |
|---|---|---|---|---|---|---|
| CDKN2A | | g.chr9:21971102_21971103insA | ENST00000304494.5 | - | 2 | 525_526 |
| CDKN2A | | g.chr9:21971175_21971182delCTCCGCCA | ENST00000304494.5 | - | 2 | 446_453 |
| CDKN2A | | g.chr9:21971182delA | ENST00000304494.5 | - | 2 | 446 |
| BRAF | | g.chr7:140453113_140453114delGG | ENST00000288602.6 | - | 15 | 1881_1882 |
| BRAF | | g.chr7:140453116_140453117insCT | ENST00000288602.6 | - | 15 | 1878_1879 |
| BRAF | | g.chr7:140453136A>T | ENST00000288602.6 | - | 15 | 1859 |
| TERT | | g.chr5:1295084G>A | ENST00000310581.5 | - | 1 | 78 |
| PTEN | | g.chr10:89624220_89624225delCCCAGA | ENST00000371953.3 | + | 0 | 1351_1356 |
| PTEN | | g.chr10:89624225_89624243delACATGACAGC CATCATCAA (SEQ ID NO: 123) | ENST00000371953.3 | + | 0 | 1356_1374 |
| PTEN | | g.chr10:89624242_89624247delAAAGAG | ENST00000371953.3 | + | 1 | 1373_1378 |
| APC | | g.chr5:112175295_112175301delGCAGACT | ENST00000457016.1 | + | 16 | 4384_4390 |
| APC | | g.chr5:112175299_112175300insC | ENST00000457016.1 | + | 16 | 4388_4389 |
| APC | | g.chr5:112175301_112175307delTGCAGGG | ENST00000457016.1 | + | 16 | 4390_4396 |
| APC | | g.chr5:112175307_112175308insG | ENST00000457016.1 | + | 16 | 4396_4397 |
| PRKD1 | | g.chr14:30103721A>T | ENST00000331968.5 | - | 8 | 1446 |
| DNAH3 | | g.chr16:21014526C>T | ENST00000261383.3 | - | 42 | 6025 |
| 5LC25A10 | | g.chr17:79684455G>T | ENST00000350690.5 | + | 8 | 647 |
| DAXX | | g.chr6:33286892G>A | ENST00000374542.5 | - | 7 | 2249 |

TABLE 18-continued

Potentially clonal, somatic single nucleotide variants identified in CBTPA tumor whole genome sequencing data.

| | | | | | |
|---|---|---|---|---|---|
| CCDC141 | g.chr2:179733893T>C | ENST00000420890.2 | - | 15 | 2462 |
| NPC1L1 | g.chr7:44578884A>G | ENST00000289547.4 | - | 2 | 1167 |
| INADL | g.chr1:62574146C>A | ENST00000371158.2 | + | 34 | 4529 |
| MOV10L1 | g.chr22:50530457G>C | ENST00000262794.5 | + | 2 | 208 |
| EXOC1 | g.chr4:56768600C>T | ENST00000381295.2 | + | 18 | 2776 |
| GCDH | g.chr19:13002786A>G | ENST00000222214.5 | + | 4 | 480 |
| UNG | g.chr12:109541372C>T | ENST00000242576.2 | + | 6 | 863 |
| C9orf85 | g.chr9:74561942T>C | ENST00000377031.3 | + | 2 | 313 |
| LRWD1 | g.chr7:102109029C>T | ENST00000292616.5 | + | 8 | 1100 |
| ERP29 | g.chr12:112460155A>T | ENST00000261735.3 | + | 3 | 635 |

| Hugo_Symbol | cDNA_Change | Codon_Change | Protein_Change | Other_Transcripts |
|---|---|---|---|---|
| CDKN2A | c.255_256insT | c.(253-258)gctgccfs | p.A86fs | CDKN2A_ENST00000497750.1_Frame_Shift_Ins_p.A35fs\|CDKN2A_ENST00000579755.1_Frame_Shift_Ins_p.C100fs\|CDKN2A_ENST00000361570.3_Frame_Shift_Ins_p.C141fs\|RP11-145E5.5_ENST00000404796.2_Intron\|CDKN2A_ENST00000479692.2_Frame_Shift_Ins_p.A35fs\|CDKN2A_ENST00000498628.2_Frame_Shift_Ins_p.A35fs\|CDKN2A_ENST00000578845.2_Frame_Shift_Ins_p.A35fs\|CDKN2A_ENST00000530628.2_Frame_Shift_Ins_p.C100fs\|CDKN2A_ENST00000494262.1_Frame_Shift_Ins_p.A35fs\|CDKN2A_ENST00000498124.1_Frame_Shift_Ins_p.A86fs\|CDKN2A_ENST00000446177.1_Frame_Shift_Ins_p.A86fs\|CDKN2A_ENST00000579122.1_Frame_Shift_Ins_p.A86fs |
| CDKN2A | c.176_183delTGGCGGAG | c.(175-183)gtggcggagfs | p.VAE59fs | CDKN2A_ENST00000497750.1_Frame_Shift_Del_p.VAE8fs\|CDKN2A_ENST00000579755.1_Frame_Shift_Del_p.GGA74fs\|CDKN2A_ENST00000361570.3_Frame_Shift_Del_p.GGA115fs\|RP11-145E5.5_ENST00000404796.2_Intron\|CDKN2A_ENST00000479692.2_Frame_Shift_Del_p.VAE8fs\|CDKN2A_ENST00000498628.2_Frame_Shift_Del_p.VAE8fs\|CDKN2A_ENST00000578845.2_Frame_Shift_Del_p.VAE8fs\|CDKN2A_ENST00000530628.2_Frame_Shift_Del_p.GGA74fs\|CDKN2A_ENST00000494262.1_Frame_Shift_Del_p.VAE8fs\|CDKN2A_ENST00000498124.1_Frame_Shift_Del_p.VAE59fs\|CDKN2A_ENST00000446177.1_Frame_Shift_Del_p.VAE59fs\|CDKN2A_ENST00000579122.1_Frame_Shift_Del_p.VAE59fs |

TABLE 18-continued

<table>
<tr><th colspan="5">Potentially clonal, somatic single nucleotide variants identified in CBTPA tumor whole genome sequencing data.</th></tr>
<tr><td>CDKN2A</td><td>c.176delT</td><td>c.(175-177)gtgfs</td><td>p.V59fs</td><td>CDKN2A_ENST00000497750.1_Frame_Shift_Del_p.V8fs|CDKN2A_ENST00000579755.1_Frame_Shift_Del_p.S73fs|CDKN2A_ENST00000361570.3_Frame_Shift_Del_p.S114fs|RP11-145E5.5_ENST00000404796.2_Intron|CDKN2A_ENST00000479692.2_Frame_Shift_Del_p.V8fs|CDKN2A_ENST00000498628.2_Frame_Shift_Del_p.V8fs|CDKN2A_ENST00000578845.2_Frame_Shift_Del_p.V8fs|CDKN2A_ENST00000530628.2_Frame_Shift_Del_p.S73fs|CDKN2A_ENST00000494262.1_Frame_Shift_Del_p.V8fs|CDKN2A_ENST00000498124.1_Frame_Shift_Del_p.V59fs_CDKN2A_ENST00000446177.1_Frame_Shift_Del_p.V59fs|CDKN2A_ENST00000579122.1_Frame_Shift_Del_p.V59fs</td></tr>
<tr><td>BRAF</td><td>c.1821_1822delCC</td><td>c.(1819-1824)tcccatfs</td><td>p.H608fs</td><td></td></tr>
<tr><td>BRAF</td><td>c.1818_1819insAG</td><td>c.(1816-1821)gggtccfs</td><td>p.GS606fs</td><td></td></tr>
<tr><td>BRAF</td><td>c.1799T>A</td><td>c.(1798-1800)gTg>gAg</td><td>p.V600E</td><td></td></tr>
<tr><td>TERT</td><td>c.210T</td><td>c.(19-21)tg>tgT</td><td>p.C7C</td><td>TERT_ENST00000296820.5_Silent_p.C7C|TERT_ENST00000334602.6_Silent_p.C7C_51 TERT_ENST00000508104.2_Silent_p.C7C|TERT_ENST00000522877.1_5'UTR</td></tr>
<tr><td>PTEN</td><td></td><td></td><td></td><td>KLLN_ENST00000445946.3_5'Flank</td></tr>
<tr><td>PTEN</td><td></td><td></td><td></td><td>KLLN_ENST00000445946.3_5'Flank</td></tr>
<tr><td>PTEN</td><td>c.16_21delAAAGAG</td><td>c.(16-21)aaagagdel</td><td>p.KE6del</td><td>KLLN_ENST00000445946.3_5'Flank</td></tr>
<tr><td>APC</td><td>c.4004_4010delGCAGACT</td><td>c.(4003-4011)agcagactgfs</td><td>p.SRL1335fs</td><td>APC_ENST00000508376.2_Frame_Shift_Del_p.SRL1335fs|APC_ENST00000257430.4_Frame_Shift_Del_p.SRL1335fs|CTC-554D6.1_ENST00000520401.1_Intron</td></tr>
<tr><td>APC</td><td>c.4008_4009insC</td><td>c.(4009-4011)ctgfs</td><td>p.L1337fs</td><td>APC_ENST00000508376.2_Frame_Shift_Ins_p.L1337fs|APC_ENST00000257430.4_Frame_Shift_Ins_p.L1337fs|CTC-554D6.1_ENST00000520401.1_Intron</td></tr>
<tr><td>APC</td><td>c.4010_4016delTGCAGGG</td><td>c.(4009-4017)ctgcagggtfs</td><td>p.LQG1337fs</td><td>APC_ENST00000508376.2_Frame_Shift_Del_p.LQG1337fs|APC_ENST00000257430.4_Frame_Shift_Del_p.LQG1337fs|CTC-554D6.1_ENST00000520401.1_Intron</td></tr>
<tr><td>APC</td><td>c.4016_4017insG</td><td>c.(4015-4020)ggttctfs</td><td>p.S1340fs</td><td>APC_ENST00000508376.2_Frame_Shift_Ins_p.S1340fs|APC_ENST00000257430.4_Frame_Shift_Ins_p.S1340fs|CTC-554D6.1_ENST00000520401.1_Intron</td></tr>
<tr><td>PRKD1</td><td>c.1217T>A</td><td>c.(1216-1218)cTc>cAc</td><td>p.L406H</td><td>PRKD1_ENST00000415220.2_Missense_Mutation_p.L414H|PRKD1_ENST00000551644.1_5'Flank</td></tr>
<tr><td>DNAH3</td><td>c.6026G>A</td><td>c.(6025-6027)aGc>aAc</td><td>p.S2009N</td><td>DNAH3_ENST00000415178.1_3'UTR</td></tr>
<tr><td>SLC25A10</td><td>c.561G>T</td><td>c.(559-561)caG>caT</td><td>p.Q187H</td><td>SLC25A10_ENST00000331531.5_Missense_Mutation_p.Q187H|SLC25A10_ENST00000571730.1_Missense_</td></tr>
</table>

TABLE 18-continued

Potentially clonal, somatic single nucleotide variants identified in CBTPA tumor whole genome sequencing data.

| | | | | |
|---|---|---|---|---|
| | | | | Mutation_p.Q342H\|SLC25A10_EN5T00000545862.1_Missense_ Mutation_p.Q144H\|SLC25A10_ ENST00000541223.1_Missense_Mutationp.Q342H |
| DAXX | c.2045C>T | c.(2044-2046)tCc>tTc | p.S682F | .2_Missense_Mutation_p.S607F\|DAXX_ENST00000266000.6_ Missense_Mutation_p.S682F\|ZBTB22_ENST00000418724.1_5'Flank |
| CCDC141 | c.2345A>G | c.(2344-2346)tAc>tGc | p.Y782C | CCDC141_ENST00000295723.5_Missense_Mutation_p.Y207C |
| NPC1L1 | c.1112T>C | c.(1111-1113)gTc>gCc | p.V371A | NPC1L1_ENST00000381160.3_Missense_Mutation_p.V371A\|NPC1L1_ ENST00000546276.1_Missense_Mutation_p.V371A\|NPC1L1_ ENST00000423141.1_Missense_Mutation_p.V371A |
| INADL | c.4415C>A | c.(4414-4416)gCa>gAa | P.A1472E | INADL_ENST00000545929.1_Intron\|INADL_ENST00000543708.1_ Missense_Mutation_p.A286E\|INADL_ENST00000316485.6_ Missense-Mutation-P.A1502E |
| MOV10L1 | c.125G>C | c.(124-126)gGt>gCt | p.G42A | MOV10L1_ENST00000395858.3_Missense_Mutation_p.G42A\|MOV10L1_ ENST00000545383.1_Missense_Mutation_p.G42A\|MOV10L1_ ENST00000540615.1_Missense_Mutation_p.G22A\|MOV10L1_ ENST00000475190.1_3'UTR\|MOV10L1_ENST00000395843.1\|5'UTR |
| EXOC1 | c.2428C>T | c.(2428-2430)Cgt>Tgt | p.R810C | EXOC1_ENST00000349598.6_Missense_Mutation_p.R795C\|EXOC1_ ENST00000346134.7_Missense_Mutation_p.R810C |
| GCDH | c.269A>G | c.(268-270)gAa>gGa | p.E90G | GCDH_ENST00000457854.1_Missense_Mutation_p.E90G\|GCDH_ ENST00000422947.2_Missense_Mutation_p.K28E\|GCDH_ ENST00000591470.1_Missense_Mutation_p.E90G |
| UNG | c.757C>T | c.(757-759)Ctc>Ttc | p.L253F | UNG_ENST00000336865.2_Missense_Mutation_p.L244F |
| C9orf85 | c.123T>C | c.(121-123)caT>caC | p.H41H | C9orf85_ENST00000486911.2_Silent_p.H41H\|C9orf85_ ENST00000334731.2_Silent_p.H41H |
| LRWD1 | c.948C>T | c.(946-948)tgC>tgT | p.C316C | MIR4467_ENST00000578629.1_RNA\|MIR5090_ENST00000582533.1_RNA |
| ERP29 | c.485A>T | c.(484-486)gAc>gTc | p.D162V | ERP29_ENST00000455836.1_3'UTR\|ERP29_ENST00000546477.1_ Missense_Mutation_p.D61V |

| Hugo_Symbol | Refseq_mRNA_Id | Refseq_prot_Id | SwissProt_ acc_Id | SwissProt_entry_Id | Description | UniProt_AApos |
|---|---|---|---|---|---|---|
| CDKN2A | NM_000077.4 | NP_000068.1 | P42771 | CD2A1_HUMAN | cyclin-dependent kinase inhibitor 2A | 86 |
| CDKN2A | NM_000077.4 | NP_000068.1 | P42771 | CD2A1_HUMAN | cyclin-dependent kinase inhibitor 2A | 59 |
| CDKN2A | NM_000077.4 | NP_000068.1 | P42771 | CD2A1_HUMAN | cyclin-dependent kinase inhibitor 2A | 59 |

TABLE 18-continued

Potentially clonal, somatic single nucleotide variants identified in CBTPA tumor whole genome sequencing data.

| | | | | | | |
|---|---|---|---|---|---|---|
| BRAF | NM_004333.4 | NP_004324.2 | P15056 | BRAF_HUMAN | B-Raf proto-oncogene, serine/threonine kinase | 608 |
| BRAF | NM_004333.4 | NP_004324.2 | P15056 | BRAF_HUMAN | B-Raf proto-oncogene, serine/threonine kinase | 606 |
| BRAF | NM_004333.4 | NP_004324.2 | P15056 | BRAF_HUMAN | B-Raf proto-oncogene, serine/threonine kinase | 600 |
| TERT | NM_001193376.1\|NM_198253.2 | NP_001180305.1\|NP_937983.2 | O14746 | TERT_HUMAN | telomerase reverse transcriptase | 7 |
| PTEN | NM_000314.4 | NP_000305.3 | P60484 | PTEN_HUMAN | phosphatase and tensin homolog | |
| PTEN | NM_000314.4 | NP_000305.3 | P60484 | PTEN_HUMAN | phosphatase and tensin homolog | |
| PTEN | NM_000314.4 | NP_000305.3 | P60484 | PTEN_HUMAN | phosphatase and tensin homolog | 6 |
| APC | | | P25054 | APC_HUMAN | adenomatous polyposis coli | 1335 |
| APC | | | P25054 | APC_HUMAN | adenomatous polyposis coli | 1337 |
| APC | | | P25054 | APC_HUMAN | adenomatous polyposis coli | 1337 |
| APC | | | P25054 | APC_HUMAN | adenomatous polyposis coli | 1340 |
| PRKD1 | NM_002742.2 | NP_002733.2 | Q15139 | KPCD1_HUMAN | protein kinase D1 | 406 |
| DNAH3 | NM_017539.1 | NP_060009.1 | Q8TD57 | DYH3_HUMAN | dynein, axonemal, heavy chain 3 | 2009 |
| SLC25A10 | NM_001270953.1\|NM_012140.4 | NP_001257882.1\|NP_036272.2 | Q9UBX3 | DIC_HUMAN | solute carrier family 25 (mitochondrial carrier; dicarboxylate transporter), member 10 | 187 |

TABLE 18-continued

Potentially clonal, somatic single nucleotide variants identified in CBTPA tumor whole genome sequencing data.

| | | | | | | |
|---|---|---|---|---|---|---|
| DAXX | NM_001141969.1\|NM_001141970.1\|NM_001350.4 | NP_001135441.11\|P_001135442.1\|NP_001341.1 | Q9UER7 | DAXX_HUMAN | death-domain associated protein | 682 |
| CCDC141 | NM_173648.3 | NP_775919.3 | Q6ZP82 | CC141_HUMAN | coiled-coil domain containing 141 | 782 |
| NPC1L1 | NM_013389.2 | NP_037521.2 | Q9UHC9 | NPCL1_HUMAN | NPC1-like 1 | 371 |
| INADL | NM_176877.2 | NP_795352 | Q8NI35 | INADL_HUMAN | InaD-like (Drosophila) | 1472 |
| MOV10L1 | NM_018995.2 | NP_061868.1 | Q9BXT6 | M10L1_HUMAN | Mov10 RISC complex RNA helicase like 1 | 42 |
| EXOC1 | NM_001024924.1 | NP_001020095.1 | Q9NV70 | EXOC1_HUMAN | exocyst complex component 1 | 810 |
| GCDH | | | Q92947 | GCDH_HUMAN | glutaryl-CoA dehydrogenase | 90 |
| UNG | NM_080911.2 | NP_550433.1 | | | uracil-DNA glycosylase | |
| C9orf85 | | | Q96MD7 | CI085_HUMAN | chromosome 9 open reading frame 85 | 41 |
| LRWD1 | NM_152892.1 | NP_690852.1 | Q9UFC0 | LRWD1_HUMAN | leucine-rich repeats and WD repeat domain containing 1 | 316 |
| ERP29 | NM_006817.3 | NP_006808.1 | P30040 | ERP29_HUMAN | endoplasmic reticulum protein 29 | 162 |

| Hugo_Symbol | UniProt_Region | UniProt_Site | UniProt_Natural_Variations | UniProt_Experimental_Info | tumor_f |
|---|---|---|---|---|---|
| CDKN2A | | | | | 0.959 |
| CDKN2A | | | V -> G (in CMM2). {ECO:0000269\|PubMed:10874641}. | | 0.532 |
| CDKN2A | | | V -> G (in CMM2). {ECO:0000269\|PubMed:10874641}. | | 0.451 |
| BRAF | Protein kinase. {ECO:0000255\|PROSITE-ProRule:PRU00159}. | | | | 1 |

TABLE 18-continued

Potentially clonal, somatic single nucleotide variants identified in CBTPA tumor whole genome sequencing data.

| | | | |
|---|---|---|---|
| BRAF | Protein kinase. {ECO:0000255\|PROSITE-ProRule:PRU00159}. | | 1 |
| BRAF | Protein kinase. {ECO:0000255\|PROSITE-ProRule:PRU00159}. | V -> D (in a melanoma cell line; requires 2 nucleotide substitutions). {ECO:0000269\|PubMed:12068308}.\|V -> E (in CRC; also found in sarcoma, metastatic melanoma, ovarian serous carcinoma, pilocytic astrocytoma; somatic mutation; most common mutation; constitutive and elevated kinase activity; efficiently induces cell transformation; suppression of mutation in melanoma causes growth arrest and promotes apoptosis; loss of regulation by PMRT5). {ECO:0000269\|PubMed:12068308, ECO:0000269\|PubMed:12198537, ECO:0000269\|PubMed:16959974, ECO:0000269\|PubMed:17344846, ECO:0000269\|PubMed:23263490, ECO:0000269\|PubMed:24455489}. | 0.988 |
| TERT | RNA-interacting domain 1. | | 0.981 |
| PTEN | | | 0.437 |
| PTEN | | | 0.496 |
| PTEN | | | 0.444 |
| APC | Responsible for down-regulation through a process mediated by direct ubiquitination.\|Ser-rich. | | 0.544 |
| APC | Responsible for down-regulation through a process mediated by direct ubiquitination.\|Ser-rich. | | 0.147 |
| APC | Responsible for down-regulation through a process mediated by direct ubiquitination.\|Ser-rich. | | 0.084 |
| APC | Ser-rich. | | 0.152 |
| PRKD1 | | | 0.363 |
| DNAH3 | | | 0.387 |

TABLE 18-continued

| Potentially clonal, somatic single nucleotide variants identified in CBTPA tumor whole genome sequencing data. | | |
|---|---|---|
| SLC25A10 | | 0.398 |
| DAXX | Interaction with SPOP. | 0.421 |
| CCDC141 | | 0.423 |
| NPC1L1 | | 0.449 |
| INADL | PDZ 8. {ECO:0000255\|PROSITE-ProRule:PRU00143}. | 0.45 |
| MOV10L1 | | 0.455 |
| EXOC1 | | 0.46 |
| GCDH | | 0.487 |
| UNG | | 0.522 |
| C9orf85 | Lys-rich. | 0.525 |
| LRWD1 | | 0.535 |
| ERP29 | | 0.572 |

Figure 7:
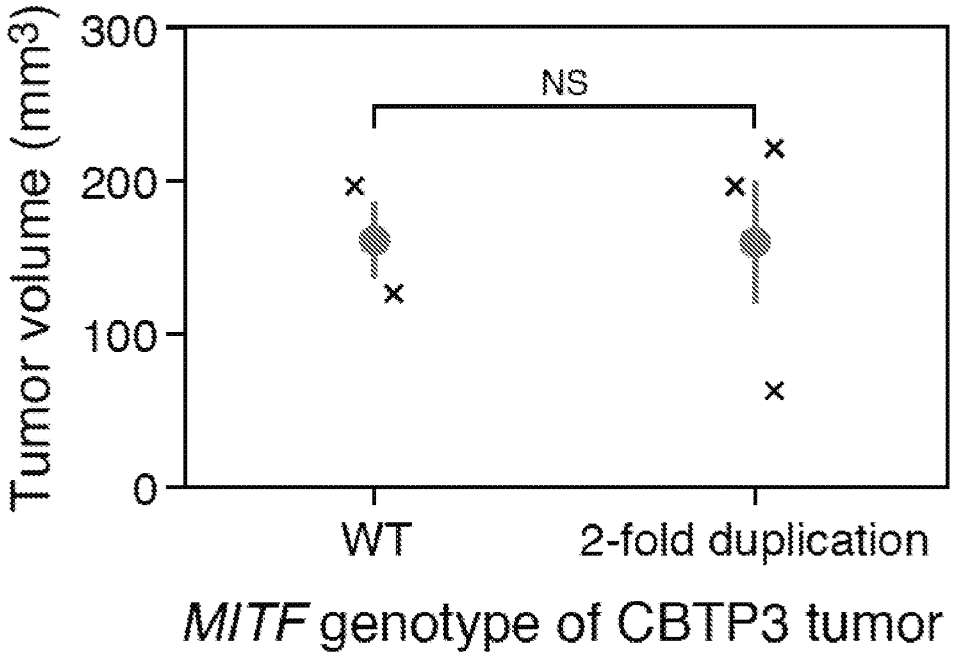
FIG. 7 is a graph showing that MITF duplication does not impact CBTP3 tumor growth. Volumes of CBTP3 primary tumors without (left) or with (right) MITF two-fold duplication at day 67 following intradermal injection into NSG mice. Black crosses: individual tumors; circles: group means error bars: SEM. NS: not significant (two-tailed, two-sample Student's t-test).
Figure 43:
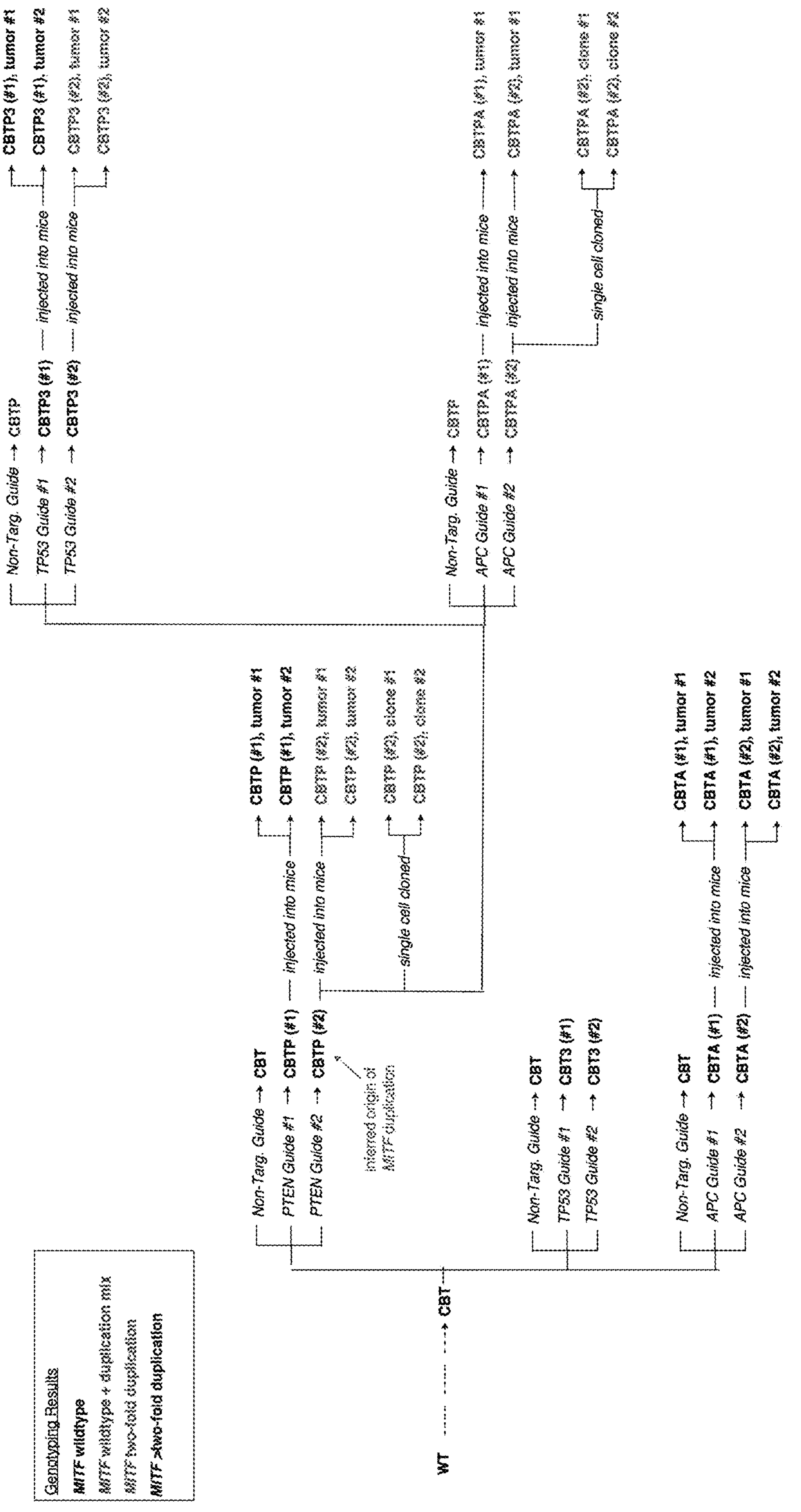
FIG. 43—MITF duplication status across samples. Mutant cell lines, tumors, and single cell clones are displayed in a tree representing their history of derivation. MITF duplication status as determined by targeted amplicon sequencing of heterozygous SNP sites (Table 19, see Materials and Methods) is indicated by color (legend). As CBTP-guide-2 was continuously grown in culture, it was first used as a parental line to generate CBTP3 cells, and later on as a parental line to generate CBTPA cells.

The spontaneous two-fold, tandem duplication of MITF—a gene amplified in 5-10% of melanomas (Hodis et al. *Cell* 150:251-263 (2012); Akbani et al. *Cell* 161:1681-1696 (2015); Garraway et al. *Nature* 436:117-122 (2005))—underscored the loyalty of Applicants' human model but had no major phenotypic consequence. Applicants screened for the duplication across the samples and determined that it arose spontaneously only in CBTP cells created using PTEN guide 2 (FIG. 43, Table 19) (Rimm et al. *Am J Pathol* 154:325-329 (1999)). In the CBTPA setting, the MITF duplication became clonal in CBTP-guide-2 cells in vitro prior to APC knockout, such that all CBTPA tumors and their matched CBTP controls exhibited the MITF two-fold duplication (FIG. 43, Table 19). However, in two other settings—CBTP and CBTP3—there were tumors where MITF was either wildtype or duplicated, and Applicants used those to compare its phenotypic impact on tumors. First, in CBTP, upon injection of CBTP-guide-2 cells into mice, the MITF duplication rose in frequency from a sub-clonal to a clonal lesion in all tested CBTP-guide-2 tumors (FIG. 43, Table 19). When Applicants compared the tumor growth rate of CBTP-guide-1 (wildtype MITF) and CBTP-guide-2 (duplicated MITF) tumors, they found no significant differences in vivo (FIG. 21G). Second, in CBTP3, we leveraged the fact that the MITF duplication was likely subclonal in CBTP-guide-2 cells in vitro when they served as parental cells for TP53 knock out (FIG. 43, Table 19) and became clonal in some CBTP3 tumors but not others. Comparing CBTP3 tumors that were wildtype to those that had the MITF duplication again ruled out an obvious effect on tumor size (FIG. 7). While the recurrence of MITF amplification in 5-10% of human melanomas suggests a consequential role for this event in melanoma pathogenesis (Akbani et al. *Cell* 161:1681-1696 (2015); Yeh et al. *Nat Commun* 8:644 (2017)), Applicants' findings imply that, in certain genetic backgrounds, low-level MITF amplification leads to increased cellular fitness (as reflected by clonal selection), but not grossly apparent phenotypic changes. These results, in concert with the rest of the whole genome sequencing results of the CBTPA tumor, suggest that genome edited mutations in CDKN2A, BRAF, TER T, PTEN, and APC were sufficient to produce the phenotypes observed in CBTPA melanocytes.

TABLE 19

MITF and TERT genotyping in a diverse sample of mutant cell lines, tumors, and single cell clones.

| Sample ID | Genotype | Guide (for most recently edited gene) | Sample Type | TERT -124C > T Zygosity "Call" | MITF Status "Call" | TERT -124C > T Mutant Allele % |
|---|---|---|---|---|---|---|
| parental, wildtype melanocytes | wildtype | none | parental cells | wildtype, homozygous | wildtype | 0.0 |
| CBT (ctrl for CBTP), pre-xenograft | CBT | non-targeting (control for PTEN) | pre-xenograft | ~hemizygous | wildtype | 49.3 |
| CBTP #1, pre-xenograft | CBTP | #1 (PTEN) | pre-xenograft | hemi/homo mix | wildtype | 67.6 |
| CBTP #2, pre-xenograft | CBTP | #2 (PTEN) | pre-xenograft | hemi/homo mix | wildtype | 59.8 |
| CBTP #1, tumor #1 | CBTP | #2 (PTEN) | tumor | hemi/homo mix | wildtype | 72.1 |
| CBTP #1, tumor #2 | CBTP | #1 (PTEN) | tumor | hemi/homo mix | wildtype | 77.3 |
| CBTP #2, tumor #1 | CBTP | #2 (PTEN) | tumor | ~homozygous | two fold duplication | 97.66856 |
| CBTP #2, tumor #2 | CBTP | #2 (PTEN) | tumor | ~homozygous | two-fold duplication | 97.69231 |
| CBTP #2, tumor #3 | CBTP | #2 (PTEN) | tumor | ~homozygous | two-fold duplication | 98.52565 |
| CBTP #2, single cell clone #1 | CBTP | #2 (PTEN) | single cell clone | ~homozygous | two-fofd duplication | 97.35642 |
| CBTP #2, single cell clone #2 | CBTP | #2 (PTEN) | single cell clone | ~homozygous | two-fold duplication | 97.19439 |
| CBT (ctrl for CBT3), pre-xenograft | CBT | non-targeting (control for TP53) | pre-xenograft | hemi/homo mix | wildtype | 63.0 |
| CBT3 #1, pre-xenograft | CBT3 | #1 (TP53) | pre-xenograft | hemi/homo mix | wildtype | 56.8 |
| CBT3 #2, pre-xenograft | CBT3 | #2 (TP53) | pre-xenograft | hemi/homo mix | wildtype | 58.7 |
| CBT (ctrl for CBTA), pre-xenograft | CBT | non-targeting (control for APC) | pre-xenograft | hemi/homo mix | wildtype | 73.1 |
| CBTA #1, pre-xenograft | CBTA | #1 (APC) | pre-xenograft | hemi/homo mix | wildtype | 81.0 |
| CBTA #2, pre-xenograft | CBTA | #2 (APC) | pre-xenograft | hemi/homo mix | wildtype | 88.9 |
| CBTA #1, tumor #1 | CBTA | #1 (APC) | tumor | hemi/homo mix | wildtype | 60.1 |
| CBTA #1, tumor #2 | CBTA | #1 (APC) | tumor | hemi/homo mix | wildtype | 55.9 |
| CBTA #1, tumor #3 | CBTA | #1 (APC) | tumor | ~homozygous | wildtype | 98.2 |
| CBTA #2, tumor #1 | CBTA | #2 (APC) | tumor | hemi/homo mix | wildtype | 84.4 |
| CBTA #2, tumor #2 | CBTA | #2 (APC) | tumor | hemi/homo mix | wildtype | 93.5 |
| CBTA #2, tumor #3 | CBTA | #2 (APC) | tumor | ~homozygous | wildtype | 99.1 |
| CBTP (ctrl for CBTP3), pre-xenograft | CBTP | non-targeting (control for TP53) | pro-xenograft | hemi/homo mix | wt + two-fold mixture? | 80.9 |
| CBTP3 #1, pre-xenograft | CBTP3 | #1 (TP53) | pre-xenograft | hemi/homo mix | wildtype | 65.1 |
| CBTP3 #2, pre-xenograft | CBTP3 | #2 (TP53) | pre-xenograft | hemi/homo mix | wildtype | 66.6 |
| CBTP3 #1, tumor #1 | CBTP3 | #1 (TP53) | tumor | ~hemizygous | wildtype | 53.7 |
| CBTP3 #1, tumor #2 | CBTP3 | #1 (TP53) | tumor | ~homozygous | >two-fold duplication | 97.4 |
| CBTP3 #1, tumor #3 | CBTP3 | #1 (TP53) | tumor | ~hemizygous | wildtype | 43.5 |
| CBTP3 #2, tumor #1 | CBTP3 | #2 (TP53) | tumor | hemi/homo mix | two fold duplication | 77.0 |
| CBTP3 #2, tumor #2 | CBTPS | #2 (TP53) | tumor | hemi/homo mix | two fold duplication | 92.7 |
| CBTP3 #2, tumor #3 | CBTP3 | #2 (TF53) | tumor | hemi/homo mix | two-fold duplication | 89.0 |
| CBTP (ctrl for CBTPA), pre-xenograft | CBTP | non-targeting (control for APC) | pre-xenograft | ~homozygous | two-fold duplication | 98.0 |
| CBTPA #1, pre-xenograft | CBTPA | #1 (APC) | pre-xenograft | ~homozygous | two fold duplication | 98.5 |
| CBTPA #2, pre-xenograft | CBTPA | #2 (APC) | pre-xenograft | ~homozygous | two-fold duplication | 97.7 |

TABLE 19-continued

MITF and TERT genotyping in a diverse sample of mutant cell lines, tumors, and single cell clones.

| | | | | | | |
|---|---|---|---|---|---|---|
| CBTPA #1, tumor #1 | CBTPA | #1 (APC) | tumor | ~homozygous | two-fold duplication | 98.0 |
| CBTPA #1, tumor #2 | CBTPA | #1 (APC) | tumor | ~homozygous | | 98.2 |
| CBTPA #1, tumor #3 | CBTPA | #1 (APC) | tumor | ~homozygous | | 98.2 |
| CBTPA #2, tumor #1 | CBTPA | #2 (APC) | tumor | ~homozygous | two-fold duplication | 98.0 |
| CBTPA #2, tumor #2 | CBTPA | #2 (APC) | tumor | ~homozygous | | 98.3 |
| CBTPA #2, tumor #3 | CBTPA | #2 (APC) | tumor | ~homozygous | | 98.2 |
| CBTPA #2, single cell clone #1 | CBTPA | #2 (APC) | single cell clone | homozygous | two-fold duplication | 98.5 |
| CBTPA #2, single cell clone #2 | CBTPA | #2 (APC) | single cell clone | homozygous | two-fold duplication | 98.7 |

| Sample ID | MITF SNP8 T | MITF SNP8 C | MITF SNP12 T | MITF SNP12 C | MITF SNP8 Ratio (in Sample/in WT cells) | MITF SNP12 Ratio (in Sample/in WT cells) |
|---|---|---|---|---|---|---|
| parental, wildtype melanocytes | 47.75 | 51.96 | 42.12 | 56.59 | 1.00 | 1.00 |
| CBT (ctrl for CBTP), pre-xenograft | 50.50 | 49.14 | 41.89 | 58.48 | 1.12 | 1.04 |
| CBTP #1, pre-xenograft | 56.96 | 42.73 | 34.46 | 65.93 | 1.45 | 1.42 |
| CBTP #2, pre-xenograft | 59.10 | 40.55 | 33.88 | 66.58 | 1.59 | 1.46 |
| CBTP #1, tumor #1 | 48.67 | 51.63 | 40.44 | 59.38 | 1.03 | 1.09 |
| CBTP #1, tumor #2 | 48.67 | 44.40 | 34.68 | 65.04 | 1.19 | 1.40 |
| CBTP #2, tumor #1 | 71.21 | 29.00 | 21.65 | 77.98 | 2.67 | 2.68 |
| CBTP #2, tumor #2 | 69.17 | 30.99 | 21.60 | 78.11 | 2.49 | 2.69 |
| CBTP #2, tumor #3 | 71.69 | 28.01 | 20.62 | 79.49 | 2.79 | 2.87 |
| CBTP #2, single cell clone #1 | 71.53 | 28.49 | 21.78 | 66.89 | 2.73 | 2.29 |
| CBTP #2, single cell clone #2 | 72.10 | 27.77 | 21.50 | 66.90 | 2.83 | 2.32 |
| CBT (ctrl for CBT3), pre-xenograft | 46.61 | 53.08 | 41.06 | 58.75 | 0.96 | 1.07 |
| CBT3 #1, pre-xenograft | 46.95 | 52.74 | 41.81 | 57.95 | 0.97 | 1.03 |
| CBT3 #2, pre-xenograft | 53.90 | 45.77 | 40.96 | 58.73 | 1.28 | 1.07 |
| CBT (ctrl for CBTA), pre-xenograft | 54.99 | 44.69 | 39.29 | 60.14 | 1.34 | 1.14 |
| CBTA #1, pre-xenograft | 48.69 | 50.95 | 43.28 | 56.29 | 1.04 | 0.97 |
| CBTA #2, pre-xenograft | 48.51 | 51.11 | 43.18 | 56.42 | 1.03 | 0.97 |
| CBTA #1, tumor #1 | 45.31 | 54.40 | 41.37 | 58.97 | 0.91 | 1.06 |
| CBTA #1, tumor #2 | 51.25 | 48.36 | 47.09 | 53.15 | 1.15 | 0.84 |
| CBTA #1, tumor #3 | 50.25 | 49.42 | 43.84 | 55.71 | 1.11 | 0.95 |
| CBTA #2, tumor #1 | 47.36 | 52.35 | 41.11 | 59.45 | 0.98 | 1.08 |
| CBTA #2. tumor #2 | 48.83 | 50.74 | 45.06 | 55.50 | 1.05 | 0.92 |
| CBTA #2, tumor #3 | 47.35 | 52.38 | NA | NA | 0.98 | NA |
| CBTP (ctrl for CBTP3), pre-xenograft | 63.55 | 36.10 | 28.36 | 71.08 | 1.92 | 1.87 |
| CBTP3 #1, pre-xenograft | 53.70 | 45.96 | 37.44 | 62.02 | 1.27 | 1.23 |
| CBTP3 #2, pre-xenograft | 46.93 | 52.67 | 40.06 | 59.40 | 0.97 | 1.10 |
| CBTP3 #1, tumor #1 | 51.63 | 48.03 | 47.51 | 51.88 | 1.17 | 0.81 |
| CBTP3 #1, tumor #2 | 93.22 | 6.47 | 4.43 | 94.96 | 15.67 | 15.96 |
| CBTP3 #1, tumor #3 | 42.79 | 57.06 | 49.03 | 51.41 | 0.82 | 0.78 |
| CBTP3 #2, tumor #1 | 78.65 | 20.96 | 15.14 | 84.16 | 4.08 | 4.14 |
| CBTP3 #2, tumor #2 | 72.29 | 27.40 | 21.40 | 77.98 | 2.87 | 2.71 |
| CBTP3 #3, tumor #3 | 67.33 | 32.47 | 25.81 | 74.45 | 2.26 | 2.15 |
| CBTP (ctrl for CBTPA), pre-xenograft | 73.49 | 26.18 | 18.26 | 80.18 | 3.05 | 3.27 |
| CBTPA #1, pre-xenograft | 73.61 | 26.08 | 18.15 | 80.21 | 3.07 | 3.29 |
| CBTPA #2, pre-xenograft | 77.06 | 22.59 | 17.07 | 81.39 | 3.71 | 3.55 |
| CBTPA #1, tumor #1 | 71.95 | 27.69 | 19.75 | 78.66 | 2.83 | 2.96 |
| CBTPA #1, tumor #2 | NA | NA | NA | NA | NA | NA |
| CBTPA #1, tumor #3 | NA | NA | NA | NA | NA | NA |
| CBTPA #2, tumor #1 | 72.82 | 26.87 | 18.56 | 79.94 | 2.95 | 3.21 |
| CBTPA #2, tumor #2 | NA | NA | NA | NA | NA | NA |
| CBTPA #2, tumor #3 | NA | NA | NA | NA | NA | NA |
| CBTPA #2, single cell clone #1 | 72.41 | 27.50 | 20.48 | 67.78 | 2.87 | 2.46 |
| CBTPA #2, single cell clone #2 | 70.91 | 29.10 | 20.10 | 68.38 | 2.65 | 2.33 |

Figure 19C:
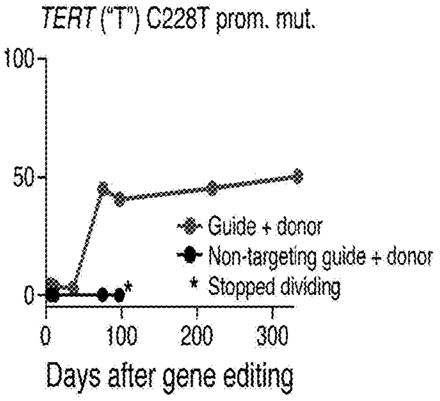
Figure 19D:
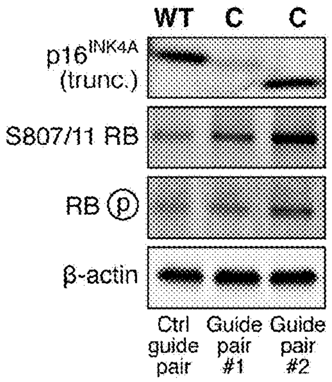
Figure 19E:
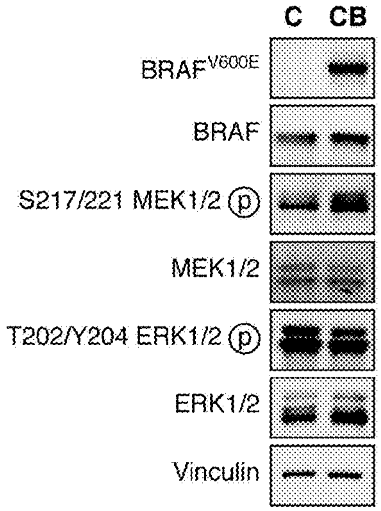
Figure 19F:
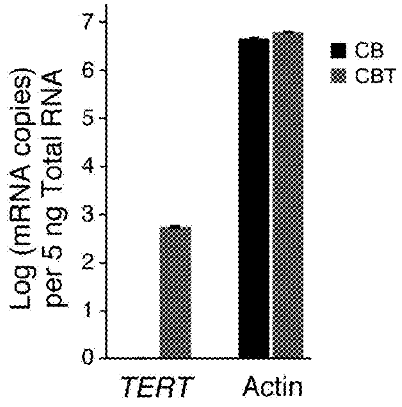
Figure 19G:
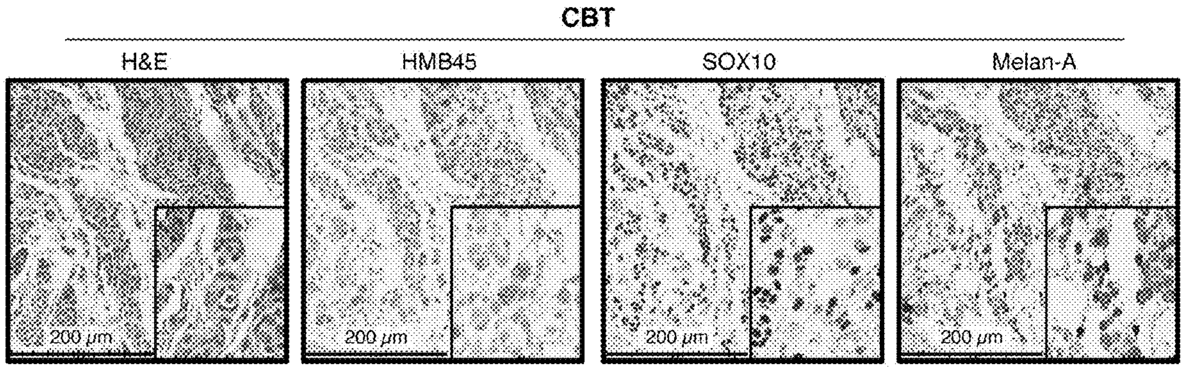

Genome sequencing of a CBTPA tumor also revealed homozygosity of the TERT −124C>T promoter allele (FIG. 40), in contrast to the ~50% TERT −124C>T frequency previously observed at the time of initial TERT editing (FIG. 19C). Sequencing the TERT promoter across the samples showed that all CBTPA tumors (and their matched CBTP non-targeting control cells) were homozygous for the TERT promoter mutation, while other samples (e.g., CBTP and CBTP3 tumors) showed varying degrees of hemi/homozygosity (Table 19). Cells with MITF duplication were more likely to be homozygous in the mutant TERT promoter allele, suggesting that the duplication may have arisen in a homozygous TERT −124C>T cell before undergoing positive, clonal selection (Table 19). A selective advantage for homozygosity of the mutant TERT promoter allele would have led to homozygosity in most of the samples, given the existence of homozygous cells in the initial CBT cell population (Table 10); however, Applicants did not observe that (Table 19). These results confirm that the CBTPA phenotypes observed in vivo were the product of homozygous mutant genotypes in all edited genes, including TERT, and furthermore suggest that a homozygous mutant TERT promoter allele may not produce a strong fitness advantage compared to a hemizygous locus.

Figure 18A:
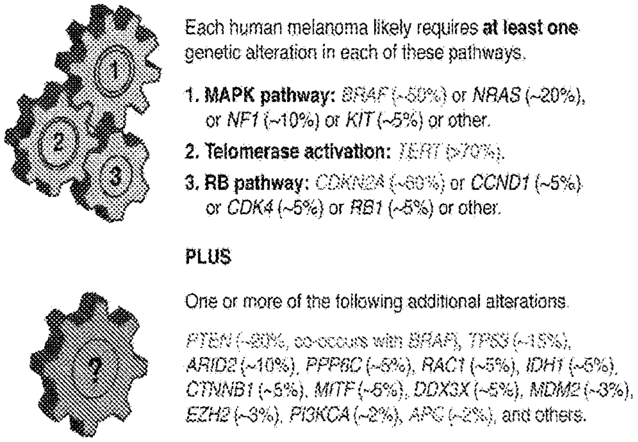
FIG. 18A-18C—illustrate the strategy for introducing melanoma mutations into human melanocytes.
Figure 18B:
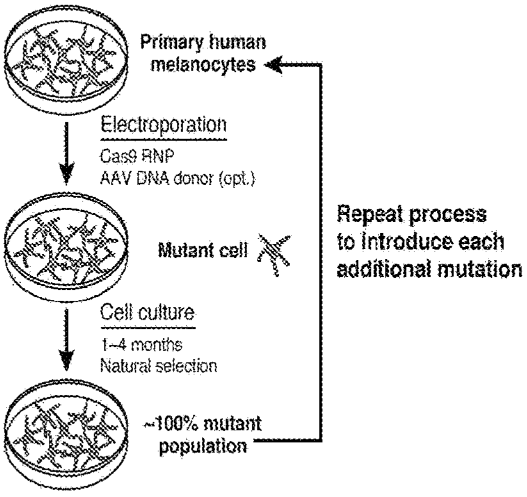
Figure 18C:
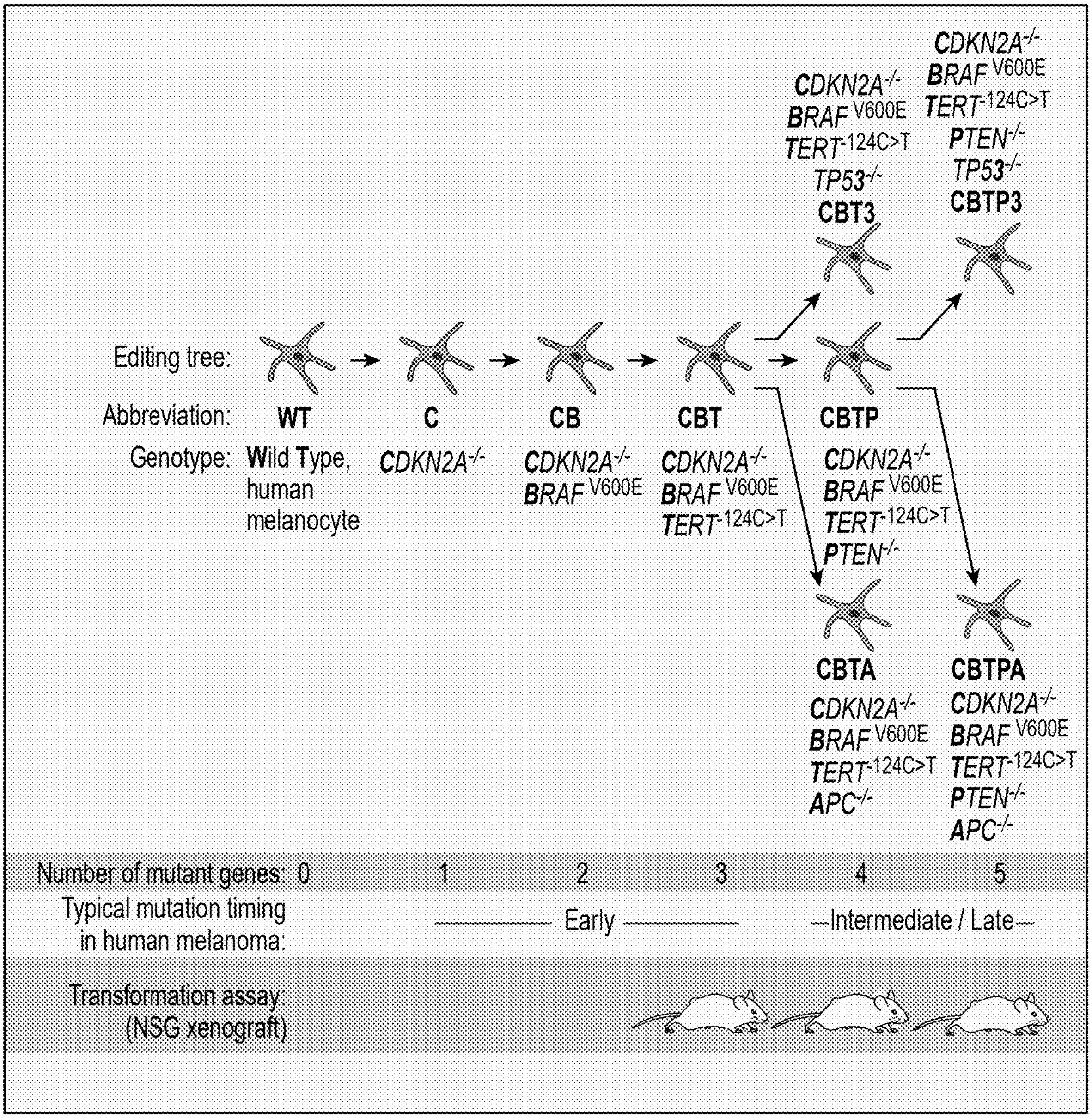

In conclusion, Applicants have shown that immortalization and malignant transformation of differentiated primary human melanocytes can be caused by precise mutations in the endogenous loci of CDKN2A, BRAF, and TERT, which satisfies the putative genetic requirements for melanoma formation—activation of the RB pathway, the MAPK pathway, and telomerase activity (FIG. 18A). Slow growth of a large primary tumor can then be triggered by further mutation of either PTEN or APC as the fourth mutation (FIG. 28N). APC knockout causes both distant metastases and dark pigmentation (FIG. 28N), and its further combination with PTEN knockout as the fourth and fifth mutations produces aggressive disease with rapid tumor growth, distant metastases, and rapid-onset weight loss (FIG. 28N).

Pathogenesis of certain aggressive human melanomas may thus depend on as few as five altered pathways: RB (CDKN2A), MAPK (BRAF), telomerase (TERT), PI3K/AKT (PTEN), and Wnt (APC), despite the highly deranged nature of most human melanoma genomes. Estimation of how many human melanomas demonstrate dysregulation of at least these five pathways is a challenge given current data. Nevertheless, it is reasonable to assume that nearly all melanomas might in some form or another dysregulate the RB, MAPK and telomerase pathways, that roughly 40% of melanomas have activated the PI3K/AKT pathway (20% through PTEN loss and 20% through activating mutations in NRAS) and that roughly 30% have Wnt activation (determined by nuclear localization of β-catenin). Under these assumptions, at least 12% of human melanomas might fall in this category (Akbani et al. *Cell* 161:1681-1696 (2015); Dankort et al. *Nat Genet* 41:544-552 (2009)).

More generally, this work establishes a model where a minimal set of mutations is known to cause an aggressive melanoma phenotype, and, therefore, permits a search for additional such sets of mutations. For example, could NRAS substitute for both BRAF and PTEN in this model? Could a non-Wnt pathway gene be found to substitute for APC? Does it matter if the order in which the mutations are introduced is changed? Applicants' genome engineered human models of melanoma also establish a cellular resource that can be leveraged in many directions, including for comparative molecular studies, genetic vulnerability screening, pooled in vitro or in vivo screens for additional combinations of cancer associated mutations, investigation of the influence of the tumor cells' genotype on its microenvironment, investigating downstream molecular mechanisms, and searching for mutation-specific interactions with the immune system in humanized mice (Rongvaux et al. *Nat Biotechnol* 32:364-372 (2014)).

Genome editing enables efforts to engineer a cancer from healthy cells. Applicants' work demonstrates that it is possible to do so starting from differentiated, primary human cells. Such genome edited human models advance knowledge of the genetic basis of human malignancy by ascribing causation of malignant phenotypes to defined sets of genetic alterations and allowing for their further study in isogenic human models of disease.

Example 5—Materials and Methods

Cell Culture. Primary human epidermal melanocytes derived from the foreskin of a neonatal, lightly pigmented donor were purchased from Thermo Fisher Scientific (Cat. C0025C, donor 1583283) and maintained in M254 media (Thermo Fisher, Cat. 5254500) supplemented with human melanocyte growth supplement (Thermo Fisher, Cat. S0025). Cells were cultured at 37° C., 5% $CO_2$, and 5% $O_2$.

Genome Editing. Cas9 protein, tracrRNA, and crRNAs ('guides', Table 20) were purchased and prepared according to manufacturer's instructions (IDT). To generate RNP complexes, 3-6 g Cas9 and 45 pmol previously annealed crRNA:trRNA were incubated together for 10 minutes at 25° C. before delivery by electroporation. To target CDKN2A, two crRNAs were mixed at a molar ratio of 1:1 (22.5 pmol crRNA 1: 22.5 pmol crRNA 2) and incubated with 3 g Cas9.

Electroporation was performed using the Lonza Nucleofector 4D System (program: EO-208) and P3 Primary Cell Nucleofector Kit (Lonza), according to manufacturer's instructions, with optional inclusion of 100 pmol electroporation enhancer (IDT 1075916). After electroporation, cells were incubated with 80 μL of warm media for 10 minutes at 37° C. to enhance recovery and were directly transferred into a tissue culture plate.

For precise editing using a DNA donor template of either the BRAF or the TERT locus, cells were transduced with rAAV (MOI=~100-10000) immediately upon plating to deliver the homologous DNA donor template. Cells were incubated at 30° C. for 48 hours to improve genome editing efficiency.

TABLE 20

Sequences of Cas9 guides used for genome editing.

| Name | Sequence (5' -> 3') | SEQ ID NO |
|---|---|---|
| CDKN2A Guide pair 1 | Guide 1: CAGCAGCAGCTCCGCCACTC<br>Guide 2: GACCCGTGCACGACGCTGCC | 124<br>125 |
| CDKN2A Guide pair 2 | Guide 1: GATGATGGGCAGCGCCCGAG<br>Guide 2: TCGGGTGAGAGTGGCGGGGT | 126<br>127 |
| BRAF Guide | AGACAACTGTTCAAACTGAT | 128 |
| TERT Guide | GCAGCAGGGAGCGCACGGCT | 129 |
| PTEN Guide 1 | TTGATGATGGCTGTCATGTC | 130 |
| PTEN Guide 2 | TGATGATGGCTGTCATGTCT | 131 |
| TP53 Guide 1 | TCCTCAGCATCTTATCCGAG | 132 |
| TP53 Guide 2 | TCCACTCGGATAAGATGCTG | 133 |
| APC Guide 1 | AACCAAATCCAGCAGACTGC | 134 |
| APC Guide 2 | GTTTATCTTCAGAATCAGCC | 135 |
| Non-targeting Guide 1 | ACGGAGGCTAAGCGTCGCAA | 136 |
| Non-targeting Guide 2 | CGCTTCCGCGGCCCGTTCAA | 137 |
| Non-targeting Guide 3 | ATCGTTTCCGCTTAACGGCG | 138 |
| Non-targeting Guide 4 | GTAGGCGCGCCGCTCTCTAC | 139 |

Generation of rAAV for DNA donor delivery. A 1.8 kb DNA donor template homologous to the BRAF exon 15 locus was designed, centered on amino acid 600, with left and right homology arms of ~900 bp each. This template harbored the V600E (T>A) mutation and a S607S (TCC>AGT) silent mutation to prevent targeting by Cas9.

A 1.8 kb DNA donor template homologous to the TERT promoter and exon 1 locus was designed, roughly centered on the TERT transcription start site, with left and right homology arms of ~900 bp each. Three variants of this DNA donor were designed, all harboring a C7C (C>T) silent mutation in exon 1 to prevent targeting by Cas9: (1) harboring the −124C>T TERT promoter mutation, (2) harboring the −146C>T TERT promoter mutation, and (3) wildtype in the TERT promoter sequence.

All DNA donor templates were synthesized (GeneWiz) and cloned into a standard rAAV transfer plasmid backbone (kind gift of R. Platt from F. Zhang lab at Broad), between the inverted terminal repeats (ITRs), using standard molecular cloning techniques. rAAV2/6.2 was produced, purified, and titered either through prior methods (Ran et al. *Nature* 520:186-191 (2015)) or by the Massachusetts Eye and Ear Institute Viral Vector Core.

Targeted Amplicon Sequencing. DNA was extracted using QuickExtract DNA Extraction Solution following recommended guidelines (Epicentre). Target genomic loci were amplified using gene-specific primers (Table 21) that included universal handles for later attachment of barcoded Illumina adaptors using an additional round of PCR. An additional first round of PCR using primers outside the DNA donor (Table 22) was included when necessary to discriminate between genomic DNA and transduced homologous DNA donor templates. All PCR products were run on an agarose gel, extracted using the MinElute Gel Extraction Kit (Qiagen), quantified by Qubit (Thermo Fisher), and pooled for sequencing on the Illumina MiSeq System. Sequencing data was demultiplexed by barcode, aligned to the expected amplicon sequence using the Needleman-Wunsch algorithm (needle, EBI), and reads were individually assessed for harboring either indels, precise desired mutations (if relevant), or wildtype sequence.

TABLE 21

Primer sequences used for targeted amplicon PCR.

| Name | Forward (5' -> 3') | SEQ ID NO | Reverse (5' -> 3') | SEQ ID NO |
|---|---|---|---|---|
| CDKN2A | GCGGGCATGGTTA CTGCCTCTG | 140 | CTTGTGTGGGGGTCTG CTTGGC | 148 |
| BRAF | TCATAATGCTTGCT CTGATAGGA | 141 | GGCCAAAAATTTAATC AGTGGA | 149 |
| TERT | ACGAACGTGGCCA GCGGCAG | 142 | GTCCTGCCCCTTCACCT TC | 150 |
| PTEN | ATTTCCATCCTGCA GAAGAAGC | 143 | CATCCGTCTACTCCCA CGTTCT | 151 |
| TP53 | CCTCCCAGAGACC CCAGTTGCA | 144 | CTGGAGAGACGACAG GGCTGGT | 152 |
| APC | AGAGGCAGAATCA GCTCCATCC | 145 | TGGACTTTTGGGTGTC TGAGCA | 153 |
| MITF SNP8 | GGAGTGTAGATAG ATGAAATCA | 146 | AATCTTACACAGTGTG TTTAGG | 154 |
| MITF SNP12 | AAGATTAAGTGTT GTGACTAGG | 147 | AGTATGTCTTCTTCTA ATGGTG | 155 |

TABLE 22

Primer sequences for BRAF and TERT that bind outside of homologous DNA donor template region.

| Name | Forward (5' -> 3') | Reverse (5' -> 3') |
|---|---|---|
| BRAF | TGAGTGGCCTGTGATTCT CCTCA (SEQ ID NO: 156) | AGTCTTTACACCCCCAAGTATG TTCTGT (SEQ ID NO: 157) |
| TERT | GGTCTGGCAGGTGACACC ACAC (SEQ ID NO: 158) | AAGTCGGGCCTCCTAGCTCTGC (SEQ ID NO: 159) |

RT-qPCR. Total RNA extraction from cultured cells and reverse transcription were performed using the RNeasy Plus Mini Kit (Qiagen) and SuperScript VILO Master Mix Kit (Thermo Fisher) according to manufacturer's instructions. TAQMAN® qPCR probes were purchased from Thermo Fisher to assess expression levels of TERT (HS00972650_m1), AXIN2 (HS00610344_m1), GAPDH (HS99999905_m1), and ACTB (HS03023943_g1).

Relative expression changes for AXIN2 were determined using the ΔΔCt method. Absolute quantification of TERT and ACTB mRNA transcripts was performed by comparison to standard curves generated using pLX304-hTERT and pDONR223-ACTB plasmids. Each experimental sample and standard was run in triplicate using the TAQMAN® Fast Advanced Mastermix (Thermo Fisher) on the QuantStudio 6 Flex Real-Time PCR System (Thermo Fisher) following manufacturer's guidelines.

Immunoblotting. Protein extraction and immunoblotting were performed as described previously (Wheeler et al. *Science* 350:211-217 (2015)). To test for differences in RB pathway regulation between CDKN2A wildtype and knockout cells, cells for the immunoblot in FIG. 19D were cultured in reduced (50%) growth factor conditions for 24 hrs. Cells were lysed using RIPA Lysis and Extraction Buffer supplemented with Halt Protease and Phosphatase Inhibitor Cocktail (Thermo Fisher). The antibodies used for protein analysis are listed in Table 23.

TABLE 23

Antibodies and dilutions used for immunohistochemistry (IHC).

| Target | Vendor; Catalog Number | Dilution |
|---|---|---|
| p16INK4A | R&D Systems; AF5779-SP | 1:250 |
| RB | Cell Signaling Technology; 9309 | 1:1000 |
| B-Actin | Cell Signaling Technology; 3700 | 1:5000 |
| Phosphor-RB | Cell Signaling Technology; 9301 | 1:1000 |
| Vinculin | Sigma-Aldrich; S-V9131 | 1:10000 |
| BRAF | Cell Signaling Technology; 14814 | 1:1000 |
| BRAFv600e | Spring Bioscience; E19290 | 1:1000 |
| MEK1/2 | Cell Signaling Technology; 8727 | 1:1000 |
| Phosphor-MEK1/2 | Cell Signaling Technology; 3958 | 1:1000 |
| p21 | Cell Signaling Technology; 2947 | 1:1000 |
| ERK1/2 | Cell Signaling Technology; 9107 | 1:1000 |
| Phosphor-ERK1/2 | Cell Signaling Technology; 4094 | 1:1000 |
| PTEN | Cell Signaling Technology; 9552 | 1:1000 |
| Phosphor-AKT S473 | Cell Signaling Technology; 4060 | 1:1000 |
| Phosphor-AKT T308 | Cell Signaling Technology; 2965 | 1:1000 |
| AKT | Cell Signaling Technology; 2920 | 1:1000 |
| P53 | Santa Cruz Biotechnology; sc-126 | 1:1000 |
| IRDye 680RD Goat anti-Mouse IgG | LI-COR; 926-68070 | 1:10000 |
| IRDye 680RD Goat anti-Rabbit IgG | LI-COR; 926-68071 | 1:10000 |
| IRDye 800CW Goat anti-Mouse IgG | LI-COR; 926-32210 | 1:10000 |
| IRDye 800CW Goat anti-Rabbit IgG | LI-COR; 926-32211 | 1:10000 |
| IRDye 800CW Donkey anti-Goat IgG | LI-COR; 925-32214 | 1:10000 |

Mouse Xenograft Studies. All mouse procedures were performed under the guidelines and approval of the Massachusetts Institute of Technology Committee for Animal Care (MIT CAC) under protocol 0036-01-15. Four to six week old female NOD.Cg-Prkdcscid Il2rgtm1Wjl/SzJ (NSG) mice were purchased from the Jackson Laboratory and housed under specific-pathogen free conditions at the Broad Institute's Vivarium. Each mouse received two intradermal injections ($1\times10^6$ cells resuspended in 50 µL of media per injection), one in each flank. All control and experimental groups were performed in replicates of n=4-8 mice. Body weight and tumor size were assessed twice per week. Tumor volumes were calculated using the ellipsoid volume formula ($(\text{Width}^2\times\text{Length})/2$).

Histopathology and Immunohistochemistry (IHC). After euthanizing the mice, solid tumors and visceral organs were collected and fixed with 10% formalin (Patterson Veterinary) for 24 hours. Samples were subsequently transferred into 70% ethanol and submitted to the Histology Core at the Koch Institute for paraffin embedding, H&E staining, and IHC using protein antibodies listed in Table 24, followed by dermatopathological review. Metastatic lesions in lung and liver sections were counted manually. Lesions of all sizes, including single cell metastases, were identified based on immunohistochemical staining patterns for melanoma protein markers HMB45, SOX10, and Melan-A and included in the metastasis count in order to avoid arbitrarily picking a threshold for qualifying lesion size.

TABLE 24

Reagents and dilutions used for immunohistochemistry (IHC).

| Target | Vendor; Catalog Number | Dilution |
|---|---|---|
| Ki-67 | BD Pharmingen; 550609 | 1:40 |
| HMB45 | Ventana; 790-4366 | 1:1 or 1:5 |
| SOX10 | Biocare Medical; AVI 3099 G | 1:1 or 1:5 |
| Melan-A | Agilent Dako; IR63361-2 | 1:1 or 1:3 |
| Mouse-on-Mouse AP-Polymer | Biocare Medical; MM624H | 1:1 |
| Mouse-on-Mouse HRP-Polymer | Biocare Medical; MM620H | 1:1 |

Whole Genome Sequencing. DNA was extracted using the QIAamp DNA Mini Kit (Qiagen) according to manufacturer's protocol. Tumors harvested from xenograft experiments were homogenized using a Precellys 24 machine (Bertin Corporation) prior to DNA extraction. Purified DNA was submitted to the Broad Institute Genomics Platform for PCR-free sequencing at 30-60× coverage.

An aliquot of genomic DNA was taken from a stock sample at a target of 350 ng in 50 µL of solution to serve as the input into shearing. Samples underwent fragmentation by acoustic shearing using the Covaris focused-ultrasonicator, targeting 385 bp fragments. Following fragmentation, additional size selection was performed using a SPRI cleanup. Library preparation was performed using the KAPA Hyper Prep without amplification module kit (KAPA Biosystems, product KK8505), and with palindromic forked adapters with unique 8 base index sequences embedded within the adapter (purchased from IDT). Following sample preparation, libraries were quantified using quantitative PCR with a KAPA Biosystems kit, with probes specific to the ends of the adapters. This assay was automated using Agilent's Bravo liquid handling platform. Based on qPCR quantification, libraries were normalized to 1.7 nM. Samples are then pooled into 24-plexes, and the pools are once again qPCRed. Samples were then combined with HiSeq X Cluster Amp Mix 1,2 and 3 into single wells on a strip tube using the Hamilton Starlet Liquid Handling system. Libraries were sequenced with 151-bp paired-end reads for whole-genome sequencing. Cluster amplification of the templates was performed according to the manufacturer's protocol (Illumina) using the Illumina cBot. Flowcells were sequenced on HiSeqX Sequencing-by-Synthesis Kits, then analyzed using RTA2. Output from Illumina software was processed by the Picard data-processing pipeline to yield BAM files containing well-calibrated, hg19-aligned reads. All sample information tracking was performed by automated LIMS messaging.

Analysis of Aligned Whole Genome Sequencing Data. Whole genome sequencing BAM files were uploaded to FireCloud (https://software.broadinstitute.org/firecloud/), where coding somatic nucleotide variant (SNV, includes indels), copy number variant (CNV), and structural variant (SV) calling was carried out. Somatic SNV and CV calling was performed using standard GATK4 workflows (https://software.broadinstitute.org/gatk/gatk4). SNV calling was restricted to coding regions and potentially clonal mutations (allelic fraction >=0.3). SV calling was performed using dRanger/BreakPointer (Drier et al. *Genome Res* 23:228-235 (2013); Berger et al. *Nature* 470:214-220 (2011)) and restricted to potentially clonal variants ([fraction of read pairs that support the variant >=0.2] and [fraction of split reads that support the variant >=0.2]).

Genotyping MITF Duplication. We performed targeted amplicon sequencing of two heterozygous SNPs in the MITF locus (primers listed in Table 21). For each SNP, the allele ratio of each sequenced sample was compared to the allele ratio observed in wildtype, parental melanocytes (to produce a ratio of ratios). A sample with a ratio of SNP ratios greater than two was interpreted as having an MITF amplification. The clonal and two-fold nature of the MITF tandem duplication in the CBTPA WGS sample was inferred by observing a consistent SNP ratio of ~3:1 (3+1=4 MITF alleles) in almost all MITF amplified samples, including several single cell clones (Table 19).

Statistical Testing. Statistical testing of RT-qPCR measurements within a single sample group (comparison to a population mean of zero) was carried out using a one-tailed, one-sample Student's t-test. Statistical comparisons of RT-qPCR or tumor volume measurements between two sample groups were carried out using a two-tailed, two-sample Student's t-test. All test calculations were performed using SciPy statistical functions.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An in vitro cell population for modeling cancer comprising human primary melanocytes, wherein the human primary melanocytes are genetically edited to comprise:

(a) a CDKN2A knockout mutation, (b) a BRAF V600E mutation, (c) a PTEN knockout mutation, (d) a CTNNB1 activating mutation selected from the group consisting of CTNNB1 S45P, CTNNB1 S45F, CTNNB1 S45Y, CTNNB1 S37F, CTNNB1 S37Y, and CTNNB1 S33C, and (e) a TERT activating mutation selected from the group consisting of a −124C>T promoter mutation and a −146C>T promoter mutation, wherein the in vitro cell population comprises pigmented cells, and wherein the in vitro cell population undergoes metastatic spread when introduced to a mouse.

2. The in vitro cell population of claim 1, wherein the melanocytes are genetically modified to comprise a polynucleotide encoding a Cas enzyme of a CRISPR-Cas system.

3. The in vitro cell population of claim 1, wherein the CDKN2A knockout mutation and the BRAF V600E mutation occur at an allelic frequency of 90-100%, and the TERT activating mutation occurs at an allelic frequency of 50%.

4. The in vitro cell population of claim 1, wherein the melanocytes further comprise an APC inactivating mutation.

5. The in vitro cell population of claim 4, wherein the APC inactivating mutation has an allelic frequency of 75-85%.

6. The in vitro cell population of claim 1, wherein the PTEN knockout mutation has an allelic frequency of 90-100%.

7. The in vitro cell population of claim 1, wherein the melanocytes further comprise a TP53 knockout mutation.

8. The in vitro cell population of claim 7, wherein the TP53 knockout mutation has an allelic frequency of 90-100%.

9. The in vitro cell population of claim 1, wherein the melanocytes further comprise an APC inactivating mutation, wherein the PTEN knockout mutation has an allelic frequency of 90-100% and the APC inactivating mutation has an allelic frequency of 75-85%.

10. The in vitro cell population of claim 1, wherein the TERT activating mutation consists of a −124C>T promoter mutation.

11. The in vitro cell population of claim 1, wherein the TERT activating mutation consists of a −146C>T promoter mutation.

12. The in vitro cell population of claim 1, wherein the CTNNB1 activating mutation is generated using a crRNA comprising the sequence set forth in SEQ ID NO: 34.

* * * * *

SEQUENCE LISTING

<160> NUMBER OF SEQ ID NOS: 244

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 1
ggcaccgagt cggtgc 16

<210> SEQ ID NO 2
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(7)
<223> OTHER INFORMATION: N = any complementary set of nucleotides that together will base pair to nucleotides 11-17
<220> FEATURE:
<221> NAME/KEY: misc_feature
<222> LOCATION: (11)..(17)
<223> OTHER INFORMATION: N = any complementary set of nucleotides that together will base pair to nucleotides 1-7

<400> SEQUENCE: 2
nnnnnnnagt nnnnnnn 17

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(5)
<223> OTHER INFORMATION: Y = pyrimidine
<220> FEATURE:
<221> NAME/KEY: misc_feature
<222> LOCATION: (8)..(8)
<223> OTHER INFORMATION: N = any nucleotide that forms part of a bulge of the duplex
<220> FEATURE:
<221> NAME/KEY: misc_feature
<222> LOCATION: (9)..(12)
<223> OTHER INFORMATION: N = any nucleotide so long as it base pairs with the corresponding NNNN portion of the tracrRNA
<220> FEATURE:
<221> NAME/KEY: misc_feature
<222> LOCATION: (13)..(16)
<223> OTHER INFORMATION: NNNN = a linker sequence
<220> FEATURE:
<221> NAME/KEY: misc_feature
<222> LOCATION: (17)..(20)
<223> OTHER INFORMATION: N = any nucleotide so long as it base pairs with the corresponding NNNN portion of the tracrRNA
<220> FEATURE:
<221> NAME/KEY: misc_feature
<222> LOCATION: (21)..(23)
<223> OTHER INFORMATION: AAN = part of the bulge of the duplex, with N being any nucleotide
<220> FEATURE:
<221> NAME/KEY: misc_feature
<222> LOCATION: (26)..(29)
<223> OTHER INFORMATION: R = any purine

<400> SEQUENCE: 3
gyyyyagnnn nnnnnnnnnn aanuurrrru 30

<210> SEQ ID NO 4
<211> LENGTH: 4
<212> TYPE: PRT
<213> ORGANISM: Artificial Sequence
<220> FEATURE:
<223> OTHER INFORMATION: Synthetic Linker

<400> SEQUENCE: 4

Gly Gly Gly Ser
1

<210> SEQ ID NO 5
<211> LENGTH: 15
<212> TYPE: PRT
<213> ORGANISM: Artificial Sequence
<220> FEATURE:
<223> OTHER INFORMATION: Synthetic Linker

<400> SEQUENCE: 5

Gly Gly Gly Gly Ser Gly Gly Gly Gly Ser Gly Gly Gly Gly Ser
1 5 10 15

<210> SEQ ID NO 6
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 6
cagcagcagc tccgccactc 20

<210> SEQ ID NO 7
<211> LENGTH: 20
<212> TYPE: RNA
<213> ORGANISM: Artificial Sequence
<220> FEATURE:
<223> OTHER INFORMATION: Synthetic Guide Sequence

<400> SEQUENCE: 7
cagcagcagc uccgccacuc 20

<210> SEQ ID NO 8
<211> LENGTH: 36
<212> TYPE: RNA
<213> ORGANISM: Artificial Sequence
<220> FEATURE:
<223> OTHER INFORMATION: Synthetic Guide

<400> SEQUENCE: 8
cagcagcagc uccgccacuc guuuuagagc uaugcu 36

<210> SEQ ID NO 9
<211> LENGTH: 20
<212> TYPE: DNA
<213> ORGANISM: Artificial Sequence
<220> FEATURE:
<223> OTHER INFORMATION: Synthetic Guide

<400> SEQUENCE: 9
gacccgtgca cgacgctgcc 20

<210> SEQ ID NO 10
<211> LENGTH: 20
<212> TYPE: RNA

<213> ORGANISM: Artificial Sequence
<220> FEATURE:
<223> OTHER INFORMATION: Synthetic Guide

<400> SEQUENCE: 10
gacccgugca cgacgcugcc 20

<210> SEQ ID NO 11
<211> LENGTH: 36
<212> TYPE: RNA
<213> ORGANISM: Artificial Sequence
<220> FEATURE:
<223> OTHER INFORMATION: Synthetic Guide

<400> SEQUENCE: 11
gacccgugca cgacgcugcc guuuuagagc uaugcu 36

<210> SEQ ID NO 12
<211> LENGTH: 20
<212> TYPE: DNA
<213> ORGANISM: Artificial Sequence
<220> FEATURE:
<223> OTHER INFORMATION: Synthetic Guide

<400> SEQUENCE: 12
gatgatgggc agcgcccgag 20

<210> SEQ ID NO 13
<211> LENGTH: 20
<212> TYPE: RNA
<213> ORGANISM: Artificial Sequence
<220> FEATURE:
<223> OTHER INFORMATION: Synthetic Guide

<400> SEQUENCE: 13
gaugaugggc agcgcccgag 20

<210> SEQ ID NO 14
<211> LENGTH: 36
<212> TYPE: RNA
<213> ORGANISM: Artificial Sequence
<220> FEATURE:
<223> OTHER INFORMATION: Synthetic Guide

<400> SEQUENCE: 14
gaugaugggc agcgcccgag guuuuagagc uaugcu 36

<210> SEQ ID NO 15
<211> LENGTH: 20
<212> TYPE: DNA
<213> ORGANISM: Artificial Sequence
<220> FEATURE:
<223> OTHER INFORMATION: Synthetic Guide

<400> SEQUENCE: 15
tcgggtgaga gtggcggggt 20

<210> SEQ ID NO 16
<211> LENGTH: 20
<212> TYPE: RNA
<213> ORGANISM: Artificial Sequence
<220> FEATURE:
<223> OTHER INFORMATION: Synthetic Guide

<400> SEQUENCE: 16
ucgggugaga guggcggggu 20

<210> SEQ ID NO 17
<211> LENGTH: 36
<212> TYPE: RNA
<213> ORGANISM: Artificial Sequence
<220> FEATURE:
<223> OTHER INFORMATION: Synthetic Guide

<400> SEQUENCE: 17
ucgggugaga guggcggggu guuuuagagc uaugcu 36

<210> SEQ ID NO 18
<211> LENGTH: 20
<212> TYPE: DNA
<213> ORGANISM: Artificial Sequence
<220> FEATURE:
<223> OTHER INFORMATION: Synthetic Guide

<400> SEQUENCE: 18
agacaactgt tcaaactgat 20

<210> SEQ ID NO 19
<211> LENGTH: 36
<212> TYPE: RNA
<213> ORGANISM: Artificial Sequence
<220> FEATURE:
<223> OTHER INFORMATION: Synthetic Guide

<400> SEQUENCE: 19
agacaacugu ucaaacugau guuuuagagc uaugcu 36

<210> SEQ ID NO 20
<211> LENGTH: 20
<212> TYPE: DNA
<213> ORGANISM: Artificial Sequence
<220> FEATURE:
<223> OTHER INFORMATION: Synthetic Guide

<400> SEQUENCE: 20
gcagcaggga gcgcacggct 20

<210> SEQ ID NO 21
<211> LENGTH: 20
<212> TYPE: RNA
<213> ORGANISM: Artificial Sequence
<220> FEATURE:
<223> OTHER INFORMATION: Synthetic Guide

<400> SEQUENCE: 21
gcagcaggga gcgcacggcu 20

<210> SEQ ID NO 22
<211> LENGTH: 36
<212> TYPE: RNA
<213> ORGANISM: Artificial Sequence
<220> FEATURE:
<223> OTHER INFORMATION: Synthetic Guide

<400> SEQUENCE: 22
gcagcaggga gcgcacggcu guuuuagagc uaugcu 36

<210> SEQ ID NO 23
<211> LENGTH: 20
<212> TYPE: DNA
<213> ORGANISM: Artificial Sequence
<220> FEATURE:

<223> OTHER INFORMATION: Synthetic Guide

<400> SEQUENCE: 23
aaacaaaagg agatatcaag 20

<210> SEQ ID NO 24
<211> LENGTH: 20
<212> TYPE: RNA
<213> ORGANISM: Artificial Sequence
<220> FEATURE:
<223> OTHER INFORMATION: Synthetic Guide

<400> SEQUENCE: 24
aaacaaaagg agauaucaag 20

<210> SEQ ID NO 25
<211> LENGTH: 36
<212> TYPE: RNA
<213> ORGANISM: Artificial Sequence
<220> FEATURE:
<223> OTHER INFORMATION: Synthetic Guide

<400> SEQUENCE: 25
aaacaaaagg agauaucaag guuuuagagc uaugcu 36

<210> SEQ ID NO 26
<211> LENGTH: 20
<212> TYPE: DNA
<213> ORGANISM: Artificial Sequence
<220> FEATURE:
<223> OTHER INFORMATION: Synthetic Guide

<400> SEQUENCE: 26
ttgatgatgg ctgtcatgtc 20

<210> SEQ ID NO 27
<211> LENGTH: 20
<212> TYPE: RNA
<213> ORGANISM: Artificial Sequence
<220> FEATURE:
<223> OTHER INFORMATION: Synthetic Guide

<400> SEQUENCE: 27
uugaugaugg cugucauguc 20

<210> SEQ ID NO 28
<211> LENGTH: 36
<212> TYPE: RNA
<213> ORGANISM: Artificial Sequence
<220> FEATURE:
<223> OTHER INFORMATION: Synthetic Guide

<400> SEQUENCE: 28
uugaugaugg cugucauguc guuuuagagc uaugcu 36

<210> SEQ ID NO 29
<211> LENGTH: 20
<212> TYPE: DNA
<213> ORGANISM: Artificial Sequence
<220> FEATURE:
<223> OTHER INFORMATION: Synthetic Guide

<400> SEQUENCE: 29
tgatgatggc tgtcatgtct 20

<210> SEQ ID NO 30
<211> LENGTH: 20
<212> TYPE: RNA
<213> ORGANISM: Artificial Sequence
<220> FEATURE:
<223> OTHER INFORMATION: Synthetic Guide

<400> SEQUENCE: 30
ugaugauggc ugucaugucu 20

<210> SEQ ID NO 31
<211> LENGTH: 36
<212> TYPE: RNA
<213> ORGANISM: Artificial Sequence
<220> FEATURE:
<223> OTHER INFORMATION: Synthetic Guide

<400> SEQUENCE: 31
ugaugauggc ugucaugucu guuuuagagc uaugcu 36

<210> SEQ ID NO 32
<211> LENGTH: 20
<212> TYPE: DNA
<213> ORGANISM: Artificial Sequence
<220> FEATURE:
<223> OTHER INFORMATION: Synthetic Guide

<400> SEQUENCE: 32
ttgcctttac cactcagaga 20

<210> SEQ ID NO 33
<211> LENGTH: 20
<212> TYPE: RNA
<213> ORGANISM: Artificial Sequence
<220> FEATURE:
<223> OTHER INFORMATION: Synthetic Guide

<400> SEQUENCE: 33
uugccuuuac cacucagaga 20

<210> SEQ ID NO 34
<211> LENGTH: 36
<212> TYPE: RNA
<213> ORGANISM: Artificial Sequence
<220> FEATURE:
<223> OTHER INFORMATION: Synthetic Guide

<400> SEQUENCE: 34
uugccuuuac cacucagaga guuuuagagc uaugcu 36

<210> SEQ ID NO 35
<211> LENGTH: 20
<212> TYPE: DNA
<213> ORGANISM: Artificial Sequence
<220> FEATURE:
<223> OTHER INFORMATION: Synthetic Guide

<400> SEQUENCE: 35
tcctcagcat cttatccgag 20

<210> SEQ ID NO 36
<211> LENGTH: 20
<212> TYPE: RNA
<213> ORGANISM: Artificial Sequence
<220> FEATURE:
<223> OTHER INFORMATION: Synthetic Guide

<400> SEQUENCE: 36
uccucagcau cuuauccgag 20

<210> SEQ ID NO 37
<211> LENGTH: 36
<212> TYPE: RNA
<213> ORGANISM: Artificial Sequence
<220> FEATURE:
<223> OTHER INFORMATION: Synthetic Guide

<400> SEQUENCE: 37
uccucagcau cuuauccgag guuuuagagc uaugcu 36

<210> SEQ ID NO 38
<211> LENGTH: 20
<212> TYPE: DNA
<213> ORGANISM: Artificial Sequence
<220> FEATURE:
<223> OTHER INFORMATION: Synthetic Guide

<400> SEQUENCE: 38
tccactcgga taagatgctg 20

<210> SEQ ID NO 39
<211> LENGTH: 20
<212> TYPE: RNA
<213> ORGANISM: Artificial Sequence
<220> FEATURE:
<223> OTHER INFORMATION: Synthetic Guide

<400> SEQUENCE: 39
uccacucgga uaagaugcug 20

<210> SEQ ID NO 40
<211> LENGTH: 36
<212> TYPE: RNA
<213> ORGANISM: Artificial Sequence
<220> FEATURE:
<223> OTHER INFORMATION: Synthetic Guide

<400> SEQUENCE: 40
uccacucgga uaagaugcug guuuuagagc uaugcu 36

<210> SEQ ID NO 41
<211> LENGTH: 1831
<212> TYPE: DNA
<213> ORGANISM: Homo sapiens

<400> SEQUENCE: 41
gttgaaggat ataaagaaaa tcttgtctca caaagggaag atcttgtgga ccctctaaaa 60
cggtgtgagg gacccttta agaatgctgt tttagggaat gattcatatg actgagcttt 120
ccacagcttg ctgcaatgca cacaagtttt tgttcccttc ttttagaact tctctttctt 180
cttttccaca aagcaaaaaa caagaagaaa gaaagagcta tgcaagacag cacaaggctg 240
ttaatctacc tctcattttt ttttgtcttt cctcttccag ctgccccata attatgagat 300
actttctagt ctaaaggaag taactttcca atttaggctt aaataagatt gcgaaacagc 360
ttctctgtta aaaggagtag ttctcttagc aaaaccataa taatggctgt ggatcacacc 420
tgccttaaat tgcatacctg ttttttttt caacagggta cacagaacat tttgaacaca 480
aaatacttta aacaatttag aataaaatat gaaacactgt ttataagaca tatatttttg 540
tttgaaatac actgaaactg gtttcaaaat attcgtttta agggttcata tttatttaag 600

```
aataaaatat gaaacactgt ttataagaca tatatttttg tttgaaatac actgaaactg    660
gtttcaaaat attcgtttta agggtaaaga aaaaagttaa aaaatctatt tacataaaaa    720
ataagaacac tgatttttgt gaatactggg aactatgaaa atactatagt tgagaccttc    780
aatgactttc tagtaactca gcagcatctc agggccaaaa atttaatcag tggaaaaata    840
gcctcaattc ttaccatcca caaaatggat ccagacaact gttcaaactg atgactccca    900
ctccatcgag atttctctgt agctagacca aaatcaccta tttttactgt gaggtcttca    960
tgaagaaata tatctgaggt gtagtaagta aaggaaaaca gtagatctca ttttcctatc   1020
agagcaagca ttatgaagag tttaggtaag agatctaatt tctataattc tgtaatataa   1080
tattctttaa aacatagtac ttcatctttc ctcttagagt caataagtat gtctaaaaca   1140
atgattagtt ctatttagcc tatataacct gcttttaaga tttttggggc ttgaaatgtg   1200
ttaggatgag gtgagatgct ttcctaagtt tataggagaa cctaaaactt tcccattaga   1260
ttttagcaat gtaggcccag atattctctt ggcactcctg ggcgagcagt aaaggctctt   1320
cattggaatg aagatgctgc agatagtatc ttagtctgca cttagggaag agaaatatta   1380
tgtttttctc acctcattgt tatataattt agagtcttca gttatatctc aactaccact   1440
gagcaaggtc agaggtctga aagggactaa tagatagcta caaaactatc agttttatag   1500
tgctgataaa atgtaagcaa gcaatcaaaa actcctacta ttgtaaagac ttctgataga   1560
ttttcttgta atgttcagtt gtcgagaaac caaaagcagg ctgtggtatc ctgctctcct   1620
atacatgcat gcacaatcct ttattaattc tctttacagt atatcgaact tagcatgaaa   1680
actgttttta cataatgtga agacaaaatg cagaagaaaa agtcaggatg ttttcaaact   1740
tcgcagacaa atttcaggaa ggatactatt actcttgagg tctctgtgga tgattgactt   1800
ggcgtgtaag taactgaaaa acaaaacatc a                                  1831
```

<210> SEQ ID NO 42
<211> LENGTH: 1834
<212> TYPE: DNA
<213> ORGANISM: Homo sapiens

<400> SEQUENCE: 42

```
cgcgtcctgc ccgggtgggc ccaggacccc tgcccaacgg gcgtccgctc cggctcaggg     60
gcagcgccac gcctgggcct cttgggcaac ggcagacttc ggctggcact gcccccgcgc    120
ctcctcgcac ccggggctgg caggcccagg gggaccccgg cctccctgac gctatggttc    180
caggcccgtt cgcatcccag acgccttcgg ggtccactag cgtgtggcgg gggccgggcc    240
tgagtggcag cgccgagctg gtacagcggc ggcccgcaca cctggtaggc gcagctggga    300
gccaccagca caaagagcgc gcagcgtgcc agcaggtgaa ccagcacgtc gtcgcccacg    360
cggcgcagca gcagccccca cgccccgctc ccccgcagtg cgtcggtcac cgtgttgggc    420
aggtagctgc gcacgctggt ggtgaaggcc tcggggggc  ccccgcgggc cccgtccagc    480
agcgcgaagc cgaaggccag cacgttcttc gcgccgcgct cgcacagcct ctgcagcact    540
cgggccacca gctccttcag gcaggacacc tgcgggggaa gcgccctgag tcgcctgcgc    600
tgctctccgc atgtcgctgg ttccccccgg ccgccctcaa ccccagccgg acgccgaccc    660
cggggaggcc cacctggcgg aaggaggggg cggcgggggg cggccgtgcg tcccagggca    720
cgcacaccag gcactgggcc accagcgcgc ggaaagccgc cgggtccccg cgctgcacca    780
gccgccagcc ctggggcccc aggcgccgca cgaacgtggc cagcggcagc acctcgcggt    840
```

agtggctgcg cagcagggag cgcacggctc gacagcgggg agcgcgcggc atcgcggggg 900
tggccggggc cagggcttcc cacgtgcgca gcaggacgca gcgctgcctg aaactcgcgc 960
cgcgaggaga gggcggggcc gcggaaagga aggggagggg ctgggagggc ccggaagggg 1020
ctgggccggg gacccgggag gggtcgggac ggggcggggt ccgcgcggag gaggcggagc 1080
tggaaggtga aggggcagga cgggtgcccg ggtccccagt ccctccgcca cgtgggaagc 1140
gcggtcctgg gcgtctgtgc ccgcgaatcc actgggagcc cggcctggcc ccgacagcgc 1200
agctgctccg ggcggacccg gggtctgggc ccgcgcttcc ccgcccgcgc gccgctcgcg 1260
ctcccagggt gcagggacgc cagcgagggc cccagcggag agaggtcgaa tcggcctagg 1320
ctgtggggta acccgaggga ggggccatga tgtggaggcc ctgggaacag gtgcgtgcgg 1380
cgaccctttg gccgctggcc tgatccggag acccagggct gcctccaggt ccggacgcgg 1440
ggcgtcgggc tccgggcacc acgaatgccg gacgtgaagg ggaggacgga ggcgcgtaga 1500
cgcggctggg gacgaacccg aggacgcatt gctccctgga cgggcacgcg ggacctcccg 1560
gagtgcctcc ctgcaacact tccccgcgac ttgggctcct tgacacaggc ccgtcatttc 1620
tctttgcagg ttctcaggcg gcgaggggtc cccaccatga gcaaaccacc ccaaatctgt 1680
taatcaccca ccggggcggt cccgtcgaga aagggtggga aatggagcca ggcgctcctg 1740
ctggccgcgc accgggcgcc tcacaccagc cacaacggcc ttgaccctgg gccccggcac 1800
tctgtctggc agatgaggcc aacatctggt caca 1834

<210> SEQ ID NO 43
<211> LENGTH: 1834
<212> TYPE: DNA
<213> ORGANISM: Homo sapiens

<400> SEQUENCE: 43
cgcgtcctgc ccgggtgggc ccaggacccc tgcccaacgg gcgtccgctc cggctcaggg 60
gcagcgccac gcctgggcct cttgggcaac ggcagacttc ggctggcact gccccgcgc 120 ctcctcgcac ccggggctgg caggcccagg gggaccccgg cctccctgac gctatggttc 180
caggcccgtt cgcatcccag acgccttcgg ggtccactag cgtgtggcgg gggccgggcc 240
tgagtggcag cgccgagctg gtacagcggc ggcccgcaca cctggtaggc gcagctggga 300
gccaccagca caaagagcgc gcagcgtgcc agcaggtgaa ccagcacgtc gtcgcccacg 360
cggcgcagca gcagccccca cgccccgctc ccccgcagtg cgtcggtcac cgtgttgggc 420
aggtagctgc gcacgctggt ggtgaaggcc tcggggggc ccccgcgggc cccgtccagc 480
agcgcgaagc cgaaggccag cacgttcttc gcgccgcgct cgcacagcct ctgcagcact 540
cgggccacca gctccttcag gcaggacacc tgcgggggaa gcgccctgag tcgcctgcgc 600
tgctctccgc atgtcgctgg ttcccccgg ccgccctcaa ccccagccgg acgccgaccc 660
cggggaggcc cacctggcgg aaggaggggg cggcgggggg cggccgtgcg tcccagggca 720
cgcacaccag gcactgggcc accagcgcgc ggaaagccgc cgggtccccg cgctgcacca 780
gccgccagcc ctggggcccc aggcgccgca cgaacgtggc cagcggcagc acctcgcggt 840
agtggctgcg cagcagggag cgcacggctc gacagcgggg agcgcgcggc atcgcggggg 900
tggccggggc cagggcttcc cacgtgcgca gcaggacgca gcgctgcctg aaactcgcgc 960
cgcgaggaga gggcggggcc gcggaaagga aggggagggg ctgggagggc ccggaggggg 1020
ctgggccggg gacccggaag gggtcgggac ggggcggggt ccgcgcggag gaggcggagc 1080
tggaaggtga aggggcagga cgggtgcccg ggtccccagt ccctccgcca cgtgggaagc 1140
gcggtcctgg gcgtctgtgc ccgcgaatcc actgggagcc cggcctggcc ccgacagcgc 1200
agctgctccg ggcggacccg ggggtctggg ccgcgcttcc ccgcccgcgc gccgctcgcg 1260
ctcccagggt gcagggacgc cagcgagggc cccagcggag agaggtcgaa tcggcctagg 1320
ctgtggggta acccgaggga ggggccatga tgtggaggcc ctgggaacag gtgcgtgcgg 1380
cgaccctttg gccgctggcc tgatccggag acccagggct gcctccaggt ccggacgcgg 1440
ggcgtcgggc tccgggcacc acgaatgccg gacgtgaagg ggaggacgga ggcgcgtaga 1500
cgcggctggg gacgaacccg aggacgcatt gctccctgga cgggcacgcg ggacctcccg 1560
gagtgcctcc ctgcaacact tccccgcgac ttgggctcct tgacacaggc ccgtcatttc 1620
tctttgcagg ttctcaggcg gcgaggggtc cccaccatga gcaaaccacc ccaaatctgt 1680
taatcaccca ccggggcggt cccgtcgaga aagggtggga aatggagcca ggcgctcctg 1740
ctggccgcgc accgggcgcc tcacaccagc cacaacggcc ttgaccctgg gccccggcac 1800
tctgtctggc agatgaggcc aacatctggt caca 1834

<210> SEQ ID NO 44
<211> LENGTH: 20
<212> TYPE: DNA
<213> ORGANISM: Artificial Sequence
<220> FEATURE:
<223> OTHER INFORMATION: Synthetic Guide

<400> SEQUENCE: 44
tgggagggcc cggagggggc 20

<210> SEQ ID NO 45
<211> LENGTH: 20
<212> TYPE: DNA
<213> ORGANISM: Artificial Sequence
<220> FEATURE:
<223> OTHER INFORMATION: Synthetic Guide

<400> SEQUENCE: 45
tgggagggcc cggagggggc 20

<210> SEQ ID NO 46
<211> LENGTH: 20
<212> TYPE: DNA
<213> ORGANISM: Artificial Sequence
<220> FEATURE:
<223> OTHER INFORMATION: Synthetic Guide

<400> SEQUENCE: 46
gtccccggcc cagccccctc 20

<210> SEQ ID NO 47
<211> LENGTH: 20
<212> TYPE: DNA
<213> ORGANISM: Artificial Sequence
<220> FEATURE:
<223> OTHER INFORMATION: Synthetic Guide

<400> SEQUENCE: 47
gtccccggcc cagccccctc 20

<210> SEQ ID NO 48
<211> LENGTH: 20
<212> TYPE: DNA
<213> ORGANISM: artificial sequence
<220> FEATURE:

<223> OTHER INFORMATION: Synthetic Guide

<400> SEQUENCE: 48
tccccggccc agccccctcc 20

<210> SEQ ID NO 49
<211> LENGTH: 20
<212> TYPE: DNA
<213> ORGANISM: Artificial Sequence
<220> FEATURE:
<223> OTHER INFORMATION: Synthetic Guide

<400> SEQUENCE: 49
tccccggccc agccccctcc 20

<210> SEQ ID NO 50
<211> LENGTH: 20
<212> TYPE: DNA
<213> ORGANISM: Artificial Sequence
<220> FEATURE:
<223> OTHER INFORMATION: Synthetic Guide

<400> SEQUENCE: 50
ggggctggga gggcccggag 20

<210> SEQ ID NO 51
<211> LENGTH: 20
<212> TYPE: DNA
<213> ORGANISM: Artificial Sequence
<220> FEATURE:
<223> OTHER INFORMATION: Synthetic Guide

<400> SEQUENCE: 51
ggggctggga gggcccggag 20

<210> SEQ ID NO 52
<211> LENGTH: 20
<212> TYPE: DNA
<213> ORGANISM: Artificial Sequence
<220> FEATURE:
<223> OTHER INFORMATION: Synthetic Guide

<400> SEQUENCE: 52
gggctgggag ggcccggagg 20

<210> SEQ ID NO 53
<211> LENGTH: 20
<212> TYPE: DNA
<213> ORGANISM: Artificial Sequence
<220> FEATURE:
<223> OTHER INFORMATION: Synthetic Guide

<400> SEQUENCE: 53
gggctgggag ggcccggagg 20

<210> SEQ ID NO 54
<211> LENGTH: 20
<212> TYPE: DNA
<213> ORGANISM: Artificial Sequence
<220> FEATURE:
<223> OTHER INFORMATION: Synthetic Guide

<400> SEQUENCE: 54
gggagggccc ggagggggct 20

<210> SEQ ID NO 55
<211> LENGTH: 20
<212> TYPE: DNA
<213> ORGANISM: Artificial Sequence
<220> FEATURE:
<223> OTHER INFORMATION: Synthetic Guide

<400> SEQUENCE: 55
gggagggccc ggagggggct 20

<210> SEQ ID NO 56
<211> LENGTH: 20
<212> TYPE: DNA
<213> ORGANISM: Artificial Sequence
<220> FEATURE:
<223> OTHER INFORMATION: Synthetic Guide

<400> SEQUENCE: 56
gaggggctgg gagggcccgg 20

<210> SEQ ID NO 57
<211> LENGTH: 20
<212> TYPE: DNA
<213> ORGANISM: Artificial Sequence
<220> FEATURE:
<223> OTHER INFORMATION: Synthetic Guide

<400> SEQUENCE: 57
gaggggctgg gagggcccgg 20

<210> SEQ ID NO 58
<211> LENGTH: 20
<212> TYPE: DNA
<213> ORGANISM: Artificial Sequence
<220> FEATURE:
<223> OTHER INFORMATION: Synthetic Guide

<400> SEQUENCE: 58
gggggctggg ccggggaccc 20

<210> SEQ ID NO 59
<211> LENGTH: 20
<212> TYPE: DNA
<213> ORGANISM: Artificial Sequence
<220> FEATURE:
<223> OTHER INFORMATION: Synthetic Guide

<400> SEQUENCE: 59
gggggctggg ccggggaccc 20

<210> SEQ ID NO 60
<211> LENGTH: 20
<212> TYPE: DNA
<213> ORGANISM: Artificial Sequence
<220> FEATURE:
<223> OTHER INFORMATION: Synthetic Guide

<400> SEQUENCE: 60
ggctgggccg gggacccggg 20

<210> SEQ ID NO 61
<211> LENGTH: 20
<212> TYPE: DNA
<213> ORGANISM: Artificial Sequence
<220> FEATURE:
<223> OTHER INFORMATION: Synthetic Guide

<400> SEQUENCE: 61
ggctgggccg gggacccggg 20

<210> SEQ ID NO 62
<211> LENGTH: 20
<212> TYPE: DNA
<213> ORGANISM: Artificial Sequence
<220> FEATURE:
<223> OTHER INFORMATION: Synthetic Guide

<400> SEQUENCE: 62
gctgggccgg ggacccggga 20

<210> SEQ ID NO 63
<211> LENGTH: 20
<212> TYPE: DNA
<213> ORGANISM: Artificial Sequence
<220> FEATURE:
<223> OTHER INFORMATION: Synthetic Guide

<400> SEQUENCE: 63
gctgggccgg ggacccggga 20

<210> SEQ ID NO 64
<211> LENGTH: 20
<212> TYPE: DNA
<213> ORGANISM: Artificial Sequence
<220> FEATURE:
<223> OTHER INFORMATION: Synthetic Guide

<400> SEQUENCE: 64
ctgggccggg gacccgggag 20

<210> SEQ ID NO 65
<211> LENGTH: 20
<212> TYPE: DNA
<213> ORGANISM: Artificial Sequence
<220> FEATURE:
<223> OTHER INFORMATION: Artificial Sequence

<400> SEQUENCE: 65
ctgggccggg gacccgggag 20

<210> SEQ ID NO 66
<211> LENGTH: 20
<212> TYPE: DNA
<213> ORGANISM: Artificial Sequence
<220> FEATURE:
<223> OTHER INFORMATION: Synthetic Guide

<400> SEQUENCE: 66
gccggggacc cgggaggggt 20

<210> SEQ ID NO 67
<211> LENGTH: 20
<212> TYPE: DNA
<213> ORGANISM: Artificial Sequence
<220> FEATURE:
<223> OTHER INFORMATION: Synthetic Guide

<400> SEQUENCE: 67
gccggggacc cgggaggggt 20

<210> SEQ ID NO 68
<211> LENGTH: 20

<212> TYPE: DNA
<213> ORGANISM: Artificial Sequence
<220> FEATURE:
<223> OTHER INFORMATION: Synthetic Guide

<400> SEQUENCE: 68
ccggggaccc gggaggggtc 20

<210> SEQ ID NO 69
<211> LENGTH: 20
<212> TYPE: DNA
<213> ORGANISM: Artificial Sequence
<220> FEATURE:
<223> OTHER INFORMATION: Synthetic Guide

<400> SEQUENCE: 69
ccggggaccc gggaggggtc 20

<210> SEQ ID NO 70
<211> LENGTH: 20
<212> TYPE: DNA
<213> ORGANISM: Artificial Sequence
<220> FEATURE:
<223> OTHER INFORMATION: Synthetic Guide

<400> SEQUENCE: 70
cgccccgtcc cgacccctcc 20

<210> SEQ ID NO 71
<211> LENGTH: 20
<212> TYPE: DNA
<213> ORGANISM: Artificial Sequence
<220> FEATURE:
<223> OTHER INFORMATION: Synthetic Guide

<400> SEQUENCE: 71
cgccccgtcc cgacccctcc 20

<210> SEQ ID NO 72
<211> LENGTH: 20
<212> TYPE: DNA
<213> ORGANISM: Artificial Sequence
<220> FEATURE:
<223> OTHER INFORMATION: Synthetic Guide

<400> SEQUENCE: 72
gccccgtccc gacccctccc 20

<210> SEQ ID NO 73
<211> LENGTH: 20
<212> TYPE: DNA
<213> ORGANISM: Artificial Sequence
<220> FEATURE:
<223> OTHER INFORMATION: Synthetic Guide

<400> SEQUENCE: 73
ggccgcggaa aggaagggga 20

<210> SEQ ID NO 74
<211> LENGTH: 20
<212> TYPE: DNA
<213> ORGANISM: Artificial Sequence
<220> FEATURE:
<223> OTHER INFORMATION: Synthetic Guide

<400> SEQUENCE: 74
ggccgcggaa aggaagggga 20

<210> SEQ ID NO 75
<211> LENGTH: 20
<212> TYPE: DNA
<213> ORGANISM: Artificial Sequence
<220> FEATURE:
<223> OTHER INFORMATION: Synthetic Guide

<400> SEQUENCE: 75
gaaactcgcg ccgcgaggag 20

<210> SEQ ID NO 76
<211> LENGTH: 20
<212> TYPE: DNA
<213> ORGANISM: Artificial Sequence
<220> FEATURE:
<223> OTHER INFORMATION: Synthetic Guide

<400> SEQUENCE: 76
gaaactcgcg ccgcgaggag 20

<210> SEQ ID NO 77
<211> LENGTH: 20
<212> TYPE: DNA
<213> ORGANISM: Artificial Sequence
<220> FEATURE:
<223> OTHER INFORMATION: Synthetic Guide

<400> SEQUENCE: 77
gcccctcccc ttcctttccg 20

<210> SEQ ID NO 78
<211> LENGTH: 20
<212> TYPE: DNA
<213> ORGANISM: Artificial Sequence
<220> FEATURE:
<223> OTHER INFORMATION: Synthetic Guide

<400> SEQUENCE: 78
gcccctcccc ttcctttccg 20

<210> SEQ ID NO 79
<211> LENGTH: 20
<212> TYPE: DNA
<213> ORGANISM: Artificial Sequence
<220> FEATURE:
<223> OTHER INFORMATION: Synthetic Guide

<400> SEQUENCE: 79
tgcctgaaac tcgcgccgcg 20

<210> SEQ ID NO 80
<211> LENGTH: 20
<212> TYPE: DNA
<213> ORGANISM: Artificial Sequence
<220> FEATURE:
<223> OTHER INFORMATION: Synthetic Guide

<400> SEQUENCE: 80
tgcctgaaac tcgcgccgcg 20

<210> SEQ ID NO 81
<211> LENGTH: 20
<212> TYPE: DNA
<213> ORGANISM: Artificial Sequence
<220> FEATURE:
<223> OTHER INFORMATION: Synthetic Guide

<400> SEQUENCE: 81
gcggggccgc ggaaaggaag 20

<210> SEQ ID NO 82
<211> LENGTH: 20
<212> TYPE: DNA
<213> ORGANISM: Artificial Sequence
<220> FEATURE:
<223> OTHER INFORMATION: Synthetic Guide

<400> SEQUENCE: 82
gcggggccgc ggaaaggaag 20

<210> SEQ ID NO 83
<211> LENGTH: 20
<212> TYPE: DNA
<213> ORGANISM: Artificial Sequence
<220> FEATURE:
<223> OTHER INFORMATION: Synthetic Guide

<400> SEQUENCE: 83
aaactcgcgc cgcgaggaga 20

<210> SEQ ID NO 84
<211> LENGTH: 20
<212> TYPE: DNA
<213> ORGANISM: Artificial Sequence
<220> FEATURE:
<223> OTHER INFORMATION: Synthetic Guide

<400> SEQUENCE: 84
aaactcgcgc cgcgaggaga 20

<210> SEQ ID NO 85
<211> LENGTH: 20
<212> TYPE: DNA
<213> ORGANISM: Artificial Sequence
<220> FEATURE:
<223> OTHER INFORMATION: Synthetic Guide

<400> SEQUENCE: 85
ggcggggccg cggaaaggaa 20

<210> SEQ ID NO 86
<211> LENGTH: 20
<212> TYPE: DNA
<213> ORGANISM: Artificial Sequence
<220> FEATURE:
<223> OTHER INFORMATION: Synthetic Guide

<400> SEQUENCE: 86
ggcggggccg cggaaaggaa 20

<210> SEQ ID NO 87
<211> LENGTH: 20
<212> TYPE: DNA
<213> ORGANISM: Artificial Sequence
<220> FEATURE:
<223> OTHER INFORMATION: Synthetic Guide

<400> SEQUENCE: 87
gccgcggaaa ggaaggggag 20

<210> SEQ ID NO 88
<211> LENGTH: 20
<212> TYPE: DNA
<213> ORGANISM: Artificial Sequence
<220> FEATURE:
<223> OTHER INFORMATION: Synthetic Guide

<400> SEQUENCE: 88
gccgcggaaa ggaaggggag 20

<210> SEQ ID NO 89
<211> LENGTH: 20
<212> TYPE: DNA
<213> ORGANISM: Artificial Sequence
<220> FEATURE:
<223> OTHER INFORMATION: Synthetic Guide

<400> SEQUENCE: 89
gggccgcgga aaggaagggg 20

<210> SEQ ID NO 90
<211> LENGTH: 20
<212> TYPE: DNA
<213> ORGANISM: Artificial Sequence
<220> FEATURE:
<223> OTHER INFORMATION: Synthetic Guide

<400> SEQUENCE: 90
gggccgcgga aaggaagggg 20

<210> SEQ ID NO 91
<211> LENGTH: 20
<212> TYPE: DNA
<213> ORGANISM: Artificial Sequence
<220> FEATURE:
<223> OTHER INFORMATION: Synthetic Guide

<400> SEQUENCE: 91
ggaaaggaag gggaggggct 20

<210> SEQ ID NO 92
<211> LENGTH: 20
<212> TYPE: DNA
<213> ORGANISM: Artificial Sequence
<220> FEATURE:
<223> OTHER INFORMATION: Synthetic Guide

<400> SEQUENCE: 92
ggaaaggaag gggaggggct 20

<210> SEQ ID NO 93
<211> LENGTH: 20
<212> TYPE: DNA
<213> ORGANISM: Artificial Sequence
<220> FEATURE:
<223> OTHER INFORMATION: Synthetic Guide

<400> SEQUENCE: 93
gctgcgcagc cactaccgcg 20

<210> SEQ ID NO 94
<211> LENGTH: 20
<212> TYPE: DNA
<213> ORGANISM: Artificial Sequence
<220> FEATURE:
<223> OTHER INFORMATION: Synthetic Guide

<400> SEQUENCE: 94
gctgcgcagc cactaccgcg 20

<210> SEQ ID NO 95
<211> LENGTH: 20
<212> TYPE: DNA
<213> ORGANISM: Artificial Sequence
<220> FEATURE:
<223> OTHER INFORMATION: Synthetic Guide

<400> SEQUENCE: 95
tggccagcgg cagcacctcg 20

<210> SEQ ID NO 96
<211> LENGTH: 20
<212> TYPE: DNA
<213> ORGANISM: Artificial Sequence
<220> FEATURE:
<223> OTHER INFORMATION: Synthetic Guide

<400> SEQUENCE: 96
tggccagcgg cagcacctcg 20

<210> SEQ ID NO 97
<211> LENGTH: 20
<212> TYPE: DNA
<213> ORGANISM: Artificial Sequence
<220> FEATURE:
<223> OTHER INFORMATION: Synthetic Guide

<400> SEQUENCE: 97
ggggagcgcg cggcatcgcg 20

<210> SEQ ID NO 98
<211> LENGTH: 20
<212> TYPE: DNA
<213> ORGANISM: Artificial Sequence
<220> FEATURE:
<223> OTHER INFORMATION: Synthetic Guide

<400> SEQUENCE: 98
ggggagcgcg cggcatcgcg 20

<210> SEQ ID NO 99
<211> LENGTH: 20
<212> TYPE: DNA
<213> ORGANISM: Artificial Sequence
<220> FEATURE:
<223> OTHER INFORMATION: Synthetic Guide

<400> SEQUENCE: 99
gctgcgcagc agggagcgca 20

<210> SEQ ID NO 100
<211> LENGTH: 20
<212> TYPE: DNA
<213> ORGANISM: Artificial Sequence
<220> FEATURE:
<223> OTHER INFORMATION: Synthetic Guide

<400> SEQUENCE: 100
gctgcgcagc agggagcgca 20

<210> SEQ ID NO 101

<211> LENGTH: 20
<212> TYPE: DNA
<213> ORGANISM: Artificial Sequence
<220> FEATURE:
<223> OTHER INFORMATION: Synthetic Guide

<400> SEQUENCE: 101
gcagcaggga gcgcacggct 20

<210> SEQ ID NO 102
<211> LENGTH: 20
<212> TYPE: DNA
<213> ORGANISM: Artificial Sequence
<220> FEATURE:
<223> OTHER INFORMATION: Synthetic Guide

<400> SEQUENCE: 102
gcagcaggga gcgcacggct 20

<210> SEQ ID NO 103
<211> LENGTH: 20
<212> TYPE: DNA
<213> ORGANISM: Artificial Sequence
<220> FEATURE:
<223> OTHER INFORMATION: Synthetic Guide

<400> SEQUENCE: 103
ccacgttcgt gcggcgcctg 20

<210> SEQ ID NO 104
<211> LENGTH: 20
<212> TYPE: DNA
<213> ORGANISM: Artificial Sequence
<220> FEATURE:
<223> OTHER INFORMATION: Synthetic Guide

<400> SEQUENCE: 104
ccacgttcgt gcggcgcctg 20

<210> SEQ ID NO 105
<211> LENGTH: 20
<212> TYPE: DNA
<213> ORGANISM: Artificial Sequence
<220> FEATURE:
<223> OTHER INFORMATION: Synthetic Guide

<400> SEQUENCE: 105
tgccgctggc cacgttcgtg 20

<210> SEQ ID NO 106
<211> LENGTH: 20
<212> TYPE: DNA
<213> ORGANISM: Artificial Sequence
<220> FEATURE:
<223> OTHER INFORMATION: Synthetic Guide

<400> SEQUENCE: 106
tgccgctggc cacgttcgtg 20

<210> SEQ ID NO 107
<211> LENGTH: 20
<212> TYPE: DNA
<213> ORGANISM: Artificial Sequence
<220> FEATURE:
<223> OTHER INFORMATION: Synthetic Guide

<400> SEQUENCE: 107
cgccgcacga acgtggccag 20

<210> SEQ ID NO 108
<211> LENGTH: 20
<212> TYPE: DNA
<213> ORGANISM: Artificial Sequence
<220> FEATURE:
<223> OTHER INFORMATION: Synthetic Guide

<400> SEQUENCE: 108
cgccgcacga acgtggccag 20

<210> SEQ ID NO 109
<211> LENGTH: 20
<212> TYPE: DNA
<213> ORGANISM: Artificial Sequence
<220> FEATURE:
<223> OTHER INFORMATION: Synthetic Guide

<400> SEQUENCE: 109
gcggtagtgg ctgcgcagca 20

<210> SEQ ID NO 110
<211> LENGTH: 20
<212> TYPE: DNA
<213> ORGANISM: Artificial Sequence
<220> FEATURE:
<223> OTHER INFORMATION: Synthetic Guide

<400> SEQUENCE: 110
gcggtagtgg ctgcgcagca 20

<210> SEQ ID NO 111
<211> LENGTH: 20
<212> TYPE: DNA
<213> ORGANISM: Artificial Sequence
<220> FEATURE:
<223> OTHER INFORMATION: Synthetic Guide

<400> SEQUENCE: 111
ctaccgcgag gtgctgccgc 20

<210> SEQ ID NO 112
<211> LENGTH: 20
<212> TYPE: DNA
<213> ORGANISM: Artificial Sequence
<220> FEATURE:
<223> OTHER INFORMATION: Synthetic Guide

<400> SEQUENCE: 112
ctaccgcgag gtgctgccgc 20

<210> SEQ ID NO 113
<211> LENGTH: 20
<212> TYPE: DNA
<213> ORGANISM: Artificial Sequence
<220> FEATURE:
<223> OTHER INFORMATION: Synthetic Guide

<400> SEQUENCE: 113
gcggcagcac ctcgcggtag 20

<210> SEQ ID NO 114
<211> LENGTH: 20
<212> TYPE: DNA

<213> ORGANISM: Artificial Sequence
<220> FEATURE:
<223> OTHER INFORMATION: Synthetic Guide

<400> SEQUENCE: 114
gcggcagcac ctcgcggtag 20

<210> SEQ ID NO 115
<211> LENGTH: 20
<212> TYPE: DNA
<213> ORGANISM: Artificial Sequence
<220> FEATURE:
<223> OTHER INFORMATION: Synthetic Guide

<400> SEQUENCE: 115
gggagcgcac ggctcggcag 20

<210> SEQ ID NO 116
<211> LENGTH: 20
<212> TYPE: DNA
<213> ORGANISM: Artificial Sequence
<220> FEATURE:
<223> OTHER INFORMATION: Synthetic Guide

<400> SEQUENCE: 116
gggagcgcac ggctcggcag 20

<210> SEQ ID NO 117
<211> LENGTH: 20
<212> TYPE: DNA
<213> ORGANISM: Artificial Sequence
<220> FEATURE:
<223> OTHER INFORMATION: Synthetic Guide

<400> SEQUENCE: 117
ggagcgcacg gctcggcagc 20

<210> SEQ ID NO 118
<211> LENGTH: 20
<212> TYPE: DNA
<213> ORGANISM: Artificial Sequence
<220> FEATURE:
<223> OTHER INFORMATION: Synthetic Guide

<400> SEQUENCE: 118
ggagcgcacg gctcggcagc 20

<210> SEQ ID NO 119
<211> LENGTH: 20
<212> TYPE: DNA
<213> ORGANISM: Artificial Sequence
<220> FEATURE:
<223> OTHER INFORMATION: Synthetic Guide

<400> SEQUENCE: 119
gagcgcacgg ctcggcagcg 20

<210> SEQ ID NO 120
<211> LENGTH: 20
<212> TYPE: DNA
<213> ORGANISM: Artificial Sequence
<220> FEATURE:
<223> OTHER INFORMATION: Synthetic Guide

<400> SEQUENCE: 120
gagcgcacgg ctcggcagcg 20

<210> SEQ ID NO 121
<211> LENGTH: 20
<212> TYPE: DNA
<213> ORGANISM: Artificial Sequence
<220> FEATURE:
<223> OTHER INFORMATION: Synthetic Guide

<400> SEQUENCE: 121
gctcggcagc ggggagcgcg 20

<210> SEQ ID NO 122
<211> LENGTH: 20
<212> TYPE: DNA
<213> ORGANISM: Artificial Sequence
<220> FEATURE:
<223> OTHER INFORMATION: Synthetic Guide

<400> SEQUENCE: 122
gctcggcagc ggggagcgcg 20

<210> SEQ ID NO 123
<211> LENGTH: 19
<212> TYPE: DNA
<213> ORGANISM: Homo sapiens

<400> SEQUENCE: 123
acatgacagc catcatcaa 19

<210> SEQ ID NO 124
<211> LENGTH: 20
<212> TYPE: DNA
<213> ORGANISM: Artificial Sequence
<220> FEATURE:
<223> OTHER INFORMATION: Synthetic Guide

<400> SEQUENCE: 124
cagcagcagc tccgccactc 20

<210> SEQ ID NO 125
<211> LENGTH: 20
<212> TYPE: DNA
<213> ORGANISM: Artificial Sequence
<220> FEATURE:
<223> OTHER INFORMATION: Synthetic Guide

<400> SEQUENCE: 125
gacccgtgca cgacgctgcc 20

<210> SEQ ID NO 126
<211> LENGTH: 20
<212> TYPE: DNA
<213> ORGANISM: Artificial Sequence
<220> FEATURE:
<223> OTHER INFORMATION: Synthetic Guide

<400> SEQUENCE: 126
gatgatgggc agcgcccgag 20

<210> SEQ ID NO 127
<211> LENGTH: 20
<212> TYPE: DNA
<213> ORGANISM: Artificial Sequence
<220> FEATURE:
<223> OTHER INFORMATION: Synthetic Guide

<400> SEQUENCE: 127
tcgggtgaga gtggcggggt 20

<210> SEQ ID NO 128
<211> LENGTH: 20
<212> TYPE: DNA
<213> ORGANISM: Artificial Sequence
<220> FEATURE:
<223> OTHER INFORMATION: Synthetic Guide

<400> SEQUENCE: 128
agacaactgt tcaaactgat 20

<210> SEQ ID NO 129
<211> LENGTH: 20
<212> TYPE: DNA
<213> ORGANISM: Artificial Sequence
<220> FEATURE:
<223> OTHER INFORMATION: Synthetic Guide

<400> SEQUENCE: 129
gcagcaggga gcgcacggct 20

<210> SEQ ID NO 130
<211> LENGTH: 20
<212> TYPE: DNA
<213> ORGANISM: Artificial Sequence
<220> FEATURE:
<223> OTHER INFORMATION: Synthetic Guide

<400> SEQUENCE: 130
ttgatgatgg ctgtcatgtc 20

<210> SEQ ID NO 131
<211> LENGTH: 20
<212> TYPE: DNA
<213> ORGANISM: Artificial Sequence
<220> FEATURE:
<223> OTHER INFORMATION: Synthetic Guide

<400> SEQUENCE: 131
tgatgatggc tgtcatgtct 20

<210> SEQ ID NO 132
<211> LENGTH: 20
<212> TYPE: DNA
<213> ORGANISM: Artificial Sequence
<220> FEATURE:
<223> OTHER INFORMATION: Synthetic Guide

<400> SEQUENCE: 132
tcctcagcat cttatccgag 20

<210> SEQ ID NO 133
<211> LENGTH: 20
<212> TYPE: DNA
<213> ORGANISM: Artificial Sequence
<220> FEATURE:
<223> OTHER INFORMATION: Synthetic Guide

<400> SEQUENCE: 133
tccactcgga taagatgctg 20

<210> SEQ ID NO 134
<211> LENGTH: 20

<212> TYPE: DNA
<213> ORGANISM: Artificial Sequence
<220> FEATURE:
<223> OTHER INFORMATION: Synthetic Guide

<400> SEQUENCE: 134
aaccaaatcc agcagactgc 20

<210> SEQ ID NO 135
<211> LENGTH: 20
<212> TYPE: DNA
<213> ORGANISM: Artificial Sequence
<220> FEATURE:
<223> OTHER INFORMATION: Synthetic Guide

<400> SEQUENCE: 135
gtttatcttc agaatcagcc 20

<210> SEQ ID NO 136
<211> LENGTH: 20
<212> TYPE: DNA
<213> ORGANISM: Artificial Sequence
<220> FEATURE:
<223> OTHER INFORMATION: Synthetic Guide

<400> SEQUENCE: 136
acggaggcta agcgtcgcaa 20

<210> SEQ ID NO 137
<211> LENGTH: 20
<212> TYPE: DNA
<213> ORGANISM: Artificial Sequence
<220> FEATURE:
<223> OTHER INFORMATION: Synthetic Guide

<400> SEQUENCE: 137
cgcttccgcg gcccgttcaa 20

<210> SEQ ID NO 138
<211> LENGTH: 20
<212> TYPE: DNA
<213> ORGANISM: Artificial Sequence
<220> FEATURE:
<223> OTHER INFORMATION: Synthetic Guide

<400> SEQUENCE: 138
atcgtttccg cttaacggcg 20

<210> SEQ ID NO 139
<211> LENGTH: 20
<212> TYPE: DNA
<213> ORGANISM: Artificial Sequence
<220> FEATURE:
<223> OTHER INFORMATION: Synthetic Guide

<400> SEQUENCE: 139
gtaggcgcgc cgctctctac 20

<210> SEQ ID NO 140
<211> LENGTH: 22
<212> TYPE: DNA
<213> ORGANISM: Artificial Sequence
<220> FEATURE:
<223> OTHER INFORMATION: Synthetic Guide

<400> SEQUENCE: 140
gcgggcatgg ttactgcctc tg 22

<210> SEQ ID NO 141
<211> LENGTH: 23
<212> TYPE: DNA
<213> ORGANISM: Artificial Sequence
<220> FEATURE:
<223> OTHER INFORMATION: Synthetic Guide

<400> SEQUENCE: 141
tcataatgct tgctctgata gga 23

<210> SEQ ID NO 142
<211> LENGTH: 20
<212> TYPE: DNA
<213> ORGANISM: Artificial Sequence
<220> FEATURE:
<223> OTHER INFORMATION: Synthetic Guide

<400> SEQUENCE: 142
acgaacgtgg ccagcggcag 20

<210> SEQ ID NO 143
<211> LENGTH: 22
<212> TYPE: DNA
<213> ORGANISM: Artificial Sequence
<220> FEATURE:
<223> OTHER INFORMATION: Synthetic Guide

<400> SEQUENCE: 143
atttccatcc tgcagaagaa gc 22

<210> SEQ ID NO 144
<211> LENGTH: 22
<212> TYPE: DNA
<213> ORGANISM: Artificial Sequence
<220> FEATURE:
<223> OTHER INFORMATION: Synthetic Guide

<400> SEQUENCE: 144
cctcccagag accccagttg ca 22

<210> SEQ ID NO 145
<211> LENGTH: 22
<212> TYPE: DNA
<213> ORGANISM: Artificial Sequence
<220> FEATURE:
<223> OTHER INFORMATION: Synthetic Guide

<400> SEQUENCE: 145
agaggcagaa tcagctccat cc 22

<210> SEQ ID NO 146
<211> LENGTH: 22
<212> TYPE: DNA
<213> ORGANISM: Artificial Sequence
<220> FEATURE:
<223> OTHER INFORMATION: Synthetic Guide

<400> SEQUENCE: 146
ggagtgtaga tagatgaaat ca 22

<210> SEQ ID NO 147
<211> LENGTH: 22
<212> TYPE: DNA
<213> ORGANISM: Artificial Sequence
<220> FEATURE:
<223> OTHER INFORMATION: Synthetic Guide

<400> SEQUENCE: 147
aagattaagt gttgtgacta gg 22

<210> SEQ ID NO 148
<211> LENGTH: 22
<212> TYPE: DNA
<213> ORGANISM: Artificial Sequence
<220> FEATURE:
<223> OTHER INFORMATION: Synthetic Guide

<400> SEQUENCE: 148
cttgtgtggg ggtctgcttg gc 22

<210> SEQ ID NO 149
<211> LENGTH: 22
<212> TYPE: DNA
<213> ORGANISM: Artificial Sequence
<220> FEATURE:
<223> OTHER INFORMATION: Synthetic Guide

<400> SEQUENCE: 149
ggccaaaaat ttaatcagtg ga 22

<210> SEQ ID NO 150
<211> LENGTH: 19
<212> TYPE: DNA
<213> ORGANISM: Artificial Sequence
<220> FEATURE:
<223> OTHER INFORMATION: Synthetic Guide

<400> SEQUENCE: 150
gtcctgcccc ttcaccttc 19

<210> SEQ ID NO 151
<211> LENGTH: 22
<212> TYPE: DNA
<213> ORGANISM: Artificial Sequence
<220> FEATURE:
<223> OTHER INFORMATION: Synthetic Guide

<400> SEQUENCE: 151
catccgtcta ctcccacgtt ct 22

<210> SEQ ID NO 152
<211> LENGTH: 22
<212> TYPE: DNA
<213> ORGANISM: Artificial Sequence
<220> FEATURE:
<223> OTHER INFORMATION: Synthetic Guide

<400> SEQUENCE: 152
ctggagagac gacagggctg gt 22

<210> SEQ ID NO 153
<211> LENGTH: 22
<212> TYPE: DNA
<213> ORGANISM: Artificial Sequence
<220> FEATURE:
<223> OTHER INFORMATION: Synthetic Guide

<400> SEQUENCE: 153
tggacttttg ggtgtctgag ca 22

<210> SEQ ID NO 154
<211> LENGTH: 22
<212> TYPE: DNA
<213> ORGANISM: Artificial Sequence
<220> FEATURE:
<223> OTHER INFORMATION: Synthetic Guide

<400> SEQUENCE: 154
aatcttacac agtgtgttta gg 22

<210> SEQ ID NO 155
<211> LENGTH: 22
<212> TYPE: DNA
<213> ORGANISM: Artificial Sequence
<220> FEATURE:
<223> OTHER INFORMATION: Synthetic Guide

<400> SEQUENCE: 155
agtatgtctt cttctaatgg tg 22

<210> SEQ ID NO 156
<211> LENGTH: 23
<212> TYPE: DNA
<213> ORGANISM: Artificial Sequence
<220> FEATURE:
<223> OTHER INFORMATION: Synthetic Guide

<400> SEQUENCE: 156
tgagtggcct gtgattctcc tca 23

<210> SEQ ID NO 157
<211> LENGTH: 28
<212> TYPE: DNA
<213> ORGANISM: Artificial Sequence
<220> FEATURE:
<223> OTHER INFORMATION: Synthetic Guide

<400> SEQUENCE: 157
agtctttaca cccccaagta tgttctgt 28

<210> SEQ ID NO 158
<211> LENGTH: 22
<212> TYPE: DNA
<213> ORGANISM: Artificial Sequence
<220> FEATURE:
<223> OTHER INFORMATION: Synthetic Guide

<400> SEQUENCE: 158
ggtctggcag gtgacaccac ac 22

<210> SEQ ID NO 159
<211> LENGTH: 22
<212> TYPE: DNA
<213> ORGANISM: Artificial Sequence
<220> FEATURE:
<223> OTHER INFORMATION: Synthetic Guide

<400> SEQUENCE: 159
aagtcgggcc tcctagctct gc 22

<210> SEQ ID NO 160
<211> LENGTH: 12
<212> TYPE: DNA
<213> ORGANISM: Artificial Sequence
<220> FEATURE:
<223> OTHER INFORMATION: Synthetic

<400> SEQUENCE: 160
acttgtttaa gt 12

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
tgggagggcc cggagggggc 20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
tgggagggcc cggagggggc 20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
gtccccggcc cagccccctc 20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
gtccccggcc cagccccctc 20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
tccccggccc agccccctcc 20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
tccccggccc agccccctcc 20

<210> SEQ ID NO 167

<211> LENGTH: 20
<212> TYPE: DNA
<213> ORGANISM: Artificial Sequence
<220> FEATURE:
<223> OTHER INFORMATION: Synthetic

<400> SEQUENCE: 167
ggggctggga gggcccggag 20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
ggggctggga gggcccggag 20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
gggctgggag ggcccggagg 20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
gggctgggag ggcccggagg 20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
gggagggccc ggagggggct 20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
gggagggccc ggagggggct 20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
gaggggctgg gagggcccgg 20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
gaggggctgg gagggcccgg 20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
gggggctggg ccggggaccc 20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gggggctggg ccggggaccc 20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
ggctgggccg gggacccggg 20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
ggctgggccg gggacccggg 20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
gctgggccgg ggacccggga 20

<210> SEQ ID NO 180
<211> LENGTH: 20
<212> TYPE: DNA

<213> ORGANISM: Artificial Sequence
<220> FEATURE:
<223> OTHER INFORMATION: Synthetic

<400> SEQUENCE: 180
gctgggccgg ggacccggga 20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
ctgggccggg gacccgggag 20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
ctgggccggg gacccgggag 20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
gccggggacc cgggaggggt 20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
gccggggacc cgggaggggt 20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
ccggggaccc gggaggggtc 20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
ccggggaccc gggaggggtc 20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
cgccccgtcc cgacccctcc 20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
cgccccgtcc cgacccctcc 20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
gccccgtccc gacccctccc 20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
ggccgcggaa aggaagggga 20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
ggccgcggaa aggaagggga 20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
gaaactcgcg ccgcgaggag 20

<210> SEQ ID NO 193
<211> LENGTH: 20
<212> TYPE: DNA
<213> ORGANISM: Artificial Sequence
<220> FEATURE:

<223> OTHER INFORMATION: Synthetic

<400> SEQUENCE: 193
gaaactcgcg ccgcgaggag 20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
gcccctcccc ttcctttccg 20

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
gcccctcccc ttcctttccg 20

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
tgcctgaaac tcgcgccgcg 20

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
tgcctgaaac tcgcgccgcg 20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
gcggggccgc ggaaaggaag 20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
gcggggccgc ggaaaggaag 20

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
aaactcgcgc cgcgaggaga 20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
aaactcgcgc cgcgaggaga 20

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
ggcggggccg cggaaaggaa 20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
ggcggggccg cggaaaggaa 20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
gccgcggaaa ggaaggggag 20

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
gccgcggaaa ggaaggggag 20

<210> SEQ ID NO 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
gggccgcgga aaggaagggg 20

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
gggccgcgga aaggaagggg 20

<210> SEQ ID NO 208
<211> LENGTH: 20
<212> TYPE: DNA
<213> ORGANISM: Artificial Sequence
<220> FEATURE:
<223> OTHER INFORMATION: Synthetic

<400> SEQUENCE: 208
ggaaaggaag gggaggggct 20

<210> SEQ ID NO 209
<211> LENGTH: 20
<212> TYPE: DNA
<213> ORGANISM: Artificial Sequence
<220> FEATURE:
<223> OTHER INFORMATION: Synthetic

<400> SEQUENCE: 209
ggaaaggaag gggaggggct 20

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
gctgcgcagc cactaccgcg 20

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
gctgcgcagc cactaccgcg 20

<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
tggccagcgg cagcacctcg 20

<210> SEQ ID NO 213
<211> LENGTH: 20

<212> TYPE: DNA
<213> ORGANISM: Artificial Sequence
<220> FEATURE:
<223> OTHER INFORMATION: Synthetic

<400> SEQUENCE: 213
tggccagcgg cagcacctcg 20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
ggggagcgcg cggcatcgcg 20

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
ggggagcgcg cggcatcgcg 20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
gctgcgcagc agggagcgca 20

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
gctgcgcagc agggagcgca 20

<210> SEQ ID NO 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
gcagcaggga gcgcacggct 20

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
gcagcaggga gcgcacggct 20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
ccacgttcgt gcggcgcctg 20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
ccacgttcgt gcggcgcctg 20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
tgccgctggc cacgttcgtg 20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
tgccgctggc cacgttcgtg 20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
cgccgcacga acgtggccag 20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
cgccgcacga acgtggccag 20

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
gcggtagtgg ctgcgcagca 20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
gcggtagtgg ctgcgcagca 20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
ctaccgcgag gtgctgccgc 20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
ctaccgcgag gtgctgccgc 20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
gcggcagcac ctcgcggtag 20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
gcggcagcac ctcgcggtag 20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
gggagcgcac ggctcggcag 20

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
gggagcgcac ggctcggcag 20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
ggagcgcacg gctcggcagc 20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
ggagcgcacg gctcggcagc 20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
gagcgcacgg ctcggcagcg 20

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
gagcgcacgg ctcggcagcg 20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
gctcggcagc ggggagcgcg 20

<210> SEQ ID NO 239
<211> LENGTH: 20
<212> TYPE: DNA
<213> ORGANISM: Artificial Sequence
<220> FEATURE:
<223> OTHER INFORMATION: Synthetic

<400> SEQUENCE: 239
gctcggcagc ggggagcgcg 20

<210> SEQ ID NO 240
<211> LENGTH: 201
<212> TYPE: DNA
<213> ORGANISM: Artificial Sequence
<220> FEATURE:
<223> OTHER INFORMATION: Synthetic

<400> SEQUENCE: 240
ccgcgccccg gcccggtgca gcaccaccag cgtgtccagg aagccctccc gggcagcgtc 60
gtgcacgggt cgggtgagag tggcggggtc ggcgcagttg ggctccgcgc cgtggagcag 120
cagcagctcc gccactcggg cgctgcccat catcatgacc tgccagagag aacagaatgg 180
tcagagccag ggtgggggcc g 201

<210> SEQ ID NO 241
<211> LENGTH: 201
<212> TYPE: DNA
<213> ORGANISM: Artificial Sequence
<220> FEATURE:
<223> OTHER INFORMATION: Synthetic

<400> SEQUENCE: 241
ccgcgccccg gcccggtgca gcaccaccag cgtgtccagg aagccctccc gggcagcgtc 60
gtgcacgggt cgggtgagag tggcggggtc ggcgcagtag ggctccgcgc cgtggagcag 120
cagcagctcc gccactcggg cgctgcccat catcatgacc tgccagagag aacagaatgg 180
tcagagccag ggtgggggcc g 201

<210> SEQ ID NO 242
<211> LENGTH: 117
<212> TYPE: DNA
<213> ORGANISM: Artificial Sequence
<220> FEATURE:
<223> OTHER INFORMATION: Synthetic

<400> SEQUENCE: 242
ccgcgccccg gcccggtgca gcaccaccag cgtgtccagg aagccctccc gggcagcgtc 60
gtgcacgggt cgggtgagag tggcggggtc ggcgcagttg ggctccgcgc cgtggag 117

<210> SEQ ID NO 243
<211> LENGTH: 200
<212> TYPE: DNA
<213> ORGANISM: Artificial Sequence
<220> FEATURE:
<223> OTHER INFORMATION: Synthetic

<400> SEQUENCE: 243
ccgcgccccg gcccggtgca gcaccaccag cgtgtccagg aagccctccc gggcagcgtc 60
gtgcacgggt cgggtgagag tggcggggtc ggcgagttgg gctccgcgcc gtggagcagc 120
agcagctccg ccactcgggc gctgcccatc atcatgacct gccagagaga acagaatggt 180
cagagccagg gtgggggccg 200

<210> SEQ ID NO 244
<211> LENGTH: 200
<212> TYPE: DNA
<213> ORGANISM: Artificial Sequence
<220> FEATURE:

```
<223> OTHER INFORMATION: Synthetic

<400> SEQUENCE: 244

ccgcgccccg gcccggtgca gcaccaccag cgtgtccagg aagccctccc gggcagcgtc      60

gtgcacgggt cgggtgagag tggcggggtc ggcgcagttg ggtccgcgcc gtggagcagc     120

agcagctccg ccactcgggc gctgcccatc atcatgacct gccagagaga acagaatggt     180

cagagccagg gtgggggccg                                                 200
```